(12) United States Patent
Balsitis et al.

(10) Patent No.: US 11,497,808 B2
(45) Date of Patent: Nov. 15, 2022

(54) HBV VACCINES AND METHODS TREATING HBV

(71) Applicant: Gilead Sciences, Inc., Foster City, CA (US)

(72) Inventors: Scott J. Balsitis, Moss Beach, CA (US); Sarah M. Ahmadi-Erber, Vienna (AT); Timo Schippers, Vienna (AT); Sarah Schmidt, Vienna (AT)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 17/034,706

(22) Filed: Sep. 28, 2020

(65) Prior Publication Data

US 2021/0093712 A1 Apr. 1, 2021

Related U.S. Application Data

(60) Provisional application No. 62/908,494, filed on Sep. 30, 2019.

(51) Int. Cl.
| | | |
|---|---|---|
| *A61K 39/29* | (2006.01) | |
| *A61P 37/04* | (2006.01) | |
| *C12N 9/12* | (2006.01) | |
| *A61K 39/00* | (2006.01) | |

(52) U.S. Cl.
CPC ............ *A61K 39/292* (2013.01); *A61P 37/04* (2018.01); *C12N 9/1252* (2013.01); *C12Y 207/07007* (2013.01); *A61K 2039/5256* (2013.01); *C12N 2730/10122* (2013.01); *C12N 2730/10134* (2013.01); *C12N 2760/10034* (2013.01); *C12N 2760/10043* (2013.01)

(58) Field of Classification Search
CPC .......... A61K 39/292; A61K 2039/5256; A61K 2039/545; A61K 39/12; A61P 37/04; A61P 31/20; C12N 9/1252; C12N 2730/10122; C12N 2730/10134; C12N 2760/10034; C12N 2760/10043; C12Y 207/07007; Y02A 50/30
See application file for complete search history.

(56) References Cited

U.S. PATENT DOCUMENTS

| | | | |
|---|---|---|---|
| 4,428,941 A | 1/1984 | Galibert et al. | |
| 5,196,194 A | 3/1993 | Rutter et al. | |
| 5,593,825 A | 1/1997 | Carman et al. | |
| 5,856,084 A | 1/1999 | Karayiannis et al. | |
| 6,060,595 A | 5/2000 | Scaglioni et al. | |
| 6,072,049 A | 6/2000 | Thoma | |
| 6,096,879 A | 8/2000 | Tiollais et al. | |
| 6,110,706 A | 8/2000 | Thoma | |
| 6,172,193 B1 | 1/2001 | Primi et al. | |
| 6,232,099 B1 | 5/2001 | Chapman et al. | |
| 6,268,122 B1 | 7/2001 | Murray | |
| 6,270,955 B1 | 8/2001 | Murray | |
| 6,297,048 B1 | 10/2001 | Jolly et al. | |
| 6,558,675 B1 | 5/2003 | Oon et al. | |
| 6,787,142 B2 | 9/2004 | Oon et al. | |
| 7,038,035 B1 | 5/2006 | Oon et al. | |
| 7,067,247 B2 | 6/2006 | Zheng | |
| 7,105,165 B2 | 9/2006 | Oon et al. | |
| 7,141,242 B2 | 11/2006 | Coleman et al. | |
| 7,202,354 B2 | 4/2007 | Coleman et al. | |
| 7,313,357 B2 | 12/2007 | Stuyver et al. | |
| 7,732,423 B2 | 6/2010 | Michel et al. | |
| 8,138,318 B2 | 3/2012 | Coleman et al. | |
| 8,216,589 B2 | 7/2012 | Yum et al. | |
| 8,729,231 B2 | 5/2014 | Bussfeld et al. | |
| 8,945,876 B2 | 2/2015 | Su et al. | |
| 9,017,695 B2 | 4/2015 | de los Rios et al. | |
| 9,238,679 B2 | 1/2016 | Weiner et al. | |
| 9,353,158 B2 | 5/2016 | Whalen et al. | |
| 9,403,879 B2 | 8/2016 | Weiner et al. | |
| 9,428,556 B2 | 8/2016 | Apelian et al. | |
| 9,512,412 B2 | 12/2016 | Martin et al. | |
| 9,512,443 B2 | 12/2016 | Richmond et al. | |
| 9,675,690 B2 | 6/2017 | Weiner et al. | |
| 9,751,914 B2 | 9/2017 | Yuan et al. | |
| 9,878,035 B2 | 1/2018 | Du et al. | |
| 10,190,105 B2 | 1/2019 | Martin et al. | |
| 10,195,268 B2 | 2/2019 | Weiner et al. | |
| 10,695,421 B2 | 6/2020 | Weiner et al. | |
| 11,020,476 B2 | 6/2021 | Boden et al. | |

(Continued)

FOREIGN PATENT DOCUMENTS

| | | |
|---|---|---|
| EP | 1294893 B1 | 3/2006 |
| EP | 1572234 B1 | 2/2012 |

(Continued)

OTHER PUBLICATIONS

Li et. al. Hepatitis B virus isolate CX003C(e204), complete genome. GenBank Acc. No. KJ173341, Dep. Jan. 22, 2014. (Year: 2014).*
Boni C et al. (2019), "Combined GS-4774 and Tenofovir Therapy Can Improve HBV-Specific T-Cell Responses in Patients With Chronic Hepatitis", Gastroenterology, vol. 157, No. 1, pp. 227-241.
Bénéchet A P et al. (2019), "Dynamics and genomic landscape of CD8+ T cells undergoing hepatic priming", Nature, vol. 574.
Chinnakannan S K et al. (2020), "The Design and Development of a Multi-HBV Antigen Encoded in Chimpanzee Adenoviral and Modified Vaccinia Ankara Viral Vectors; A Novel Therapeutic Vaccine Strategy against HBV", Vaccines, vol. 8, No. 2, 184.
Clark D N et al. (2017), "Mapping of Functional Subdomains in the Terminal Protein Domain of Hepatitis B Virus Polymerase", Journal of Virology, vol. 91, Issue 3, e01785-16.

(Continued)

*Primary Examiner* — Rachel B Gill

(57) ABSTRACT

Provided are HBV immunogenic polypeptides, polynucleotides encoding such polypeptides, vectors expressing such immunogenic polypeptides for use in eliciting an immune response against HBV; pharmaceutical and immunogenic compositions and kits comprising such polypeptides, polynucleotides or vectors, and methods of use in treating and/or preventing HBV.

19 Claims, 49 Drawing Sheets

Specification includes a Sequence Listing.

(56) References Cited

U.S. PATENT DOCUMENTS

| | | | |
|---|---|---|---|
| 2012/0251569 A1* | 10/2012 | Martin | A61P 37/02 |
| | | | 435/235.1 |
| 2013/0011435 A1 | 1/2013 | Martin et al. | |
| 2017/0056493 A1* | 3/2017 | Robek | C12N 15/86 |
| 2021/0154290 A1 | 5/2021 | Ammendola et al. | |

FOREIGN PATENT DOCUMENTS

| | | |
|---|---|---|
| EP | 2057268 B1 | 8/2014 |
| TW | I555531 B | 11/2016 |
| WO | WO-97/00698 A1 | 1/1997 |
| WO | WO-2009/083210 A1 | 7/2009 |
| WO | WO-2011/015656 A2 | 2/2011 |
| WO | WO-2013/007772 A1 | 1/2013 |
| WO | WO-2016/075250 A1 | 5/2016 |
| WO | WO-2016/090470 A1 | 6/2016 |
| WO | WO-2017/040815 A1 | 3/2017 |
| WO | WO-2017/076988 A1 | 5/2017 |
| WO | WO-2017/132332 A1 | 8/2017 |
| WO | WO-2017/198726 A1 | 11/2017 |
| WO | WO-2018/189522 A1 | 10/2018 |
| WO | WO-2019/115816 A1 | 6/2019 |
| WO | WO-2020/255023 A1 | 12/2020 |
| WO | WO-2021/045969 A1 | 3/2021 |

OTHER PUBLICATIONS

Intl. Search Report—Written Opinion dated Jan. 25, 2021 for Intl. Appl. No. PCT/US2020/053060.

Jones S A et al. (2014), "Comparative Analysis of Hepatitis B Virus Polymerase Sequences Required for Viral RNA Binding, RNA Packaging, and Protein Priming", Journal of Virology, vol. 88, No. 3, pp. 1564-1572.

Kosinska A D et al. (2017), "Therapeutic vaccination for chronic hepatitis B", Current Opinion in Virology, vol. 23, pp. 75-81.

Kwon T K et al. (2002), "Intramuscular co-injection of naked DNA encoding HBV core antigen and Flt3 ligand suppresses anti-HBc antibody response", Immunology Letters 81(3): 229-234.

Lanford R E et al. (1999), "Mapping of the Hepatitis B Virus Reverse Transcriptase TP and RT Domains by Transcomplementation for Nucleotide Priming and by Protein-Protein Interaction", Journal of Virology, vol. 73, No. 3, p. 1885-1893.

McNaughton A L et al. (2018), "Insights From Deep Sequencing of the HBV Genome-Unique, Tiny, and Misunderstood", Gastroenterology, Elsevier Inc, US, vol. 156, No. 2, pp. 384-399.

Radoshitzky S R et al. (2015), "Past, present, and future of arenavirus taxonomy", Arch Virol 160:1851-1874.

Radziwill G et al. (1990), "Mutational analysis of the hepatitis B virus P gene product: domain structure and RNase H activity", Journal of Virology, vol. 64, No. 2, pp. 613-620.

Vörös J et al. (2014), "Large-Scale Production and Structural and Biophysical Characterizations of the Human Hepatitis B Virus Polymerase", Journal of Virology, vol. 88, No. 5, p. 2584-2599.

Examination Report dated Oct. 13, 2021 for GCC Appl. No. 40546.

Office Action and Search Report dated Oct. 15, 2021 for Taiwanese Appl. No. 109133810.

Intl. Preliminary Report on Patentability—Written Opinion dated Apr. 14, 2022 for Intl. Appl. No. PCT/US2020/053060.

Office Action dated Apr. 11, 2022 for Panamanian Appl. No. 93895-01.

* cited by examiner

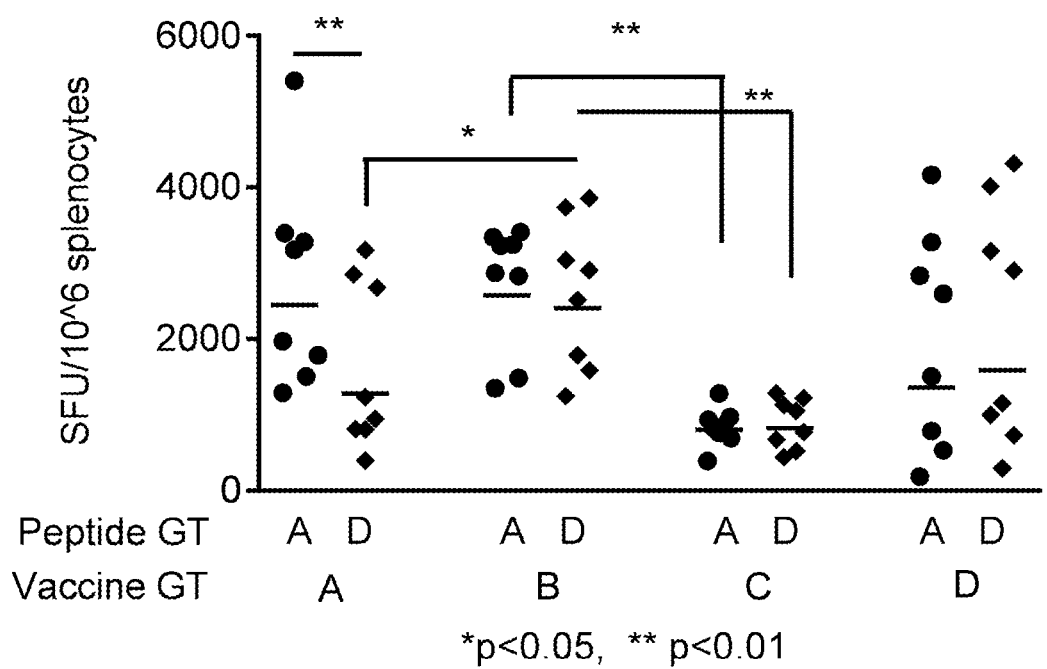
*Fig. 4A*
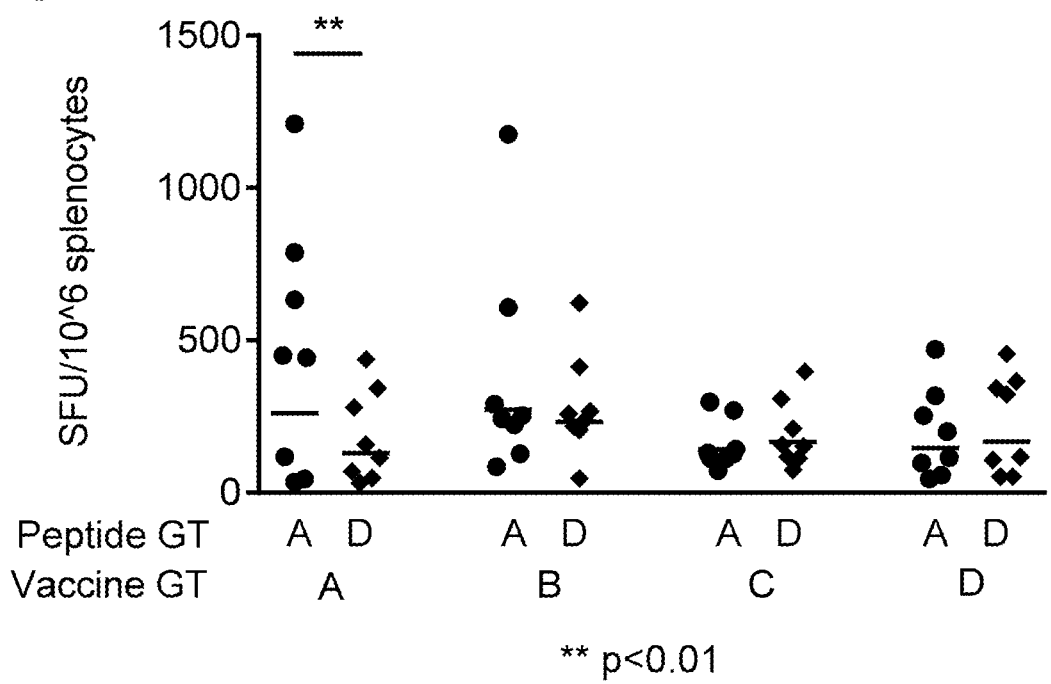
*Fig. 4B*
Figs. 4A-4B

Fig. 9A

Fig. 9B
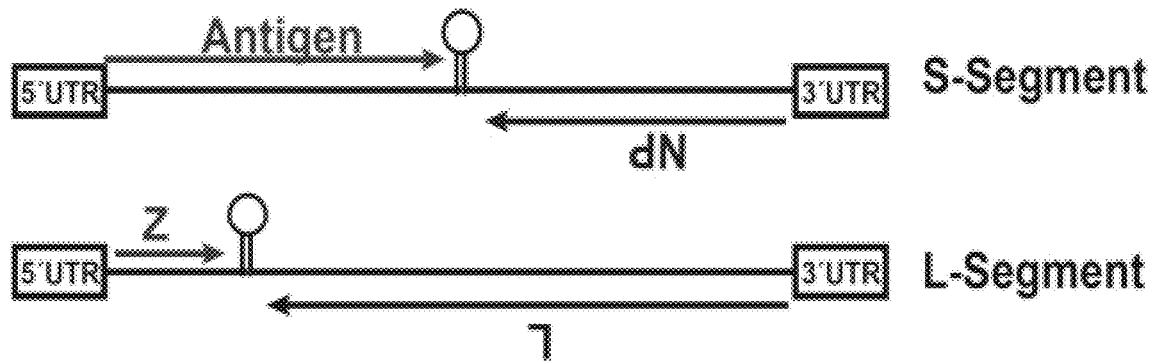
+ viral GP is delivered *in trans*
Fig. 9C
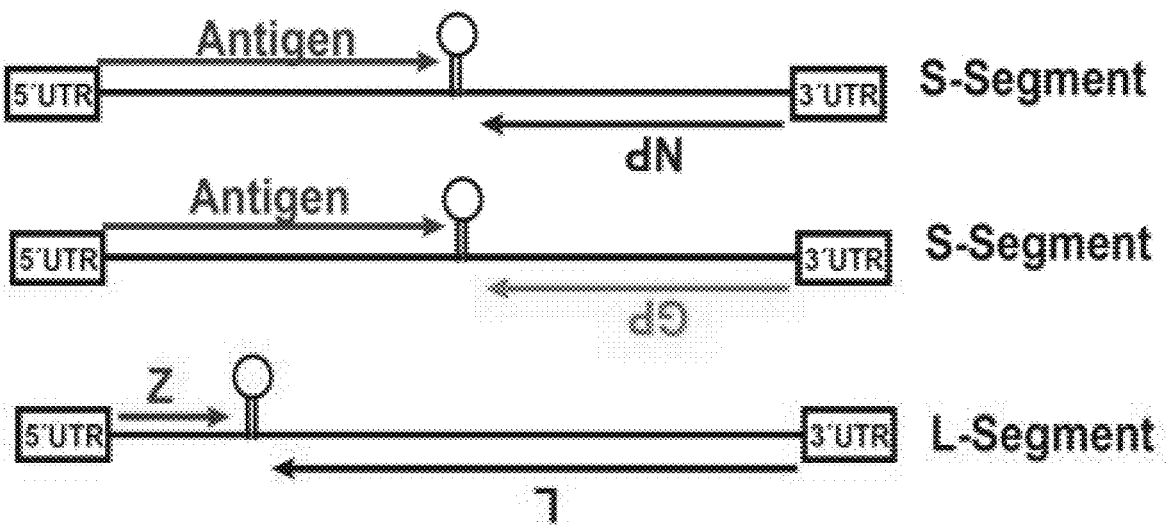
Figs. 9B-9C

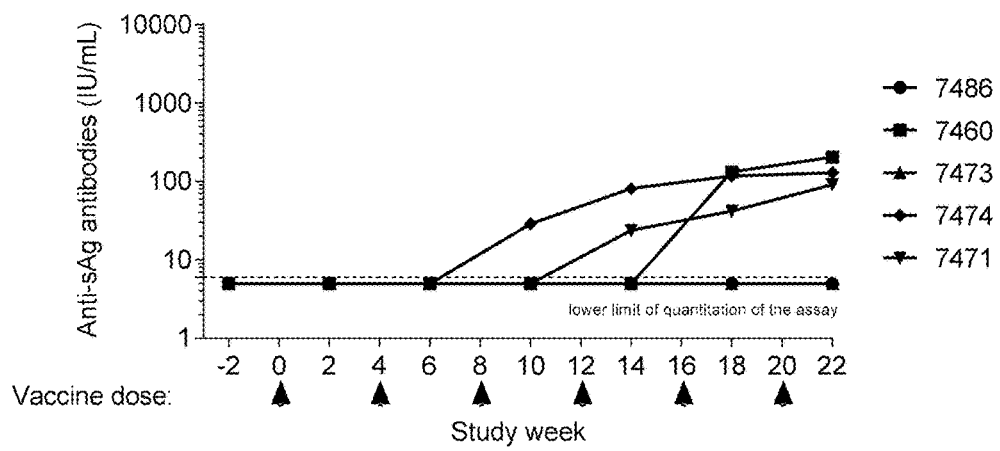
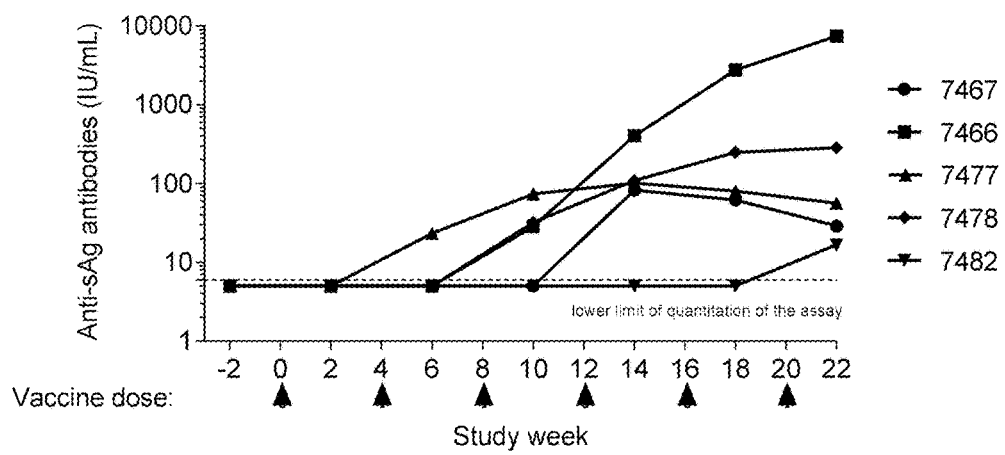
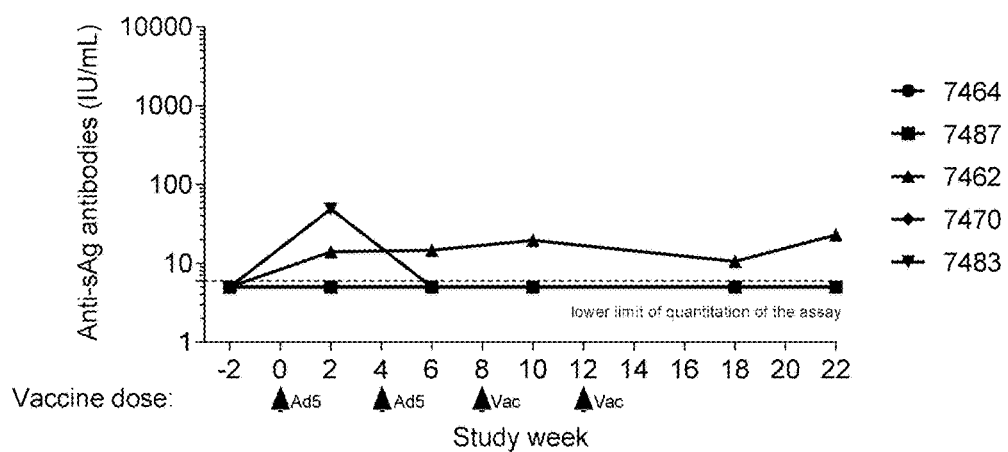
Figs. 22A-C

Fig. 27

HBV VACCINES AND METHODS TREATING HBV

CROSS-REFERENCE TO RELATED APPLICATIONS

This application claims the benefit under 35 U.S.C. § 119(e) of U.S. provisional application No. 62/908,494, filed on Sep. 30, 2019, which is hereby incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Sep. 4, 2020, is named 1324_PC_SL.txt and is 294,167 bytes in size.

BACKGROUND

There have been many attempts to use vaccination to treat patients with chronic hepatitis B virus (HBV) infection to improve rates of HBV surface antigen (sAg) loss, the primary marker of functional cure. Such attempts have included vaccination with recombinant proteins (Dikici, et al., *J Gastroenterol Hepatol.* (2003) 18(2):218-22; Pol, et al., *J Hepatol.* (2001) 34(6):917-21; Vandepapeliere, et al., *Vaccine* (2007) 25(51):8585-97; Yalcin, et al., *J Clin Gastroenterol.* (2003) 37(4):330-5; Al-Mahtab, *Hepatol Int.* (2013) 7(4):981-9; Hoa, et al., *Antimicrob Agents Chemother.* (2009) 53(12):5134-40; and Yalcin, et al., *Infection.* (2003) 31(4):221-5), recombinant DNA (Mancini-Bourgine, et al., *Hepatology.* (2004) 40(4):874-82; Yang, et al., *World J Gastroenterol.* (2017) 23(2):306-17; Yang, et al., *J Viral Hepat.* (2012) 19(8):581-93; Yoon, et al., *Liver Int.* (2015) 35(3):805-15; Cavenaugh, et al., *PLoS One.* (2011) 6(2):e14626; and Godon, et al., *Mol Ther.* (2014) 22(3):675-84), dendritic cells (Luo, et al., *Vaccine.* (2010) 28(13):2497-504; and Wei, et al., *Int Immunopharmacol.* (2015) 27(2):238-43), a yeast vector (Gane. et al., *J Hepatol.* (2019) Epub 2019/07/16. doi: 10.1016/j.jhep.2019.06.028. PubMed PMID: 31306680), and some viral vectors (Cavenaugh, et al., supra; and Zoulim, et al., *Hum Vaccin Immunother.* (2019) Epub Aug. 3, 2019. doi: 10.1080/21645515.2019.1651141. PubMed PMID: 31373537). Despite these many attempts, to date no therapeutic vaccination approach has shown consistent benefit in chronic HBV infection (CHB). Deficits in previous vaccine approaches may explain the failures of previous vaccine approaches.

Such deficits include limitations in the antigen designs and in the vaccine technologies used. An optimal antigen will contain highly conserved portions of HBV proteins and exclude poorly conserved regions, because highly conserved regions can induce responses against epitopes that are identical in the vaccine antigen and in the virus present in the treated patient, while poorly conserved regions may elicit immunodominant T cell responses against epitopes that are not present in the patient's infecting virus strain (Swadling, et al., *Vaccines* (Basel). (2016) 4(3). Epub 2016/08/05. doi: 10.3390/vaccines4030027. PubMed PMID: 27490575). However, some prior vaccines used antigen designs that do not meet these criteria (Yalcin, et al., *J Clin Gastroenterol.* (2003) 37(4):330-5; Hoa, et al., supra; Yalcin, et al., *Infection.* (2003) 31(4):221-5; Mancini-Bourgine, et al., supra; Yang, et al., *J Viral Hepat.* (2012) 19(8):581-93; Cavenaugh, et al., supra; Godon, et al., supra; Gane. et al., supra; and Obeng-Adjei, et al., *Cancer Gene Ther.* (2013) 20(12):652-62). Additionally, many prior vaccines have failed to induce a full combination of virus-specific CD4+ T cells, CD8+ T cells, and antibody responses (Dikici, et al., supra; Pol, et al., supra; Vandepapeliere, et al., supra; Yalcin, et al., *J Clin Gastroenterol.* (2003) 37(4):330-5; Al-Mahtab, supra; Hoa, et al., supra; Yalcin, et al., *Infection.* (2003) 31(4):221-5; Mancini-Bourgine, et al., supra; Yang, et al., *J Viral Hepat.* (2012) 19(8):581-93; Gane. et al., supra; and Zoulim, et al., supra). These immune components are particularly important for curing chronic HBV infection as CD8+ T cells have been shown to be the main effector cells responsible for viral clearance during acute HBV infection in chimpanzees (Thimme, et al., *J Virol.* (2003) 77(1):68-76). In addition, antibodies that bind to HBV surface antigen (HBsAg) facilitate HBsAg clearance and prevent spread of residual HBV. Moreover, a high magnitude of immune response is likely necessary to achieve a therapeutic effect, but many prior CHB vaccines have failed to induce such a robust response (Mancini-Bourgine, et al., supra; Yang, et al., *J Viral Hepat.* (2012) 19(8):581-93; Cavenaugh, et al., supra; Gane. et al., supra; and Zoulim, et al., supra). Lastly, some prior CHB vaccine antigens have not been sufficiently stable in the delivery vectors to enable commercial-scale vaccine manufacture.

SUMMARY

In one aspect, provided are truncated hepatitis B virus (HBV) polymerase polypeptides, e.g., capable of inducing or eliciting an immune response in a human upon administration. In some embodiments, the truncated HBV polymerase polypeptide comprises an inactivated reverse transcriptase domain and an inactivated RNase H, and does not comprise all of the terminal protein (TP) domain and all or part of the Spacer domain. In some embodiments, the polypeptide is no longer than 600 amino acids in length, e.g., no longer than 595, 590, 585, 580, 575, 570, 565, 560, 555, 550, 545, 540 or 535 amino acids in length. In some embodiments, the reverse transcriptase domain does not comprise a YMDD motif (SEQ ID NO: 97) and the RNase H domain does not comprise an AELL motif (SEQ ID NO: 98). In some embodiments, the YMDD motif (SEQ ID NO: 97) in the reverse transcriptase domain is mutated to YMHD (SEQ ID NO: 99) and wherein the AELL motif (SEQ ID NO: 98) in the RNase H domain is mutated to AHLL (SEQ ID NO: 100). In some embodiments, the polypeptide is from an HBV genotype A, B, C or D. In some embodiments, (a) the polypeptide is from HBV genotype B and does not comprise a polypeptide sequence (e.g., the sequence is removed or deleted or not included) of SEQ ID NO: 50, or a sequence that is at least 90%, 91%, 92%, 93%, 94%, 95%, 96%, 97%, 98% or 99% identical to any one of SEQ ID NO: 50; or (b) the polypeptide is from HBV genotype D and does not comprise a polypeptide sequence of SEQ ID NO: 51, or a sequence that is at least 90%, 91%, 92%, 93%, 94%, 95%, 96%, 97%, 98% or 99% identical to any one of SEQ ID NO: 51. In some embodiments, the truncated HBV polymerase polypeptide comprises or consists of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14.

In another aspect, provided are HBV polymerase deletion mutant polypeptides. In some embodiments, the HBV polymerase deletion mutant polypeptide comprises in sequential order from the N-terminus to the C-terminus, a terminal protein (TP) domain, an inactivated reverse transcriptase domain, and an inactivated RNase H, wherein the mutant polypeptide does not comprise all or part of a Spacer domain. In some embodiments, the polypeptide is no longer than 800 amino acids in length, e.g., no longer than 795, 790, 785, 780, 775, 770, 765, 760, 755, 750, 745, 740, 735, 730, 725, 720, 715, 710 or 705 amino acids in length. In some embodiments, the reverse transcriptase domain does not comprise a YMDD motif (SEQ ID NO: 97) and the RNase H domain does not comprise an AELL motif (SEQ ID NO: 98). In some embodiments, the YMDD motif (SEQ ID NO: 97) in the reverse transcriptase domain is mutated to YMHD (SEQ ID NO: 99) and wherein the AELL motif (SEQ ID NO: 98) in the RNase H domain is mutated to AHLL (SEQ ID NO: 100). In some embodiments, the polypeptide is from an HBV genotype A, B, C or D. In some embodiments, (a) the polypeptide is from HBV genotype A and does not comprise a polypeptide of SEQ ID NO: 42 or 46, or a sequence that is at least 90%, 91%, 92%, 93%, 94%, 95%, 96%, 97%, 98% or 99% identical to any one of SEQ ID NO: 42 or 46; (b) the polypeptide is from HBV genotype B and does not comprise a polypeptide of SEQ ID NO: 43 or 47, or a sequence that is at least 90%, 91%, 92%, 93%, 94%, 95%, 96%, 97%, 98% or 99% identical to any one of SEQ ID NO: 43 or 47; (c) the polypeptide is from HBV genotype C and does not comprise a polypeptide of SEQ ID NO: 44 or 48, or a sequence that is at least 90%, 91%, 92%, 93%, 94%, 95%, 96%, 97%, 98% or 99% identical to any one of SEQ ID NO: 44 or 48; or (d) the polypeptide is from HBV genotype D and does not comprise a polypeptide of SEQ ID NO: 45 or 49, or a sequence that is at least 90%, 91%, 92%, 93%, 94%, 95%, 96%, 97%, 98% or 99% identical to any one of SEQ ID NO: 45 or 49. In some embodiments, the HBV polymerase deletion mutant polypeptide comprises or consists of an amino acid sequence of any one of SEQ ID NOs: 5-12, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-12. In some embodiments, HBV polymerase deletion mutant polypeptide further comprises (e.g., is a fusion protein including) an HBV core polypeptide. In some embodiments, the HBV polymerase deletion mutant polypeptide comprises in sequential order from the N-terminus to the C-terminus, an HBV core polypeptide and the HBV polymerase deletion mutant polypeptide, as described herein. In some embodiments, the HBV polymerase deletion mutant polypeptide comprises or consists of an amino acid sequence of any one of SEQ ID NOs: 19-26, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 19-26.

In a further aspect, provided is an HBV core-sAg fusion protein. In some embodiments, the core-sAg fusion protein comprises in sequential order from the N-terminus to the C-terminus, an HBV core polypeptide and an HBV small surface antigen (sAg) polypeptide. In various embodiments, the core polypeptide is from an HBV genotype B or C and the sAg polypeptide is from an HBV genotype C. In some embodiments, the core polypeptide is from an HBV genotype D and the sAg polypeptide is from an HBV genotype D. In some embodiments, the core-sAg fusion protein comprises: (a) a core polypeptide comprising or consisting of an amino acid sequence of SEQ ID NO: 65, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 65, and a sAg polypeptide comprising or consisting of an amino acid sequence of SEQ ID NO: 3, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical SEQ ID NO: 3; or (b) a core polypeptide comprising or consisting of an amino acid sequence of SEQ ID NO: 66, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 66, and a sAg polypeptide comprising or consisting of an amino acid sequence of SEQ ID NO: 4, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical SEQ ID NO: 4. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In various embodiments, the sAg polypeptide does not comprise a pre-S1 polypeptide. In various embodiments, the sAg polypeptide does not comprise a pre-S2 polypeptide. In some embodiments, the sAg polypeptide does not comprise an HBV pre-S2 polypeptide comprising or consisting of an amino acid sequence of any one of SEQ ID NOs: 79-83, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79-83. In some embodiments, the sAg polypeptide does not comprise both of an HBV pre-S1 polypeptide and an HBV pre-S2 polypeptide. In some embodiments, the sAg polypeptide does not comprise an HBV pre-S1-pre-S2 polypeptide comprising or consisting of an amino acid sequence of any one of SEQ ID NO: 84-88, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84-88. In various embodiments, the core-sAg fusion protein comprises a cleavable linker operably linked to and positioned between the HBV core polypeptide and the HBV sAg polypeptide. In some embodiments, the cleavable linker is a 2A cleavable peptide. In some embodiments, the cleavable linker is a 2A cleavable peptide selected from foot-and-mouth disease virus (F2A), equine rhinitis A virus (E2A), porcine teschovirus-1 (P2A) and *Thosea asigna* virus (T2A). In some embodiments, the cleavable linker is a porcine teschovirus-1 (P2A) linker. In some embodiments, the cleavable linker comprises or consists of an amino acid sequence of ATNFSLLKQAGDVEENPGP (SEQ ID NO: 56), APVKQTLNFDLLKLAGDVESNPGP (SEQ ID NO: 57), QCTNYALLKLAGDVESNPGP (SEQ ID NO: 58), or EGRGSLLTCGDVEENPGP (SEQ ID NO: 59), or an amino acid sequence that is at least 90%, 91%, 92%, 93%, 94%, 95%, 96%, 97%, 98% or at least 99% identical to ATNFSLLKQAGDVEENPGP (SEQ ID NO: 56), APVKQTLNFDLLKLAGDVESNPGP (SEQ ID NO: 57), QCTNYALLKLAGDVESNPGP (SEQ ID NO: 58), or EGRGSLLTCGDVEENPGP (SEQ ID NO: 59). In some embodiments, the cleavable linker comprises or consists of an amino acid sequence of ATNFSLLKQAGDVEENPGP (SEQ ID NO: 56), or an amino acid sequence that is at least 90%, 91%, 92%, 93%, 94%, 95%, 96%, 97%, 98% or at least 99% identical to ATNFSLLKQAGDVEENPGP (SEQ ID NO: 56). In some embodiments, the core-sAg fusion protein comprises a flexible linker and/or a furin recognition/cleavage site operably linked to and positioned N-terminal to the cleavable linker and C-terminal to the HBV core polypeptide. In some embodiments, the furin recognition/cleavage site comprises or consists of an amino acid sequence selected from RAKR (SEQ ID NO: 60), REKR (SEQ ID NO: 61) and RRKR (SEQ ID NO: 62). In some embodiments, the flexible linker comprises a polyglycine or polyalanine sequence. In some embodiments, the flexible linker comprises or consists of a polyglycine or polyalanine sequence selected from AA, AAA, AAY, GG, GGG, GGS, GSG and GGGS (SEQ ID NO: 63). In some embodiments, the core-sAg fusion protein is no longer than 450 amino acids in length, e.g., no longer than 445, 440, 435, 430, 425, 420, 415 or 410 amino acids in length. In some embodiments, the core-sAg fusion protein comprises or consists of an amino acid sequence of any one of SEQ ID NOs: 38-41, e.g., SEQ ID NO: 41, or a sequence that is at least 90%, 91%, 92%, 93%, 94%, 95%, 96%, 97%, 98% or 99% identical to any one of SEQ ID NOs: 38-41, e.g., SEQ ID NO:41. In some embodiments, the fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41. In various embodiments, the core-sAg fusion polypeptide does not comprise an amino sequence or fragment thereof from an HBV protein selected from the group consisting of X, pre-core, pre-S1 and pre-S2.

With respect to the immunogenic HBV polypeptides, in some embodiments, the truncated HBV polymerase polypeptide, the HBV polymerase deletion mutant polypeptide, or the core-sAg fusion protein, as described herein, further comprise an N-terminal signal peptide or leader sequence. In various embodiments, the signal peptide or leader sequence is from a source protein selected from a serum protein, a cytokine, a chemokine, a chaperone protein, an invariant protein, and a protein that directs proteins to the lysosomal compartment. In various embodiments, the signal peptide or leader sequence is from a source protein selected from colony stimulating factor 2 (CSF2, GM-CSF), tissue type plasminogen activator (PLAT, t-PA), C—C motif chemokine ligand 7 (CCL7, MCP-3), C—X—C motif chemokine ligand 10 (CXCL10, IP-10), catenin beta 1 (CTNNB1), CD74 (p33; DHLAG; HLADG; Ia-GAMMA, invariant chain), serum albumin (ALB), polyubiquitin B/C (UBB/UBC), calreticulin (CALR), vesicular stomatitis virus G protein (VSV-G), lysosomal associated membrane protein 1 (LAMP-1) and lysosomal associated membrane protein 2 (LAMP-2). In some embodiments, the signal peptide or leader sequence is selected from an amino acid sequence of any one of SEQ ID NOs: 67-78, or a sequence that is at least 95%, 96%, 97%, 98%, or 99% identical to any one of SEQ ID NOs: 67-78. In various embodiments, the truncated HBV polymerase polypeptide, the HBV polymerase deletion mutant polypeptide, and/or the core-sAg fusion protein, as described herein, can be recombinantly produced or chemically synthesized. In various embodiments, the truncated HBV polymerase polypeptide, the HBV polymerase deletion mutant polypeptide, and/or the core-sAg fusion protein, as described herein, are capable of inducing, promoting or stimulating an immune response (e.g., expansion and/or activation of CD8+ and/or CD4+ T cells; production of antibodies that bind to and/or neutralize one or more of HBV polymerase, HBV core and HBV sAg) in a human. In various embodiments, the truncated HBV polymerase polypeptide, the HBV polymerase deletion mutant polypeptide, and/or the core-sAg fusion protein, as described herein, are capable of inducing, promoting or stimulating an immune response against HBV (e.g., that prevents, delays progression of, inhibits and/or reverses HBV infection) in a human. In various embodiments, the truncated HBV polymerase polypeptide, the HBV polymerase deletion mutant polypeptide, and/or the core-sAg fusion protein, as described herein, are capable of inducing, promoting or stimulating proliferation and/or activation of one or more cell types selected from monocyte-derived dendritic cells (DCs), CD8+ T cells and CD4+ T cells.

In a further aspect, provided are polynucleotides encoding the immunogenic HBV polypeptides, as described herein. For example, provided are polynucleotides encoding one or more of the truncated HBV polymerase polypeptides, the HBV polymerase deletion mutant polypeptide, or the core-sAg fusion protein, as described herein. In some embodiments, the polynucleotide comprises cDNA, mRNA, self-amplifying RNA (SAM), self-replicating RNA, or self-amplifying replicon RNA (RepRNA). In some embodiments, polynucleotide comprises self-replicating or self-amplifying alphavirus replicons. In some embodiments, the polynucleotide comprises or consists of a nucleic acid sequence of any one of SEQ ID NOs: 27-37, e.g., SEQ ID NOs: 37 and 89-94, e.g., SEQ ID NOs: 29, 89, 90 or 92, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-37, e.g., SEQ ID NO:37 and 89-94, e.g., SEQ ID NOs: 29, 89, 90 or 92.

In another aspect, provided is a lipid nanoparticle (LNP) comprising one or more of the polynucleotides encoding an immunogenic HBV polypeptide, as described herein.

In another aspect, provided are expression cassettes comprising one or more of the polynucleotides encoding an immunogenic HBV polypeptide, as described herein, operably linked to one or more regulatory sequences. In some embodiments, the polynucleotide is operably linked to and under the control of a constitutive promoter. In some embodiments, the promoter is selected from cytomegalovirus major immediate-early (CMV), the CMV enhancer fused to the chicken beta-actin promoter (CAG), human elongation factor-1α (HEF-1α), mouse cytomegalovirus (mouse CMV), Chinese hamster elongation factor-1α (CHEF-1α), and phosphoglycerate kinase (PGK).

In another aspect, provided are comprising one or more of the polynucleotides encoding an immunogenic HBV polypeptide, as described herein, or one or more expression cassettes comprising such polynucleotides. In various embodiments, the vector is a plasmid vector, a bacterial vector or a viral vector. In some embodiments, the vector is a viral vector. In various embodiments, the viral vector is a DNA virus or an RNA virus. In some embodiments, the viral vector is from a virus selected from adenovirus, adeno-associated virus, arenavirus, alphavirus, poxvirus, cytomegalovirus, rhabdovirus, vesicular stomatitis virus, flavivirus, maraba virus and vaccinia virus. In some embodiments, the viral vector is from a virus from a taxonomic family selected from Adenoviridae, Arenaviridae, Herpesviridae (e.g. Cytomegalovirus), Poxviridae (e.g. Vaccinia virus, e.g. modified vaccinia Ankara (MVA)), Flaviviridae (e.g. Yellow fever virus), Rhabdoviridae (e.g. Vesiculovirus, e.g. Maraba vesiculovirus), Togaviridae (e.g., Alphavirus). In some embodiments, the viral vector is an arenavirus vector selected from Lymphocytic choriomeningitis mammarenavirus (LCMV), Cali mammarenavirus (a.k.a., Pichinde mammarenavirus or Pichinde arenavirus (PICV)), Guanarito virus (GTOV), Junin virus (JUNV), Lassa virus (LASV), Lujo virus (LUJV), Machupo virus (MACV), Sabia virus (SABV), and Whitewater Arroyo virus (WWAV). In some embodiments, the viral vector is an arenavirus vector selected from Lymphocytic choriomeningitis mammarenavirus (LCMV) or Cali mammarenavirus (a.k.a., Pichinde mammarenavirus or Pichinde arenavirus (PICV)). In some embodiments, the viral vector is a human adenovirus or a simian adenovirus (e.g., a chimpanzee adenovirus, a gorilla adenovirus or a rhesus adenovirus). In some embodiments, the viral vector is an adenovirus vector selected from adenovirus serotype 5 (Ad5), adenovirus serotype 26 (Ad26), adenovirus serotype 34 (Ad34), adenovirus serotype 35 (Ad35), adenovirus serotype 48 (Ad48), chimpanzee adenovirus (e.g. ChAdOx1, ChAdOx2, ChAd3 (AdC3), ChAd5 (AdC5), ChAd6 (AdC6), ChAd7 (AdC7), ChAd8 (AdC8), ChAd9 (AdC9), ChAd10 (AdC10), ChAd11 (AdC11), ChAd17 (AdC17), ChAd16 (AdC16), ChAd19 (AdC19), ChAd20 (AdC20), ChAd22 (AdC22), ChAd24 (AdC24), ChAdY25, ChAd26 (AdC26), ChAd28 (AdC28), ChAd30 (AdC30), ChAd31 (AdC31), ChAd37 (AdC37), ChAd38 (AdC38), ChAd43 (AdC43), ChAd44 (AdC44), ChAd55 (AdC55), ChAd63 (AdC63), ChAdV63, ChAd68 (AdC68), ChAd73 (AdC73), ChAd82 (AdC82), ChAd83 (AdC83), ChAd143 (AdC143), ChAd144 (AdC144), ChAd145 (AdC145), ChAd147 (AdC147)), gorilla adenovirus (e.g. GC44, GC45, GC46) and rhesus adenovirus (e.g., RhAd51, RhAd52, RhAd53, RhAd54, RhAd55, RhAd56, RhAd57, RhAd58, RhAd59, RhAd60, RhAd61, RhAd62, RhAd63, RhAd64, RhAd65, RhAd66). In some embodiments, the viral vector is replication-defective, replication-deficient, replication-attenuated or replication-competent. In some embodiments, the viral vector is a replication-defective arenavirus having a bi-segmented genome. In some embodiments, the viral vector is a replication-attenuated arenavirus having a tri-segmented genome.

In a further aspect, provided are arenavirus vectors. In one embodiment, provided is an arenavirus vector comprising a polynucleotide encoding an HBV core-sAg fusion polypeptide comprising or consisting of an amino acid sequence of any one of SEQ ID NOs: 38-41, e.g., SEQ ID NO:41, or a sequence that is at least 90%, 91%, 92%, 93%, 94%, 95%, 96%, 97%, 98% or 99% identical to any one of SEQ ID NOs: 38-41, e.g., SEQ ID NO:41, and wherein the sAg polypeptide does not comprise an HBV pre-S1 polypeptide and/or an HBV pre-S2 polypeptide. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41. In some embodiments, the polynucleotide comprises or consists of a nucleic acid sequence of any one of SEQ ID NOs: 33-37, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37. In some embodiments, the polynucleotide comprises or consists of a nucleic acid sequence of SEQ ID NO: 37, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments, the arenavirus vector has a bisegmented genome and further comprises a polynucleotide encoding a truncated HBV polymerase comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14, and wherein the truncated HBV polymerase does not comprise all of an HBV polymerase terminal protein (TP) domain and does not comprise all or part of an HBV polymerase Spacer domain. In some embodiments, the truncated HBV polymerase does not comprise a polypeptide sequence of SEQ ID NO: 50 or SEQ ID NO:51, or a sequence that is at least 90%, 91%, 92%, 93%, 94%, 95%, 96%, 97%, 98% or 99% identical to any one of SEQ ID NO: 50 or SEQ ID NO: 51. In some embodiments, the polynucleotide comprises or consists of a nucleic acid sequence of any one of SEQ ID NOs: 29 and 89-94, e.g., SEQ ID NOs: 29, 89, 90 or 92, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 29 and 89-94, e.g., SEQ ID NOs: 29, 89, 90 or 92. In some embodiments, the arenavirus vector is a Lymphocytic choriomeningitis mammarenavirus (LCMV) vector and the polynucleotide comprises or consists of a nucleic acid sequence of SEQ ID NO: 29, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 29. In some embodiments, the arenavirus vector is a Cali mammarenavirus (a.k.a., Pichinde mammarenavirus or Pichinde arenavirus (PICV)) vector and the polynucleotide comprises or consists of a nucleic acid sequence of SEQ ID NO: 90, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90.

Further provided is an arenavirus vector comprising a polynucleotide encoding a truncated HBV polymerase comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14, and wherein the truncated HBV polymerase does not comprise all of an HBV polymerase terminal protein (TP) domain and does not comprise all or part of an HBV polymerase Spacer domain. In some embodiments, the truncated HBV polymerase does not comprise a polypeptide sequence of SEQ ID NO: 50 or SEQ ID NO:51, or a sequence that is at least 90%, 91%, 92%, 93%, 94%, 95%, 96%, 97%, 98% or 99% identical to any one of SEQ ID NO: 50 or SEQ ID NO: 51. In some embodiments, the polynucleotide comprises or consists of a nucleic acid sequence of any one of SEQ ID NOs: 29 and 89-94, e.g., SEQ ID NOs: 29, 89, 90 or 92, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 29 and 89-94, e.g., SEQ ID NOs: 29, 89, 90 or 92. In some embodiments, the arenavirus vector is a Lymphocytic choriomeningitis mammarenavirus (LCMV) vector and the polynucleotide comprises or consists of a nucleic acid sequence of SEQ ID NO: 29, or that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 29. In some embodiments, the arenavirus vector is a Cali mammarenavirus vector and the polynucleotide comprises or consists of a nucleic acid sequence of SEQ ID NO: 90, or that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90. In some embodiments, the arenavirus vector is replication-defective, replication-deficient, or replication-incompetent.

In a further aspect, provided are host cells comprising one or more polynucleotides encoding one or more immunogenic HBV polypeptides, as described herein, or one or more vectors comprising such polynucleotides. In some embodiments, the one or more polynucleotides encoding one or more immunogenic HBV polypeptides, as described herein, are not integrated into the host cell genome, e.g., are episomal. In some embodiments, the one or more polynucleotides are integrated into the host cell genome. In some embodiments, the host cell is a mammalian cell, e.g., a human cell. In various embodiments, the host cell can be in vitro or in vivo.

In another aspect, provided are immunogenic compositions comprising one or more of the immunogenic HBV polypeptides, as described herein. In some embodiments, the immunogenic composition comprises one or more, e.g., two or more, of the truncated HBV polymerase polypeptides, one or more, e.g., two or more, of the HBV polymerase deletion mutant polypeptides, and/or one or more, e.g., two or more, of the core-sAg fusion protein, as described herein. In some embodiments, the immunogenic composition comprises one or more, e.g., two or more, polynucleotides encoding one or more, e.g., two or more, of the truncated HBV polymerase polypeptides, one or more, e.g., two or more, of the HBV polymerase deletion mutant polypeptides, and/or one or more, e.g., two or more, of the core-sAg fusion protein, as described herein. In some embodiments, the immunogenic composition comprises one or more, e.g., two or more, one or more, e.g., two or more, vectors comprising one or more, e.g., two or more, polynucleotides encoding one or more, e.g., two or more, of the truncated HBV polymerase polypeptides, one or more, e.g., two or more, of the HBV polymerase deletion mutant polypeptides, and/or one or more, e.g., two or more, of the core-sAg fusion protein, as described herein. The immunogenic compositions further comprise a pharmaceutically acceptable carrier. In some embodiments, the immunogenic composition comprises one or more polynucleotides in the form of DNA, cDNA, mRNA, or self-replicating RNA. In various embodiments, the immunogenic composition comprises a first viral expression vector and a second viral expression vector, wherein: (a) the first viral expression vector comprises a polynucleotide encoding a truncated HBV polymerase polypeptide or an HBV polymerase deletion mutant polypeptide, as described herein; and (b) the second viral expression vector comprises a polynucleotide encoding the core-sAg fusion protein, as described. In some embodiments, the immunogenic composition comprises a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the immunogenic composition comprises a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the immunogenic compositions comprise a first viral expression vector and a second viral expression vector, wherein: (a) the first viral expression vector comprises a polynucleotide encoding an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) the second viral expression vector comprises a polynucleotide encoding the core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41. In some embodiments, the immunogenic compositions comprise a first viral expression vector and a second viral expression vector, wherein: (a) the first viral expression vector comprises a polynucleotide comprising or consisting of a nucleic acid sequence of any one of SEQ ID NOs: 27-32 and 89-94 e.g., SEQ ID NOs: 29, 89, 90 or 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94 e.g., SEQ ID NOs: 29, 89, 90 or 92; and (b) the second viral expression vector comprises a polynucleotide comprising or consisting of a nucleic acid sequence of any one of SEQ ID NOs: 33-37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37. In some embodiments, the immunogenic composition comprises a first viral expression vector and a second viral expression vector, wherein: (a) the first viral expression vector comprises a polynucleotide comprising or consisting of a nucleic acid sequence of SEQ ID NO: 29 or 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29 or 90; and (b) the second viral expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 37. In various embodiments, the first viral expression vector and the second viral expression vector are independently from a taxonomic family selected from Adenoviridae, Arenaviridae, Herpesviridae (e.g. Cytomegalovirus), Poxviridae (e.g. Vaccinia virus, e.g. modified vaccinia Ankara (MVA)), Flaviviridae (e.g. Yellow fever virus), Rhabdoviridae (e.g. Vesiculovirus, e.g. Maraba vesiculovirus), Togaviridae (e.g., Alphavirus). In various embodiments, the first viral expression vector and the second viral expression vector in the immunogenic composition can be from the same taxonomic family or different taxonomic families. In some embodiments, the first viral expression vector and the second viral expression vector in the immunogenic composition are from Arenaviridae. In some embodiments, the first viral expression vector and the second viral expression vector in the immunogenic composition are independently from an arenavirus vector selected from Lymphocytic choriomeningitis mammarenavirus (LCMV), Cali mammarenavirus (a.k.a., Pichinde mammarenavirus or Pichinde arenavirus (PICV)), Guanarito virus (GTOV), Junin virus (JUNV), Lassa virus (LASV), Lujo virus (LUJV), Machupo virus (MACV), Sabia virus (SABV), and Whitewater Arroyo virus (WWAV). In some embodiments, the first viral expression vector and the second viral expression vector are independently from an arenavirus vector selected from Lymphocytic choriomeningitis mammarenavirus (LCMV) or Cali mammarenavirus (a.k.a., Pichinde mammarenavirus or Pichinde arenavirus (PICV)). In some embodiments, the first viral expression vector and the second viral expression vector are replication-defective or replication-deficient. In some embodiments, the first viral expression vector and the second viral expression vector are replication-attenuated. In some embodiments, the immunogenic composition comprises a first LCMV arenavirus expression vector and a second LCMV arenavirus expression vector, wherein: (a) the first LCMV arenavirus expression vector comprises a polynucleotide comprising or consisting of a nucleic acid sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 37. In some embodiments, the immunogenic composition comprises a first Pichinde arenavirus expression vector and a second Pichinde arenavirus expression vector, wherein: (a) the first Pichinde arenavirus expression vector comprises a polynucleotide comprising or consisting of a nucleic acid sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 37. In various embodiments, the first viral expression vector and the second viral expression vector are provided in the immunogenic composition in a ratio in the range of from 1:10 to 10:1, e.g., 1:9 to 9:1, 1:8 to 8:1, 1:7 to 7:1, 1:6 to 6:1, 1:5 to 5:1, 1:4 to 4:1, 1:3 to 3:1, 1:2 to 2:1 or 1:1. In some embodiments, the immunogenic composition comprises in the range of about $10^3$ to about $10^{12}$ viral focus forming units (FFU) or plaque forming units (PFU) or infectious units (IU) or viral particles (vp) per milliliter, e.g. from about $10^4$ to about $10^7$ viral FFU or PFU or IU or vp per milliliter, e.g. from about $10^3$ to about $10^4$, $10^5$, $10^6$, $10^7$, $10^8$, $10^9$, $10^{10}$, $10^{11}$ or $10^{12}$ viral FFU or PFU or IU or vp per milliliter, of each of the first viral expression vector and the second viral expression vector. In some embodiments, the immunogenic composition further comprises one or more of an adjuvant, a detergent, a micelle-forming agent, and an oil. In various embodiments, the immunogenic composition is formulated for administration via a route selected from intravenous, intramuscular, intradermal, subcutaneous and mucosal (e.g. buccal, intranasal, intrarectal, intravaginal). In some embodiments, the immunogenic composition is an aqueous solution or suspension, e.g., is formulated as a liquid. In some embodiments, the immunogenic composition is lyophilized.

In a further aspect, provided are kits. In various embodiments, the kit comprises one or more, e.g., two or more, unitary doses of one or more, e.g., two or more, of a truncated HBV polymerase polypeptide, one or more, e.g., two or more, of an HBV polymerase deletion mutant polypeptide and/or one or more, e.g., two or more, of a core-sAg fusion protein, as described herein. In some embodiments, the kit comprises one or more, e.g., two or more, unitary doses of one or more, e.g., two or more, polynucleotides encoding one or more, e.g., two or more, of a truncated HBV polymerase polypeptide, one or more, e.g., two or more, of an HBV polymerase deletion mutant polypeptide and/or one or more, e.g., two or more, of a core-sAg fusion protein, as described herein. In some embodiments, the kit comprises one or more, e.g., two or more, unitary doses of one or more, e.g., two or more, vectors comprising one or more, e.g., two or more, polynucleotides encoding one or more, e.g., two or more, of a truncated HBV polymerase polypeptide, one or more, e.g., two or more, of an HBV polymerase deletion mutant polypeptide and/or one or more, e.g., two or more, of a core-sAg fusion protein, as described herein. In various embodiments, the kit comprises one or more, e.g., two or more, unitary doses of one or more, e.g., two or more, immunogenic compositions, as described herein. In some embodiments, the one or more unitary doses in the kit are in a single container. In some embodiments, the one or more unitary doses in the kit are in two or more separate containers. In some embodiments, the kit comprises one or more containers selected from vials, ampules and pre-loaded syringes. In some embodiments, the kit comprises one or more containers comprising the one or more polypeptides, one or more polynucleotides, one or more vectors or one or more immunogenic compositions in an aqueous solution or suspension, or as a lyophilized preparation. In various embodiments, the one or more unitary doses can be the same or different. In some embodiments, the kit comprises one or more unitary doses of one or more viral vectors, as described herein, wherein the unitary doses are in the range of about $10^3$ to about $10^{12}$ viral focus forming units (FFU) or plaque forming units (PFU) or infectious units (IU) or viral particles (vp), e.g. from about $10^4$ to about $10^7$ viral FFU or PFU or IU or vp, e.g. from about $10^3$ to about $10^4$, $10^5$, $10^6$, $10^7$, $10^8$, $10^9$, $10^{10}$, $10^{11}$, or $10^{12}$ viral FFU or PFU or IU or vp. In some embodiments, the kit comprises one or more polynucleotides encoding, or one or more vectors expressing, or an immunogenic composition comprising, at least two immunogenic polypeptides, the immunogenic polypeptides comprising: (a) an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the kit comprises one or more polynucleotides encoding, or one or more vectors expressing, or an immunogenic composition comprising, at least two immunogenic polypeptides, the immunogenic polypeptides comprising: (a) an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the kit comprises one or more polynucleotides encoding, or one or more vectors expressing, or an immunogenic composition comprising, at least two immunogenic polypeptides, the immunogenic polypeptides comprising: (a) an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) an HBV core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41. In some embodiments, the kit comprises first and second vectors encoding first and second immunogenic polypeptides, respectively, the first and second immunogenic polypeptides comprising, respectively: (a) an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) an HBV core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41. In some embodiments, the kit comprises a first viral expression vector and a second viral expression vector, wherein: (a) the first viral expression vector comprises a polynucleotide comprising or consisting of a nucleic acid sequence of any one of SEQ ID NOs: 27-32 and 89-94, e.g., SEQ ID NOs: 29, 89, 90 or 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94, e.g., SEQ ID NOs: 29, 89, 90 or 92; and (b) the second viral expression vector comprises a polynucleotide comprising or consisting of a nucleic acid sequence of any one of SEQ ID NOs: 33-37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37. In some embodiments, the kit comprises a first viral expression vector and a second viral expression vector, wherein: (a) the first viral expression vector comprises a polynucleotide comprising or consisting of a nucleic acid sequence of SEQ ID NO: 29 or 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29 or 90; and (b) the second viral expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments, the kit comprises one or more unitary doses of an immunogenic composition comprising first and second viral expression vectors, as described herein, wherein the first and second viral expression vectors comprise a replication-deficient or replication-defective Cali mammarenavirus (a.k.a., Pichinde mammarenavirus or Pichinde arenavirus (PICV)). In some embodiments, the kit comprises one or more unitary doses of an immunogenic composition comprising first and second viral expression vectors, as described herein, wherein the first and second viral expression vectors comprise a replication-deficient or replication-defective Lymphocytic choriomeningitis mammarenavirus (LCMV). In some embodiments, the kit comprises (a) one or more unitary doses of an immunogenic composition, as described herein, wherein the first and second viral expression vectors are from Adenoviridae; and (b) one or more unitary doses of an immunogenic composition, as described herein, wherein the first and second viral expression vectors are from Poxviridae (e.g., Vaccinia virus, e.g., modified vaccinia Ankara (MVA)). In some embodiments, the kit comprises (a) one or more unitary doses of an immunogenic composition, as described herein, wherein the first and second viral expression vectors are from Arenaviridae; and (b) one or more unitary doses of an immunogenic composition, as described herein, wherein the first and second viral expression vectors are from Adenoviridae. In some embodiments, the kit comprises a first LCMV arenavirus expression vector and a second LCMV arenavirus expression vector, wherein: (a) the first LCMV arenavirus expression vector comprises a polynucleotide comprising or consisting of a nucleic acid sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments, the kit comprises a first Pichinde arenavirus expression vector and a second Pichinde arenavirus expression vector, wherein: (a) the first Pichinde arenavirus expression vector comprises a polynucleotide comprising or consisting of a nucleic acid sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In various embodiment, the kit further comprises one or more unitary doses of one or more additional therapeutic agents. In some embodiments, the kit further comprises one or more agonists or activators of one or more toll-like receptors (TLRs). In some embodiments, the kit further comprises one or more TLR agonists or activators selected from a TLR2 agonist, a TLR3 agonist, a TLR4 agonist, a TLR5 agonist, a TLR7 agonist, a TLR8 agonist and a TLR9 agonist. In some embodiments, the kit further comprises a TLR7 agonist selected from GS 9620 (vesatolimod), R848 (Resiquimod), DS-0509, LHC-165 and TMX-101 (imiquimod). In some embodiments, the kit further comprises a TLR8 agonist selected from GS-9688, R848 (Resiquimod) and NKTR-262 (dual TLR7/TLR8 agonist). In some embodiments, the kit further comprises one or more interleukin receptor agonists of an interleukin receptor selected from IL-2, IL-7, IL-12 and IL-15. In some embodiments, the kit further comprises one or more cytokines selected from IL-2, IL-7, IL-12, IL-15, and variants thereof. In some embodiments, the kit further comprises one or more innate immune activators. In some embodiments, the kit further comprises one or more innate immune activators comprising an agonist of a receptor selected from fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the kit further comprises one or more unitary doses of GS-3583 and/or GS-9992. In some embodiments, the kit further comprises one or more antagonists or inhibitors of an inhibitory immune checkpoint protein or receptor and/or one or more activators or agonists of a stimulatory immune checkpoint protein or receptor. In some embodiments, the kit further comprises one or more immune checkpoint proteins or receptors selected from CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MEW class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7). In some embodiments, the kit further comprises one or more blockers or inhibitors of one or more T-cell inhibitory immune checkpoint proteins or receptors. In some embodiments, the kit further comprises one or more T-cell inhibitory immune checkpoint proteins or receptors selected from CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the kit further comprises one or more agonists or activators of one or more T-cell stimulatory immune checkpoint proteins or receptors. In some embodiments, the kit further comprises one or more T-cell stimulatory immune checkpoint proteins or receptors selected from CD27, CD70; CD40, CD40LG; inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the kit further comprises one or more unitary doses of AGEN-2373 and/or AGEN-1223. In some embodiments, the kit further comprises one or more blockers or inhibitors of one or more NK-cell inhibitory immune checkpoint proteins or receptors. In some embodiments, the kit further comprises one or more NK-cell inhibitory immune checkpoint proteins or receptors selected from killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, the kit further comprises one or more agonists or activators of one or more NK-cell stimulatory immune checkpoint proteins or receptors. In some embodiments, the kit further comprises one or more NK-cell stimulatory immune checkpoint proteins or receptors selected from CD16, CD226 (DNAM-1); killer cell lectin like receptor K1 (KLRK1, NKG2D, CD314); and SLAM family member 7 (SLAMF7). In some embodiments, the kit further comprises one or more proteinaceous inhibitors of PD-L1 (CD274), PD-1 (PDCD1) and/or CTLA4. In some embodiments, the kit further comprises one or more proteinaceous inhibitors of CTLA4 selected from ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the kit further comprises one or more proteinaceous inhibitors of PD-L1 (CD274) or PD-1 (PDCD1) selected from zimberelimab (AB122), pembrolizumab, nivolumab, cemiplimab, pidilizumab, AMP-224, MEDI0680 (AMP-514), spartalizumab, atezolizumab, avelumab, ASC22, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments, the kit further comprises one or more small molecule inhibitors of CD274 (PDL1, PD-L1), programmed cell death 1 (PDCD1, PD1, PD-1) and/or CTLA4. In some embodiments, the kit further comprises one or more small molecule inhibitors of CD274 or PDCD1 selected from GS-4224, GS-4416, INCB086550 and MAX10181. In some embodiments, the kit further comprises the small molecule inhibitor of CTLA4, BPI-002. In some embodiments, the kit further comprises one or more one or more anti-viral agents. In some embodiments, the kit further comprises one or more antiviral agents selected from lamivudine (LAM), adefovir dipivoxil (ADV), entecavir (ETV), telbivudine (LdT), tenofovir disoproxil fumarate (TDF), tenofovir alafenamide (TAF or VEMLIDY®) and ledipasvir+sofosbuvir (HARVONI®). In some embodiments, the kit further comprises one or more therapeutic agents selected from HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), gene editors targeting HBV (e.g., CRISPR-Cas (e.g., Cas9, Cas12, Cascade, Cas13), zinc finger nucleases, homing endonucleases, homing meganucleases (e.g., ARCUS), synthetic nucleases, TALENs), covalently closed circular DNA (cccDNA) inhibitors and HBsAg secretion or assembly inhibitors and HBV viral entry inhibitors.

In a further aspect, provided are methods for eliciting an immune response to human hepatitis B virus (HBV) in a subject in need thereof. Also provided are methods of treating or preventing human hepatitis B virus (HBV) in a subject in need thereof. In some embodiments, the methods comprise administering to the subject a therapeutically effective amount of one or more immunogenic compositions, as described herein. In some embodiments, the methods entail administering one or more immunogenic compositions comprising a mixture comprising a first viral expression vector and a second viral expression vector, wherein: (a) the first viral expression vector comprises a polynucleotide encoding a truncated HBV polymerase polypeptide or a HBV polymerase deletion mutant polypeptide, as described herein; and (b) the second viral expression vector comprises a polynucleotide encoding the core-sAg fusion protein, as described herein. In some embodiments, the methods entail administering to the subject a therapeutically effective amount of one or more immunogenic compositions comprising a mixture comprising a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the methods entail administering to the subject a therapeutically effective amount of one or more immunogenic compositions comprising a mixture comprising a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. In some embodiments, the methods entail administering to the subject a therapeutically effective amount of one or more immunogenic compositions comprising a mixture comprising a first viral expression vector and a second viral expression vector, wherein: (a) the first viral expression vector comprises a polynucleotide encoding an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) the second viral expression vector comprises a polynucleotide encoding the core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41. In some embodiments, the methods entail administering to the subject a therapeutically effective amount of one or more immunogenic compositions comprising a mixture comprising a first viral expression vector and a second viral expression vector, wherein: (a) the first viral expression vector comprises a polynucleotide comprising or consisting of a nucleic sequence of any one of SEQ ID NOs: 27-32 and 89-94, e.g., SEQ ID NOs: 29, 89, 90 or 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94, e.g., SEQ ID NOs: 29, 89, 90 or 92; and (b) the second viral expression vector comprises a polynucleotide comprising or consisting of a nucleic acid sequence of any one of SEQ ID NOs: 33-37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37. In some embodiments, the methods comprise administering to the subject a therapeutically effective amount of one or more immunogenic compositions comprising a mixture comprising a first viral expression vector and a second viral expression vector, wherein: (a) the first viral expression vector comprises a polynucleotide comprising or consisting of a nucleic sequence of SEQ ID NO: 29 or 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29 or 90; and (b) the second viral expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments of the methods, the first viral expression vector and the second viral expression vector are from Arenaviridae. In some embodiments of the methods, the first viral expression vector and the second viral expression vector are from an arenavirus vector selected from Lymphocytic choriomeningitis mammarenavirus (LCMV), Cali mammarenavirus (a.k.a., Pichinde mammarenavirus or Pichinde arenavirus (PICV)), Guanarito virus (GTOV), Junin virus (JUNV), Lassa virus (LASV), Lujo virus (LUJV), Machupo virus (MACV), Sabia virus (SABV), and Whitewater Arroyo virus (WWAV). In some embodiments of the methods, the first viral expression vector and the second viral expression vector are from an arenavirus vector selected from Lymphocytic choriomeningitis mammarenavirus (LCMV) or Cali mammarenavirus (a.k.a., Pichinde mammarenavirus or Pichinde arenavirus (PICV)). In some embodiments of the methods, the first viral expression vector and the second viral expression vector are replication-defective or replication-deficient. In some embodiments of the methods, the first viral expression vector and the second viral expression vector are replication-attenuated. In some embodiments, the methods comprise administering to the subject a therapeutically effective amount of one or more immunogenic compositions comprising a mixture comprising a first LCMV arenavirus expression vector and a second LCMV arenavirus expression vector, wherein: (a) the first LCMV arenavirus expression vector comprises a polynucleotide comprising or consisting of a nucleic sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments, the methods comprise administering to the subject a therapeutically effective amount of one or more immunogenic compositions comprising a mixture comprising a first Pichinde arenavirus expression vector and a second Pichinde arenavirus expression vector, wherein: (a) the first Pichinde arenavirus expression vector comprises a polynucleotide comprising or consisting of a nucleic sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. In some embodiments of the methods, the subject is infected with HBV, is suspected of being infected with HBV, or is at risk of being infected with HBV. In some embodiments of the methods, the subject is asymptomatic. In some embodiments of the methods, the subject is chronically infected with HBV. In some embodiments of the methods, the subject is exhibiting or experiencing one or more symptoms selected from hepatic failure, hepatic cancer, hepatic fibrosis and hepatic cirrhosis. In some embodiments of the methods, the subject is acutely infected with HBV. In some embodiments of the methods, the subject is exhibiting or experiencing one or more symptoms selected from jaundice, visible webs of swollen blood vessels in the skin, dark-colored (e.g., orange or brown) urine, light-colored feces, fever, persistent fatigue, malaise, abdominal pain, abdominal fluid, loss of appetite, nausea, and vomiting. In some embodiments of the methods, the subject is co-infected with hepatitis D virus (HDV). In some embodiments of the methods, the composition is administered via a route selected from intravenous, intramuscular, intradermal, subcutaneous and mucosal (e.g. buccal, intranasal, intrarectal, intravaginal). In some embodiments, the methods entail administering to the subject from about $10^3$ to about $10^{12}$ viral focus forming units (FFU) or plaque forming units (PFU) or infectious units (IU) or viral particles (vp), e.g. from about $10^4$ to about $10^7$ viral FFU or PFU or IU or vp, e.g. from about $10^3$ to about $10^4$, $10^5$, $10^6$, $10^7$, $10^8$, $10^9$, $10^{10}$, $10^{11}$ or $10^{12}$ viral FFU or PFU or IU or vp, per administration. In some embodiments of the methods, the one or more compositions are administered multiple times. In some embodiments, the methods entail administering intravenously or intramuscularly from about $10^6$ to about $10^8$ viral FFU or PFU or IU or vp per administration every other week (Q2W) or monthly (Q4W). In some embodiments, the methods entail multiple administrations of the one or more immunogenic compositions over a time period of at least about 2 weeks, 3 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, or longer, or until sAg is not detectable in the serum or plasma of the subject. In some embodiments, the methods comprise a prime-boost regimen comprising administering a priming composition at a first time point and administering one or more boosting compositions at one or more subsequent time points. As appropriate, the methods can entail repeating the prime-boost regimen one or more iterations. In some embodiments of the methods, the administrations of the priming composition and the one or more boosting compositions are spaced at least 1 week and up to at least 2 weeks, 3 weeks, 1 month, 2 months, 3 months, 4 months, 5 months or 6 months apart. In some embodiments of the methods, the priming composition and the boosting composition can comprise the same immunogenic composition or can comprise different immunogenic compositions. In some embodiments of the methods, the priming composition and the boosting composition comprise the same one or more polypeptides and same viral expression vector. In some embodiments of the methods, the priming composition and the boosting composition comprise different polypeptides and/or different viral expression vectors. In some embodiments, the methods entail priming with a priming composition comprising one or more (e.g., first and second) viral expression vectors, and boosting with a boosting composition comprising one or more (e.g., third and fourth) viral expression vectors. In various embodiments, the prime-boost regimen comprises: (a) Priming with a priming composition comprising one or more viral expression vectors and boosting with a boosting composition comprising one or more polynucleotides, wherein the one or more polynucleotides comprise DNA, cDNA, mRNA or self-replicating RNA; (b) Priming with a priming composition comprising one or more polynucleotides, wherein the one or more polynucleotides comprise DNA, cDNA, mRNA or self-replicating RNA, and boosting with a boosting composition comprising one or more viral expression vectors; (c) Priming with a priming composition comprising one or more viral expression vectors, and boosting with a boosting composition comprising one or more viral expression vectors, wherein the one or more viral expression vectors in the priming composition and the one or more viral expression vectors in the boosting composition are from identical, related or unrelated taxonomical families; (d) Priming with a priming composition comprising one or more replication-deficient viral expression vectors and boosting with a boosting composition comprising one or more replication-deficient viral expression vectors, wherein the one or more replication-deficient viral expression vectors in the priming composition and the one or more replication-deficient viral expression vectors in the boosting composition are from identical, related or unrelated taxonomical families; (e) Priming with a priming composition comprising one or more replication-attenuated viral expression vectors and boosting with a boosting composition comprising one or more replication-attenuated viral expression vectors, wherein the one or more replication-attenuated viral expression vectors in the priming composition and the one or more replication-attenuated viral expression vectors in the boosting composition are from identical, related or unrelated taxonomical families; (f) Priming with a priming composition comprising one or more replication-deficient viral expression vectors and boosting with a boosting composition comprising one or more replication-attenuated viral expression vectors; (g) Priming with a priming composition comprising one or more replication-attenuated viral expression vectors and boosting with a boosting composition comprising one or more replication-deficient viral expression vectors; (h) Priming with a priming composition comprising one or more Lymphocytic choriomeningitis mammarenavirus (LCMV) viral expression vectors and boosting with a boosting composition comprising one or more Pichinde mammarenavirus (PICV) viral expression vectors; (i) Priming with a priming composition comprising one or more Pichinde mammarenavirus (PICV)

viral expression vectors and boosting with a boosting composition comprising one or more Lymphocytic choriomeningitis mammarenavirus (LCMV) viral expression vectors; (j) Priming with a priming composition comprising one or more replication deficient Pichinde mammarenavirus (PICV) viral expression vectors and boosting with a boosting composition comprising one or more replication deficient Lymphocytic choriomeningitis mammarenavirus (LCMV) viral expression vectors; (k) Priming with a priming composition comprising one or more replication deficient Lymphocytic choriomeningitis mammarenavirus (LCMV) viral expression vectors and boosting with a boosting composition comprising one or more replication deficient Pichinde mammarenavirus (PICV) viral expression vectors; (l) Priming with a priming composition comprising one or more arenavirus viral expression vectors and boosting with a boosting composition comprising one or more adenovirus viral expression vectors; (m) Priming with a priming composition comprising one or more adenovirus viral expression vectors and boosting with boosting composition comprising one or more arenavirus viral expression vectors; (n) Priming with a priming composition comprising one or more poxvirus viral expression vectors and boosting with a boosting composition comprising one or more arenavirus viral expression vectors; (o) Priming with a priming composition comprising one or more arenavirus viral expression vectors and boosting with boosting composition comprising one or more poxvirus viral expression vectors; (p) Priming with a priming composition comprising one or more poxvirus viral expression vectors and boosting with a boosting composition comprising one or more adenovirus viral expression vectors; or (q) Priming with a priming composition comprising one or more adenovirus viral expression vectors and boosting with boosting composition comprising one or more poxvirus viral expression vectors. In some embodiments, the methods entail a prime-boost regimen that comprises: (a) Priming with a priming composition comprising one or more Lymphocytic choriomeningitis mammarenavirus (LCMV) viral expression vectors and boosting with a boosting composition comprising one or more Pichinde mammarenavirus (PICV) viral expression vectors; (b) Priming with a priming composition comprising one or more Pichinde mammarenavirus (PICV) viral expression vectors and boosting with a boosting composition comprising one or more Lymphocytic choriomeningitis mammarenavirus (LCMV) viral expression vectors; (c) Priming with a priming composition comprising one or more replication deficient Pichinde mammarenavirus (PICV) viral expression vectors and boosting with a boosting composition comprising one or more replication deficient Lymphocytic choriomeningitis mammarenavirus (LCMV) viral expression vectors; or (d) Priming with a priming composition comprising one or more replication deficient Lymphocytic choriomeningitis mammarenavirus (LCMV) viral expression vectors and boosting with a boosting composition comprising one or more replication deficient Pichinde mammarenavirus (PICV) viral expression vectors. In some embodiments, the priming composition and the boosting composition comprise an immunogenic composition as described herein. In some embodiments, the subject is not receiving antiviral therapy or antiviral therapy is discontinued prior to administration of the one or more immunogenic compositions. In some embodiments of the methods, antiviral therapy is discontinued after one or more administrations of the one or more immunogenic compositions. In some embodiments, the methods further comprise administering to the subject one or more additional therapeutic agents, e.g. two, three, four, or more additional therapeutic agents. In some embodiments, the methods comprise co-administering one or more agonists or activators of one or more toll-like receptors (TLRs). In some embodiments, the methods comprise co-administering one or more TLR agonists or activators selected from a TLR2 agonist, a TLR3 agonist, a TLR4 agonist, a TLR5 agonist, a TLR7 agonist, a TLR8 agonist and a TLR9 agonist. In some embodiments, the methods entail co-administering a TLR7 agonist selected from GS-9620 (vesatolimod), R848 (Resiquimod), DS-0509, LHC-165 and TMX-101 (imiquimod). In some embodiments, the methods entail co-administering a TLR8 agonist selected from GS-9688, R848 (Resiquimod) and NKTR-262 (dual TLR7/TLR8 agonist). In some embodiments, the methods entail co-administering one or more interleukin receptor agonists of an interleukin receptor selected from IL-2, IL-7, IL-12 and IL-15. In some embodiments, the methods entail co-administering one or more cytokines selected from IL-2, IL-7, IL-12, IL-15, and variants thereof. In some embodiments, the methods entail co-administering one or more innate immune activators. In some embodiments, the methods entail co-administering one or more innate immune activators comprising an agonist of a receptor selected from fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the methods entail co-administering GS-3583 and/or GS-9992. In some embodiments, the methods entail co-administering one or more antagonists or inhibitors of an inhibitory immune checkpoint protein or receptor and/or one or more activators or agonists of a stimulatory immune checkpoint protein or receptor. In some embodiments, the methods entail co-administering one or more immune checkpoint proteins or receptors selected from: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7). In some embodiments, the methods entail co-administering one or more blockers or inhibitors of one or more T-cell inhibitory immune checkpoint proteins or receptors. In some embodiments, the methods entail co-administering one or more T-cell inhibitory immune checkpoint proteins or receptors selected from CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the methods entail co-administering one or more agonists or activators of one or more T-cell stimulatory immune checkpoint proteins or receptors. In some embodiments, the methods entail co-administering one or more T-cell stimulatory immune checkpoint proteins or receptors selected from CD27, CD70; CD40, CD40LG; inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the methods entail co-administering AGEN-2373 and/or AGEN-1223. In some embodiments, the methods entail co-administering one or more blockers or inhibitors of one or more NK-cell inhibitory immune checkpoint proteins or receptors. In some embodiments, the methods entail co-administering one or more NK-cell inhibitory immune checkpoint proteins or receptors selected from killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In some embodiments, the methods entail co-administering one or more agonists or activators of one or more NK-cell stimulatory immune checkpoint proteins or receptors. In some embodiments, the methods entail co-administering one or more NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7). In some embodiments, the methods entail co-administering one or more proteinaceous inhibitors of PD-L1 (CD274), PD-1 (PDCD1) or CTLA4. In some embodiments, the methods entail co-administering one or more proteinaceous inhibitors of CTLA4 selected from ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the methods entail co-administering one or more proteinaceous inhibitors of PD-L1 (CD274) or PD-1 (PDCD1) selected from zimberelimab (AB122), pembrolizumab, nivolumab, cemiplimab, pidilizumab, AMP-224, MEDI0680 (AMP-514), spartalizumab, atezolizumab, avelumab, ASC22, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments, the methods entail co-administering one or more small molecule inhibitors of CD274 (PDL1, PD-L1), programmed cell death 1 (PDCD1, PD1, PD-1) or CTLA4. In some embodiments, the methods entail co-administering one or more small molecule inhibitors of CD274 or PDCD1 selected from GS-4224, GS-4416, INCB086550 and MAX10181. In some embodiments, the methods entail co-administering BPI-002 (a small molecule inhibitor of CTLA4). In some embodiments, the methods comprise co-administering to the subject one or more antiviral agents. In some embodiments, the methods comprise co-administering one or more antiviral agents selected from lamivudine (LAM), adefovir dipivoxil (ADV), entecavir (ETV), telbivudine (LdT), tenofovir disoproxil fumarate (TDF), tenofovir alafenamide (TAF or VEMLIDY®) and ledipasvir+sofosbuvir (HARVONI®). In some embodiments, the methods comprise co-administering to the subject one or more therapeutic agents selected from HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), gene editors targeting HBV (e.g., CRISPR-Cas (e.g., Cas9, Cas12, Cascade, Cas13), zinc finger nucleases, homing endonucleases, homing meganucleases (e.g., ARCUS), synthetic nucleases, TALENs), covalently closed circular DNA (cccDNA) inhibitors and HBsAg secretion or assembly inhibitors and HBV viral entry inhibitors. In some embodiments, the method activates in the subject CD8+ T cells and/or CD4+ T cells targeting one or more HBV polypeptide epitopes. In some embodiments, the method elicits in the subject production of antibodies that bind one or more HBV polypeptides.

BRIEF DESCRIPTION OF THE DRAWINGS

FIGS. 4A-4B illustrate the immunogenicity of Core-Pol fusion protein-expressing adenovirus vectors in DO mice. Five- to seven-week-old DO mice (n=8 per group) were injected intramuscularly with $1 \times 10^8$ viral particles (vp) of adenovirus encoding GT-A core-Pol$^{Δ3}$ or GT-B, C, or D core-Pol$^{Δ1}$. On day 14 after injection, splenocytes were harvested and T cell responses evaluated by IFN-γ ELISPOT (BD mouse IFN-γ ELISPOT kit, catalog #551083) responses to overlapping peptide pools corresponding to GT-A and D core and Pol. Statistical comparisons between responses to peptides of different genotypes within mice receiving the same vaccine were assessed with Wilcoxon signed-rank tests. Statistical comparisons between mice receiving different vaccines were assessed with Mann-Whitney tests. (A) Responses to Pol peptides. (B) Responses to Core peptides. SFU, spot forming units.

FIGS. 9A-9C illustrate an overview of the arenavirus vector platforms demonstrated in the examples provided herein. (A) Schematic of a phylogenetic tree of the arenavirus family (Arenaviridae). In the examples provided herein, Lymphocytic choriomeningitis mammarenavirus (LCMV)(NCBI:txid11623) from the Old World (OW) clade and Cali mammarenavirus (a.k.a., Pichinde mammarenavirus or Pichinde arenavirus (PICV)) (NCBI:txid2169993) from the New World (NW) clade were selected for generation of HBV antigen encoding vectors. See, e.g., Buchmeier et al., 2001, "Arenaviridae: The Viruses and Their Replication," *Fields Virology* Vol 2, 1635-1668. Arenavirus taxonomy is more recently reviewed in, e.g., Radoshitzky, et al., *Arch Virol*. (2015) 160(7):1851-74. Phylogenetic information for Arenaviridae is also available at the Virus Pathogen Resource website, located at viprbrc.org. (B) Schematic of replication-defective arenavirus vectors having a bi-segmented genome, described in WO2009083210, and (C) replication-attenuated arenavirus vectors having a tri-segmented genome, described in WO2016075250 and WO2017198726. Replication-defective arenavirus vectors having a bi-segmented genome, described in WO2009083210 and used in the examples provided herein, encode three of the four viral proteins (L, Z and NP) and an open reading frame for insertion of a heterologous polynucleotide, e.g., encoding an antigen. The replication-defective arenavirus vectors having a bi-segmented genome can only propagate when viral GP is delivered in trans. Replication-attenuated arenavirus vectors having a tri-segmented genome, described in WO2016075250 and WO2017198726, have an artificial duplication of the genomic S-segment, encode all four viral proteins (L, Z, NP & GP) and have two open reading frames for insertion of one or two heterologous polynucleotides, e.g., encoding one or two antigens.

FIGS. 18A-18F focus on IFN-γ ELISPOT obtained after stimulation with core peptide pools. 18A: Group 1; 18B: Group 2; 18C: Group 3; 18D; Group 4; 18E: Group 5; 18F: Group 6.

FIGS. 19A-19F focus on IFN-γ ELISPOT obtained after stimulation with sAg peptide pools. 19A: Group 1; 19B: Group 2; 19C: Group 3; 19D; Group 4; 19E: Group 5; 19F: Group 6.

FIGS. 20A-20F focus on IFN-γ ELISPOT obtained after stimulation with Pol peptide pools. 20A: Group 1; 20B: Group 2; 20C: Group 3; 20D; Group 4; 20E: Group 5; 20F: Group 6.

Figure 1:
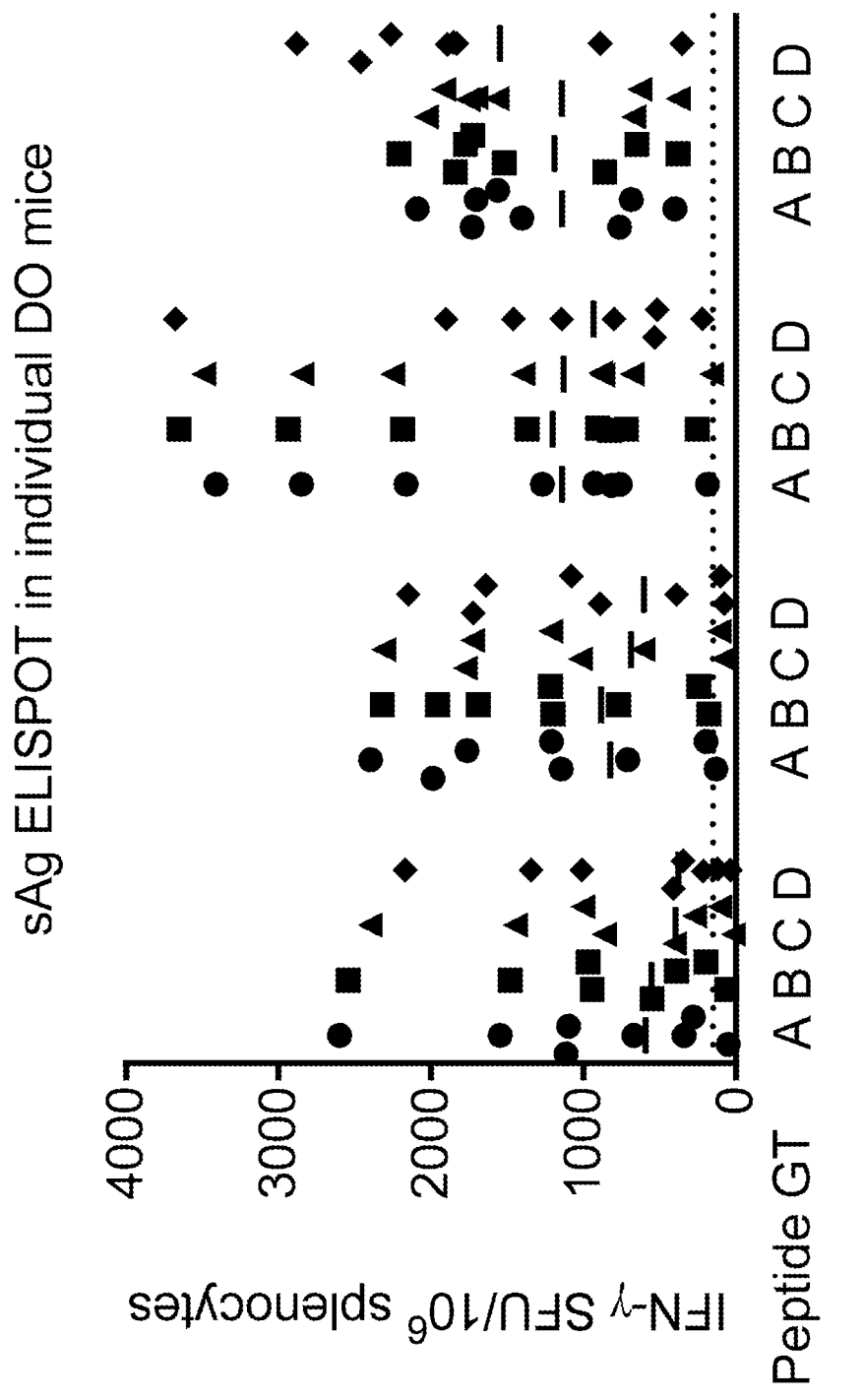
FIG. 1 illustrates the immunogenicity of HBsAg-expressing adenovirus vectors from genotypes (GT) A, B, C and D in DO mice. Five- to seven-week-old Diversity Outbred (DO) mice (n=8 per group) were injected intramuscularly with $1 \times 10^8$ viral particles (vp) of adenovirus encoding HBsAg consensus sequences of HBV genotypes (GT)-A, B, C, D (SEQ ID NOs: 1-4, respectively). On day 14 after injection, splenocytes were harvested and T cell responses were evaluated by interferon (IFN)-γ ELISPOT (BD mouse IFN-γ ELISPOT kit, catalog #551083). Each symbol corresponds to an individual mouse which was assessed for responses to overlapping peptide pools corresponding to GT-A, B, C, and D HBsAg.

F and polymerase peptide pools. The lower limit of quantitation (LLOQ) ELISPOT (dashed line) was defined as 200 IFN-γ+SFU/$10^6$ PBMC.

DETAILED DESCRIPTION

1. Introduction

Provided are polypeptides useful to elicit a protective immune response against one or more hepatitis B virus (HBV) antigens in a human. The immunogenic polypeptides described herein are capable of eliciting preventative and/or therapeutic immune responses in a human against one or more hepatitis B virus (HBV) antigens. Generally, the immunogenic polypeptides described herein contain highly conserved portions of HBV proteins in order to induce responses against epitopes that are identical in the vaccine antigen and in the infecting HBV present in the patient, while also excluding poorly conserved regions, thereby avoiding eliciting immunodominant T cell responses targeting epitopes that are not present in the patient's infecting HBV strain. The herein described immunogenic polypeptides furthermore induce both CD4+ and CD8+ T cell responses to facilitate infected cell elimination, and additionally anti-sAg antibody responses that facilitate sAg clearance, thereby reducing or eliminating spread of residual virus if sterilizing viral clearance is not completely achieved. Moreover, the herein described immunogenic polypeptides are demonstrated to be immunogenic when delivered using vaccine technologies capable of inducing the desired responses in humans, and stable in the delivery vectors through sufficient rounds of vector replication to enable commercial-scale vaccine manufacture. The immunogenic polypeptides can be used in various vector systems known to induce CD4+ and CD8+ T cell, and antibody responses in humans and other non-human primates. In certain embodiments, the immunogenic polypeptides are expressed from arenavirus vectors that can be repeatedly dosed without inducing anti-vector antibodies, thereby overcoming a limitation of many previous viral vector technologies and providing the possibility of enhancing therapeutic benefit with repeated dosing.

2. Polypeptides Useful to Promote Immune Response Against Hepatitis B Virus (HBV)

Provided are immunogenic polypeptides useful to promote, induce and/or elicit an immunogenic response against one or more hepatitis B virus (HBV) antigens. In various embodiments, the immunogenic polypeptides comprise variants and/or fragments of polypeptides encoded by an HBV polymerase (Pol) gene and fusion polypeptides having in sequential order, from the N-terminus to the C-terminus, a variant and/or fragment of a polypeptide encoded by an HBV core gene and a variant and/or fragment of a polypeptide encoded by the surface antigen (sAg) gene. The immunogenic polypeptides can contain amino acid sequences based on consensus or near-consensus sequences from HBV A, B, C or D genotypes, and combinations thereof. Generally, the immunogenic polypeptides described herein do not comprise sequences of HBV X protein (HBx), pre-core, pre-S1, pre-S2, or fragments thereof.

In various embodiments, immunogenic polypeptides described herein, and/or the polynucleotides encoding such polypeptides, are provided in isolated form. This means that such the polypeptide or polynucleotide is at least 50% w/w pure of interfering proteins, cellular and other contaminants arising from its production or purification but does not exclude the possibility that the agent is combined with an excess of pharmaceutical acceptable carrier(s) or other vehicle intended to facilitate its use. The term "isolated," when applied to a polypeptide or polynucleotide, as described herein, denotes that the polypeptide or polynucleotide is essentially free of cellular components with which it is associated in the natural state. It can be, for example, in a homogeneous state and may be in either a dry or aqueous solution. Purity and homogeneity can be determined using known methods, e.g., analytical chemistry techniques such as polyacrylamide gel electrophoresis, column chromatography, thin layer chromatography, or high-performance liquid chromatography (HPLC) analysis. A protein that is the predominant species present in a preparation is substantially purified. An "isolated" or "purified" polypeptide or polynucleotide is substantially free of other cellular material, or culture medium when produced by recombinant techniques, or chemical precursors or other chemicals when chemically synthesized. In various embodiments, purified polypeptides and/or polynucleotides are at least 60%, 70%, 75%, 80%, 85%, 90%, 91%, 92%, 93%, 94%, 95%, 96%, 97%, 98%, 99%, or 100% (w/w), separated from, purified of, or free of interfering proteins and contaminants from production or purification. Often an agent is the predominant macromolecular species remaining after its purification.

HBV Polymerase Polypeptide Variants

In various embodiments, provided are truncated and/or internal deletion mutant hepatitis B virus (HBV) polymerase polypeptides.

Wild-type HBV polymerase has four domains, arranged in tandem in a single polypeptide from N-terminus to C-terminus: the terminal protein (TP) domain conserved across the hepadnaviridae (amino acid residues 1 to 177), the Spacer region (amino acid residues 178 to 335), linking TP to the reverse transcriptase (RT) domain (amino acid residues 336 to 678; comprising NCBI conserved domain pfam00078 or cd01645) and the C-terminal RNase H (RH) domain (amino acid residues 679 to 832). See, e.g., Lanford, et al., *J. Virol.* (1999) 73(3): 1885-93; Vörös, et al., *J Virol.* (2014) 88(5):2584-99 and Jones, et al., *J Virol.* (2014) 88(3):1564-72. In the HBV polymerase variants described herein, all or part of the Spacer region has been deleted or removed. In the HBV polymerase truncation mutants, the entire TP domain has been deleted or removed.

Generally, the enzymatic domains, i.e., the reverse transcriptase and RNase H domains, are inactivated in the HBV polymerase protein mutants described herein. In various embodiments, the reverse transcriptase domain does not comprise a YMDD motif (SEQ ID NO: 97). In some embodiments, the YMDD motif (SEQ ID NO: 97) in the reverse transcriptase domain is changed to YMHD (SEQ ID NO: 99). In some embodiments, the RNase H domain does not comprise an AELL motif (SEQ ID NO: 98). In some embodiments, the AELL motif (SEQ ID NO: 98) in the RNase H domain is changed to AHLL (SEQ ID NO: 100).

Truncated Polymerase Mutants

In some embodiments, the truncated HBV polymerase polypeptides comprise an inactivated reverse transcriptase domain and an inactivated RNase H, wherein the polypeptide does not comprise all of the terminal protein (TP) domain and does not comprise all or part of the Spacer domain (i.e., the terminal protein (TP) domain and all or part of the Spacer domain is removed, excised or excluded). In the truncated HBV polymerase polypeptides described herein, all of the TP domain and all or part of the Spacer domain or region is deleted or removed. For example, in some embodiments, the N-terminal 300 amino acids of a native or wild-type HBV polymerase are deleted or removed from the truncated HBV polymerase polypeptides described herein. In various embodiments, the inactivated reverse transcriptase domain and the inactivated RNase H can be directly fused or operably linked or connected via a linker, as described herein. In some embodiments, the truncated HBV polymerase polypeptide is no longer than 600 amino acids in length, e.g., no longer than 595, 590, 585, 580, 575, 570, 565, 560, 555, 550, 545, 540 or 535 amino acids in length. In some embodiments, the truncated HBV polymerase polypeptides comprise the C-terminal 528, 529, 530, 531, 532, 533, 534 or 535 amino acids of a native or wild-type HBV polymerase.

In some embodiments, the truncated HBV polymerase polypeptides comprise an amino acid sequence corresponding to amino acid residues 300-832, 301-832, 302-832, 303-832, 304-832, 305-832, 306-832, 307-832, 308-832, 309-832, 310-832, 311-832, 312-832, 313-832, 314-832, 315-832, 316-832, 317-832, 318-832, 319-832, 320-832, 325-832, 326-832, 327-832, 328-832, 329-832, 330-832, 331-832, 332-832, 333-832, 334-832, 335-832 or 336-832 of a native or wild-type HBV polymerase. As used herein, numbering of a given amino acid polymer or nucleic acid polymer "corresponds to", is "corresponding to" or is "relative to" the numbering of a selected or reference amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer. In various embodiments, the truncated HBV polymerase polypeptides comprise an amino acid sequence corresponding to amino acid residues 300-832. In such embodiments, the N-terminus corresponds to amino acid position 300 of the prototype genotype D pol protein. The N-terminal 6 amino acid residues of this sequence is SAR-SQS (SEQ ID NO: 95) in the genotype D Pol antigen, and SSRSQS (SEQ ID NO: 96) in the genotype B Pol antigen. Literature reports have indicated that this N-terminal start site allows for function of the RT domain (see, e.g., Lanford, et al., supra) and expression of the truncated protein in vitro (see, e.g., Vörös, et al., supra).

In some embodiments, the truncated HBV polymerase polypeptide is from HBV genotype B and comprises or consists of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13. In some embodiments, the truncated HBV polymerase polypeptide is from HBV genotype B and does not comprise a polypeptide sequence (i.e., the sequence is excluded, excised or removed; the sequence is not included) of SEQ ID NO: 50, or a sequence that is at least 90%, 91%, 92%, 93%, 94%, 95%, 96%, 97%, 98% or 99% identical to any one of SEQ ID NO: 50.

In some embodiments, the truncated HBV polymerase polypeptide is from HBV genotype D and comprises or consists of an amino acid sequence of SEQ ID NO: 14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 14. In some embodiments, the truncated HBV polymerase polypeptide is from HBV genotype D and does not comprise a polypeptide sequence of SEQ ID NO: 51, or a sequence that is at least 90%, 91%, 92%, 93%, 94%, 95%, 96%, 97%, 98% or 99% identical to any one of SEQ ID NO: 51.

Modifications may be made in the structure of the polypeptides and polynucleotides encoding such polypeptides, described herein, and still obtain a functional molecule that encodes a variant or derivative polypeptide with desirable (e.g., immunogenic) characteristics. When it is desired to alter the amino acid sequence of a polypeptide to create an equivalent, or even an improved, variant or portion of a polypeptide described herein, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed polypeptides, or corresponding DNA sequences that encode such polypeptides without appreciable loss of their biological utility or activity.

A "substitution," as used herein, denotes the replacement of one or more amino acids or nucleotides by different amino acids or nucleotides, respectively.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

As used herein, "identity" means the percentage of identical nucleotide or amino acid residues at corresponding positions in two or more sequences when the sequences are aligned to maximize sequence matching, i.e., taking into account gaps and insertions. Sequences are generally aligned for maximum correspondence over a designated region, e.g., a region at least 20, 25, 30, 35, 40, 45, 50, 55, 60, 65 or more amino acids or nucleotides in length, and can be up to the full length of the reference polypeptide or polynucleotide sequence. For sequence comparison, typically one sequence acts as a reference sequence, to which test sequences are compared. When using a sequence comparison algorithm, test and reference sequences are input into a computer program, subsequence coordinates are designated, if necessary, and sequence algorithm program parameters are designated. Otherwise, standard parameters can be used. The sequence comparison algorithm then calculates the percent sequence identity for the test sequence(s) relative to the reference sequence, based on the designated program parameters.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, or over the full length of a sequence, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5: 151-153; Myers, E. W. and Muller W. (1988) CABIOS 4:11-17; Robinson, E. D. (1971) Comb. Theor 77: 105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides described herein. Software for performing BLAST analyses is publicly available through the National Center for Biotechnology Information (blast.ncbi.nlm.nih.gov/Blast.cgi).

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff (1989) Proc. Natl. Acad. Sci. USA 89: 10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, e.g., at least 50 positions, at least 100 positions, or over the full length of a reference sequence, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

A "polypeptide variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences described herein and evaluating one or more biological activities of the polypeptide as described herein and/or using any of a number of techniques well known in the art. The term "variant" may also refer to any naturally occurring or engineered molecule comprising one or more nucleotide or amino acid mutations.

Illustrative HBV polymerase truncation mutants for use in promoting, inducing or eliciting an immunogenic response, e.g., against a polymerase antigen expressed by HBV, are provided in Table A. Illustrative N-terminal sequence segments deleted or removed from, and therefore not contained in, the HBV polymerase truncation mutants described herein are provided in Table B.

TABLE A

Pol$^{300}$-mutants-Motifs containing inactivating mutations are underlined (YMDD mutated to YMHD, AELL mutated to AHLL).

| SEQ ID NO: | HBV genotype | Length (# amino acids) | Polypeptide sequence |
|---|---|---|---|
| 13 | B | 534 | MSSRSQSQGPVLSCWWLQFRNSEPCSEYCLCHIVNLIEDWGPCTE<br>HGEHRIRTPRTPARVTGGVFLVDKNPHNTTESRLVVDFSQFSRGN<br>TRVSWPKFAVPNLQSLTNLLSSNLSWLSLDVSAAFYHLPLHPAAM<br>PHLLVGSSGLSRYVARLSSNSRIINNQHRTMQNLHDSCSRNLYVS<br>LMLLYKTYGRKLHLYSHPIILGFRKIPMGVGLSPFLLAQFTSAIC<br>SVVRRAFPHCLAFS<u>YMHD</u>VVLGAKSVQHLESLYAAVTNFLLSLGI |

TABLE A-continued

Pol³⁰⁰-mutants-Motifs containing inactivating mutations are underlined (YMDD mutated to YMHD, AELL mutated to AHLL).

| SEQ ID NO: | HBV genotype | Length (# amino acids) | Polypeptide sequence |
|---|---|---|---|
| | | | HLNPHKTKRWGYSLNFMGYVIGSWGTLPQEHIVQKIKMCFRKLPV NRPIDWKVCQRIVGLLGFAAPFTQCGYPALMPLYACIQAKQAFTF SPTYKAFLSKQYLHLYPVARQRPGLCQVFADATPTGWGLAIGHQR MRGAFVSPLPIHT<u>AHLL</u>AACFARSRSGAKLIGTDNSVVLSRKYTS FPWLLGCAANWILRGTSFVYVPSALNPADDPSRGRLGLYRPLLRL LYRPTTGRTSLYADSPSVPSHLPDRVHFASPLHVAWRPP |
| 14 | D | 534 | MSARSQSERPVFPCWWLQFRNSKPCSDYCLSHIVNLLEDWGPCAE HGEHHIRIPRTPARVTGGVFLVDKNPHNTAESRLVVDFSQFSRGN YRVSWPKFAVPNLQSLTNLLSSNLSWLSLDVSAAFYHLPLHPAAM PHLLVGSSGLSRYVARLSSNSRIFNYQHGTMQNLHDSCSRNLYVS LMLLYQTFGRKLHLYSHPIILGFRKIPMGVGLSPFLLAQFTSAIC SVVRRAFPHCLAFS<u>YMHD</u>VVLGAKSVQHLESLFTAVTNFLLSLGI HLNPNKTKRWGYSLHFMGYVIGCYGSLPQDHIIQKIKECFRKLPV NRPIDWKVCQRIVGLLGFAAPFTQCGYPALMPLYACIQSKQAFTF SPTYKAFLCKQYLNLYPVARQRPGLCQVFADATPTGWGLVMGHQR MRGTFKAPLPIHT<u>AHLL</u>AACFARSRSGANILGTDNSVVLSRKYTS FPWLLGCAANWILRGTSFVYVPSALNPADDPSRGRLGLYRPLLRL PFRPTTGRTSLYADSPSVPSHLPDRVHFASPLHVAWRPP |

TABLE B

N-terminal polypeptide sequence removed from Pol³⁰⁰ truncated mutants

| SEQ ID NO: | HBV genotype | Polypeptide sequence |
|---|---|---|
| 50 | B | PLSYQHFRKLLLLDDEAGPLEEELPRLADEGLNRRVAEDLNLGNLNVSIPWTHKV GNFTGLYSSTVPVFNPEWQTPSFPHIHLQEDIINRCQQYVGPLTVNEKRRLKLIM PARFYPNLTKYLPLDKGIKPYYPEHVVNHYFQTRHYLHTLWKAGILYKRESTRSA SFCGSPYSWEQDLQHGRLVFQTSKRHGDKSFCPQSPGILPRSSVGPCIQNQLRKS RLGPQPAQGQLAGRQQGGSGSIRARVHPSPWGTVGVEPSGSGHIHNCASNSSSCL HQSAVRKAAYSHISTSKGHSSSGHAVELHHFPPS |
| 51 | D | PLSYQHFRRLLLLDDEAGPLEEELPRLADEGLNRRVAEDLNLGNLNVSIPWTHKV GNFTGLYSSTVPVFNPHWKTPSFPNIHLHQDIIKKCEQFVGPLTVNEKRRLQLIM PARFYPNVTKYLPLDKGIKPYYPEHLVNHYFQTRHYLHTLWKAGILYKRETTHSA SFCGSPYSWEQELQHGAESFHQQSSGILSRPPVGSSLQSKHRKSRLGLQSQQGHL ARRQQGRGWSIRAGIHPTARRPFGVEPSGSGHTANLASKSASCLYQSAVRKAAYP VVSTFKKHSSSGHAVELHNLPPN |

In some embodiments, the truncated HBV polymerase polypeptide does not comprise an amino sequence or fragment thereof from another HBV protein. In some embodiments, truncated HBV polymerase polypeptide does not comprise an amino sequence or fragment thereof from an HBV protein selected from the group consisting of pre-core, core, X and envelope (e.g., small, medium or large surface antigen (sAg)).

Internal Deletion Polymerase Mutants

Further provided are HBV polymerase internal deletion mutant polypeptides. In various embodiments, the HBV polymerase internal deletion mutant polypeptides comprise in sequential order, from the N-terminus to C-terminus, a terminal protein (TP) domain, an inactivated reverse transcriptase domain, an inactivated RNase H, wherein the mutant polypeptide does not comprise all or part of a Spacer domain (i.e., all or part of the Spacer domain or region is deleted or removed). In various embodiments, the HBV polymerase deletion mutant polypeptide is no longer than 800 amino acids in length, e.g., no longer than 795, 790, 785, 780, 775, 770, 765, 760, 755, 750, 745, 740, 735, 730, 725, 720, 715, 710 or 705 amino acids in length. In some embodiments, the HBV polymerase internal deletion mutant polypeptides comprise in sequential order, from the N-terminus to C-terminus, a terminal protein (TP) domain, and an amino acid sequence corresponding to amino acid residues 300-832, 301-832, 302-832, 303-832, 304-832, 305-832, 306-832, 307-832, 308-832, 309-832, 310-832, 311-832, 312-832, 313-832, 314-832, 315-832, 316-832, 317-832, 318-832, 319-832, 320-832, 325-832, 326-832, 327-832, 328-832, 329-832, 330-832, 331-832, 332-832, 333-832, 334-832, 335-832 or 336-832 of a native or wild-type HBV polymerase. In various embodiments, the terminal protein (TP) domain, the inactivated reverse transcriptase domain, and the inactivated RNase H independently can be directly fused or operably linked or connected via a linker, e.g., as described herein, e.g., as provided in Table J.

In some embodiments, the HBV polymerase internal deletion mutant polypeptide is from HBV genotype A and comprises or consists of an amino acid sequence of any one of SEQ ID NOs: 5 and 9, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5 and 9. In some embodiments, the HBV polymerase internal deletion mutant polypeptide is from HBV genotype A and does not comprise a polypeptide of SEQ ID NO: 42 or 46, or a sequence that is at least 90%, 91%, 92%, 93%, 94%, 95%, 96%, 97%, 98% or 99% identical to any one of SEQ ID NO: 42 or 46.

In some embodiments, the HBV polymerase internal deletion mutant polypeptide is from HBV genotype B and comprises or consists of an amino acid sequence of any one of SEQ ID NOs: 6 and 10, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 6 and 10. In some embodiments, the HBV polymerase internal deletion mutant polypeptide is from HBV genotype B and does not comprise a polypeptide of SEQ ID NO: 43 or 47, or a sequence that is at least 90%, 91%, 92%, 93%, 94%, 95%, 96%, 97%, 98% or 99% identical to any one of SEQ ID NO: 43 or 47.

In some embodiments, the HBV polymerase internal deletion mutant polypeptide is from HBV genotype C and comprises or consists of an amino acid sequence of any one of SEQ ID NOs: 8 and 11, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 8 and 11. In some embodiments, the HBV polymerase internal deletion mutant polypeptide is from HBV genotype C and does not comprise a polypeptide of SEQ ID NO: 44 or 48, or a sequence that is at least 90%, 91%, 92%, 93%, 94%, 95%, 96%, 97%, 98% or 99% identical to any one of SEQ ID NO: 44 or 48.

In some embodiments, the HBV polymerase internal deletion mutant polypeptide is from HBV genotype D and comprises or consists of an amino acid sequence of any one of SEQ ID NOs: 9 and 12, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 9 and 12. In some embodiments, the HBV polymerase internal deletion mutant polypeptide is from HBV genotype D and does not comprise a polypeptide of SEQ ID NO: 45 or 49, or a sequence that is at least 90%, 91%, 92%, 93%, 94%, 95%, 96%, 97%, 98% or 99% identical to any one of SEQ ID NO: 45 or 49.

In some embodiments, the HBV polymerase internal deletion mutant polypeptide does not comprise an amino sequence or fragment thereof from another HBV protein. In some embodiments, HBV polymerase internal deletion mutant polypeptide does not comprise an amino sequence or fragment thereof from an HBV protein selected from the group consisting of pre-core, core, X and envelope (e.g., small, medium or large surface antigen (sAg)).

Illustrative HBV polymerase internal deletion mutants for use in promoting, inducing or eliciting an immunogenic response, e.g., against a polymerase antigen expressed by HBV, are provided in Tables C and E. Illustrative internal amino acid sequence segments deleted or removed from, and therefore not contained in, the HBV polymerase internal deletion mutants described herein, e.g., corresponding to all or part of an HBV polymerase Spacer region, are provided in Tables D and F.

Core-Polymerase Fusion Polypeptides

In various embodiments, the truncated and internal deletion HBV polymerase polypeptide variants described herein are fused to an HBV core polypeptide. The core polypeptide can be positioned either N-terminal or C-terminal to the HBV polymerase. Further provided are fusion polypeptides comprising in sequential order from the N-terminus to the C-terminus, an HBV core polypeptide and a truncated or internal deletion HBV polymerase polypeptide mutant, as described herein. In some embodiments, the core-Pol fusion polypeptide comprises the HBV polymerase deletion mutant polypeptide, described herein, comprises in sequential order from the N-terminus to the C-terminus, an HBV core polypeptide and an internal deletion HBV polymerase polypeptide mutant, as described herein.

In some embodiments, the core-Pol fusion polypeptide comprises or consists of an amino acid sequence of any one of SEQ ID NOs: 19-26, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 19-26.

In some embodiments, the HBV core-polymerase internal deletion mutant fusion protein does not comprise an amino sequence or fragment thereof from an HBV protein selected from the group consisting of X, pre-core, and envelope (e.g., small, medium or large surface antigen (sAg)).

Illustrative core-polymerase fusion proteins for use in promoting, inducing or eliciting an immunogenic response, e.g., against a core and/or polymerase antigen expressed by HBV, are provided in Table G.

TABLE C

Pol$^{A1}$ mutants: Motifs containing inactivating mutations are underlined (YMDD mutated to YMHD, AELL mutated to AHLL). Amino acids in bold + underline + italic mark the site of deletion (last amino acid prior to the deleted region, and the first amino acid after the deleted region).

| SEQ ID NO: | HBV genotype | Length (# amino acids) | Polypeptide sequence |
|---|---|---|---|
| 5 | A | 755 | MPLSYQHFRKLLLLDDETEAGPLEEELPRLADEDLNRRVAEDLNLGNLNVSIPWTHKVGNFTGLYSSTVP IFNPEWQTPSFPKIHLHEDIANRCQQFVGPLTVNEKRRLRLIMPARFYPNSTKYLPLDKGIKPYYPDHVV NHYFQTRHYLHTLWKAGILYKRETTRSASFCGSPYSWEQELHHGRLVIKTSQRHGDEPFCSQPSGILSRS SVG*PE*FHSFPPSSARSQSQGPVFSCWWLQFRNTQPCSKYCLSHLVNLLEDWGPCDEHGEHHIRIPRTPAR VTGGVFLVDKNPHNTAESRLVVDFSQFSRGITRVSWPKFAVPNLQSLTNLLSSNLSWLSLDVSAAFYHIP LHPAAMPHLLVGSSGLSRYVARLSSNSRIHNNQHGTLQNLHDSCSRQLYVSLMLLYKTYGRKLHLYSHPI ILGFRKIPMGVGLSPFLLAQFTSAICSVVRRAFPHCLAFS<u>YMHD</u>VVLGAKSVQHLESLYTAVINFLLSLG IHLNPNKTKRWGYSLNFMGYVIGSWGTLPQDHIVQKIKHCFRKLPINRPIDWKVCQRIVGLLGFAAPFTQ CGYPALMPLYACIQAKQAFTFSPTYKAFLSKQYLNLYPVARQRPGLCQVFADATPTGWGLAIGHQRMRGT FVAPLPIHT<u>AHLL</u>AACFARSRSGAKLIGTDNSVVLSRKYTSFPWLLGCTANWILRGTSFVYVPSALNPAD DPSRGRLGLYRPLLRLPYRPTTGRTSLYAVSPSVPSHLPVRVHFASPLHVAWRPP |

TABLE C-continued

Pol^A1 mutants: Motifs containing inactivating mutations are underlined (YMDD mutated to YMHD, AELL mutated to AHLL). Amino acids in bold + underline + italic mark the site of deletion (last amino acid prior to the deleted region, and the first amino acid after the deleted region).

| SEQ ID NO: | HBV genotype | Length (# amino acids) | Polypeptide sequence |
|---|---|---|---|
| 6 | B | 749 | MPLSYQHFRKLLLLLDDEAGPLEEELPRLADEGLNRRVAEDLNLGNLNVSIPWTHKVGNFTGLYSSTVPVF NPEWQTPSFPHIHLQEDIINRCQQYVGPLTVNEKRRLKLIMPARFYPNLTKYLPLDKGIKPYYPEHVVNH YFQTRHYLHTLWKAGILYKRESTRSASFCGSPYSWEQDLQHGRLVFQTSKRHGDKSFCPQSPGILPR_SE_ HHFPPSSSRSQSQGPVLSCWWLQFRNSEPCSEYCLCHIVNLIEDWGPCTEHGEHRIRTPRTPARVTGGVF LVDKNPHNTTESRLVVDFSQFSRGNTRVSWPKFAVPNLQSLTNLLSSNLSWLSLDVSAAFYHLPLHPAAM PHLLVGSSGLSRYVARLSSNSRIINNQHRTMQNLHDSCSRNLYVSLMLLYKTYGRKLHLYSHPIILGFRK IPMGVGLSPFLLAQFTSAICSVVRRAFPHCLAFS<u>YMHD</u>VVLGAKSVQHLESLYAAVINFLLSLGIHLNPH KTKRWGYSLNFMGYVIGSWGTLPQEHIVQKIKMCFRKLPVNRPIDWKVCQRIVGLLGFAAPFTQCGYPAL MPLYACIQAKQAFTFSPTYKAFLSKQYLHLYPVARQRPGLCQVFADATPTGWGLAIGHQRMRGAFVSPLP IHT<u>AHLL</u>AACFARSRSGAKLIGTDNSVVLSRKYTSFPWLLGCAANWILRGTSFVYVPSALNPADDPSRGR LGLYRPLLRLLYRPTTGRTSLYADSPSVPSHLPDRVHFASPLHVAWRPP |
| 7 | C | 753 | MPLSYQHFRKLLLLLDDEAGPLEEELPRLADEDLNRRVAEDLNLGNLNVSIPWTHKVGNFTGLYSSTVPVF NPEWQTPSFPHIHLQEDIINRCQQYVGPLTVNEKRRLKLIMPARFYPNLTKYLPLDKGIKPYYPEHTVNH YFKTRHYLHTLWKAGILYKRETTRSASFCGSPYSWEQELQHGRLVFQTSTRHGDESFCSQSSGILSRSPV G_PE_IHNFPPSSARSQSEGPLLSCWWLQFRNSKPCSDYCLSHIVNLLEDWGPCTEHGEHNIRIPRTPARVT GGVFLVDKNPHNTTESRLVVDFSQFSRGSTHVSWPKFAVPNLQSLTNLLSSNLSWLSLDVSAAFYHLPLH PAAMPHLLVGSSGLSRYVARLSSTSRNINYQHGAMQDLHDSCSRNLYVSLLLLYKTFGRKLHLYSHPIIL GFRKIPMGVGLSPFLLAQFTSAICSVVRRAFPHCLAFS<u>YMHD</u>VVLGAKSVQHLESLFTAVTNFLLSLGTH LNPNKTKRWGYSLNFMGYVIGSWGTLPQEHIVLKIKIQCFRKLPVNRPIDWKVCQRIVGLLGFAAPFTQCG YPALMPLYACIQAKQAFTFSPTYKAFLCKQYLNLYPVARQRSGLCQVFADATPTGWGLAVGHQRMRGTFV SPLPIHT<u>AHLL</u>AACFARSRSGAKLIGTDNSVVLSRKYTSFPWLLGCAANWILRGTSFVYVPSALNPADDP SRGRLGLYRPLLRLPFRPTTGRTSLYAVSPSVPSHLPVRVHFASPLHVAWRPP |
| 8 | D | 742 | MPLSYQHFRRLLLLLDDEAGPLEEELPRLADEGLNRRVAEDLNLGNLNVSIPWTHKVGNFTGLYSSTVPVF NPHWKTPSFPNIHLHQDIIKKCEQFVGPLTVNEKRRLQLIMPARFYPNVTKYLPLDKGIKPYYPEHVNH YFQTRHYLHTLWKAGILYKRETTHSASFCGSPYSWEQELQHGAESFHQQSSGILSRPPVG_SE_IHNLPPNS ARSQSERPVFPCWWLQFRNSKPCSDYCLSHIVNLLEDWGPCAEHGEHHIRIPRTPARVTGGVFLVDKNPH NTAESRLVVDFSQFSRGNYRVSWPKFAVPNLQSLTNLLSSNLSWLSLDVSAAFYHLPLHPAAMPHLLVGS SGLSRYVARLSSNSRIFNYQHGTMQNLHDSCSRNLYVSLMLLYQTFGRKLHLYSHPIILGFRKIPMGVGL SPFLLAQFTSAICSVVRRAFPHCLAFS<u>YMHD</u>VVLGAKSVQHLESLFTAVTNFLLSLGIHLNPNKTKRWGY SLHFMGYVIGCYGSLPQDHIIQKIKECFRKLPVNRPIDWKVCQRIVGLLGFAAPFTQCGYPALMPLYACI QSKQAFTFSPTYKAFLCKQYLNLYPVARQRPGLCQVFADATPTGWGLVMGHQRMRGTFKAPLPIHT<u>AHLL</u> AACFARSRSGANILGTDNSVVLSRKYTSFPWLLGCAANWILRGTSFVYVPSALNPADDPSRGRLGLYRPL LRLPFRPTTGRTSLYADSPSVPSHLPDRVHFASPLHVAWRPP |

TABLE D

Internal Spacer polypeptide sequences removed from Pol^A1 mutants and Core-Pol^A1 fusion proteins

| SEQ ID NO: | HBV genotype | Polypeptide sequence |
|---|---|---|
| 42 | A | CIRSQFKQSRLGLQPHQGPLATSQSGRSGSIRAR VHSPIRRCFGVEPSGSGHIGHSASSSSSCLHQSA VRKAAYSHLSTSKRQSSSGHAV |
| 43 | B | SVGPCIQNQLRKSRLGPQPAQGQLAGRQQGGSGS IRARVHPSPWGTVGVEPSGSGHIHNCASNSSSCL HQSAVRKAAYSHISTSKGHSSSGHAV |
| 44 | C | CIRSQLKQSRLGLQPQQGSLARSKSGRSGSIRAR VHPITRQSFGVEPSGSGHIDNSASSASSCLHQSA VRKTAYSHLSTSKRQSSSGHAV |
| 45 | D | SLQSKHRKSRLGLQSQQGHLARRQQGRGWSIRAG IHPTARRPFGVEPSGSGHTANLASKSASCLYQSA VRKAAYPVVSTFKKHSSSGHAV |

TABLE E

Pol^A3 mutants-Motifs containing inactivating mutations are underlined (YMDD mutated to YMHD, AELL mutated to AHLL). Amino acids in bold + nderline + italic mark the site of deletion (last amino acid prior to the deleted region, and the first amino acid after the deleted region).

| SEQ ID NO: | HBV genotype | Length (# amino acids) | Polypeptide sequence |
|---|---|---|---|
| 9 | A | 705 | MPLSYQHFRKLLLLLDDETEAGPLEEELPRLADEDLNRRVAEDLNLGNLNVSIPWTHKVGNFTGLYSST VPIFNPEWQTPSFPKIHLHEDIANRCQQFVGPLIVNEKRRLRLIMPARFYPNSTKYLPLDKGIKPYYP DHVVNHYFQTRHYLHILWKAGILYKRETTRSASFCGSPYSWEQELHH_GC_WWLQFRNTQPCSKYCLSHL |

TABLE E-continued

Pol^Δ3 mutants-Motifs containing inactivating mutations are underlined
(YMDD mutated to YMHD, AELL mutated to AHLL). Amino acids in bold +
underline + italic mark the site of deletion (last amino acid prior to
the deleted region, and the first amino acid after the deleted region).

| SEQ ID NO: | HBV genotype | Length (# amino acids) | Polypeptide sequence |
|---|---|---|---|
|  |  |  | VNLLEDWGPCDEHGEHHIRIPRTPARVTGGVFLVDKNPHNTAESRLVVDFSQFSRGITRVSWPKFAVP NLQSLTNLLSSNLSWLSLDVSAAFYHIPLHPAAMPHLLVGSSGLSRYVARLSSNSRIHNNQHGTLQNL HDSCSRQLYVSLMLLYKTYGRKLHLYSHPIILGFRKIPMGVGLSPFLLAQFTSAICSVVRRAFPHCLA FS<u>YMHD</u>VVLGAKSVQHLESLYTAVTNFLLSLGIHLNPNKTKRWGYSLNFMGYVIGSWGTLPQDHIVQK IKHCFRKLPINRPIDWKVCQRIVGLLGFAAPFTQCGYPALMPLYACIQAKQAFTFSPTYKAFLSKQYL NLYPVARQRPGLCQVFADATPTGWGLAIGHQRMRGTFVAPLPIHT<u>AHLL</u>AACFARSRSGAKLIGTDNS VVLSRKYTSFPWLLGCTANWILRGTSFVYVPSALNPADDSRGRLGLYRPLLRLPYRPTTGRTSLYAV SPSVPSHLPVRVHFASPLHVAWRPP |
| 10 | B | 703 | MPLSYQHFRKLLLLLDDEAGPLEEELPRLADEGLNRRVAEDLNLGNLNVSIPWTHKVGNFTGLYSSTVP VFNPEWQTPSFPHIHLQEDIINRCQQYVGPLIVNEKRRLKLIMPARFYPNLIKYLPLDKGIKPYYPEH VVNHYFQTRHYLHILWKAGILYKRESTRSASFCGSPYSWEQDLQH<u>GC</u>WWLQFRNSEPCSEYCLCHIVN LIEDWGPCTEHGEHRIRTPRTPARVTGGVFLVDKNPHNTTESRLVVDFSQFSRGNTRVSWPKFAVPNL QSLTNLLSSNLSWLSLDVSAAFYHLPLHPAAMPHLLVGSSGLSRYVARLSSNSRIINNQHRTMQNLHD SCSRNLYVSLMLLYKTYGRKLHLYSHPIILGFRKIPMGVGLSPFLLAQFTSAICSVVRRAFPHCLAFS <u>YMHD</u>VVLGAKSVQHLESLYAAVTNFLLSLGIHLNPHKTKRWGYSLNFMGYVIGSWGTLPQEHIVQKIK MCFRKLPVNRPIDWKVCQRIVGLLGFAAPFTQCGYPALMPLYACIQAKQAFTFSPTYKAFLSKQYLHL YPVARQRPGLCQVFADATPTGWGLAIGHQRMRGAFVSPLPIHT<u>AHLL</u>AACFARSRSGAKLIGTDNSVV LSRKYTSFPWLLGCAANWILRGTSFVYVPSALNPADDSRGRLGLYRPLLRLLYRPTTGRTSLYADSP SVPSHLPDRVHFASPLHVAWRPP |
| 11 | C | 703 | MPLSYQHFRKLLLLLDDEAGPLEEELPRLADEDLNRRVAEDLNLGNLNVSIPWTHKVGNFTGLYSSTVP VFNPEWQTPSFPHIHLQEDIINRCQQYVGPLIVNEKRRLKLIMPARFYPNLIKYLPLDKGIKPYYPEH TVNHYFKIRHYLHILWKAGILYKRETTRSASFCGSPYSWEQELQH<u>GC</u>WWLQFRNSKPCSDYCLSHIVN LLEDWGPCTEHGEHNIRIPRTPARVTGGVFLVDKNPHNTTESRLVVDFSQFSRGSTHVSWPKFAVPNL QSLTNLLSSNLSWLSLDVSAAFYHLPLHPAAMPHLLVGSSGLSRYVARLSSTSRNINYQHGAMQDLHD SCSRNLYVSLLLLYKTFGRKLHLYSHPIILGFRKIPMGVGLSPFLLAQFTSAICSVVRRAFPHCLAFS <u>YMHD</u>VVLGAKSVQHLESLFTAVTNFLLSLGIHLNPNKTKRWGYSLNFMGYVIGSWGTLPQEHIVLKIK QCFRKLPVNRPIDWKVCQRIVGLLGFAAPFTQCGYPALMPLYACIQAKQAFTFSPTYKAFLCKQYLNL YPVARQRSGLCQVFADATPTGWGLAVGHQRMRGTFVSPLPIHT<u>AHLL</u>AACFARSRSGAKLIGTDNSVV LSRKYTSFPWLLGCAANWILRGTSFVYVPSALNPADDSRGRLGLYRPLLRLPFRPTTGRTSLYAVSP SVPSHLPVRVHFASPLHVAWRPP |
| 12 | D | 703 | MPLSYQHFRRLLLLLDDEAGPLEEELPRLADEGLNRRVAEDLNLGNLNVSIPWTHKVGNFTGLYSSTVP VFNPHWKTPSFPNIHLHQDIIKKCEQFVGPLIVNEKRRLQLIMPARFYPNVIKYLPLDKGIKPYYPEH LVNHYFQTRHYLHILWKAGILYKRETTHSASFCGSPYSWEQELQH<u>GC</u>WWLQFRNSKPCSDYCLSHIVN LLEDWGPCAEHGEHHIRIPRTPARVTGGVFLVDKNPHNTAESRLVVDFSQFSRGNYRVSWPKFAVPNL QSLTNLLSSNLSWLSLDVSAAFYHLPLHPAAMPHLLVGSSGLSRYVARLSSNSRIFNYQHGTMQNLHD SCSRNLYVSLMLLYQTFGRKLHLYSHPIILGFRKIPMGVGLSPFLLAQFTSAICSVVRRAFPHCLAFS <u>YMHD</u>VVLGAKSVQHLESLFTAVTNFLLSLGIHLNPNKTKRWGYSLHFMGYVIGCYGSLPQDHIIQKIK ECFRKLPVNRPIDWKVCQRIVGLLGFAAPFTQCGYPALMPLYACIQSKQAFTFSPTYKAFLCKQYLNL YPVARQRPGLCQVFADATPTGWGLVMGHQRMRGTFKAPLPIHT<u>AHLL</u>AACFARSRSGANILGTDNSVV LSRKYTSFPWLLGCAANWILRGTSFVYVPSALNPADDSRGRLGLYRPLLRLPFRPTTGRTSLYADSP SVPSHLPDRVHFASPLHVAWRPP |

TABLE F

Internal Spacer polypeptide sequences removed
from Pol^Δ3 mutants and Core-Pol^Δ3 fusion proteins

| SEQ ID NO: | HBV genotype | Polypeptide sequence |
|---|---|---|
| 46 | A | RLVIKTSQRHGDEPPFCSQPSGILSRSSVGPCIRS QFKQSRLGLQPHQGPLATSQSGRSGSIRARVHSP IRRCFGVEPSGSGHIGHSASSSSSCLHQSAVRKA AYSHLSTSKRQSSSGHAVEFHSFPPSSARSQSQG PVFS |
| 47 | B | RLVFQTSKRHGDKSFCPQSPGILPRSSVGPCIQN QLRKSRLGPQPAQGQLAGRQQGGSGSIRARVHPS PWGTVGVEPSGSGHIHNCASNSSSCLHQSAVRKA AYSHISTSKGHSSSGHAVELHHPPSSSRSQSQSG PVLS |
| 48 | C | RLVFQTSTRHGDESFCSQSSGILSRSPVGPCIRS QLKQSRLGLQPQQGSLARSKSGRSGSIRARVHPI TRQSFGVEPSGSGHIDNSASSASSCLHQSAVRKT AYSHLSTSKRQSSSGHAVELHNFPPSSARSQSEG PLLS |
| 49 | D | AESFHQQSSGILSRPPVGSSLQSKHRKSRLGLQS QQGHLARRQQGRGWSIRAGIHPTARRPFGVEPSG SGHTANLASKSASCLYQSAVRKAAYPVVSTFKKH SSSGHAVELHNLPPNSARSQSERPVFP |

TABLE G

Core-Pol fusion proteins

| SEQ ID NO: | HBV genotype | Length (# amino acids) | Polypeptide sequence |
|---|---|---|---|

Core-Pol$^{mut}$ fusion proteins-Core sequences are indicated with bold + underline. Motifs containing inactivating mutations in Pos are underlined (UMDD mutated to YMHD, AELL mutated to AHLL).

| | | | |
|---|---|---|---|
| 15 | A | 1030 | MDIDPYKEFGASVELLSELPSDFFPSVRDLLDTASALYREALESPEHCSP<br>HHTALRQAILQWGELMTLATWVGNNLEDPASRDLVVNYVNTNMGLKIRQL<br>LWFHISCLTEGRETVLEYLVSEGVWIRTPPAYRPPNAPILSTLPETTVVR<br>RRDRGRSPRRRTPSPRRRRSQSPRRRRSQSRESQCMPLSYQHFRKLLLLD<br>DETEAGPLEEELPRLADEDLNRRVAEDLNLGNLNVSIPWTHKVGNFTGLY<br>SSTVPIFNPEWQTPSFPKIHLHEDIANRCQQFVGPLTVNEKRRLRLIMPA<br>RFYPNSTKYLPLDKGIKPYYPDHVVNHYFQTRHYLHTLWKAGILYKRETT<br>RSASFCGSPYSWEQELHHGRLVIKTSQRHGDEPFCSQPSGILSRSSVGPC<br>IRSQFKQSRLGLQPHQGPLATSQSGRSGSIRARVHSPIRRCFGVEPSGSG<br>HIGHSASSSSSCLHQSAVRKAAYSHLSTSKRQSSSGHAVEFHSFPPSSAR<br>SQSQGPVFSCWWLQFRNTQPCSKYCLSHLVNLLEDWGPCDEHGEHHIRIP<br>RTPARVTGGVFLVDKNPHNTAESRLVVDFSQFSRGITRVSWPKFAVPNLQ<br>SLTNLLSSNLSWLSLDVSAAFYHIPLHPAAMPHLLVGSSGLSRYVARLSS<br>NSRIHNNQHGTLQNLHDSCSRQLYVSLMLLYKTYGRKLHLYSHPIILGFR<br>KIPMGVGLSPFLLAQFTSAICSVVRRAFPHCLAFS<u>YMHD</u>VVLGAKSVQHL<br>ESLYTAVTNFLLSLGIHLNPNKTKRWGYSLNFMGYVIGSWGTLPQDHIVQ<br>KIKHCFRKLPINRPIDWKVCQRIVGLLGFAAPFTQCGYPALMPLYACIQA<br>KQAFTFSPTYKAFLSKQYLNLYPVARQRPGLCQVFADATPTGWGLAIGHQ<br>RMRGIFVAPLPIHT<u>AHLL</u>AACFARSRSGAKLIGIDNSVVLSRKYTSFPWL<br>LGCTANWILRGISFVYVPSALNPADDPSRGRLGLYRPLLRLPYRPTTGRT<br>SLYAVSPSVPSHLPVRVHFASPLHVAWRPP |
| 16 | B | 1026 | MDIDPYKEFGASVELLSELPSDFFPSVRDLLDTASALYREALESPEHCSP<br>HHTALRQAILQWGELMNLATWVGSNLEDPASRELVVSYVNVNMGLKIRQL<br>LWFHISCLTEGRETVLEYLVSFGVWIRTPPAYRPPNAPILSTLPETTVVR<br>RRGRSPRRRTPSPRRRRSQSPRRRRSQSRESQCMPLSYQHFRKLLLLDDE<br>AGPLEEELPRLADEGLNRRVAEDLNLGNLNVSIPWTHKVGNFTGLYSSTV<br>PVFNPEWQTPSFPHIHLQEDIINRCQQYVGPLTVNEKRRLKLIMPARFYP<br>NLTKYLPLDKGIKPYYPEHVVNHYFQTRHYLHTLWKAGILYKRESTRSAS<br>FCGSPYSWEQDLQHGRLVFQTSKRHGDKSFCPQSPGILPRSSVGPCIQNQ<br>LRKSRLGPQPAQGQLAGRQQGGSGSIRARVHPSPWGTVGVEPSGSGHIHN<br>CASNSSSCLHQSAVRKAAYSHISTSKGHSSSGHAVELHHPPSSSRSQSQ<br>GPVLSCWWLQFRNSEPCSEYCLCHIVNLIEDWGPCTEHGEHRIRTPRTPA<br>RVTGGVFLVDKNPHNTTESRLVVDFSQFSRGNTRVSWPKFAVPNLQSLTN<br>LLSSNLSWLSLDVSAAFYHLPLHPAAMPHLLVGSSGLSRYVARLSSNSRI<br>INNQHRTMQNLHDSCSRNLYVSLMLLYKTYGRKLHLYSHPIILGFRKIPM<br>GVGLSPFLLAQFTSAICSVVRRAFPHCLAFS<u>YMHD</u>VVLGAKSVQHLESLY<br>AAVINFLLSLGIHLNPHKTKRWGYSLNFMGYVIGSWGILPQEHIVQKIKM<br>CFRKLPVNRPIDWKVCQRIVGLLGFAAPFTQCGYPALMPLYACIQAKQAF<br>TFSPTYKAFLSKQYLHLYPVARQRPGLCQVFADATPTGWGLAIGHQRMRG<br>AFVSPLPIHT<u>AHLL</u>AACFARSRSGAKLIGIDNSVVLSRKYTSFPWLLGCA<br>ANWILRGISFVYVPSALNPADDPSRGRLGLYRPLLRLLYRPTTGRTSLYA<br>DSPSVPSHLPDRVHFASPLHVAWRPP |
| 17 | C | 1026 | MDIDPYKEFGASVELLSELPSDFFPSVRDLLDTASALYREALESPEHCSP<br>HHTALRQAILQWGELMNLATWVGSNLEDPASRELVVSYVNVNMGLKIRQL<br>LWFHISCLTEGRETVLEYLVSFGVWIRTPPAYRPPNAPILSTLPETTVVR<br>RRGRSPRRRTPSPRRRRSQSPRRRRSQSRESQCMPLSYQHFRKLLLLDDE<br>AGPLEEELPRLADEDLNRRVAEDLNLGNLNVSIPWTHKVGNFTGLYSSTV<br>PVFNPEWQTPSFPHIHLQEDIINRCQQYVGPLTVNEKRRLKLIMPARFYP<br>NLTKYLPLDKGIKPYYPEHTVNHYFKTRHYLHTLWKAGILYKRETTRSAS<br>FCGSPYSWEQELQHGRLVFQTSTRHGDESFCSQSSGILSRSPVGPCIRSQ<br>LKQSRLGLQPQQGSLARSKSGRSGSIRARVHPTTRQSFGVEPSGSGHIDN<br>SASSASSCLHQSAVRKTAYSHLSTSKRQSSSGHAVELHNFPPSSARSQSE<br>GPLLSCWWLQFRNSKPCSDYCLSHIVNLLEDWGPCTEHGEHNIRIPRTPA<br>RVTGGVFLVDKNPHNTTESRLVVDFSQFSRGSTHVSWPKFAVPNLQSLTN<br>LLSSNLSWLSLDVSAAFYHLPLHPAAMPHLLVGSSGLSRYVARLSSTSRN<br>INYQHGAMQDLHDSCSRNLYVSLLLLYKTFGRKLHLYSHPIILGFRKIPM<br>GVGLSPFLLAQFTSAICSVVRRAFPHCLAFS<u>YMHD</u>VVLGAKSVQHLESLF<br>TAVTNFLLSLGIHLNPNKTKRWGYSLNFMGYVIGSWGTLPQEHIVLKIKQ<br>CFRKLPVNRPIDWKVCQRIVGLLGFAAPFTQCGYPALMPLYACIQAKQAF<br>TFSPTYKAFLCKQYLNLYPVARQRSGLCQVFADATPTGWGLAVGHQRMRG<br>TFVSPLPIHT<u>AHLL</u>AACFARSRSGAKLIGIDNSVVLSRKYTSFPWLLGCA<br>ANWILRGISFVYVPSALNPADDPSRGRLGLYRPLLRLPFRPTTGRTSLYA<br>VSPSVPSHLPVRVHFASPLHVAWRPP |
| 18 | D | 1015 | MDIDPYKEFGASVELLSFLPSDFFPSVRDLLDTASALYREALESPEHCSP<br>HHTALRQAILCWGELMNLATWVGVNLEDPASRDLVVSYVNTNMGLKFRQL<br>LWFHISCLTFGRETVLEYLVSFGVWIRTPPAYRPPNAPILSTLPETTVVR<br>RRGRSPRRRTPSPRRRRSQSPRRRRSQSRESQCMPLSYQHFRRLLLLDDE<br>AGPLEEELPRLADEGLNRRVAEDLNLGNLNVSIPWTHKVGNFTGLYSSTV<br>PVFNPHWKTPSFPNIHLHQDIIKKCEQFVGPLTVNEKRRLQLIMPARFYP<br>NVTKYLPLDKGIKPYYPEHLVNHYFQTRHYLHTLWKAGILYKRETTHSAS |

TABLE G-continued

Core-Pol fusion proteins

| SEQ ID NO: | HBV genotype | Length (# amino acids) | Polypeptide sequence |
|---|---|---|---|
| | | | FCGSPYSWEQELQHGAESFHQQSSGILSRPPVGSSLQSKHRKSRLGLQSQ QGHLARRQQGRGWSIRAGIHPTARRPFGVEPSGSGHTANLASKSASCLYQ SAVRKAAYPVVSTFKKHSSSGHAVELHNLPPNSARSQSERPVFPCWWLQF RNSKPCSDYCLSHIVNLLEDWGPCAEHGEHHIRIPRTPARVTGGVFLVDK NPHNTAESRLVVDFSQFSRGNYRVSWPKFAVPNLQSLTNLLSSNLSWLSL DVSAAFYHLPLHPAAMPHLLVGSSGLSRYVARLSSNSRIFNYQHGTMQNL HDSCSRNLYVSLMLLYQTFGRKLHLYSHPIILGFRKIPMGVGLSPFLLAQ FTSAICSVVRRAFPHCLAFS<u>YMHD</u>VVLGAKSVQHLESLFTAVTNFLLSLG IHLNPNKTKRWGYSLHFMGYVIGCYGSLPQDHIIQKIKECFRKLPVNRPI DWKVCQRIVGLLGFAAPFTQCGYPALMPLYACIQSKQAFTFSPTYKAFLC KQYLNLYPVARQRPGLCQVFADATPTGWGLVMGHQRMRGTFKAPLPIHT<u>A HLL</u>AACFARSRSGANILGTDNSVVLSRKYTSFPWLLGCAANWILRGTSFV YVPSALNPADDPSRGRLGLYRPLLRLPFRPTTGRTSLYADSPSVPSHLPD RVHFASPLHVAWRPP |

Core-Pol^Al fusion proteins-Core sequences are indicated with bold + underline. Motifs containing inactivating mutations in Pol are underlined (YMDD mutated to YMHD, AELL mutated to AHLL). Amino acids in bold + italic mark the site of deltion (last amino acid prior to the deleted region, and the first amino acid after the deleted region).

| SEQ ID NO: | HBV genotype | Length (# amino acids) | Polypeptide sequence |
|---|---|---|---|
| 19 | A | 940 | <u>MDIDPYKEFGASVELLSFLPSDFFPSVRDLLDTASALYREALESPEHCSP HHTALRQAILCWGELMTLATWVGNNLEDPASRDLVVNYVNTNMGLKIRQL LWFHISCLTFGRETVLEYLVSFGVWIRTPPAYRPPNAPILSTLPETTVVR RRDRGRSPRRRTPSPRRRRSQSPRRRRSQSRESQC</u>MPLSYQHFRKLLLLD DETEAGPLEEELPRLADEDLNRRVAEDLNLGNLNVSIPWTHKVGNFTGLY SSTVPIFNPEWQTPSFPKIHLHEDIANRCQQFVGPLTVNEKRRLRLIMPA RFYPNSTKYLPLDKGIKPYYPDHVVNHYFQTRHYLHTLWKAGILYKRETT RSASFCGSPYSWEQELHHGRLVIKTSQRHGDEPFCSQPSGILSRSSVG_PE_ FHSFPPSSARSQSQGPVFSCWWLQFRNTQPCSKYCLSHLVNLLEDWGPCD EHGEHHIRIPRTPARVTGGVFLVDKNPHNTAESRLVVDFSQFSRGITRVS WPKFAVPNLQSLTNLLSSNLSWLSLDVSAAFYHIPLHPAAMPHLLVGSSG LSRYVARLSSNSRIHNNQHGTLQNLHDSCSRQLYVSLMLLYKTYGRKLHL YSHPIILGFRKIPMGVGLSPFLLAQFTSAICSVVRRAFPHCLAFS<u>YMHD</u>V VLGAKSVQHLESLYTAVTNFLLSLGIHLNPNKTKRWGYSLNFMGYVIGSW GTLPQDHIVQKIKHCFRKLPINRPIDWKVCQRIVGLLGFAAPFTQCGYPA LMPLYACIQAKQAFTFSPTYKAFLSKQYLNLYPVARQRPGLCQVFADATP TGWGLAIGHQRMRGIFVAPLPIHT<u>AHLL</u>AACFARSRSGAKLIGIDNSVVL SRKYTSFPWLLGCTANWILRGISFVYVPSALNPADDPSRGRLGLYRPLLR LPYRPTTGRTSLYAVSPSVPSHLPVRVHFASPLHVAWRPP |
| 20 | B | 932 | <u>MDIDPYKEFGASVELLSELPSDFFPSVRDLLDTASALYREALESPEHCSP HHTALRQAILQWGELMNLATWVGSNLEDPASRELVVSYVNVNMGLKIRQL LWFHISCLTEGRETVLEYLVSFGVWIRTPPAYRPPNAPILSTLPETTVVR RRGRSPRRRTPSPRRRRSQSPRRRRSQSRESQC</u>MPLSYQHFRKLLLLDDE AGPLEEELPRLADEGLNRRVAEDLNLGNLNVSIPWTHKVGNFTGLYSSTV PVFNPEWQTPSFPHIHLQEDIINRCQQYVGPLTVNEKRRLKLIMPARFYP NLTKYLPLDKGIKPYYPEHVVNHYFQTRHYLILWKAGILYKRESTRSAS FCGSPYSWEQDLQHGRLVFQTSKRHGDKSFCPQSPGILPR_SE_LHHFPPSS SRSQSQGPVLSCWWLQFRNSEPCSEYCLCHIVNLIEDWGPCTEHGEHRIR TPRTPARVTGGVFLVDKNPHNTTESRLVVDFSQFSRGNTRVSWPKFAVPN LQSLTNLLSSNLSWLSLDVSAAFYHLPLHPAAMPHLLVGSSGLSRYVARL SSNSRIINNQHRTMQNLHDSCSRNLYVSLMLLYKTYGRKLHLYSHPIILG FRKIPMGVGLSPFLLAQFTSAICSVVRRAFPHCLAFS<u>YMHD</u>VVLGAKSVQ HLESLYAAVTNFLLSLGIHLNPHKTKRWGYSLNFMGYVIGSWGTLPQEHI VQKIKMCFRKLPVNRPIDWKVCQRIVGLLGFAAPFTQCGYPALMPLYACI QAKQAFTFSPTYKAFLSKQYLHLYPVARQRPGLCQVFADATPTGWGLAIG HQRMRGAFVSPLPIHT<u>AHLL</u>AACFARSRSGAKLIGIDNSVVLSRKYTSFP WLLGCAANWILRGISFVYVPSALNPADDPSRGRLGLYRPLLRLLYRPTTG RTSLYADSPSVPSHLPDRVHFASPLHVAWRPP |
| 21 | C | 936 | <u>MDIDPYKEFGASVELLSELPSDFFPSVRDLLDTASALYREALESPEHCSP HHTALRQAILQWGELMNLATWVGSNLEDPASRELVVSYVNVNMGLKIRQL LWFHISCLTEGRETVLEYLVSFGVWIRTPPAYRPPNAPILSTLPETTVVR RRGRSPRRRTPSPRRRRSQSPRRRRSQSRESQC</u>MPLSYQHFRKLLLLDDE AGPLEEELPRLADEDLNRRVAEDLNLGNLNVSIPWTHKVGNFTGLYSSTV PVFNPEWQTPSFPHIHLQEDIINRCQQYVGPLTVNEKRRLKLIMPARFYP NLTKYLPLDKGIKPYYPEHVNHYFKTRHYLILWKAGILYKRETTRSAS FCGSPYSWEQELQHGRLVFQTSTRHGDESFCSQSSGILSRSPVG_PE_LHNF PPSSARSQSEGPLLSCWWLQFRNSKPCSDYCLSHIVNLLEDWGPCTEHGE HNIRIPRTPARVTGGVFLVDKNPHNTTESRLVVDFSQFSRGSTHVSWPKF AVPNLQSLTNLLSSNLSWLSLDVSAAFYHLPLHPAAMPHLLVGSSGLSRY VARLSSTSRNINYQHGAMQDLHDSCSRNLYVSLLLLYKTFGRKLHLYSHP IILGFRKIPMGVGLSPFLLAQFTSAICSVVRRAFPHCLAFS<u>YMHD</u>VVLGA KSVQHLESLFTAVTNFLLSLGIHLNPNKTKRWGYSLNFMGYVIGSWGTLP QEHIVLKIKQCFRKLPVNRPIDWKVCQRIVGLLGFAAPFTQCGYPALMPL |

TABLE G-continued

Core-Pol fusion proteins

| SEQ ID NO: | HBV genotype | Length (# amino acids) | Polypeptide sequence |
|---|---|---|---|
| | | | YACIQAKQAFTFSPTYKAFLCKQYLNLYPVARQRSGLCQVFADATPTGWG<br>LAVGHQRMRGIFVSPLPIHT<u>AHLL</u>AACFARSRSGAKLIGIDNSVVLSRKY<br>TSFPWLLGCAANWILRGISFVYVPSALNPADDPSRGRLGLYRPLLRLPFR<br>PTTGRTSLYAVSPSVPSHLPVRVHFASPLHVAWRPP |
| 22 | D | 925 | MDIDPYKEFGASVELLSFLPSDFFPSVRDLLDTASALYREALESPEHCSP<br>HHTALRQAILCWGELMNLATWVGVNLEDPASRDLVVSYVNTNMGLKFRQL<br>LWFHISCLTFGRETVLEYLVSFGVWIRTPPAYRPPNAPILSTLPETTVVR<br>RRGRSPRRRTPSPRRRRSQSPRRRRSQSRESQC MPLSYQHFRRLLLLDDE<br>AGPLEEELPRLADEGLNRRVAEDLNLGNLNVSIPWTHKVGNFTGLYSSTV<br>PVFNPHWKTPSFPNIHLHQDIIKKCEQFVGPLTVNEKRRLQLIMPARFYP<br>NVTKYLPLDKGIKPYYPEHLVNHYFQTRHYLHILWKAGILYKRETTHSAS<br>FCGSPYSWEQELQHGAESFHQQSSGILSRPPVG*SE*LHNLPPNSARSQSER<br>PVFPCWWLQFRNSKPCSDYCLSHIVNLLEDWGPCAEHGEHHIRIPRTPAR<br>VTGGVFLVDKNPHNTAESRLVVDFSQFSRGNYRVSWPKFAVPNLQSLTNL<br>LSSNLSWLSLDVSAAFYHLPLHPAAMPHLLVGSSGLSRYVARLSSNSRIF<br>NYQHGTMQNLHDSCSRNLYVSLMLLYQTFGRKLHLYSHPIILGFRKIPMG<br>VGLSPFLLAQFTSAICSVVRRAFPHCLAFS<u>YMHD</u>VVLGAKSVQHLESLFT<br>AVTNFLLSLGIHLNPNKTKRWGYSLHFMGYVIGCYGSLPQDHIIQKIKEC<br>FRKLPVNRPIDWKVCQRIVGLLGFAAPFTQCGYPALMPLYACIQSKQAFT<br>FSPTYKAFLCKQYLNLYPVARQRPGLCQVFADATPTGWGLVMGHQRMRGT<br>FKAPLPIHT<u>AHLL</u>AACFARSRSGANILGTDNSVVLSRKYTSFPWLLGCAA<br>NWILRGTSFVYVPSALNPADDPSRGRLGLYRPLLRLPFRPTTGRTSLYAD<br>SPSVPSHLPDRVHFASPLHVAWRPP |

Core-Pol<sup>Δ3</sup> fusion proteins-Core sequences are indicated with bold + underline. Motifs containing inactivating mutations in Pos are underlined (YMDD mutated to YMHD, AELL mutated to AHLL). Amino acids in bold + underline + italic mark the site of deletion (last amino acid prior to the deleted region, and the first amino acid after the deleted region).

| SEQ ID NO: | HBV genotype | Length (# amino acids) | Polypeptide sequence |
|---|---|---|---|
| 23 | A | 890 | MDIDPYKEFGASVELLSFLPSDFFPSVRDLLDTASALYREALESPEHCSP<br>HHTALRQAILCWGELMTLATWVGNNLEDPASRDLVVNYVNTNMGLKIRQL<br>LWFHISCLTFGRETVLEYLVSFGVWIRTPPAYRPPNAPILSTLPETTVVR<br>RRDRGRSPRRRTPSPRRRRSQSPRRRRSQSRESQC MPLSYQHFRKLLLLD<br>DETEAGPLEEELPRLADEDLNRRVAEDLNLGNLNVSIPWTHKVGNFTGLY<br>SSTVPIFNPEWQTPSFPKIHLHEDIANRCQQFVGPLTVNEKRRLRLIMPA<br>RFYPNSTKYLPLDKGIKPYYPDHVVNHYFQTRHYLHILWKAGILYKRETT<br>RSASFCGSPYSWEQELHH<u>*GC*</u>WWLQFRNIQPCSKYCLSHLVNLLEDWGPCD<br>EHGEHHIRIPRTPARVTGGVFLVDKNPHNTAESRLVVDFSQFSRGITRVS<br>WPKFAVPNLQSLTNLLSSNLSWLSLDVSAAFYHIPLHPAAMPHLLVGSSG<br>LSRYVARLSSNSRIHNNQHGTLQNLHDSCSRQLYVSLMLLYKTYGRKLHL<br>YSHPIILGFRKIPMGVGLSPFLLAQFTSAICSVVRRAFPHCLAFS<u>YMHD</u>V<br>VLGAKSVQHLESLYTAVTNFLLSLGIHLNPNKTKRWGYSLNFMGYVIGSW<br>GTLPQDHIVQKIKHCFRKLPINRPIDWKVCQRIVGLLGFAAPFTQCGYPA<br>LMPLYACIQAKQAFTFSPTYKAFLSKQYLNLYPVARQRPGLCQVFADATP<br>TGWGLAIGHQRMRGIFVAPLPIHT<u>AHLL</u>AACFARSRSGAKLIGIDNSVVL<br>SRKYTSFPWLLGCTANWILRGTSFVYVPSALNPADDPSRGRLGLYRPLLR<br>LPYRPTTGRTSLYAVSPSVPSHLPVRVHFASPLHVAWRPP |
| 24 | B | 886 | MDIDPYKEFGASVELLSELPSDFFPSVRDLLDTASALYREALESPEHCSP<br>HHTALRQAILQWGELMNLATWVGSNLEDPASRELVVSYVNVNMGLKIRQL<br>LWFHISCLTEGRETVLEYLVSEGVWIRTPPAYRPPNAPILSTLPETTVVR<br>RRGRSPRRRTPSPRRRRSQSPRRRRSQSRESQC MPLSYQHFRKLLLLDDE<br>AGPLEEELPRLADEGLNRRVAEDLNLGNLNVSIPWTHKVGNFTGLYSSTV<br>PVFNPEWQTPSFPHIHLQEDIINRCQQYVGPLTVNEKRRLKLIMPARFYP<br>NLTKYLPLDKGIKPYYPEHVVNHYFQTRHYLHILWKAGILYKRESTRSAS<br>FCGSPYSWEQDLQH<u>*GC*</u>WWLQFRNSEPCSEYCLCHIVNLIEDWGPCTEHGE<br>HRIRTPRIPARVTGGVFLVDKNPHNTTESRLVVDFSQFSRGNTRVSWPKF<br>AVPNLQSLTNLLSSNLSWLSLDVSAAFYHLPLHPAAMPHLLVGSSGLSRY<br>VARLSSNSRIINNQHRTMQNLHDSCSRNLYVSLMLLYKTYGRKLHLYSHP<br>IILGFRKIPMGVGLSPFLLAQFTSAICSVVRRAFPHCLAFS<u>YMHD</u>VVLGA<br>KSVQHLESLYAAVTNFLLSLGIHLNPHKTKRWGYSLNFMGYVIGSWGTLP<br>QEHIVQKIKMCFRKLPVNRPIDWKVCQRIVGLLGFAAPFTQCGYPALMPL<br>YACIQAKQAFTFSPTYKAFLSKQYLHLYPVARQRPGLCQVFADATPTGWG<br>LAIGHQRMRGAFVSPLPIHT<u>AHLL</u>AACFARSRSGAKLIGIDNSVVLSRKY<br>TSFPWLLGCAANWILRGISFVYVPSALNPADDPSRGRLGLYRPLLRLLYR<br>PTTGRTSLYADSPSVPSHLPDRVHFASPLHVAWRPP |
| 25 | C | 886 | MDIDPYKEFGASVELLSELPSDFFPSVRDLLDTASALYREALESPEHCSP<br>HHTALAQAILQWGELMNLATWVGSNLEDPASRELVVSYVNVNMGLKIRQL<br>LWFHISCLTEGRETVLEYLVSEGVWIRTPPAYRPPNAPILSTLPETTVVR<br>RRGRSPRRRTPSPRRRRSQSPRRRRSQSRESQC MPLSYQHFRKLLLLDDE<br>AGPLEEELPRLADEDLNRRVAEDLNLGNLNVSIPWTHKVGNFTGLYSSTV<br>PVFNPEWQTPSFPHIHLQEDIINRCQQYVGPLTVNEKRRLKLIMPARFYP<br>NLTKYLPLDKGIKPYYPEHTVNHYFKTRHYLHILWKAGILYKRETTRSAS |

TABLE G-continued

Core-Pol fusion proteins

| SEQ ID NO: | HBV genotype | Length (# amino acids) | Polypeptide sequence |
|---|---|---|---|
| | | | FCGSPYSWEQELQH*GC*WWLQFRNSKPCSDYCLSHIVNLLEDWGPCTEHGE HNIRIPRIPARVTGGVFLVDKNPHNTTESRLVVDFSQFSRGSTHVSWPKF AVPNLQSLTNLLSSNLSWLSLDVSAAFYHLPLHPAAMPHLLVGSSGLSRY VARLSSTSRNINYQHGAMQDLHDSCSRNLYVSLLLLYKTFGRKLHLYSHP IILGFRKIPMGVGLSPFLLAQFTSAICSVVRRAFPHCLAFS<u>YMHD</u>VVLGA KSVQHLESLFTAVTNFLLSLGIHLNPNKTKRWGYSLNFMGYVIGSWGTLP QEHIVLKIKQCFRKLPVNRPIDWKVCQRIVGLLGFAAPFTQCGYPALMPL YACIQAKQAFTFSPTYKAFLCKQYLNLYPVARQRSGLCQVFADATPTGWG LAVGHQRMRGIFVSPLPIHT<u>AHLL</u>AACFARSRSGAKLIGIDNSVVLSRKY TSFPWLLGCAANWILRGISFVYVPSALNPADDPSRGRLGLYRPLLRLPFR PTTGRTSLYAVSPSVPSHLPVRVHFASPLHVAWRPP |
| 26 | D | 886 | MDIDPYKEFGASVELLSELPSDFFPSVRDLLDTASALYREALESPEHCSP HHTALRQAILQWGELMNLATWVGVNLEDPASRDLVVSYVNTNMGLKFRQL LWFHISCLTEGRETVLEYLVSEGVWIRTPPAYRPPNAPILSTLPETTVVR RRGRSPRRRTPSPRRRRSQSPRRRRSQSRESQCMPLSYQHFRRLLLLDDE AGPLEEELPRLADEGLNRRVAEDLNLGNLNVSIPWTHKVGNFTGLYSSTV PVFNPHWKTPSFPNIHLHQDIIKKCEQFVGPLTVNEKRRLQLIMPARFYP NVTKYLPLDKGIKPYYPEHLVNHYFQTRHYLHILWKAGILYKRETTHSAS FCGSPYSWEQELQH*GC*WWLQFRNSKPCSDYCLSHIVNLLEDWGPCAEHGE HHIRIPRIPARVTGGVFLVDKNPHNTAESRLVVDFSQFSRGNYRVSWPKF AVPNLQSLTNLLSSNLSWLSLDVSAAFYHLPLHPAAMPHLLVGSSGLSRY VARLSSNSRIFNYQHGTMQNLHDSCSRNLYVSLMLLYQTFGRKLHLYSHP IILGFRKIPMGVGLSPFLLAQFTSAICSVVRRAFPHCLAFS<u>YMHD</u>VVLGA KSVQHLESLFTAVINFLLSLGIHLNPNKTKRWGYSLHFMGYVIGCYGSLP QDHIIQKIKECFRKLPVNRPIDWKVCQRIVGLLGFAAPFTQCGYPALMPL YACIQSKQAFTFSPTYKAFLCKQYLNLYPVARQRPGLCQVFADATPTGWG LVMGHQRMRGIFKAPLPIHT<u>AHLL</u>AACFARSRSGANILGIDNSVVLSRKY TSFPWLLGCAANWILRGISFVYVPSALNPADDPSRGRLGLYRPLLRLPFR PTTGRISLYADSPSVPSHLPDRVHFASPLHVAWRPP |

Core-sAg Fusion Proteins

Further provided are fusion proteins composed of an N-terminal portion comprising an HBV core polypeptide, or an immunogenic fragment thereof, and a C-terminal portion comprising an HBV small surface antigen, or an immunogenic fragment thereof. In various embodiments, the HBV core polypeptide or fragment thereof and the HBV small surface antigen (sAg), or fragment thereof, are directly fused or abutted. In some embodiments, the HBV core polypeptide or fragment thereof and the HBV small surface antigen, or fragment thereof, are connected via a linker.

HBV Core Polypeptide, or an Immunogenic Fragment Thereof

In various embodiments, the HBV core polypeptide, or immunogenic fragment thereof, of the core-sAg fusion protein independently can be from an HBV genotype A, B/C or D. Illustrative HBV core polypeptide amino acid sequences that can be used in the herein described core-sAg fusion proteins are provided in Table H.

TABLE H

Illustrative HBV core polypeptide sequences

| SEQ ID NO: | HBV genotype | Polypeptide sequence |
|---|---|---|
| 64 | A | MDIDPYKEFGASVELLSFLPSDFFPSVRDLLDTA SALYREALESPEHCSPHHTALRQAILCWGELMTL ATWVGNNLEDPASRDLVVNYVNTNMGLKIRQLLW FHISCLTFGRETVLEYLVSFGVWIRTPPAYRPPN APILSTLPETTVVRRRDRGRSPRRRTPSPRRRS QSPRRRRSQSRESQC |
| 65 | B/C | MDIDPYKEFGASVELLSFLPSDFFPSVRDLLDTA SALYREALESPEHCSPHHTALRQAILCWGELMNL ATWVGSNLEDPASRELVVSYVNVNMGLKIRQLLW FHISCLTFGRETVLEYLVSFGVWIRTPPAYRPPN APILSTLPETTVVRRRGRSPRRRTPSPRRRRSQS PRRRRSQSRESQC |
| 66 | D | MDIDPYKEFGASVELLSFLPSDFFPSVRDLLDTA SALYREALESPEHCSPHHTALRQAILCWGELMNL ATWVGVNLEDPASRDLVVSYVNTNMGLKFRQLLW FHISCLTFGRETVLEYLVSFGVWIRTPPAYRPPN APILSTLPETTVVRRRGRSPRRRTPSPRRRRSQS PRRRRSQSRESQC |

In some embodiments, the core polypeptide in the core-sAg fusion polypeptide comprises or consists of an amino acid sequence of any one of SEQ ID NOs: 64-66, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 64-66. In some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66.

HBV Small Surface Antigen, or an Immunogenic Fragment Thereof

In various embodiments, the HBV sAg polypeptide, or immunogenic fragment thereof, of the core-sAg fusion protein independently can be from an HBV genotype A, B, C or D. Illustrative HBV sAg polypeptide amino acid sequences that can be used in the herein described core-sAg fusion proteins are provided in Table 1, in Example 1 below.

In some embodiments, the sAg polypeptide in the core-sAg fusion polypeptide comprises or consists of an amino acid sequence of any one of SEQ ID NOs: 1-4, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 1-4, e.g., comprising one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213.

With respect to the core-sAg fusion proteins, the HBV core polypeptide and the HBV sAg polypeptide can be from the same or different HBV genotypes. In some embodiments, the core-sAg fusion protein comprises in sequential order, from the N-terminus to the C-terminus, an HBV core polypeptide and an HBV small surface antigen (sAg) polypeptide, wherein:

- the core polypeptide is from an HBV genotype A and the sAg polypeptide is from an HBV genotype A;
- the core polypeptide is from an HBV genotype B or C and the sAg polypeptide is from an HBV genotype B;
- the core polypeptide is from an HBV genotype B or C and the sAg polypeptide is from an HBV genotype C;
- the core polypeptide is from an HBV genotype D and the sAg polypeptide is from an HBV genotype D;
- the core polypeptide is from an HBV genotype A and the sAg polypeptide is from an HBV genotype B;
- the core polypeptide is from an HBV genotype A and the sAg polypeptide is from an HBV genotype C;
- the core polypeptide is from an HBV genotype A and the sAg polypeptide is from an HBV genotype D;
- the core polypeptide is from an HBV genotype B or C and the sAg polypeptide is from an HBV genotype A;
- the core polypeptide is from an HBV genotype B or C and the sAg polypeptide is from an HBV genotype D;
- the core polypeptide is from an HBV genotype D and the sAg polypeptide is from an HBV genotype A;
- the core polypeptide is from an HBV genotype D and the sAg polypeptide is from an HBV genotype B; or
- the core polypeptide is from an HBV genotype D and the sAg polypeptide is from an HBV genotype C.

In some embodiments, the core-sAg fusion protein comprises in sequential order, from the N-terminus to the C-terminus, an HBV core polypeptide and an HBV small surface antigen (sAg) polypeptide, wherein:

- the core polypeptide is from an HBV genotype B or C and the sAg polypeptide is from an HBV genotype C; or
- the core polypeptide is from an HBV genotype D and the sAg polypeptide is from an HBV genotype D.

In some embodiments, the core-sAg fusion protein comprises in sequential order, from the N-terminus to the C-terminus, (i) an HBV core polypeptide comprising or consisting of an amino acid sequence of SEQ ID NO: 65, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 65; and (ii) an HBV small surface antigen (sAg) polypeptide comprising or consisting of an amino acid sequence of SEQ ID NO: 3, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 3.

In some embodiments, the core-sAg fusion protein comprises in sequential order, from the N-terminus to the C-terminus, (i) an HBV core polypeptide comprising or consisting of an amino acid sequence of SEQ ID NO: 66, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 66; and (ii) an HBV small surface antigen (sAg) polypeptide comprising or consisting of an amino acid sequence of SEQ ID NO: 4, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 4.

In various embodiments, the core-sAg fusion proteins described herein comprise an HBV small surface antigen isoform but do not comprise an HBV medium surface antigen isoform or an HBV large surface antigen isoform. Accordingly, in some embodiments, the core-sAg fusion proteins described herein do not comprise an HBV pre-S1 polypeptide. In some embodiments, the core-sAg fusion proteins described herein do not comprise an HBVpre-S2 polypeptide. In some embodiments, the core-sAg fusion proteins described herein do not comprise both of an HBV pre-S1 polypeptide and an HBV pre-S2 polypeptide.

An illustrative HBV pre-S2 polypeptide not included in the herein described core-sAg fusion protein is provided below:

```
                                              (SEQ ID NO: 79)
MQWNST[A/T]FHQ[T/A]LQDPRVR[A/G]LYFP[A/G]GGSS[L/S]

G[A/T][V/I]NPV[L/P]TT[A/V]S[P/H][L/I]SSIF[S/A]RIG

DP[A/V][L/M/P/T]N.
```

An illustrative HBV pre-S2 consensus polypeptide from HBV genotype A not included in the herein described core-sAg fusion protein is provided below:

```
                                              (SEQ ID NO: 80)
MQWNSTAFHQALQDPRVRGLYFPAGGSSSGTVNPAPNIASHISSISART

GDPVTN.
```

An illustrative HBV pre-S2 consensus polypeptide from HBV genotype B not included in the herein described core-sAg fusion protein is provided below:

```
                                              (SEQ ID NO: 81)
MQWNSTTFHQTLQDPRVRALYFPAGGSSSGTVSPAQNTVSAISSILSKT

GDPVPN.
```

An illustrative HBV pre-S2 consensus polypeptide from HBV genotype C not included in the herein described core-sAg fusion protein is provided below:

```
                                              (SEQ ID NO: 82)
MQWNSTTFHQALLDPRVRGLYFPAGGSSSGTVNPVPTTASPISSIFSRTG

DPAPN.
```

An illustrative HBV pre-S2 consensus polypeptide from HBV genotype D not included in the herein described core-sAg fusion protein is provided below:

(SEQ ID NO: 83)
MQWNSTTFHQTLQDPRVRGLYFPAGGSSSGTVNPVPTTASPISSIFSRIG
DPALN.

In some embodiments, the core-sAg fusion proteins described herein do not comprise an HBV pre-S2 polypeptide comprising or consisting of an amino acid sequence of any one of SEQ ID NOs: 79-83, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 79-83.

An illustrative HBV pre-S1-pre-S2 polypeptide not included in the herein described core-sAg fusion protein is provided below:

(SEQ ID NO: 84)
MGQNLSTSNPLGFFPDHQL[D/A]PAFRANT[A/G/R]NPDWDFNPNKDT
WPDANKVGAGAFGLGFTPPHGGLLGWSPQAQGI[I/L]QT[L/V]PANPP
PAS[T/A]NRQ[S/T]GRQPTPLSPPLR[N/D]THPQAMQWNST[A/T]F
HQ[T/A]LQDPRVR[A/G]LYFP[A/G]GGSS[L/S]G[A/T][V/I]NP
V[L/P]TT[A/V]S[P/H][L/I]SSIF[S/A]RIGDP[A/V][L/M/
P/T]N.

An illustrative HBV pre-S1-pre-S2 consensus polypeptide from HBV genotype A not included in the herein described core-sAg fusion protein is provided below:

(SEQ ID NO: 85)
MGGWSSKPRKGMGTNLSVPNPLGFFPDHQLDPAFGANSNNPDWDFNPIK
DHWPAANQVGVGAFGPGLTPPHGGILGWSPQAQGILTTVSTIPPPASTN
RQSGRQPTPISPPLRDSHPQAMQWNSTAFHQALQDPRVRGLYFPAGGSS
SGTVNPAPNIASHISSISARTGDPVTN.

An illustrative HBV pre-S1-pre-S2 consensus polypeptide from HBV genotype B not included in the herein described core-sAg fusion protein is provided below:

(SEQ ID NO: 86)
MGGWSSKPRKGMGTNLSVPNPLGFFPDHQLDPAFKANSENPDWDLNPHK
DNWPDANKVGVGAFGPGFTPPHGGLLGWSPQAQGLLTIVPAAPPPASTN
RQSGRQPIPLSPPLRDTHPQAMQWNSTIFHQTLQDPRVRALYFPAGGSS
SGTVSPAQNTVSAISSILSKTGDPVPN.

An illustrative HBV pre-S1-pre-S2 consensus polypeptide from HBV genotype C not included in the herein described core-sAg fusion protein is provided below:

(SEQ ID NO: 87)
MGGWSSKPRQGMGTNLSVPNPLGFFPDHQLDPAFGANSNNPDWDFNPNK
DHWPEANQVGAGAFGPGFTPPHGGLLGWSPQAQGILTTVPAAPPPASTN
RQSGRQPTPISPPLRDSHPQAMQWNSTTFHQALLDPRVRGLYFPAGGSS
SGTVNPVPTTASPISSIFSRTGDPAPN.

An illustrative HBV pre-S1-pre-S2 consensus polypeptide from HBV genotype D not included in the herein described core-sAg fusion protein is provided below:

(SEQ ID NO: 88)
MGQNLSTSNPLGFFPDHQLDPAFRANTANPDWDFNPNKDTWPDANKVGA
GAFGLGFTPPHGGLLGWSPQAQGILQTLPANPPPASTNRQSGRQPTPLS
PPLRNTHPQAMQWNSTTFHQTLQDPRVRGLYFPAGGSSSGTVNPVPTTA
SPISSIFSRIGDPALN.

In some embodiments, the core-sAg fusion proteins described herein do not comprise an HBV pre-S1-pre-S2 polypeptide comprising or consisting of an amino acid sequence of any one of SEQ ID NOs: 84-88, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 84-88.

Optional Polypeptide Linker

As appropriate, the HBV core polypeptide and the HBV sAg polypeptide in the core-sAg fusion protein can be directly abutted or fused, or can be joined, connected or linked by one or more peptide linkers. In various embodiments, the one or more peptide linkers is selected from one or more of a polyalanine linker, a polyglycine linker, a cleavable linker, a flexible linker, a rigid linker, and combinations thereof, e.g., within a linker or within a full-length fusion polypeptide. Illustrative fusion protein linkers that can be used in the present fusion polypeptides to connect the HBV core polypeptide and the HBV sAg polypeptide are described, e.g., in Chen, et al., *Adv Drug Deliv Rev.* (2013) 65(10): 1357-1369. In some embodiments, the polyalanine linker comprises or consists of 2 or 3 contiguous alanine residues, e.g. AA, AAA, AAY or AAX, wherein X is any amino acid (e.g., A, C, D, E, F, G, H, I, K, L, M, N, P, Q, R, S, T, V, Y). In some embodiments, a polyglycine linker is used, e.g., GG, GGG, GGS, GSG or GGGS (SEQ ID NO:63). In some embodiments, the cleavable linker is selected from a 2A cleavable peptide. Illustrative 2A cleavable peptides that can be used to connect the HBV core polypeptide and the HBV sAg polypeptide are described, e.g., in Donnelly, et al., *J. Gen. Virol* (2001), 82, 1027-1041 and Chng, et al., mAbs (2015) 7:2, 403-412. Illustrative 2A cleavable peptides that can be used to link the HBV core polypeptide and the HBV sAg polypeptide include without limitation 2A cleavage sequences (e.g., foot-and-mouth disease virus (F2A), equine rhinitis A virus (E2A), porcine teschovirus-1 (P2A) and *Thosea asigna* virus (T2A)), optionally in combination with a furin recognition/cleavage sequences (e.g. RAKR (SEQ ID NO: 60), REKR (SEQ ID NO: 61) and RRKR (SEQ ID NO: 62)). In certain embodiments, a furin recognition/cleavage sequence (e.g., RAKR (SEQ ID NO: 60), REKR (SEQ ID NO: 61) and RRKR (SEQ ID NO: 62)) is combined or fused with a 2A cleavable peptide (e.g., foot-and-mouth disease virus (F2A), equine rhinitis A virus (E2A), porcine teschovirus-1 (P2A) and *Thosea asigna* virus (T2A)) in a single linker. See, e.g., Chng, et al., mAbs (2015) 7:2, 403-412. In some embodiments, the linker comprises a porcine teschovirus-1 (P2A) linker. In various embodiments, the 2A cleavable linker comprises or consists of an amino acid sequence of ATNFSLLKQAGDVEENPGP (SEQ ID NO: 56), APVKQTLNFDLLKLAGDVESNPGP (SEQ ID NO: 57), QCTNYALLKLAGDVESNPGP (SEQ ID NO: 58), or EGRGSLLTCGDVEENPGP (SEQ ID NO: 59), or an amino acid sequence that is at least 90%, 91%, 92%, 93%, 94%, 95%, 96%, 97%, 98% or at least 99% identical to ATNFSLLKQAGDVEENPGP (SEQ ID NO: 56), APVKQTLNFDLLKLAGDVESNPGP (SEQ ID NO: 57), QCTNYALLKLAGDVESNPGP (SEQ ID NO: 58), or EGRGSLLTCGDVEENPGP (SEQ ID NO: 59). In various embodiments, the 2A cleavable linker comprises or consists of an amino acid sequence of ATNFSLLKQAGDVEENPGP (SEQ ID NO: 56), or an amino acid sequence that is at least 90%, 91%, 92%, 93%, 94%, 95%, 96%, 97%, 98% or at least 99% identical to ATNFSLLKQAGDVEENPGP (SEQ ID NO: 56). As appropriate, in certain embodiments, a furin recognition/cleavage sequence can be positioned either at the N-terminus or the C-terminus of a 2A linker. In some embodiments, the cleavable linker comprises or consists of a furin recognition/cleavage site selected from RAKR (SEQ ID NO: 60), REKR (SEQ ID NO: 61) and RRKR (SEQ ID NO: 62). Illustrative linkers that can be used to link or connect the HBV core polypeptide and the HBV sAg polypeptide are provided in Table J.

an HBV protein selected from the group consisting of X, pre-core, pre-S1, pre-S2 and polymerase.

In some embodiments, the core-sAg fusion protein comprises or consists of an amino acid sequence of any one of SEQ ID NOs: 38-41, e.g., SEQ ID NO: 41, or a sequence that is at least 90%, 91%, 92%, 93%, 94%, 95%, 96%, 97%, 98% or 99% identical to any one of SEQ ID NOs: 38-41, SEQ ID NO: 41. In some embodiments, the fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372,

TABLE J illustrative linkers for connecting HBV core and HBV sAg polypeptides in the core-sAg fusion protein

| SEQ ID NO: | NAME | SEQUENCE |
|---|---|---|
| | poly-alanine (2) | AA |
| | poly-alanine (3) | AAA |
| | poly-alanine-Tyr | AY |
| | poly-alanine-XXX | AAX (X = any amino acid) |
| | poly-glycine (2) | GG |
| | poly-glycine (3) | GGG |
| | poly-glycine/serine (3) | GGS |
| | poly-glycine/serine (3) | GSG |
| 63 | Gly3Ser | GGGS |
| 60 | furin recognition site | RAKR |
| 61 | furin recognition site | REKR |
| 62 | furin recognition site | RRKR |
| 56 | P2A | ATNFSLLKQAGDVEENPGP |
| 57 | F2A | APVKQTLNFDLLKLAGDVESNPGP |
| 58 | E2A | QCTNYALLKLAGDVESNPGP |
| 59 | T2A | EGRGSLLTCGDVEENPGP |

In some embodiments, the core-sAg fusion protein is no longer than 450 amino acids in length, e.g., no longer than 445, 440, 435, 430, 425, 420, 415 or 410 amino acids in length.

In some embodiments, the core-sAg fusion protein does not comprise an amino sequence or fragment thereof from wherein the position numbers are with reference to SEQ ID NO:41.

Illustrative core-sAg fusion proteins, e.g., for use in promoting, inducing or eliciting an immunogenic response, e.g., against core and/or small surface antigens expressed by HBV, are provided in Table K.

TABLE K

Core-sAg fusion proteins

Core-sAg fusion proteins-Core sequences are indicated with bold + underline. Flexible GSG linker indicated by italics. Cleavable P2A linker indicated by underlining.

| SEQ ID NO: | HBV geno-type | Length (#amino acids) | Polypeptide sequence |
|---|---|---|---|
| 38 | Core: B/C<br>sAg: C | 409 | MDIDPYKEFGASVELLSFLPSDFFPSVRDLLDTASALYREALESPEHCSPHHTALRQAILCWGEL<br>MNLATWVGSNLEDPASRELVVSYVNVNMGLKIRQLLWFHISCLTFGRETVLEYLVSFGVWIRTPP<br>AYRPPNAPILSTLPETTVVRRRGRSPRRRTPSPRRRRSQSPRRRRSQSRESQCMESTTSGFLGPL<br>LVLQAGFFLLTRILTIPQSLDSWWTSLNFLGGAPTCPGQNSQSPTSNHSPTSCPPICPGYRWMCL<br>RRFIIFLCILLLCLIFLLVLLDYQGMLPVCPLIPGSSTTSTGPCKTCTTPAQGTSMFPSCCCTKP<br>TDGNCTCIPIPSSWAFARFLWEWASVRFSWLSLLVPFVQWFVGLSPTVWLSVIWMMWYWGPSLYN<br>ILSPFLPLLPIFFCLWVYI |
| 39 | Core: B/C<br>sAg: C | 430 | MDIDPYKEFGASVELLSFLPSDFFPSVRDLLDTASALYREALESPEHCSPHHTALRQAILCWGEL<br>MNLATWVGSNLEDPASRELVVSYVNVNMGLKIRQLLWFHISCLTFGRETVLEYLVSFGVWIRTPP<br>AYRPPNAPILSTLPETTVVRRRGRSPRRRTPSPRRRRSQSPRRRRSQSRESQC*GSG*ATNFSLLKQ<br>AGDVEENPGPESTTSGFLGPLLVLQAGFFLLTRILTIPQSLDSWWTSLNFLGGAPTCPGQNSQSP<br>TSNHSPTSCPPICPGYRWMCLRRFIIFLCILLLCLIFLLVLLDYQGMLPVCPLIPGSSTTSTGPC<br>KTCTTPAQGTSMFPSCCCTKPTDGNCTCIPIPSSWAFARFLWEWASVRFSWLSLLVPFVQWFVGL<br>SPTVWLSVIWMMWYWGPSLYNILSPFLPLLPIFFCLWVYI |
| 40 | Core: D<br>sAg: D | 409 | MDIDPYKEFGASVELLSFLPSDFFPSVRDLLDTASALYREALESPEHCSPHHTALRQAILCWGEL<br>MNLATWVGVNLEDPASRDLVVSYVNTNMGLKFRQLLWFHISCLTFGRETVLEYLVSFGVWIRTPP<br>AYRPPNAPILSTLPETTVVRRRGRSPRRRTPSPRRRRSQSPRRRRSQSRESQCMENITSGFLGPL<br>LVLQAGFFLLTRILTIPQSLDSWWTSLNFLGGTTVCLGQNSQSPTSNHSPTSCPPICPGYRWMCL<br>RRFIIFLFILLLCLIFLLVLLDYQGMLPVCPLIPGSSTTSTGPCRTCTTPAQGTSMYPSCCCTKP<br>SDGNCTCIPIPSSWAFGKFLWEWASARFSWLSLLVPFVQWFVGLSPTVWLSVIWMMWYWGPSLYS<br>ILSPFLPLLPIFFCLWVYI |
| 41 | Core: D<br>sAg: D | 430 | MDIDPYKEFGASVELLSFLPSDFFPSVRDLLDTASALYREALESPEHCSPHHTALRQAILCWGEL<br>MNLATWVGVNLEDPASRDLVVSYVNTNMGLKFRQLLWFHISCLTFGRETVLEYLVSFGVWIRTPP<br>AYRPPNAPILSTLPETTVVRRRGRSPRRRTPSPRRRRSQSPRRRRSQSRESQC*GSG*ATNFSLLKQ<br>AGDVEENPGPENITSGFLGPLLVLQAGFFLLTRILTIPQSLDSWWTSLNFLGGTTVCLGQNSQSP<br>TSNHSPTSCPPICPGYRWMCLRRFIIFLFILLLCLIFLLVLLDYQGMLPVCPLIPGSSTTSTGPC<br>RTCTTPAQGTSMYPSCCCTKPSDGNCTCIPIPSSWAFGKFLWEWASARFSWLSLLVPFVQWFVGL<br>SPTVWLSVIWMMWYWGPSLYSILSPFLPLLPIFFCLWVYI |

Signal or Leader Sequences

In various embodiments, the immunogenic polypeptides described herein comprise a signal sequence or signal peptide, e.g., to direct intracellular trafficking of the polypeptide to a proteasomal or lysosomal compartment. In various embodiments, the immunogenic polypeptide comprises a signal sequence at the N-terminus and/or the C-terminus. In some embodiments, the immunogenic polypeptide comprises an N-terminal signal peptide or leader sequence. In various embodiments, the signal peptide or leader sequence is from a source protein selected from a serum protein, a cytokine, a chemokine, a chaperone protein, an invariant protein, and a protein that directs proteins to the lysosomal compartment. In some embodiments, the signal peptide or leader sequence is from a source protein selected from colony stimulating factor 2 (CSF2, GM-CSF), tissue type plasminogen activator (PLAT, t-PA), C—C motif chemokine ligand 7 (CCL7, MCP-3), C—X—C motif chemokine ligand 10 (CXCL10, IP-10), catenin beta 1 (CTNNB1), CD74 (p33; DHLAG; HLADG; Ia-GAMMA, invariant chain), serum albumin (ALB), polyubiquitin B/C (UBB/UBC), calreticulin (CALR), vesicular stomatitis virus G protein (VSV-G), lysosomal associated membrane protein 1 (LAMP-1) and lysosomal associated membrane protein 2 (LAMP-2). In various embodiments, the signal peptide or leader sequence is selected from an amino acid sequence of any one of SEQ ID NOs: 67-76, or a sequence that is at least 95%, 96%, 97%, 98%, or 99% identical to any one of SEQ ID NOs: 67-76. In certain embodiments, the immunogenic polypeptide comprises N-terminal and C-terminal signal sequences from LAMP-1, e.g, SEQ ID NOs: 77 and 78, respectively. Illustrative signal sequences that can be used in the present immunogenic polypeptides are provided in Table L.

TABLE L illustrative signal sequences

| SEQ ID NO: | source protein name | SEQUENCE |
|---|---|---|
| 67 | CSF2, GM-CSF | MWLQSLLLLGTVACSISV |
| 68 | PLAT, t-PA | MDAMKRGLCCVLLLCGAVFVSAR |
| 69 | CD74 | MHRRRSRSCREDQKPV |
| 70 | albumin | KWVTFISLLFLFSSAYS |

TABLE L-continued illustrative signal sequences

| SEQ ID NO: | source protein name | SEQUENCE |
|---|---|---|
| 71 | β-catenin | MRKAAVSHWQQQSYLDSGIHSGATTTAPSLS |
| 72 | CCL7, MCP-3 | MNPSAAVIFCLILLGLSGTQGILDMAQPVGINTSTTCCYRFI NKKIPKQRLESYRRTTSSHCPREAVIFKTKLDKEICADPTQK WVQDFMKHLDKKTQTPKLASAGA |
| 73 | ubiquitin | MQIFVKTLIGKTITLEVEPSDTIENVKAKIQDKEGIPPDQQR LIFAGKQLEDGRTLSDYNIQKESTLHLVLRLRGG |
| 74 | calreticulin | MLLSVPLLLGLLGLAVA |
| 75 | VSV-G | MKCLLYLAFLFIGVNC |
| 76 | CXCL10, IP-10 | MNQTAILICCLIFLTLSGIQG |
| 77 | LAMP-1 N-terminal | MAPRSARRPLLLLLLLLLGLMHCASAAMFMVKNGNGTACIM ANFSAAFSVNYDTKSGPKNMTLDLPSDATVVLNRSSCGKENT SDPSLVIAFGRGHTLTLNFTRNATRYSVQLMSFVYNLSDTHL FPNASSKEIKTVESITDIRADIDKKYRCVSGTQVHMNNVTVT LHDATIQAYLSNSSFSRGETRCEQDRPSPTTAPPAPPSPSPS PVPKSPSVDKYNVSGTNGTCLLASMGLQLNLTYERKDNTTVT RLLNINPNKTSASGSCGAHLVTLELHSEGTTVLLFQFGMNAS SSRFFLQGIQLNT1LPDARDPAFKAANGSLRALQATVGNSYK CNAEEHVRVTKAFSVNIFKVWVQAFKVEGGQFGSVEECLLDE NSLEDI |
| 78 | LAMP-1 C-terminal | GSEFTLIPIAVGGALAGLVIVLIAYLVGRKRSHAGYQTI |

Further provided are methods for making the immunogenic polypeptides described herein. In some implementations, the methods comprise constructing the immunogenic polypeptides using peptide synthesis. In some implementations, the methods comprise constructing, using synthetic or recombinant DNA technology, polynucleotides encoding each of the polypeptides of the bivalent antigen and expressing the polypeptides from an expression vector. In some implementations, the methods may further comprise inserting the polynucleotides into one or more vectors and expressing the encoded polypeptides in a cell. This can be done employing known recombinant techniques.

3. Polynucleotides Encoding Immunogenic Polypeptides

Provided are polynucleotides encoding the immunogenic polypeptides, described herein, vectors comprising such polynucleotides, and host cells (e.g., human cells, mammalian cells, yeast cells, plant cells, insect cells, bacterial cells, e.g., *E. coli*) comprising such polynucleotides or expression vectors. Provided herein are polynucleotides comprising nucleotide sequence(s) encoding any of the immunogenic polypeptides provided herein, as well as expression cassettes and vector(s) comprising such polynucleotide sequences, e.g., expression vectors for their efficient expression in host cells, e.g., mammalian cells. In various embodiments, the polynucleotide is a DNA, a cDNA, an mRNA, a self-amplifying RNA (SAM), a self-replicating RNA, or a self-amplifying replicon RNA (RepRNA). In some embodiments, the polynucleotide comprises or is expressed from an alphavirus self-replicating or self-amplifying replicon RNA (RepRNA). Self-replicating RNA and self-amplifying replicon RNA as modes of vaccine delivery are described, e.g., by Tews, et al., *Methods Mol Biol*. (2017) 1499:15-35; Démoulins, et al., *Methods Mol Biol*. (2017) 1499:37-75; Englezou, et al., *Mol Ther Nucleic Acids*. (2018) 12:118-134; McCollough, et al., Vaccines (Basel). (2014) 2(4):735-54; and McCollough, et al., *Mot Ther Nucleic Acids*. (2014) 3:e173.

The terms "polynucleotide" and "nucleic acid molecule" interchangeably refer to a polymeric form of nucleotides and includes both sense and anti-sense strands of RNA, cDNA, genomic DNA, and synthetic forms and mixed polymers of the above. As used herein, the term nucleic acid molecule may be interchangeable with the term polynucleotide. In some embodiments, a nucleotide refers to a ribonucleotide, deoxynucleotide or a modified form of either type of nucleotide, and combinations thereof. The terms also include without limitation, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-biased polynucleotides for improved expression in a desired viral expression vector or host cell.

A "substitution," as used herein, denotes the replacement of one or more amino acids or nucleotides by different amino acids or nucleotides, respectively.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location. "Isolated nucleic acid encoding an immunogenic polypeptide" refers to one or more nucleic acid molecules encoding such immunogenic polypeptides, including such nucleic acid molecule(s) in a single vector or multiple separate vectors, and such nucleic acid molecule(s) present at one or more locations in a host cell.

A "polynucleotide variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences described herein and evaluating one or more biological activities of the encoded polypeptide as described herein and/or using any of a number of techniques well known in the art.

In some embodiments, the nucleic acid molecule is codon-biased to enhance expression in a desired host cell, e.g., in human cells, mammalian cells, yeast cells, plant cells, insect cells, or bacterial cells, e.g., *E. coli* cells. Accordingly, provided are polynucleotides encoding an immunogenic polypeptide, described herein, wherein the polynucleotides are codon-biased, comprise replacement heterologous signal sequences, and/or have mRNA instability elements eliminated. Methods to generate codon-biased nucleic acids can be carried out by adapting the methods described in, e.g., U.S. Pat. Nos. 5,965,726; 6,174,666; 6,291,664; 6,414,132; and 6,794,498. Preferred codon usage for expression of the immunogenic polypeptides from desired viral expression vectors and/or in desired host cells is provided, e.g., at kazusa.or.jp/codon/; and genscript.com/tools/codon-frequency-table.

In some embodiments, the polynucleotide encoding an immunogenic polypeptide, as described herein, has at least 80%, at least 85%, at least 90%, at least 91%, at least 92%, at least 93%, at least 94%, at least 95%, at least 96%, at least 97%, at least 98%, at least 99% identical, or 100% identical to a nucleic acid sequence selected from the group consisting of SEQ ID NOs: 27-37 and 89-94, as provided in Table M.

As appropriate, in certain embodiments, the 3'-end of a polynucleotide encoding one or more of the immunogenic polypeptides described herein comprises one or multiple tandem stop codons, e.g., two or more tandem TAG ("amber"), TAA ("ochre") or TGA ("opal" or "umber") stop codons. The multiple tandem stop codons can be the same or different.

Further provided are expression cassettes, comprising a polynucleotide encoding an immunogenic polypeptide, as described herein, operably linked to one or more regulatory sequences. In some embodiments, the polynucleotide is operably linked to and under the control of a constitutive promoter. In some embodiments, the promoter is selected from cytomegalovirus major immediate-early (CMV), the CMV enhancer fused to the chicken beta-actin promoter (CAG), human elongation factor-1α (HEF-1α), mouse cytomegalovirus (mouse CMV), Chinese hamster elongation factor-1α (CHEF-1α), and phosphoglycerate kinase (PGK).

TABLE M

Polynucleotides encoding immunogenic polypeptides

| SEQ ID NO: | HBV genotype | name | Polynucleotide sequence |
|---|---|---|---|
| 27 | B | Pol$^{A1}$ | ATGCCCCTGAGCTACCAGCACTTCAGGAAGCTGCTGCTGCTGGATGATGAGGCTGGCCCTCTGGAGGAGGAGC TGCCCAGGCTGGCAGATGAGGGCCTCAACAGGAGAGTGGCAGAGGACCTGAACCTGGGCAACCTGAATGTGAG CATCCCCTGGACCCACAAAGTGGGGAACTTCACTGGCCTCTACAGCAGCACAGTGCCAGTGTTCAACCCTGAG TGGCAGACCCCCTCCTTCCCCCACATCCACCTCCAGGAGGACATCATCAACAGATGTCAGCAGTATGTGGGCC CTCTGACAGTCAATGAGAAGAGGAGGCTGAAGCTGATCATGCCTGCCAGGTTCTACCCCAACCTGACCAAGTA CCTCCCACTGGACAAGGGCATCAAGCCATACTATCCTGAGCATGTGGTGAACCACTACTTTCAGACCAGGCAC TACCTGCACACACTGTGGAAGGCTGGCATCCTGTACAAGAGGGAGAGCACCAGATCAGCCTCTTTCTGTGGCT CCCCCTACAGCTGGGAGCAGGATCTCCAGCATGGCAGACTGGTGTTCCAGACCTCCAAGAGGCATGGGGACAA GTCCTTTTGCCCCCAGAGCCCTGGCATCCTGCCCAGGAGCGAGCTCCACCACTTCCCCCCCTCCTCCAGCAGA AGCCAGTCCCAGGGACCTGTGCTGTCCTGCTGGTGGCTCCAGTTCAGGAACAGTGAGCCCTGCAGTGAGTACT GTCTGTGTCACATTGTGAACCTGATTGAGGACTGGGGGCCCTGCACTGAGCATGGAGAGCACAGGATCAGAAC CCCCAGGACCCCAGCCAGAGTGACTGGAGGTGTGTTCCTGGTGGACAAGAACCCCCACAACACCACAGAGAGC AGACTGGTGGTGGACTTCTCCCAGTTTTCAAGGGGCAACACCAGAGTGTCCTGGCCCAAGTTTGCAGTGCCCA ACCTCCAGAGCCTGACCAACCTGCTGTCATCAAACCTGAGCTGGCTGTCCCTGGATGTGTCTGCTGCCTTCTA CCACCTGCCCCTGCACCCTGCAGCCATGCCTCACCTCCTGGTGGGCAGCTCAGGCCTGAGCAGGTATGTGGCC AGGCTGTCAAGCAACTCCAGAATCATCAACAACCAGCACAGGACCATGCAGAACCTGCATGACTCTTGCAGCA GGAACCTGTATGTGAGCCTGATGCTGCTGTACAAGACCTATGGCAGGAAGCTGCACCTGTACTCCCACCCCAT CATCCTGGGTTTCAGGAAGATCCCCATGGGAGTGGGACTGTCCCCCTTCCTGCTGGCCCAGTTCACCTCTGCC ATCTGCTCTGTGGTGAGGAGAGCCTTCCCCCACTGCCTGGCCTTCTCCTACATGCATGATGTGGTGCTGGGGG CCAAGTCAGTGCAGCACCTGGAGTCTCTGTATGCTGCAGTCACCAACTTCCTGCTCAGCCTGGGCATCCACCT GAACCCCCACAAGACCAAGAGGTGGGGCTACTCTCTGAACTTCATGGGCTATGTGATAGGCAGCTGGGGCACC CTGCCACAGGAGCACATAGTGCAGAAGATCAAGATGTGCTTCAGGAAGCTGCCAGTGAACAGGCCCATTGATT GGAAGGTGTGCCAGAGGATTGTGGGCCTGCTGGGCTTTGCAGCACCCTTCACACAGTGTGGCTACCCAGCTCT GATGCCCCTGTATGCCTGCATCCAGGCCAAGCAGGCCTTCACCTTCTCCCCACTTACAAGGCCTTCCTGTCC AAGCAGTACCTGCACCTGTACCCTGTGGCAAGGCAGAGGCCAGGCCTCTGCCAGGTGTTTGCAGATGCCACCC CCACAGGCTGGGGCCTGGCCATTGGCCACCAGAGGATGAGAGGGGCCTTTGTGAGCCCACTGCCAATCCACAC AGCCCACCTGCTGGCAGCATGCTTTGCCAGGTCCAGGTCTGGTGCAAAGCTGATTGGCACTGACAACAGTGTG |

TABLE M-continued

Polynucleotides encoding immunogenic polypeptides

| SEQ ID NO: | HBV genotype | name | Polynucleotide sequence |
|---|---|---|---|
| | | | GTGCTGTCCAGAAAGTACACCAGCTTCCCCTGGCTGCTGGGATGTGCTGCCAACTGGATTCTGAGGGGCACCA GCTTTGTCTATGTGCCCTCTGCACTGAACCCTGCAGATGACCCCTCCAGGGGCAGACTGGGGCTGTACAGGCC ACTGCTCAGACTGCTGTACAGGCCCACCACTGGCAGAACCTCCCTGTATGCAGACAGCCCCTCAGTGCCCTCT CACCTGCCAGACAGAGTGCACTTTGCCAGCCCCCTGCATGTTGCCTGGAGGCCCCCC |
| 28 | B | Pol$^{\Delta 3}$ | ATGCCCCTGAGCTACCAGCACTTCAGGAAGCTGCTGCTGCTGGATGATGAGGCTGGCCCTCTGGAGGAGGAGC TGCCCAGGCTGGCAGATGAGGGCCTCAACAGGAGAGTGGCAGAGGACCTGAACCTGGGCAACCTGAATGTGAG CATCCCCTGGACCCACAAAGTGGGGAACTTCACTGGCCTCTACAGCAGCACAGTGCCAGTGTTCAACCCTGAG TGGCAGACCCCCTCCTTCCCCCACATCCACCTCCAGGAGGACATCATCAACGATGTCAGCAGTATGTGGGCC CTCTGACAGTCAATGAGAAGAGGAGGCTGAAGCTGATCATGCCTGCCAGGTTCTACCCCAACCTGACCAAGTA CCTCCCACTGGACAAGGGCATCAAGCCATACTATCCTGAGCATGTGGTGAACCACTACTTTCAGACCAGGCAC TACCTGCACACACTGTGGAAGGCTGGCATCCTGTACAAGAGGGAGAGCACCAGATCAGCCTCTTTCTGTGGCT CCCCCTACAGCTGGGAGCAGGATCTCCAGCATGGCTGCTGGTGGCTCCAGTTCAGGAACAGTGAGCCCTGCAG TGAGTACTGTCTGTGTCACATTGTGAACCTGATTGAGGACTGGGGGCCCTGCACTGAGCATGGAGAGCACAGG ATCAGAACCCCCAGGACCCCAGCCAGAGTGACTGGAGGTGTGTTCCTGGTGGACAAGAACCCCCACAACACCA CAGAGAGCAGACTGGTGGTGGACTTCTCCCAGTTTTCAAGGGGCAACACCAGAGTGTCCTGGCCCAAGTTTGC AGTGCCCAACCTCCAGAGCCTGACCAACCTGCTGTCATCAAACCTGAGCTGGCTGTCCCTGGATGTGTCTGCT GCCTTCTACCACCTGCCCCTGCACCCTGCAGCCATGCCTCACCTCCTGGTGGGCAGCTCAGGCCTGAGCAGGT ATGTGGCCAGGCTGTCAAGCAACTCCAGAATCATCAACAACCAGCACAGGACCATGCAGAACCTGCATGACTC TTGCAGCAGGAACCTGTATGTGAGCCTGATGCTGCTGTACAAGACCTATGGCAGGAAGCTGCACCTGTACTCC CACCCCATCATCCTGGGTTTCAGGAAGATCCCCATGGGAGTGGGACTGTCCCCCTTCCTGCTGGCCCAGTTCA CCTCTGCCATCTGCTCTGTGGTGAGGAGAGCCTTCCCCCACTGCCTGGCCTTCTCCTACATGCATGATGTGGT GCTGGGGGCCAAGTCAGTGCAGCACCTGGAGTCTCTGTATGCTGCAGTCACCAACTTCCTGCTCAGCCTGGGC ATCCACCTGAACCCCCACAAGACCAAGAGGTGGGGCTACTCTCTGAACTTCATGGGCTATGTGATAGGCAGCT GGGGCACCCTGCCACAGGAGCACATAGTGCAGAAGATCAAGATGTGCTTCAGGAAGCTGCCAGTGAACAGGCC CATTGATTGGAAGGTGTGCCAGAGGATTGTGGGCCTGCTGGGCTTTGCAGCACCCTTCACACAGTGTGGCTAC CCAGCTCTGATGCCCCTGTATGCCTGCATCCAGGCCAAGCAGGCCTTCACCTTCTCCCCCACTTACAAGGCCT TCCTGTCCAAGCAGTACCTGCACCTGTACCCTGTGGCAAGGCAGAGGCCAGGCCTCTGCCAGGTGTTTGCAGA TGCCACCCCACAGGCTGGGGCCTGGCCATTGGCCACCAGAGGATGAGAGGGGCCTTTGTGAGCCCACTGCCA ATCCACACAGCCCACCTGCTGGCAGCATGCTTTGCCAGGTCCAGGTCTGGTGCAAAGCTGATTGGCACTGACA ACAGTGTGGTGCTGTCCAGAAAGTACACCAGCTTCCCCTGGCTGCTGGGATGTGCTGCCAACTGGATTCTGAG GGGCACCAGCTTTGTCTATGTGCCCTCTGCACTGAACCCTGCAGATGACCCCTCCAGGGGCAGACTGGGGCTG TACAGGCCACTGCTCAGACTGCTGTACAGGCCCACCACTGGCAGAACCTCCCTGTATGCAGACAGCCCCTCAG TGCCCTCTCACCTGCCAGACAGAGTGCACTTTGCCAGCCCCCTGCATGTTGCCTGGAGGCCCCCC |
| 29 | B | Pol$^{300}$ | ATGTCCAGCAGAAGCCAGTCCCAGGGACCTGTGCTGTCCTGCTGGTGGCTCCAGTTCAGGAACAGTGAGCCCT GCAGTGAGTACTGTCTGTGTCACATTGTGAACCTGATTGAGGACTGGGGGCCCTGCACTGAGCATGGAGAGCA CAGGATCAGAACCCCCAGGACCCCAGCCAGAGTGACTGGAGGTGTGTTCCTGGTGGACAAGAACCCCCACAAC ACCACAGAGAGCAGACTGGTGGTGGACTTCTCCCAGTTTTCAAGGGGCAACACCAGAGTGTCCTGGCCCAAGT TTGCAGTGCCCAACCTCCAGAGCCTGACCAACCTGCTGTCATCAAACCTGAGCTGGCTGTCCCTGGATGTGTC TGCTGCCTTCTACCACCTGCCCCTGCACCCTGCAGCCATGCCTCACCTCCTGGTGGGCAGCTCAGGCCTGAGC AGGTATGTGGCCAGGCTGTCAAGCAACTCCAGAATCATCAACAACCAGCACAGGACCATGCAGAACCTGCATG ACTCTTGCAGCAGGAACCTGTATGTGAGCCTGATGCTGCTGTACAAGACCTATGGCAGGAAGCTGCACCTGTA CTCCCACCCCATCATCCTGGGTTTCAGGAAGATCCCCATGGGAGTGGGACTGTCCCCCTTCCTGCTGGCCCAG TTCACCTCTGCCATCTGCTCTGTGGTGAGGAGAGCCTTCCCCCACTGCCTGGCCTTCTCCTACATGCATGATG TGGTGCTGGGGGCCAAGTCAGTGCAGCACCTGGAGTCTCTGTATGCTGCAGTCACCAACTTCCTGCTCAGCCT GGGCATCCACCTGAACCCCCACAAGACCAAGAGGTGGGGCTACTCTCTGAACTTCATGGGCTATGTGATAGGC AGCTGGGGCACCCTGCCACAGGAGCACATAGTGCAGAAGATCAAGATGTGCTTCAGGAAGCTGCCAGTGAACA GGCCCATTGATTGGAAGGTGTGCCAGAGGATTGTGGGCCTGCTGGGCTTTGCAGCACCCTTCACACAGTGTGG CTACCCAGCTCTGATGCCCCTGTATGCCTGCATCCAGGCCAAGCAGGCCTTCACCTTCTCCCCCACTTACAAG GCCTTCCTGTCCAAGCAGTACCTGCACCTGTACCCTGTGGCAAGGCAGAGGCCAGGCCTCTGCCAGGTGTTTG CAGATGCCACCCCCACAGGCTGGGGCCTGGCCATTGGCCACCAGAGGATGAGAGGGGCCTTTGTGAGCCCACT GCCAATCCACACAGCCCACCTGCTGGCAGCATGCTTTGCCAGGTCCAGGTCTGGTGCAAAGCTGATTGGCACT GACAACAGTGTGGTGCTGTCCAGAAAGTACACCAGCTTCCCCTGGCTGCTGGGATGTGCTGCCAACTGGATTC TGAGGGGCACCAGCTTTGTCTATGTGCCCTCTGCACTGAACCCTGCAGATGACCCCTCCAGGGGCAGACTGGG GCTGTACAGGCCACTGCTCAGACTGCTGTACAGGCCCACCACTGGCAGAACCTCCCTGTATGCAGACAGCCCC TCAGTGCCCTCTCACCTGCCAGACAGAGTGCACTTTGCCAGCCCCCTGCATGTTGCCTGGAGGCCCCCC |
| 89 | B | Pol$^{300}$ ori | ATGTCTTCAAGATCCCAGAGTCAGGGCCCTGTACTTTCCTGCTGGTGGCTCCAGTTCAGGAACAGTGAGCCCT GCTCCGAATACTGTCTCTGCCATATCGTCAATCTTATCGAAGACTGGGGACCCTGTACCGAACATGGAGAACA TCGCATCAGGACTCCTAGGACCCCTGCTCGTGTTACAGGCGGGGTTTTTCTTGTTGACAAAAATCCTCACAAT ACCACAGAGTCTAGACTCGTGGTGGACTTCTCTCAATTTTCTAGGGGGAACACCCGTGTGTCTTGGCCAAAAT TCGCAGTCCCAAATCTCCAGTCACTCACCAACCTGTTGTCCTCCAATTTGTCCTGGTTATCGCTGGATGTGTC TGCGGCGTTTTATCATCTTCCTCTGCATCCTGCTGCTATGCCTCATCTTCTTGTTGGTTCTTCTGGACTATCA AGGTATGTTGCCCGTTTGTCCTCTAATTCCAGGATCATCAACAACCAGCACGGGACCATGCAAAACCTGCACG ACTCCTGCTCAAGGAACCTCTATGTTTCCCTCATGTTGCTGTACAAAACCTACGGACGGAAACTGCACTTGTA TTCCCATCCCATCATCTTGGGCTTTCGCAAAATTCCTATGGGAGTGGGCCTCAGTCCGTTTCTCTTGGCTCAG TTTACTAGTGCCATTTGTTCAGTGGTTCGTAGGGCTTTCCCCCACTGTCTGGCTTTCAGTTATATGCATGATG TGGTATTGGGGGCCAAGTCTGTACAACATCTTGAGTCCCTTTTTACCGCTGTTACCAATTTTCTTTTGTCTTT GGGTATACATTTAAACCCTCACAAAACAAAAAGATGGGGATATTCCCTTAACTTCATGGGATATGTAATTGGG AGTTGGGGCACATTGCCGCAGGAACATATTGTACAAAAAATCAAAATGTTTTAGGAAACTTCCTGTAAACC GGCCTATTGATTGGAAATATGTCAACGAATTGTGGGTCTTTTGGGGTTTGCCGCCCCTTTCACGCAATGTGG ATATCCTGCTTTAATGCCTTTATATGCATGTATACAAGCAAAACAGGCTTTTACTTTCTCGCCAACTTACAAG GCCTTCCTAAGTAAACAGTATCTGCACCTTTACCCCGTTGCTCGGCAACGGCCTGGTCTGTGCCAAGTGTTTG |

TABLE M-continued

Polynucleotides encoding immunogenic polypeptides

| SEQ ID NO: | HBV genotype | name | Polynucleotide sequence |
|---|---|---|---|
| | | | CTGACGCAACCCCCACTGGTTGGGGCTTGGCCATAGGCCATCAGCGCATGCGTGGAGCCTTCGTGTCTCCTCT<br>GCCGATCCATACTGCGCATCTCCTGGCCGCTTGTTTTGCTCGCAGCAGGTCTGGGGCAAAACTCATCGGGACT<br>GACAATTCTGTCGTGCTCTCCCGCAAGTATACATTCCTTTCCATGGCTGCTAGGCTGTGCTGCCAACTGGATCC<br>TGCGCGGGACGTCCTTTGTTTACGTCCCGTCGGCGCTGAATCCCGCGGACGACCCCTCCCGGGGCCGCTTGGG<br>GCTCTACCGCCCGCTTCTCCGCTTGTTGTACCGACCGACTACGGGGCGCACCTCTCTCTACGCGGACTCCCCG<br>TCTGTGCCTTCTCATCTGCCGGACCGTGTGCACTTCGCTTCACCTCTGCACGTCGCATGGAGACCACCGT |
| 90 | B | Pol300 dint | ATGTCATCCAGATCCCAGAGTCAGGGCCCTGTCCTTTCCTGTTGGTGGCTCCAGTTCAGGAACAGTGAGCCCT<br>GTTCTGAGTACTGTCTCTGCCACATTGTCAATCTGATTGAGGACTGGGGCCCCTGCACAGAGCATGGTGAACA<br>CAGGATCAGGACTCCCAGGACCCCTGCCAGGGTGACTGGTGGGGTTTTCCTTGTTGACAAAAATCCTCACAAC<br>ACCACAGAGTCAAGGCTTGTGGTGGACTTCTCTCAATTTTCAAGGGGGAACACAAGGGTGTCTTGGCCCAAAT<br>TTGCAGTCCCAAATCTCCAGTCTCTGACCAACCTGTTGTCCTCCAATTTGTCCTGGTTGTCTCTGGATGTCTC<br>TGCTGCCTTTTATCATCTTCCTCTCCATCCTGCTGCCATGCCTCATCTTCTTGTTGGTTCTTCTGGCTCTCT<br>AGGTATGTTGCCAGATTGTCCTCCAATTCCAGGATCATCAACAACCAGCACAGGACCATGCAAAACCTGCATG<br>ACTCCTGCTCCAGAAACCTCTATGTTTCTCTCATGTTGCTGTACAAAACCTATGGCAGGAAACTGCATTTGTA<br>TTCCCATCCCATCATCTTGGGCTTCAGGAAAATTCCCATGGGAGTGGGCCTCAGTCCCTTCCTCTTGGCTCAG<br>TTCACCAGTGCCATTTGTTCTGTTGTCAGGAGGGCTTTCCCCCACTGTCTTGCTTTCAGTTACATGCATGATG<br>TGGTCTTGGGGGCCAAGTCTGTCCAACATCTTGAGTCACTTTATGCTGCTGTGACCAACTTTCTTTTGTCTTT<br>GGGCATCCATTTGAACCCTCACAAAACCAAAAGATGGGGCTATTCCCTCAATTTCATGGGCTATGTCATTGGG<br>AGTTGGGGCACTTTGCCCCAGGAACACATTGTGCAAAAAATCAAGATGTGTTTCAGGAAACTTCCTGTGAACA<br>GGCCAATTGACTGGAAAGTCTGTCAGAGAATTGTGGGTCTTTTGGGGTTTGCAGCTCCTTTCACCCAATGTGG<br>CTATCCTGCTTTGATGCCCTTGTATGCCTGCATCCAGGCCAAACAGGCTTTCACTTTCTCCCCCACTTACAAG<br>GCCTTCCTCAGCAAACAGTATCTCCACCTTTACCCTGTTGCAAGGCAGGGCCTGGTCTGTGCCAAGTGTTTG<br>CTGATGCAACCCCCACTGGTTGGGGCTTGGCCATTGGCCATCAGAGAATGAGAGGTGCCTTTGTGTCTCCTCT<br>CCCCATCCACACTGCTCATCTCCTGGCAGCTTGCTTTGCAAGGAGCAGGTCTGGAGCCAAACTCATAGGGACT<br>GACAATTCTGTGGTGCTCTCCAGAAAGTACACCTCCTTTCCTTGGCTGCTGGGCTGTGCAGCCAACTGGATCC<br>TGAGGGGGACTTCCTTTGTTTATGTCCCCTCTGCCCTGACCTGACGATGACCCCTCCAGGGGCAGGTTGGG<br>GCTCTACAGACCCCTTCTCAGGTTGTGTACAGACCAACAACAGGGAGGACCTCTCTCTATGCAGATTCCCC<br>TCTGTTCCTTCTCATCTTCCAGACAGAGTGCACTTTGCTTCTCCTCTGCATGTGGCTTGGAGACCTCCC |
| 91 | B | Pol300 huCo low GC | ATGTCTAGCAGAAGCCAGTCCCAGGGACCTGTGCTGTCTTGTTGGTGGCTTCAGTTTCGGAATAGCGAGCCAT<br>GTAGCGAGTATTGCCTGTGTCACATCGTGAATCTGATTGAGGATTGGGGACCATGCACAGAGCACGGAGAGCA<br>CCGGATCAGAACCCCTAGGACACCAGCCCGCGTGACAGGAGGCGTGTTCCTGGTGGATAAGAACCCCCATAAT<br>ACAACAGAGAGCAGACTGGTGGTGGATTTTCTCAGTTTTCTCGGGGCAATACAAGAGTGTCCTGGCCAAAGT<br>TTGCCGTGCCCAATCTCCAGAGCCTGACAAACCTGCTGTCTTCTAATCTGAGCTGGCTGTCCCTGGACGTGTC<br>CGCCGCCTTTTACCACCTGCCACTGCACCCTGCCGCCACCTGCTGGTGGGCAGCTCCGGACTGAGC<br>AGATACGTGGCAAGGCTGTCTAGCAATTCTAGAATTATTAATAATCAGCACAGAACAATGCAGAATCTGCATG<br>ATTCTTGTAGCAGGAATCTGTACGTGAGCCTGATGCTGCTGTATAAGACATATGGACGCAAGCTGCACCTGTA<br>TTCTCACCCTATTATTCTGGGCTTCCGGAAGATCCCTATGGGCGTGGGACTGTCCCCATTCCTGCTGGCCCAG<br>TTTACCTCCGCCATCTGCTCTGTGGTGCGGAGAGCCTTTCCCACATTGTCTGGCCTTTTCTTACATGCACGATG<br>TGGTGCTGGGCGCCAAATCCGTGCAGCACCTGGAGTCTCTGTATGCCGCCGTGACAAACTTCCTGCTGAGCCT<br>GGGCATCCACCTGAATCCACATAAGACAAAGCGGTGGGGCTATTCTCTGAATTTTATGGGCTATGTGATCGGC<br>AGCTGGGGAACCCTGCCACAGGAGCACATTGTGCAGAAGATCAAGATGTGCTTTCGCAAGCTGCCCGTGAATC<br>GGCCTATCGATTGGAAGGTGTGCCAGAGGATCGTGGGACTGCTGGGATTCGCAGCACCCTTTACCCAGTGCGG<br>CTACCCAGCCTGATGCCACTGTATGCCTGTATCCAGGCCAAACAGGCCTTCACCTTTTCCCCTACATATAAG<br>GCTTTTCTGTCTAAGCAGTACCTGCATCTGTATCCAGTGGCAAGGCAGAGGCCAGGACTGTGCCAGGTGTTTG<br>CAGATGCAACACCAACAGGATGGGGACTGGCAATCGGACACCAGAGGATGAGAGGAGCCTTCGTGAGCCCACT<br>GCCAATTCACACCGCCCACCTGCTGGCAGCATGCTTTGCAAGGTCCCGCTCTGGAGCAAAGCTGATTGGCACC<br>GATAACAGCGTGGTGCTGTCAGAAAATACACCAGCTTCCCCTGGCTGCTGGGATGTGCAGCAATTGGATTC<br>TGAGGGGCACCAGCTTCGTGTATGTGCCTTCCGCCCTGAATCCTGCCGATGATCCATCTCGAGGCAGACTGGG<br>ACTGTATAGGCCACTGCTGAGCACTGCTGTATAGGCCTACCACAGGCAGAACATCCCTGTATGCCGACAGCCCA<br>TCCGTGCCCTCTCACCTGCCAGATAGAGTGCATTTCGCAAGCCCACTGCATGTGGCATGGAGGCCACCC |
| 92 | B | Pol300 ori_ del CpG | ATGTCTTCAAGATCCCAGAGTCAGGGCCCTGTACTTTCCTGCTGGTGGCTCCAGTTCAGGAACAGTGAGCCCT<br>GCTCTGAATACTGTCTCTGCCATATTGTCAATCTTATAGAAGACTGGGGACCCTGTACTGAACATGGAGAACA<br>TAGGATCAGGACTCCTAGGACCCCTGCTAGAGTTACAGGGGGGGTTTTCTTGTTGACAAAAATCCTCACAAT<br>ACCACAGAGTCTAGACTTGTGGTGGACTTCTCTCAATTTTCTAGGGGGAACACCAGGGTGTCTTGGCCAAAAT<br>TTGCAGTCCCAAATCTCCAGTCACTCACCAACCTGTTGTCCTCCAATTTGTCCTGGTTATCCCTGGATGTGTC<br>TGCAGCCTTTTATCATCTTCCTCTGCATCCTGCTGCTATGCCTCATCTTCTTGTTGGTTCTTCTGGACTATCA<br>AGGTATGTTGCCAGGTTGTCCTCTAATTCCAGGATCATCAACAACCAGCACAGGACCATGCAAAACCTGCATG<br>ACTCCTGCTCAAGGAACCTCTATGTTTCCTGCATGTTGCTGTACAAAACCTATGGAAGGAAACTGCACTTGTA<br>TTCCCATCCCATCATCTTGGGCTTTAGAAAATTCCTATGGGAGTGGGCCTCAGTCCCTTTCCTCTTGGCTCAG<br>TTTACTAGTGCCATTTGTTCAGTGGTTAGAAGGGCTTTCCCCACTGTCTGGCTTTCAGTTATATGCATGATG<br>TGGTATTGGGGGCCAAGTCTGTACAACATCTTGAGTCCCTTTATGCTGCTGTTACCAATTTTCTTTTGTCTTT<br>GGGTATACATTTAAACCCTCACAAAACAAAAGATGGGGATATTCCCTTAACTTCATGGGATATGTAATTGGG<br>AGTTGGGGCACATTGCCTCAGGAACATATTGTACAAAAAATCAAATGTGTTTAGGAAACTTCCTGTAAACA<br>GGCCATTGATTGGAAAGTATGTCAAAGAATTGTGGGTCTTTTGGGGTTTGCAGCCCCTTTCACCCAATGTGG<br>ATATCCTGCTTTAATGCCTTTATATGCATGTATACAAGCAAAACAGGCTTTTACTTTCTCCCCAACTTACAAG<br>GCCTTCCTAAGTAAACAGTATCTGCACCTTTACCCTGTTGCTAGGCAAAGGCCTGGTCTGTGCCAAGTGTTTG<br>CTGATGCAACCCCCACTGGTTGGGCTTGGCCATAGGCCATCAGAGGATGAGGGGAGCCTTTGTGTCTCCTCT<br>GCCTCCATACTGCCCATCTCCTGGCAGCTTGTTTTGCTAGGAGCAGGTCTGGGCAAAACTCATTGGGACT<br>GACAATTCTGTTGTGCTCTCCAGAAAGTATACATCCTTTCCATGGCTGCTAGGCTGTGCTGCCAACTGGATCC |

TABLE M-continued

Polynucleotides encoding immunogenic polypeptides

| SEQ ID NO: | HBV geno-type | name | Polynucleotide sequence |
|---|---|---|---|
| | | | TGAGGGGGACATCCTTTGTTTATGTCCCTTCAGCACTGAATCCTGCTGATGACCCCTCCAGGGGCAGATTGGG<br>GCTCTACAGGCCCCTTCTCAGGTTGTTGTACAGACCCACTACTGGGAGAACCTCTCTCTATGCAGACTCCCCC<br>TCTGTGCCTTCTCATCTGCCTGACAGGGTGCACTTTGCTTCACCTCTGCATGTTGCATGGAGACCACCT |
| 93 | B | Pol300 IDT | ATGAGTTCCCGATCACAGAGTCAGGGGCCCGTCCTTTCATGTTGGTGGCTTCAGTTTCGAAACTCCGAGCCAT<br>GTTCTGAGTATTGTCTCTGCCACATTGTGAATCTTATTGAAGACTGGGGCCCCTGCACCGAGCACGGCGAGCA<br>CCGAATACGGACACCTCGAACGCCAGCAAGAGTGACGGGCGGAGTGTTCCTCGTCGACAAGAATCCACACAAC<br>ACGACGGAGAGTAGATTGGTCGTTGATTTCAGTCAATTTTCAAGAGGCAATACACGAGTTTCTTGGCCGAAAT<br>TCGCCGTACCGAATCTGCAATCCTTGACAAATTTGCTTAGTTCTAATTTGTCTTGGCTTTCTCTCGATGTTTC<br>CGCCGCTTTCTATCACTTGCCCCTTCACCCAGCCGCGATGCCGCATCTCTTGGTGGGCAGCTCTGGACTTAGT<br>AGATACGTAGCTAGACTCAGTTCTAACTCACGGATAATAAATAACCAACATCGCACTATGCAGAACCTGCATG<br>ATTCTTGTTCCCGGAACTTGTATGTCTCCTTGATGTTGTTGTATAAAACTTATGGGCGAAAGCTTCATCTGTA<br>TAGCCATCCGATTATATTGGGTTTTAGGAAAATTCCTATGGGTGTTGGCTTGAGCCCTTTTCTGCTGGCGCAA<br>TTTACTTCAGCTATCTGCTCAGTAGTACGCCGGGCGTTTCCCCATTGTCTTGCTTTCTCATACATGCATGATG<br>TAGTACTTGGGGCCAAGTCTGTACAACACCTTGAGAGTTTGTATGCCGCCGTAACTAATTTCCTTCTCTCTCT<br>CGGGATCCATCTTAACCCTCACAAAACGAAGAGGTGGGGTTATTCTCTGAATTTCATGGGATATGTTATCGGG<br>TCTTGGGGAACGCTGCCTCAGGAACACATCGTCCAGAAATCAAGATGTGTTTCAGAAAGTTGCCAGTGAACA<br>GACCGATAGATTGGAAGGTTTGCCAAAGAATTGTTGGCTTGTTGGGATTCGCAGCCCCATTCACACAGTGCGG<br>GTATCCGGCTTTGATGCCCCTTTATGCTTGTATCCAGGCAAAACAGGCATTCACCTTTTCACCGACTTACAAA<br>GCATTTCTTTCTAAGCAGTATCTCCATCTTTACCCTGTCGCTCGACAGCGGCCGGGGCTTTGCCAGGTTTTCG<br>CAGACGCAACCCCAACTGGTTGGGGTCTTGCGATCGGCCACCAGAGGATGCGCGGTGCATTCGTGTCCCGCT<br>CCCAATCCATACGGCCCACTTGCTGGCGGCGTGCTTCGCTCGAAGTAGAAGCGGGGCTAAATTGATCGGCACG<br>GACAATTCAGTCGTGTTGTCACGCAAATATACCTCCTTTCCCTGGTTGCTCGGTTGCGCAGCAAACTGGATAC<br>TTCGGGGAACTAGTTTCGTTTATGTGCCCTCTGCTCTCAACCCCGCCGACGATCCTTCACGAGGGAGGCTGGG<br>TCTTTTACCGCCCATTGCTCAGGCTGCTTTACCGGCCTACCACTGGGAGAACAAGCTTGTACGCCGACAGCCCG<br>AGCGTCCCGTCTCATCTGCCCGACAGAGTTCACTTTGCGAGTCCATTGCACGTCGCTTGGCGCCCGCCG |
| 94 | B | Pol300_IDT_CpGdel | ATGAGTTCCAGATCACAGAGTCAGGGGCCTGTCCTTTCATGTTGGTGGCTTCAGTTTAGAAACTCAGAGCCAT<br>GTTCTGAGTATTGTCTCTGCCACATTGTGAATCTTATTGAAGACTGGGGCCCCTGCACAGAGCATGGAGAGCA<br>CAGAATAAGGACACCTAGAACCCCAGCAAGAGTGACAGGTGGAGTGTTCCTGGTAGACAAGAATCCACACAAC<br>ACAACTGAGAGTAGATTGGTGGTTGATTTCAGTCAATTTTCAAGAGGCAATACAAGAGTTTCTTGGCCAAAAT<br>TTGCTCGTACCAATCTGCAATCCTTGACAAATTTGCTTAGTTCTAATTTGTCTTGGCTTTCTCTAGATGTTTC<br>TGCAGCTTTCTATCACTTGCCCCTTCACCCAGCAGCTATGCCTCATCTCTTGGTGGGCAGCTCTGGACTTAGT<br>AGATATGTAGCTAGACTCAGTTCTAACTCAAGGATAATAAATAACCAACATAGGACTATGCAGAACCTGCATG<br>ATTCTTGTTCCAGGAACTTGTATGTCTCCTTGATGTTGTTGTATAAAACTTATGGGAGAAAGCTTCATCTGTA<br>TAGCCATCCTATTATATTGGGTTTTAGGAAAATTCCTATGGGTGTTGGCTTGAGCCCTTTTCTGCTGGCCCAA<br>TTTACTTCAGCTATCTGCTCAGTAGTAAGGAGGGCCTTTCCCCATTGTCTTGCTTTCTCATACATGCATGATG<br>TAGTACTTGGGGCCAAGTCTGTACAACACCTTGAGAGTTTGTATGCAGCAGTAACTAATTTCCTTCTCTCTCT<br>TGGGATCCATCTTAACCCTCACAAAACCAAGAGGTGGGGTATTCTCTGAATTTCATGGGATATGTTATAGGG<br>TCTTGGGGAACCCTGCCTCAGGAACACATTGTCCAGAAATCAAGATGTGTTTCAGAAAGTTGCCAGTGAACA<br>GACCAATAGATTGGAAGGTTTGCCAAAGAATTGTTGGCTTGTTGGGATTTGCAGCCCCATTCACACAGTGTGG<br>GTATCCTGCTTTGATGCCCCTTTATGCTTGTATCCAGGCAAAACAGGCATTCACCTTTTCACCCACTTACAAA<br>GCATTTCTTTCTAAGCAGTATCTCCATCTTTACCCTGTGGCTAGACAGAGGCCAGGGCTTTGCCAGGTTTTTG<br>CAGATGCAACCCCAACTGGTTGGGGTCTTGCAATTGGCCACCAGAGGATGAGAGGTGCATTTGTGTCCCCACT<br>CCCAATCCATACTGCCCACTTGCTGGCAGCTTGCTTTGCTAGAAGTAGAAGTGGGGCTAAATTGATTGGCACA<br>GACAATTCAGTTGTGTTGTCAAGGAAATATACCTCCTTTCCCTGGTTGCTTGGTTGTGCAGCAAACTGGATAC<br>TTAGGGGAACTAGTTTTGTTTATGTGCCCTCTGCTCTCAACCCTGCAGATGATCCTTCAAGAGGGAGGCTGGG<br>TCTTTTACAGGCCATTGCTCAGGCTGCTTTACAGGCCTACCACTGGGAGAACAAGCTTGTATGCAGACAGCCCC<br>AGTGTCCCCTCTCATCTGCCTGACAGAGTTCACTTTGCAAGTCCATTGCATGTTGCTTGGAGACCTCCA |
| 30 | D | PolΔ1 | ATGCCCCTGAGCTACCAACACTTCAGGAGACTGCTGCTGCTGGATGATGAGGCAGGCCCTCTGGAGGAGGAGC<br>TGCCCAGGCTGGCAGATGAGGGCCTGAACAGGAGGGTGGCTGAGGAACCTGAATGTGAG<br>CATCCCTTGGACCCACAAAGTGGGCAACTTCACAGGCCTGTACAGCAGCACTGTGCCTGTGTTCAACCCCCAC<br>TGGAAGACACCCAGCTTCCCCAACATCCACCTGCACCAGGACATCATCAAGAAGTGTGAGCAGTTTGTGGGCC<br>CCCTGACAGTCAATGAGAAGAGGAGGCTCCAGCTGATCATGCCAGCCAGGTTCTACCCCAATGTGACCAAGTA<br>CCTCCCCCTGGACAAGGGCATCAAGCCTTACTATCCAGAGCACCTGGTGAACCACTACTTCCAGACCAGACAC<br>TACCTGCACACTGTGGAAGGCAGGCATCCTGTACAAGAGGGAGACCACACACAGTGCCTCCTTCTGTGGCA<br>GCCCCTACTCCTGGGAGCAGGACTGCAACATGGAGCTGAGTCCTTCCACCAGCAGTCCAGTGGCATCCTGAG<br>CAGGCCCCTGTGGGCAGCGAGCTGCACAACCTGCCCCCCAACTCTGCCAGATCCCAGTCGAGAGGCCAGTG<br>TTCCCTTGCTGGTGGCTCCAGTTCAGGAACAGCAAGCCCTGCTCAGACTACTGCCTGAGCCACATTGTGAACC<br>TGCTGGAGGACTGGGGCCCCTGTGCAGAGCATGGGGAGCACCACATCAGAATCCCCAGGAACCCTGCCAGGGT<br>GACAGGAGGGGTGTTCCTGGTGGACAAGAACCCCCACAACACTGCAGAGTCCAGGCTGGTGGTGGACTTCTCC<br>CAGTTCAGCAGGGGCAACTACAGAGTCTCCTGGCCAAAGTTTGCTGTGCCCAACCTCCAGAGCCTGACAAACC<br>TGCTGAGCAGCAACCTGTCCTGGCTCTCCCTGGATGTGAGTGCAGCCTTCTATCACCTGCCCCTGCACCCAGC<br>AGCCATGCCACACCTGCTGGTGGGCTCCAGTGGCCTGTCCAGGTATGTGGCCAGGCTCTCCTCCAACTCCAGG<br>ATCTTCAACTATCAGCATGGCACCATGCAGAACCTGCATGACAGCTGCTCCAGGAACCTGTATGTGTCCCTGA<br>TGCTGCTCTATCAGACCTTTGGCAGGAAGCTGCACCTGTACAGCCACCCCATCATCCTGGGGTTCAGGAAGAT<br>CCCCATGGGTGTGGGCCTGTCCCCCTTCCTGCTGGCCCAGTTCACCAGTGCCATCTGCTCAGTGGTGAGGAGG<br>GCCTTCCCACACTGCCTGGCCTTCTCTTACATGGATGATGTGGTGCTGGGAGCCAAGTCTGTGCAGCACCTGG<br>AGAGCCTGTTCACAGCTGTGACAAACTTTCTCCTGAGCCTGGGCATCCACCTGAACCCCAACAAGACCAAGAG<br>GTGGGGTTATTCACTGCACTTCATGGGCTATGTGATTGGCTGCTATGGCTCTCTGCCACAGGACCACATCATC<br>CAGAAGATCAAGGAGTGCTTCAGAAAGCTGCCAGTGAACAGGCCAATTGACTGGAAGGTGTGCCAGAGGATTG<br>TGGGCCTGCTGGGCTTTGCAGCCCCCTTCACCCAGTGTGGCTACCCTGCCCTGATGCCCCTGTATGCCTGCAT<br>CCAGAGCAAGCAGGCCTTCACCTTTTCCCCCACTTACAAGGCCTTCCTGTGCAAGCAGTACCTGAACCTGTAC |

TABLE M-continued

Polynucleotides encoding immunogenic polypeptides

| SEQ ID NO: | HBV geno-type | name | Polynucleotide sequence |
|---|---|---|---|
| | | | CCTGTGGCCAGGCAGAGACCTGGGCTGTGCCAGGTGTTTGCAGATGCCACCCCCACAGGATGGGGACTGGTCA<br>TGGGACACCAGAGGATGAGGGGCACCTTCAAGGCACCCCTGCCCATCCACACAGCCCACCTGCTGGCTGCCTG<br>CTTTGCCAGGAGCAGGAGTGGGGCCAACATCCTGGGCACAGACAACTCTGTGGTGCTGAGCAGGAAGTACACA<br>TCCTTCCCCTGGCTGCTGGGATGTGCAGCCAACTGGATCCTGAGGGGCACCAGCTTTGTGTATGTGCCCTCTG<br>CCCTCAACCCTGCAGATGATCCAAGCAGGGGCAGGCTGGGACTGTACAGGCCACTGCTCAGACTGCCCTTCAG<br>GCCCACCACTGGCAGGACCAGCCTGTATGCTGACTCCCCATCTGTGCCCTCCCACCTGCCTGACAGAGTGCAC<br>TTTGCCTCCCCACTGCATGTGGCCTGGAGGCCCCCA |
| 31 | D | Pol$^{\Delta 3}$ | ATGCCCCTGAGCTACCAACACTTCAGGAGACTGCTGCTGCTGGATGATGAGGCAGGCCCTCTGGAGGAGGAGC<br>TGCCCAGGCTGGCAGATGAGGGCCTGAACAGGAGGGTGGCTGAGGACCTGAACCTGGGCAACCTGAATGTGAG<br>CATCCCTTGGACCCACAAAGTGGGCAACTTCACAGGCCTGTACAGCACACTGTGCCTGTGTTCAACCCCCAC<br>TGGAAGACACCCCAGCTTCCCCAACATCCACCTGCACCAGGACATCATCAAGAAGTGTGAGCAGTTTGTGGGCC<br>CCCTGACAGTCAATGAGAAGAGGAGGCTCCAGCTGATCATGCCAGCCAGGTTCTACCCCAATGTGACCAAGTA<br>CCTCCCCCTGGACAAGGGCATCAAGCCTTACTATCCAGAGCACCTGGTGAACCACTACTTCCAGACCAGACAC<br>TACCTGCACACACTGTGAAGGCAGGCATCCTGTACAAGAGGGAGACCACACAGTGCCTCCTTCTGTGGCA<br>GCCCCTACTCCTGGGAGCAGGAGCTGCAACATGGATGCTGGTGGCTCCAGTTCAGGACAGCAAGCCCTGCTC<br>AGACTACTGCCTGAGCCACATTGTGAACCTGCTGGAGGACTGGGGCCCCTGTGCAGAGCATGGGGAGCACCAC<br>ATCAGAATCCCCAGGACCCCTGCCAGGGTGACAGGAGGGGTGTTCCTGGTGGACAAGAACCCCCACAACACTG<br>CAGAGTCCAGGCTGGTGGTGGACTTCTCCCAGTTCAGCAGGGGCAACTACAGAGTCTCCTGGCCAAAGTTTGC<br>TGTGCCCAACCTCCAGAGCCTGACAAACCTGCTGAGCAGCAACCTGTCCTGGCTCTCCCTGGATGTGAGTGCA<br>GCCTTCTATCACCTGCCCCTGCACCCAGCAGCCATGCCACACCTGCTGGTGGGCTCCAGTGGCCTGTCCAGGT<br>ATGTGGCCAGGCTCTCCTCCAACTCCAGGATCTTCAACTATCAGCATGGCACCATGCAGAACCTGCATGACAG<br>CTGCTCCAGGAACCTGTATGTGTCCCTGATGCTGCTCTATCAGACCTTTGGCAGGAAGCTGCACCTGTACAGC<br>CACCCCATCATCCTGGGGTTCAGGAAGATCCCCATGGGTGTGGGCCTGTCCCCCTTCCTGCTGGCCCAGTTCA<br>CCAGTGCCATCTGCTCAGTGGTGAGGAGGGCCTTCCCACACTGCCTGGCCTTCTCTTACATGCATGATGTGGT<br>CCTGGGTGCCAAGTCTGTGCAGCACCTGGAGAGCCTGTTCACAGCTGTGACAAACTTTCTCCTGAGCCTGGGC<br>ATCCACCTGAACCCCAACAAGACCAAGAGGTGGGGTTATTCACTGCACTTCATGGGCTATGTGATTGGCTGCT<br>ATGGCTCTCTGCCACAGGACCACATCATCCAGAAGATCAAGGAGTGCTTCAGAAAGCTGCCAGTGAACAGGCC<br>AATTGACTGGAAGGTGTGCCAGAGGATTGTGGGCCTGCTGGGCTTTGCAGCCCCCTTCACCCAGTGTGGCTAC<br>CCTGCCCTGATGCCCCTGTATGCCTGCATCCAGAGCAAGCAGGCCTTCACCTTTTCCCCACTTACAAGGCCT<br>TCCTGTGCAAGCAGTACCTGAACCTGTACCCTGTGGCCAGGCAGAGACCTGGGCTGTGCCAGGTGTTTGCAGA<br>TGCCACCCCCACAGGATGGGGACTGGTCATGGGACACCAGAGGATGAGGGGCACCTTCAAGGCACCCCTGCCC<br>ATCCACACAGCCCACCTGCTGGCTGCCTGCTTTGCCAGGAGCAGGAGTGGGGCCAACATCCTGGGCACAGACA<br>ACTCTGTGGTGCTGAGCAGGAAGTACACATCCTTCCCCTGGCTGCTGGGATGTGCAGCCAACTGGATCCTGAG<br>GGGCACCAGCTTTGTGTATGTGCCCTCTGCCCTCAACCCTGCAGATGATCCAAGCAGGGGCAGGCTGGGACTG<br>TACAGGCCACTGCTCAGACTGCCCTTCAGGCCCACCACTGGCAGGACCAGCCTGTATGCTGACTCCCCATCTG<br>TGCCCTCCCACCTGCCTGACAGAGTGCACTTTGCCTCCCCACTGCATGTGGCCTGGAGGCCCCCA |
| 32 | D | Pol$^{300}$ | ATGTCTGCCAGATCCCAGTCTGAGAGGCCAGTGTTCCCTTGCTGGTGGCTCCAGTTCAGGAACAGCAAGCCCT<br>GCTCAGACTACTGCCTGAGCCACATTGTGAACCTGCTGGAGGACTGGGGCCCCTGTGCAGAGCATGGGGAGCA<br>CCACATCAGAATCCCCAGGACCCCTGCCAGGGTGACAGGAGGGGTGTTCCTGGTGGACAAGAACCCCCACAAC<br>ACTGCAGAGTCCAGGCTGGTGGTGGACTTCTCCCAGTTCAGCAGGGGCAACTACAGAGTCTCCTGGCCAAAGT<br>TTGCTGTGCCCAACCTCCAGAGCCTGACAAACCTGCTGAGCAGCAACCTGTCCTGGCTCTCCCTGGATGTGAG<br>TGCAGCCTTCTATCACCTGCCCCTGCACCCAGCAGCCATGCCACACCTGCTGGTGGGCTCCAGTGGCCTGTCC<br>AGGTATGTGGCCAGGCTCTCCTCCAACTCCAGGATCTTCAACTATCAGCATGGCACCATGCAGAACCTGCATG<br>ACAGCTGCTCCAGGAACCTGTATGTGTCCCTGATGCTGCTCTATCAGACCTTTGGCAGGAAGCTGCACCTGTA<br>CAGCCACCCCATCATCCTGGGGTTCAGGAAGATCCCCATGGGTGTGGGCCTGTCCCCCTTCCTGCTGGCCCAG<br>TTCACCAGTGCCATCTGCTCAGTGGTGAGGAGGGCCTTCCCACACTGCCTGGCCTTCTCTTACATGCATGATG<br>TGGTCCTGGGTGCCAAGTCTGTGCAGCACCTGGAGAGCCTGTTCACAGCTGTGACAAACTTTCTCCTGAGCCT<br>GGGCATCCACCTGAACCCCAACAAGACCAAGAGGTGGGGTTATTCACTGCACTTCATGGGCTATGTGATTGGC<br>TGCTATGGCTCTCTGCCACAGGACCACATCATCCAGAAGATCAAGGAGTGCTTCAGAAAGCTGCCAGTGAACA<br>GGCCAATTGACTGGAAGGTGTGCCAGAGGATTGTGGGCCTGCTGGGCTTTGCAGCCCCCTTCACCCAGTGTGG<br>CTACCCTGCCCTGATGCCCCTGTATGCCTGCATCCAGAGCAAGCAGGCCTTCACCTTTTCCCCACTTACAAG<br>GCCTTCCTGTGCAAGCAGTACCTGAACCTGTACCCTGTGGCCAGGCAGAGACCTGGGCTGTGCCAGGTGTTTG<br>CAGATGCCACCCCCACAGGATGGGGACTGGTCATGGGACACCAGAGGATGAGGGGCACCTTCAAGGCACCCCT<br>GCCCATCCACACAGCCCACCTGCTGGCTGCCTGCTTTGCCAGGAGCAGGAGTGGGGCCAACATCCTGGGCACA<br>GACAACTCTGTGGTGCTGAGCAGGAAGTACACATCCTTCCCCTGGCTGCTGGGATGTGCAGCCAACTGGATCC<br>TGAGGGGCACCAGCTTTGTGTATGTGCCCTCTGCCCTCAACCCTGCAGATGATCCAAGCAGGGGCAGGCTGGG<br>ACTGTACAGGCCACTGCTCAGACTGCCCTTCAGGCCCACCACTGGCAGGACCAGCCTGTATGCTGACTCCCCA<br>TCTGTGCCCTCCCACCTGCCTGACAGAGTGCACTTTGCCTCCCCACTGCATGTGGCCTGGAGGCCCCCA |
| 33 | B/C | Core-sAg | ATGGACATTGACCCCTACAAGGAGTTTGGGGCCAGTGTGGAGCTGCTGTCTTTTCTGCCATCTGACTTCTTCC<br>CCAGTGTGAGGGACCTGCTGGACACTGCCTCAGCACTGTACAGAGAGGCCCTGGAGAGCCCAGAGCACTGCTC<br>CCCCCACCACACAGCCCTGAGGCAGGCCATCCTCTGCTGGGGGAGCTGATGAACCTGGCCACCTGGGTGGGC<br>TCCAACCTGGAGGACCCTGCCTCAAGGGAGCTGGTGGTCAGCTATGTCAATGTGAACATGGGCCTCAAGATCA<br>GGCAGCTGCTGTGGTTCCACATCTCCTGCCTGACCTTTGGCAGGGAGACAGTCCTGGAGTACCTGGTGAGCTT<br>TGGGGTGTGGATCAGGACCCCCCCTGCCTACAGGCCCCCCAATGCTCCCATCCTGTCCACCCTGCCAGAGACC<br>ACTGTGGTCAGGAGAAGGGGCAGGTCCCCAGGAGGAGAACCCCTCTCCCAGGAGGAGGAGAAGCCAGTCCC<br>CCAGGAGGAGGAGGAGCCAGAGCAGAGAGTCTCAGTGCATGGAGGCACCACATCAGGCTTCCTGGGCCCCT<br>GCTGGTGCTCCAGGCAGGCTTCTTTCTGCTGACCAGGATTCTGACCATCCCCCAGTCCCTGGACAGCTGGTGG<br>ACCTCCTGAATTTTCTGGGGGGGCCCCTACCTGTCCTGGCCAGAACTCTCAGTCTCCCACCTGAATCACT<br>CACCAACCAGCTGTCCCCCATCGTCCTGGCTACAGGTGGATGTGCCTGAGGAGATTCATCATCTTCCTGTG<br>CATCCTGCTGCTGTGCCTGATCTTTCTGCTGGTGCTGCTGGACTACCAGGGCATGCTGCCAGTGTGCCCTCTC<br>ATCCCAGGCAGCTCCACCACATCCACAGGACCTTGCAAGACATGCACCACACCAGCCCAGGGCACCAGCATGT |

TABLE M-continued

Polynucleotides encoding immunogenic polypeptides

| SEQ ID NO: | HBV genotype | name | Polynucleotide sequence |
|---|---|---|---|
| | | | TCCCCTCCTGCTGTTGCACCAAGCCAACAGATGGCAACTGCACATGCATTCCCATCCCCTCCAGCTGGGCCTTT TGCCAGGTTTCTGTGGGAGTGGGCCAGTGTGAGATTTTCCTGGCTGTCTCTTCTGGTGCCCTTTGTGCAGTGG TTTGTGGGCCTGTCCCCTACAGTGTGGCTGAGTGTCATCTGGATGATGTGGTACTGGGGCCCCTCCCTGTACA ACATCCTCTCTCCCTTTCTGCCTCTGCTGCCAATCTTCTTTTGCCTGTGGGTGTACATC |
| 34 | B/C | Core-P2A-sAg | ATGGACATTGACCCCTACAAGGAGTTTGGGGCCAGTGTGGAGCTGCTGTCTTTTCTGCCATCTGACTTCTTCC CCAGTGTGAGGGACCTGCTGGACACTGCCTCAGCACTGTACAGAGAGGCCCTGGAGAGCCCAGAGCACTGCTC CCCCCACCACACAGCCCTGAGGCAGGCCATCCTCTGCTGGGGGGAGCTGATGAACCTGGCCACCTGGGTGGGC TCCAACCTGGAGGACCCTGCCTCAAGGGAGCTGGTGGTCAGCTATGTCAATGTGAACATGGGCCTCAAGATCA GGCAGCTGCTGTGGTTCCACATCTCCTGCCTGACCTTTGGCAGGGAGACAGTCCTGGAGTACCTGGTGAGCTT TGGGGTGTGGATCAGGACCCCCCCTGCCTACAGGCCCCCCAATGCTCCCATCCTGTCCACCCTGCCAGAGACC ACTGTGGTCAGGAGAAGGGGCAGGTCCCCAGGAGGAGAACCCCCTCTCCCAGGAGGAGGAGAAGCCAGTCCC CCAGGAGGAGGAGGAGCCAGAGCAGAGAGTCTCAGTCGGCAGTGGGCAACCAACTTCAGCCTCCTGAAACA GGCAGGGGATGTGGAGGAAAACCCAGGCCCCGAGAGCACCACATCAGGCTTCCTGGGCCCCCTGCTGGTGCTC CAGGCAGGCTTCTTTCTGCTGACCAGGATTCTGACCATCCCCCAGTCCTGGACAGCTGGTGGACCTCCCTGA ATTTTCTGGGGGGGGCCCCTACCTGTCCTGGCCAGAACTCTCAGTCTCCCACCTCGAATCACTCACCAACCAG CTGTCCCCCATCTGTCCTGGCTACAGGTGGATGTGCCTGAGGAGATTCATCATCTTCCTGTGCATCCTGCTG CTGTGCCTGATCTTTCTGCTGGTGCTGCTGGACTACCAGGGCATGCTGCCAGTGTGCCCTCTCATCCCAGGCA GCTCCACCACAAGCACCTTGCAAGACATGCACCACACCTGCCAGGGCACCAGCATGTTCCCCTCCTG CTGTTGCACCAAGCCAACAGATGGCAACTGCACATGCATTCCCATCCCCTCCAGCTGGGCCTTTGCCAGGTTT CTGTGGGAGTGGGCCAGTGTGAGATTTTCCTGGCTGTCTCTTCTGGTGCCCTTTGTGCAGTGGTTTGTGGGCC TGTCCCCTACAGTGTGGCTGAGTGTCATCTGGATGATGTGGTACTGGGGCCCCTCCCTGTACAACATCCTCTC TCCCTTTCTGCCTCTGCTGCCAATCTTCTTTTGCCTGTGGGTGTACATC |
| 35 | D/D | Core-sAg | ATGGACATTGACCCCTACAAGGAGTTTGGGGCCAGTGTGGAGCTGCTCTCCTTCCTGCCCTCAGACTTCTTTC CCAGTGTGAGGGACCTGCTTGACACAGCCTCTGCCCTCTACAGAGAGGCCCTGGAGAGCCCAGAGCATTGCTC CCCCCACCACACAGCACTGAGGCAGGCCATCCTCTGTGGGGGGAGCTCATGAACCTGGCCACCTGGGTGGGT GTCAACCTGGAGGACCCAGCTTCCAGGGATCTGGTGGTCAGCTATGTGAACACAAACATGGGCCTCAAGTTCA GGCAGCTGCTCTGGTTCCACATCTCCTGCCTGACCTTTGGCAGGGAGACTGTGCTGGAGTACCTGGTGAGCTT TGGAGTGTGGATCAGGACCCCCACCTGCCTACAGGCCCCCCAATGCCCCCATCCTGTCCACCCTGCCTGAGACC ACAGTGGTGAGGAGGAGGGGGAGGTCCCCCAGAAGGAGGACCCCTTCTCCCAGGAGGAGGAGGAGTCAGTCTC CCAGGAGGAGGAGGAGCCAGAGCAGAGAGTCCCAGTGTATGGAGAACATCACCTCTGGCTTTCTGGGACCCCT GCTGGTGCTCCAGGCAGGCTTTTTCCTGCTGACCAGGATCCTGACCATCCCTCAGAGCCTGGACTCCTGGTGG ACATCTCTGAATTTTCTTGGGGGCACCACTGTGTGCCTGGGACAGAACTCCCAGTCTCCCACCTCCAACCACA GCCCAACATCCTGTCCCCCATCTGCCCAGGCTACAGGTGGATGTGCCTGAGGAGGTTCATCATCTTCCTGTT CATCCTGCTGCTGTGCCTGATCTTTCTGCTGGTGATCTGGATCTATCAGGGCATGCTGCCAGTGTGCCCACTG ATCCCAGGCAGCTCCACCACAAGCACAGGACCTTGCAGGACATGCACCACACCTGCCAGGGCACTTCCATGT ACCCATCTTGCTGTTGCACCAAGCCATCTGATGGCAATTGCACCTGCATCCCCATCCCCTCAAGCTGGGCCTT TGGCAAGTTCCTGTGGGAGTGGGCAAGTGCCAGATTCTCTTGGCTGAGCCTGCTGGTCCCTTTTGTGCAGTGG TTTGTGGGCCTGAGCCCCACTGTGTGGCTGTCTGTGATCTGGATGATGTGGTACTGGGGCCCCTCCCTGTATT CAATCCTGAGCCCTTTTCTGCCACTGCTGCCCATCTTCTTTTGTCTGTGGGTGTACATC |
| 36 | D/D | Core-P2A-sAg | ATGGACATTGACCCCTACAAGGAGTTTGGGGCCAGTGTGGAGCTGCTCTCCTTCCTGCCCTCAGACTTCTTTC CCAGTGTGAGGGACCTGCTTGACACAGCCTCTGCCCTCTACAGAGAGGCCCTGGAGAGCCCAGAGCATTGCTC CCCCCACCACACAGCACTGAGGCAGGCCATCCTCTGTGGGGGAGCTCATGAACCTGGCCACCTGGGTGGGT GTCAACCTGGAGGACCCAGCTTCCAGGGATCTGGTGGTCAGCTATGTGAACACAAACATGGGCCTCAAGTTCA GGCAGCTGCTCTGGTTCCACATCTCCTGCCTGACCTTTGGCAGGGAGACTGTGCTGGAGTACCTGGTGAGCTT TGGAGTGTGGATCAGGACCCCCACCTGCCTACAGGCCCCCAATGCCCCCATCCTGTCCACCCTGCCTGAGACC ACAGTGGTGAGGAGGAGGGGGAGGTCCCCCAGAAGGAGGACCCCTTCTCCCAGGAGGAGGAGGAGTCAGTCTC CCAGGAGGAGGAGGAGCCAGAGCAGAGAGTCCCAGTGTGGCAGTGGGCAACCAACTTCAGCCTCCTGAAACA GGCAGGGGATGTGGAGGAAAACCCAGGCCCCGAGAACATCACCTCTGGCTTTCTGGGACCCCTGCTGGTGCTC CAGGCAGGCTTTTTCCTGCTGACCAGGATCCTGACCATCCCTCAGAGCCTGGACTCCTGGTGGACATCTCTGA ATTTTCTTGGGGGCACCACTGTGTGCCTGGGACAGAACTCCCAGTCTCCCACCTCCAACCACAGCCCAACATC CTGTCCCCCATCTGCCCAGGCTACAGGTGGATGTGCCTGAGGAGGTTCATCATCTTCCTGTTCATCCTGCTG CTGTGCCTGATCTTTCTGCTGGTGCTCCTGGACTATCAGGGCATGCTGCCAGTGTGCCCACTGATCCCAGGCA GCTCCACCACAAGCACAGGACCTTGCAGGACATGCACCACACCTGCCAGGGCACTTCCATGTACCCATCTTG CTGTTGCACCAAGCCATCTGATGGCAATTGCACCTGCATCCCCATCCCCTCAAGCTGGGCCTTTGGCAAGTTC CTGTGGGAGTGGGCAAGTGCCAGATTCTCTTGGCTGAGCCTGCTGGTCCCTTTTGTGCAGTGGTTTGTGGGCC TGAGCCCCACTGTGTGGCTGTCTGTGATCTGGATGATGTGGTACTGGGGCCCCTCCCTGTATTCAATCCTGAG CCCTTTTCTGCCACTGCTGCCCATCTTCTTTTGTCTGTGGGTGTACATC |
| 37 | D/D | iCore-P2A-sAg | ATGGACATTGACCCCTACAAGGAGTTTGGGGCCAGTGTGGAGCTGCTGTCTTTTCTGCCATCTGACTTCTTCC CCAGTGTGAGGGACCTGCTGGACACTGCCTCAGCACTGTACAGAGAGGCCCTGGAGAGCCCAGAGCACTGCTC CCCCCACCACACAGCCCTGAGGCAGGCCATCCTCTGCTGGGGGAGCTGATGAACCTGGCCACCTGGGTGGGC GTCAACCTGGAGGACCTGCCTCAAGGGACCTGGTGGTCAGCTATGTCAATGTGAACATGGGCCTCAAGTTCA GGCAGCTGCTGTGGTTCCACATCTCCTGCCTGACCTTTGGCAGGGAGACAGTCCTGGAGTACCTGGTGAGCTT TGGGGTGTGGATCAGGACCCCCCTGCCTACAGGCCCCCAATGCTCCCATCCTGTCCACCCTGCCAGAGACC ACTGTGGTCAGGAGAAGGGGCAGGTCCCCAGGAGGAGAACCCCCTCTCCCAGGAGGAGGAGAAGCCAGTCCC CCAGGAGGAGGAGGAGCCAGAGCAGAGAGTCTCAGTCTGGCAGTGGGCAACCAACTTCAGCCTCCTGAAACA GGCAGGGGATGTGGAGGAAAACCCAGGCCCCGAGAACATCACATCAGGCTTCCTGGGCCCCCTGCTGGTGCTC CAGGCAGGCTTCTTTCTGCTGACCAGGATTCTGACCATCCCCCAGTCCTGGACAGCTGGTGGACCTCCCTGA ATTTTCTGGGGGGACCACTGTCTGTCTTGGCCAGAACTCTCAGTCTCCCACCTCGAATCACTCACCAACCAG CTGTCCCCCATCTGTCCTGGCTACAGGTGGATGTGCCTGAGGAGATTCATCATCTTCCTGTTCATCCTGCTG CTGTGCCTGATCTTTCTGCTGGTGCTGCTGGACTACCAGGGCATGCTGCCAGTGTGCCCTCTCATCCCAGGCA |

TABLE M-continued

Polynucleotides encoding immunogenic polypeptides

| SEQ ID NO: | HBV geno-type | name | Polynucleotide sequence |
|---|---|---|---|
| | | | GCTCCACCACATCCACAGGACCTTGCAGGACATGCACCACACCAGCCCAGGGCACCAGCATGTACCCCTCCTG CTGTTGCACCAAGCCATCAGATGGCAACTGCACATGCATTCCCATCCCCTCCAGCTGGGCCTTTGGCAAGTTT CTGTGGGAGTGGGCCAGTGCGAGATTTTCCTGGCTGTCTCTTCTGGTGCCCTTTGTGCAGTGGTTTGTGGGCC TGTCCCCTACAGTGTGGCTGAGTGTCATCTGGATGATGTGGTACTGGGGCCCCTCCCTGTACAGCATCCTCTC TCCCTTTCTGCCTCTGCTGCCAATCTTCTTTTGCCTGTGGGTGTACATC |

4. Vectors and Host Cells

Further provided are vectors comprising one or more polynucleotides encoding one or more of the immunogenic polypeptides, described herein, or an expression cassette comprising such polynucleotides. A vector can be of any type, for example, a recombinant vector such as an expression vector. Vectors include without limitation, plasmids, cosmids, bacterial artificial chromosomes (BAC) and yeast artificial chromosomes (YAC) and vectors derived from bacteriophages or plant or animal (including human) viruses. Vectors can comprise an origin of replication recognized by the proposed host cell and in the case of expression vectors, promoter and other regulatory regions recognized by the host cell. In additional embodiments, a vector comprises one or more polynucleotides encoding one or more immunogenic polypeptides of the disclosure operably linked to a promoter and optionally additional regulatory elements. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome. Vectors include without limitation, those suitable for recombinant production of the immunogenic polypeptides disclosed herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Some vectors are suitable for delivering the nucleic acid molecule or polynucleotide of the present application. Certain vectors are capable of directing the expression of nucleic acids to which they are operatively linked. Such vectors are referred to herein as expression vectors.

The term "operably linked" refers to two or more nucleic acid sequence or polypeptide sequence elements that are usually physically linked and are in a functional relationship with each other. For instance, in the context of nucleic acid sequence elements, a promoter is operably linked to a coding sequence if the promoter is able to initiate or regulate the transcription or expression of a coding sequence, in which case, the coding sequence should be understood as being "under the control of" the promoter.

The choice of the vector is dependent on the recombinant procedures followed and the host used. Introduction of vectors into host cells can be effected by inter alia calcium phosphate transfection, DEAE-dextran-mediated transfection, lipofectamine transfection, electroporation, virus infection, or via administration to a subject, as described herein. Vectors may be autonomously replicating or may replicate together with the chromosome into which they have been integrated. In certain embodiments, the vectors contain one or more selection markers. The choice of the markers may depend on the host cells of choice. These include without limitation, kanamycin, neomycin, puromycin, hygromycin, zeocin, thymidine kinase gene from Herpes simplex virus (HSV-TK), and dihydrofolate reductase gene from mouse (dhfr). Vectors comprising one or more nucleic acid molecules encoding the immunogenic polypeptides described herein, operably linked to one or more nucleic acid molecules encoding proteins or peptides that can be used to isolate the immunogenic polypeptides, are also covered by the disclosure. These proteins or peptides include without limitation, glutathione-S-transferase, maltose binding protein, metal-binding polyhistidine, green fluorescent protein, luciferase and beta-galactosidase.

In other embodiments, the vector that is used is pcDNA™3.1+(ThermoFisher, MA).

In some embodiments, the vector is viral vector. As appropriate, the viral vector can be a DNA virus or a RNA virus, including a self-replicating RNA virus. Self-replicating RNA viruses include Alphaviruses, and are described, e.g., in Lundstrom, *Molecules*. (2018) 23(12). pii: E3310 (PMID: 30551668); and Ljungberg, et al., *Expert Rev Vaccines*. (2015) 14(2):177-94). In various embodiments, the viral vector is from a virus selected from the group consisting of adenovirus, adeno-associated virus, arenavirus, alphavirus, self-replicating alphavirus, poxvirus, cytomegalovirus, rhabdovirus, vesicular stomatitis virus, flavivirus, maraba virus and vaccinia virus. In some embodiments, the viral vector is from a viral family selected from the group consisting of: Adenoviridae (e.g., Adenovirus, adeno-associated virus), Arenaviridae (e.g., lymphocytic choriomeningitis mammarenavirus, Cali mammarenavirus (a.k.a., Pichinde mammarenavirus (PICV)), Poxviridae (e.g., Vaccinia virus), Herpesviridae (e.g., Cytomegalovirus, Herpesvirus, e.g., HSV-1), Parvoviridae (e.g., Parvovirus H1), Poxviridae (e.g. Vaccinia virus, e.g. modified vaccinia Ankara (MVA)), Flaviviridae (e.g. Yellow fever virus), Reoviridae (e.g., Reovirus), Retroviridae (e.g., Lentivirus), Picornaviridae (e.g., Coxsackievirus, Seneca Valley Virus, Poliovirus), Paramyxoviridae (e.g., Measles virus, Newcastle disease virus (NDV)), Rhabdoviridae (e.g., Vesiculovirus, including Maraba vesiculovirus and Vesicular stomatitis virus (VSV)), Togaviridae (e.g., Alphavirus, e.g., self-replicating Alphavirus; Sindbis virus), Enteroviridae (e.g., Echovirus). Illustrative modified vaccinia viral vectors of use for expressing the present immunogenic polypeptides are described, e.g., in WO 2019/134049.

In some embodiments, the viral expression vector is an arenavirus vector selected from Lymphocytic choriomeningitis mammarenavirus (LCMV)(NCBI:txid11623), Cali mammarenavirus (a.k.a., Pichinde mammarenavirus or Pichinde arenavirus) (NCBI:txid2169993), Guanarito virus (GTOV) (NCBI:txid45219), Argentinian mammarenavirus (a.k.a., Junin virus (JUNV))(NCBI:txid2169991), Lassa virus (LASV)(NCBI:txid11620), Lujo virus (LUJV)(NCBI:txid649188), Machupo virus (MACV)(NCBI:txid11628), Brazilian mammarenavirus (a.k.a., Sabia virus (SABV)) (NCBI:txid2169992), and Whitewater Arroyo virus (WWAV)(NCBI:txid46919). In some embodiments, the viral expression vector is an arenavirus vector selected from Lymphocytic choriomeningitis mammarenavirus (LCMV) or Cali mammarenavirus (a.k.a., Pichinde mammarenavirus or Pichinde arenavirus (PICV)). Illustrative arenavirus vectors that can be used as delivery and expression vehicles for the herein described immunogenic polypeptides are described, e.g., in WO 2009/083210; WO 2015/183895; WO 2016/075250; WO 2017/198726; and U.S. Pat. Nos. 9,943,585 and 10,342,861, which are hereby incorporated herein by reference in their entireties for all purposes.

In some embodiments, the viral expression vector is an adenovirus vector, e.g., from a human adenovirus or a simian adenovirus (e.g., a chimpanzee adenovirus, a gorilla adenovirus or a rhesus monkey adenovirus). In various embodiments, the adenovirus vector is selected from adenovirus serotype 5 (Ad5), adenovirus serotype 26 (Ad26), adenovirus serotype 34 (Ad34), adenovirus serotype 35 (Ad35), adenovirus serotype 48 (Ad48), chimpanzee adenovirus (e.g. ChAdOx1, ChAdOx2, ChAd3 (AdC3), ChAd5 (AdC5), ChAd6 (AdC6), ChAd7 (AdC7), ChAd8 (AdC8), ChAd9 (AdC9), ChAd10 (AdC10), ChAd11 (AdC11), ChAd17 (AdC17), ChAd16 (AdC16), ChAd19 (AdC19), ChAd20 (AdC20), ChAd22 (AdC22), ChAd24 (AdC24), ChAdY25, ChAd26 (AdC26), ChAd28 (AdC28), ChAd30 (AdC30), ChAd31 (AdC31), ChAd37 (AdC37), ChAd38 (AdC38), ChAd43 (AdC43), ChAd44 (AdC44), ChAd55 (AdC55), ChAd63 (AdC63), ChAdV63, ChAd68 (AdC68), ChAd73 (AdC73), ChAd82 (AdC82), ChAd83 (AdC83), ChAd143 (AdC143), ChAd144 (AdC144), ChAd145 (AdC145), ChAd147 (AdC147)), gorilla adenovirus (e.g. GC44, GC45, GC46) and rhesus adenovirus (e.g., RhAd51, RhAd52, RhAd53, RhAd54, RhAd55, RhAd56, RhAd57, RhAd58, RhAd59, RhAd60, RhAd61, RhAd62, RhAd63, RhAd64, RhAd65, RhAd66). Illustrative Chimpanzee, Gorilla and Rhesus monkey adenovirus vectors that can be used as delivery and expression vehicles for the herein described immunogenic polypeptides are described, e.g., in WO2012/172277 (ChAdOx1), WO2017/221031 (ChAdOx2), WO2019/076880; WO2019/076877; Andrabi et al., (2019) *Cell Reports* 27:2426-2441 Guo, et al., *Hum Vaccin Immunother*. (2018) 14(7):1679-1685; Abbink, et al., *J Virol*. (2015) 89(3):1512-22; and Abbink et al., *J Virol*. (2018) 92(6). pii: e01924-17.

In various embodiments, the viral expression vector is incapable of replication (i.e., replication-defective or replication-deficient), has reduced or diminished capacity for replication, e.g., in comparison to a wild-type viral vector (i.e., replication-attenuated) or is replication competent. In various embodiments, the viral expression vector is a replication-defective or replication-deficient arenavirus vector having a bi-segmented genome, e.g., as described in WO 2009/083210 and WO 2017/076988. In various embodiments, the viral expression vector is a replication-attenuated arenavirus vector having a tri-segmented genome, e.g., as described in WO 2016/075250, WO 2017/076988 and WO 2017/198726.

Further provided are host cells comprising one or more polynucleotides encoding one or more of the immunogenic polypeptides or one or more vectors expressing the immunogenic polypeptides, as described herein. Any of a variety of host cells can be used. In one embodiment, a host cell is a prokaryotic cell, for example, *E. coli*. In another embodiment, a host cell is a eukaryotic cell, for example, a yeast cell, a plant cell, an insect cell, a mammalian cell, such as a Chinese Hamster Ovary (CHO)-based or CHO-origin cell line (e.g., CHO—S, CHO DG44, ExpiCHO™, CHOZN® ZFN-modified GS-/- CHO cell line, CHO-K1, CHO-K1a), COS cells, BHK cells, NSO cells or Bowes melanoma cells. Examples of human host cells are, inter alia, HeLa, 911, AT1080, A549 and HEK293 (e.g., HEK293E, HEK293F, HEK293H, HEK293T, Expi293™). In addition, the immunogenic polypeptides can be expressed in a yeast cell such as *Pichia* (see, e.g., Powers et al., *J Immunol Methods*. 251:123-35 (2001)), *Hanseula*, or *Saccharomyces*.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As appropriate, the host cells can be stably or transiently transfected with one or more polynucleotides encoding one or more immunogenic polypeptides, as described herein. As appropriate, the host cells can be infected with one or more vectors expressing one or more immunogenic polypeptides, as described herein. In some embodiments, the host cells are capable of being infected with and propagating one or more replication-attenuated or replication competent vectors expressing one or more immunogenic polypeptides, as described herein. Illustrative cells useful for infecting with and/or propagating viral vectors include without limitation BHK-21, A549, Vero and HEK293 (e.g., HEK293E, HEK293F, HEK293H, HEK293T, Expi293™) cells. In certain embodiments, the host cells express the Coxsackievirus and adenovirus receptor (CAR), e.g., MDCK, Caco-2 or Calu-3 host cells. In certain embodiments, the polynucleotides integrate into the genome of the host cell.

5. Pharmaceutical Compositions/Immunogenic Compositions

Provided are pharmaceutical compositions or immunogenic compositions comprising one or more of the immunogenic HBV polypeptides, as described herein, or a polynucleotide encoding one or more of the immunogenic HBV polypeptides, as described herein, or a viral expression vector comprising one or more of such polynucleotides, and a pharmaceutically acceptable diluent, carrier or excipient. "Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Generally, the pharmaceutical compositions described herein are immunogenic. In certain embodiments, the pharmaceutical composition comprises a therapeutically effective amount of the one or more (e.g., two or more, three or more) immunogenic HBV polypeptides, or one or more (e.g., two or more, three or more) polynucleotides encoding one or more (e.g., two or more, three or more) of the immunogenic HBV polypeptides, or one or more (e.g., two or more, three or more) viral expression vectors containing one or more (e.g., two or more, three or more) of the polynucleotides encoding one or more of the immunogenic HBV polypeptides.

Various pharmaceutically acceptable diluents, carriers, and excipients, and techniques for the preparation and use of pharmaceutical compositions will be known to those of skill in the art in light of the present disclosure. Illustrative pharmaceutical compositions and pharmaceutically acceptable diluents, carriers, and excipients are also described in, e.g., Loyd V. Allen Jr (Editor), "Remington: The Science and Practice of Pharmacy," 22$^{nd}$ Edition, 2012, Pharmaceutical Press; Brunton, Knollman and Hilal-Dandan, "Goodman and Gilman's The Pharmacological Basis of Therapeutics," 13th Edition, 2017, McGraw-Hill Education/Medical; McNally and Hastedt (Editors), "Protein Formulation and Delivery, 2nd Edition, 2007, CRC Press; Banga, "Therapeutic Peptides and Proteins: Formulation, Processing, and Delivery Systems," 3rd Edition, 2015, CRC Press; Lars Hovgaard, Frokjaer and van de Weert (Editors), "Pharmaceutical Formulation Development of Peptides and Proteins," 2nd Edition, 2012, CRC Press; Carpenter and Manning (Editors), "Rational Design of Stable Protein Formulations: Theory and Practice," 2002, Springer (Pharmaceutical Biotechnology (Book 13)); Meyer (Editor), "Therapeutic Protein Drug Products: Practical Approaches to Formulation in the Laboratory, Manufacturing, and the Clinic, 2012, Woodhead Publishing.

In certain embodiments, the polynucleotides or vectors are formulated into lipid nanoparticles. For example, in some embodiments where the immunogenic HBV polypeptides are expressed from self-replicating or self-amplifying RNA molecules, the self-replicating or self-amplifying RNA can be formulated into lipid nanoparticles (LNPs). As used herein, the term "lipid nanoparticle" refers to one or more spherical nanoparticles with an average diameter of between about 10 to about 1000 nanometers, and which comprise a solid lipid core matrix that can solubilize lipophilic molecules. In certain embodiments, the lipid core is stabilized by surfactants (e.g., emulsifiers), and can comprise one or more of triglycerides (e.g., tristearin), diglycerides (e.g., glycerol bahenate), monoglycerides (e.g., glycerol monostearate), fatty acids (e.g., stearic acid), steroids (e.g., cholesterol), and waxes (e.g., cetyl palmitate), including combinations thereof. Lipid nanoparticles are described, for example, in Petrilli et al., Curr Pharm Biotechnol. 15:847-55, 2014; and U.S. Pat. Nos. 6,217,912; 6,881,421; 7,402,573; 7,404,969; 7,550,441; 7,727,969; 8,003,621; 8,691,750; 8,871,509; 9,017,726; 9,173,853; 9,220,779; 9,227,917; and 9,278,130, each of which is incorporated by reference in its entirety. In one embodiment, a self-replicating or self-amplifying RNA molecule encoding one or more of the immunogenic HBV polypeptides described herein is formulated or condensed into polyethylenimine (PEI)-polyplex delivery vehicles, e.g., as described in Demoulins, et al., *Nanomedicine.* (2016) April; 12(3):711-722 and Demoulins, et al., *J Control Release.* (2017) Nov. 28; 266:256-271, which can be nanoparticulate.

In embodiments where the immunogenic HBV polypeptides are expressed from a viral expression vector, the viral expression vector can be formulated for the desired route of administration, e.g., as an isotonic pharmaceutically acceptable aqueous solution or suspension suitable for intravenous, intramuscular, subcutaneous or intradermal administration. In some embodiments, the viral expression vector can be formulated for mucosal, e.g., buccal, intranasal, intravaginal or intra-rectal delivery. Illustrative formulations for viral expression vectors that can be used in the herein described pharmaceutical compositions and methods are described, e.g., in Manfredsson and Benskey, editors, "Viral Vectors for Gene Therapy: Methods and Protocols (Methods in Molecular Biology)," 2019, Book 1937 in Methods in Molecular Biology Series, Humana Press; WO 2017/013169 (formulation of Adenoviral vectors in an aqueous mixture or freeze dried composition in the presence of amorphous sugar and low salt concentration); and Kumru, et al., *J Pharm Sci.* (2018) November; 107(11):2764-2774 (aqueous formulations buffered in Tris and containing proline, lactose, and mannitol as stabilizing additives). Formulation of arenavirus vectors is described, e.g., in WO 2009/083210; WO 2016075250 and WO 2017/198726. In certain embodiments, the viral expression vectors are delivered via microneedle-mediated delivery, e.g., as described in Zaric, et al., *Expert Opin Drug Deliv.* (2017) October; 14(10): 1177-1187.

In some embodiments, each carrier, diluent or excipient is "acceptable" in the sense of being compatible with the other ingredients of the pharmaceutical composition and not injurious to the subject. Often, the pharmaceutically acceptable carrier is an aqueous pH-buffered solution. Some examples of materials which can serve as pharmaceutically-acceptable carriers, diluents or excipients include: water; buffers, e.g., a buffer having a pKa in the range of about 6.0 to about 8.0, e.g., a physiologically acceptable buffer, e.g., selected from phosphate, carbonate, bicarbonate, citrate, maleate, glycine-glycine, HEPES, HEPPSO, HEPPS, imidazole, BICINE, TRICINE, Tris, and BIS-Tris; sugars, such as lactose, trehalose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Hank's solution, Ringer's solution; ethyl alcohol; phosphate buffer solutions; amino acids (e.g., charged amino acids, including without limitation, aspartate, asparagine, glutamate, glutamine, histidine, arginine, lysine); and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

In one particular formulation, an arenavirus vector (e.g., a LCMV or Pichinde mammarenavirus vector (PICV)) described herein is formulated in an isotonic aqueous solution comprising a biologically compatible buffer having a pKa in the range of about 6.0 to about 8.0 (e.g., HEPES and NaCl), at a neutral or near-neutral pH and a non-ionic surfactant (e.g., PLURONIC® F68 (a.k.a., poloxamer 188)). In one particular formulation, an arenavirus vector (e.g., a LCMV or Pichinde mammarenavirus vector) described herein is formulated in an isotonic aqueous solution comprising HEPES buffer at pH 7.4, NaCl, and PLURONIC® F68 (a.k.a., poloxamer 188). Schleiss, et al. (*Clin Vaccine Immunol.* 2017 Jan. 5; 24 (1):e00300-16) describes an LCMV formulating LCMV vectors in a diluent of 25 mM HEPES, 150 mM NaCl, 0.01% PLURONIC® F68; pH 7.4), which can be used to formulate the herein described arenavirus vectors. A final concentration of 10% sorbitol was added before freezing below −60° C.

The formulation of and delivery methods of pharmaceutical compositions will generally be adapted according to the site and the disease to be treated. Exemplary formulations include without limitation, those suitable for parenteral administration, e.g., intravenous, intra-arterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. In some embodiments, the pharmaceutical compositions are formulated for parenteral, e.g., intravenous, subcutaneous, or oral administration. In some embodiments, the pharmaceutical compositions are formulated for mucosal, e.g., buccal, intranasal, intrarectal and/or intravaginal administration.

In certain embodiments, pharmaceutical compositions are sterile. In certain embodiments, the pharmaceutical composition has a pH in the range of 4.5 to 8.5, 4.5 to 6.5, 6.5 to 8.5, 6.0 to 8.0, 6.5 to 8.5, or a pH of about 5.0, about 5.5, about 6.0, about 6.5, about 6.6, about 6.7, about 6.8, about 6.9, about 7.0, about 7.1, about 7.2, about 7.3, about 7.5, about 8.0 or about 8.5. In one embodiment, the pharmaceutical composition has an osmolarity in the range of 240-260 or 250-330 mOsmol/L. In certain embodiments, the pharmaceutical composition is isotonic or near isotonic.

In some embodiments, the pharmaceutical compositions are liquids or solids. In some embodiments, the pharmaceutical composition comprises an aqueous solution or suspension. In some embodiments, the pharmaceutical composition is lyophilized or is a frozen liquid.

In some embodiments, the pharmaceutical composition further comprises one or more additional therapeutic agents, e.g., a second therapeutic agent, or second and third therapeutic agents, for use in combination therapies, as described herein.

In certain embodiments, the pharmaceutical composition further comprises an adjuvant. Illustrative adjuvants that can be co-formulated or co-administered with the herein described immunogenic HBV polypeptides, polynucleotides encoding such immunogenic HBV polypeptides and vectors expressing such immunogenic HBV polypeptides include without limitation cytokines, chemokines, immune co-stimulatory molecules, toll-like receptor agonists or inhibitors of immune suppressive pathways, as described herein, and in Li, et al., *Curr Issues Mol Biol.* (2017) 22:17-40. Other adjuvants that can be co-formulated or co-administered with the herein described immunogenic HBV polypeptides, polynucleotides encoding such immunogenic HBV polypeptides and vectors expressing such immunogenic HBV polypeptides include without limitation mineral salts (e.g., aluminum salts (e.g., alum), calcium phosphate, incomplete Freunds's adjuvant), lipid particles (e.g., MF59, cochleates, virus-like particles), microparticles (e.g., virosomes, polylactic acid (PLA), poly[lactide-coglycolide] (PLG)), immune potentiators (e.g., dsRNA:Poly(I:C), Poly-IC:LC, Monophosphoryl lipid A (MPL), LPS, Flagellin, Imidazoquinolines: imiquimod (R837), resiquimod (848), CpG oligodeoxynucleotides (ODN), Muramyl dipeptide (MDP), Saponins (QS-21)), and mucosal adjuvants (e.g., Cholera toxin (CT), Heat-labile enterotoxin (LTK3 and LTR72), Chitosan). Adjuvants that can be co-formulated or co-administered with the herein described immunogenic HBV polypeptides, polynucleotides encoding such immunogenic HBV polypeptides and vectors expressing such immunogenic HBV polypeptides are summarized in Apostólico, et al., *J Immunol Res.* (2016) 2016:1459394.

In some embodiments, the pharmaceutical compositions or immunogenic compositions comprise mixtures of two or more immunogenic HBV polypeptides, two or more polynucleotides encoding such immunogenic HBV polypeptides, or two or more vectors expressing such immunogenic HBV polypeptides. In some embodiments, the pharmaceutical composition comprises two or more immunogenic HBV polypeptides, two or more polynucleotides encoding such immunogenic HBV polypeptides, or two or more vectors expressing such immunogenic HBV polypeptides.

In various embodiments, the immunogenic composition comprises one or more polynucleotides encoding, or one or more vectors capable of expressing, two immunogenic polypeptides, the immunogenic polypeptides comprising: (a) an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41.

In various embodiments, the immunogenic composition comprises one or more polynucleotides encoding, or one or more vectors capable of expressing, two immunogenic polypeptides, the immunogenic polypeptides comprising: (a) an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41.

In various embodiments, the immunogenic composition comprises one or more polynucleotides encoding, or one or more vectors capable of expressing, two immunogenic polypeptides, the immunogenic polypeptides comprising: (a) an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) an HBV core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41.

With respect to the core-sAg fusion polypeptide in the immunogenic composition, in some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41.

In some embodiments, the immunogenic composition comprises a first viral expression vector and a second viral expression vector, wherein: (a) the first viral expression vector comprises a polynucleotide comprising or consisting of a nucleic acid sequence of any one of SEQ ID NOs: 27-32 and 89-94, e.g., SEQ ID NOs: 29, 89, 90 and 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94, e.g., SEQ ID NOs: 29, 89, 90 and 92; and (b) the second viral expression vector comprises a polynucleotide comprising or consisting of a nucleic acid sequence of any one of SEQ ID NOs: 33-37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37.

In some embodiments, the immunogenic composition comprises a first viral expression vector and a second viral expression vector, wherein: (a) the first viral expression vector comprises a polynucleotide comprising or consisting of a nucleic acid sequence of SEQ ID NO: 29 or 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 29, 89, 90 or 92; and (b) the second viral expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 37.

In some embodiments, the immunogenic composition comprises a first LCMV arenavirus expression vector and a second LCMV arenavirus expression vector, wherein: (a) the first LCMV arenavirus expression vector comprises a polynucleotide comprising or consisting of a nucleic acid sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 37.

In some embodiments, the immunogenic composition comprises a first Pichinde arenavirus expression vector and a second Pichinde arenavirus expression vector, wherein: (a) the first Pichinde arenavirus expression vector comprises a polynucleotide comprising or consisting of a nucleic acid sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37 or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NO: 37.

As appropriate or desired, the HBV polymerase polypeptide mutant and the HBV core-sAg fusion protein can be provided in the immunogenic composition in a ratio in the range of from 1:10 to 10:1, e.g., in the range of 1:9 to 9:1, 1:8 to 8:1, 1:7 to 7:1, 1:6 to 6:1, 1:5 to 5:1, 1:4 to 4:1, 1:3 to 3:1, 1:2 to 2:1 or 1:1. In various embodiments, ratios can be measured be measured in units of plaque forming units (PFU), focus forming units (FFU), infectious units (IU), or viral particles (vp).

In various embodiments, the one or more polynucleotides are DNA, cDNA, mRNA, or self-replicating RNA.

In some embodiments, the immunogenic composition comprises a first viral expression vector and a second viral expression vector, wherein: (a) the first viral expression vector comprises a polynucleotide encoding a truncated HBV polymerase polypeptide or an HBV polymerase deletion mutant polypeptide, as described herein; and (b) the second viral expression vector comprises a polynucleotide encoding the core-sAg fusion protein, as described herein. As appropriate or desired, the first viral expression vector and the second viral expression vector can be provided in a ratio in the range of from 1:10 to 10:1, e.g., in the range of 1:9 to 9:1, 1:8 to 8:1, 1:7 to 7:1, 1:6 to 6:1, 1:5 to 5:1, 1:4 to 4:1, 1:3 to 3:1, 1:2 to 2:1 or 1:1.

In some embodiments, the immunogenic composition comprise in the range of about $10^3$ to about $10^{12}$ viral focus forming units (FFU) or plaque forming units (PFU) or infectious units (IU) or viral particles (vp), e.g. from about $10^4$ to about $10^7$ viral FFU or PFU, e.g. from about $10^3$ to about $10^4$, $10^5$, $10^6$, $10^7$, $10^8$, $10^9$, $10^{10}$, $10^{11}$ or $10^{12}$ viral FFU or PFU or IU or vp per milliliter, of each of the first viral expression vector and the second viral expression vector.

In various embodiments, the first viral expression vector and the second viral expression vector in the immunogenic composition independently are from a taxonomic family selected from Adenoviridae, Arenaviridae, Herpesviridae (e.g. Cytomegalovirus), Poxviridae (e.g. Vaccinia virus, e.g. modified vaccinia Ankara (MVA)), Flaviviridae (e.g. Yellow fever virus), Rhabdoviridae (e.g. Vesiculovirus, e.g. Maraba vesiculovirus), Togaviridae (e.g., Alphavirus). In various embodiments, the first viral expression vector and the second viral expression vector can be from the same taxonomic family or from different taxonomic families. For example, in some embodiments, both the first viral expression vector and the second viral expression vector in the immunogenic composition are from Adenoviridae, Arenaviridae, or Poxviridae (e.g. Vaccinia virus, e.g. modified vaccinia Ankara (MVA)).

In some embodiments, the first viral expression vector and the second viral expression vector in the immunogenic composition are from Arenaviridae. In some embodiments, the first viral expression vector and the second viral expression vector are from an arenavirus vector selected from Lymphocytic choriomeningitis mammarenavirus (LCMV), Cali mammarenavirus (a.k.a., Pichinde mammarenavirus or Pichinde arenavirus (PICV)), Guanarito virus (GTOV), Junin virus (JUNV), Lassa virus (LASV), Lujo virus (LUJV), Machupo virus (MACV), Sabia virus (SABV), and Whitewater Arroyo virus (WWAV). In some embodiments, the first viral expression vector and the second viral expression vector are from an arenavirus vector selected from Lymphocytic choriomeningitis mammarenavirus (LCMV) or Cali mammarenavirus (a.k.a., Pichinde mammarenavirus or Pichinde arenavirus (PICV)).

In various embodiments, the first viral expression vector and the second viral expression vector in the immunogenic composition are replication-defective or replication-deficient. In some embodiments, the first viral expression vector and the second viral expression vector in the immunogenic composition are replication-attenuated.

6. Methods of Treatment

Further provided are methods for eliciting an immune response to human hepatitis B virus (HBV) in a subject in need thereof. Also provided are methods of treating or preventing human hepatitis B virus (HBV) in a subject in need thereof. Also provided are methods of inhibiting HBV replication in an infected individual. Further provided are methods for reducing the viral load associated with HBV infection. In various embodiments, the methods comprise administering to the subject an effective amount of an immunogenic composition, as described herein. In various embodiments, the "subject" or the "individual" is a human, a woodchuck, a Peking duck, a mouse or a non-human primate (e.g., a chimpanzee).

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom, delaying of progression and/or preventing a worsening of a symptom associated with a disease or condition. "Treatment" or "treating" can include one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Delaying" as used herein refers to development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

"Prevent" or "prevention" or "preventing" as used herein refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, in certain embodiments, the term "preventing HBV infection" refers to administering to a subject who does not have a detectable HBV infection an anti-HBV therapeutic substance. It is understood that the subject for anti-HBV preventative therapy may be an individual at risk of contracting the HBV virus. It is also understood that prevention does not require a 100% success rate. In some instances, prevention may be understood as a reduction of the risk of infection, but not a complete elimination the occurrence of an infection.

"Therapeutically effective amount" or "effective amount" as used herein refers to an amount that is effective to elicit the desired biological or medical response, including the amount of an immunogenic composition that, when administered to a subject for treating a disease, is sufficient to effect such treatment for the disease. The effective amount will vary depending on the immunogenic composition, the disease, and its severity and the age, weight, etc., of the subject to be treated. The effective amount can include a range of amounts. An effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

In various embodiments, the administered immunogenic composition comprises a mixture comprising a first viral expression vector and a second viral expression vector, wherein: (a) the first viral expression vector comprises a polynucleotide encoding the truncated HBV polymerase polypeptide, as described herein, or the HBV polymerase deletion mutant polypeptide as described herein; and (b) the second viral expression vector comprises a polynucleotide encoding the core-sAg fusion protein, as described herein.

In various embodiments, the administered immunogenic composition comprises a mixture comprising a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. Such an immunogenic composition can be administered in a priming composition and/or in a boosting composition.

In various embodiments, the administered immunogenic composition comprises a first viral expression vector and a second viral expression vector, wherein: (a) the first viral expression vector comprises a polynucleotide encoding an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) the second viral expression vector comprises a polynucleotide encoding the core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41. Such an immunogenic composition can be administered in a priming composition and/or in a boosting composition.

With respect to the core-sAg fusion polypeptide in the administered immunogenic composition, in some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41.

In various embodiments, the administered immunogenic composition comprises a mixture comprising a first viral expression vector and a second viral expression vector, wherein: (a) the first viral expression vector comprises a polynucleotide encoding an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) the second viral expression vector comprises a polynucleotide encoding the core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41. Such an immunogenic composition can be administered in a priming composition and/or in a boosting composition.

In various embodiments, the administered immunogenic composition comprises a mixture comprising a first viral expression vector and a second viral expression vector, wherein: (a) the first viral expression vector comprises a polynucleotide comprising or consisting of a nucleic sequence of any one of SEQ ID NOs: 27-32 and 89-94, e.g., SEQ ID NOs: 29, 89, 90 and 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94, e.g., SEQ ID NOs: 29, 89, 90 and 92; and (b) the second viral expression vector comprises a polynucleotide comprising or consisting of a nucleic acid sequence of any one of SEQ ID NOs: 33-37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37. Such an immunogenic composition can be administered in a priming composition and/or in a boosting composition.

In various embodiments, the administered immunogenic composition comprises a mixture comprising a first viral expression vector and a second viral expression vector, wherein: (a) the first viral expression vector comprises a polynucleotide comprising or consisting of a nucleic sequence of SEQ ID NOs: 29, 89, 90 or 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 29, 89, 90 or 92; and (b) the second viral expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. Such an immunogenic composition can be administered in a priming composition and/or in a boosting composition.

In various embodiments, the first viral expression vector and the second viral expression vector in the administered immunogenic composition independently are from a taxonomic family selected from Adenoviridae, Arenaviridae, Herpesviridae (e.g. Cytomegalovirus), Poxviridae (e.g. Vaccinia virus, e.g. modified vaccinia Ankara (MVA)), Flaviviridae (e.g. Yellow fever virus), Rhabdoviridae (e.g. Vesiculovirus, e.g. Maraba vesiculovirus), Togaviridae (e.g., Alphavirus), as described above and herein. In various embodiments, the first viral expression vector and the second viral expression vector can be from the same taxonomic family or from different taxonomic families. For example, in some embodiments, both the first viral expression vector and the second viral expression vector in the administered immunogenic composition are from Adenoviridae, Arenaviridae, or Poxviridae (e.g. Vaccinia virus, e.g. modified vaccinia Ankara (MVA)).

In some embodiments, the first viral expression vector and the second viral expression vector are from Arenaviridae. In some embodiments, the first viral expression vector and the second viral expression vector in the administered immunogenic composition are from an arenavirus vector selected from Lymphocytic choriomeningitis mammarenavirus (LCMV), Cali mammarenavirus (a.k.a., Pichinde mammarenavirus or Pichinde arenavirus (PICV)), Guanarito virus (GTOV), Junin virus (JUNV), Lassa virus (LASV), Lujo virus (LUJV), Machupo virus (MACV), Sabia virus (SABV), and Whitewater Arroyo virus (WWAV). In some embodiments, the first viral expression vector and the second viral expression vector in the administered immunogenic composition are from an arenavirus vector selected from Lymphocytic choriomeningitis mammarenavirus (LCMV) or Cali mammarenavirus (a.k.a., Pichinde mammarenavirus or Pichinde arenavirus (PICV)).

In various embodiments, the first viral expression vector and the second viral expression vector in the administered immunogenic composition are replication-defective or replication-deficient. In some embodiments, the first viral expression vector and the second viral expression vector in the administered immunogenic composition are replication-attenuated.

In various embodiments, the administered immunogenic composition comprises a mixture comprising a first LCMV arenavirus expression vector and a second LCMV arenavirus expression vector, wherein: (a) the first LCMV arenavirus expression vector comprises a polynucleotide comprising or consisting of a nucleic sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. Such an immunogenic composition can be administered in a priming composition and/or in a boosting composition.

In various embodiments, the administered immunogenic composition comprises a mixture comprising a first Pichinde arenavirus expression vector and a second Pichinde arenavirus expression vector, wherein: (a) the first Pichinde arenavirus expression vector comprises a polynucleotide comprising or consisting of a nucleic sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37. Such an immunogenic composition can be administered in a priming composition and/or in a boosting composition.

In various embodiments, the subject is infected with HBV, is suspected of being infected with HBV, or is at risk of being infected with HBV. "At risk individual" as used herein refers to an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). In various embodiments, the subject is chronically infected with HBV, e.g., infected with HBV for longer than 6 months. Typically, the individual is suffering from a chronic hepatitis B infection, although it is within the scope of the present disclosure to treat people who are acutely infected with HBV. Accordingly, in some embodiments, the subject is acutely infected with HBV. In some embodiments, the subject is co-infected with hepatitis D virus (HDV).

In various embodiments, the subject may be asymptomatic. In some embodiments, the subject is experiencing or exhibiting symptoms associated with HBV infection. Symptoms of HBV can include, e.g., jaundice, visible webs of swollen blood vessels in the skin, dark-colored (e.g., orange or brown) urine, light-colored feces, fever, persistent fatigue, malaise, abdominal pain, abdominal fluid, loss of appetite, nausea, and vomiting. Chronic infection with HBV can lead to one or more symptoms including, e.g., hepatic failure, hepatic cancer, hepatic fibrosis and hepatic cirrhosis. One or more administrations of the immunogenic polypeptides, polynucleotides encoding such polypeptides, vectors, LNPs and immunogenic compositions comprising such polypeptides or polynucleotides, as described herein, can prevent, delay, alleviate, mitigate, inhibit, reverse or eliminate one or more symptoms associated with or caused by HBV infection.

In some embodiments, the immunogenic composition is administered via a route selected from intravenous, intramuscular, intradermal, subcutaneous and mucosal (e.g. buccal, intranasal, intrarectal, intravaginal).

In some embodiments, the administered dose of the immunogenic composition comprises in the range of about $10^3$ to about $10^{12}$ viral focus forming units (FFU) or plaque forming units (PFU) or infectious units (IU) or viral particles (vp), e.g., from about $10^4$ to about $10^7$ viral FFU or PFU, e.g., from about $10^3$ to about $10^4$, $10^5$, $10^6$, $10^7$, $10^8$, $10^9$, $10^{10}$, $10^{11}$ or $10^{12}$ viral FFU or PFU or IU or vp per milliliter, of each of the first viral expression vector and the second viral expression vector. In some embodiments, the methods entail administering intravenously or intramuscularly from about $10^6$ to about $10^8$ viral FFU or PFU or IU or vp per administration every other week (Q2W) or monthly (Q4W).

In various embodiments, the methods comprise a prime-boost regimen. In some embodiments, the prime-boost regimen entails administering a priming composition at a first time point and administering one or more boosting compositions at one or more subsequent time points. As appropriate, the methods can entail repeating the prime-boost regimen one or more iterations. In various embodiments, the administrations of the priming composition and the one or more boosting compositions are spaced at least 1 week and up to at least 2 weeks, 3 weeks, 1 month, 2 months, 3 months, 4 months, 5 months or 6 months apart. As appropriate, the dosage or dosing frequency of the immunogenic composition may be adjusted over the course of the treatment, based on the judgment of the administering physician. As appropriate, a subject can be treated with multiple administrations over a time period of at least about 2 weeks to 3 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, or longer, or until sAg is no longer detectable in the serum or plasma of the subject.

In some embodiments, after one or more administrations of the one or more immunogenic polypeptides, as described herein, or one or more polynucleotides encoding one or more immunogenic polypeptides, as described herein, or one or more vectors expressing one or more immunogenic polypeptides, as described herein, optionally with one or more additional therapeutic agents, described herein, the subject does not exhibit symptoms of HBV in the absence of antiviral treatment for at least 6 months, at least 1 year, at least 2 years, at least 3 years, or more. In some embodiments, after one or more administrations of the one or more immunogenic polypeptides, as described herein, or one or more polynucleotides encoding one or more immunogenic polypeptides, as described herein, or one or more vectors expressing one or more immunogenic polypeptides, as described herein, optionally with one or more additional therapeutic agents, described herein, sAg is no longer detectable in the serum or plasma of the subject, in the absence of antiviral treatment for at least 6 months, e.g., at least 1 year, at least 2 years, at least 3 years, or more.

As appropriate or desired, the priming composition and the boosting composition can comprise the same immunogenic composition or different immunogenic compositions. In various embodiments, the priming composition and the boosting composition comprise the same one or more polypeptides and same expression vector (e.g., viral expression vector). In some embodiments, the priming composition and the boosting composition comprise different polypeptides and/or different expression vectors (e.g., viral expression vectors). For example, in some embodiments, the priming composition and the boosting composition comprise the same one or more polypeptides and different expression vectors (e.g., viral vectors from different virus species within a taxonomic family, viral vectors from different taxonomic families, viral vectors with different replication competencies). In some embodiments, the priming composition and the boosting composition comprise different immunogenic polypeptides and the same expression vector (e.g., viral expression vector).

In some embodiments, the methods comprise priming with a priming composition comprising one or more viral expression vectors, and boosting with a boosting composition comprising one or more viral expression vectors. In some embodiments, the prime-boost regimen comprises:

a) Priming with a priming composition comprising one or more viral expression vectors and boosting with a boosting composition comprising one or more polynucleotides, wherein the one or more polynucleotides comprise DNA, cDNA, mRNA or self-replicating RNA;

b) Priming with a priming composition comprising one or more polynucleotides, wherein the one or more polynucleotides comprise DNA, cDNA, mRNA or self-replicating RNA, and boosting with a boosting composition comprising one or more viral expression vectors;

c) Priming with a priming composition comprising one or more viral expression vectors, and boosting with a boosting composition comprising one or more viral expression vectors, wherein the one or more viral expression vectors in the priming composition and the one or more viral expression vectors in the boosting composition are from identical, related or unrelated taxonomical families;

d) Priming with a priming composition comprising one or more replication-deficient viral expression vectors and boosting with a boosting composition comprising one or more replication-deficient viral expression vectors, wherein the one or more replication-deficient viral expression vectors in the priming composition and the one or more replication-deficient viral expression vectors in the boosting composition are from identical, related or unrelated taxonomical families;

e) Priming with a priming composition comprising one or more replication-attenuated viral expression vectors and boosting with a boosting composition comprising one or more replication-attenuated viral expression vectors, wherein the one or more replication-attenuated viral expression vectors in the priming composition and the one or more replication-attenuated viral expression vectors in the boosting composition are from identical, related or unrelated taxonomical families; Priming with a priming composition comprising one or more replication-deficient viral expression vectors and boosting with a boosting composition comprising one or more replication-attenuated viral expression vectors;

g) Priming with a priming composition comprising one or more replication-attenuated viral expression vectors and boosting with a boosting composition comprising one or more replication-deficient viral expression vectors;

h) Priming with a priming composition comprising one or more Lymphocytic choriomeningitis mammarenavirus (LCMV) viral expression vectors and boosting with a boosting composition comprising one or more Pichinde mammarenavirus (PICV) viral expression vectors;

i) Priming with a priming composition comprising one or more Pichinde mammarenavirus (PICV) viral expression vectors and boosting with a boosting composition comprising one or more Lymphocytic choriomeningitis mammarenavirus (LCMV) viral expression vectors;

j) Priming with a priming composition comprising one or more replication deficient Pichinde mammarenavirus (PICV) viral expression vectors and boosting with a boosting composition comprising one or more replication deficient Lymphocytic choriomeningitis mammarenavirus (LCMV) viral expression vectors;

k) Priming with a priming composition comprising one or more replication deficient Lymphocytic choriomeningitis mammarenavirus (LCMV) viral expression vectors and boosting with a boosting composition comprising one or more replication deficient Pichinde mammarenavirus (PICV) viral expression vectors;

l) Priming with a priming composition comprising one or more arenavirus viral expression vectors and boosting with a boosting composition comprising one or more adenovirus viral expression vectors;

m) Priming with a priming composition comprising one or more adenovirus viral expression vectors and boosting with boosting composition comprising one or more arenavirus viral expression vectors;

n) Priming with a priming composition comprising one or more poxvirus viral expression vectors and boosting with a boosting composition comprising one or more arenavirus viral expression vectors;

o) Priming with a priming composition comprising one or more arenavirus viral expression vectors and boosting with boosting composition comprising one or more poxvirus viral expression vectors; Priming with a priming composition comprising one or more poxvirus viral expression vectors and boosting with a boosting composition comprising one or more adenovirus viral expression vectors; or q) Priming with a priming composition comprising one or more adenovirus viral expression vectors and boosting with boosting composition comprising one or more poxvirus viral expression vectors.

In some embodiments, the methods comprise priming with a priming composition comprising one or more viral expression vectors, and boosting with a boosting composition comprising one or more viral expression vectors. In some embodiments, the prime-boost regimen comprises:

a) Priming with a priming composition comprising one or more Lymphocytic choriomeningitis mammarenavirus (LCMV) viral expression vectors and boosting with a boosting composition comprising one or more Pichinde mammarenavirus (PICV) viral expression vectors;

b) Priming with a priming composition comprising one or more Pichinde mammarenavirus (PICV) viral expression vectors and boosting with a boosting composition comprising one or more Lymphocytic choriomeningitis mammarenavirus (LCMV) viral expression vectors;

c) Priming with a priming composition comprising one or more replication deficient Pichinde mammarenavirus (PICV) viral expression vectors and boosting with a boosting composition comprising one or more replication deficient Lymphocytic choriomeningitis mammarenavirus (LCMV) viral expression vectors; or d) Priming with a priming composition comprising one or more replication deficient Lymphocytic choriomeningitis mammarenavirus (LCMV) viral expression vectors and boosting with a boosting composition comprising one or more replication deficient Pichinde mammarenavirus (PICV) viral expression vectors.

In various embodiments, the priming composition and the boosting composition comprise an immunogenic composition as described herein.

In some embodiments, the subject is not receiving antiviral therapy or antiviral therapy is discontinued prior to administration of the one or more immunogenic compositions. In some embodiments, the antiviral therapy is discontinued after one or more administrations of the compositions.

In some embodiments, the treatment methods activate in the subject CD8+ T cells targeting one or more HBV polypeptide epitopes. In some embodiments, the treatment methods elicit in the subject production of antibodies that bind one or more HBV polypeptides.

7. Combination Therapies

In certain embodiments, the immunogenic polypeptides, polynucleotides encoding such polypeptides, vectors, LNPs and immunogenic compositions comprising such polypeptides or polynucleotides, as described herein, are combined or co-administered with one, two, three, four or more additional therapeutic agents. In certain embodiments, the immunogenic polypeptides, polynucleotides encoding such polypeptides, vectors, LNPs and immunogenic compositions comprising such polypeptides or polynucleotides, as described herein, are combined or co-administered with two additional therapeutic agents. In certain embodiments, the immunogenic polypeptides, polynucleotides encoding such polypeptides, vectors, LNPs and immunogenic compositions comprising such polypeptides or polynucleotides, as described herein, are combined or co-administered with three additional therapeutic agents. In certain embodiments, the immunogenic polypeptides, polynucleotides encoding such polypeptides, vectors, LNPs and immunogenic compositions comprising such polypeptides or polynucleotides, as described herein, are combined or co-administered with four additional therapeutic agents. The one, two, three, four or more additional therapeutic agents can be different therapeutic agents selected from the same class of therapeutic agents, and/or they can be selected from different classes of therapeutic agents.

"Co-administration" as used herein refers to administration of unit dosages of the immunogenic polypeptides, polynucleotides encoding such polypeptides, vectors, LNPs and immunogenic compositions comprising such polypeptides or polynucleotides, as described herein, before or after administration of unit dosages of one or more additional therapeutic agents. For example, administration of the immunogenic composition disclosed herein within seconds, minutes, or hours of the administration of one or more additional therapeutic agents. For example, in some embodiments, a unit dose of an immunogenic composition of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of an immunogenic composition of the present disclosure within seconds or minutes. In some embodiments, a unit dose of the immunogenic polypeptides, polynucleotides encoding such polypeptides, vectors, LNPs and immunogenic compositions comprising such polypeptides or polynucleotides, as described herein, is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of the immunogenic polypeptides, polynucleotides encoding such polypeptides, vectors, LNPs and immunogenic compositions comprising such polypeptides or polynucleotides, as described herein.

Co-administration of the immunogenic polypeptides, polynucleotides encoding such polypeptides, vectors, LNPs and immunogenic compositions comprising such polypeptides or polynucleotides, as described herein, with one or more additional therapeutic agents generally refers to simultaneous or sequential administration of an immunogenic composition disclosed herein and one or more additional therapeutic agents, such that therapeutically effective amounts of each agent are present in the body of the patient.

In various embodiments, the immunogenic polypeptides, polynucleotides encoding such polypeptides, vectors, LNPs and immunogenic compositions comprising such polypeptides or polynucleotides, as described herein, are combined or co-administered with one or more additional therapeutic agents as described herein, the components of the composition are administered as a simultaneous or sequential regimen. When administered sequentially, the combination may be administered in two or more administrations.

In various embodiments, the immunogenic polypeptides, polynucleotides encoding such polypeptides, vectors, LNPs and immunogenic compositions comprising such polypeptides or polynucleotides, as described herein, are combined or co-administered with one, two, three, four or more additional therapeutic agents selected from HBV combination drugs, HBV vaccines, HBV DNA polymerase inhibitors, immunomodulators, toll-like receptor (TLR) modulators, interferon alpha receptor ligands, hyaluronidase inhibitors, HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), HBsAg secretion or assembly inhibitors, HBV viral entry inhibitors, immune checkpoint inhibitor, cytotoxic T-lymphocyte-associated protein 4 (CTLA4) inhibitors, cyclophilin inhibitors, endonuclease modulators, ribonucleotide reductase inhibitors, covalently closed circular DNA (cccDNA) inhibitors, farnesoid X receptor (FXR) agonists, STING agonists, anti-HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2,3-dioxygenase (IDO) pathway inhibitors, ZCCHC14 inhibitors, inducers of tertiary lymphoid aggregates, nucleic acid polymers (e.g., NAPs and STOPS), PD-1 inhibitors, PD-L1 inhibitors, recombinant thymosin alpha-1, Bruton's tyrosine kinase (BTK) inhibitors, lysine demethylase (KDM) inhibitors, HBV replication inhibitors, arginase inhibitors, gene therapy and cell therapy, gene editors, cellular therapy, TCR-T cell therapy, and other HBV drugs.

In certain embodiments, the immunogenic polypeptides, polynucleotides encoding such polypeptides, vectors, LNPs and immunogenic compositions comprising such polypeptides or polynucleotides, as described herein, may be combined or co-administered with one or more of a chemotherapeutic agent, an immunomodulator, an immunotherapeutic agent, a therapeutic antibody, a therapeutic vaccine, a bispecific antibody and "antibody-like" therapeutic protein (such as DARPins®, anti-pMHC TCR-like antibodies, DARTs®, Duobodies®, Bites®, XmAbs®, TandAbs®, Fab derivatives), an antibody-drug conjugate (ADC), gene modifiers or gene editors targeting HBV (e.g., CRISPR-Cas (e.g., Cas9, Cas12, Cascade, Cas13), zinc finger nucleases, homing endonucleases, homing meganucleases (e.g., ARCUS), synthetic nucleases, TALENs), cell therapies (e.g., T-cells, NK cells, macrophages having a chimeric antigen receptor (CAR)), and TCR-T (an engineered T cell receptor) or any combination thereof.

In certain embodiments, the immunogenic polypeptides, polynucleotides encoding such polypeptides, vectors, LNPs and immunogenic compositions comprising such polypeptides or polynucleotides, as described herein, are combined or co-administered with one, two, three, four or more additional therapeutic agents, e.g., as 3-dioxygenase (IDO) inhibitors, apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (CTLA4) inhibitors, DNA polymerase inhibitor, endonuclease modulators, epigenetic modifiers, farnesoid X receptor (FXR) agonists, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, inhibitor of apoptosis proteins family proteins (IAPs) inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, OX-40 receptor agonist, PD-1 inhibitors, PD-L1 inhibitors, peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonists, TLR-7 agonists, TLR-9 agonists, TLR9 agonists or gene stimulator, toll-like receptor (TLR) modulators, viral ribonucleotide reductase inhibitors, and combinations thereof.

HBV Inhibiting Antiviral Drugs

In various embodiments, the immunogenic polypeptides, polynucleotides encoding such polypeptides, vectors, LNPs and immunogenic compositions comprising such polypeptides or polynucleotides, as described herein, are combined or co-administered with one or more antiviral agents. In some embodiments, the one or more antiviral agents are selected from the group consisting of lamivudine (LAM), adefovir dipivoxil (ADV), entecavir (ETV), telbivudine (LdT), tenofovir disoproxil fumarate (TDF), tenofovir disoproxil fumarate and emtricitabine (TRUVADA®), tenofovir alafenamide (TAF or VEMLIDY®) and ledipasvir and sofosbuvir (HARVONI®).

Other HBV Drugs

Examples of other drugs for the treatment of HBV that can be combined or co-administered include alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, NCO-48 Fumarate, XTYW-001, SFA-001, TCM-800B, reduced glutathione, RO-6864018, ENOB-HB-01, RG-7834, QL-007sofosbuvir, ledipasvir, UB-551, PA-1010, HPN-BV1, STSG-0002, and ZH-2N, and the compounds disclosed in US20150210682, (Roche), U.S.

2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

Examples of combination drugs for the treatment of HBV that can be combined or co-administered include tenofovir disoproxil fumarate and emtricitabine (TRUVADA®), ledipasvir and sofosbuvir (HARVONI®); ABX-203 (NASVAC), lamivudine and PEG-IFNα; adefovir and PEG-IFNα; and INO-1800 (INO-9112 and RG7944).

HBV Vaccines

In various embodiments, the immunogenic polypeptides, polynucleotides encoding such polypeptides, vectors, LNPs and immunogenic compositions comprising such polypeptides or polynucleotides, as described herein, are combined or co-administered with one or more HBV vaccines. HBV vaccines that can be combined or co-administered (e.g., in a prime-boost prevention regimen) include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, CARG-101, Euforavac, Eutravac, anrix-DTaP—IPV-Hep B, HBAI-20, Infanrix-DTaP—IPV-Hep B-Hib, Pentabio Vaksin DTP—HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, YS-HBV-001, IR-101H, TVAX-008, and DTaP-rHB-Hib vaccine.

Examples of HBV therapeutic vaccines that can be combined or co-administered (e.g., in a prime-boost treatment regimen) include HBsAG-HBIG complex, ARB-1598, Bio-Hep-B, abi-HB (intravenous), ABX-203 (NASVAC), Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2 (HepTcell), NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, VVX-001, GSK-3528869A (ChAd155-hli-HBV+MVA-HBV+Hbc-HBs/AS01B-4), VBI-2601, VTP-300 (ChAdOx1-SIi-HBV-CPmut-TPA-Ssh prime and MVA-SIi-HBV-CPmut-TPA-Ssh boost), Lm HBV and BM32 (Tulaeva, et al., EBioMedicine (2020) 102953). HBV Arenavirus vaccines are described, e.g., in WO2017076988 and WO2017198726.

HBV DNA Polymerase Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more polymerase inhibitors. Examples of HBV DNA polymerase inhibitors that can be combined or co-administered include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, AiB-001, and HS-10234.

Immunomodulators

In various embodiments, the immunogenic polypeptides, polynucleotides encoding such polypeptides, vectors, LNPs and immunogenic compositions comprising such polypeptides or polynucleotides, as described herein, are combined or co-administered with one or more immunomodulators (e.g., an immune checkpoint inhibitor, a tumor necrosis factor (TNF) receptor superfamily (TNFRSF) agonist, an immune stimulator, e.g., a TLR agonist). Examples of immunomodulators that can be combined or co-administered include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440, WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785 and corresponding prodrug RO-702053, RG-7854, RO-6871765, AIC-649, and IR-103.

Toll-Like Receptor (TLR) Agonists

In various embodiments, the immunogenic polypeptides, polynucleotides encoding such polypeptides, vectors, LNPs and immunogenic compositions comprising such polypeptides or polynucleotides, as described herein, are combined or co-administered with one or more agonists or stimulators of a toll-like receptor (TLR). In various embodiments, the immunogenic polypeptides, polynucleotides encoding such polypeptides, vectors, LNPs and immunogenic compositions comprising such polypeptides or polynucleotides, as described herein, are combined or co-administered with an agonist of a TLR, e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793), TLR11, TLR12 and TLR13.

Examples of TLR3 agonists that can be combined or co-administered include rintatolimod, poly-ICLC, RIBOXXON®, Apoxxim, RIBOXXIM®, IPH-33, MCT-465, MCT-475 and ND-1.1.

Examples of TLR4 agonists that can be combined or co-administered include G-100, and GSK-1795091.

Example TLR7 agonists that can be combined or co-administered include without limitation AL-034, DSP-0509, GS-9620 (vesatolimod), LHC-165, TMX-101 (imiquimod), GSK-2245035, resiquimod, DSR-6434, DSP-3025, IMO-4200, MCT-465, telratolimod (MEDI-9197), 3M-051, SB-9922, 3M-052, Limtop, TMX-30X, TMX-202, RG-7863, RG-7854, RG-7795, RO-7011785 and corresponding prodrug RO-702053, and the compounds disclosed in US20100143301 (Gilead Sciences), US20110098248

(Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Example dual TLR7/TLR8 agonists that can be combined or co-administered is NKTR-262, telratolimod and BDB-001.

Example TLR8 agonists that can be co-administered include without limitation E-6887, IMO-4200, IMO-8400, IMO-9200, MCT-465, telratolimod (MEDI-9197), motolimod, resiquimod, selgantolimod (GS-9688), HRS-9950, VTX-1463, VTX-763, 3M-051, 3M-052, SBT6050, and the compounds disclosed in US2016289229 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics), U.S. Pat. No. 9,670,205 (Gilead Sciences, Inc.), US20160289229 (Gilead Sciences, Inc.), WO2017/048727 (Gilead Sciences, Inc.), US20180065938 (Gilead Sciences, Inc.), and US20180086755 (Gilead Sciences, Inc.).

Example TLR9 agonists that can be combined or co-administered include without limitation AST-008, cobitolimod, CMP-001, IMO-2055, IMO-2125, S-540956, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042.

Additional examples of TLR7, TLR8 and TLR9 modulators that can be combined or co-administered include the compounds disclosed in WO2017047769 (Teika Seiyaku), WO2015014815 (Janssen), WO2018045150 (Gilead Sciences Inc), WO2018045144 (Gilead Sciences Inc), WO2015162075 (Roche), WO2017034986 (University of Kansas), WO2018095426 (Jiangsu Hengrui Medicine Co Ltd), WO2016091698 (Roche), WO2016075661 (GlaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607 (Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (BristolMyers Squibb), WO2015057655 (Eisai Co Ltd), WO2017001307 (Roche), WO2018005586 (BristolMyers Squibb), WO201704023 (3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO201804163 (Roche), WO2018038877 (3M Co), WO2015057659 (Eisai Co Ltd), WO2017202704 (Roche), WO2018026620 (BristolMyers Squibb), WO2016029077 (Janus Biotherapeutics), WO201803143 (Merck), WO2016096778 (Roche), WO2017190669 (Shanghai De Novo Pharmatech), U.S. Ser. No. 09/884,866 (University of Minnesota), WO2017219931 (Sichuan KelunBiotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909 (Takeda Pharmaceutical), WO2015095780 (University of Kansas), WO2015023958 (University of Kansas).

In certain embodiments, the immunogenic polypeptides, polynucleotides encoding such polypeptides, vectors, LNPs and immunogenic compositions comprising such polypeptides or polynucleotides, as described herein, are combined or co-administered with a TLR7, TLR8 or TLR9 agonist.

Interferon Alpha Receptor Ligands

In various embodiments, the immunogenic polypeptides, polynucleotides encoding such polypeptides, vectors, LNPs and immunogenic compositions comprising such polypeptides or polynucleotides, as described herein, are combined or co-administered with one or more interferon alpha receptor ligands. Examples of interferon alpha receptor ligands that can be combined or co-administered include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), PEG-IFN-alpha, rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more hyaluronidase inhibitors. Examples of hyaluronidase inhibitors that can be combined or co-administered include astodrimer.

Hepatitis B Surface Antigen (HBsAg) Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more HBsAg inhibitors. Examples of HBsAg inhibitors that can be combined or co-administered include AK-074, HBF-0259, GP-605, PBHBV-001, PBHBV-2-15, PBHBV-2-1, REP-9AC, REP-9C, REP-9, REP-2139, REP-2139-Ca, REP-2055, REP-2163, REP-2165, REP-2053, REP-2031 and REP-006, and REP-9AC'. Examples of HBsAg secretion inhibitors that can be combined or co-administered include BM601, GST-HG-131, AB-452 and ALG-010093.

Cyclophilin Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more cyclophilin inhibitors. Examples of cyclophilin inhibitors that can be combined or co-administered include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more HBV viral entry inhibitors. Examples of HBV viral entry inhibitors that can be combined or co-administered include bulevirtide (Hepcludex; Myrcludex B).

Inhibitory Nucleic Acids

In various embodiments, the immunogenic polypeptides, polynucleotides encoding such polypeptides, vectors, LNPs and immunogenic compositions comprising such polypeptides or polynucleotides, as described herein, are combined or co-administered with one or more inhibitory nucleic acids (e.g., antisense oligonucleotide, short interfering RNA (siRNA), DNA-directed RNA interference (ddRNAi)) specifically targeting an HBV polynucleotide. In some embodiments, the HBV polynucleotide encodes and HBV protein (i.e., is in a coding region within the HBV genome).

Antisense Oligonucleotide Targeting Viral mRNA

In various embodiments, the immunogenic polypeptides, polynucleotides encoding such polypeptides, vectors, LNPs and immunogenic compositions comprising such polypeptides or polynucleotides, as described herein, are combined or co-administered with one or more antisense oligonucleotides. Examples of antisense oligonucleotide targeting viral mRNA that can be combined or co-administered include ISIS-HBVRx, IONIS-HBVRx, IONIS-HBV-LRx, IONIS-GSK6-LRx, GSK-3389404, BNC-1701 and RG-6004.

Short Interfering RNAs (siRNA)

In various embodiments, the immunogenic polypeptides, polynucleotides encoding such polypeptides, vectors, LNPs and immunogenic compositions comprising such polypeptides or polynucleotides, as described herein, are combined or co-administered with one or more siRNAs specifically targeting an HBV polynucleotide. Examples of siRNA specifically targeting an HBV polynucleotide that can be combine or co-administered include TKM-HBV (TKM-HepB), ALN-HBV, SR-008, HepB-nRNA, ARC-520, ARC-521, ARB-1740, ARB-1467, AB-729, DCR-HBVS, RG-6084 (PD-L1), RG-6217, ALN-HBV-02, JNJ-3989 (ARO-HBV), STSG-0002, LUNAR-HBV and DCR-HBVS (DCR-5219).

DNA-Directed RNA Interference (ddRNAi)

In various embodiments, the immunogenic polypeptides, polynucleotides encoding such polypeptides, vectors, LNPs and immunogenic compositions comprising such polypeptides or polynucleotides, as described herein, are combined or co-administered with one or more ddRNAi specifically targeting an HBV polynucleotide. Examples of ddRNAi specifically targeting an HBV polynucleotide that can be combined or co-administered include BB-HB-331.

Endonuclease Modulators

In various embodiments, the immunogenic polypeptides, polynucleotides encoding such polypeptides, vectors, LNPs and immunogenic compositions comprising such polypeptides or polynucleotides, as described herein, are combined or co-administered with one or more endonuclease modulators. Examples of endonuclease modulators that can be combined or co-administered include PGN-514.

Ribonucleotide Reductase Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more ribonucleotide reductase inhibitors. Examples of inhibitors of ribonucleotide reductase that can be combined or co-administered include Trimidox.

Non-Nucleoside Reverse Transcriptase Inhibitors (NNRTIs)

In various embodiments, the immunogenic polypeptides, polynucleotides encoding such polypeptides, vectors, LNPs and immunogenic compositions comprising such polypeptides or polynucleotides, as described herein, are combined or co-administered with one or more NNRTIs. Examples of NNRTIs that can be combined or co-administered include the compounds disclosed in WO2018118826 (Merck), WO2018080903 (Merck), WO2018119013 (Merck), WO2017100108 (Idenix), WO2017027434 (Merck), WO2017007701 (Merck), WO2008005555 (Gilead).

HBV Replication Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more HBV replication inhibitors. Examples of HBV replication inhibitors that can be combined or co-administered include GP-31502, isothiafludine, IQP-HBV, RM-5038, and Xingantie.

Covalently Closed Circular DNA (cccDNA) Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more cccDNA inhibitors. Examples of cccDNA inhibitors that can be combined or co-administered include BSBI-25, ccc-R08, and CHR-101.

Farnesoid X Receptor (FXR) Agonists

In various embodiments, the immunogenic polypeptides, polynucleotides encoding such polypeptides, vectors, LNPs and immunogenic compositions comprising such polypeptides or polynucleotides, as described herein, are combined or co-administered with one or more FXR agonists. Examples of FXR agonists that can be combined or co-administered include EYP-001, cilofexor (GS-9674), EDP-305, MET-409, Tropifexor, AKN-083, RDX-023, BWD-100, LMB-763, INV-3, NTX-023-1, EP-024297 and GS-8670.

Anti-HBV Antibodies

In various embodiments, the immunogenic polypeptides, polynucleotides encoding such polypeptides, vectors, LNPs and immunogenic compositions comprising such polypeptides or polynucleotides, as described herein, are combined or co-administered with one or more antibodies that specifically binds to an HBV antigen, including an HBV peptide presented in a major histocompatibility molecule (MHC) molecule (pMHC). Examples of HBV antibodies targeting the surface antigens of the hepatitis B virus that can be combined or co-administered include lenvervimab (GC-1102), XTL-17, XTL-19, KN-003, IV Hepabulin SN, and fully human monoclonal antibody therapy (hepatitis B virus infection, Humabs BioMed). Antibodies targeting HBV X protein (HBx) that can be combined or co-administered are described, e.g., in Kornyeyev, et al., *J Virol.* Jul. 30, 2019; 93 (16). pii: e00248-19.

Examples of HBV antibodies, including monoclonal antibodies and polyclonal antibodies, that can be combined or co-administered include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Examples of fully human monoclonal HBV antibodies that can be combined or co-administered include HBC-34.

Antibodies against HBV viral peptide/major histocompatibility complex (MHC) class I (pMHC) complexes that can be combined or co-administered are described, e.g., in Sastry, et al., *J Virol.* 2011 March; 85(5):1935-42 and in WO2011062562.

CCR2 Chemokine Antagonists

In various embodiments, the immunogenic polypeptides, polynucleotides encoding such polypeptides, vectors, LNPs and immunogenic compositions comprising such polypeptides or polynucleotides, as described herein, are combined or co-administered with one or more CCR2 chemokine antagonists. Examples of CCR2 chemokine antagonists that can be combined or co-administered include propagermanium.

Thymosin Agonists

In various embodiments, the immunogenic polypeptides, polynucleotides encoding such polypeptides, vectors, LNPs and immunogenic compositions comprising such polypeptides or polynucleotides, as described herein, are combined or co-administered with one or more thymosin agonists, e.g., a recombinant thymosin alpha-1. Examples of thymosin agonists that can be combined or co-administered include Thymalfasin, and recombinant thymosin alpha 1 (GeneScience). Examples of recombinant thymosin alpha-1 include NL-004 and PEGylated thymosin alpha-1.

Interleukin Receptor Agonists (e.g., Cytokines)

In some embodiments, the immunogenic polypeptides, polynucleotides encoding such polypeptides, vectors, LNPs and immunogenic compositions comprising such polypeptides or polynucleotides, as described herein, are combined or co-administered with one or more interleukin receptor agonists of an interleukin receptor selected from IL-2, IL-7, IL-12 and IL-15. In some embodiments, the immunogenic polypeptides, polynucleotides encoding such polypeptides, vectors, LNPs and immunogenic compositions comprising such polypeptides or polynucleotides, as described herein, are combined or co-administered with one or more cytokines selected from the group consisting of IL-2, IL-7, IL-12, IL-15, IL-21, IL-24, and variants thereof. Examples of IL-2 receptor agonists that can be combined or co-administered include proleukin (aldesleukin, IL-2); celmoleukin; pegylated IL-2 (e.g., NKTR-214); modified variants of IL-2 (e.g., THOR-707), bempegaldesleukin, AIC-284, ALKS-4230, CUI-101 and Neo-2/15. Examples of IL-15 receptor agonists that can be combined or co-administered include ALT-803, NKTR-255, and hetIL-15, interleukin-15/Fc fusion protein, AM-0015, NIZ-985, SO-C101, IL-15 Synthorin (pegylated I1-15), P-22339, and an IL-15-PD-1 fusion protein N-809. Examples of IL-7 receptor agonists that can be combined or co-administered include CYT-107.

Nucleoprotein Modulators

In various embodiments, the immunogenic polypeptides, polynucleotides encoding such polypeptides, vectors, LNPs and immunogenic compositions comprising such polypeptides or polynucleotides, as described herein, are combined or co-administered with one or more nucleoprotein modulators. Nucleoprotein modulators may be either HBV core or capsid protein inhibitors. Examples of nucleoprotein modulators that can be combined or co-administered include GS-4882, AB-423, AB-836, AT-130, ALG-001075, ALG-001024, ALG-000184, EDP-514, GLS4, NVR-1221, NVR-3778, AL-3778, BAY 41-4109, morphothiadine mesilate, ARB-168786, ARB-880, ARB-1820, GST-HG-141, JNJ-379, JNJ-632, RG-7907, GST-HG-141, HEC-72702, KL-060332, AB-506, ABI-H0731, ABI-H3733, JNJ-440, AK-0605, HRS-5091, VNRX-9945, ABI-H2158, CB-HBV-001, AK-0605, SOC-10, SOC-11 and DVR-23.

Examples of capsid inhibitors that can be combined or co-administered include ALG-000184, ABI-H0731, NVR 3-778, and compounds disclosed in US2018161307 (Gilead Sciences), US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140188337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), U.S. 20170334882 (Novira), US20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors that can be combined or co-administered include compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297

(Ginkgo Pharma), WO2018022282 (Newave Pharma), US20180030053 (Novartis), WO2018045911 (Zhejiang Pharma).

Innate Immune Activators

In some embodiments, the immunogenic polypeptides, polynucleotides encoding such polypeptides, vectors, LNPs and immunogenic compositions comprising such polypeptides or polynucleotides, as described herein, are combined or co-administered with one or more innate immune activators. In various embodiments, the one or more innate immune activators comprises an agonist of a receptor selected from the group consisting of fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the methods entail co-administering GS-3583 and/or GS-9992. In some embodiments, the methods entail combining or co-administering a FLT3 agonist, e.g., GS-3583 or CDX-301.

STING Agonists, RIG-I and NOD2 Modulators

In some embodiments, the immunogenic polypeptides, polynucleotides encoding such polypeptides, vectors, LNPs and immunogenic compositions comprising such polypeptides or polynucleotides, as described herein, are combined or co-administered with a stimulator of interferon response cGAMP interactor 1 (STING or STING1; NCBI Gene ID: 340061) agonist. In some embodiments, the STING/STING1 agonist or activator is selected from the group consisting of ADU-S100 (MIW-815), SB-11285, MK-1454, SR-8291, AdVCA0848, STINGVAX, GSK-532, SYN-STING, MSA-1, SR-8291, 5,6-dimethylxanthenone-4-acetic acid (DMXAA), cyclic-GAMP (cGAMP) and cyclic-di-AMP. Examples of STING agonists that can be combined or co-administered include the compounds disclosed in WO 2018065360 (Biolog Life Science Institute Forschungslabor and Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), U.S. 20170158724 (Glaxo Smithkline), WO 2017075477 (Aduro Biotech), U.S. 20170044206 (Merck), WO 2014179760 (University of California), WO2018098203 (Janssen), WO2018118665 (Merck), WO2018118664 (Merck), WO2018100558 (Takeda), WO2018067423 (Merck), WO2018060323 (Boehringer).

In some embodiments, the immunogenic polypeptides, polynucleotides encoding such polypeptides, vectors, LNPs and immunogenic compositions comprising such polypeptides or polynucleotides, as described herein, are combined or co-administered with a DExD/H-box helicase 58 (DDX58; a.k.a., retinoic acid-inducible gene 1 (RIG-I), RIG1, RIGI, RLR-1, SGMRT2; NCBI Gene ID: 23586). Illustrative RIG-I agonists that can be combined or co-administered include inarigivir soproxil (SB-9200; GS-9992); SB-40, SB-44, ORI-7246, ORI-9350, ORI-7537, ORI-9020, ORI-9198, ORI-7170, and RGT-100.

In some embodiments, the immunogenic polypeptides, polynucleotides encoding such polypeptides, vectors, LNPs and immunogenic compositions comprising such polypeptides or polynucleotides, as described herein, are combined or co-administered with a nucleotide binding oligomerization domain containing 2 (NOD2; NCBI Gene ID: 64127) agonist, such as inarigivir soproxil (SB-9200; GS-9992), and IR-103.

Phosphatidylinositol 3-Kinase (PI3K) Inhibitors

In some embodiments, the immunogenic polypeptides, polynucleotides encoding such polypeptides, vectors, LNPs and immunogenic compositions comprising such polypeptides or polynucleotides, as described herein, are combined or co-administered with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWSS, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments, the PI3K inhibitor is a pan-PI3K inhibitor. Examples of PI3K inhibitors include without limitation, ACP-319, AEZA-129, AMG-319, AS252424, AZD8186, BAY 1082439, BEZ235, bimiralisib (PQR309), buparlisib (BKM120), BYL719 (alpelisib), carboxyamidotriazole orotate (CTO), CH5132799, CLR-457, CLR-1401, copanlisib (BAY 80-6946), DS-7423, duvelisib (IPI-145), fimepinostat (CUDC-907), gedatolisib (PF-05212384), GDC-0032, GDC-0084 (RG7666), GDC-0077, pictilisib (GDC-0941), GDC-0980, GSK2636771, GSK2269577, idelalisib (Zydelig®), INCB040093, INCB50465, IPI-443, IPI-549, KAR4141, LY294002, LY3023414, NERLYNX® (neratinib), nemiralisib (GSK2269557), omipalisib (GSK2126458, GSK458), OXY111A, panulisib (P7170, AK151761), PA799, perifosine (KRX-0401), Pilaralisib (SAR245408; XL147), puquitinib mesylate (XC-302), SAR260301, seletalisib (UCB-5857), serabelisib (INK-1117, MLN-1117, TAK-117), SF1126, sonolisib (PX-866), RG7604, rigosertib sodium (ON-01910 sodium), RP5090, tenalisib (RP6530), RV-1729, SRX3177, taselisib, TG100115, umbralisib (TGR-1202), TGX221, voxtalisib (SAR245409), VS-5584, WX-037, X-339, X-414, XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Immune Checkpoint Modulators

In some embodiments, the immunogenic polypeptides, polynucleotides encoding such polypeptides, vectors, LNPs and immunogenic compositions comprising such polypeptides or polynucleotides, as described herein, are combined or co-administered with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu, et al., J Exp Clin Cancer Res. (2018) 37:110). In various embodiments, the immune checkpoint proteins or receptors regulate NK cell responses (e.g., reviewed in Davis, et al., Semin Immunol. (2017) 31:64-75 and Chiossone, et al., Nat Rev Immunol. (2018) 18(11):671-688).

Examples of immune checkpoint proteins or receptors include without limitation CD27 (NCBI Gene ID: 939); CD70 (NCBI Gene ID: 970); CD40 (NCBI Gene ID: 958);

CD40LG (NCBI Gene ID: 959); CD47 (NCBI Gene ID: 961); CD48 (SLAMF2; NCBI Gene ID: 962); transmembrane and immunoglobulin domain containing 2 (TMIGD2, CD28H; NCBI Gene ID: 126259); CD84 (LY9B, SLAMF5; NCBI Gene ID: 8832); CD96 (NCBI Gene ID: 10225); CD160 (NCBI Gene ID: 11126); MS4A1 (CD20; NCBI Gene ID: 931); CD244 (SLAMF4; NCBI Gene ID: 51744); CD276 (B7H3; NCBI Gene ID: 80381); V-set domain containing T cell activation inhibitor 1 (VTCN1, B7H4; NCBI Gene ID: 79679); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943); TNFSF8 (CD30L; NCBI Gene ID: 944); TNFRSF10A (CD261, DR4, TRAILR1; NCBI Gene ID: 8797); TNFRSF9 (CD137; NCBI Gene ID: 3604); TNFSF9 (CD137L; NCBI Gene ID: 8744); TNFRSF10B (CD262, DR5, TRAILR2; NCBI Gene ID: 8795); TNFRSF10 (TRAIL; NCBI Gene ID: 8743); TNFRSF14 (HVEM, CD270; NCBI Gene ID: 8764); TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608); TNFSF13B (BAFF; NCBI Gene ID: 10673); TNFRSF18 (GITR; NCBI Gene ID: 8784); TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941); CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMF1, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAET1E; ULBP4; NCBI Gene ID: 135250); retinoic acid early transcript 1G (RAET1G; ULBP5; NCBI Gene ID: 353091); retinoic acid early transcript 1L (RAET1L; ULBP6; NCBI Gene ID: 154064); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1, KIR, CD158E1; NCBI Gene ID: 3811) (e.g., Lirilumab (IPH2102/BMS-986015), IPH-4102); and killer cell lectin like receptor D1 (KLRD1; NCBI Gene ID: 3824).

In some embodiments, the immunogenic polypeptides, polynucleotides encoding such polypeptides, vectors, LNPs and immunogenic compositions comprising such polypeptides or polynucleotides, as described herein, are combined or co-administered with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., J Exp Clin Cancer Res. (2018) 37:110.

In some embodiments, the immunogenic polypeptides, polynucleotides encoding such polypeptides, vectors, LNPs and immunogenic compositions comprising such polypeptides or polynucleotides, as described herein, are combined or co-administered with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94).

In some embodiments, the immunogenic polypeptides, polynucleotides encoding such polypeptides, vectors, LNPs and immunogenic compositions comprising such polypeptides or polynucleotides, as described herein, are combined or co-administered with one or more agonists or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., Semin Immunol. (2017) 31:64-75; Fang, et al., Semin Immunol. (2017) 31:37-54; and Chiossone, et al., Nat Rev Immunol. (2018) 18(11):671-688.

Inhibitors of Cytotoxic T-Lymphocyte-Associated Protein 4 (CTLA4)

In various embodiments, the immunogenic polypeptides, polynucleotides encoding such polypeptides, vectors, LNPs and immunogenic compositions comprising such polypeptides or polynucleotides, as described herein, are combined or co-administered with one or more Inhibitors of cytotoxic T-lymphocyte-associated protein 4 (CTLA4) (CD152; NCBI Gene ID: 1493). Examples of inhibitors of CTLA4 that can be co-administered include without limitation ipilimumab, tremelimumab, BMS-986218, AGEN1181, AGEN1884, AGEN2041, BMS-986249, MK-1308, REGN-4659, ADU-1604, CS-1002, BCD-145, APL-509, JS-007, BA-3071, ONC-392, JHL-1155, KN-044, CG-0161, ATOR-1144, PBI-5D3H5, BPI-002, belatacept, PSI-001, PRS-010, JHL-1155, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Inhibitors of PD-L1 (CD274) or PD-1 (PDCD1; CD279)

In various embodiments, the immunogenic polypeptides, polynucleotides encoding such polypeptides, vectors, LNPs and immunogenic compositions comprising such polypeptides or polynucleotides, as described herein, are combined or co-administered with one or more inhibitors of programmed cell death 1 ligand 1 (PD-L1; CD274; NCBI Gene ID: 29126) or programmed cell death 1 (PD-1; PDCD1; CD279; NCBI Gene ID: 5133). Examples of inhibitors of PD-L1 (CD274) or PD-1 (PDCD1) that can be combined or co-administered include without limitation zimberelimab (AB122), pembrolizumab, nivolumab, cemiplimab, pidilizumab, AMP-224, MEDI0680 (AMP-514), spartalizumab, atezolizumab, avelumab (MSB0010718C), ASC22, durvalumab, ALN-PDL, BMS-936559, CK-301, PF-06801591, BGB-108, BGB-A317 (tislelizumab), GLS-010 (WBP-3055), AK-103 (HX-008), GB-226, AK-105, CS-1003, HLX-10, MGA-012, BI-754091, PDR-001, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, RO-6084 (PD-L1 antisense oligonucleotide), STI-1110, GX-P2, RG-7446, mDX-400, CX-072, CBT-502, TSR-042 (dostarlimab), MSB-2311, JTX-4014, BGB-A333, SHR-1316, CS-1001 (WBP-3155), MEDI-0680, envafolimab (KN-035), KD-033, KY-1003, IBI-308 (sintilimab), HLX-20, KL-A167, STI-A1014, STI-A1015 (IMC-001), BCD-135, FAZ-053, TQB-2450, MDX1105-01, MSB-0010718C, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), GNS-1480 (Epidermal growth factor receptor antagonist; Programmed cell death ligand 1 inhibitor), M-7824 (PD-L1/TGF-β bifunctional fusion protein), and INBRX-105 (4-1BB/PDL1).

Examples of PD-1 inhibitors that can be combined or co-administered further include the compounds disclosed in WO2017112730 (Incyte Corp), WO2017087777 (Incyte Corp), WO2017017624, WO2014151634 (BristolMyers Squibb Co), WO201317322 (BristolMyers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (BristolMyers Squibb Co), WO20161266460 (BristolMyers Squibb Co), WO2017087678 (BristolMyers Squibb Co), WO2016149351 (BristolMyers Squibb Co), WO2015033299 (Aurigene Discovery Technologies Ltd), WO2015179615 (Eisai Co Ltd; Eisai Research Institute), WO2017066227 (BristolMyers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), WO2018026971 (Arising International).

In various embodiments, the immunogenic polypeptides, polynucleotides encoding such polypeptides, vectors, LNPs and immunogenic compositions comprising such polypeptides or polynucleotides, as described herein, are combined or co-administered with one or more proteinaceous (e.g., antibody or fragment thereof, or antibody mimetic) inhibitors of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. Additional examples of small molecule PD-L1 inhibitors include those disclosed in U.S. Publication No. US2018305315 (Gilead Sciences), US2020017471 (Gilead Sciences) and US2019270727 (Gilead Sciences). In some embodiments, the small molecule inhibitor of CTLA4 comprises BPI-002.

Inhibitors of T Cell Immunoreceptor with Ig and ITIM Domains (TIGIT)

In various embodiments, the immunogenic polypeptides, polynucleotides encoding such polypeptides, vectors, LNPs and immunogenic compositions comprising such polypeptides or polynucleotides, as described herein, are combined or co-administered with one or more inhibitors of T cell immunoreceptor with Ig and ITIM domains (TIGIT) (NCBI Gene ID: 201633). Example anti-TIGIT antibodies, that can be combined or co-administered include etigilimab, BMS-986207, tiragolumab (a.k.a., MTIG-7192A; RG-6058; RO 7092284), AGEN1307, AGEN1327, AGEN1777, COM-902, IBI-939, AB154, MG1131 and E05884448 (EOS-448).

TNF Receptor Superfamily (TNFRSF) Member Agonists or Activators

In various embodiments, the immunogenic polypeptides, polynucleotides encoding such polypeptides, vectors, LNPs and immunogenic compositions comprising such polypeptides or polynucleotides, as described herein, are combined or co-administered with one or more agonists of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be combined or co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be combined or co-administered include without limitation RG7876, SEA-CD40, APX-005M and ABBV-428.

In some embodiments, the anti-TNFRSF7 (CD27) antibody varlilumab (CDX-1127) is combined or co-administered.

Example anti-TNFRSF9 (4-1BB, CD137) antibodies that can be combined or co-administered include without limitation urelumab, utomilumab (PF-05082566), AGEN-2373 and ADG-106.

Example anti-TNFRSF18 (GITR) antibodies that can be combined or co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Indoleamine-Pyrrole-2,3-Dioxygenase (IDO1) Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with one or more inhibitors of indoleamine 2,3-dioxygenase 1 (IDO1; NCBI Gene ID: 3620). Examples of IDO1 inhibitors that can be combined or co-administered include without limitation, BLV-0801, epacadostat, resminostat, F-001287, GBV-1012, GBV-1028, GDC-0919, indoximod, NKTR-218, NLG-919-based vaccine, PF-06840003, pyranonaphthoquinone derivatives (SN-35837), SBLK-200802, BMS-986205, and shIDO-ST, EOS-200271, KHK-2455, LY-3381916, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

LAG-3 and TIM-3 Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with an anti-TIM-3 antibody, such as TSR-022, LY-3321367, MBG-453, INCAGN-2390. In various embodiments, the immunogenic polypeptides, polynucleotides encoding such polypeptides, vectors, LNPs and immunogenic compositions comprising such polypeptides or polynucleotides, as described herein, are combined or co-administered with an anti-LAG-3 (Lymphocyte-activation) antibody, such as relatlimab (ONO-4482), LAG-525, MK-4280, REGN-3767, INCAGN2385.

Inhibitors of Apoptosis Proteins Family Proteins (IAPs)

In various embodiments, the immunogenic polypeptides, polynucleotides encoding such polypeptides, vectors, LNPs and immunogenic compositions comprising such polypeptides or polynucleotides, as described herein, are combined or co-administered with an inhibitor of apoptosis proteins family protein (TAP). Examples of IAP inhibitors include APG-1387.

Bruton's Tyrosine Kinase (BTK) Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include without limitation, (S)-6-amino-9-(1-(but-2-ynoyl)pyrrolidin-3-yl)-7-(4-phenoxyphenyl)-7H-purin-8 (9H)-one, ABBV-105, acalabrutinib (ACP-196), AC-058, AC-0025, ARQ-531, BMS-986142, dasatinib, ibrutinib (PCI-32765, CRA-032765), GDC-0853, PRN-1008, SNS-062, BGB-3111, CB988, HM71224, KBP-7536, M-2951 (evobrutinib), M7583, tirabrutinib (ONO-4059), ML-319, MSC-2364447, PRN-1008, RDX-022, RG-7845, spebrutinib (CC-292), TAK-020, TAS-5315, TP-0158, TP-4207, vecabrutinib (SNS-062), ARQ-531, SHR-1459, DTRMWXHS-12, and the compounds disclosed in US20140330015 (Ono Pharmaceutical), US20130079327 (Ono Pharmaceutical), and US20130217880 (Ono Pharmaceutical).

Lysine Demethylase (KDM) Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with an inhibitor of a lysine demethylase (KDM). Examples of KDM5 inhibitors that can be combined or co-adminstered include the compounds disclosed in WO2016057924 (Genentech/Constellation Pharmaceuticals), US20140275092 (Genentech/Constellation Pharmaceuticals), US20140371195 (Epitherapeutics), US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), and WO2014164708 (Quanticel).

Examples of KDM1 inhibitors that can be combined or co-administered include the compounds disclosed in U.S. Pat. No. 9,186,337B2 (Oryzon Genomics), GSK-2879552, RG-6016, and ORY-2001.

Arginase Inhibitors

In various embodiments, the immunogenic polypeptides, polynucleotides encoding such polypeptides, vectors, LNPs and immunogenic compositions comprising such polypeptides or polynucleotides, as described herein, are combined or co-administered with an arginase inhibitor. Examples of Arginase inhibitors include CB-1158, C-201, and resminostat.

Bi- and Tri-Specific Natural Killer (NK)-Cell Engagers

In various embodiments, the immunogenic polypeptides, polynucleotides encoding such polypeptides, vectors, LNPs and immunogenic compositions comprising such polypeptides or polynucleotides, as described herein, are combined or co-administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HBV-associated antigens as described herein. BiKEs and TriKEs are described, e.g., in Felices, et al., Methods Mol Biol. (2016) 1441:333-346; Fang, et al., Semin Immunol. (2017) 31:37-54.

Long Acting Treatments

In various embodiments, the immunogenic polypeptides, polynucleotides encoding such polypeptides, vectors, LNPs and immunogenic compositions comprising such polypeptides or polynucleotides, as described herein, are combined or co-administered with a long acting treatment. Long acting entecavir (subcutaneous depot), long acting tenofovir (TFD and TAF) implants (devices) or subcutaneous depot. An example of long acting entecavir is described in Henry, et al., *Eur J Pharm Sci.* (2019) 136:104958.

Gene Therapy and Cell Therapy

In various embodiments, the immunogenic polypeptides, polynucleotides encoding such polypeptides, vectors, LNPs and immunogenic compositions comprising such polypeptides or polynucleotides, as described herein, are combined or co-administered with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Gene Editors

The genome editing system can be selected from the group consisting of: a CRISPR/Cas9 system, a zinc finger nuclease system, a TALEN system, a homing endonucleases system, and a meganuclease system (e.g., an ARCU.S. system); e.g., cccDNA elimination via targeted cleavage, and altering one or more of the hepatitis B virus (HBV) viral genes. Altering (e.g., knocking out and/or knocking down) the PreC, C, X, PreSI, PreS2, S, P or SP gene refers to (1) reducing or eliminating PreC, C, X, PreSI, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreSI, PreS2, S, P and/or SP gene(s) is performed by targeting the gene(s) within HBV cccDNA and/or integrated HBV DNA. Additional examples genome editing systems include, but are not limited to those disclosed in US2019284543 (Gilead Sciences), and US2019338263 (Gilead Sciences).

Examples of gene therapy, such as liver targeted anti-HBV gene therapy (using ARCU.S. technology), or using CRISPR/Cas9 gene editing technology, or EBT-106 (LNP-delivered CRISPR/CasX nuclease.

CAR-T Cell Therapy

CAR-T cell therapy includes a population of immune effector cells engineered to express a chimeric antigen receptor (CAR), wherein the CAR includes an HBV antigen-binding domain. In certain embodiments, the antigen-binding domain is a domain disclosed herein. In certain embodiments, the antigen-binding domain is other than a domain disclosed herein. In certain embodiments, the antigen is HBsAg (i.e. HbsAg-CART). The immune effector cell is a T-cell or an NK cell. In certain embodiments, the T-cell is a CD4+ T-cell, a CD8+ T-cell, a NK cell or a combination thereof. Cells can be autologous or allogeneic. An example of a CART directed to HBV is described in Kruse, et al., *Cytotherapy*. (2018) 20(5):697-705.

TCR-T Cell Therapy

TCR-T cell therapy includes T cells expressing HBV-specific T cell receptors. TCR-T cells are engineered to target HBV derived peptides presented on the surface of virus-infected cells. An example of a TCR directed to HBV is described in Wisskirchen, et al., *J Clin Invest*. (2019) 129(7):2932-2945.

TCR-T cell therapy includes T-Cells expressing HBV surface antigen (HBsAg)-specific TCR, such as IMC-I109V.

TCR-T cell therapy includes TCR-T therapy directed to treatment of HBV, such as LTCR-H2-1.

In another specific embodiment, the immunogenic polypeptides, polynucleotides encoding such polypeptides, vectors, LNPs and immunogenic compositions comprising such polypeptides or polynucleotides, as described herein, are combined or co-administered with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, the immunogenic polypeptides, polynucleotides encoding such polypeptides, vectors, LNPs and immunogenic compositions comprising such polypeptides or polynucleotides, as described herein, are combined or co-administered with at least a second additional therapeutic agent selected from the group consisting of: HBV DNA polymerase inhibitors, immunomodulator, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARPins®, anti-pMHC TCR-like antibodies, DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, the immunogenic polypeptides, polynucleotides encoding such polypeptides, vectors, LNPs and immunogenic compositions comprising such polypeptides or polynucleotides, as described herein, are combined or co-administered with at least a second additional therapeutic agent selected from the group consisting of: HBV DNA polymerase inhibitors, HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment the immunogenic polypeptides, polynucleotides encoding such polypeptides, vectors, LNPs and immunogenic compositions comprising such polypeptides or polynucleotides, as described herein, are combined or co-administered with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics)., US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In certain embodiments, the immunogenic polypeptides, polynucleotides encoding such polypeptides, vectors, LNPs and immunogenic compositions comprising such polypeptides or polynucleotides, as described herein, are combined or co-administered with 5-30 mg tenofovir alafenamide fumarate, tenofovir alafenamide hemifumarate, or tenofovir alafenamide. In certain embodiments, the immunogenic polypeptides, polynucleotides encoding such polypeptides, vectors, LNPs and immunogenic compositions comprising such polypeptides or polynucleotides, as described herein, are combined or co-administered with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, the immunogenic polypeptides, polynucleotides encoding such polypeptides, vectors, LNPs and immunogenic compositions comprising such polypeptides or polynucleotides, as described herein, are combined or co-administered with 10 mg tenofovir alafenamide fumarate, tenofovir alafenamide hemifumarate, or tenofovir alafenamide. In certain embodiments, the immunogenic polypeptides, polynucleotides encoding such polypeptides, vectors, LNPs and immunogenic compositions comprising such polypeptides or polynucleotides, as described herein, are combined or co-administered with 25 mg tenofovir alafenamide fumarate, tenofovir alafenamide hemifumarate, or tenofovir alafenamide. An agent as disclosed herein may be combined with the immunogenic polypeptides, polynucleotides encoding such polypeptides, vectors, LNPs and immunogenic compositions comprising such polypeptides or polynucleotides, as described herein, in any dosage amount of the compound (e.g., from 50 mg to 500 mg of compound) the same as if each combination of dosages were specifically and individually listed.

In certain embodiments, the immunogenic polypeptides, polynucleotides encoding such polypeptides, vectors, LNPs and immunogenic compositions comprising such polypeptides or polynucleotides, as described herein, are combined or co-administered with 100-400 mg tenofovir disoproxil fumarate, tenofovir disoproxil hemifumarate, or tenofovir disoproxil. In certain embodiments, an agent disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, an agent disclosed herein, or a pharmaceutically acceptable salt thereof, is combined with 300 mg tenofovir disoproxil fumarate, tenofovir disoproxil hemifumarate, or tenofovir disoproxil. In certain embodiments, an agent disclosed herein, or a pharmaceutically acceptable salt thereof, is combined with 250 mg tenofovir disoproxil fumarate, tenofovir disoproxil hemifumarate, or tenofovir disoproxil. In certain embodiments, an agent herein, or a pharmaceutically acceptable salt thereof, is combined with 150 mg tenofovir disoproxil fumarate, tenofovir disoproxil hemifumarate, or tenofovir disoproxil. An agent as disclosed herein may be combined with the immunogenic polypeptides, polynucleotides encoding such polypeptides, vectors, LNPs and immunogenic compositions comprising such polypeptides or polynucleotides, as described herein, in any dosage amount of the compound (e.g., from 50 mg to 500 mg of compound) the same as if each combination of dosages were specifically and individually listed.

8. Kits

Further provided is a kit comprising one or more unitary doses of one or more of the truncated HBV polymerase polypeptide, one or more of the HBV polymerase deletion mutant polypeptide, one or more of the core-sAg fusion protein, one or more polynucleotides, one or more vectors, or one or more immunogenic compositions, as described herein. In some embodiments, the kit comprises one or more unitary doses of two or more of the truncated HBV polymerase polypeptide, the HBV polymerase deletion mutant polypeptide, the core-sAg fusion protein, the polynucleotides, the vectors, or the immunogenic compositions, described herein.

In various embodiments, as appropriate or desired, the one or more unitary doses can be in a single container or in two or more separate containers. In various embodiments, the one or more containers can be selected from the group consisting of vials, ampules and pre-loaded syringes.

In some embodiments, the one or more containers comprise the one or more polypeptides, one or more polynucleotides, one or more vectors or one or more immunogenic compositions in an aqueous solution. In some embodiments, the one or more containers comprise the one or more polypeptides, one or more polynucleotides, one or more vectors or one or more immunogenic compositions as a lyophilized preparation.

As appropriate or desired, the one or more unitary doses can be the same or different. In some embodiments, the kit comprises one or more unitary doses of one or more viral vectors capable of expressing the immunogenic polypeptides. In kits comprising viral vectors, the unitary doses can be in the range of about $10^3$ to about $10^{12}$ viral focus forming units (FFU) or plaque forming units (PFU) or infectious units (IU) or viral particles (vp), e.g. from about $10^4$ to about $10^7$ viral FFU or PFU, e.g. from about $10^3$ to about $10^4$, $10^5$, $10^6$, $10^7$, $10^8$, $10^9$, $10^{10}$, $10^{11}$ or $10^{12}$ viral FFU or PFU or IU or vp.

In various embodiments, the kit comprises one or more polynucleotides encoding, or one or more vectors capable of expressing, or an immunogenic composition comprising, two immunogenic polypeptides, the immunogenic polypeptides comprising: (a) an HBV polymerase polypeptide mutant comprising or consisting of an amino acid sequence of any one of SEQ ID NOs: 5-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 5-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41.

In various embodiments, the kit comprises one or more polynucleotides encoding, or one or more vectors capable of expressing, or an immunogenic composition comprising, two immunogenic polypeptides, the immunogenic polypeptides comprising: (a) an HBV polymerase polypeptide mutant comprising or consisting of an amino acid sequence of any one of SEQ ID NOs: 13-14, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 13-14; and (b) an HBV core-sAg fusion protein comprising or consisting of an amino acid sequence of any one of SEQ ID NOs: 38-41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 38-41.

In various embodiments, the kit comprises one or more polynucleotides encoding, or one or more vectors capable of expressing, or an immunogenic composition comprising, two immunogenic polypeptides, the immunogenic polypeptides comprising: (a) an HBV polymerase polypeptide mutant comprising or consisting of an amino acid sequence of SEQ ID NO: 13, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 13; and (b) an HBV core-sAg fusion protein comprising or consisting of an amino acid sequence of SEQ ID NO: 41, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 41.

With respect to the core-sAg fusion polypeptide in the kit (e.g., expressable from a vector; in an immunogenic composition), in some embodiments, the core polypeptide comprises a serine (S) residue at the amino acid position corresponding to position 12, and an asparagine (N) residue at the amino acid position corresponding to position 67, wherein the position numbers are with reference to SEQ ID NO:65 or SEQ ID NO:66. In some embodiments, the sAg polypeptide comprises an isoleucine (I) residue at the amino acid position corresponding to position 68, wherein the position numbers are with reference to SEQ ID NO:3 or SEQ ID NO:4. In some embodiments, the sAg polypeptide comprises one or more of a serine (S) residue at the amino acid position corresponding to position 53, an isoleucine (I) residue at the amino acid position corresponding to position 68, a threonine (T) residue at the amino acid position corresponding to position 125, a proline (P) residue at the amino acid position corresponding to position 127, an phenylalanine (F) residue at the amino acid position corresponding to position 161, a tyrosine (Y) residue at the amino acid position corresponding to position 200, a serine (S) residue at the amino acid position corresponding to position 210, and a leucine (L) residue at the amino acid position corresponding to position 213, wherein the position numbers are with reference to SEQ ID NO:3 or SEQ ID NO:4. In some embodiments, the core-sAg fusion polypeptide comprises one or more of a serine (S) residue at the amino acid position corresponding to position 12, an asparagine (N) residue at the amino acid position corresponding to position 67, a valine (V) residue at the amino acid position corresponding to position 74, a phenylalanine (F) residue at the amino acid position corresponding to position 97, a threonine (T) residue at the amino acid position corresponding to position 249, a threonine (T) residue at the amino acid position corresponding to position 250, a serine (S) residue at the amino acid position corresponding to position 317, a serine (S) residue at the amino acid position corresponding to position 318, an arginine (R) residue at the amino acid position corresponding to position 326, a tyrosine (Y) residue at the amino acid position corresponding to position 338, a glycine (G) residue at the amino acid position corresponding to position 363, and an alanine (A) residue at the amino acid position corresponding to position 372, wherein the position numbers are with reference to SEQ ID NO:41.

In some embodiments, the kit comprises a first viral expression vector and a second viral expression vector, wherein: (a) the first viral expression vector comprises a polynucleotide comprising or consisting of a nucleic acid sequence of any one of SEQ ID NOs: 27-32 and 89-94, e.g., SEQ ID NOs: 29, 89, 90 and 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 27-32 and 89-94, e.g., SEQ ID NOs: 29, 89, 90 and 92; and (b) the second viral expression vector comprises a polynucleotide comprising or consisting of a nucleic acid sequence of any one of SEQ ID NOs: 33-37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to any one of SEQ ID NOs: 33-37.

In some embodiments, the kit comprises a first viral expression vector and a second viral expression vector, wherein: (a) the first viral expression vector comprises a polynucleotide comprising or consisting of a nucleic acid sequence of SEQ ID NOs: 29, 89, 90 or 92, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NOs: 29, 89, 90 or 92; and (b) the second viral expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37.

In some embodiments, the kit comprises: (a) one or more unitary doses of an immunogenic composition as described above and herein, wherein the first and second viral expression vectors comprise a replication-deficient or replication-defective Cali mammarenavirus (a.k.a., Pichinde mammarenavirus or Pichinde arenavirus (PICV)); and (b) one or more unitary doses of an immunogenic composition as described above and herein, wherein the first and second viral expression vectors comprise a replication-deficient or replication-defective Lymphocytic choriomeningitis mammarenavirus (LCMV).

In some embodiments, the kit comprises: (a) one or more unitary doses of an immunogenic composition as described above and herein, wherein the first and second viral expression vectors are from Adenoviridae; and (b) one or more unitary doses of an immunogenic composition as described above and herein, wherein the first and second viral expression vectors are from Poxviridae (e.g., Vaccinia virus, e.g., modified vaccinia Ankara (MVA)).

In some embodiments, the kit comprises: (a) one or more unitary doses of an immunogenic composition as described above and herein, wherein the first and second viral expression vectors are from Arenaviridae; and (b) one or more unitary doses of an immunogenic composition as described above and herein, wherein the first and second viral expression vectors are from Adenoviridae.

In some embodiments, the kit comprises: (a) one or more unitary doses of an immunogenic composition as described above and herein, wherein the first and second viral expression vectors are from Arenaviridae; and (b) one or more unitary doses of an immunogenic composition as described above and herein, wherein the first and second viral expression vectors are from Poxviridae (e.g., Vaccinia virus, e.g., modified vaccinia Ankara (MVA)).

In some embodiments, the kit comprises a first LCMV arenavirus expression vector and a second LCMV arenavirus expression vector, wherein: (a) the first LCMV arenavirus expression vector comprises a polynucleotide comprising or consisting of a nucleic acid sequence of SEQ ID NO: 29, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 29; and (b) the second LCMV arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37.

In some embodiments, the kit comprises a first Pichinde arenavirus expression vector and a second Pichinde arenavirus expression vector, wherein: (a) the first Pichinde arenavirus expression vector comprises a polynucleotide comprising or consisting of a nucleic acid sequence of SEQ ID NO: 90, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 90; and (b) the second Pichinde arenavirus expression vector comprises a polynucleotide comprising or consisting of a nucleic acid sequence of SEQ ID NO: 37, or a sequence that is at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO: 37.

In various embodiments, the kit comprises one or more unitary doses of one or more additional therapeutic agents.

For example, in some embodiments, the kit comprises one or more agonists or activators of one or more toll-like receptors (TLRs). In various embodiments, the TLR agonist or activator is selected from the group consisting of a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from the group consisting of GS 9620 (vesatolimod), R848 (Resiquimod), DS-0509, LHC-165 and TMX-101 (imiquimod), and/or wherein the TLR8 agonist is selected from the group consisting of GS-9688, R848 (Resiquimod) and NKTR-262 (dual TLR7/TLR8 agonist).

In some embodiments, the kit comprises one or more interleukin receptor agonists of an interleukin receptor selected from IL-2, IL-7, IL-12 and IL-15. In some embodiments, the kit comprises one or more cytokines selected from the group consisting of IL-2, IL-7, IL-12, IL-15, and variants thereof.

In some embodiments, the kit comprises one or more innate immune activators. In various embodiments, the one or more innate immune activators comprises an agonist of a receptor selected from the group consisting of fms related tyrosine kinase 3 (FLT3), stimulator of interferon genes (STING) receptor, DExD/H-box helicase 58 (DDX58; a.k.a., RIG-I), nucleotide binding oligomerization domain containing 2 (NOD2). In some embodiments, the kit comprises one or more unitary doses of GS-3583 and/or GS-9992.

In some embodiments, the kit comprises one or more antagonists or inhibitors of an inhibitory immune checkpoint protein or receptor and/or one or more activators or agonists of a stimulatory immune checkpoint protein or receptor. In various embodiments, the one or more immune checkpoint proteins or receptors are selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

In some embodiments, the kit comprises one or more blockers or inhibitors of one or more T-cell inhibitory immune checkpoint proteins or receptors. In various embodiments, the blockers or inhibitors of one or more T-cell inhibitory immune checkpoint proteins or receptors are selected from the group consisting of CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1).

In some embodiments, the kit comprises one or more agonists or activators of one or more T-cell stimulatory immune checkpoint proteins or receptors. In various embodiments, the agonists or activators of one or more T-cell stimulatory immune checkpoint proteins or receptors are selected from the group consisting of CD27, CD70; CD40, CD40LG; inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNF SF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the kit comprises one or more unitary doses of AGEN-2373 and/or AGEN-1223.

In some embodiments, the kit comprises one or more blockers or inhibitors of one or more NK-cell inhibitory immune checkpoint proteins or receptors. In various embodiments, the NK-cell inhibitory immune checkpoint proteins or receptors are selected from the group consisting of killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94).

In some embodiments, the kit comprises one or more agonists or activators of one or more NK-cell stimulatory immune checkpoint proteins or receptors. In various embodiments, the NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7).

In various embodiments of the kits, the one or more immune checkpoint inhibitors comprises a proteinaceous inhibitor of PD-L1 (CD274), PD-1 (PDCD1) or CTLA4. In some embodiments, the proteinaceous inhibitor of CTLA4 is selected from the group consisting of ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the proteinaceous inhibitor of PD-L1 (CD274) or PD-1 (PDCD1) is selected from the group consisting of zimberelimab (AB122), pembrolizumab, nivolumab, cemiplimab, pidilizumab, AMP-224, MEDI0680 (AMP-514), spartalizumab, atezolizumab, avelumab, ASC22, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1). In some embodiments, the one or more immune checkpoint inhibitors comprises a small molecule inhibitor of CD274 (PDL1, PD-L1), programmed cell death 1 (PDCD1, PD1, PD-1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

In various embodiments, the kit comprises one or more anti-viral agents. Illustrative anti-viral agents that can be in the kit include lamivudine (LAM), adefovir dipivoxil (ADV), entecavir (ETV), telbivudine (LdT), tenofovir disoproxil fumarate (TDF), tenofovir alafenamide (TAF or VEMLIDY®) and ledipasvir+sofosbuvir (HARVONI®). In some embodiments, the kit comprises one or more therapeutic agents selected from the group consisting of HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), gene editors targeting HBV (e.g., CRISPR-Cas (e.g., Cas9, Cas12, Cascade, Cas13), zinc finger nucleases, homing endonucleases, homing meganucleases (e.g., ARCUS), synthetic nucleases, TALENs), covalently closed circular DNA (cccDNA) inhibitors and HBsAg secretion or assembly inhibitors and HBV viral entry inhibitors.

Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

The following examples are offered to illustrate, but not to limit the claimed invention.

Example 1

Identification of HBV sAg Sequences that Induce Robust, Genotype Cross-Reactive T Cell Responses In this example, we identified near-consensus, naturally occurring sequences of HBV sAg in genotypes A, B, C, and D, generated adenovirus type 5 vectors encoding each antigen, and tested the magnitude and genotype cross-reactivity of the T cells induced by each of these vectors in outbred mice.

Selection of near-consensus, naturally occurring HBV sAg sequences. In selecting the specific amino acid sequence of an HBV sAg to be used for therapeutic vaccination, we sought an sAg sequence that was both efficiently expressed and processed for antigen presentation, while also inducing T cell responses that react broadly across a range of HBV genotypes. Although consensus sequences or mosaic antigens can be designed to attempt to improve T cell genotype reactivity, such sequences do not occur in nature and have a risk of being inefficiently expressed or poorly processed into T-cell epitopes. Consequently, we identified near-consensus, naturally occurring HBV sAg sequences from genotypes (GT) A, B, C and D. Using a database of sAg sequences from 14207 individuals infected with these HBV genotypes, we constructed consensus sequences for each genotype, then identified the naturally occurring sAg sequence closest to the consensus for each genotype. The naturally occurring, near-consensus sAg sequences for HBV genotypes A, B, C and D are provided in Table 1 as SEQ ID NOs: 1-4, respectively.

TABLE 1

Naturally-occurring, near-consensus sAg polypeptide sequences

| SEQ ID NO: | HBV genotype | Polypeptide sequence |
|---|---|---|
| 1 | A | MENITSGFLGPLLVLQAGFFLLTRILTIPQSLDSWWTSLNFLGGTPVC LGQNSQSPTSNHSPTSCPPICPGYRWMCLRRFIIFLFILLLCLIFLLV LLDYQGMLPVCPLIPGSTTTSTGPCKTCTTPAQGNSMFPSCCCTKPTD GNCTCIPIPSSWAFAKYLWEWASVRFSWLSLLVPFVQWFVGLSPTVWL SVIWMMWYWGPSLYNILSPFIPLLPIFFCLWVYI |
| 2 | B | MESTTSGFLGPLLVLQAGFFLLTRILTIPQSLDSWWTSLNFLGGAPTC PGQNLQSPTSNHSPTSCPPICPGYRWMCLRRFIIFLFILLLCLIFLLV LLDYQGMLPVCPLIPGSSTTSTGPCRTCTTPAQGTSMFPSCCCTKPTD GNCTCIPIPSSWAFAKYLWEWASVRFSWLSLLVPFVQWFVGLSPTVWL SVIWMMWYWGPSLYNILSPFMPLLPIFFCLWVYI |
| 3 | C | MESTTSGFLGPLLVLQAGFFLLTRILTIPQSLDSWWTSLNFLGGAPTC PGQNSQSPTSNHSPTSCPPICPGYRWMCLRRFIIFLCILLLCLIFLLV LLDYQGMLPVCPLIPGSSTTSTGPCKTCTTPAQGTSMFPSCCCTKPTD GNCTCIPIPSSWAFARFLWEWASVRFSWLSLLVPFVQWFVGLSPTVWL SVIWMMWYWGPSLYNILSPFLPLLPIFFCLWVYI |
| 4 | D | MENITSGFLGPLLVLQAGFFLLTRILTIPQSLDSWWTSLNFLGGTTVC LGQNSQSPTSNHSPTSCPPICPGYRWMCLRRFIIFLFILLLCLIFLLV LLDYQGMLPVCPLIPGSSTTSTGPCRTCTTPAQGTSMYPSCCCTKPSD GNCTCIPIPSSWAFGKFLWEWASARFSWLSLLVPFVQWFVGLSPTVWL SVIWMMWYWGPSLYSILSPFLPLLPIFFCLWVYI |

Methods

To evaluate the immunogenicity of each antigen and assess the genotype cross-reactivity of induced T cells across a broad range of epitopes in vivo, Diversity Outbred mice (DO mice) from Jackson Laboratories were used for vaccination. DO mice were developed by random outcross matings of 160 Collaborative Cross recombinant inbred mouse lines, and the colony is maintained by continued random matings that avoid crosses between siblings. The DO parental lines, the Collaborative Cross strains, were developed by crossing eight unique and genetically diverse inbred mouse strains (A/J, C57BL/6J, 129S1/SvImJ, NOD/ShiLtJ, NZO/HlLtJ, CAST/EiJ, PWK/PhJ, and WSB/EiJ). Therefore, DO mice capture the diversity of epitope selection and magnitude of T cell responses present in a highly genetically diverse population.

Results

All four naturally occurring, near-consensus sequences of HBV sAg were robustly immunogenic in DO mice (FIG. 1). Induced T cells reacted to GT-A, B, C, and D HBV sAg peptides with approximately equal magnitude, demonstrating excellent genotype cross-reactivity of the T cell response. Geometric mean response magnitude was largest for GT-C and GT-D sAg.

Example 2

Identification of HBV Core and Pol Sequences that Induce Robust, Genotype Cross-Reactive T Cell Responses In this example, we identified near-consensus, naturally occurring sequences of HBV core and HBV polymerase (Pol) in genotypes A, B, C, and D, generated Adenovirus type 5 expression vectors encoding Pol antigens or core-Pol fusion proteins, and tested the magnitude and genotype cross-reactivity of the T cells induced in inbred and outbred animals.

Selection of near-consensus, naturally occurring HBV core and Pol sequences. In selecting the specific amino acid sequence of an HBV core and Pol antigens to be used for therapeutic vaccination, we sought core and Pol sequences that were both efficiently expressed and processed for antigen presentation, while also inducing T cell responses that react broadly across a range of HBV genotypes. Although consensus sequences or mosaic antigens can be designed to attempt to improve T cell genotype reactivity, such sequences do not occur in nature and have a risk of being inefficiently expressed or poorly processed into T cell epitopes. Consequently, we identified near-consensus, naturally occurring HBV core and Pol sequences from genotypes A, B, C and D. Using a database of core sequences from 5528 individuals infected with HBV genotypes A-D, and Pol sequences from 4713 individuals infected with HBV genotypes A-D, we constructed consensus sequences for core and Pol for each genotype, then identified the naturally occurring core and Pol sequences closest to the consensus for each genotype.

GT-A, B, C, and D Pol sequences were then modified to improve antigen performance. The enzymatic activity of polymerases can induce toxicity when overexpressed, so the enzymatic activity of the reverse transcriptase (RT) and RNase H (RNH) domains was ablated by mutations in the catalytic domains. The YMDD motif in RT was mutated to YMHD, and the AELL motif in RNH was mutated to AHLL (Radziwill, et al., *J Virol.* (1990) 64(2):613-20). The resulting Pol sequences are referred to as Pol$^{mut}$. The Pol$^{mut}$ sequences for HBV genotypes A, B, C and D are provided in Table 2 as SEQ ID NOs: 52-55, respectively.

TABLE 2

Pol^mut polypeptide sequence

| SEQ ID NO: | HBV genotype | Polypeptide sequence-Motifs containing inactivating mutations in Pol are underlined (YMDD mutated to YMHD, AELL mutated to AHLL) |
|---|---|---|
| 52 | A | MPLSYQHFRKLLLLDDETEAGPLEEELPRLADEDLNRRVAEDLNLGNLNV SIPWTHKVGNFTGLYSSTVPIFNPEWQTPSFPKIHLHEDIANRCQQFVGP LTVNEKRRLRLIMPARFYPNSTKYLPLDKGIKPYYPDHVVNHYFQTRHYL HTLWKAGILYKRETTRSASFCGSPYSWEQELHHGRLVIKTSQRHGDEPFC SQPSGILSRSSVGPCIRSQFKQSRLGLQPHQGPLATSQSGRSGSIRARVH SPTRRCFGVEPSGSGHIGHSASSSSSCLHQSAVRKAAYSHLSTSKRQSSS GHAVEFHSFPPSSARSQSQGPVFSCWWLQFRNTQPCSKYCLSHLVNLLED WGPCDEHGEHHIRIPRTPARVTGGVFLVDKNPHNTAESRLVVDFSQFSRG ITRVSWPKFAVPNLQSLTNLLSSNLSWLSLDVSAAFYHIPLHPAAMPHLL VGSSGLSRYVARLSSNSRIHNNQHGTLQNLHDSCSRQLYVSLMLLYKTYG RKLHLYSHPIILGFRKIPMGVGLSPFLLAQFTSAICSVVRRAFPHCLAFS <u>YMHD</u>VVLGAKSVQHLESLYTAVTNFLLSLGIHLNPNKTKRWGYSLNFMGY VIGSWGTLPQDHIVQKIKHCFRKLPINRPIDWKVCQRIVGLLGFAAPFTQ CGYPALMPLYACIQAKQAFTFSPTYKAFLSKQYLNLYPVARQRPGLCQVF ADATPTGWGLAIGHQRMRGTFVAPLPIHT<u>AHLL</u>AACFARSRSGAKLIGTD NSVVLSRKYTSFPWLLGCTANWILRGTSFVYVPSALNPADDPSRGRLGLY RPLLRLPYRPTTGRTSLYAVSPSVPSHLPVRVHFASPLHVAWRPP |
| 53 | B | MPLSYQHFRKLLLLDDEAGPLEEELPRLADEGLNRRVAEDLNLGNLNVSI PWTHKVGNFTGLYSSTVPVFNPEWQTPSFPHIHLQEDIINRCQQYVGPLT VNEKRRLKLIMPARFYPNLTKYLPLDKGIKPYYPEHVVNHYFQTRHYLHT LWKAGILYKRESTRSASFCGSPYSWEQDLQHGRLVFQTSKRHGDKSFCPQ SPGILPRSSVGPCIQNQLRKSRLGPQPAQGQLAGRQQGGSGSIRARVHPS PWGTVGVEPSGSGHIHNCASNSSSCLHQSAVRKAAYSHISTSKGHSSSGH AVELHHFPPSSSRSQSQGPVLSCWWLQFRNSEPCSEYCLCHIVNLIEDWG PCTEHGEHRIRTPRTPARVTGGVFLVDKNPHNTTESRLVVDFSQFSRGNT RVSWPKFAVPNLQSLTNLLSSNLSWLSLDVSAAFYHLPLHPAAMPHLLVG SSGLSRYVARLSSNSRIINNQHRTMQNLHDSCSRNLYVSLMLLYKTYGRK LHLYSHPIILGFRKIPMGVGLSPFLLAQFTSAICSVVRRAFPHCLAFS<u>YM HD</u>VVLGAKSVQHLESLYAAVTNFLLSLGIHLNPHKTKRWGYSLNFMGYVI GSWGTLPQEHIVQKIKMCFRKLPVNRPIDWKVCQRIVGLLGFAAPFTQCG YPALMPLYACIQAKQAFTFSPTYKAFLSKQYLHLYPVARQRPGLCQVFAD ATPTGWGLAIGHQRMRGAFVSPLPIHT<u>AHLL</u>AACFARSRSGAKLIGTDNS VVLSRKYTSFPWLLGCAANWILRGTSFVYVPSALNPADDPSRGRLGLYRP LLRLLYRPTTGRTSLYADSPSVPSHLPDRVHFASPLHVAWRPP |
| 54 | C | MPLSYQHFRKLLLLDDEAGPLEEELPRLADEDLNRRVAEDLNLGNLNVSI PWTHKVGNFTGLYSSTVPVFNPEWQTPSFPHIHLQEDIINRCQQYVGPLT VNEKRRLKLIMPARFYPNLTKYLPLDKGIKPYYPEHTVNHYFKTRHYLHT LWKAGILYKRETTRSASFCGSPYSWEQELQHGRLVFQTSTRHGDESFCSQ SSGILSRSPVGPCIRSQLKQSRLGLQPQQGSLARSKSGRSGSIRARVHPT TRQSFGVEPSGSGHIDNSASSASSCLHQSAVRKTAYSHLSTSKRQSSSGH AVELHNFPPSSARSQSEGPLLSCWWLQFRNSKPCSDYCLSHIVNLLEDWG PCTEHGEHNIRIPRTPARVTGGVFLVDKNPHNTTESRLVVDFSQFSRGST HVSWPKFAVPNLQSLTNLLSSNLSWLSLDVSAAFYHLPLHPAAMPHLLVG SSGLSRYVARLSSTSRNINYQHGAMQDLHDSCSRNLYVSLLLLYKTFGRK LHLYSHPIILGFRKIPMGVGLSPFLLAQFTSAICSVVRRAFPHCLAFS<u>YM HD</u>VVLGAKSVQHLESLFTAVTNFLLSLGIHLNPNKTKRWGYSLNFMGYVI GSWGTLPQEHIVLKIKQCFRKLPVNRPIDWKVCQRIVGLLGFAAPFTQCG YPALMPLYACIQAKQAFTFSPTYKAFLCKQYLNLYPVARQRSGLCQVFAD ATPTGWGLAVGHQRMRGTFVSPLPIHT<u>AHLL</u>AACFARSRSGAKLIGTDNS VVLSRKYTSFPWLLGCAANWILRGTSFVYVPSALNPADDPSRGRLGLYRP LLRLPFRPTTGRTSLYAVSPSVPSHLPVRVHFASPLHVAWRPP |
| 55 | D | MPLSYQHFRRLLLLDDEAGPLEEELPRLADEGLNRRVAEDLNLGNLNVSI PWTHKVGNFTGLYSSTVPVFNPHWKTPSFPNIHLHQDIIKKCEQFVGPLT VNEKRRLQLIMPARFYPNVIKYLPLDKGIKPYYPEHLVNHYFQTRHYLHT LWKAGILYKRETTHSASFCGSPYSWEQELQHGAESFHQQSSGILSRPPVG SSLQSKHRKSRLGLQSQQGHLARRQQGRGWSIRAGIHPTARRPFGVEPSG SGHTANLASKSASCLYQSAVRKAAYPVVSTFKKHSSSGHAVELHNLPPNS ARSQSERPVFPCWWLQFRNSKPCSDYCLSHIVNLLEDWGPCAEHGEHHIR IPRTPARVTGGVFLVDKNPHNTAESRLVVDFSQFSRGNYRVSWPKFAVPN LQSLTNLLSSNLSWLSLDVSAAFYHLPLHPAAMPHLLVGSSGLSRYVARL SSNSRIFNYQHGTMQNLHDSCSRNLYVSLMLLYQTFGRKLHLYSHPIILG FRKIPMGVGLSPFLLAQFTSAICSVVRRAFPHCLAFS<u>YMHD</u>VVLGAKSVQ HLESLFTAVTNFLLSLGIHLNPNKTKRWGYSLHFMGYVIGCYGSLPQDHI IQKIKECFRKLPVNRPIDWKVCQRIVGLLGFAAPFTQCGYPALMPLYACI QSKQAFTFSPTYKAFLCKQYLNLYPVARQRPGLCQVFADATPTGWGLVMG HQRMRGTFKAPLPIHT<u>AHLL</u>AACFARSRSGANILGTDNSVVLSRKYTSFP WLLGCAANWILRGTSFVYVPSALNPADDPSRGRLGLYRPLLRLPFRPTTG RTSLYADSPSVPSHLPDRVHFASPLHVAWRPP |

Figure 2:
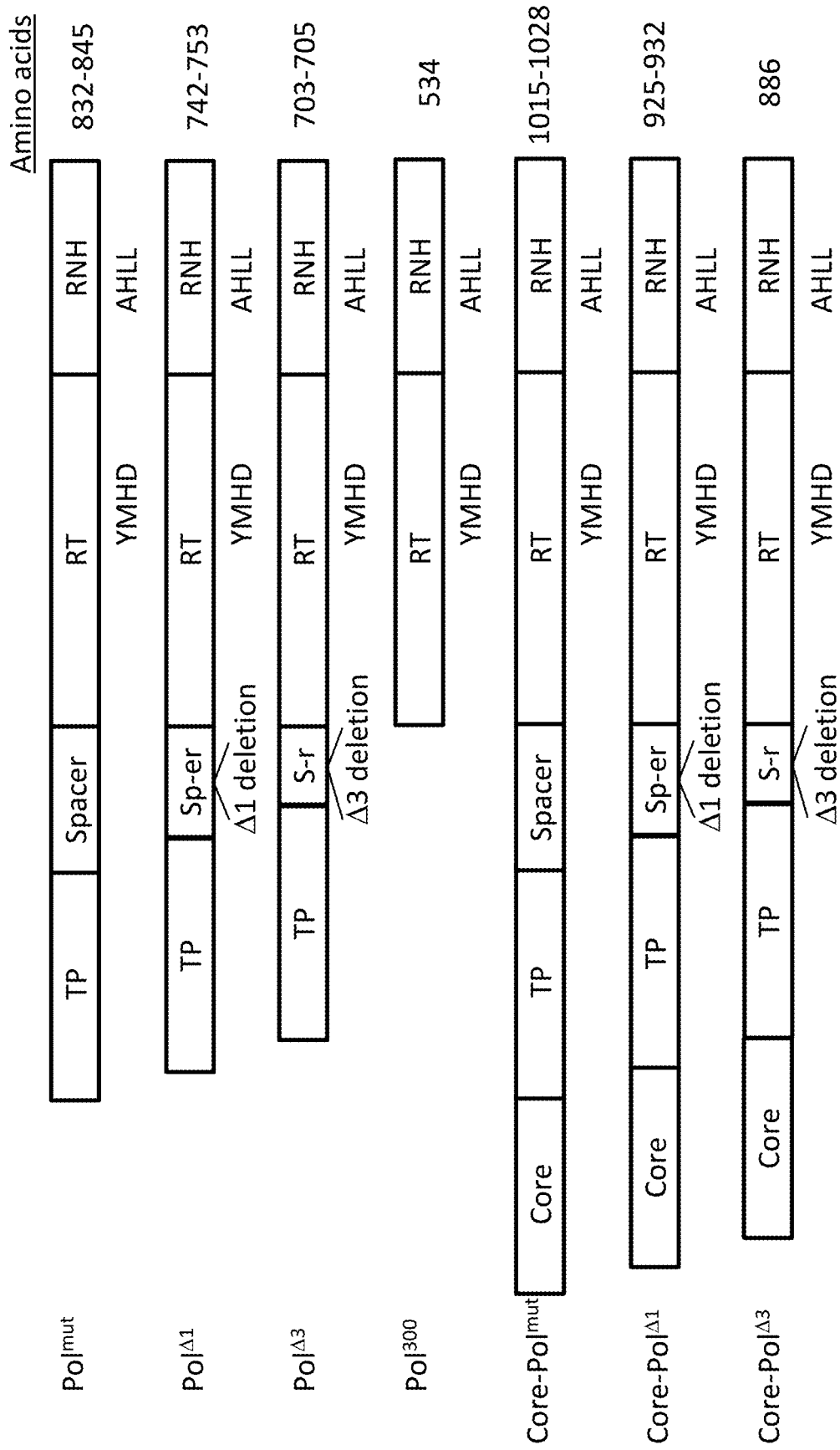
FIG. 2 illustrates schematics of each Pol-containing antigen design. Each Pol domain is indicated separately (TP, terminal protein; RT, Reverse Transcriptase; RNH, RNase H). Approximate location of the D to H mutation in the YMDD motif (SEQ ID NO: 97) in RT and of the E to H mutation in the AELL motif (SEQ ID NO: 98) in RNH are indicated below the RT and RNH domains. Designation of each construct is shown at left, and the amino acid size range of the GT-A, B, C, and D constructs is shown at right. "YMHD" and "AHLL" disclosed as SEQ ID NOS 99 and 100, respectively.

Pol$^{mut}$ sequences were then further modified to remove amino acid regions that are poorly conserved among HBV strains and genotypes, to generate Pol sequences of varying length to accommodate viral vectors with differing constraints on encoded antigen size, and to create core-Pol fusions in order to encode two antigens with a single open reading frame. Pol consists of four functional domains, Terminal Protein (TP), Spacer, RT, and RNH. Of these three, TP, RT, and RNH are highly conserved amongst HBV strains and genotypes and so are likely to induce strain- and genotype-cross-reactive T cells, whereas the Spacer domain is highly variable. We generated GT-A, B, C, and D Pol sequences with deletions in the Spacer region. In one set of sequences, designated Pol$^{\Delta 1}$, the deletion was based on a previously reported deletion mutant that retains enzymatic function in vitro, indicating that the deletion is not disruptive to the expression, structure and folding of the remaining protein (Radziwill, et al., *J Virol.* (1990) 64(2):613-20). In a second set of vectors designated Pol$^{\Delta 3}$, the entire poorly conserved region was identified by sequence alignment and deleted. Core-Pol fusions were generated by fusing the near-consensus core sequences to the Pol$^{mut}$, Pol$^{\Delta 1}$ and Pol$^{\Delta 3}$ sequences for GT-A, B, C, and D. Lastly, to accommodate viral vectors with smaller packaging limits, we constructed shorter versions of each near-consensus inactivated Pol sequence, designated as Pol$^{300}$. The Pol$^{300}$ variants have large N-terminal deletions in which the entire TP and most of the Spacer domain is removed, but the RT and RNaseH domains are maintained (Lanford et al., *J Virol.* (1999); 73(3):1885-93). A listing of Pol-containing antigen sequences tested in adenovirus or arenavirus vectors is shown in Table 3 and FIG. 2. Sequences of the amino acids removed from each Pol deletion constructs are provided in SEQ ID NOs: 42-51.

TABLE 3

Sequences of Pol-containing antigens

| Polypeptide SEQ ID NOs | Polypeptide |
|---|---|
| 5-8 for Genotype A-D, respectively | Pol$^{\Delta 1}$ |
| 9-12 for Genotype A-D, respectively | Pol$^{\Delta 3}$ |
| 13-14 for Genotype B and D, respectively | Pol$^{300}$ |
| 15-18 for Genotype A-D, respectively | Core-Pol$^{mut}$ |
| 19-22 for Genotype A-D, respectively | Core-Pol$^{\Delta 1}$ |
| 23-26 for Genotype A-D, respectively | Core-Pol$^{\Delta 3}$ |

Methods

Figure 3:
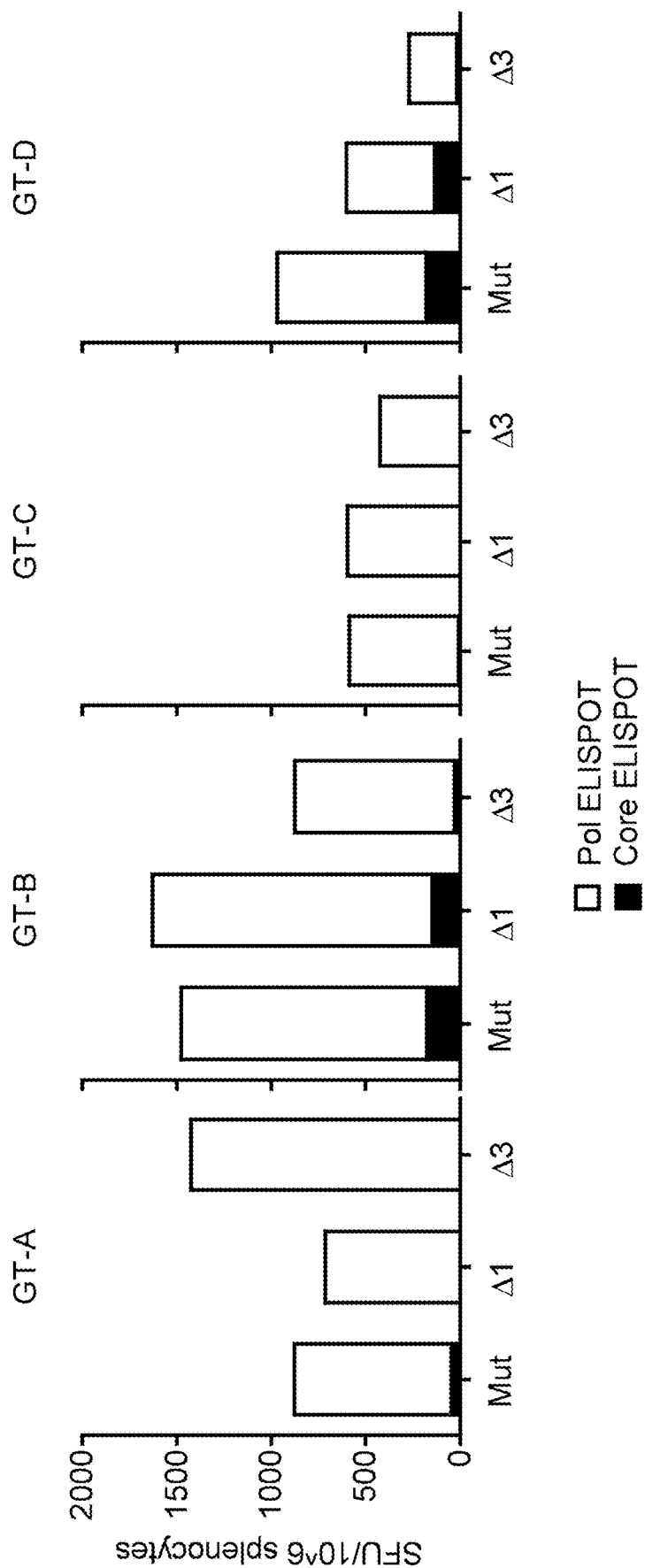
FIG. 3 illustrates the immunogenicity of Core-Pol fusion protein-expressing adenovirus vectors in C57BL/6 mice. Six- to eight-week-old C57BL/6 mice (n=5 per group) were injected with $1 \times 10^8$ viral particles (vp) of adenovirus encoding core-Pol fusion variants of SEQ ID NOs: 15-26. The genotype of each antigen is shown above each graph, while the antigen designations are shown on the horizontal axis (Mut: core-Pol$^{mut}$, Δ1: core-Pol$^{Δ1}$, Δ3: core-Pol$^{Δ3}$). On day 14 after injection, splenocytes were harvested and T cell responses evaluated by IFN-γ ELISPOT (BD mouse IFN-γ ELISPOT kit, catalog #551083) using overlapping peptide pools corresponding to GT-D core and Pol. Bars show stacked geometric mean responses for each group. SFU, spot forming units.

The immunogenicity of each GT-A, B, C, and D core-Pol fusion construct was initially tested in C57BL/6 mice for induction of T cell responses reactive with GT-D core and Pol peptide pools, to identify the variant within each genotype inducing the largest immunogenic response (FIG. 3). In all genotypes, a robust Pol response was detected but core responses were weaker or absent. The weak or absent core responses likely resulted from the fact that C57BL/6 mice are known to only respond to a single peptide from GT-D HBV core, namely, MGLKFRQL (Chiale, et al., Antiviral Res. 2019 August; 168:156-167). Responses to this peptide in C57BL/6 mice are often weak or absent, and the peptide has an alternate sequence in the GT-A, B, and C core sequences of MGLKIRQL.

Results

All antigen genotypes showed little change in immunogenicity between core-Pol$^{mut}$ and core Pol$^{\Delta 1}$. GT-A antigen had an increased response to core-Pol$^{\Delta 3}$ vs core-Pol$^{mut}$ and core-Pol$^{\Delta 1}$, whereas GT-B, C, and D all demonstrated reduced immunogenicity with core-Pol$^{\Delta 3}$.

T cell responses in inbred mouse strains are not ideal for comparing antigen immunogenicity across different genotypes because responses can be dominated by one or a few epitopes, which could vary in sequence among the antigens. To better compare the immunogenicity of core-Pol antigens across genotypes, immunogenicity was tested in DO mice to capture responses across a wide range of epitopes. DO mice were immunized with GT-A core-Pol$^{\Delta 3}$ or GT-B, C, or D core-Pol$^{\Delta 1}$, and T cell responses were assessed for IFN-γ ELISPOT response using GT-A and GT-D peptide pools (FIG. 4). GT-B core-Pol$^{\Delta 1}$ gave the best overall responses to Pol, with equally robust ELISPOT responses to GT-A and GT-D peptide pools (FIG. 4A). Pol responses to GT-B core-Pol$^{\Delta 1}$ were statistically significantly higher than responses to GT-A core-Pol$^{\Delta 3}$ using GT-D peptides, and to GT-C core-Pol$^{\Delta 1}$ using both peptide genotypes. The geometric mean Pol ELISPOT responses to GT-D core-Pol$^{\Delta 1}$ were numerically lower than GT-B core-Pol$^{\Delta 1}$, but the difference was not statistically significant. Responses to core were clearly detectable in the DO mice for all four antigen genotypes (FIG. 4B). The pattern of core responses was similar to the Pol responses with GT-B core-Pol$^{\Delta 1}$ yielding the overall best results, although for core no comparisons between antigen genotypes reached statistical significance.

Example 3

Identification of Smaller Immunogenic Pol Antigens

Different viral vector systems have differing limits on the maximum size of encoded antigens.

Methods

Figure 5:
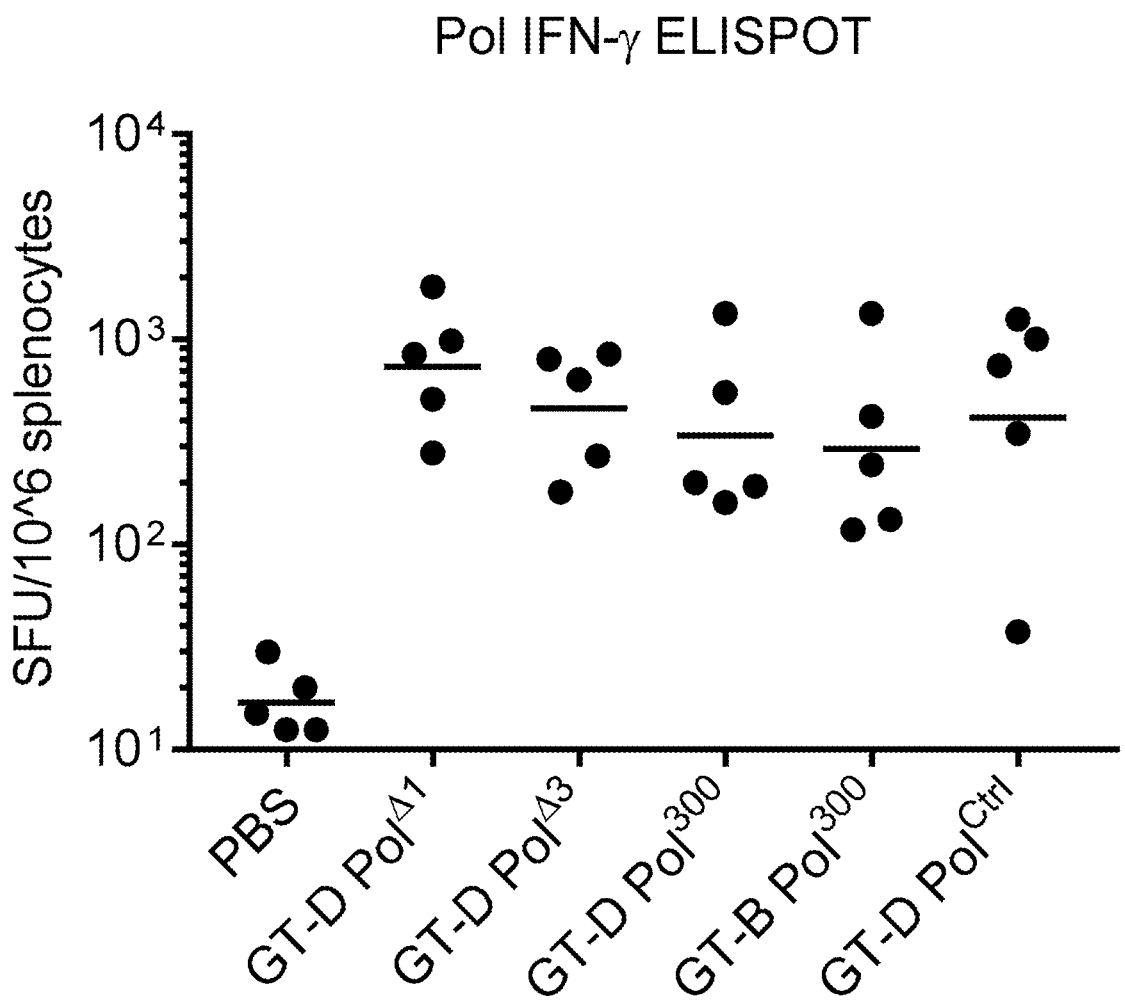
FIG. 5 illustrates the immunogenicity of Pol-expressing adenovirus vectors. Six- to eight-week-old C57BL/6 mice (n=5 per group) were injected with $1 \times 10^8$ viral particles (vp) of adenovirus expressing Pol antigen variants of SEQ ID NOs: 8, 12, 13, 14, or a full-length, unmodified GT-D Pol sequence (GT-D Pol$^{Ctrl}$). On day 14 after injection, splenocytes were harvested and T cell responses evaluated by IFN-γ ELISPOT (BD mouse IFN-γ ELISPOT kit, catalog #551083) using overlapping peptide pools corresponding to GT-D Pol. SFU: spot forming units.

To identify additional Pol variants that are smaller in size, and thus could be used in a wider range of vector systems, we evaluated the immunogenicity of Pol variants expressed without fusion to core. C57BL/6 mice were immunized with Adenovirus type 5 vectors encoding GT-D Pol$^{\Delta 1}$, Pol$^{\Delta 3}$, and Pol$^{300}$, and GT-B Pol$^{300}$, and compared to a control vector encoding a full-length, unmodified GT-D Polymerase (GT-D Pol$^{Ctrl}$) and mock vaccination with phosphate buffered saline (PBS) as a negative control. IFN-γ ELISPOT responses were measured 14 days after immunization with GT-D Pol peptide pools (FIG. 5).

Results

All tested Pol antigen designs were immunogenic, with no statistically significant differences between groups.

Example 4

Efficacy of Vaccination with Near-Consensus Antigens in Combination with Anti-PD-1 in Adeno-Associated Virus (AAV)-HBV Mice We used an Adeno-Associated Virus (AAV)-HBV model (Dion, et al., *J Virol.* (2013) 87(10):5554-63; and Yang, et al., *Cell Mol Immunol.* (2014) 11(1):71-8) to determine if our near-consensus antigen designs could have antiviral effects in a model of chronic HBV infection.

Methods

Figure 6:
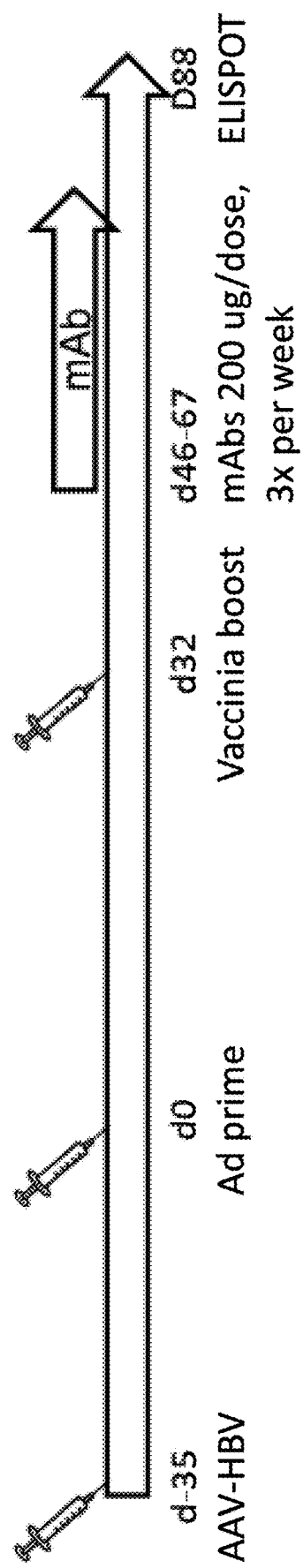
FIG. 6 illustrates the study design assessing the efficacy of HBV-expressing Ad5 and vaccinia vectors in the AAV mouse model of CHB (AAV-HBV). Six- to eight-week-old C57BL/6 mice were transduced with $10^{12}$ genome copies of AAV-HBV on day −35. Mice were randomized to treatment groups based on serum HBsAg levels at day −7. Adenovirus type 5 priming vaccines expressing HBV antigens were administered intramuscularly (i.m.) in 50 μl on day 0, and vaccinia boost vaccines expressing the same HBV antigens were administered i.m. in 50 μl on day 32. From days 46-67, mice were given either anti-PD-1 (anti-CD279) monoclonal antibody RMP1-14 or isotype control mAb. Blood samples were collected for viral antigen testing on days −7, 14, 27, 46, 60, 67, and 88. Splenocytes were harvested on day 88 and assessed for IFN-γ ELISPOT.

In this model, C57BL/6 mice were transduced with AAV vectors encoding a 1.2× length GT-D HBV genome, resulting in persistent HBV protein and virion production in hepatocytes, accompanied by antigenemia and viremia in serum. Heterologous viral vector prime-boost regimens consisting of an adenovirus (Ad) prime and poxvirus boost have yielded strong T cell responses in humans (see, e.g., Barnes, et al., *Sci Transl Med.* (2012) 4(115):115ra1; Ewer, et al., *N Engl J Med.* (2016) 374(17):1635-46; Ewer, et al. *Nat Commun.* (2013) 4:2836; Green, et al., *Sci Transl Med.* (2015) 7(300):300ra126; Swadling, et al., *Sci Transl Med.* (2014) 6(261):261ra153), so we generated vaccinia vectors based on the Western Reserve strain (NCBI:txid696871) expressing GT-C sAg and GT-B core-Pol$^{\Delta1}$. AAV-HBV mice were vaccinated with Ad5 prime and vaccinia boost vectors encoding GT-C sAg and GT-B core-Pol$^{\Delta1}$ or irrelevant control antigens beta-galactosidase and green fluorescent protein. Mice were further treated with either anti-mouse PD-1 monoclonal antibody or an isotype control antibody after the boost vaccination. A diagram of the AAV-HBV efficacy study is shown in FIG. 6, and treatment groups are shown in Table 4. A control group received HBV vaccine but no AAV-HBV to determine if vaccine responses were reduced in the presence of persistent HBV.

TABLE 4

Study Groups in AAV-HBV Efficacy Study

| Group | N | AAV-HBV | Prime | Boost | Antibody |
|---|---|---|---|---|---|
| 1 | 12 | Y | Ad-β-gal | Vac-GFP | Isotype ctrl |
| 2 | 12 | Y | Ad-sAg GT-C Ad-core-pol$^{\Delta1}$ GT-B | Vac-sAg GT-C Vac-core-pol$^{\Delta1}$ GT-B | Isotype ctrl |
| 3 | 12 | Y | Ad-β-gal | Vac-GFP | α-PD-1 |
| 4 | 12 | Y | Ad-sAg GT-C Ad-core-pol$^{\Delta1}$ GT-B | Vac-sAg GT-C Vac-core-pol$^{\Delta1}$ GT-B | α-PD-1 |
| 5 | 12 | N | Ad-sAg GT-C Ad-core-pol$^{\Delta1}$ GT-B | Vac-sAg GT-C Vac-core-pol$^{\Delta1}$ GT-B | None |

Ad: Adenovirus 5 vector. Vac: vaccinia vector. β-gal: beta-galactosidase. GFP: green fluorescent protein.

Results

Figure 7:
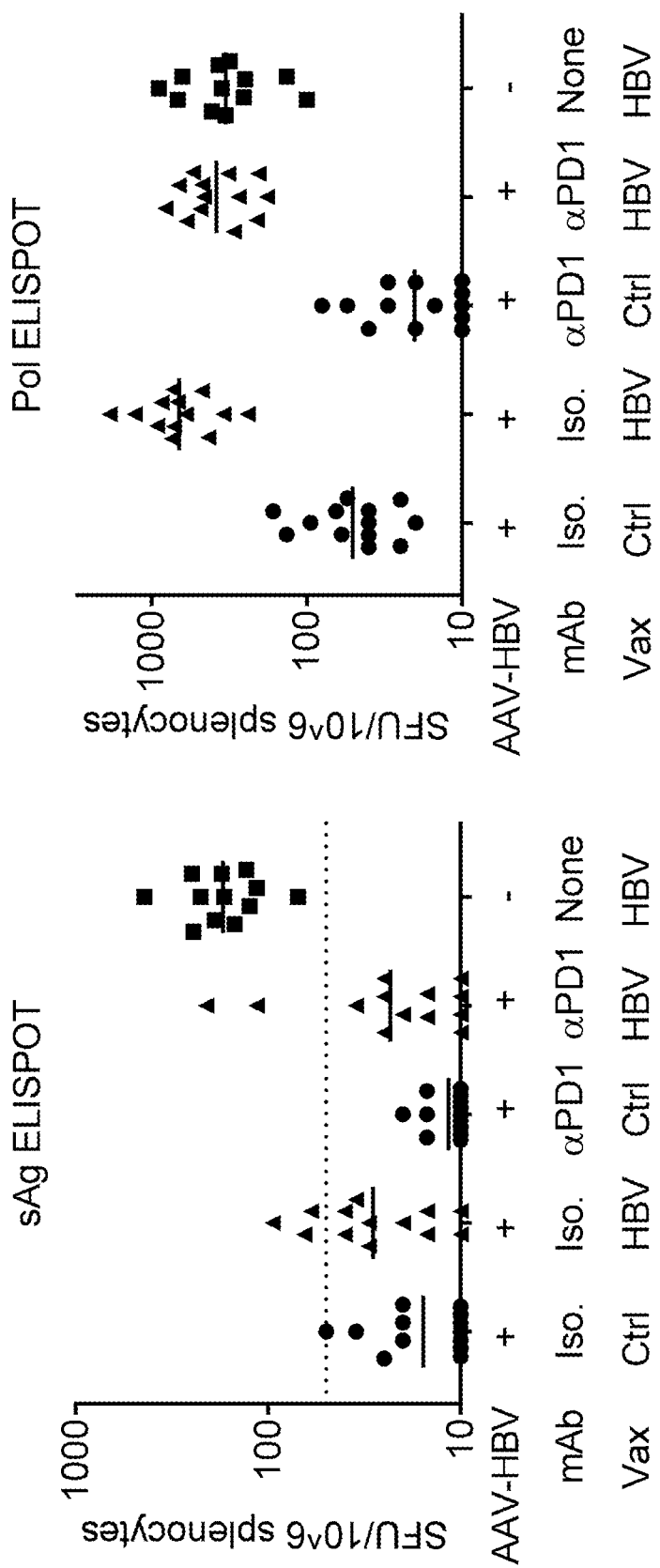
FIG. 7 illustrates the immunogenicity of Ad5 prime-vaccinia boost vaccination in AAV-HBV mice. Splenocytes were harvested on day 88 in the study shown in FIG. 6. T cell responses to HBsAg and Pol were evaluated by IFN-γ ELISPOT (BD mouse IFN-γ ELISPOT kit, catalog #551083) using overlapping peptide pools corresponding to GT-D sAg and Pol. Dashed line indicates the highest signal in HBsAg ELISPOT observed in mice receiving control vaccine. mAb: monoclonal antibody administered. Iso: isotype control. αPD-1: anti-PD-1. Vax: indicates whether the vaccine contained HBV antigens or control (Ctrl) antigens. SFU, spot forming units.

FIG. 7 shows the IFN-γ ELISPOT responses in each group. Note that responses were evaluated using GT-D peptide pools matched to the HBV strain in the AAV-HBV vector, so T cell responses are detected only if they react with the virus present in the AAV-HBV mice. Responses to core were tested but none were detected in any group, consistent with the poor immunogenicity of core in C57BL/6 mice (Chiale, et al., supra). Robust Pol ELISPOT responses were detected in all groups receiving Ad prime and vaccinia boost vectors encoding HBV antigens. Pol ELISPOT magnitude was similar in AAV-HBV mice and in control mice that did not receive AAV-HBV, indicating that the AAV-HBV does not result in T-cell tolerance to Pol. In contrast, ELISPOT responses to sAg were greatly reduced in AAV-HBV mice compared to control mice, demonstrating that AAV-HBV induces T cell tolerance to sAg. Nevertheless, in mice that received AAV-HBV and Adenovirus prime-vaccinia boost HBV vaccine, 2-3 mice per group demonstrated sAg ELISPOT responses above those detected in control-vaccinated mice. ELISPOT response magnitudes were not changed by anti-PD-1 treatment.

Figure 8:
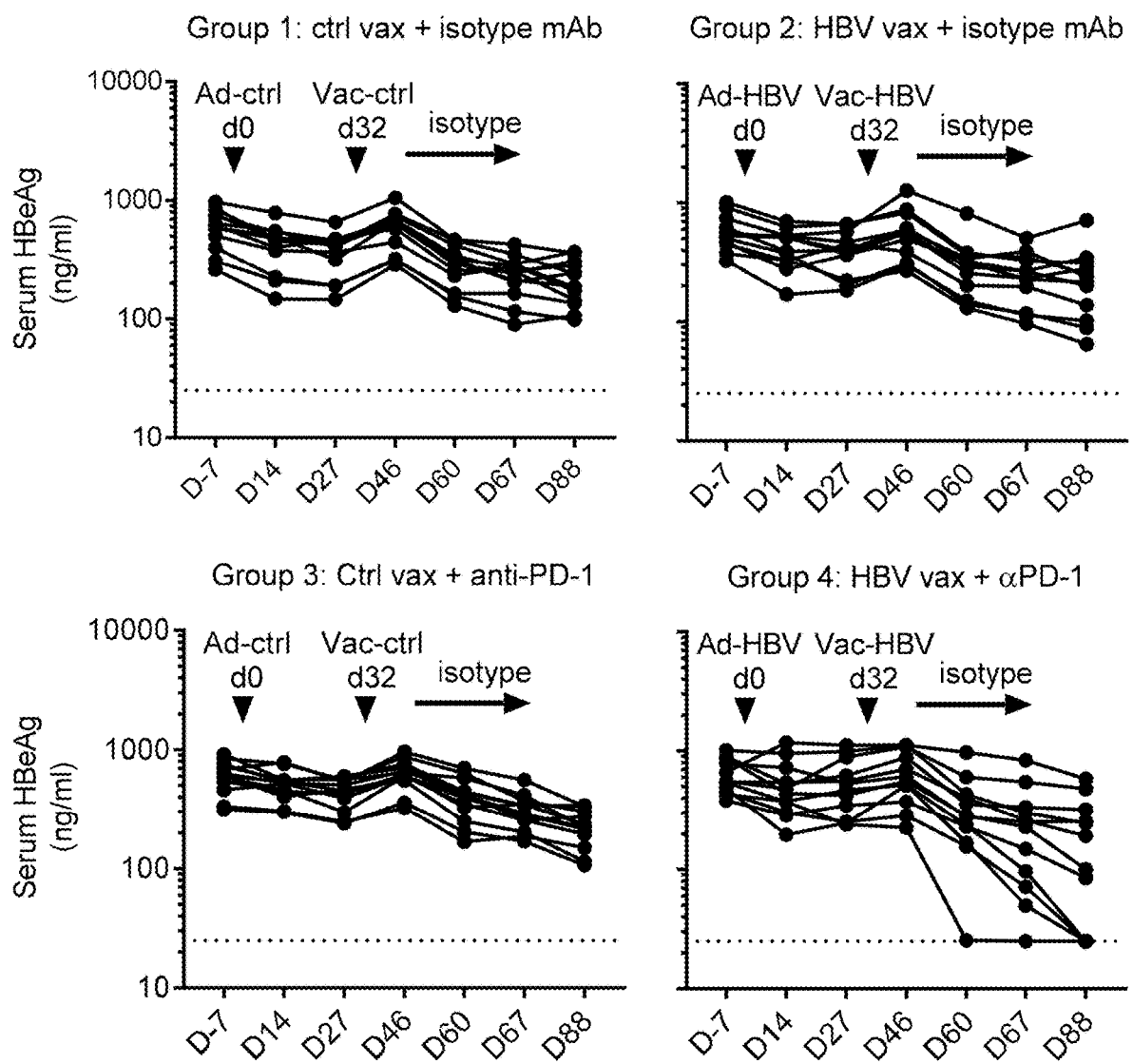
FIG. 8 illustrates the effects of HBV-expressing Ad5 prime-vaccinia boost vaccination in combination with PD-1 blockade in AAV-HBV mice. Serum HBeAg levels in the study shown in FIG. 6 were determined by ELISA (International Immunodiagnostics) at the indicated timepoints. Dashed line indicates the lower limit of detection. Ad: adenovirus 5 vector. Vac: vaccinia vector. Ctrl: control antigen. Isotype: isotype control antibody. αPD-1: anti-mouse PD-1 antibody.

To evaluate any antiviral effects of the HBV-specific T cells induced by vaccination, we measured serum e antigen (HBeAg). Serum HBeAg is a better marker of T-cell mediated antiviral efficacy than serum HBsAg, since the latter may be reduced by the action of anti-HBsAg antibodies induced by vaccination. Neither HBV vaccine alone nor anti-PD-1 alone caused any reduction in serum HBeAg compared to mice receiving control vaccine and isotype control antibody. However, the combination of HBV vaccine+anti-PD-1 resulted in loss of detectable HBeAg in serum in 4 of 12 mice (FIG. 8). These data demonstrate that vaccination with viral vectors encoding our improved antigen sequences contributed to HBV clearance as part of a combination therapy strategy.

Example 5

Immunogenicity of Pol Antigens in Arenavirus Vectors

Figure 9A:
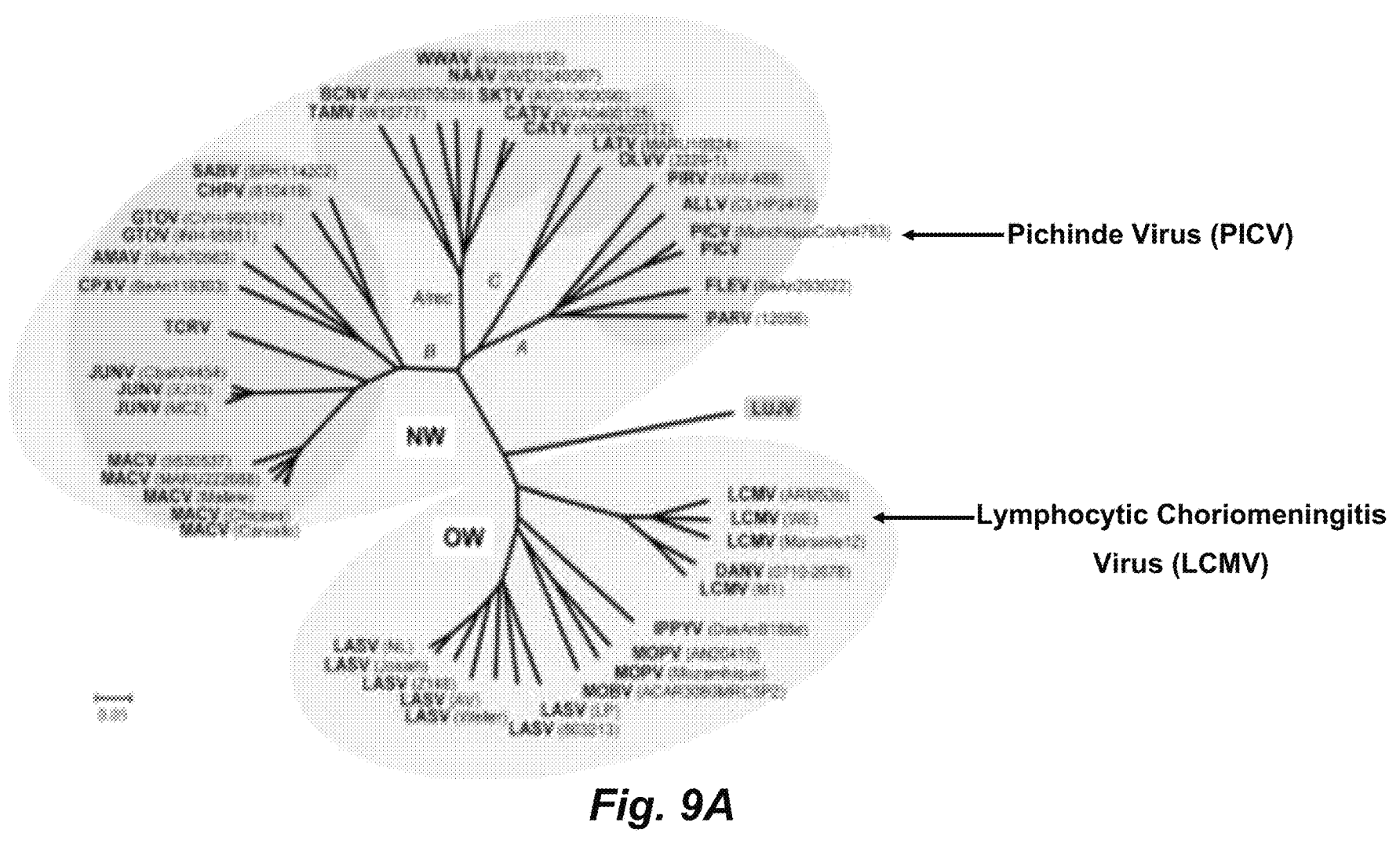

We further improved our HBV antigen designs for use in arenavirus vectors. Unlike adenovirus vectors and most other viral vector systems, arenavirus vectors can be repeatedly administered without inducing neutralizing anti-vector antibodies. Additionally, arenavirus vectors can be produced in several variants differing in the source virus used to generate the vector, e.g., replication-incompetent with a two-segment (i.e., bi-segmented) genome (Flatz, et al., *Nat Med.* (2010) 16(3):339-45), or replication-attenuated with a three-segment (i.e., tri-segmented) genome (Kallert, et al., *Nat Commun.* (2017) 8:15327) (FIG. 9). Certain HBV antigens were expressed in tri-segmented replication-attenuated or bi-segmented replication-defective arenavirus platforms with either a Lymphocytic choriomeningitis mammarenavirus (LCMV) or Cali mammarenavirus (a.k.a., Pichinde mammarenavirus or Pichinde arenavirus (PICV)) vector backbone. Replication-defective arenavirus vectors used are described in WO 2009/083210. Replication-attenuated arenavirus vectors used are described in WO 2016075250 (LCMV) and WO 2017/198726 (Pichinde).

Figure 10:
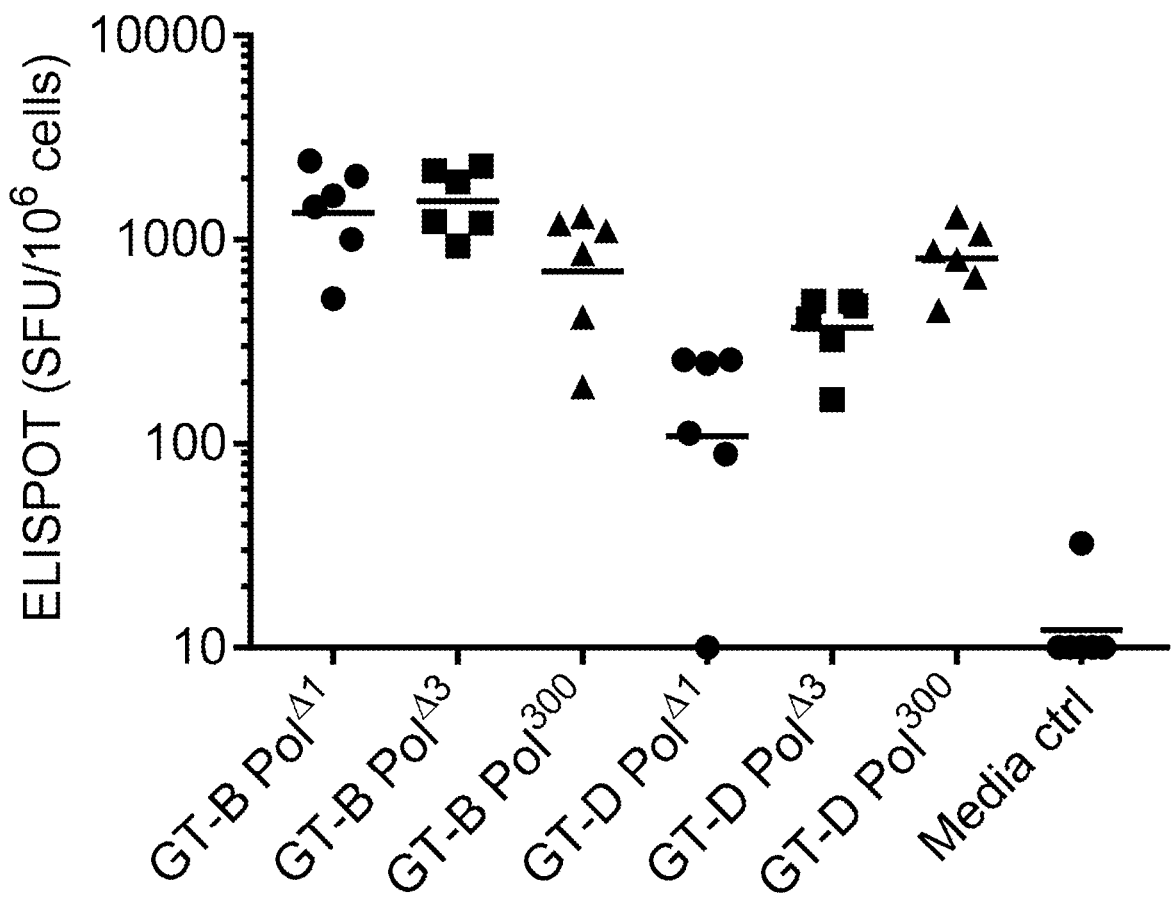
FIG. 10 illustrates the immunogenicity of Pol antigens in replication-incompetent lymphocytic choriomeningitis mammarenavirus (LCMV) vectors. Six- to eight-week-old C57BL/6 mice (n=6 per group) were injected intravenously with 1×10$^6$ focus forming units (FFU) of replication-incompetent LCMV vectors expressing Pol antigen variants GT-D and GT-B Pol$^{A1}$ (SEQ ID NOs: 6 and 8), Pol$^{A3}$ (SEQ ID NOs: 10 and 12), and Pol$^{300}$ (SEQ ID NOs: 13 and 14), or with media as a negative control. On day 7 after injection, splenocytes were harvested and T cell responses evaluated by IFN-γ ELISPOT (BD mouse IFN-γ ELISPOT kit, catalog #551083) using Pol overlapping peptide pools corresponding to the immunization antigen genotype in each group. SFU, spot forming units.

Arenavirus vectors can accommodate antigens of approximately 500-800 amino acids per open reading frame. Therefore, we tested GT-D and GT-B Pol$^{\Delta1}$ (SEQ ID NOs: 6 and 8), Pol$^{\Delta3}$ (SEQ ID NOs: 10 and 12), and Pol$^{300}$ (SEQ ID NOs: 13 and 14) for immunogenicity in replication-incompetent LCMV vectors. C57BL/6 mice were immunized intravenously with 10$^6$ focus forming units (FFU) of replication-incompetent LCMV vectors and IFN-γ ELISPOT responses were measured at day 7 post-immunization. All GT-B antigens and GT-D Pol$^{300}$ induced robust T cell responses, while GT-D Pol$^{\Delta1}$ and Pol$^{\Delta3}$ elicited reduced ELISPOT responses compared to the other antigen designs (FIG. 10).

Example 6

Identification of Genetically Stable Replication-Incompetent LCMV Vectors Encoding Immunogenic Pol Antigens The stability of various immunogenic Pol transgenes within replication-incompetent LCMV vectors (VV1) was evaluated by polymerase chain reaction (PCR) after serial passaging of vector containing supernatant. Genetic stability was defined by the major band showing at the correct size of the full-length transgene (TG). Results are shown in Table 6.

TABLE 6

Overview Table for Assessment of Genetic Stability of Pol Transgenes

| Genotype | Vector | Stable TG insertion until |
|---|---|---|
| GT-B | VV1*-Pol$^{\Delta 1}$ | P1 |
| GT-B | VV1-Pol$^{\Delta 3}$ | P1 |
| GT-B | VV1-Pol$^{300}$ | P5 |
| GT-D | VV1-Pol$^{\Delta 1}$ | P1 |
| GT-D | VV1-Pol$^{\Delta 3}$ | P1 |
| GT-D | VV1-Pol$^{300}$ | P2 |

*VV1 refers to replication-incompetent LCMV vectors.
"P#" indicates the number of passages (e.g., P1 equals 1 passage).

Example 7

Immunogenicity of Core-sAg Fusion Proteins in Replication-Incompetent LCMV Vectors Having identified stable, immunogenic Arenavirus vectors encoding HBV Pol, we additionally tested a series of core-sAg fusion proteins for immunogenicity in replication-incompetent LCMV vectors. Core-sAg fusions were generated by fusing near-consensus GT-B core and GT-C sAg, or GT-D core and GT-D sAg, with core at the N-terminus and sAg at the C-terminus. Direct fusions are expected to elicit T cell responses, but may not induce anti-sAg antibodies since the fusion protein will not secrete sAg. Therefore, additional antigen designs were tested with the core and sAg separated by a GSG linker followed by a 2A translational skip site derived from Porcine teschovirus-1 (P2A) (Kim, et al., PLoS ONE. (2011) 6: e18556). This orientation will yield a 21 amino acid extension on the C-terminus of core, while enabling normal sAg secretion to elicit antibody responses. Sequence identification numbers for the amino acid sequences of antigens tested in Arenavirus vectors, and the nucleotide sequences used to encode antigens in Arenavirus vectors, is shown in Table 7.

TABLE 7

Sequences vector antigens and antigen-encoding genes used in LCMV vectors

| Polynucleotide SEQ ID NO: | Polypeptide SEQ ID NO: | Polypeptide |
|---|---|---|
| 27 | 6 | GT-B Pol$^{\Delta 1}$ |
| 28 | 10 | GT-B Pol$^{\Delta 3}$ |
| 29 | 13 | GT-B Pol$^{300}$ |
| 30 | 8 | GT-D Pol$^{\Delta 1}$ |
| 31 | 12 | GT-D Pol$^{\Delta 3}$ |
| 32 | 14 | GT-D Pol$^{300}$ |
| 33 | 38 | GT-B/C core-sAg |
| 34 | 39 | GT-B/C core-P2A-sAg |
| 35 | 40 | GT-D core-sAg |
| 36 | 41 | GT-D core-P2A-sAg |
| 37 | 41 | GT-D iCore-P2A-sAg |

Figure 11:
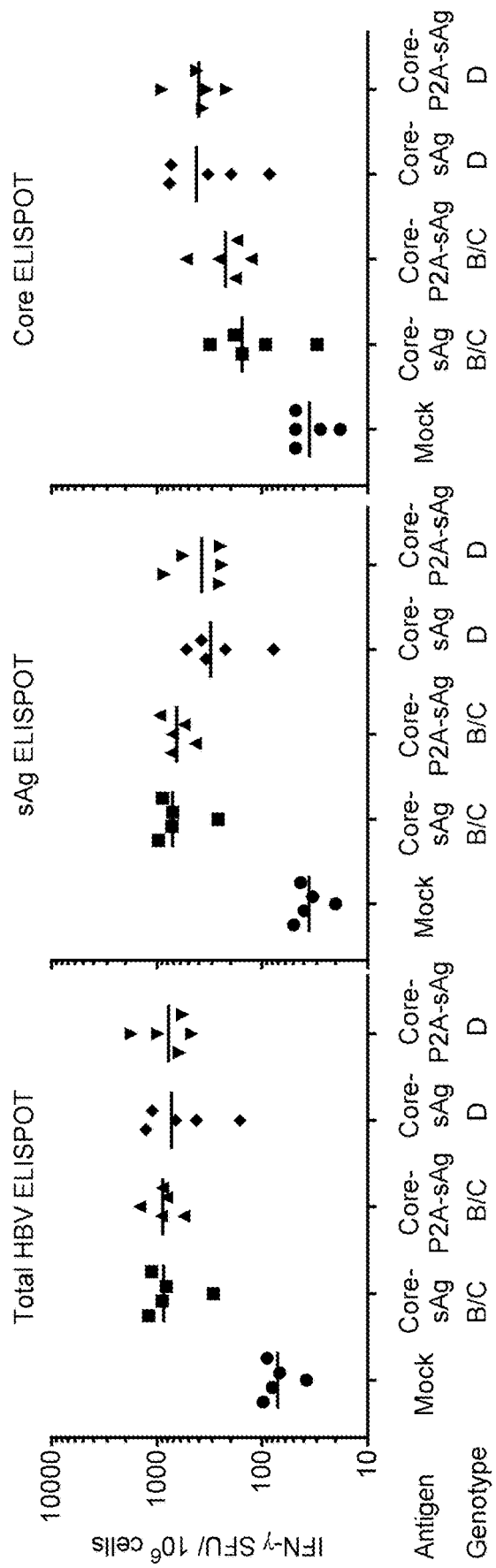
FIG. 11 illustrates the immunogenicity of Core-HBsAg fusion protein-expressing LCMV vectors in C57BL/6 mice. Six- to eight-week-old C57BL/6 mice (n=6 per group) were injected with 1×10$^6$ focus forming units (FFU) of replication-incompetent LCMV vectors expressing core-HBsAg fusion variants of SEQ ID NOs: 38-41 or mock immunized as a negative control. On day 7 after injection, splenocytes were harvested and T cell responses evaluated by IFN-γ ELISPOT (BD mouse IFN-γ ELISPOT kit, catalog #551083) using core and HBsAg overlapping peptide pools corresponding to the immunization antigen genotype in each group. SFU, spot forming units.

Replication-incompetent LCMV vectors encoding core-sAg variants were tested for immunogenicity by immunizing C57BL/6 mice (FIG. 11). The total HBV-specific IFN-γ ELISPOT responses were indistinguishable for all tested vectors, and inclusion of a P2A site had no impact on ELISPOT responses for either GT-B/C or GT-D antigens. Responses to both core and sAg were observed for all tested vectors. Detection of core responses was notable, as core T cell responses tend to be weak and difficult to detect in this mouse strain (Chiale, et al., supra). Similar results were seen in Balb/c mice immunized with the same vectors.

Figure 12:
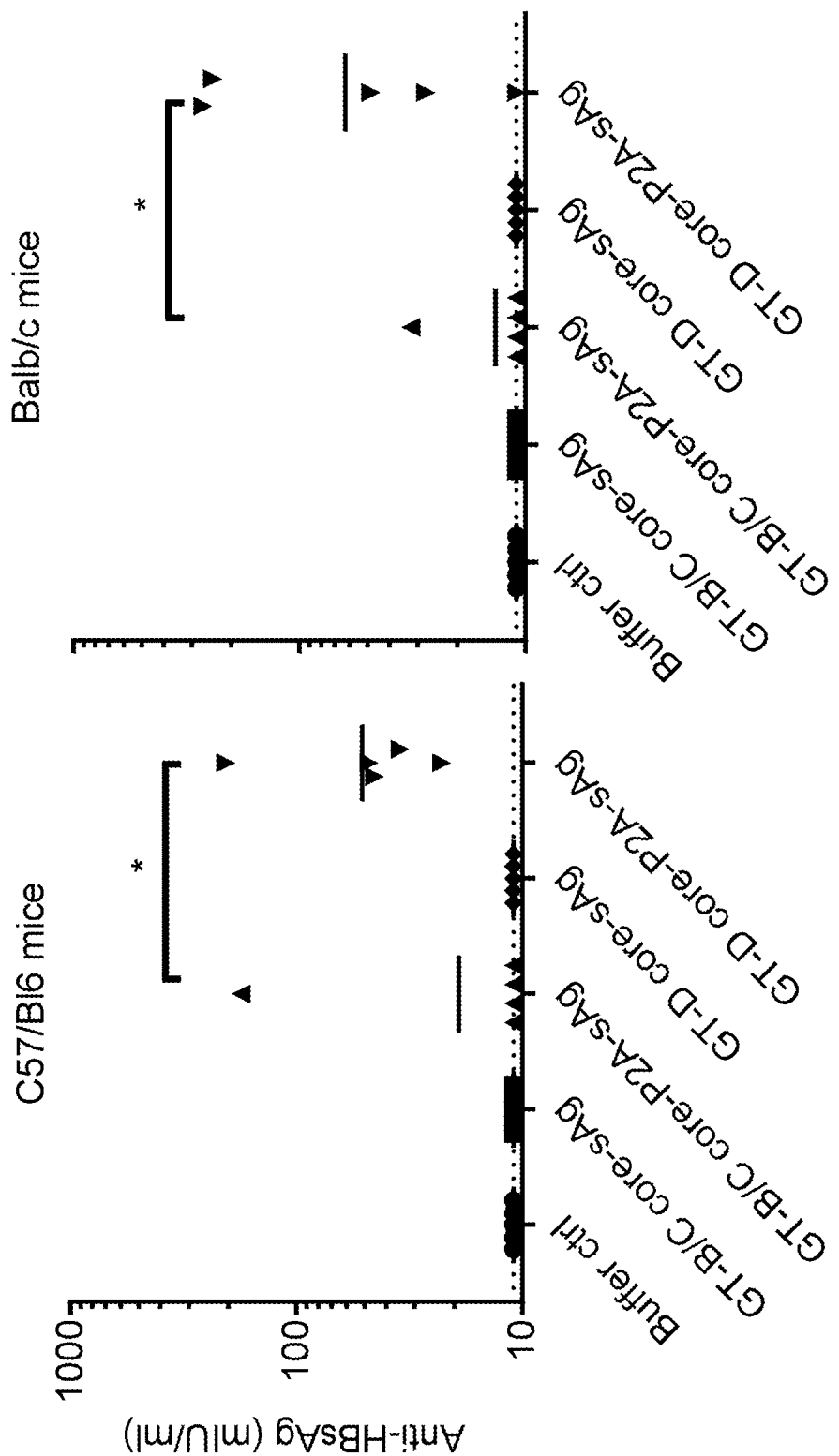
FIG. 12 illustrates the antibody response to HBsAg obtained in mice administered with core-sAg fusion protein-expressing replication-incompetent LCMV vectors. Six- to eight-week-old C57BL/6 (left) or Balb/c (right) mice (n=5 per group) were injected with 1×10$^6$ focus forming units (FFU) of replication-incompetent LCMV vectors expressing core-sAg fusion variants of SEQ ID NOs: 38-41 or with media as a negative control. On day 17 after injection, serum was collected and tested for anti-HBsAg antibody by ELISA (International Immunodiagnostics). Dashed line indicates the lower limit of detection of 11 mIU/ml. *p<0.05 by Mann-Whitney test.

Antibody responses develop more slowly than T-cell responses after replication-incompetent LCMV vector vaccination, so an additional set of C57BL/6 mice was immunized and antibody responses were measured at day 17 post-immunization (FIG. 12). As expected, direct core-sAg fusions did not elicit anti-sAg antibody responses. Among the P2A-containing constructs, only the GT-D core-P2A-sAg vector consistently induced anti-sAg antibodies, while anti-sAg antibodies were observed in only one of five mice immunized with GT-B/C core-P2A-sAg. This result was unexpected, since Western Blots showed efficient separation of core and sAg in both the GT-D and GT-B/C core-P2A-sAg vectors. To confirm that the difference in anti-sAg antibody responses was not an artifact of the mouse strain selected, the same experiment was run in Balb/c mice. Results in the Balb/c mice were similar to the results in C57BL/6 mice: anti-sAg antibodies were detected in 4 of 5 Balb/c mice immunized with GT-D core-P2A-sAg, but only 1 of 5 mice immunized with GT-B/C core-P2A-sAg (FIG. 12).

Example 8

Identification of Genetically Stable Replication-Incompetent LCMV Vectors Encoding Immunogenic Core-sAg Fusion Proteins The stability of various immunogenic core-sAg fusion transgenes within replication-incompetent LCMV vectors (VV1) was evaluated by PCR after serial passaging of vector containing supernatant. Genetic stability was defined by the major band showing at the correct size of the full-length transgene (TG). Results are shown in Table 8.

TABLE 8

Overview Table for Assessment of Genetic Stability of Core-sAg Transgenes

| Genotype | Vector | Stable TG insertion until |
|---|---|---|
| GT-B/C | VV1-Core-sAg | P6 |
| GT-B/C | VV1-Core-P2A-sAg | P7 |
| GT-D | VV1-Core-sAg | P4 |
| GT-D | VV1-Core-P2A-sAg | P2 |
| GT-D | VV1-iCore-P2A-sAg | P6 |

*VV1 refers to replication-incompetent LCMV vectors.
"P#" indicates the number of passages (e.g., P1 equals 1 passage).

GT-D core-P2A sAg induced robust T cell responses and the highest anti-sAg antibody responses of the tested core-sAg fusion designs, but did not have favorable genetic stability in this analysis. However, the modified transgene GT-D iCore-P2A-sAg (polynucleotide SEQ ID NO:37, encoding polypeptide SEQ ID NO:41) showed improved genetic stability in a replication-incompetent LCMV vector (Table 8).

Figure 13:
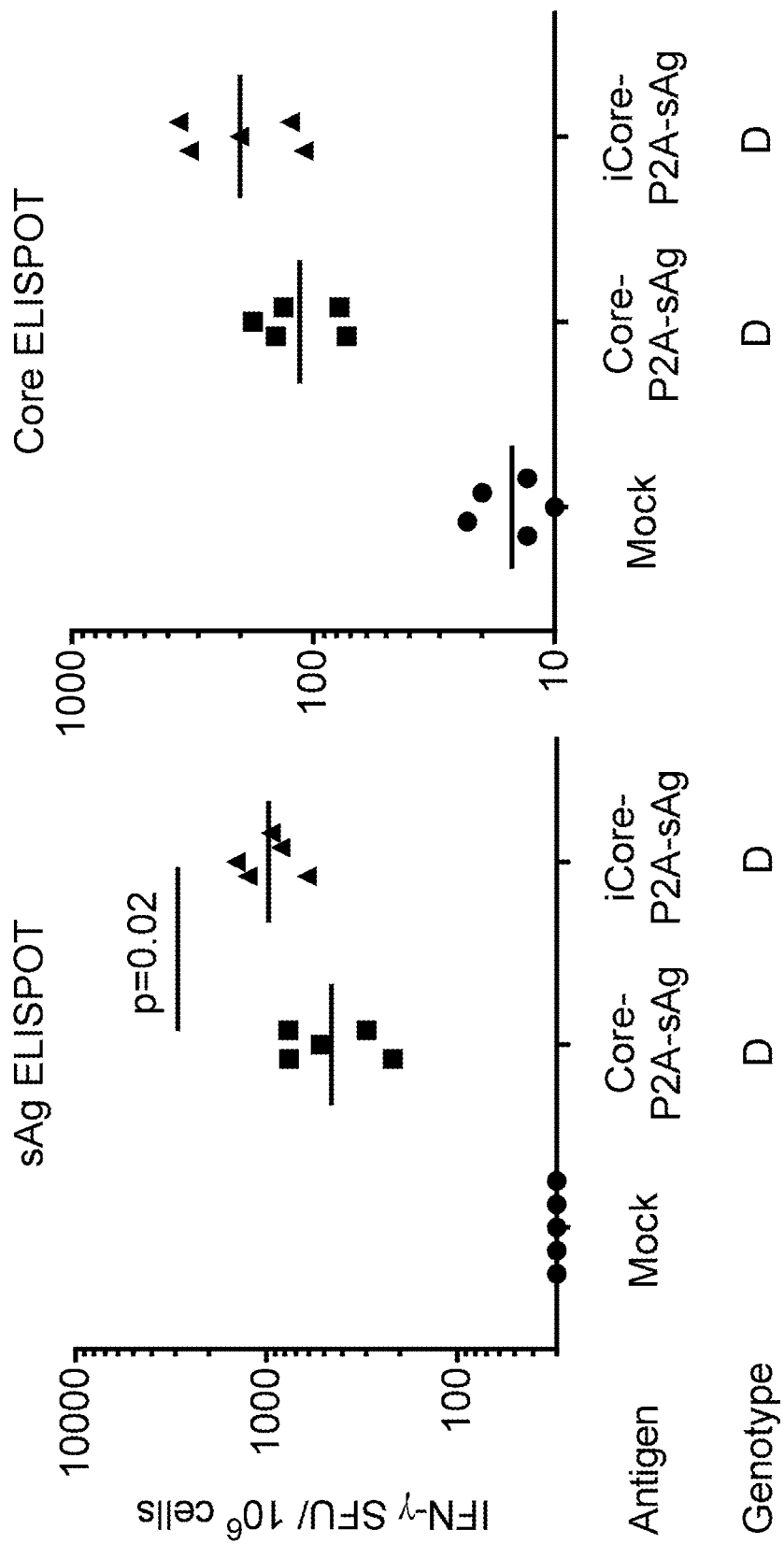
FIG. 13 illustrates the effect of nucleotide sequence modification on T-cell immunogenicity of core-P2A-sAg fusion proteins. Six- to eight-week old C57BL/6 mice (n=6 per group) were injected with 1×10$^6$ focus forming units (FFU) of replication-incompetent LCMV vectors with GT-D core-P2A-sAg (SEQ ID NO:36) or GT-D iCore-P2A-sAg (SEQ ID NO: 37), or mock immunized as a negative control. On day 7 after injection, splenocytes were harvested and T cell responses evaluated by IFN-γ ELISPOT (BD mouse IFN-γ ELISPOT kit, catalog #551083) using core and sAg overlapping peptide pools. Statistical analyses were performed with Mann-Whitney Tests.

To confirm that the modified transgene did not impair T-cell immunogenicity of GT-D iCore-P2A-sAg, C57BL/6 mice were immunized using replication-incompetent LCMV vectors with the GT-D core-P2A-sAg and GT-D iCore-P2A-sAg designs, or mock immunized, and T cell responses were measured 7 days later by IFN-γ ELISPOT (FIG. 13). sAg ELISPOT responses were significantly higher with GT-D iCore-P2A-sAg, and core ELISPOT responses were numerically higher as well. Thus, the modified transgene of GT-D iCore-P2A-sAg resulted in both improved genetic stability and improved immunogenicity.

Example 9

Immunogenicity of Replication-Incompetent LCMV Vectors in Outbred Mice

The immunogenicity of the replication-incompetent LCMV (VV1) vectors encoding various HBV antigens were evaluated in Diversity Outbred (DO) mice. These mice have more diverse MEW alleles than inbred C57BL/6 mice, so are better for evaluating genotype cross-reactivity of the T cell responses induced by vaccination.

Methods

DO mice were immunized twice at day 0 and day 28 with replication-incompetent LCMV vectors as indicated in Table 9. HBV-specific T cell responses were measured at day 42 by IFN-γ ELISPOT using splenocytes.

TABLE 9

Study Groups in Immunogenicity Study

| Group | N | Prime vector - Day 0 | Boost vector - Day 28 | Harvest Day | Dose/ vector |
|---|---|---|---|---|---|
| 1 | 8 | Mock | Mock | 42 | — |
| 2 | 8 | VV1-GT-B/ C Core-P2A-sAg | VV1-GT-B/ C Core-P2A-sAg | 42 | $10^6$ FFU |
| 3 | 8 | VV1-GT-D iCore-P2A-sAg | VV1-GT-D iCore-P2A-sAg | 42 | $10^6$ FFU |
| 4 | 8 | VV1-GT-B Pol$^{\Delta 3}$ | VV1-GT-B Pol$^{\Delta 3}$ | 42 | $10^6$ FFU |
| 5 | 8 | VV1-GT-B Pol$^{300}$ | VV1-GT-B Pol$^{300}$ | 42 | $10^6$ FFU |

Results

Figure 14A:
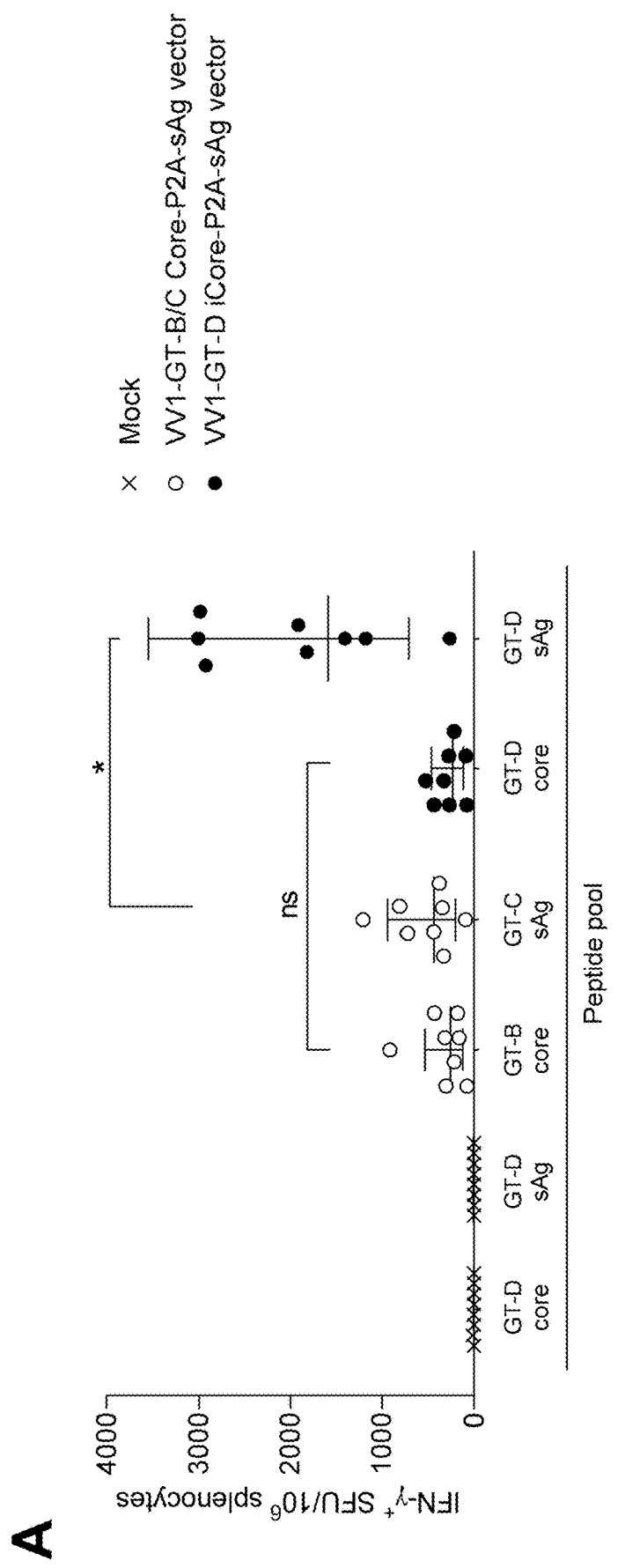
FIGS. 14A-14B illustrate the immunogenicity of prime/boost vaccination with replication-incompetent LCMV vectors (VV1) encoding GT-B/C Core-P2A-sAg or GT-D iCore-P2A-sAg (FIG. 14A) and GT-B Pol$^{A3}$ or GT-B Pol$^{300}$ (FIG. 14B) in diversity outbred mice. Animals were administered with 2 doses of each vaccine at day 0 and day 28 as described in Table 9. Splenocytes were harvested at day 42 and T cell responses to HBV antigens were measured by IFN-γ ELISPOT using sAg, core and polymerase peptide pools from various viral genotypes as indicated. Data are expressed as background (no peptide)-subtracted values. Statistical analyses were performed with Mann-Whitney tests. ns: not statistically significant; *p<0.0332.
Figure 14B:
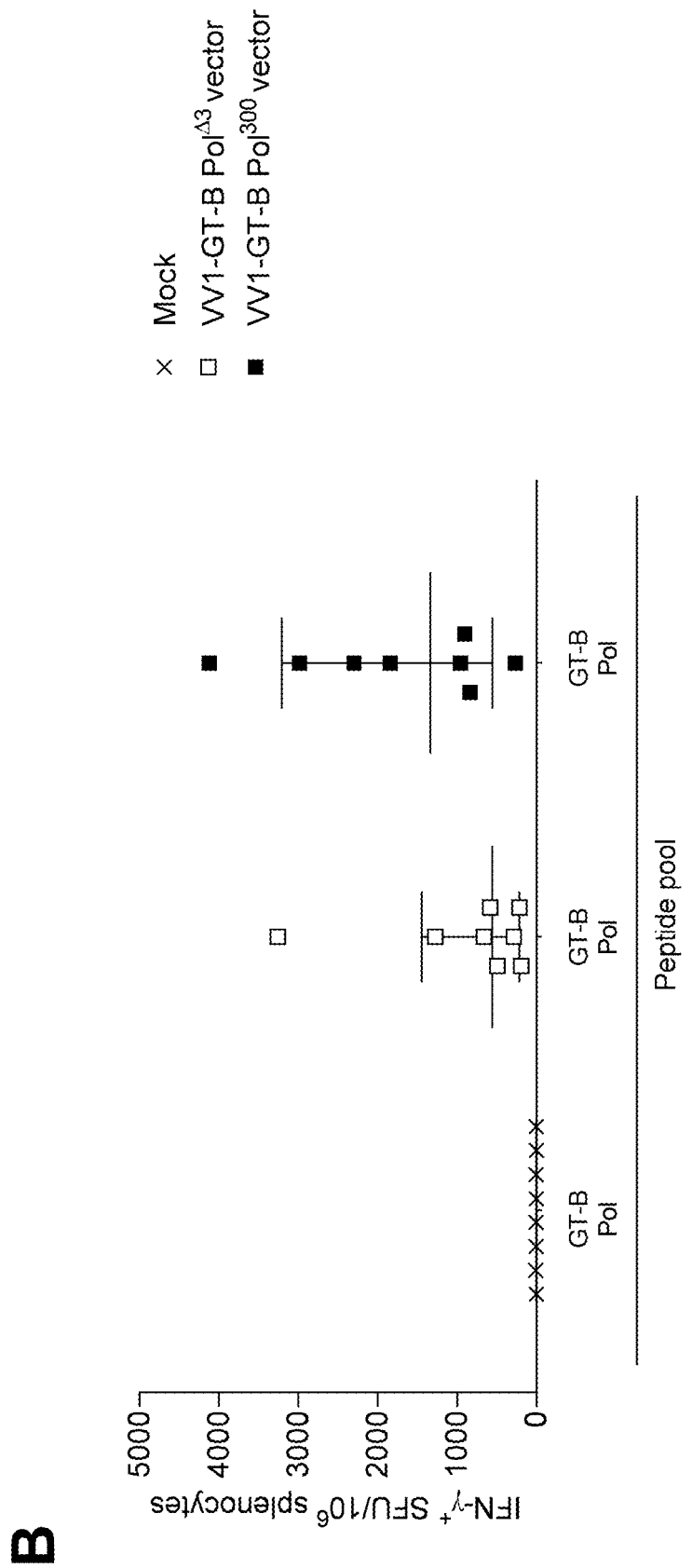

Replication-incompetent LCMV vectors encoding GT-B/C Core-P2A-sAg and GT-D iCore-P2A-sAg induced comparable T cell responses specific for their respective core antigen (FIG. 14A). The vector encoding GT-D iCore-P2A-sAg induced a higher frequency of T cells specific for its respective sAg antigen when compared to the vector encoding GT-B/C Core-P2A-sAg (FIG. 14A). The vector encoding GT-B Pol$^{300}$ induced a numerically superior T cell response specific to pol antigens than the vector encoding GT-B Pol$^{\Delta 3}$ (FIG. 14B). Thus, the vectors encoding for GT-D iCore-P2A-sAg and GT-B Pol$^{300}$ are more immunogenic than the vectors encoding for GT-B/C Core-P2A-sAg and GT-B Pol$^{\Delta 3}$ in outbred mice.

Figure 15A:
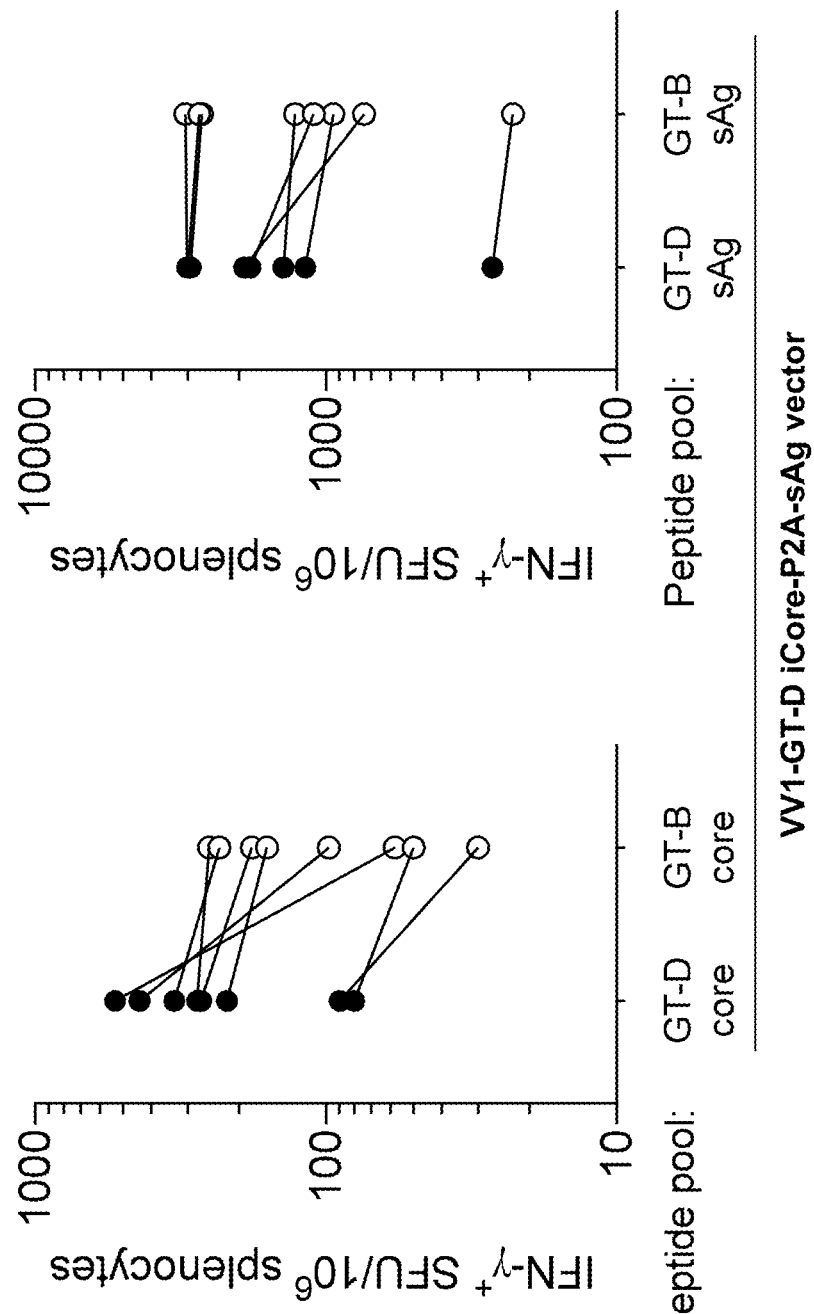
FIGS. 15A-15B illustrate the breadth of HBV-specific T cell responses generated upon prime/boost vaccination with replication-incompetent LCMV (VV1) vectors encoding GT-D iCore-P2A-sAg (FIG. 15A) or GT-B Pol$^{300}$ (FIG. 15B) in diversity outbred mice. IFN-γ ELISPOT was performed using peptides from the same viral genotype (filled circles) or from a different viral genotype (open circles).
Figure 15B:
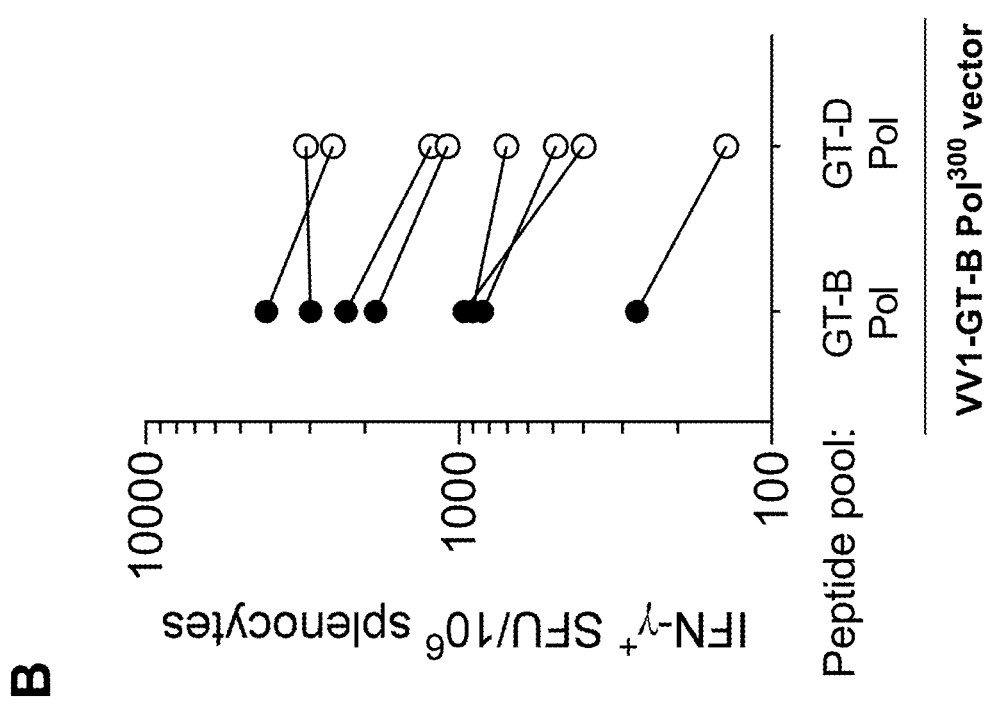

In addition to inducing T cells responses specific to their cognate antigens (i.e., GT-D core, GT-D sAg, GT-B Pol antigens), the GT-D iCore-sAg and GT-B Pol$^{300}$ vectors were also able to generate T cells responses specific for antigens obtained from different viral genotypes of HBV (i.e., GT-B core, GT-B sAg, GT-D Pol antigens) (FIGS. 15A and 15B). Thus, the vectors coding for GT-D iCore-sAg and GT-B Pol$^{300}$ produce T cells which are cross-reactive for different genotypes of HBV.

Example 10

Immunogenicity of Replication-Incompetent LCMV Vectors Administered as Single Vector or Co-Formulated in C57BL/6 Mice Replication-incompetent LCMV vectors encoding GT-D iCore-P2A-sAg and GT-B Pol300 are immunogenic in mice. We next compared their immunogenicity of both vectors when delivered either as single vectors or as a co-formulated mixture in C57BL/6 mice.

Methods

C57BL/6 mice were immunized twice at day 0 and day 21 with replication-incompetent LCMV vectors as indicated in Table 10. HBV-specific T cell responses were measured at day 28 by IFN-γ ELISPOT using splenocytes.

TABLE 10

Study Groups in Immunogenicity Study

| Group | N | Vector Format | Prime vector D 0 | Boost vector D 21 | Harvest Day | Dose/ vector |
|---|---|---|---|---|---|---|
| 1 | 5 | — | Mock | Mock | 28 | $10^6$ FFU |
| 2 | 5 | Single vector | VV1-GT-D iCore_P2A_sAg | VV1-GT-D iCore_P2A_sAg | 28 | $10^6$ FFU |
| 3 | 5 | Single vector | VV1-GT-B Pol$^{300}$ | VV1-GT-B Pol$^{300}$ | 28 | $10^6$ FFU |
| 4 | 5 | Co-formulated | VV1-GT-D iCore_P2A_sAg + VV1-GT-B Pol$^{300}$ | VV1-GT-D iCore_P2A_sAg + VV1-GT-B Pol$^{300}$ | 28 | $10^6$ FFU |

Results

Figure 16A:
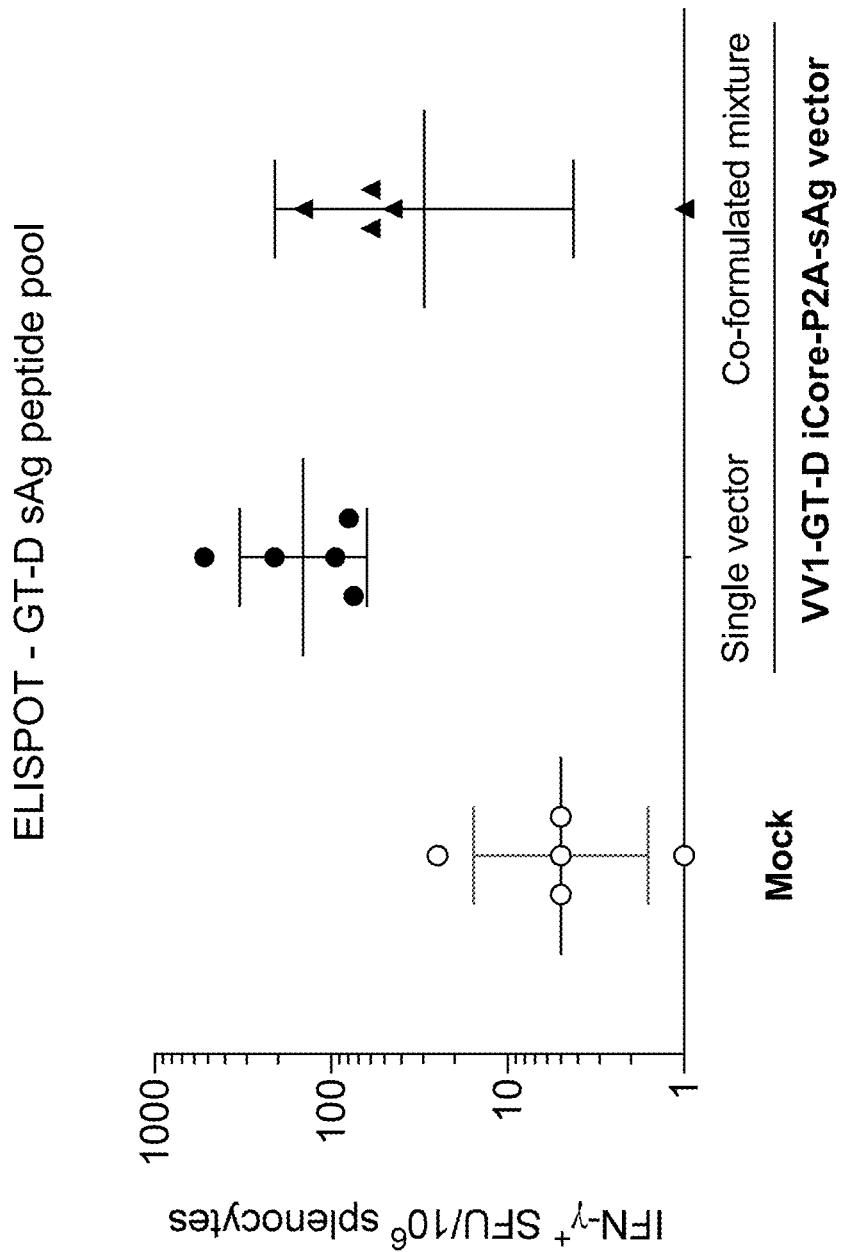
FIGS. 16A-16C illustrate the immunogenicity of prime/boost vaccination with replication-incompetent LCMV (VV1) vectors encoding GT-D iCore-P2A-sAg and GT-B Pol$^{300}$ when delivered either as single vectors or as a co-formulated mixture in C57BL/6 mice. Animals were administered with 2 doses of the vectors at day 0 and day 21 as described in Table 10. Splenocytes were harvested at day 28 and HBV-specific T cell responses were measured by IFN-γ ELISPOT using core (FIG. 16A), sAg (FIG. 16B) and Pol (FIG. 16C) peptide pools.
Figure 16B:
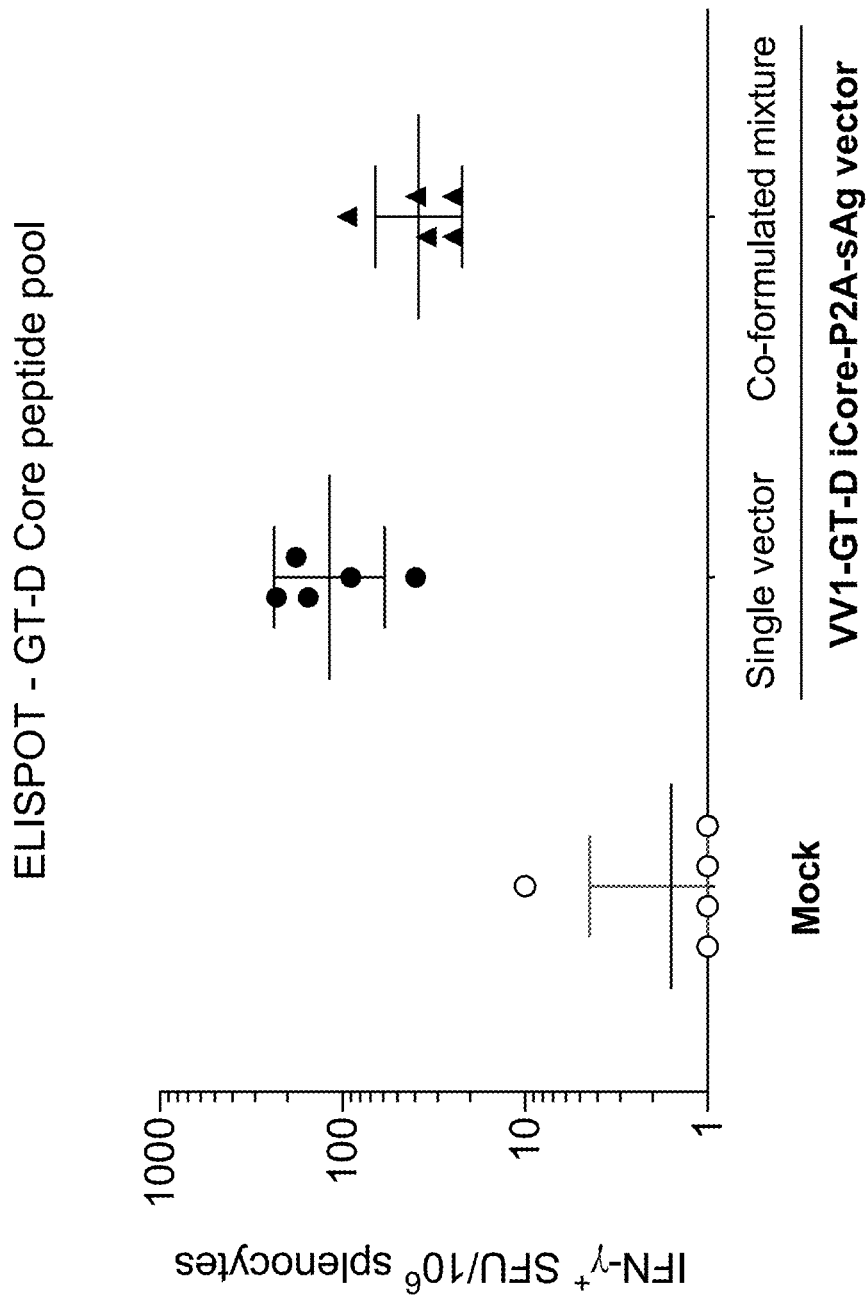
Figure 16C:
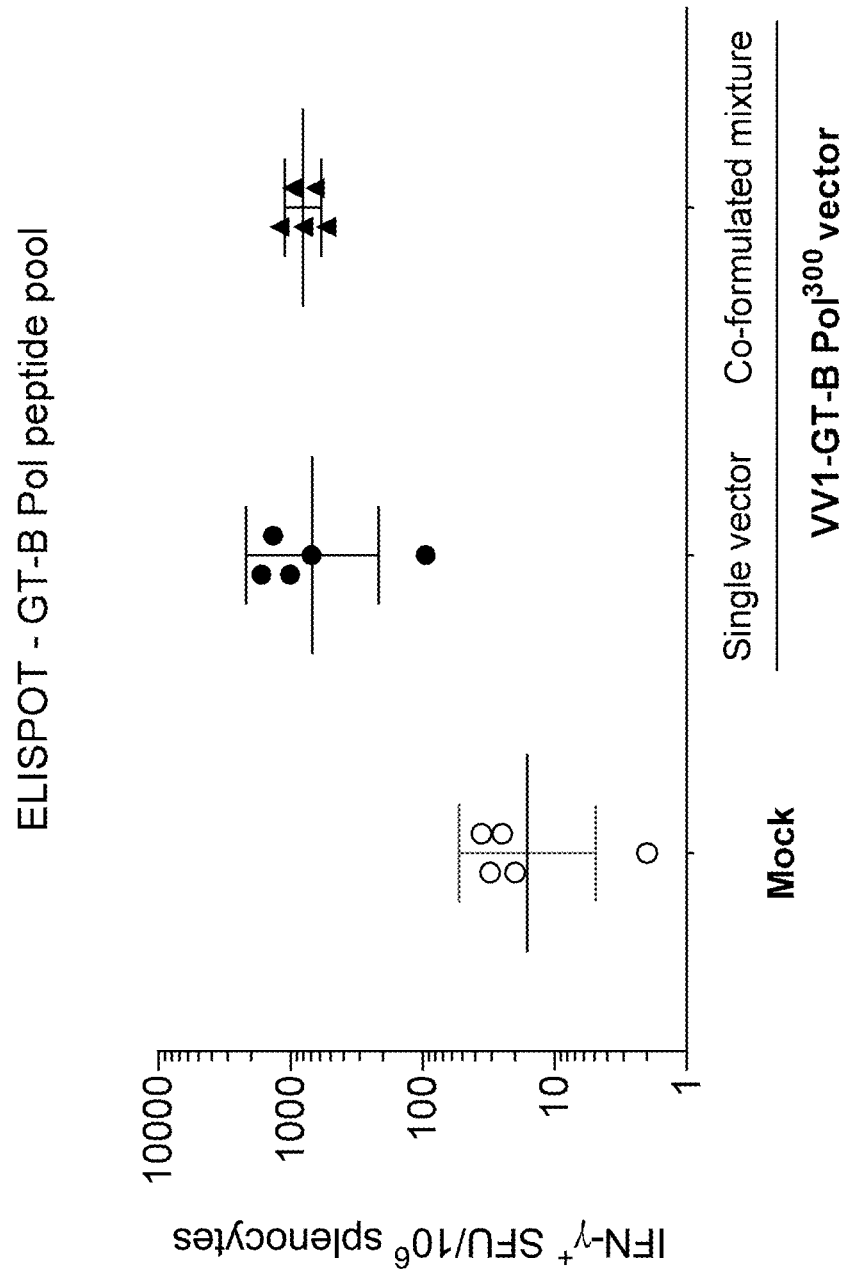

Consistent with data described above, vectors encoding GT-D iCore-P2A-sAg and GT-B Pol$^{300}$ induced T cells responses specific for sAg, core and Pol when administered as single vectors (FIGS. 16A-16C). Administration of the same vectors as a co-formulated mixture induced comparable T cell responses (FIGS. 16A-C). Thus, co-formulation of the LCMV vectors encoding GT-D iCore-P2A-sAg and GT-B Pol$^{300}$ does not interfere with their immunogenicity in C57BL/6 mice.

Example 11

Immunogenicity of Replication-Incompetent LCMV Vectors in Cynomolgus Macaques We evaluated the immunogenicity of the replication-incompetent LCMV (VV1) vectors GT-D iCore-P2A-sAg and GT-B Pol$^{300}$ vectors in cynomolgus macaques. Ad5 and vaccinia vectors encoding for the core, sAg, and Pol$^{300}$ antigens were also tested.

Methods

Cynomolgus macaques were immunized using different routes, different doses and different immunization schedules as indicated in Table 11. HBV-specific T cell responses were measured using PBMC every 2 weeks by IFN-γ ELISPOT. Intracellular cytokine staining was also performed on CD4+ and CD8+ T cells at week 14 by flow cytometry. Anti-sAg antibody responses were quantified every 4 weeks by ELISA.

TABLE 11

Study Groups in Immunogenicity Study

| Group | N | Vaccine | Dose | Route | Immunization schedule (week) |
|---|---|---|---|---|---|
| 1 | 5 | VV1-GT-D iCore-P2A-sAg + | $5 \times 10^6$ FFU/vector | i.m. | Every 4 weeks: 0, 4, 8, 12, 16, 20 |
| 2 | 5 | VV1-GT-B Pol$^{300}$ | $10^8$ FFU/vector | i.m. | Every 4 weeks: 0, 4, 8, 12, 16, 20 |
| 3 | 5 | | $5 \times 10^6$ FFU/vector | i.m. | Every 8 weeks: 0, 8, 16, 24 |
| 4 | 5 | | $10^8$ FFU/vector | i.m. | Every 8 weeks: 0, 8, 16, 24 |
| 5 | 5 | | $10^8$ FFU/vector | i.v. | Every 8 weeks: 0, 8, 16, 24 |
| 6 | 5 | 1. Ad5-GT-D core-sAg + Ad5-GT-B Pol$^{300}$ (days 0 and 5) 2. Vaccinia GT-D core-sAg + Vaccinia GT-B Pol$^{300}$ (days 8 and 12) | $10^{11}$ vp/vector $10^8$ PFU/vector | i.m. | 0 (Ad5), 4 (Ad5), 8 (Vac), 12 (Vac) |

Results

Figure 17A:
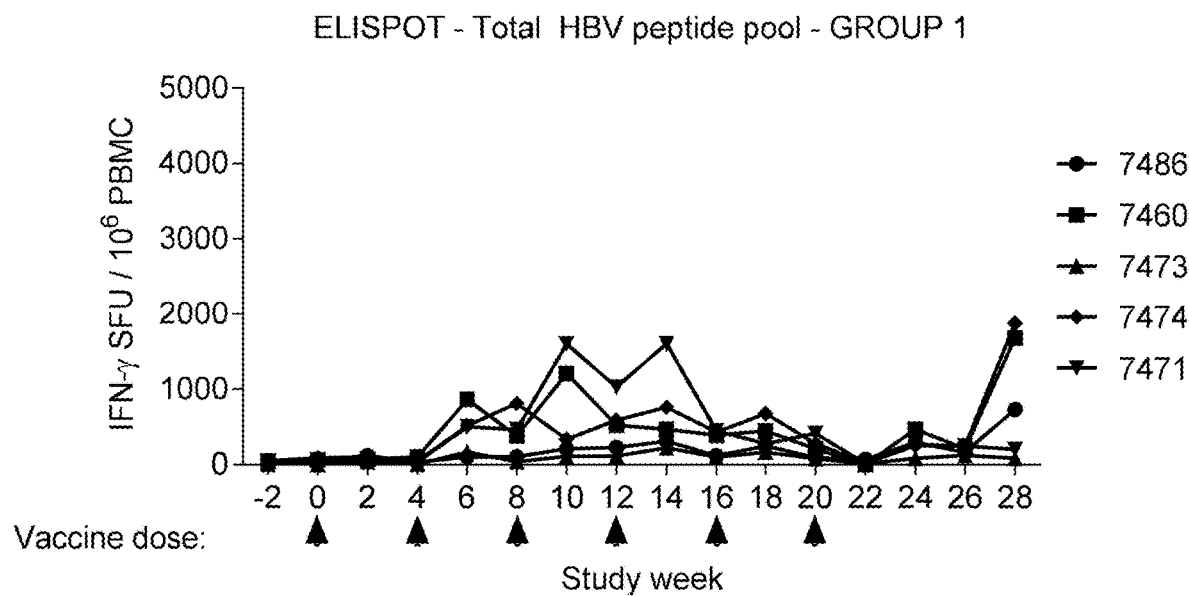
FIGS. 17A-17F illustrate the immunogenicity of repeat vaccinations with replication-incompetent LCMV vectors encoding GT-D iCore-P2A-sAg and GT-B Pol$^{300}$ in cynomolgus macaques. A group of animals was also vaccinated with Ad5 and vaccinia vectors encoding the same HBV antigens. Animals were administered with the vectors as described Table 11. 17A: Group 1; 17B: Group 2; 17C: Group 3; 17D: Group 4; 17E: Group 5; 17F: Group 6. T cell responses to HBV antigens were assessed by performing IFN-γ ELISPOT using sAg, core and Pol peptide pools at the indicated timepoints. Data are expressed at total HBV-specific T cell responses defined as the sum of IFN-γ ELISPOT values obtained after stimulation with sAg, core and polymerase peptide pools.
Figure 17B:
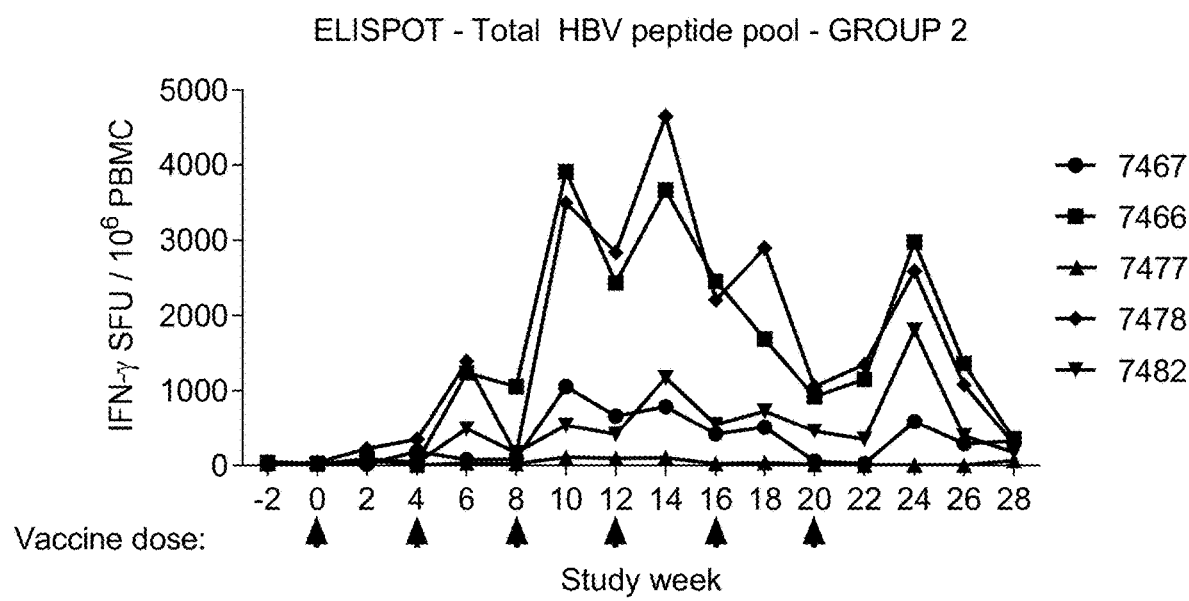
Figure 17C:
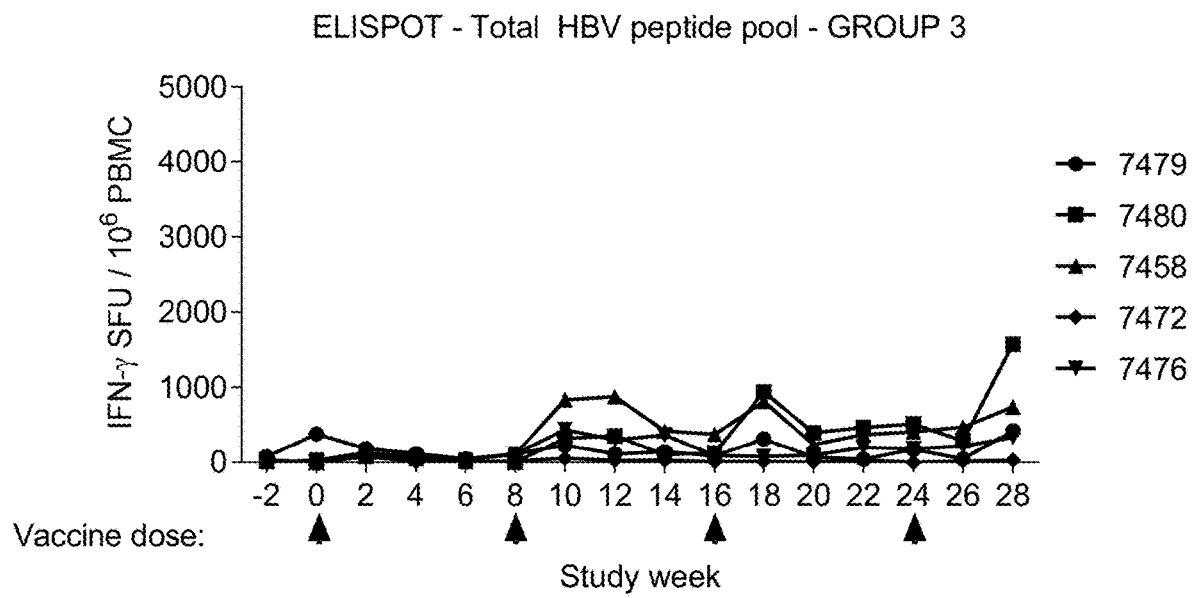
Figure 17D:
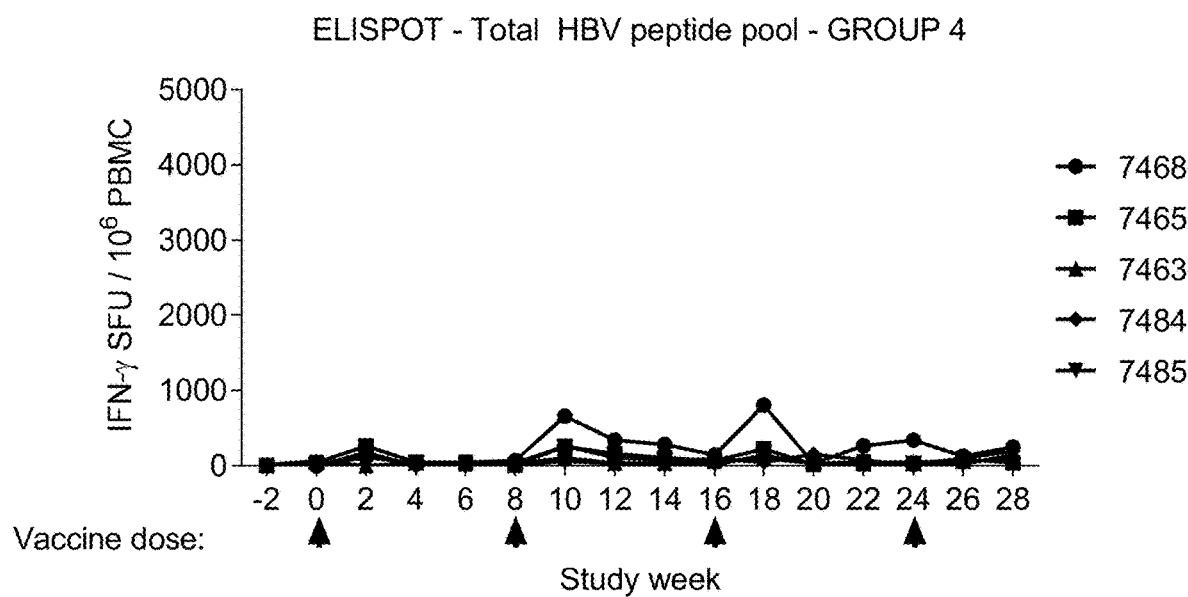
Figure 17E:
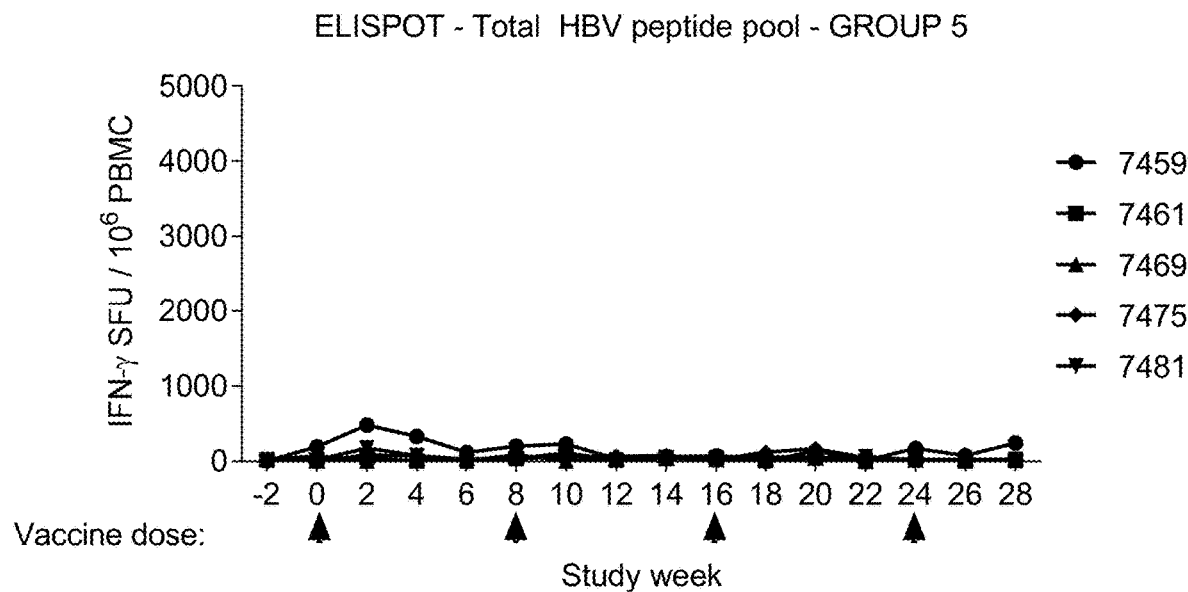
Figure 17F:
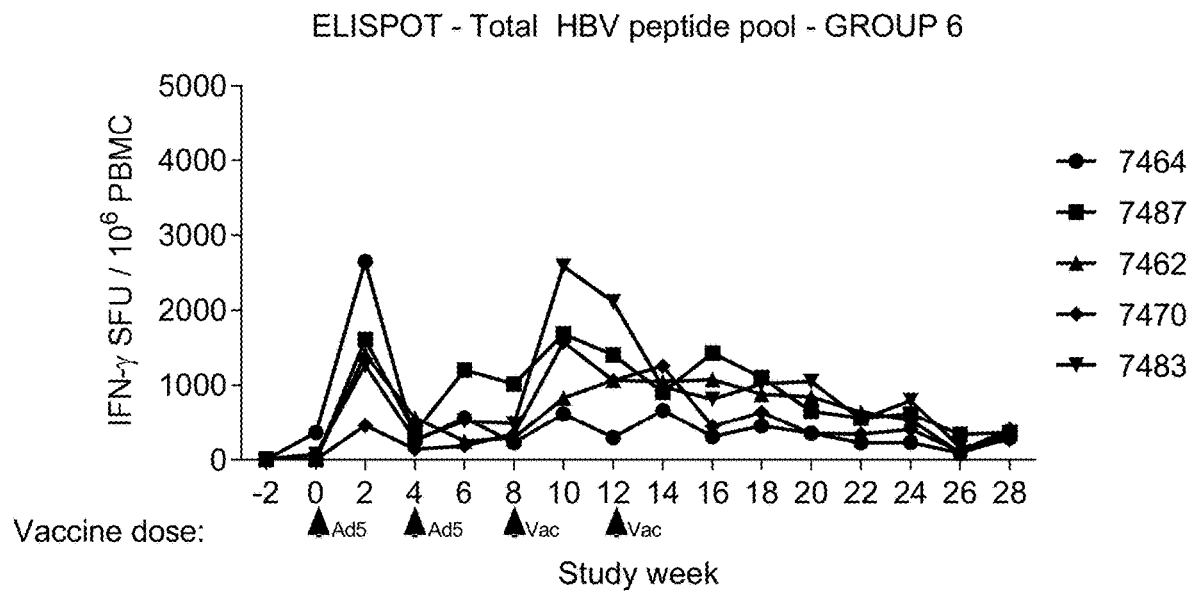
Figure 18A:
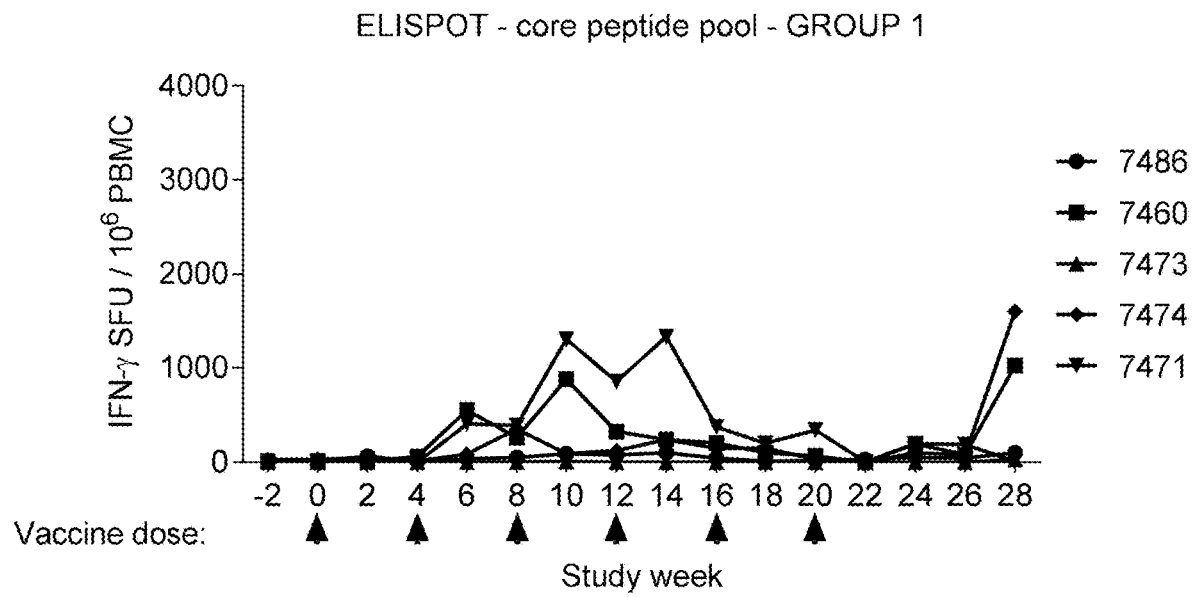
FIGS. 18A-18F illustrate the immunogenicity of repeat vaccinations with replication-incompetent LCMV vectors encoding GT-D iCore-P2A-sAg and GT-B Pol$^{300}$ in cynomolgus macaques as described in FIG. 17 and Table 11.
Figure 18B:
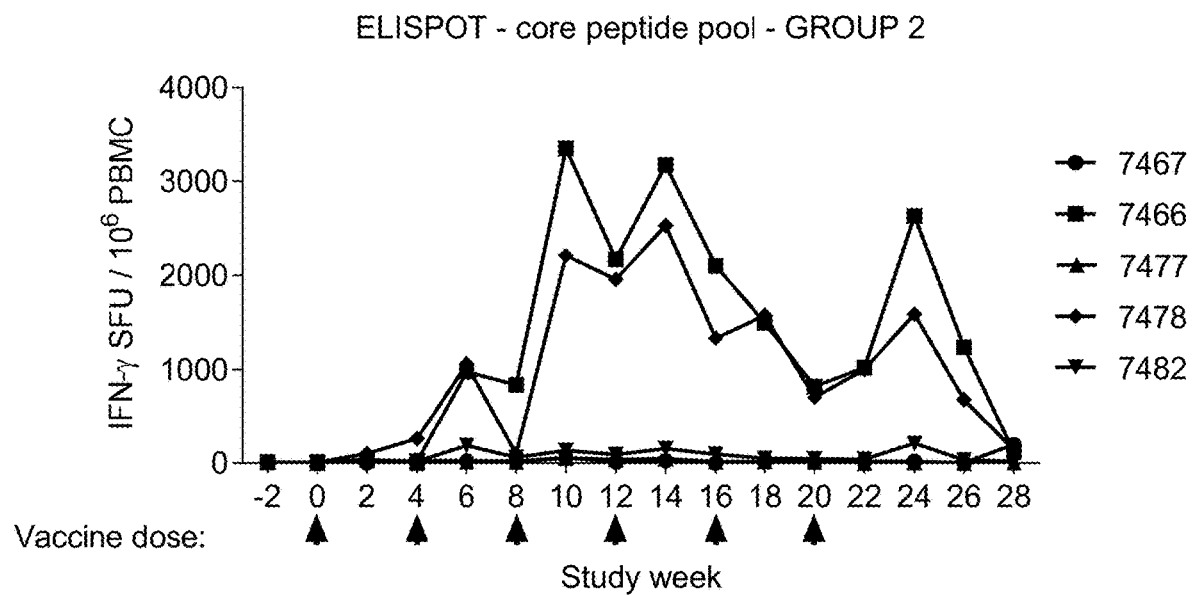
Figure 18C:
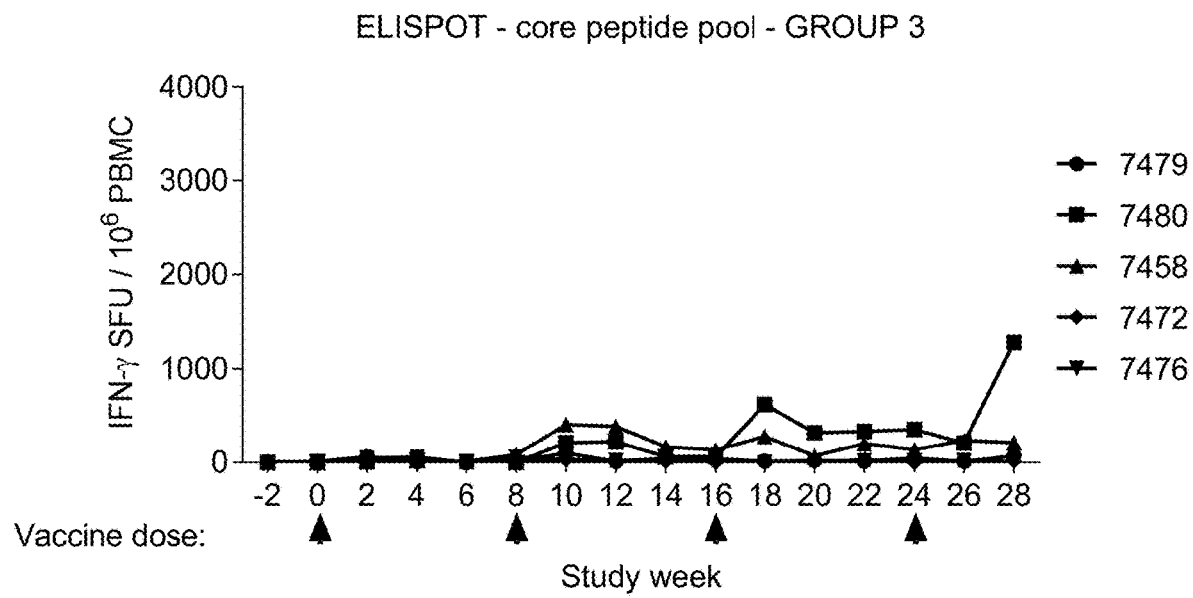
Figure 18D:
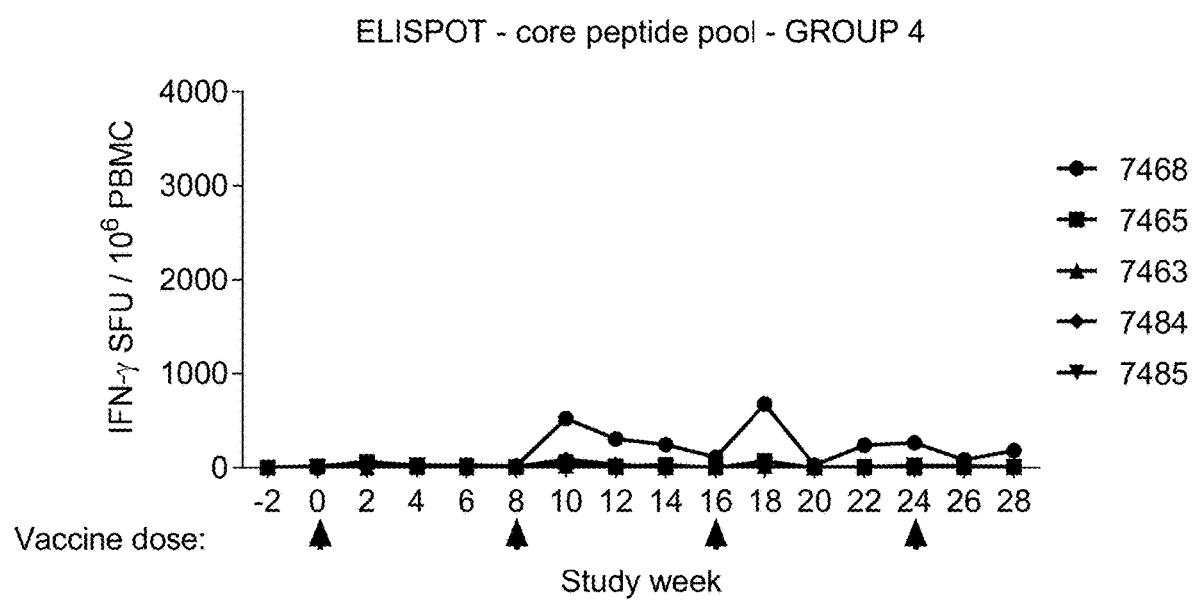
Figure 18E:
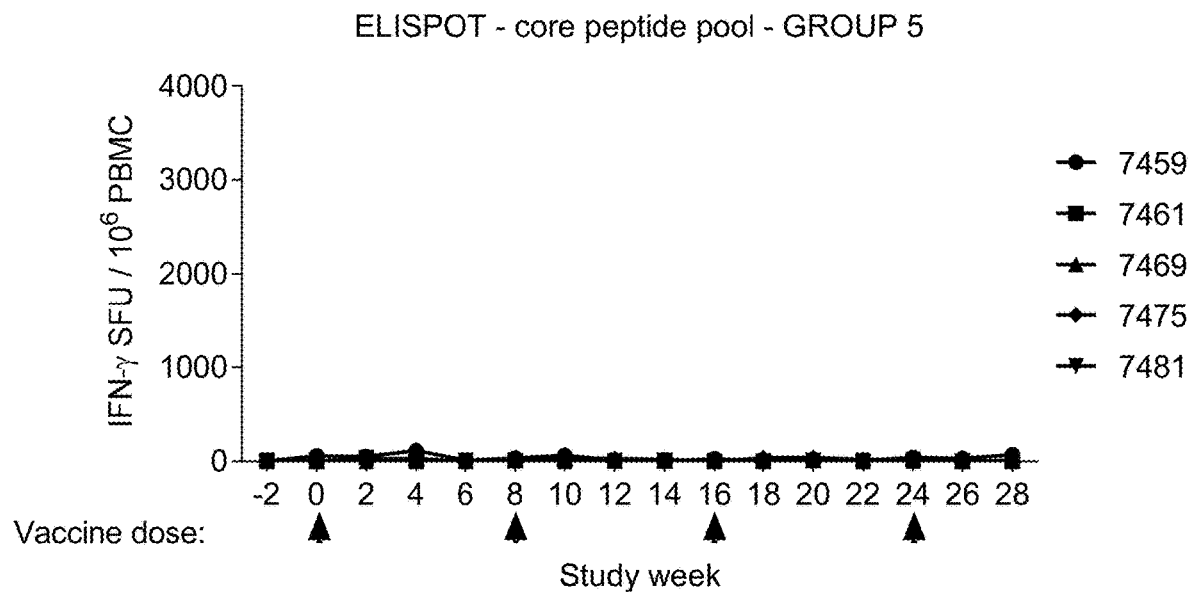
Figure 18F:
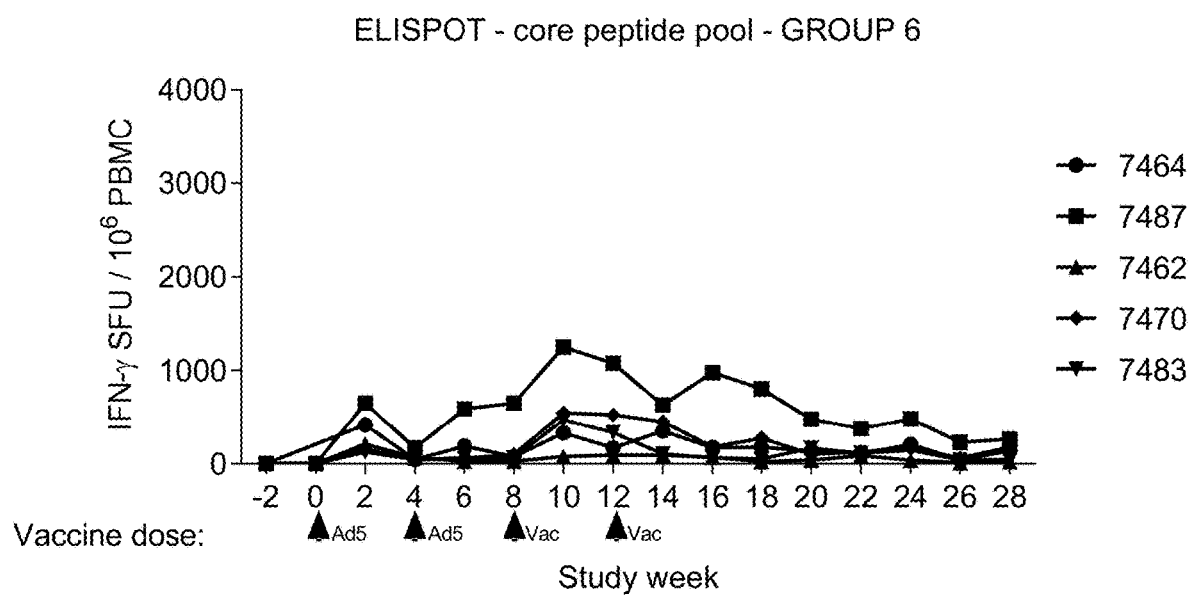
Figure 19A:
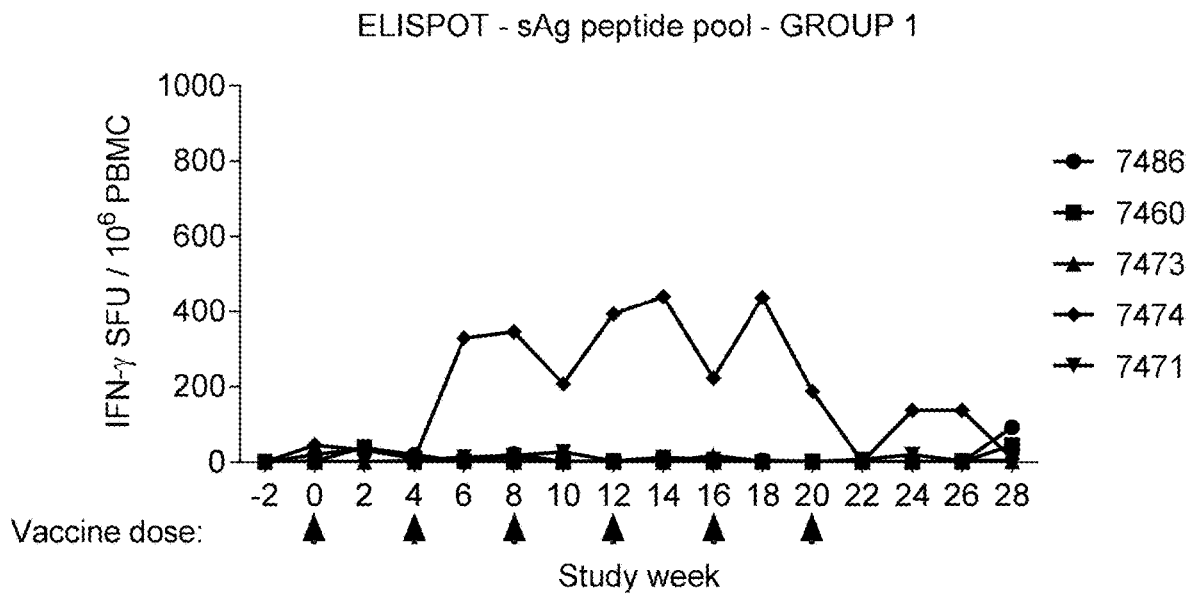
FIGS. 19A-19F illustrate the immunogenicity of repeat vaccinations with replication-incompetent LCMV vectors encoding GT-D iCore-P2A-sAg and GT-B Pol$^{300}$ in cynomolgus macaques as described in FIG. 17 and Table 11.
Figure 19B:
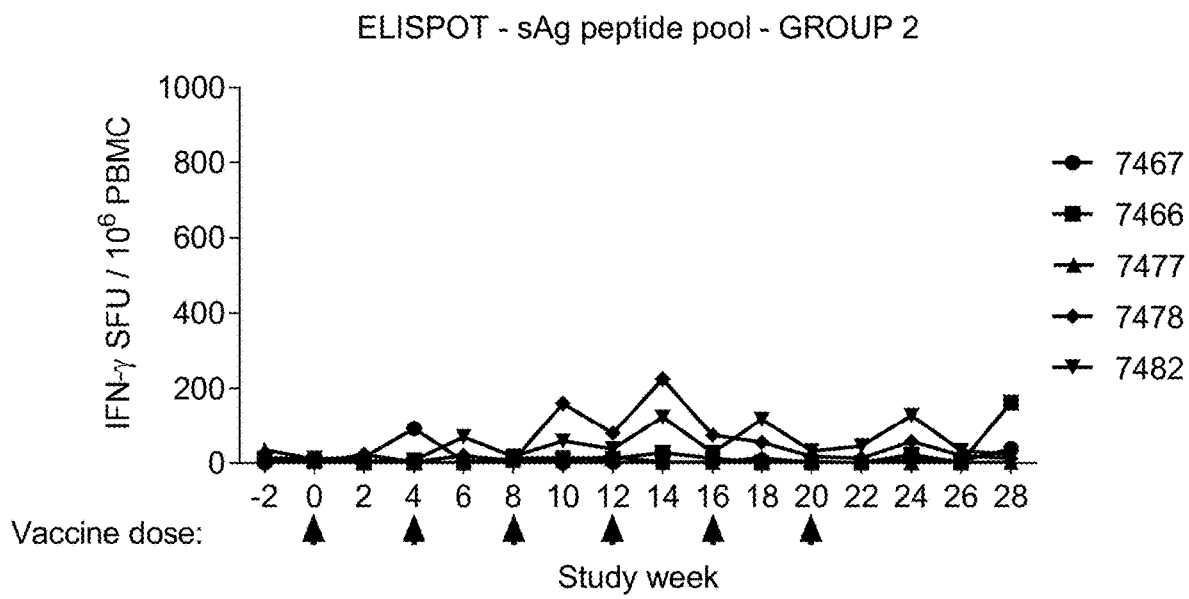
Figure 19C:
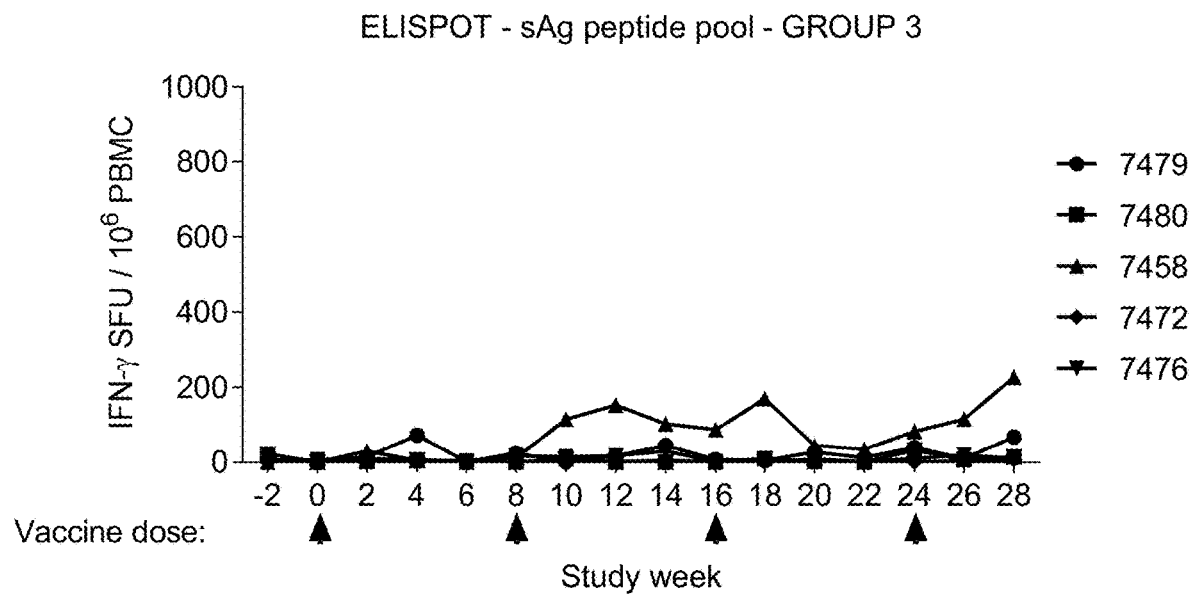
Figure 19D:
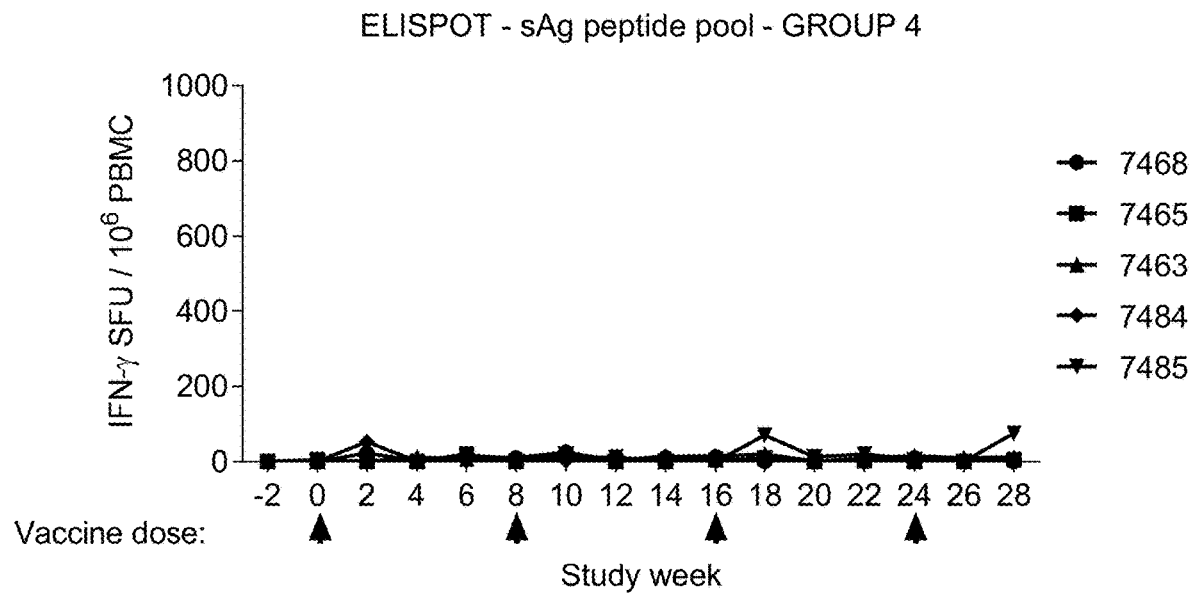
Figure 19E:
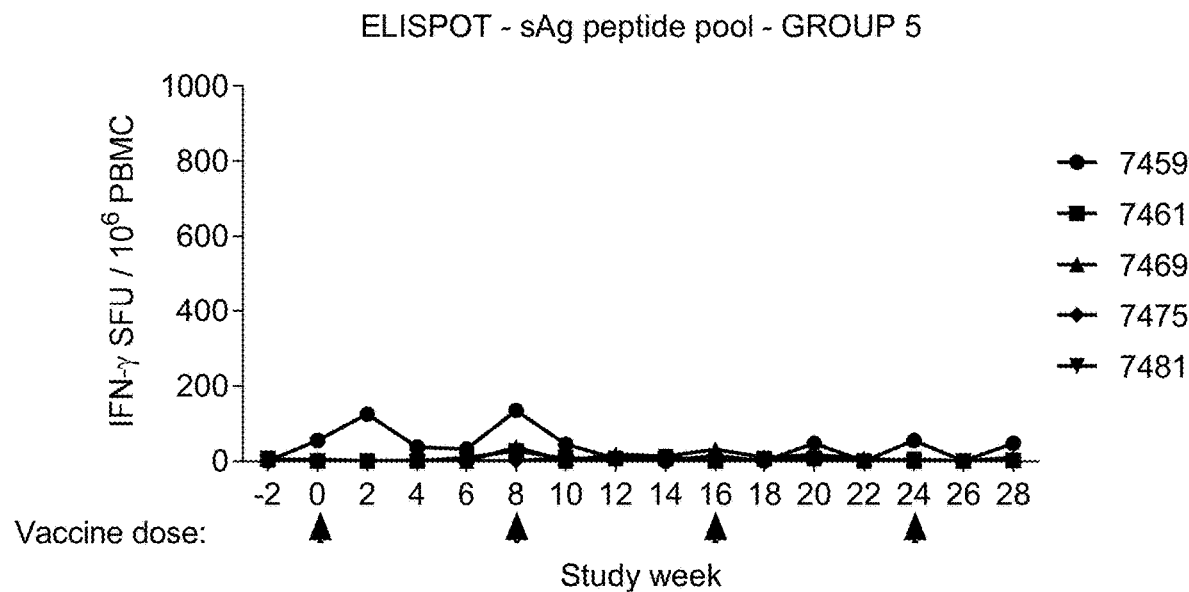
Figure 19F:
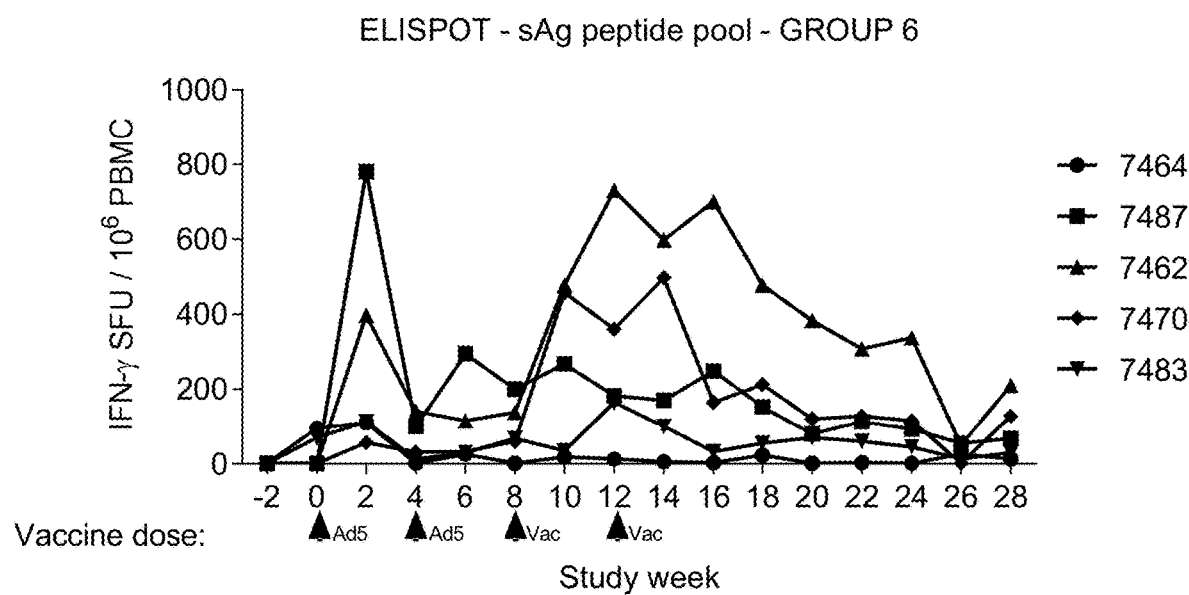
Figure 20A:
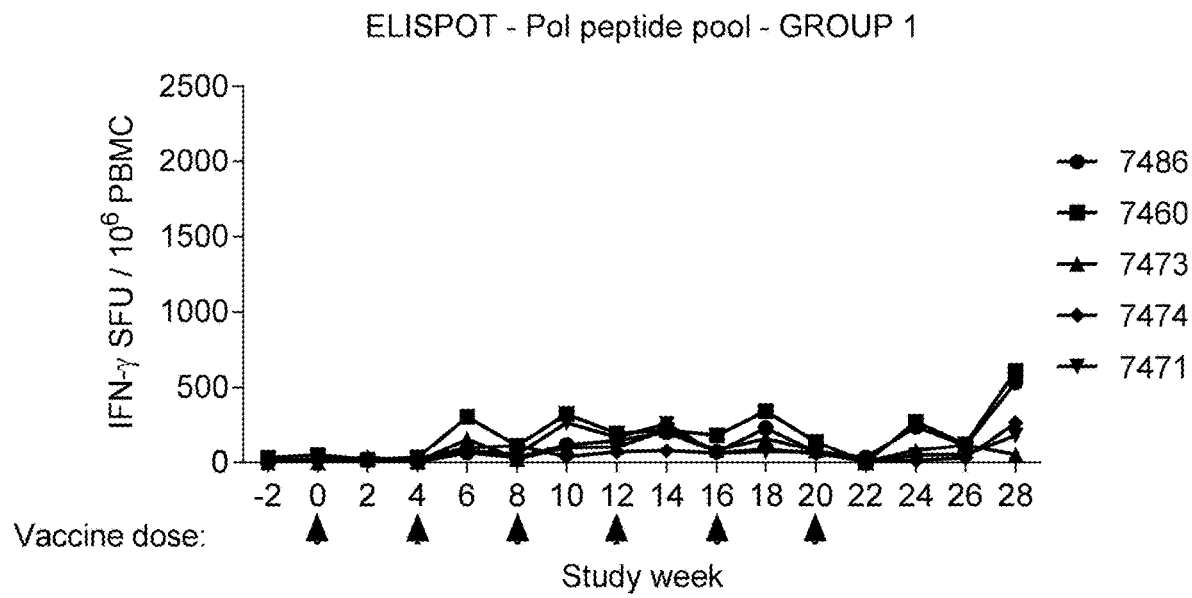
FIGS. 20A-20F illustrate the immunogenicity of repeat vaccinations with replication-incompetent LCMV vectors encoding GT-D iCore-P2A-sAg and GT-B Pol300 in cynomolgus macaques as described in FIG. 17 and Table 11.
Figure 20B:
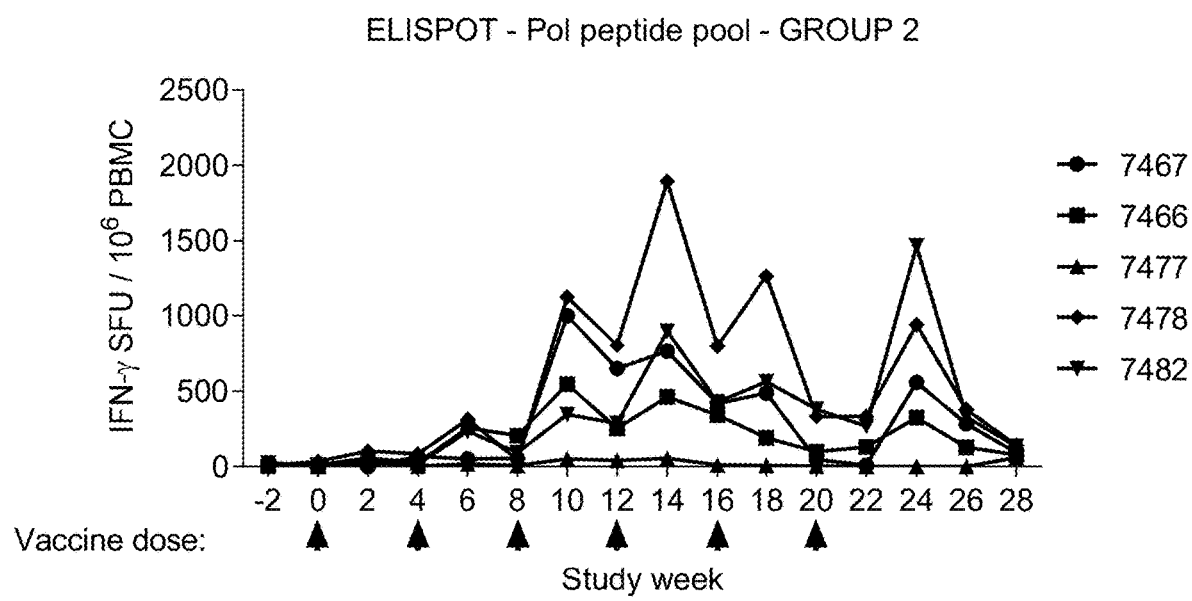
Figure 20C:
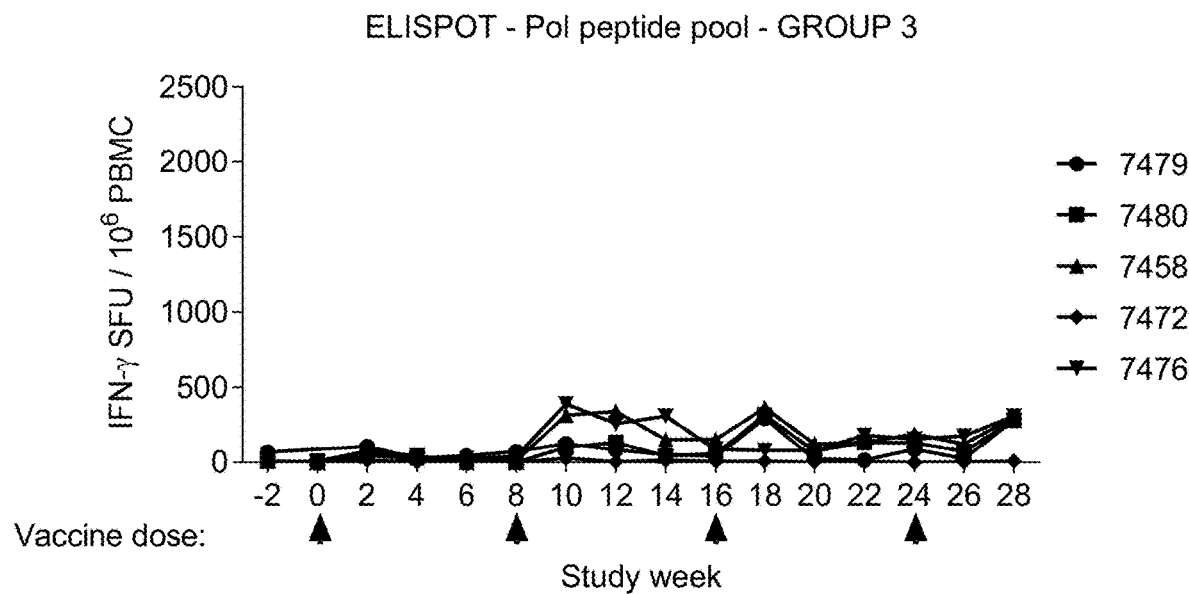
Figure 20D:
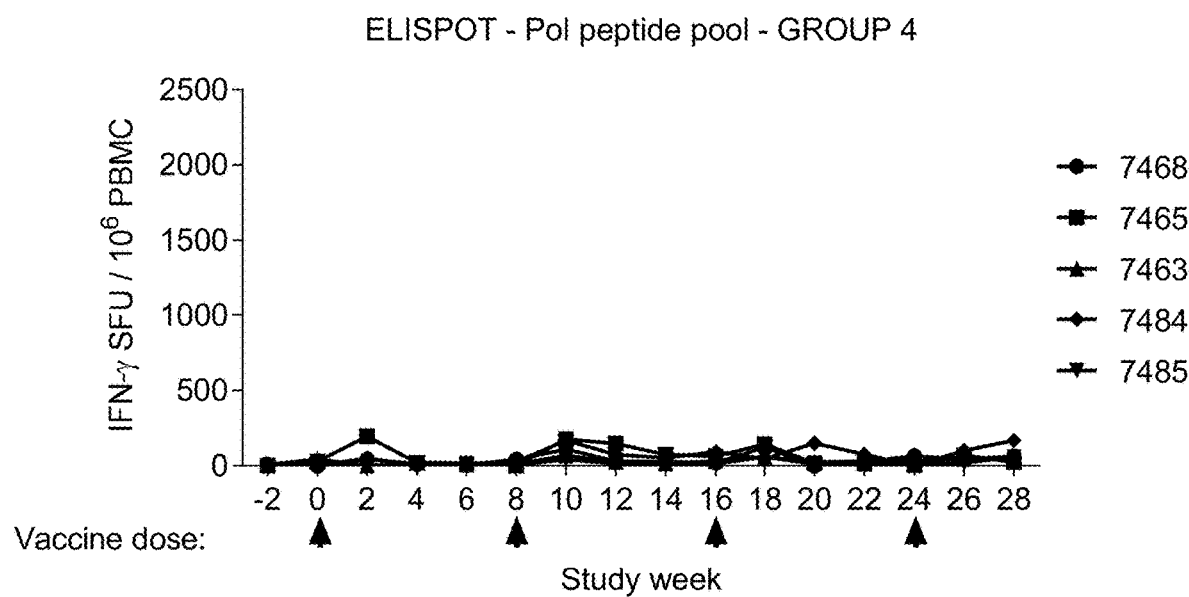
Figure 20E:
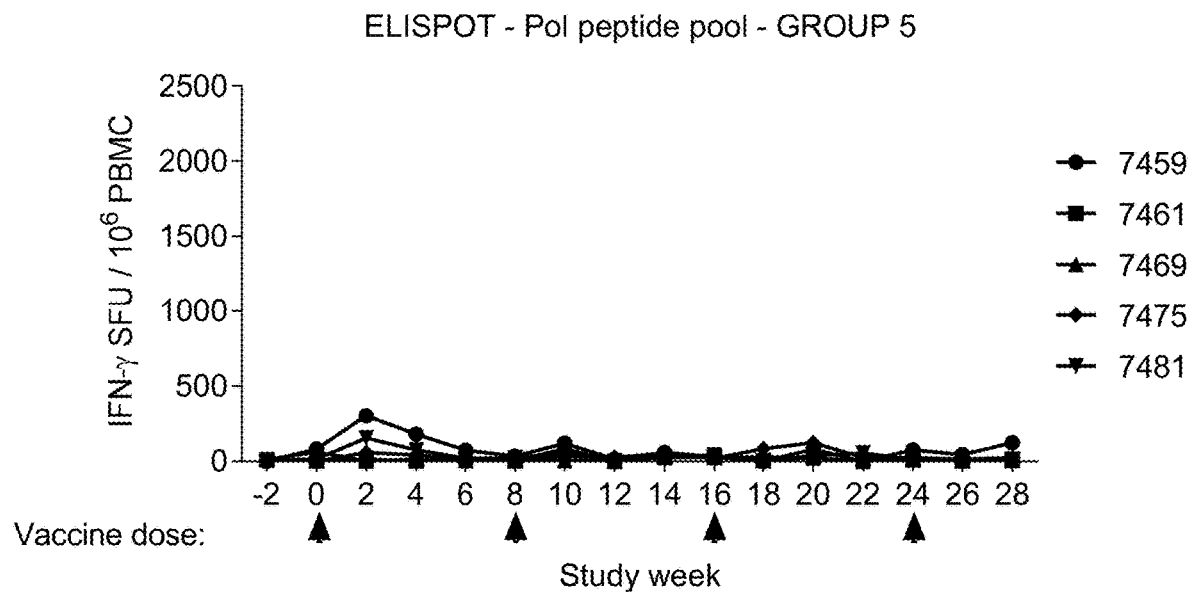
Figure 20F:
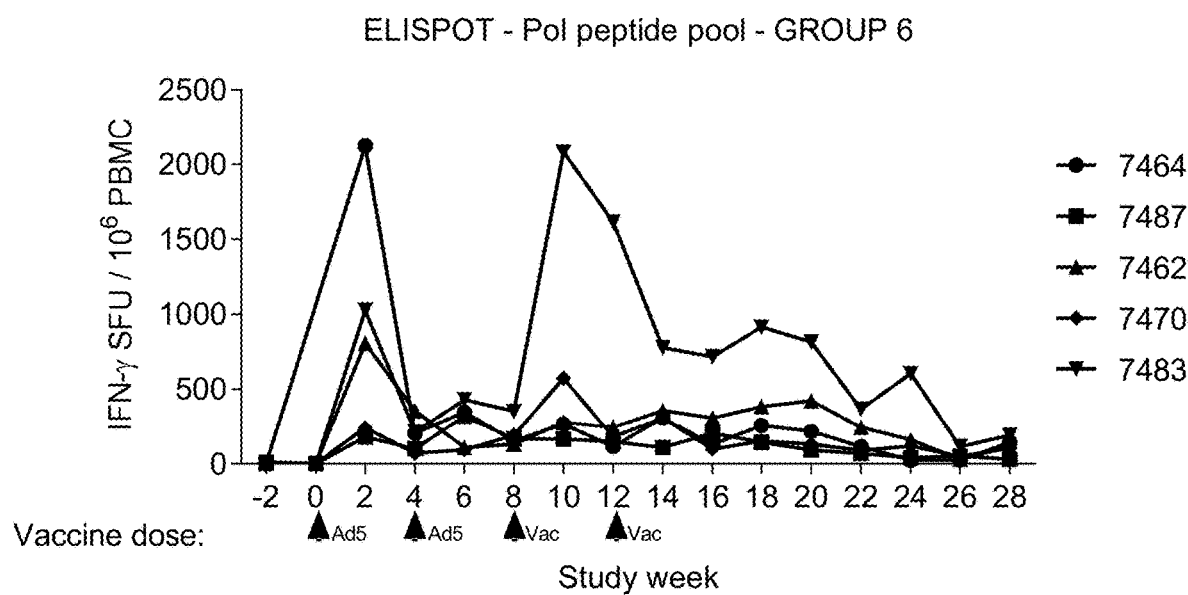

Total HBV-specific T cell responses (defined as the sum of core, sAg and polymerase-specific responses shown in FIGS. 18A-18F to 20A-20F) to the VV1 GT-D iCore-P2A-sAg and GT-B Pol$^{300}$ vectors were highest when administered via the intramuscular route (i.m.) and every 4 weeks (groups 1 and 2) (FIGS. 17A-B). Ad5 and vaccinia vectors encoding for the same antigens also induced comparable T cell responses. HBV-specific immune responses were detected after the first dose of VV1 GT-D iCore-P2A-sAg and GT-B Pol$^{300}$ vectors, and doses two through four induced progressive increases in the HBV-specific ELISPOT magnitude. The fifth and sixth doses did not further increase responses, indicating that the peak response to our vectors was reached after the fourth dose. The geometric mean response by week 14 was 1206 SFU/$10^6$ PBMC in animals administered the full human dose ($10^8$ FFU, Group 2), and approximately 2-fold lower at the lower dose $5 \times 10^6$ FFU (group 1) indicating dose-responsiveness.

Figure 21A:
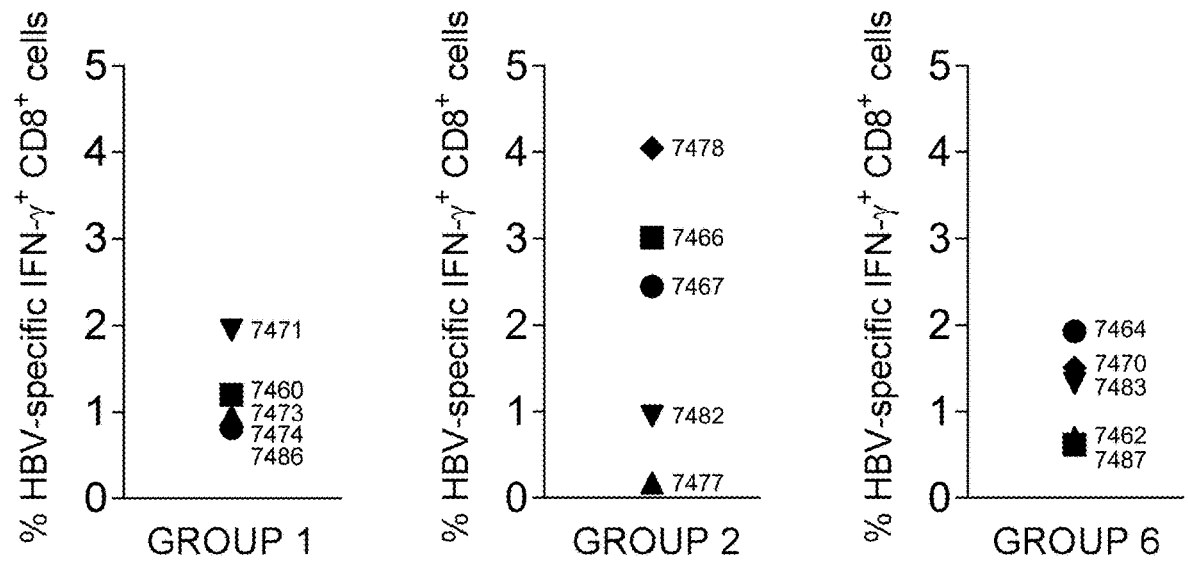
Figure 21B:
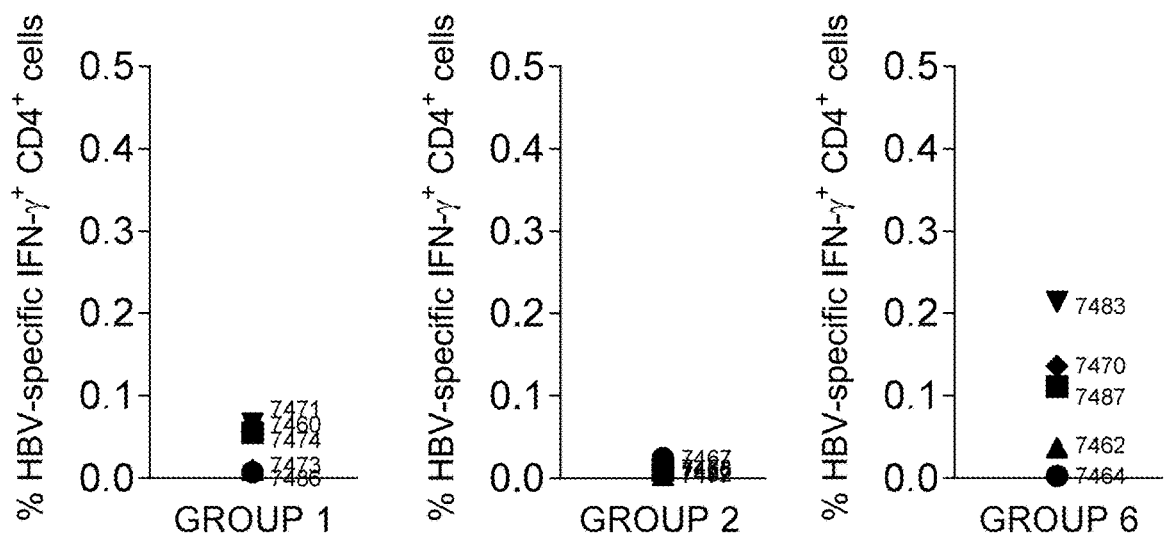
Figure 23:
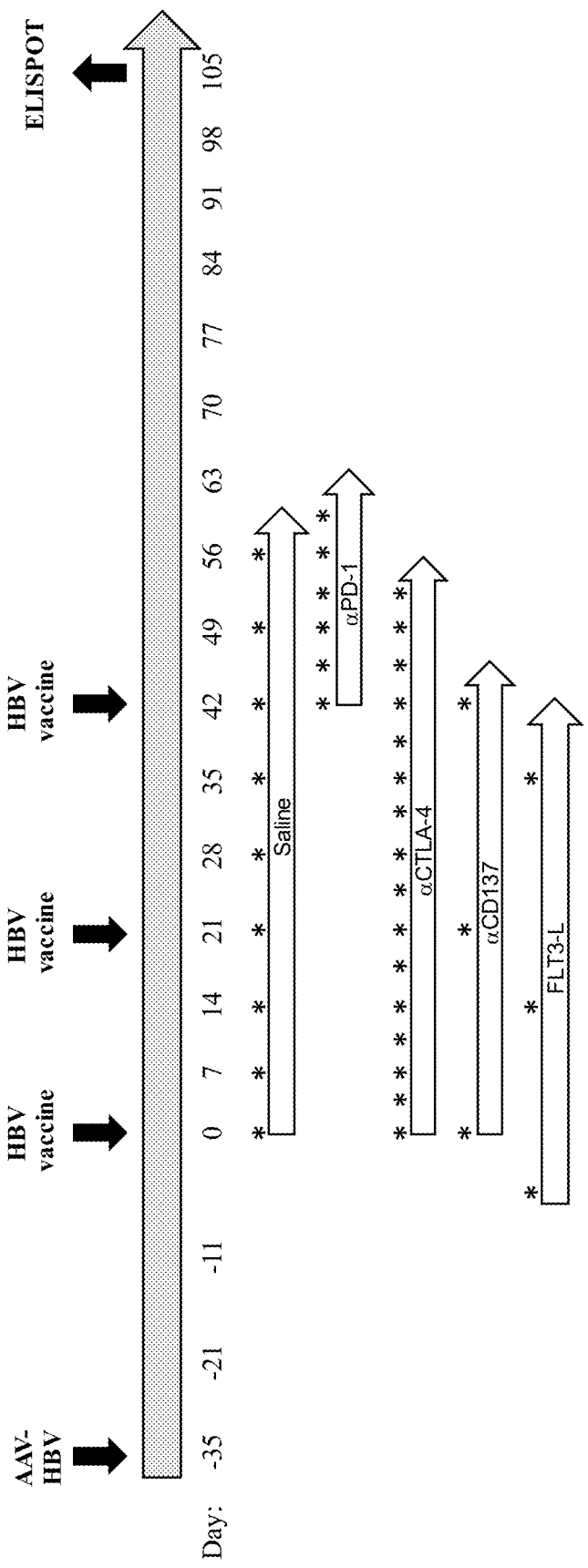

To quantify the contribution of CD4+ and CD8+ T cells to the total T cell response, PBMCs from animals from group 1, 2 and 6 were analyzed by intracellular cytokine staining (ICS) on study week 14, when T cell responses were the highest. Both groups 1 and 2 had increased levels of IFN-γ+CD8+ T cells in response to stimulation with HBV peptides. The background-corrected frequency of these cells ranged from 0.8% to 1.9% in Group 1 and from 0.2% to 4% in Group 2 (FIG. 21A). In contrast, IFN-γ+CD4+ T cells specific for HBV were detectable but at less than 0.1% of total CD4+ T cells (FIG. 21B). Thus, the T cell response induced by our vectors in non-human primates is predominantly composed of CD8+ T cells.

Anti-HBsAg antibodies were also induced by dosing with our vectors. Anti-sAg responses increased with dose level and with repeated administration of the vectors (FIG. 22).

Example 12

Immunogenicity of Replication-Incompetent LCMV Vectors in Combination with Immunomodulators in C57BL/6 Mice We evaluated the immunogenicity of replication-incompetent LCMV (VV1) vectors GT-D iCore-P2A-sAg and GT-B Pol300 alone or in combination with various immunomodulators (anti-PD-1, anti-CTLA-4 and anti-CD137 and FLT3 ligand) in the AAV-HBV mouse model.

Methods

AAV-HBV C57BL/6 mice were administered 3 doses of VV1-GT-D iCore-P2A-sAg and GT-B Pol300 vectors at day 0, day 21 and day 42. Mice were also treated with saline, anti-mouse inhibitory PD-1 antibody, anti-mouse inhibitory CTLA-4 antibody, anti-mouse stimulatory CD137 antibody and mouse FLT3-L as indicated in Table 12 and FIG. 23. A control group of mice received the HBV vaccine alone but no AAV-HBV to determine how the immunogenicity of the HBV vaccine was affected in the context of chronic HBV. HBV-specific T cell responses were measured at day 105 post first vaccination by IFN-γ ELISPOT using splenocytes. Data are expressed after subtraction of background signal in no-peptide control wells. Serum levels of HBeAg were measured at day −11 and day 105 by ELISA.

TABLE 12

| Study Groups in AAV-HBV Immunogenicity Study | | | | | |
|---|---|---|---|---|---|
| Group | N | AAV-HBV | HBV Vaccine | Immuno-modulator | Molecule and Dose |
| 1 | 11 | Yes | VV1-GT-D iCore-P2A-sAg + VV1-GT-B $Pol^{300}$ | Vehicle | Saline |
| 2 | 12 | Yes | | α-PD-1 | Clone RMP1-14 8 mg/kg/dose |
| 3 | 12 | Yes | | α-CTLA4 | Clone 9D9 10 mg/kg/dose |
| 4 | 12 | Yes | | α-CD137 | Clone mAb8 2.5 mg/kg/dose |
| 5 | 12 | Yes | | FLT3L | Murine FLT3L-Fc 1 mg/kg/dose |
| 6 | 5 | No | | Vehicle | Saline |

Results

Figure 24A:
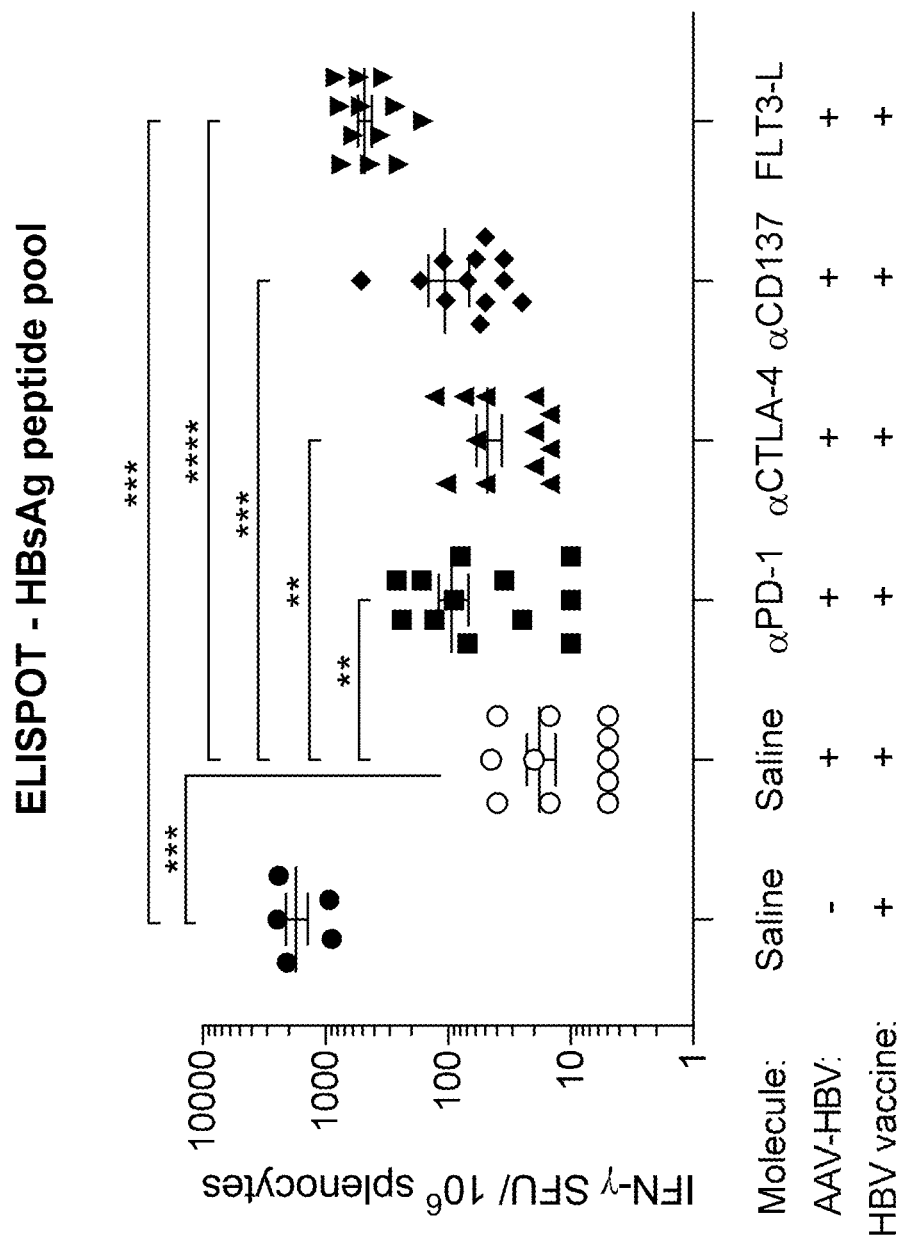
Figure 24B:
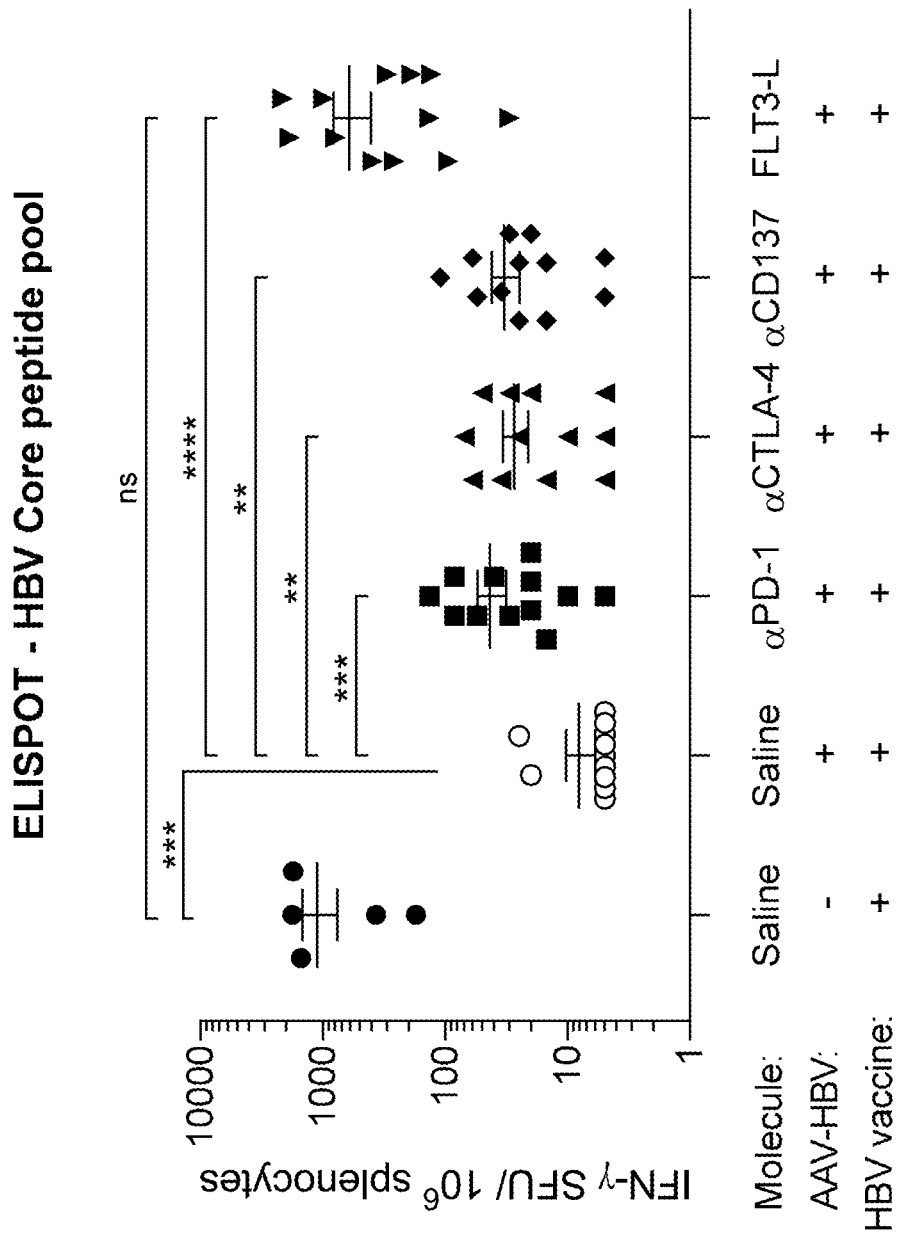
Figure 24C:
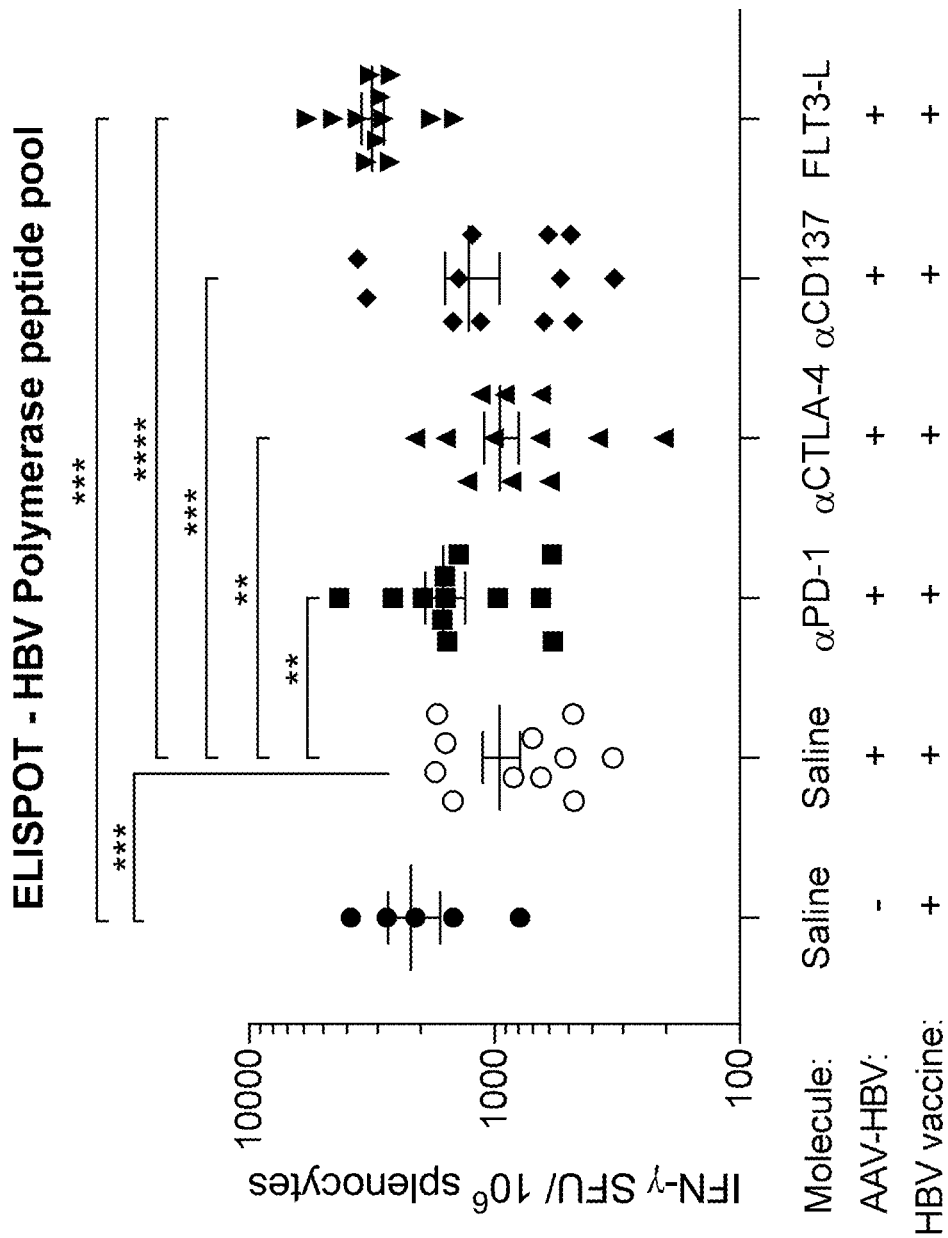

Robust IFN-γ ELISPOT responses were observed for all 3 HBV antigens in mice in the absence of persistent HBV (FIG. 24). The IFN-γ ELISPOT responses obtained from AAV-HBV mice that received the HBV vaccine alone were reduced but still present, demonstrating that VV1 GT-D iCore-P2A-sAg and GT-B Pol300 were immunogenic even in the context of an immune system tolerized to HBV. Combined administration of VV1 GT-D iCore-P2A-sAg and GT-B Pol300 with anti-PD-1, anti-CTLA-4 or anti-CD137 antibodies further improved the HBV-specific IFN-γ ELISPOT responses to core and sAg, while combination of VV1 GT-D iCore-P2A-sAg and GT-B Pol300 with FLT3-L gave the highest ELISPOT magnitude for all 3 HBV antigens.

In addition, administration of VV1 GT-D iCore-P2A-sAg and GT-B Pol300 reduced the serum levels of HBeAg in those AAV-HBV mice as measured at baseline day −11 and at day 105 (Table 13). Importantly, combined administration of VV1 GT-D iCore-P2A-sAg and GT-B Pol300 vectors with anti-PD-1, anti-CTLA-4, anti-CD137 antibodies or FTL3-L further reduced the serum levels of HBeAg (Table 13). Thus, VV1 GT-D iCore-P2A-sAg and GT-B Pol300 vectors show antiviral efficacy in the AAV-HBV mouse model which can be enhanced in combination with some immunomodulators.

TABLE 13

| Overview Table of Serum HBeAg Levels in AAV-HBV Mice | | | |
|---|---|---|---|
| | Serum HBeAg Level (geometric mean, ng/mL) | | Animals with serum HBeAg <100 ng/mL |
| Group | Day −11 | Day 105 | at day 105 |
| HBV vaccine + saline | 868 | 528 | 0/11 |
| HBV vaccine + α-PD-1 | 879 | 337 | 3/12 |
| HBV vaccine + α-CTLA4 | 661 | 341 | 2/12 |
| HBV vaccine + α-CD137 | 1069 | 500 | 1/12 |
| HBV vaccine + FLT3L-Fc | 773 | 315 | 3/12 |

Example 13

Figure 25:
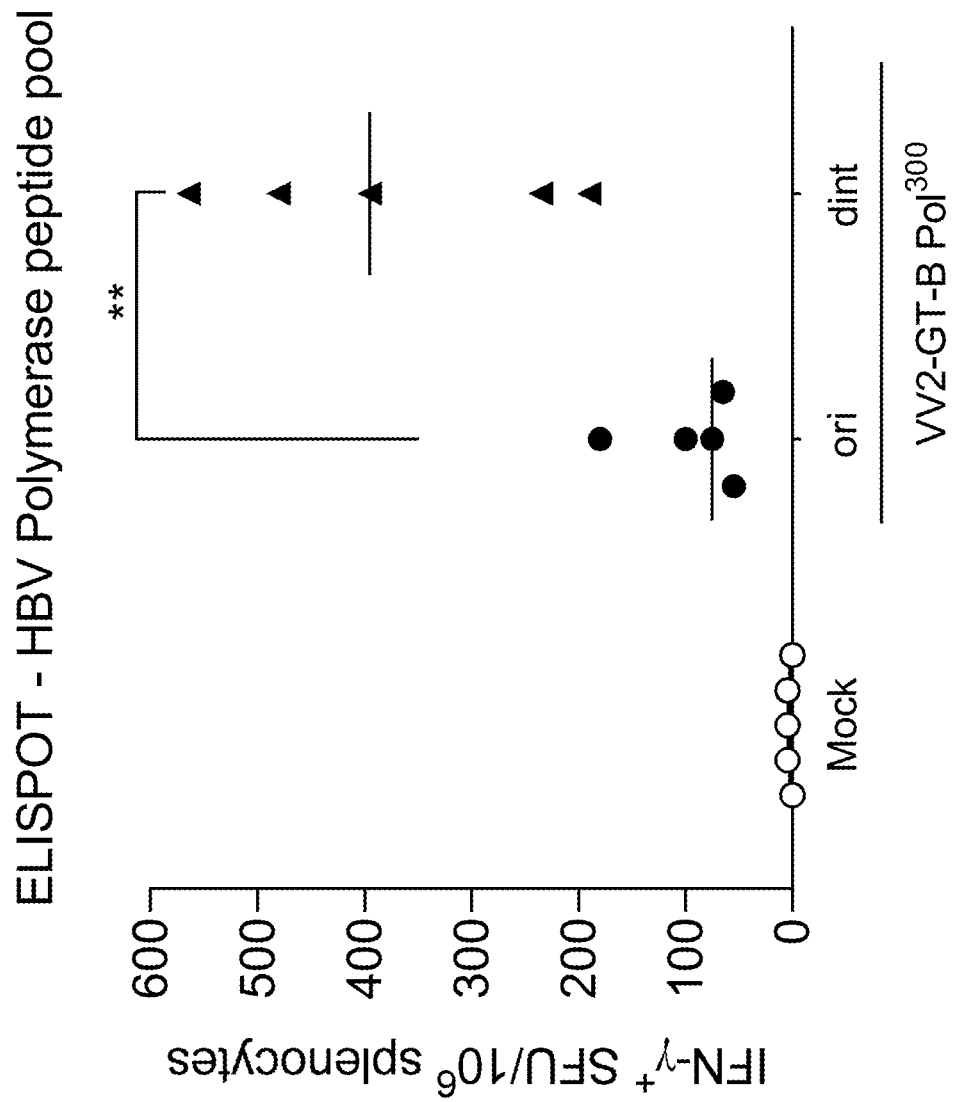

Identification of Replication-Incompetent Pichinde (PICV) Vectors Encoding Immunogenic Nucleotide-Optimized HBV Antigens We generated replication-incompetent PICV (VV2) vectors encoding the GT-D core-P2A-sAg antigen (SEQ ID NO: 41) and the GT-B Pol300 antigen (SEQ ID NO: 13), initially using the same nucleotide sequences identified to be stable and immunogenic in the replication-incompetent LCMV (VV1) vectors. The stability of the iCore-P2A-sAg transgene in VV2 vectors (SEQ ID NO: 37) was evaluated by PCR after serial passaging of vector containing supernatant and found to be sufficiently stable for manufacture (Table 13). Genetic stability was defined by the major band showing at the correct size of the full-length transgene (TG).

In contrast, when the same GT-B $Pol^{300}$ transgene used in the VV1 vectors (SEQ ID NO: 29) was used in VV2 vectors, the transgene rapidly became unstable during serial passage (Table 14). To identify VV2 vectors with sufficient genetic stability for manufacturing, we generated three additional VV2 vectors encoding the same GT-B $Pol^{300}$ antigen using different nucleotide sequences, designated VV2-Pol300 IDT CpGdel (SEQ ID NO: 94), $Pol^{300}$ ori (SEQ ID NO: 89), and $Pol^{300}$ dint (SEQ ID NO: 90), Pol300 huCo low GC (SEQ ID NO: 91), and Pol300 oridel CpG (SEQ ID NO: 92). Each vector was evaluated for transgene stability by PCR after serial passaging of vector containing supernatant, with genetic stability defined by the major band showing at the correct size of the full-length transgene (TG). Results are shown in Table 14. Surprisingly, major differences in the stability of $Pol^{300}$ transgenes in VV2 vectors were evident between the different nucleotide sequences despite encoding the identical polypeptide antigen, with $Pol^{300}$ dint, $Pol^{300}$ ori, and $Pol^{300}$ oridel CpG polynucleotide sequences demonstrating the greatest stability, e.g., at least through five passages.

TABLE 14

| Overview Table for Assessment of Genetic Stability of VV2-Core-P2A-sAg and Pol300 Transgenes | | | |
|---|---|---|---|
| Genotype | Nucleic acid SEQ ID NO: | Vector | Stable TG insertion until |
| GT-D | 37 | VV2-iCore-P2A-sAg | P5 |
| GT-B | 29 | VV2-$Pol^{300}$ | P1 |
| GT-B | 94 | VV2-Pol300__IDT__CpGdel | P3 |
| GT-B | 91 | VV2-$Pol^{300}$ huColowGC | P4 |
| GT-B | 89 | VV2-$Pol^{300}$ ori | P5 |
| GT-B | 92 | VV2-$Pol^{300}$ oridel CpG | P5 |
| GT-B | 90 | VV2-$Pol^{300}$ dint | P5 |

*VV2 refers to replication-incompetent PICV vectors.
"P#" indicates the number of passages (e.g. , P1 equals 1 passage).

Next, to assess potential differences in immunogenicity between vectors carrying the $Pol^{300}$ dint and $Pol^{300}$ ori transgenes, C57BL/6 mice were immunized twice at day 0 and day 21 with replication-incompetent PICV (VV2) vectors encoding GT-B Pol$^{300}$ ori or GT-B Pol$^{300}$ dint. HBV-specific T cell responses were then measured from splenocytes by IFN-γ ELISPOT using Pol peptide pools. Surprisingly, VV2-GT-B Pol$^{300}$ dint induced a much stronger T cell response than VV2-GT-B Pol$^{300}$ ori despite encoding identical amino acid sequences (FIG. 25). Thus, VV2-GT-B Pol$^{300}$ dint is more immunogenic than VV2-GT-B Pol$^{300}$ ori in C57BL/6 mice.

Example 14

Immunogenicity of Replication-Incompetent LCMV and PICV Arenavirus Vectors Using Homologous or Heterologous Prime-Boost Immunization Regimens in C57BL/6 Mice We evaluated the immunogenicity of replication-incompetent LCMV (VV1) and PICV (VV2) vectors encoding GT-D iCore-P2A-sAg and GT-B Pol$^{300}$ using homologous prime/boost (VV1 vector followed by VV1 vector) or heterologous prime-boost (VV2 vector followed by VV1 vector) immunization regimens in C57BL/6 mice.
Methods
C57BL/6 mice were immunized twice with replication-incompetent LCMV and PICV vectors encoding GT-D iCore-P2A-sAg and GT-B Poi' as indicated in Table 15. HBV-specific T cell responses were measured at day 28 by IFN-γ ELISPOT using splenocytes. Anti-sAg antibody responses were quantified at day 28 by ELISA.

TABLE 15

Study Groups in Immunogenicity Study

| Group | N | Immunization Regimen | Prime vector Day 0 | Boost vector Day 21 | Harvest Day | Dose/vector |
|---|---|---|---|---|---|---|
| 1 | 5 | — | Mock | Mock | 28 | 10$^6$ FFU |
| 2 | 5 | Homologous Prime/Boost | VV1-GT-D iCore-P2A-sAg | VV1-GT-D iCore-P2A-sAg | 28 | 10$^6$ FFU |
| 3 | 5 | Heterologous Prime/Boost | VV2-GT-D iCore-P2A-sAg | VV1-GT-D iCore-P2A-sAg | 28 | 10$^6$ FFU |
| 4 | 5 | Homologous Prime/Boost | VV1-GT-B Pol$^{300}$ | VV1-GT-B Pol$^{300}$ | 28 | 10$^6$ FFU |
| 5 | 5 | Heterologous Prime/Boost | VV2-GT-B Pol$^{300}$ dint | VV1-GT-B Pol$^{300}$ | 28 | 10$^6$ FFU |

Results

Figure 26A:
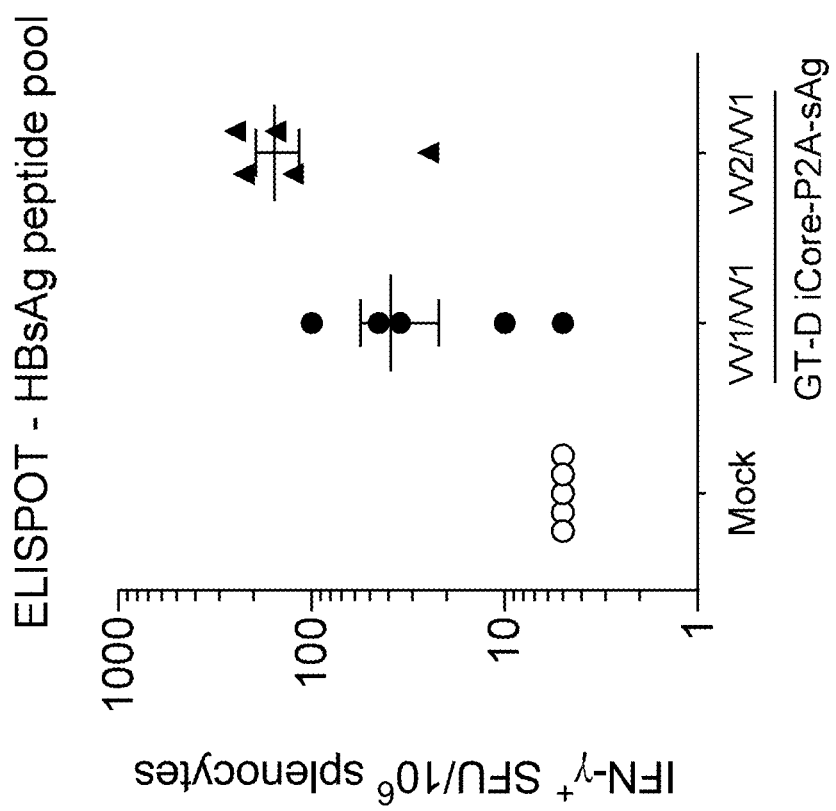
Figure 26B:
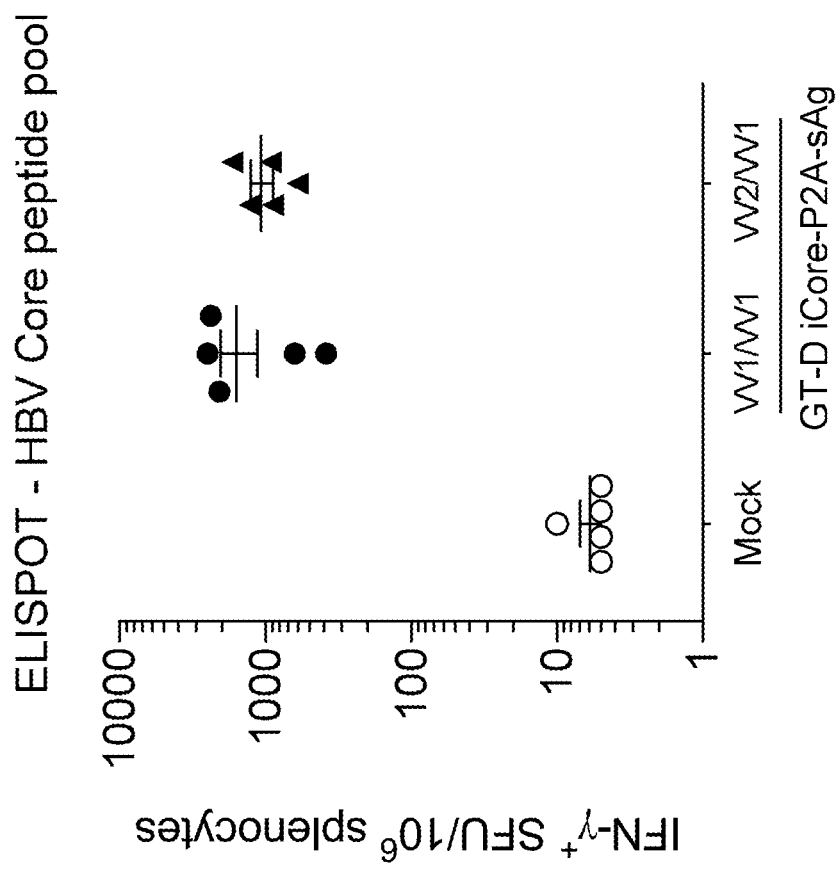
Figure 26C:
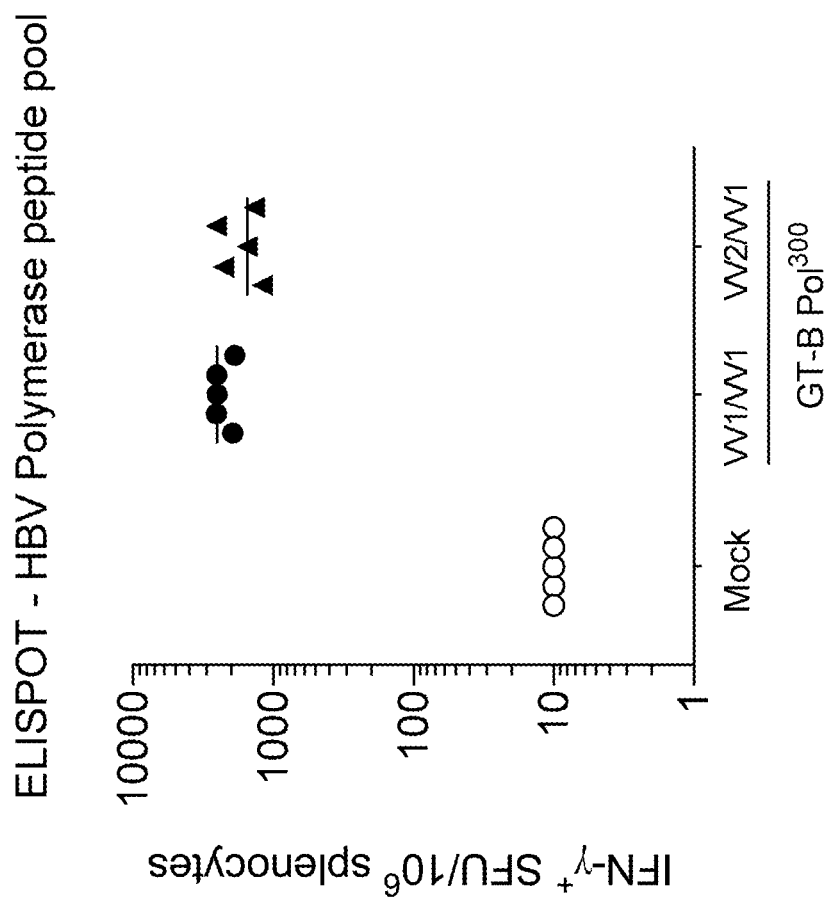
Figure 27:
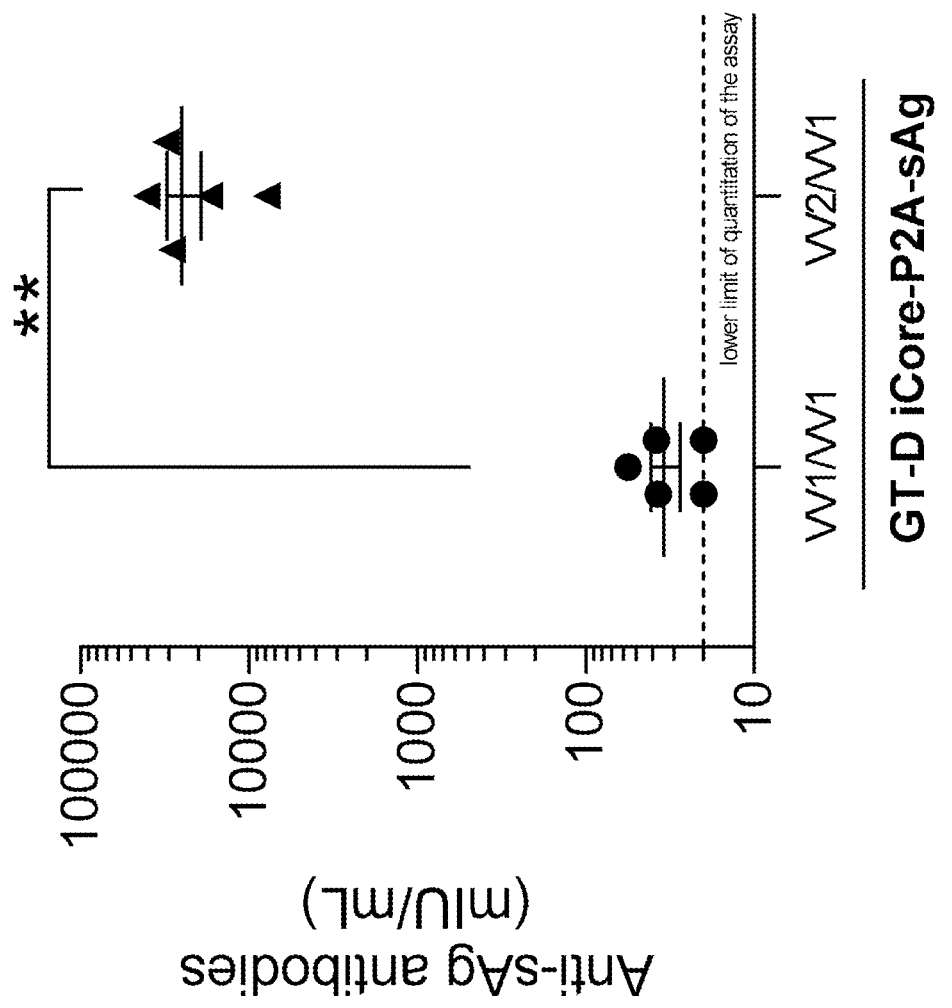

Administration of the replication-incompetent LCMV vector (VV1) encoding GT-D iCore-P2A-sAg or encoding GT-B Pol$^{300}$ using a homologous prime/boost regimen (VV1/VV1) induced robust T cell responses in C57BL/6 mice (FIGS. 26A-C). Administration of the replication-incompetent PICV vector (VV2) followed by the administration of VV1 (heterologous prime-boost regimen VV2/VV1) yielded greater sAg-specific T cell response (FIG. 26A) and similar core and Pol-specific T cell responses (FIGS. 26B-26C) compared to the VV1/VV1 regimen. Furthermore, while administration of the replication-incompetent LCMV vector using a homologous prime/boost regimen (VV1/VV1) inconsistently induced anti-sAg antibodies at low levels, immunization using the heterologous prime/boost regimen (VV2/VV1) unexpectedly led to robust and consistent induction of anti-sAg antibodies in all animals and an approximately 1000-fold increase in the average anti-sAg antibody titer (FIG. 27).

Example 15

Immunogenicity of Replication-Attenuated LCMV and PICV Arenavirus Vectors Using Homologous or Heterologous Prime-Boost Immunization Regimens in C57BL/6 Mice In addition to the replication-incompetent arenavirus vectors LCMV (VV1) and PICV (VV2), replication-competent but attenuated vectors LCMV (TT1) and PICV (TT2) encoding HBV antigens can also be engineered. Unlike VV1 and VV2 vectors, TT1 and TT2 vectors contain three genomic segments allowing genomic space to insert the two HBV antigens (the fusion protein GT-D core-P2A-sAg and the protein GT-B Pol$^{300}$) into the same vector. Because each antigen can be inserted into two different genomic segments, vectors covering the different combinations of insertion within both arenavirus vectors were generated as follows: i) GT-D core-P2A-sAg inserted into segment 1 and GT-B Pol$^{300}$ inserted into segment 2 into the LCMV backbone (TT1-GT-D core-P2A-sAg/GT-B Pol$^{300}$), ii) GT-D core-P2A-sAg inserted into segment 1 and GT-B Pol$^{300}$ inserted into segment 2 into the PICV backbone (TT2-GT-D core-P2A-sAg/GT-B Pol$^{300}$), iii) GT-D core-P2A-sAg inserted into segment 2 and GT-B Pol$^{300}$ inserted into segment 1 into the LCMV backbone (TT1-GT-B Pol$^{300}$/GT-D core-P2A-sAg) and iv) GT-D core-P2A-sAg inserted into segment 2 and GT-B Pol$^{300}$ inserted into segment 1 into the PICV backbone (TT2-GT-B Pol$^{300}$/GT-D core-P2A-sAg). We next evaluated the immunogenicity of these 4 vectors using homologous or heterologous prime-boost immunization regimens in C57BL/6 mice.
Methods
C57BL/6 mice were immunized twice with replication-attenuated LCMV and PICV vectors encoding GT-D Core-P2A-sAg and GT-B Pol$^{300}$ as indicated in Table 16. HBV-specific T cell responses were measured at day 28 by IFN-γ ELISPOT using splenocytes.

TABLE 16

Study Groups in Immunogenicity Study

| Group | N | Prime vector Day 0 | Boost vector Day 21 | Harvest Day | Dose/ vector (RCV/FFU) |
|---|---|---|---|---|---|
| 1 | 5 | Mock | Mock | 28 | — |
| 2 | 5 | TT1-GT-D core-P2A-sAg/GT-B Pol$^{300}$ | TT1-GT-D core-P2A-sAg/GT-B Pol$^{300}$ | 28 | $5 \times 10^4$ |
| 3 | 5 | TT2-GT-D core-P2A-sAg/GT-B Pol$^{300}$ | TT2-GT-D core-P2A-sAg/GT-B Pol$^{300}$ | 28 | $5 \times 10^4$ |
| 4 | 5 | TT2-GT-D core-P2A-sAg/GT-B Pol$^{300}$ | TT1-GT-D core-P2A-sAg/GT-B Pol$^{300}$ | 28 | $5 \times 10^4$ |
| 5 | 5 | TT1-GT-B Pol$^{300}$/ GT-D core-P2A-sAg | TT1-GT-B Pol$^{300}$/ GT-D core-P2A-sAg | 28 | $5 \times 10^4$ |
| 6 | 5 | TT2-GT-B Pol$^{300}$/ GT-D core-P2A-sAg | TT2-GT-B Pol$^{300}$/ GT-D core-P2A-sAg | 28 | $5 \times 10^4$ |
| 7 | 5 | TT2-GT-B Pol$^{300}$/ GT-D core-P2A-sAg | TT1-GT-B Pol$^{300}$/ GT-D core-P2A-sAg | 28 | $5 \times 10^4$ |

Results

Figure 28A:
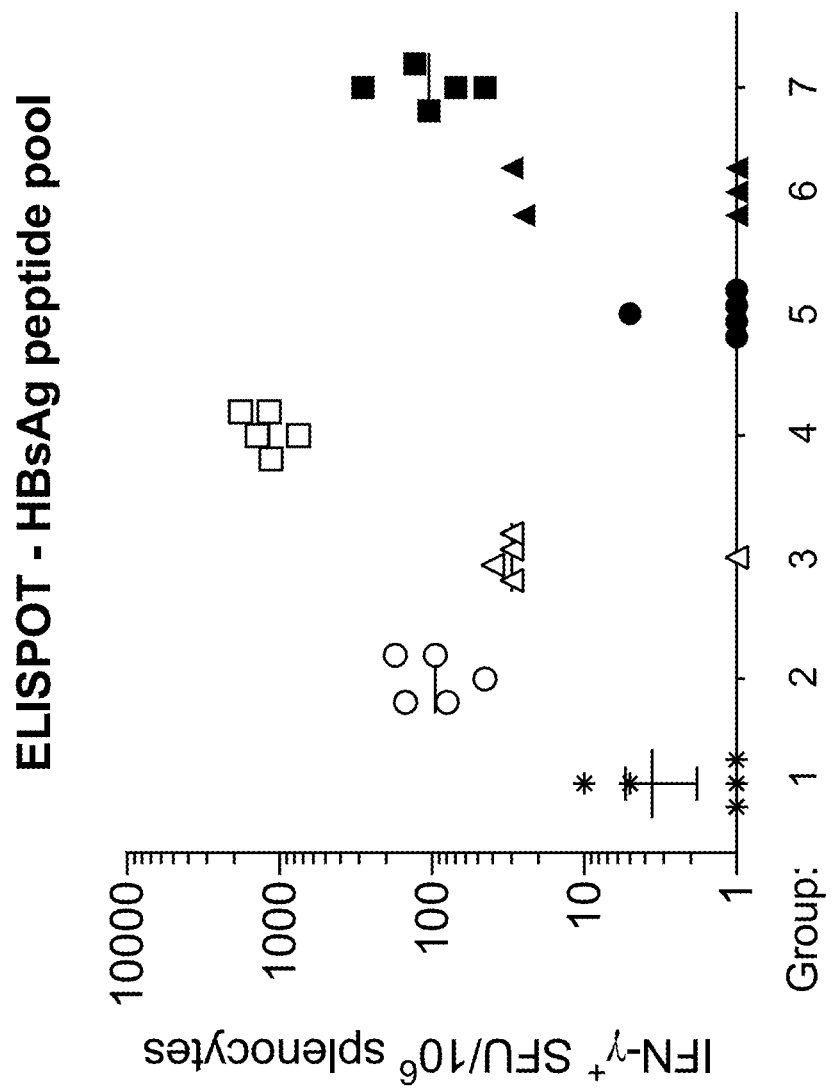
Figure 28B:
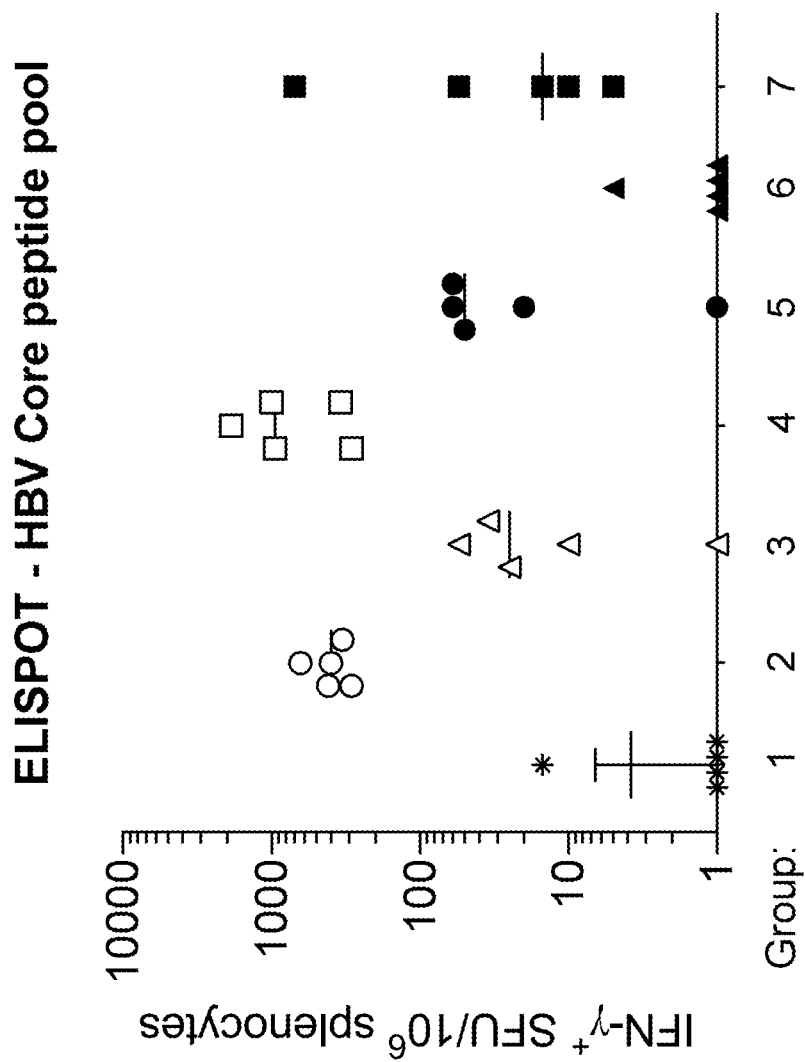
Figure 28C:
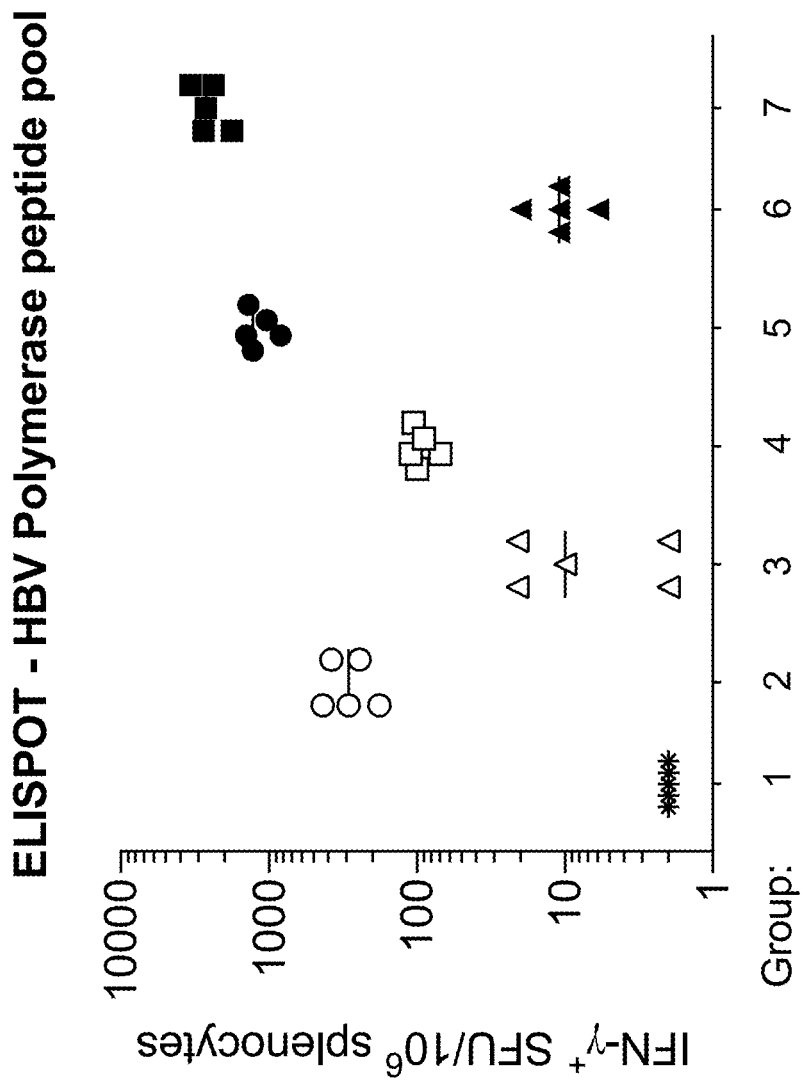

Administration of all replication-competent vectors resulted in robust T cells responses specific for the 3 HBV antigens sAg, core and Pol (FIGS. 28A-28C). Thus, TT1 and TT2 vectors expressing HBV antigens are strongly immunogenic in C57BL/6 mice.

Example 16

Figure 29:
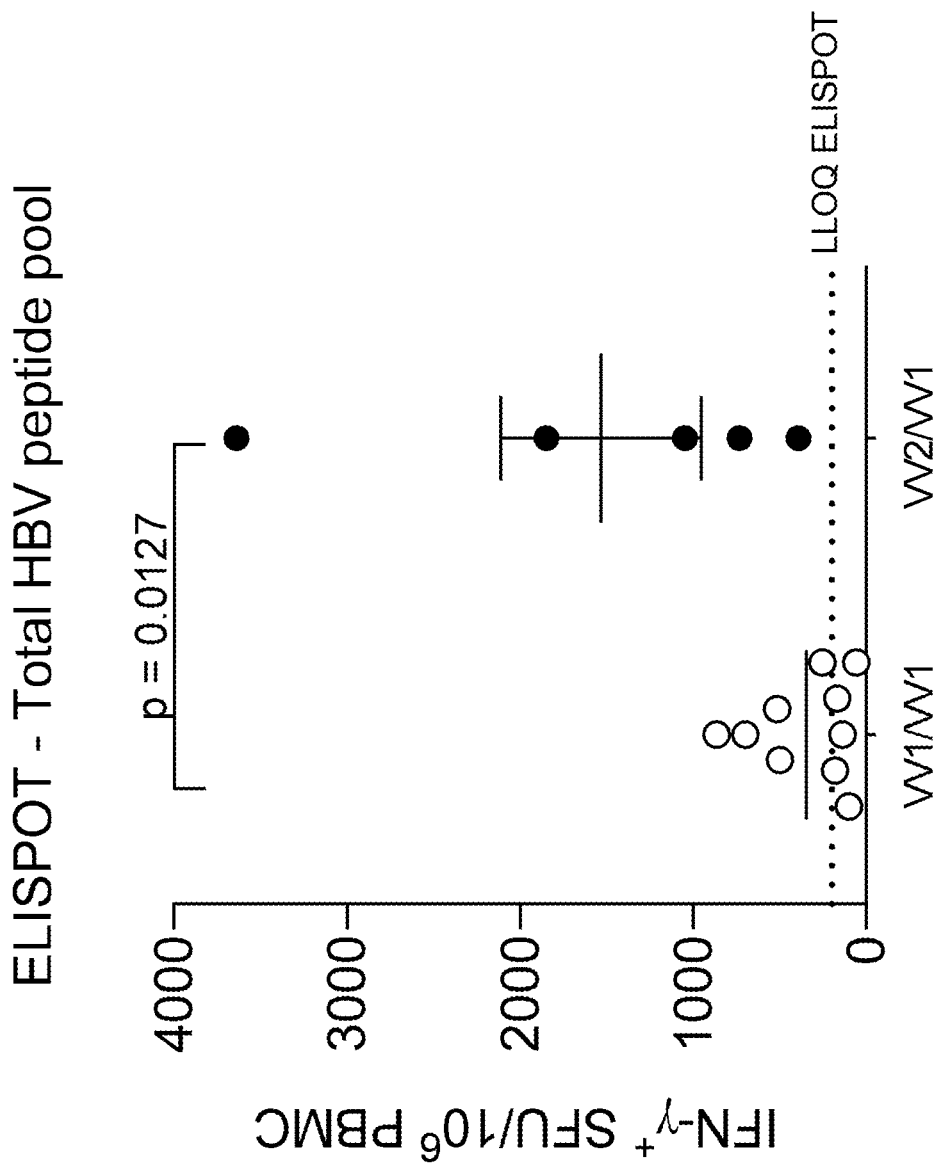

Immunogenicity of Replication-Incompetent LCMV and PICV Arenavirus Vectors Using Homologous or Heterologous Prime-Boost Immunization Regimens in Cynomolgus Macaques We evaluated the immunogenicity of replication-incompetent LCMV (VV1) and PICV (VV2) vectors encoding GT-D iCore-P2A-sAg and GT-B Pol300 using homologous prime/boost (VV1 vector followed by VV1 vector) or heterologous prime-boost (VV2 vector followed by VV1 vector) immunization regimens in cynomolgus macaques.
Methods Cynomolgus macaques (n=5) were immunized with VV2 vectors ($5 \times 10^6$ FFU/vector) at week 0 and then immunized with VV1 vectors ($5 \times 10^6$ FFU/vector) at week 4, and HBV-specific T cell responses were measured using PBMC by IFN-γ ELISPOT at week 6. Data were compared to ELISPOTs from 10 cynomolgus macaques immunized with VV1 vectors only ($5 \times 10^6$ FFU/vector) at both week 0 and week 4 (homologous prime boost regimen).
Results Administration of the replication-incompetent LCMV vectors (VV1) encoding GT-D iCore-P2A-sAg and GT-B Pol300 using a homologous prime/boost regimen (VV1/VV1) induced HBV-specific T cell responses in 5 out of 10 cynomolgus macaques (FIG. 29). In contrast, administration of the replication-incompetent PICV vector (VV2) followed by VV1 (heterologous prime/boost regimen VV2/VV1) yielded statistically greater HBV-specific T cell responses in all 5 animals compared to the VV1/VV1 homologous prime boot regimen (FIG. 29).

Example 17

Immunogenicity of Replication-Incompetent LCMV and PICV Arenavirus Vectors Using Homologous or Heterologous Prime-Boost Immunization Regimens with 1-Week Dosing Intervals in Cynomolgus Macaques We evaluated the immunogenicity of replication-incompetent LCMV (VV1) and PICV (VV2) vectors encoding GT-D iCore-P2A-sAg and GT-B Pol300 using homologous prime/boost (VV1 vector followed by VV1 vector) or heterologous prime-boost (VV2 vector followed by VV1 vector) immunization regimens administered with a 1-week dosing interval in cynomolgus macaques.
Methods Cynomolgus macaques were immunized as described in Table 17. HBV-specific T cell responses were measured using PBMC by IFN-γ ELISPOT at week 4.

TABLE 17

Study Groups in Immunogenicity Study

| Group | N | Vaccine Prime | Vaccine Boost | Dose/ vector | Immunization schedule (week) | ELISPOT analysis |
|---|---|---|---|---|---|---|
| 1 | 5 | VV1 | VV1 | $10^8$ FFU | 0 (VV1) 1 (VV1) 2 (VV1) 3 (VV1) | Week 4 |
| 2 | 5 | VV2 | VV1 | $10^8$ FFU | 0 (VV2) 1 (VV1) 2 (VV2) 3 (VV1) | Week 4 |

Results

Figure 30:
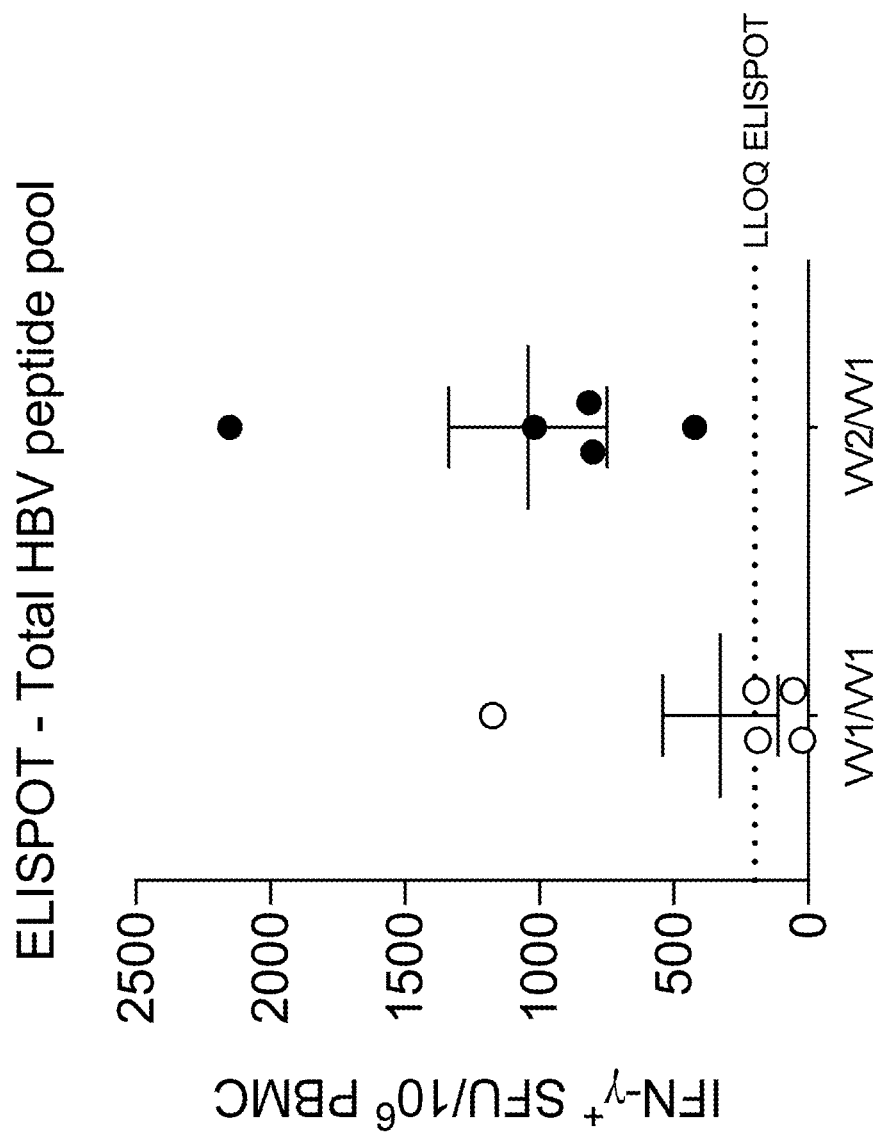

Administration of the replication-incompetent PICV vector (VV2) followed by VV1 (heterologous prime/boost regimen VV2/VV1) yielded greater HBV-specific T cell responses compared to vaccination with VV1 vector alone (FIG. 30).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An immunogenic composition comprising a first viral expression vector and a second viral expression vector, wherein:
   the first viral expression vector comprises a polynucleotide encoding a truncated HBV polymerase polypeptide mutant, wherein the polypeptide is no longer than 600 amino acids in length, does not comprise all of the terminal protein (TP) domain and does not comprise all or part of the Spacer domain, wherein the polypeptide comprises or consists of the amino acid sequence of any one of SEQ ID NOs: 13-14; and
   the second viral expression vector comprises a polynucleotide encoding a core-sAg fusion protein comprising in sequential order from the N-terminus to the C terminus, an HBV core polypeptide and an HBV small surface antigen (sAg) polypeptide, wherein the fusion protein is no longer than 450 amino acids in length, and wherein the core polypeptide is from an HBV genotype D and the sAg polypeptide is from an HBV genotype D, wherein the fusion protein comprises or consists of an amino acid sequence of any one of SEQ ID NOs: 40-41, or an amino acid sequence that is at least 97%, 98% or 99% identical to the full length of any one of SEQ ID NOs: 40-41.

2. The immunogenic composition of claim 1, comprising a first viral expression vector and a second viral expression vector, wherein:
   the first viral expression vector comprises a polynucleotide encoding an HBV polymerase polypeptide mutant comprising or consisting of the amino acid sequence of SEQ ID NO: 13; and
   the second viral expression vector comprises a polynucleotide encoding the core-sAg fusion protein comprising or consisting of an amino acid sequence of SEQ ID NO: 41, or an amino acid sequence that is at least 97%, 98% or 99% identical to the full length of SEQ ID NO: 41.

3. The immunogenic composition of claim 1, comprising a first viral expression vector and a second viral expression vector, wherein:
   a) the first viral expression vector comprises a polynucleotide comprising or consisting of a nucleic acid sequence of any one of SEQ ID NOs: 29, 32, 89, 90, 91, 92, 93 and 94, or a nucleic acid sequence that is at least 99% identical to the full length of any one of SEQ ID NOs: 29, 32, 89, 90, 91, 92, 93 and 94;
   b) the second viral expression vector comprises a polynucleotide comprising or consisting of a nucleic acid sequence of any one of SEQ ID NOs: 33-37 or a nucleic acid sequence that is at least 85%, 86%, 87%, 88%, 89%, 90%, 91%, 92%, 93%, 94%, 95%, 96%, 97%, 98% or 99% identical to the full length of any one of SEQ ID NOs: 33-37.

4. The immunogenic composition of claim 1, comprising a first viral expression vector and a second viral expression vector, wherein:
   a) the first viral expression vector comprises a polynucleotide comprising or consisting of a nucleic acid sequence of SEQ ID NOs: 29, 89, 90 or 92, or a nucleic acid sequence that is at least 99% identical to the full length of SEQ ID NOs: 29, 89, 90 or 92; and
   b) the second viral expression vector comprises a polynucleotide comprising or consisting of a nucleic acid sequence of SEQ ID NO: 37 or a nucleic acid sequence that is at least 85%, 86%, 87%, 88%, 89%, 90%, 91%, 92%, 93%, 94%, 95%, 96%, 97%, 98% or 99% identical to the full length of any one of SEQ ID NO: 37.

5. The immunogenic composition of claim 1, wherein the first viral expression vector and the second viral expression vector are independently from a taxonomic family selected from Adenoviridae, Arenaviridae, Herpesviridae, Poxviridae, Flaviviridae, Rhabdoviridae, and Togaviridae.

6. The immunogenic composition of claim 1, wherein the first viral expression vector and the second viral expression vector are from the same taxonomic family.

7. The immunogenic composition of claim 6, wherein the first viral expression vector and the second viral expression vector are from Arenaviridae.

8. The immunogenic composition of claim 6, wherein the first viral expression vector and the second viral expression vector are independently from an arenavirus vector selected from Lymphocytic choriomeningitis mammarenavirus (LCMV), Pichinde mammarenavirus (PICV), Guanarito virus (GTOV), Junin virus (JUNV), Lassa virus (LASV), Lujo virus (LUJV), Machupo virus (MACV), Sabia virus (SABV), and Whitewater Arroyo virus (WWAV).

9. The immunogenic composition of claim 6, wherein the first viral expression vector and the second viral expression vector are from an arenavirus vector selected from Lymphocytic choriomeningitis mammarenavirus (LCMV) or Pichinde mammarenavirus (PICV).

10. The immunogenic composition of claim 6, wherein the first viral expression vector and the second viral expression vector are replication-defective or replication-deficient.

11. The immunogenic composition of claim 6, wherein the first viral expression vector and the second viral expression vector are replication-attenuated.

12. The immunogenic composition of claim 1, wherein the first viral expression vector and the second viral expression vector are from different taxonomic families.

13. The immunogenic composition of claim 1, wherein the first viral expression vector and the second viral expression vector are provided in a ratio in the range of from 1:10 to 10:1.

14. The immunogenic composition of claim 1, comprising in the range of about $10^3$ to about $10^{12}$ viral focus forming units (ffu) or plaque forming units (pfu) or infectious units (iu) or viral particles (vp) per milliliter of each of the first viral expression vector and the second viral expression vector.

15. The immunogenic composition of claim 1, further comprising one or more of an adjuvant, a detergent, a micelle-forming agent, and an oil.

16. The immunogenic composition of claim 1, formulated for administration via a route selected from the group consisting of intravenous, intramuscular, intradermal, subcutaneous and mucosal.

17. The immunogenic composition of claim 1, formulated as a liquid.

18. The immunogenic composition of claim 1, wherein the composition is lyophilized.

19. A kit comprising one or more unitary doses of the immunogenic composition of claim 1.

* * * * *

SEQUENCE LISTING

<160> NUMBER OF SEQ ID NOS: 102

<210> SEQ ID NO 1
<211> LENGTH: 226
<212> TYPE: PRT
<213> ORGANISM: Hepatitis B virus

<400> SEQUENCE: 1

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
        195                 200                 205

Leu Ser Pro Phe Ile Pro Leu Leu Pro Ile Phe Phe Cys Leu Trp Val
    210                 215                 220

Tyr Ile
225

<210> SEQ ID NO 2
<211> LENGTH: 226
<212> TYPE: PRT
<213> ORGANISM: Hepatitis B virus

<400> SEQUENCE: 2

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ala Pro Thr Cys
        35                  40                  45

Pro Gly Gln Asn Leu Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val

```
                         85                  90                  95
Leu Leu Asp Tyr Gln Gly Met Leu Pro Val Cys Pro Leu Ile Pro Gly
                100                 105                 110

Ser Ser Thr Thr Ser Thr Gly Pro Cys Arg Thr Cys Thr Thr Pro Ala
                115                 120                 125

Gln Gly Thr Ser Met Phe Pro Ser Cys Cys Cys Thr Lys Pro Thr Asp
                130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Val Ile Trp Met Met Trp Tyr Trp Gly Pro Ser Leu Tyr Asn Ile
                195                 200                 205

Leu Ser Pro Phe Met Pro Leu Leu Pro Ile Phe Phe Cys Leu Trp Val
                210                 215                 220

Tyr Ile
225

<210> SEQ ID NO 3
<211> LENGTH: 226
<212> TYPE: PRT
<213> ORGANISM: Hepatitis B virus

<400> SEQUENCE: 3

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Ala Pro Thr Cys
                35                  40                  45

Pro Gly Gln Asn Ser Gln Ser Pro Thr Ser Asn His Ser Pro Thr Ser
50                  55                  60

Cys Pro Pro Ile Cys Pro Gly Tyr Arg Trp Met Cys Leu Arg Arg Phe
65                  70                  75                  80

Ile Ile Phe Leu Cys Ile Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Ser Thr Thr Ser Thr Gly Pro Cys Lys Thr Cys Thr Thr Pro Ala
                115                 120                 125

Gln Gly Thr Ser Met Phe Pro Ser Cys Cys Cys Thr Lys Pro Thr Asp
                130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Val Ile Trp Met Met Trp Tyr Trp Gly Pro Ser Leu Tyr Asn Ile
                195                 200                 205

Leu Ser Pro Phe Leu Pro Leu Leu Pro Ile Phe Phe Cys Leu Trp Val
                210                 215                 220
```

Tyr Ile
225

<210> SEQ ID NO 4
<211> LENGTH: 226
<212> TYPE: PRT
<213> ORGANISM: Hepatitis B virus

<400> SEQUENCE: 4

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Thr Thr Pro Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
    210                 215                 220

Tyr Ile
225
```

<210> SEQ ID NO 5
<211> LENGTH: 755
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Met Pro Leu Ser Tyr Gln His Phe Arg Lys Leu Leu Leu Leu Asp Asp
1               5                   10                  15

Glu Thr Glu Ala Gly Pro Leu Glu Glu Glu Leu Pro Arg Leu Ala Asp
            20                  25                  30

Glu Asp Leu Asn Arg Arg Val Ala Glu Asp Leu Asn Leu Gly Asn Leu
        35                  40                  45

Asn Val Ser Ile Pro Trp Thr His Lys Val Gly Asn Phe Thr Gly Leu
    50                  55                  60
```

```
Tyr Ser Ser Thr Val Pro Ile Phe Asn Pro Glu Trp Gln Thr Pro Ser
 65                  70                  75                  80

Phe Pro Lys Ile His Leu His Glu Asp Ile Ala Asn Arg Cys Gln Gln
                 85                  90                  95

Phe Val Gly Pro Leu Thr Val Asn Glu Lys Arg Arg Leu Arg Leu Ile
            100                 105                 110

Met Pro Ala Arg Phe Tyr Pro Asn Ser Thr Lys Tyr Leu Pro Leu Asp
            115                 120                 125

Lys Gly Ile Lys Pro Tyr Tyr Pro Asp His Val Val Asn His Tyr Phe
            130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
                165                 170                 175

Trp Glu Gln Glu Leu His His Gly Arg Leu Val Ile Lys Thr Ser Gln
                180                 185                 190

Arg His Gly Asp Glu Pro Phe Cys Ser Gln Pro Ser Gly Ile Leu Ser
            195                 200                 205

Arg Ser Ser Val Gly Pro Glu Phe His Ser Phe Pro Pro Ser Ser Ala
210                 215                 220

Arg Ser Gln Ser Gln Gly Pro Val Phe Ser Cys Trp Trp Leu Gln Phe
225                 230                 235                 240

Arg Asn Thr Gln Pro Cys Ser Lys Tyr Cys Leu Ser His Leu Val Asn
                245                 250                 255

Leu Leu Glu Asp Trp Gly Pro Cys Asp Glu His Gly Glu His His Ile
            260                 265                 270

Arg Ile Pro Arg Thr Pro Ala Arg Val Thr Gly Gly Val Phe Leu Val
            275                 280                 285

Asp Lys Asn Pro His Asn Thr Ala Glu Ser Arg Leu Val Val Asp Phe
            290                 295                 300

Ser Gln Phe Ser Arg Gly Ile Thr Arg Val Ser Trp Pro Lys Phe Ala
305                 310                 315                 320

Val Pro Asn Leu Gln Ser Leu Thr Asn Leu Leu Ser Ser Asn Leu Ser
                325                 330                 335

Trp Leu Ser Leu Asp Val Ser Ala Ala Phe Tyr His Ile Pro Leu His
            340                 345                 350

Pro Ala Ala Met Pro His Leu Leu Val Gly Ser Ser Gly Leu Ser Arg
            355                 360                 365

Tyr Val Ala Arg Leu Ser Ser Asn Ser Arg Ile His Asn Asn Gln His
            370                 375                 380

Gly Thr Leu Gln Asn Leu His Asp Ser Cys Ser Arg Gln Leu Tyr Val
385                 390                 395                 400

Ser Leu Met Leu Leu Tyr Lys Thr Tyr Gly Arg Lys Leu His Leu Tyr
                405                 410                 415

Ser His Pro Ile Ile Leu Gly Phe Arg Lys Ile Pro Met Gly Val Gly
            420                 425                 430

Leu Ser Pro Phe Leu Leu Ala Gln Phe Thr Ser Ala Ile Cys Ser Val
            435                 440                 445

Val Arg Arg Ala Phe Pro His Cys Leu Ala Phe Ser Tyr Met His Asp
            450                 455                 460

Val Val Leu Gly Ala Lys Ser Val Gln His Leu Glu Ser Leu Tyr Thr
465                 470                 475                 480

Ala Val Thr Asn Phe Leu Leu Ser Leu Gly Ile His Leu Asn Pro Asn
```

```
                        485           490           495
Lys Thr Lys Arg Trp Gly Tyr Ser Leu Asn Phe Met Gly Tyr Val Ile
                500               505               510

Gly Ser Trp Gly Thr Leu Pro Gln Asp His Ile Val Gln Lys Ile Lys
            515               520               525

His Cys Phe Arg Lys Leu Pro Ile Asn Arg Pro Ile Asp Trp Lys Val
        530               535               540

Cys Gln Arg Ile Val Gly Leu Leu Gly Phe Ala Ala Pro Phe Thr Gln
545               550               555               560

Cys Gly Tyr Pro Ala Leu Met Pro Leu Tyr Ala Cys Ile Gln Ala Lys
                565               570               575

Gln Ala Phe Thr Phe Ser Pro Thr Tyr Lys Ala Phe Leu Ser Lys Gln
            580               585               590

Tyr Leu Asn Leu Tyr Pro Val Ala Arg Gln Arg Pro Gly Leu Cys Gln
        595               600               605

Val Phe Ala Asp Ala Thr Pro Thr Gly Trp Gly Leu Ala Ile Gly His
        610               615               620

Gln Arg Met Arg Gly Thr Phe Val Ala Pro Leu Pro Ile His Thr Ala
625               630               635               640

His Leu Leu Ala Ala Cys Phe Ala Arg Ser Arg Ser Gly Ala Lys Leu
                645               650               655

Ile Gly Thr Asp Asn Ser Val Val Leu Ser Arg Lys Tyr Thr Ser Phe
            660               665               670

Pro Trp Leu Leu Gly Cys Thr Ala Asn Trp Ile Leu Arg Gly Thr Ser
        675               680               685

Phe Val Tyr Val Pro Ser Ala Leu Asn Pro Ala Asp Asp Pro Ser Arg
        690               695               700

Gly Arg Leu Gly Leu Tyr Arg Pro Leu Leu Arg Leu Pro Tyr Arg Pro
705               710               715               720

Thr Thr Gly Arg Thr Ser Leu Tyr Ala Val Ser Pro Ser Val Pro Ser
                725               730               735

His Leu Pro Val Arg Val His Phe Ala Ser Pro Leu His Val Ala Trp
            740               745               750

Arg Pro Pro
        755

<210> SEQ ID NO 6
<211> LENGTH: 749
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
        50                  55                  60

Ser Thr Val Pro Val Phe Asn Pro Glu Trp Gln Thr Pro Ser Phe Pro
65                  70                  75                  80
```

```
His Ile His Leu Gln Glu Asp Ile Ile Asn Arg Cys Gln Gln Tyr Val
             85                  90                  95
Gly Pro Leu Thr Val Asn Glu Lys Arg Leu Lys Leu Ile Met Pro
            100                 105                 110
Ala Arg Phe Tyr Pro Asn Leu Thr Lys Tyr Leu Pro Leu Asp Lys Gly
            115                 120                 125
Ile Lys Pro Tyr Tyr Pro Glu His Val Val Asn His Tyr Phe Gln Thr
            130                 135                 140
Arg His Tyr Leu His Thr Leu Trp Lys Ala Gly Ile Leu Tyr Lys Arg
145                 150                 155                 160
Glu Ser Thr Arg Ser Ala Ser Phe Cys Gly Ser Pro Tyr Ser Trp Glu
                165                 170                 175
Gln Asp Leu Gln His Gly Arg Leu Val Phe Gln Thr Ser Lys Arg His
            180                 185                 190
Gly Asp Lys Ser Phe Cys Pro Gln Ser Pro Gly Ile Leu Pro Arg Ser
            195                 200                 205
Glu Leu His His Phe Pro Pro Ser Ser Arg Ser Gln Ser Gln Gly
            210                 215                 220
Pro Val Leu Ser Cys Trp Trp Leu Gln Phe Arg Asn Ser Glu Pro Cys
225                 230                 235                 240
Ser Glu Tyr Cys Leu Cys His Ile Val Asn Leu Ile Glu Asp Trp Gly
                245                 250                 255
Pro Cys Thr Glu His Gly Glu His Arg Ile Arg Thr Pro Arg Thr Pro
            260                 265                 270
Ala Arg Val Thr Gly Gly Val Phe Leu Val Asp Lys Asn Pro His Asn
            275                 280                 285
Thr Thr Glu Ser Arg Leu Val Val Asp Phe Ser Gln Phe Ser Arg Gly
290                 295                 300
Asn Thr Arg Val Ser Trp Pro Lys Phe Ala Val Pro Asn Leu Gln Ser
305                 310                 315                 320
Leu Thr Asn Leu Leu Ser Ser Asn Leu Ser Trp Leu Ser Leu Asp Val
                325                 330                 335
Ser Ala Ala Phe Tyr His Leu Pro Leu His Pro Ala Ala Met Pro His
            340                 345                 350
Leu Leu Val Gly Ser Ser Gly Leu Ser Arg Tyr Val Ala Arg Leu Ser
            355                 360                 365
Ser Asn Ser Arg Ile Ile Asn Asn Gln His Arg Thr Met Gln Asn Leu
            370                 375                 380
His Asp Ser Cys Ser Arg Asn Leu Tyr Val Ser Leu Met Leu Leu Tyr
385                 390                 395                 400
Lys Thr Tyr Gly Arg Lys Leu His Leu Tyr Ser His Pro Ile Ile Leu
            405                 410                 415
Gly Phe Arg Lys Ile Pro Met Gly Val Gly Leu Ser Pro Phe Leu Leu
            420                 425                 430
Ala Gln Phe Thr Ser Ala Ile Cys Ser Val Val Arg Arg Ala Phe Pro
            435                 440                 445
His Cys Leu Ala Phe Ser Tyr Met His Asp Val Val Leu Gly Ala Lys
            450                 455                 460
Ser Val Gln His Leu Glu Ser Leu Tyr Ala Ala Val Thr Asn Phe Leu
465                 470                 475                 480
Leu Ser Leu Gly Ile His Leu Asn Pro His Lys Thr Lys Arg Trp Gly
                485                 490                 495
Tyr Ser Leu Asn Phe Met Gly Tyr Val Ile Gly Ser Trp Gly Thr Leu
```

```
                500                 505                 510
Pro Gln Glu His Ile Val Gln Lys Ile Lys Met Cys Phe Arg Lys Leu
            515                 520                 525

Pro Val Asn Arg Pro Ile Asp Trp Lys Val Cys Gln Arg Ile Val Gly
        530                 535                 540

Leu Leu Gly Phe Ala Ala Pro Phe Thr Gln Cys Gly Tyr Pro Ala Leu
545                 550                 555                 560

Met Pro Leu Tyr Ala Cys Ile Gln Ala Lys Gln Ala Phe Thr Phe Ser
                565                 570                 575

Pro Thr Tyr Lys Ala Phe Leu Ser Lys Gln Tyr Leu His Leu Tyr Pro
            580                 585                 590

Val Ala Arg Gln Arg Pro Gly Leu Cys Gln Val Phe Ala Asp Ala Thr
        595                 600                 605

Pro Thr Gly Trp Gly Leu Ala Ile Gly His Gln Arg Met Arg Gly Ala
    610                 615                 620

Phe Val Ser Pro Leu Pro Ile His Thr Ala His Leu Leu Ala Ala Cys
625                 630                 635                 640

Phe Ala Arg Ser Arg Ser Gly Ala Lys Leu Ile Gly Thr Asp Asn Ser
                645                 650                 655

Val Val Leu Ser Arg Lys Tyr Thr Ser Phe Pro Trp Leu Leu Gly Cys
            660                 665                 670

Ala Ala Asn Trp Ile Leu Arg Gly Thr Ser Phe Val Tyr Val Pro Ser
        675                 680                 685

Ala Leu Asn Pro Ala Asp Asp Pro Ser Arg Gly Arg Leu Gly Leu Tyr
    690                 695                 700

Arg Pro Leu Leu Arg Leu Leu Tyr Arg Pro Thr Thr Gly Arg Thr Ser
705                 710                 715                 720

Leu Tyr Ala Asp Ser Pro Ser Val Pro Ser His Leu Pro Asp Arg Val
                725                 730                 735

His Phe Ala Ser Pro Leu His Val Ala Trp Arg Pro Pro
            740                 745

<210> SEQ ID NO 7
<211> LENGTH: 753
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Asp
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
            100                 105                 110
```

```
Ala Arg Phe Tyr Pro Asn Leu Thr Lys Tyr Leu Pro Leu Asp Lys Gly
            115                 120                 125

Ile Lys Pro Tyr Tyr Pro Glu His Thr Val Asn His Tyr Phe Lys Thr
        130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Glu Ser Phe Cys Ser Gln Ser Ser Gly Ile Leu Ser Arg Ser
        195                 200                 205

Pro Val Gly Pro Glu Leu His Asn Phe Pro Pro Ser Ser Ala Arg Ser
    210                 215                 220

Gln Ser Glu Gly Pro Leu Leu Ser Cys Trp Trp Leu Gln Phe Arg Asn
225                 230                 235                 240

Ser Lys Pro Cys Ser Asp Tyr Cys Leu Ser His Ile Val Asn Leu Leu
                245                 250                 255

Glu Asp Trp Gly Pro Cys Thr Glu His Gly Glu His Asn Ile Arg Ile
            260                 265                 270

Pro Arg Thr Pro Ala Arg Val Thr Gly Gly Val Phe Leu Val Asp Lys
        275                 280                 285

Asn Pro His Asn Thr Thr Glu Ser Arg Leu Val Val Asp Phe Ser Gln
    290                 295                 300

Phe Ser Arg Gly Ser Thr His Val Ser Trp Pro Lys Phe Ala Val Pro
305                 310                 315                 320

Asn Leu Gln Ser Leu Thr Asn Leu Leu Ser Ser Asn Leu Ser Trp Leu
                325                 330                 335

Ser Leu Asp Val Ser Ala Ala Phe Tyr His Leu Pro Leu His Pro Ala
            340                 345                 350

Ala Met Pro His Leu Leu Val Gly Ser Ser Gly Leu Ser Arg Tyr Val
        355                 360                 365

Ala Arg Leu Ser Ser Thr Ser Arg Asn Ile Asn Tyr Gln His Gly Ala
    370                 375                 380

Met Gln Asp Leu His Asp Ser Cys Ser Arg Asn Leu Tyr Val Ser Leu
385                 390                 395                 400

Leu Leu Leu Tyr Lys Thr Phe Gly Arg Lys Leu His Leu Tyr Ser His
                405                 410                 415

Pro Ile Ile Leu Gly Phe Arg Lys Ile Pro Met Gly Val Gly Leu Ser
            420                 425                 430

Pro Phe Leu Leu Ala Gln Phe Thr Ser Ala Ile Cys Ser Val Val Arg
        435                 440                 445

Arg Ala Phe Pro His Cys Leu Ala Phe Ser Tyr Met His Asp Val Val
    450                 455                 460

Leu Gly Ala Lys Ser Val Gln His Leu Glu Ser Leu Phe Thr Ala Val
465                 470                 475                 480

Thr Asn Phe Leu Leu Ser Leu Gly Ile His Leu Asn Pro Asn Lys Thr
                485                 490                 495

Lys Arg Trp Gly Tyr Ser Leu Asn Phe Met Gly Tyr Val Ile Gly Ser
            500                 505                 510

Trp Gly Thr Leu Pro Gln Glu His Ile Val Leu Lys Ile Lys Gln Cys
        515                 520                 525

Phe Arg Lys Leu Pro Val Asn Arg Pro Ile Asp Trp Lys Val Cys Gln
```

```
            530                 535                 540
Arg Ile Val Gly Leu Leu Gly Phe Ala Ala Pro Phe Thr Gln Cys Gly
545                 550                 555                 560

Tyr Pro Ala Leu Met Pro Leu Tyr Ala Cys Ile Gln Ala Lys Gln Ala
                565                 570                 575

Phe Thr Phe Ser Pro Thr Tyr Lys Ala Phe Leu Cys Lys Gln Tyr Leu
                580                 585                 590

Asn Leu Tyr Pro Val Ala Arg Gln Arg Ser Gly Leu Cys Gln Val Phe
                595                 600                 605

Ala Asp Ala Thr Pro Thr Gly Trp Gly Leu Ala Val Gly His Gln Arg
                610                 615                 620

Met Arg Gly Thr Phe Val Ser Pro Leu Pro Ile His Thr Ala His Leu
625                 630                 635                 640

Leu Ala Ala Cys Phe Ala Arg Ser Arg Ser Gly Ala Lys Leu Ile Gly
                645                 650                 655

Thr Asp Asn Ser Val Val Leu Ser Arg Lys Tyr Thr Ser Phe Pro Trp
                660                 665                 670

Leu Leu Gly Cys Ala Ala Asn Trp Ile Leu Arg Gly Thr Ser Phe Val
                675                 680                 685

Tyr Val Pro Ser Ala Leu Asn Pro Ala Asp Asp Pro Ser Arg Gly Arg
                690                 695                 700

Leu Gly Leu Tyr Arg Pro Leu Leu Arg Leu Pro Phe Arg Pro Thr Thr
705                 710                 715                 720

Gly Arg Thr Ser Leu Tyr Ala Val Ser Pro Ser Val Pro Ser His Leu
                725                 730                 735

Pro Val Arg Val His Phe Ala Ser Pro Leu His Val Ala Trp Arg Pro
                740                 745                 750

Pro

<210> SEQ ID NO 8
<211> LENGTH: 742
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Pro Leu Ser Tyr Gln His Phe Arg Arg Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
                35                  40                  45

Ser Ile Pro Trp Thr His Lys Val Gly Asn Phe Thr Gly Leu Tyr Ser
            50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
                100                 105                 110

Ala Arg Phe Tyr Pro Asn Val Thr Lys Tyr Leu Pro Leu Asp Lys Gly
                115                 120                 125

Ile Lys Pro Tyr Tyr Pro Glu His Leu Val Asn His Tyr Phe Gln Thr
```

-continued

```
            130                 135                 140
Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Glu Leu Gln His Gly Ala Glu Ser Phe His Gln Ser Ser Gly
            180                 185                 190

Ile Leu Ser Arg Pro Pro Val Gly Ser Glu Leu His Asn Leu Pro Pro
            195                 200                 205

Asn Ser Ala Arg Ser Gln Ser Glu Arg Pro Val Phe Pro Cys Trp Trp
210                 215                 220

Leu Gln Phe Arg Asn Ser Lys Pro Cys Ser Asp Tyr Cys Leu Ser His
225                 230                 235                 240

Ile Val Asn Leu Leu Glu Asp Trp Gly Pro Cys Ala Glu His Gly Glu
                245                 250                 255

His His Ile Arg Ile Pro Arg Thr Pro Ala Arg Val Thr Gly Gly Val
                260                 265                 270

Phe Leu Val Asp Lys Asn Pro His Asn Thr Ala Glu Ser Arg Leu Val
            275                 280                 285

Val Asp Phe Ser Gln Phe Ser Arg Gly Asn Tyr Arg Val Ser Trp Pro
290                 295                 300

Lys Phe Ala Val Pro Asn Leu Gln Ser Leu Thr Asn Leu Leu Ser Ser
305                 310                 315                 320

Asn Leu Ser Trp Leu Ser Leu Asp Val Ser Ala Ala Phe Tyr His Leu
                325                 330                 335

Pro Leu His Pro Ala Ala Met Pro His Leu Leu Val Gly Ser Ser Gly
            340                 345                 350

Leu Ser Arg Tyr Val Ala Arg Leu Ser Ser Asn Ser Arg Ile Phe Asn
            355                 360                 365

Tyr Gln His Gly Thr Met Gln Asn Leu His Asp Ser Cys Ser Arg Asn
            370                 375                 380

Leu Tyr Val Ser Leu Met Leu Leu Tyr Gln Thr Phe Gly Arg Lys Leu
385                 390                 395                 400

His Leu Tyr Ser His Pro Ile Ile Leu Gly Phe Arg Lys Ile Pro Met
                405                 410                 415

Gly Val Gly Leu Ser Pro Phe Leu Leu Ala Gln Phe Thr Ser Ala Ile
            420                 425                 430

Cys Ser Val Val Arg Arg Ala Phe Pro His Cys Leu Ala Phe Ser Tyr
            435                 440                 445

Met His Asp Val Val Leu Gly Ala Lys Ser Val Gln His Leu Glu Ser
450                 455                 460

Leu Phe Thr Ala Val Thr Asn Phe Leu Leu Ser Leu Gly Ile His Leu
465                 470                 475                 480

Asn Pro Asn Lys Thr Lys Arg Trp Gly Tyr Ser Leu His Phe Met Gly
                485                 490                 495

Tyr Val Ile Gly Cys Tyr Gly Ser Leu Pro Gln Asp His Ile Ile Gln
                500                 505                 510

Lys Ile Lys Glu Cys Phe Arg Lys Leu Pro Val Asn Arg Pro Ile Asp
            515                 520                 525

Trp Lys Val Cys Gln Arg Ile Val Gly Leu Leu Gly Phe Ala Ala Pro
530                 535                 540

Phe Thr Gln Cys Gly Tyr Pro Ala Leu Met Pro Leu Tyr Ala Cys Ile
545                 550                 555                 560
```

```
Gln Ser Lys Gln Ala Phe Thr Phe Ser Pro Thr Tyr Lys Ala Phe Leu
                565                 570                 575

Cys Lys Gln Tyr Leu Asn Leu Tyr Pro Val Ala Arg Gln Arg Pro Gly
            580                 585                 590

Leu Cys Gln Val Phe Ala Asp Ala Thr Pro Thr Gly Trp Gly Leu Val
        595                 600                 605

Met Gly His Gln Arg Met Arg Gly Thr Phe Lys Ala Pro Leu Pro Ile
    610                 615                 620

His Thr Ala His Leu Leu Ala Ala Cys Phe Ala Arg Ser Arg Ser Gly
625                 630                 635                 640

Ala Asn Ile Leu Gly Thr Asp Asn Ser Val Val Leu Ser Arg Lys Tyr
                645                 650                 655

Thr Ser Phe Pro Trp Leu Leu Gly Cys Ala Ala Asn Trp Ile Leu Arg
            660                 665                 670

Gly Thr Ser Phe Val Tyr Val Pro Ser Ala Leu Asn Pro Ala Asp Asp
        675                 680                 685

Pro Ser Arg Gly Arg Leu Gly Leu Tyr Arg Pro Leu Leu Arg Leu Pro
    690                 695                 700

Phe Arg Pro Thr Thr Gly Arg Thr Ser Leu Tyr Ala Asp Ser Pro Ser
705                 710                 715                 720

Val Pro Ser His Leu Pro Asp Arg Val His Phe Ala Ser Pro Leu His
                725                 730                 735

Val Ala Trp Arg Pro Pro
                740

<210> SEQ ID NO 9
<211> LENGTH: 705
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Pro Leu Ser Tyr Gln His Phe Arg Lys Leu Leu Leu Leu Asp Asp
1               5                   10                  15

Glu Thr Glu Ala Gly Pro Leu Glu Glu Glu Leu Pro Arg Leu Ala Asp
                20                  25                  30

Glu Asp Leu Asn Arg Arg Val Ala Glu Asp Leu Asn Leu Gly Asn Leu
            35                  40                  45

Asn Val Ser Ile Pro Trp Thr His Lys Val Gly Asn Phe Thr Gly Leu
50                  55                  60

Tyr Ser Ser Thr Val Pro Ile Phe Asn Pro Glu Trp Gln Thr Pro Ser
65                  70                  75                  80

Phe Pro Lys Ile His Leu His Glu Asp Ile Ala Asn Arg Cys Gln Gln
                85                  90                  95

Phe Val Gly Pro Leu Thr Val Asn Glu Lys Arg Arg Leu Arg Leu Ile
            100                 105                 110

Met Pro Ala Arg Phe Tyr Pro Asn Ser Thr Lys Tyr Leu Pro Leu Asp
        115                 120                 125

Lys Gly Ile Lys Pro Tyr Tyr Pro Asp His Val Val Asn His Tyr Phe
    130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
```

```
                165                 170                 175
Trp Glu Gln Glu Leu His His Gly Cys Trp Trp Leu Gln Phe Arg Asn
            180                 185                 190

Thr Gln Pro Cys Ser Lys Tyr Cys Leu Ser His Leu Val Asn Leu Leu
        195                 200                 205

Glu Asp Trp Gly Pro Cys Asp Glu His Gly Glu His His Ile Arg Ile
    210                 215                 220

Pro Arg Thr Pro Ala Arg Val Thr Gly Gly Val Phe Leu Val Asp Lys
225                 230                 235                 240

Asn Pro His Asn Thr Ala Glu Ser Arg Leu Val Val Asp Phe Ser Gln
                245                 250                 255

Phe Ser Arg Gly Ile Thr Arg Val Ser Trp Pro Lys Phe Ala Val Pro
            260                 265                 270

Asn Leu Gln Ser Leu Thr Asn Leu Leu Ser Ser Asn Leu Ser Trp Leu
        275                 280                 285

Ser Leu Asp Val Ser Ala Ala Phe Tyr His Ile Pro Leu His Pro Ala
    290                 295                 300

Ala Met Pro His Leu Leu Val Gly Ser Ser Gly Leu Ser Arg Tyr Val
305                 310                 315                 320

Ala Arg Leu Ser Ser Asn Ser Arg Ile His Asn Asn Gln His Gly Thr
                325                 330                 335

Leu Gln Asn Leu His Asp Ser Cys Ser Arg Gln Leu Tyr Val Ser Leu
            340                 345                 350

Met Leu Leu Tyr Lys Thr Tyr Gly Arg Lys Leu His Leu Tyr Ser His
        355                 360                 365

Pro Ile Ile Leu Gly Phe Arg Lys Ile Pro Met Gly Val Gly Leu Ser
    370                 375                 380

Pro Phe Leu Leu Ala Gln Phe Thr Ser Ala Ile Cys Ser Val Val Arg
385                 390                 395                 400

Arg Ala Phe Pro His Cys Leu Ala Phe Ser Tyr Met His Asp Val Val
                405                 410                 415

Leu Gly Ala Lys Ser Val Gln His Leu Glu Ser Leu Tyr Thr Ala Val
            420                 425                 430

Thr Asn Phe Leu Leu Ser Leu Gly Ile His Leu Asn Pro Asn Lys Thr
        435                 440                 445

Lys Arg Trp Gly Tyr Ser Leu Asn Phe Met Gly Tyr Val Ile Gly Ser
    450                 455                 460

Trp Gly Thr Leu Pro Gln Asp His Ile Val Gln Lys Ile Lys His Cys
465                 470                 475                 480

Phe Arg Lys Leu Pro Ile Asn Arg Pro Ile Asp Trp Lys Val Cys Gln
                485                 490                 495

Arg Ile Val Gly Leu Leu Gly Phe Ala Ala Pro Phe Thr Gln Cys Gly
            500                 505                 510

Tyr Pro Ala Leu Met Pro Leu Tyr Ala Cys Ile Gln Ala Lys Gln Ala
        515                 520                 525

Phe Thr Phe Ser Pro Thr Tyr Lys Ala Phe Leu Ser Lys Gln Tyr Leu
    530                 535                 540

Asn Leu Tyr Pro Val Ala Arg Gln Arg Pro Gly Leu Cys Gln Val Phe
545                 550                 555                 560

Ala Asp Ala Thr Pro Thr Gly Trp Gly Leu Ala Ile Gly His Gln Arg
                565                 570                 575

Met Arg Gly Thr Phe Val Ala Pro Leu Pro Ile His Thr Ala His Leu
            580                 585                 590
```

```
Leu Ala Ala Cys Phe Ala Arg Ser Arg Ser Gly Ala Lys Leu Ile Gly
            595                 600                 605

Thr Asp Asn Ser Val Val Leu Ser Arg Lys Tyr Thr Ser Phe Pro Trp
        610                 615                 620

Leu Leu Gly Cys Thr Ala Asn Trp Ile Leu Arg Gly Thr Ser Phe Val
625                 630                 635                 640

Tyr Val Pro Ser Ala Leu Asn Pro Ala Asp Asp Pro Ser Arg Gly Arg
                645                 650                 655

Leu Gly Leu Tyr Arg Pro Leu Leu Arg Leu Pro Tyr Arg Pro Thr Thr
            660                 665                 670

Gly Arg Thr Ser Leu Tyr Ala Val Ser Pro Ser Val Pro Ser His Leu
        675                 680                 685

Pro Val Arg Val His Phe Ala Ser Pro Leu His Val Ala Trp Arg Pro
    690                 695                 700

Pro
705

<210> SEQ ID NO 10
<211> LENGTH: 703
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
            100                 105                 110

Ala Arg Phe Tyr Pro Asn Leu Thr Lys Tyr Leu Pro Leu Asp Lys Gly
        115                 120                 125

Ile Lys Pro Tyr Tyr Pro Glu His Val Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Ser Thr Arg Ser Ala Ser Phe Cys Gly Ser Pro Tyr Ser Trp Glu
                165                 170                 175

Gln Asp Leu Gln His Gly Cys Trp Trp Leu Gln Phe Arg Asn Ser Glu
            180                 185                 190

Pro Cys Ser Glu Tyr Cys Leu Cys His Ile Val Asn Leu Ile Glu Asp
        195                 200                 205

Trp Gly Pro Cys Thr Glu His Gly Glu His Arg Ile Arg Thr Pro Arg
    210                 215                 220

Thr Pro Ala Arg Val Thr Gly Gly Val Phe Leu Val Asp Lys Asn Pro
```

-continued

```
            225                 230                 235                 240
        His Asn Thr Thr Glu Ser Arg Leu Val Val Asp Phe Ser Gln Phe Ser
                        245                 250                 255
        Arg Gly Asn Thr Arg Val Ser Trp Pro Lys Phe Ala Val Pro Asn Leu
                        260                 265                 270
        Gln Ser Leu Thr Asn Leu Leu Ser Asn Leu Ser Trp Leu Ser Leu
                        275                 280                 285
        Asp Val Ser Ala Ala Phe Tyr His Leu Pro Leu His Pro Ala Ala Met
                        290                 295                 300
        Pro His Leu Leu Val Gly Ser Ser Gly Leu Ser Arg Tyr Val Ala Arg
        305                 310                 315                 320
        Leu Ser Ser Asn Ser Arg Ile Ile Asn Asn Gln His Arg Thr Met Gln
                        325                 330                 335
        Asn Leu His Asp Ser Cys Ser Arg Asn Leu Tyr Val Ser Leu Met Leu
                        340                 345                 350
        Leu Tyr Lys Thr Tyr Gly Arg Lys Leu His Leu Tyr Ser His Pro Ile
                        355                 360                 365
        Ile Leu Gly Phe Arg Lys Ile Pro Met Gly Val Gly Leu Ser Pro Phe
                        370                 375                 380
        Leu Leu Ala Gln Phe Thr Ser Ala Ile Cys Ser Val Val Arg Arg Ala
        385                 390                 395                 400
        Phe Pro His Cys Leu Ala Phe Ser Tyr Met His Asp Val Val Leu Gly
                        405                 410                 415
        Ala Lys Ser Val Gln His Leu Glu Ser Leu Tyr Ala Ala Val Thr Asn
                        420                 425                 430
        Phe Leu Leu Ser Leu Gly Ile His Leu Asn Pro His Lys Thr Lys Arg
                        435                 440                 445
        Trp Gly Tyr Ser Leu Asn Phe Met Gly Tyr Val Ile Gly Ser Trp Gly
                        450                 455                 460
        Thr Leu Pro Gln Glu His Ile Val Gln Lys Ile Lys Met Cys Phe Arg
        465                 470                 475                 480
        Lys Leu Pro Val Asn Arg Pro Ile Asp Trp Lys Val Cys Gln Arg Ile
                        485                 490                 495
        Val Gly Leu Leu Gly Phe Ala Ala Pro Phe Thr Gln Cys Gly Tyr Pro
                        500                 505                 510
        Ala Leu Met Pro Leu Tyr Ala Cys Ile Gln Ala Lys Gln Ala Phe Thr
                        515                 520                 525
        Phe Ser Pro Thr Tyr Lys Ala Phe Leu Ser Lys Gln Tyr Leu His Leu
                        530                 535                 540
        Tyr Pro Val Ala Arg Gln Arg Pro Gly Leu Cys Gln Val Phe Ala Asp
        545                 550                 555                 560
        Ala Thr Pro Thr Gly Trp Gly Leu Ala Ile Gly His Gln Arg Met Arg
                        565                 570                 575
        Gly Ala Phe Val Ser Pro Leu Pro Ile His Thr Ala His Leu Leu Ala
                        580                 585                 590
        Ala Cys Phe Ala Arg Ser Arg Ser Gly Ala Lys Leu Ile Gly Thr Asp
                        595                 600                 605
        Asn Ser Val Val Leu Ser Arg Lys Tyr Thr Ser Phe Pro Trp Leu Leu
                        610                 615                 620
        Gly Cys Ala Ala Asn Trp Ile Leu Arg Gly Thr Ser Phe Val Tyr Val
        625                 630                 635                 640
        Pro Ser Ala Leu Asn Pro Ala Asp Asp Pro Ser Arg Gly Arg Leu Gly
                        645                 650                 655
```

```
Leu Tyr Arg Pro Leu Leu Arg Leu Leu Tyr Arg Pro Thr Thr Gly Arg
            660                 665                 670

Thr Ser Leu Tyr Ala Asp Ser Pro Ser Val Pro Ser His Leu Pro Asp
        675                 680                 685

Arg Val His Phe Ala Ser Pro Leu His Val Ala Trp Arg Pro Pro
    690                 695                 700

<210> SEQ ID NO 11
<211> LENGTH: 703
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Pro Leu Ser Tyr Gln His Phe Arg Lys Leu Leu Leu Leu Asp Asp
1               5                   10                  15

Glu Ala Gly Pro Leu Glu Glu Leu Pro Arg Leu Ala Asp Glu Asp
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
            100                 105                 110

Ala Arg Phe Tyr Pro Asn Leu Thr Lys Tyr Leu Pro Leu Asp Lys Gly
        115                 120                 125

Ile Lys Pro Tyr Tyr Pro Glu His Thr Val Asn His Tyr Phe Lys Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Cys Trp Trp Leu Gln Phe Arg Asn Ser Lys
            180                 185                 190

Pro Cys Ser Asp Tyr Cys Leu Ser His Ile Val Asn Leu Leu Glu Asp
        195                 200                 205

Trp Gly Pro Cys Thr Glu His Gly Glu His Asn Ile Arg Ile Pro Arg
    210                 215                 220

Thr Pro Ala Arg Val Thr Gly Gly Val Phe Leu Val Asp Lys Asn Pro
225                 230                 235                 240

His Asn Thr Thr Glu Ser Arg Leu Val Val Asp Phe Ser Gln Phe Ser
                245                 250                 255

Arg Gly Ser Thr His Val Ser Trp Pro Lys Phe Ala Val Pro Asn Leu
            260                 265                 270

Gln Ser Leu Thr Asn Leu Leu Ser Asn Leu Ser Trp Leu Ser Leu
        275                 280                 285

Asp Val Ser Ala Ala Phe Tyr His Leu Pro Leu His Pro Ala Ala Met
    290                 295                 300

Pro His Leu Leu Val Gly Ser Ser Gly Leu Ser Arg Tyr Val Ala Arg
```

```
            305                 310                 315                 320
Leu Ser Ser Thr Ser Arg Asn Ile Asn Tyr Gln His Gly Ala Met Gln
                325                 330                 335

Asp Leu His Asp Ser Cys Ser Arg Asn Leu Tyr Val Ser Leu Leu Leu
                340                 345                 350

Leu Tyr Lys Thr Phe Gly Arg Lys Leu His Leu Tyr Ser His Pro Ile
                355                 360                 365

Ile Leu Gly Phe Arg Lys Ile Pro Met Gly Val Gly Leu Ser Pro Phe
                370                 375                 380

Leu Leu Ala Gln Phe Thr Ser Ala Ile Cys Ser Val Val Arg Arg Ala
385                 390                 395                 400

Phe Pro His Cys Leu Ala Phe Ser Tyr Met His Asp Val Val Leu Gly
                405                 410                 415

Ala Lys Ser Val Gln His Leu Glu Ser Leu Phe Thr Ala Val Thr Asn
                420                 425                 430

Phe Leu Leu Ser Leu Gly Ile His Leu Asn Pro Asn Lys Thr Lys Arg
                435                 440                 445

Trp Gly Tyr Ser Leu Asn Phe Met Gly Tyr Val Ile Gly Ser Trp Gly
                450                 455                 460

Thr Leu Pro Gln Glu His Ile Val Leu Lys Ile Lys Gln Cys Phe Arg
465                 470                 475                 480

Lys Leu Pro Val Asn Arg Pro Ile Asp Trp Lys Val Cys Gln Arg Ile
                485                 490                 495

Val Gly Leu Leu Gly Phe Ala Ala Pro Phe Thr Gln Cys Gly Tyr Pro
                500                 505                 510

Ala Leu Met Pro Leu Tyr Ala Cys Ile Gln Ala Lys Gln Ala Phe Thr
                515                 520                 525

Phe Ser Pro Thr Tyr Lys Ala Phe Leu Cys Lys Gln Tyr Leu Asn Leu
                530                 535                 540

Tyr Pro Val Ala Arg Gln Arg Ser Gly Leu Cys Gln Val Phe Ala Asp
545                 550                 555                 560

Ala Thr Pro Thr Gly Trp Gly Leu Ala Val Gly His Gln Arg Met Arg
                565                 570                 575

Gly Thr Phe Val Ser Pro Leu Pro Ile His Thr Ala His Leu Leu Ala
                580                 585                 590

Ala Cys Phe Ala Arg Ser Arg Ser Gly Ala Lys Leu Ile Gly Thr Asp
                595                 600                 605

Asn Ser Val Val Leu Ser Arg Lys Tyr Thr Ser Phe Pro Trp Leu Leu
610                 615                 620

Gly Cys Ala Ala Asn Trp Ile Leu Arg Gly Thr Ser Phe Val Tyr Val
625                 630                 635                 640

Pro Ser Ala Leu Asn Pro Ala Asp Asp Pro Ser Arg Gly Arg Leu Gly
                645                 650                 655

Leu Tyr Arg Pro Leu Leu Arg Leu Pro Phe Arg Pro Thr Thr Gly Arg
                660                 665                 670

Thr Ser Leu Tyr Ala Val Ser Pro Ser Val Pro Ser His Leu Pro Val
                675                 680                 685

Arg Val His Phe Ala Ser Pro Leu His Val Ala Trp Arg Pro Pro
                690                 695                 700

<210> SEQ ID NO 12
<211> LENGTH: 703
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 12

Met Pro Leu Ser Tyr Gln His Phe Arg Arg Leu Leu Leu Asp Asp
1               5                   10                  15

Glu Ala Gly Pro Leu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
            100                 105                 110

Ala Arg Phe Tyr Pro Asn Val Thr Lys Tyr Leu Pro Leu Asp Lys Gly
        115                 120                 125

Ile Lys Pro Tyr Tyr Pro Glu His Leu Val Asn His Tyr Phe Gln Thr
130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Glu Leu Gln His Gly Cys Trp Trp Leu Gln Phe Arg Asn Ser Lys
            180                 185                 190

Pro Cys Ser Asp Tyr Cys Leu Ser His Ile Val Asn Leu Leu Glu Asp
        195                 200                 205

Trp Gly Pro Cys Ala Glu His Gly Glu His His Ile Arg Ile Pro Arg
210                 215                 220

Thr Pro Ala Arg Val Thr Gly Gly Val Phe Leu Val Asp Lys Asn Pro
225                 230                 235                 240

His Asn Thr Ala Glu Ser Arg Leu Val Val Asp Phe Ser Gln Phe Ser
                245                 250                 255

Arg Gly Asn Tyr Arg Val Ser Trp Pro Lys Phe Ala Val Pro Asn Leu
            260                 265                 270

Gln Ser Leu Thr Asn Leu Leu Ser Ser Asn Leu Ser Trp Leu Ser Leu
        275                 280                 285

Asp Val Ser Ala Ala Phe Tyr His Leu Pro Leu His Pro Ala Ala Met
290                 295                 300

Pro His Leu Leu Val Gly Ser Ser Gly Leu Ser Arg Tyr Val Ala Arg
305                 310                 315                 320

Leu Ser Ser Asn Ser Arg Ile Phe Asn Tyr Gln His Gly Thr Met Gln
                325                 330                 335

Asn Leu His Asp Ser Cys Ser Arg Asn Leu Tyr Val Ser Leu Met Leu
            340                 345                 350

Leu Tyr Gln Thr Phe Gly Arg Lys Leu His Leu Tyr Ser His Pro Ile
        355                 360                 365

Ile Leu Gly Phe Arg Lys Ile Pro Met Gly Val Gly Leu Ser Pro Phe
370                 375                 380

Leu Leu Ala Gln Phe Thr Ser Ala Ile Cys Ser Val Val Arg Arg Ala

```
                385                 390                 395                 400
        Phe Pro His Cys Leu Ala Phe Ser Tyr Met His Asp Val Val Leu Gly
                        405                 410                 415

Ala Lys Ser Val Gln His Leu Glu Ser Leu Phe Thr Ala Val Thr Asn
                    420                 425                 430

Phe Leu Leu Ser Leu Gly Ile His Leu Asn Pro Asn Lys Thr Lys Arg
                        435                 440                 445

Trp Gly Tyr Ser Leu His Phe Met Gly Tyr Val Ile Gly Cys Tyr Gly
                    450                 455                 460

Ser Leu Pro Gln Asp His Ile Ile Gln Lys Ile Lys Glu Cys Phe Arg
        465                 470                 475                 480

Lys Leu Pro Val Asn Arg Pro Ile Asp Trp Lys Val Cys Gln Arg Ile
                        485                 490                 495

Val Gly Leu Leu Gly Phe Ala Ala Pro Phe Thr Gln Cys Gly Tyr Pro
                    500                 505                 510

Ala Leu Met Pro Leu Tyr Ala Cys Ile Gln Ser Lys Gln Ala Phe Thr
                    515                 520                 525

Phe Ser Pro Thr Tyr Lys Ala Phe Leu Cys Lys Gln Tyr Leu Asn Leu
                    530                 535                 540

Tyr Pro Val Ala Arg Gln Arg Pro Gly Leu Cys Gln Val Phe Ala Asp
        545                 550                 555                 560

Ala Thr Pro Thr Gly Trp Gly Leu Val Met Gly His Gln Arg Met Arg
                        565                 570                 575

Gly Thr Phe Lys Ala Pro Leu Pro Ile His Thr Ala His Leu Leu Ala
                    580                 585                 590

Ala Cys Phe Ala Arg Ser Arg Ser Gly Ala Asn Ile Leu Gly Thr Asp
                    595                 600                 605

Asn Ser Val Val Leu Ser Arg Lys Tyr Thr Ser Phe Pro Trp Leu Leu
                    610                 615                 620

Gly Cys Ala Ala Asn Trp Ile Leu Arg Gly Thr Ser Phe Val Tyr Val
        625                 630                 635                 640

Pro Ser Ala Leu Asn Pro Ala Asp Asp Pro Ser Arg Gly Arg Leu Gly
                        645                 650                 655

Leu Tyr Arg Pro Leu Leu Arg Leu Pro Phe Arg Pro Thr Thr Gly Arg
                    660                 665                 670

Thr Ser Leu Tyr Ala Asp Ser Pro Ser Val Pro Ser His Leu Pro Asp
                    675                 680                 685

Arg Val His Phe Ala Ser Pro Leu His Val Ala Trp Arg Pro Pro
                    690                 695                 700

<210> SEQ ID NO 13
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ser Ser Arg Ser Gln Ser Gln Gly Pro Val Leu Ser Cys Trp Trp
1               5                   10                  15

Leu Gln Phe Arg Asn Ser Glu Pro Cys Ser Glu Tyr Cys Leu Cys His
                20                  25                  30

Ile Val Asn Leu Ile Glu Asp Trp Gly Pro Cys Thr Glu His Gly Glu
            35                  40                  45
```

His Arg Ile Arg Thr Pro Arg Thr Pro Ala Arg Val Thr Gly Gly Val
    50                  55                  60

Phe Leu Val Asp Lys Asn Pro His Asn Thr Thr Glu Ser Arg Leu Val
65              70                  75                  80

Val Asp Phe Ser Gln Phe Ser Arg Gly Asn Thr Arg Val Ser Trp Pro
                85                  90                  95

Lys Phe Ala Val Pro Asn Leu Gln Ser Leu Thr Asn Leu Leu Ser Ser
                100                 105                 110

Asn Leu Ser Trp Leu Ser Leu Asp Val Ser Ala Ala Phe Tyr His Leu
            115                 120                 125

Pro Leu His Pro Ala Ala Met Pro His Leu Leu Val Gly Ser Ser Gly
    130                 135                 140

Leu Ser Arg Tyr Val Ala Arg Leu Ser Ser Asn Ser Arg Ile Ile Asn
145                 150                 155                 160

Asn Gln His Arg Thr Met Gln Asn Leu His Asp Ser Cys Ser Arg Asn
                165                 170                 175

Leu Tyr Val Ser Leu Met Leu Leu Tyr Lys Thr Tyr Gly Arg Lys Leu
            180                 185                 190

His Leu Tyr Ser His Pro Ile Ile Leu Gly Phe Arg Lys Ile Pro Met
    195                 200                 205

Gly Val Gly Leu Ser Pro Phe Leu Leu Ala Gln Phe Thr Ser Ala Ile
    210                 215                 220

Cys Ser Val Val Arg Arg Ala Phe Pro His Cys Leu Ala Phe Ser Tyr
225                 230                 235                 240

Met His Asp Val Val Leu Gly Ala Lys Ser Val Gln His Leu Glu Ser
                245                 250                 255

Leu Tyr Ala Ala Val Thr Asn Phe Leu Leu Ser Leu Gly Ile His Leu
            260                 265                 270

Asn Pro His Lys Thr Lys Arg Trp Gly Tyr Ser Leu Asn Phe Met Gly
    275                 280                 285

Tyr Val Ile Gly Ser Trp Gly Thr Leu Pro Gln Glu His Ile Val Gln
    290                 295                 300

Lys Ile Lys Met Cys Phe Arg Lys Leu Pro Val Asn Arg Pro Ile Asp
305             310                 315                 320

Trp Lys Val Cys Gln Arg Ile Val Gly Leu Leu Gly Phe Ala Ala Pro
                325                 330                 335

Phe Thr Gln Cys Gly Tyr Pro Ala Leu Met Pro Leu Tyr Ala Cys Ile
            340                 345                 350

Gln Ala Lys Gln Ala Phe Thr Phe Ser Pro Thr Tyr Lys Ala Phe Leu
    355                 360                 365

Ser Lys Gln Tyr Leu His Leu Tyr Pro Val Ala Arg Gln Arg Pro Gly
    370                 375                 380

Leu Cys Gln Val Phe Ala Asp Ala Thr Pro Thr Gly Trp Gly Leu Ala
385                 390                 395                 400

Ile Gly His Gln Arg Met Arg Gly Ala Phe Val Ser Pro Leu Pro Ile
                405                 410                 415

His Thr Ala His Leu Leu Ala Ala Cys Phe Ala Arg Ser Arg Ser Gly
            420                 425                 430

Ala Lys Leu Ile Gly Thr Asp Asn Ser Val Val Leu Ser Arg Lys Tyr
    435                 440                 445

Thr Ser Phe Pro Trp Leu Leu Gly Cys Ala Ala Asn Trp Ile Leu Arg
    450                 455                 460

Gly Thr Ser Phe Val Tyr Val Pro Ser Ala Leu Asn Pro Ala Asp Asp

```
                465                 470                 475                 480
Pro Ser Arg Gly Arg Leu Gly Leu Tyr Arg Pro Leu Leu Arg Leu Leu
                    485                 490                 495

Tyr Arg Pro Thr Thr Gly Arg Thr Ser Leu Tyr Ala Asp Ser Pro Ser
                500                 505                 510

Val Pro Ser His Leu Pro Asp Arg Val His Phe Ala Ser Pro Leu His
                515                 520                 525

Val Ala Trp Arg Pro Pro
    530

<210> SEQ ID NO 14
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Ser Ala Arg Ser Gln Ser Glu Arg Pro Val Phe Pro Cys Trp Trp
1               5                   10                  15

Leu Gln Phe Arg Asn Ser Lys Pro Cys Ser Asp Tyr Cys Leu Ser His
                20                  25                  30

Ile Val Asn Leu Leu Glu Asp Trp Gly Pro Cys Ala Glu His Gly Glu
            35                  40                  45

His His Ile Arg Ile Pro Arg Thr Pro Ala Arg Val Thr Gly Gly Val
        50                  55                  60

Phe Leu Val Asp Lys Asn Pro His Asn Thr Ala Glu Ser Arg Leu Val
65                  70                  75                  80

Val Asp Phe Ser Gln Phe Ser Arg Gly Asn Tyr Arg Val Ser Trp Pro
                85                  90                  95

Lys Phe Ala Val Pro Asn Leu Gln Ser Leu Thr Asn Leu Leu Ser Ser
                100                 105                 110

Asn Leu Ser Trp Leu Ser Leu Asp Val Ser Ala Ala Phe Tyr His Leu
            115                 120                 125

Pro Leu His Pro Ala Ala Met Pro His Leu Leu Val Gly Ser Ser Gly
        130                 135                 140

Leu Ser Arg Tyr Val Ala Arg Leu Ser Ser Asn Ser Arg Ile Phe Asn
145                 150                 155                 160

Tyr Gln His Gly Thr Met Gln Asn Leu His Asp Ser Cys Ser Arg Asn
                165                 170                 175

Leu Tyr Val Ser Leu Met Leu Leu Tyr Gln Thr Phe Gly Arg Lys Leu
                180                 185                 190

His Leu Tyr Ser His Pro Ile Ile Leu Gly Phe Arg Lys Ile Pro Met
            195                 200                 205

Gly Val Gly Leu Ser Pro Phe Leu Leu Ala Gln Phe Thr Ser Ala Ile
        210                 215                 220

Cys Ser Val Val Arg Arg Ala Phe Pro His Cys Leu Ala Phe Ser Tyr
225                 230                 235                 240

Met His Asp Val Val Leu Gly Ala Lys Ser Val Gln His Leu Glu Ser
                245                 250                 255

Leu Phe Thr Ala Val Thr Asn Phe Leu Leu Ser Leu Gly Ile His Leu
                260                 265                 270

Asn Pro Asn Lys Thr Lys Arg Trp Gly Tyr Ser Leu His Phe Met Gly
            275                 280                 285
```

-continued

Tyr Val Ile Gly Cys Tyr Gly Ser Leu Pro Gln Asp His Ile Ile Gln
    290                 295                 300

Lys Ile Lys Glu Cys Phe Arg Lys Leu Pro Val Asn Arg Pro Ile Asp
305                 310                 315                 320

Trp Lys Val Cys Gln Arg Ile Val Gly Leu Leu Gly Phe Ala Ala Pro
                325                 330                 335

Phe Thr Gln Cys Gly Tyr Pro Ala Leu Met Pro Leu Tyr Ala Cys Ile
            340                 345                 350

Gln Ser Lys Gln Ala Phe Thr Phe Ser Pro Thr Tyr Lys Ala Phe Leu
        355                 360                 365

Cys Lys Gln Tyr Leu Asn Leu Tyr Pro Val Ala Arg Gln Arg Pro Gly
    370                 375                 380

Leu Cys Gln Val Phe Ala Asp Ala Thr Pro Thr Gly Trp Gly Leu Val
385                 390                 395                 400

Met Gly His Gln Arg Met Arg Gly Thr Phe Lys Ala Pro Leu Pro Ile
                405                 410                 415

His Thr Ala His Leu Leu Ala Ala Cys Phe Ala Arg Ser Arg Ser Gly
            420                 425                 430

Ala Asn Ile Leu Gly Thr Asp Asn Ser Val Val Leu Ser Arg Lys Tyr
        435                 440                 445

Thr Ser Phe Pro Trp Leu Leu Gly Cys Ala Ala Asn Trp Ile Leu Arg
    450                 455                 460

Gly Thr Ser Phe Val Tyr Val Pro Ser Ala Leu Asn Pro Ala Asp Asp
465                 470                 475                 480

Pro Ser Arg Gly Arg Leu Gly Leu Tyr Arg Pro Leu Leu Arg Leu Pro
                485                 490                 495

Phe Arg Pro Thr Thr Gly Arg Thr Ser Leu Tyr Ala Asp Ser Pro Ser
            500                 505                 510

Val Pro Ser His Leu Pro Asp Arg Val His Phe Ala Ser Pro Leu His
        515                 520                 525

Val Ala Trp Arg Pro Pro
    530

<210> SEQ ID NO 15
<211> LENGTH: 1030
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

```
Glu Thr Val Leu Glu Tyr Leu Ser Phe Gly Val Trp Ile Arg Thr
            115                 120                 125
Pro Pro Ala Tyr Arg Pro Asn Ala Pro Ile Leu Ser Thr Leu Pro
130                 135                 140
Glu Thr Thr Val Val Arg Arg Arg Asp Arg Gly Arg Ser Pro Arg Arg
145                 150                 155                 160
Arg Thr Pro Ser Pro Arg Arg Arg Ser Gln Ser Pro Arg Arg
                165                 170                 175
Arg Ser Gln Ser Arg Glu Ser Gln Cys Met Pro Leu Ser Tyr Gln His
            180                 185                 190
Phe Arg Lys Leu Leu Leu Asp Asp Glu Thr Glu Ala Gly Pro Leu
            195                 200                 205
Glu Glu Glu Leu Pro Arg Leu Ala Asp Glu Asp Leu Asn Arg Arg Val
210                 215                 220
Ala Glu Asp Leu Asn Leu Gly Asn Leu Asn Val Ser Ile Pro Trp Thr
225                 230                 235                 240
His Lys Val Gly Asn Phe Thr Gly Leu Tyr Ser Ser Thr Val Pro Ile
                245                 250                 255
Phe Asn Pro Glu Trp Gln Thr Pro Ser Phe Pro Lys Ile His Leu His
            260                 265                 270
Glu Asp Ile Ala Asn Arg Cys Gln Gln Phe Val Gly Pro Leu Thr Val
            275                 280                 285
Asn Glu Lys Arg Arg Leu Arg Leu Ile Met Pro Ala Arg Phe Tyr Pro
290                 295                 300
Asn Ser Thr Lys Tyr Leu Pro Leu Asp Lys Gly Ile Lys Pro Tyr Tyr
305                 310                 315                 320
Pro Asp His Val Val Asn His Tyr Phe Gln Thr Arg His Tyr Leu His
                325                 330                 335
Thr Leu Trp Lys Ala Gly Ile Leu Tyr Lys Arg Glu Thr Thr Arg Ser
            340                 345                 350
Ala Ser Phe Cys Gly Ser Pro Tyr Ser Trp Glu Gln Glu Leu His His
            355                 360                 365
Gly Arg Leu Val Ile Lys Thr Ser Gln Arg His Gly Asp Glu Pro Phe
            370                 375                 380
Cys Ser Gln Pro Ser Gly Ile Leu Ser Arg Ser Ser Val Gly Pro Cys
385                 390                 395                 400
Ile Arg Ser Gln Phe Lys Gln Ser Arg Leu Gly Leu Gln Pro His Gln
                405                 410                 415
Gly Pro Leu Ala Thr Ser Gln Ser Gly Arg Ser Gly Ser Ile Arg Ala
            420                 425                 430
Arg Val His Ser Pro Thr Arg Arg Cys Phe Gly Val Glu Pro Ser Gly
            435                 440                 445
Ser Gly His Ile Gly His Ser Ala Ser Ser Ser Ser Cys Leu His
            450                 455                 460
Gln Ser Ala Val Arg Lys Ala Ala Tyr Ser His Leu Ser Thr Ser Lys
465                 470                 475                 480
Arg Gln Ser Ser Ser Gly His Ala Val Glu Phe His Ser Phe Pro Pro
                485                 490                 495
Ser Ser Ala Arg Ser Gln Ser Gln Gly Pro Val Phe Ser Cys Trp Trp
            500                 505                 510
Leu Gln Phe Arg Asn Thr Gln Pro Cys Ser Lys Tyr Cys Leu Ser His
            515                 520                 525
```

-continued

```
Leu Val Asn Leu Leu Glu Asp Trp Gly Pro Cys Asp Glu His Gly Glu
    530                 535                 540
His His Ile Arg Ile Pro Arg Thr Pro Ala Arg Val Thr Gly Gly Val
545                 550                 555                 560
Phe Leu Val Asp Lys Asn Pro His Asn Thr Ala Glu Ser Arg Leu Val
                565                 570                 575
Val Asp Phe Ser Gln Phe Ser Arg Gly Ile Thr Arg Val Ser Trp Pro
            580                 585                 590
Lys Phe Ala Val Pro Asn Leu Gln Ser Leu Thr Asn Leu Leu Ser Ser
        595                 600                 605
Asn Leu Ser Trp Leu Ser Leu Asp Val Ser Ala Ala Phe Tyr His Ile
    610                 615                 620
Pro Leu His Pro Ala Ala Met Pro His Leu Leu Val Gly Ser Ser Gly
625                 630                 635                 640
Leu Ser Arg Tyr Val Ala Arg Leu Ser Ser Asn Ser Arg Ile His Asn
                645                 650                 655
Asn Gln His Gly Thr Leu Gln Asn Leu His Asp Ser Cys Ser Arg Gln
            660                 665                 670
Leu Tyr Val Ser Leu Met Leu Leu Tyr Lys Thr Tyr Gly Arg Lys Leu
        675                 680                 685
His Leu Tyr Ser His Pro Ile Ile Leu Gly Phe Arg Lys Ile Pro Met
    690                 695                 700
Gly Val Gly Leu Ser Pro Phe Leu Leu Ala Gln Phe Thr Ser Ala Ile
705                 710                 715                 720
Cys Ser Val Val Arg Arg Ala Phe Pro His Cys Leu Ala Phe Ser Tyr
                725                 730                 735
Met His Asp Val Val Leu Gly Ala Lys Ser Val Gln His Leu Glu Ser
            740                 745                 750
Leu Tyr Thr Ala Val Thr Asn Phe Leu Leu Ser Leu Gly Ile His Leu
        755                 760                 765
Asn Pro Asn Lys Thr Lys Arg Trp Gly Tyr Ser Leu Asn Phe Met Gly
    770                 775                 780
Tyr Val Ile Gly Ser Trp Gly Thr Leu Pro Gln Asp His Ile Val Gln
785                 790                 795                 800
Lys Ile Lys His Cys Phe Arg Lys Leu Pro Ile Asn Arg Pro Ile Asp
                805                 810                 815
Trp Lys Val Cys Gln Arg Ile Val Gly Leu Leu Gly Phe Ala Ala Pro
            820                 825                 830
Phe Thr Gln Cys Gly Tyr Pro Ala Leu Met Pro Leu Tyr Ala Cys Ile
        835                 840                 845
Gln Ala Lys Gln Ala Phe Thr Phe Ser Pro Thr Tyr Lys Ala Phe Leu
    850                 855                 860
Ser Lys Gln Tyr Leu Asn Leu Tyr Pro Val Ala Arg Gln Arg Pro Gly
865                 870                 875                 880
Leu Cys Gln Val Phe Ala Asp Ala Thr Pro Thr Gly Trp Gly Leu Ala
                885                 890                 895
Ile Gly His Gln Arg Met Arg Gly Thr Phe Val Ala Pro Leu Pro Ile
            900                 905                 910
His Thr Ala His Leu Leu Ala Ala Cys Phe Ala Arg Ser Arg Ser Gly
        915                 920                 925
Ala Lys Leu Ile Gly Thr Asp Asn Ser Val Val Leu Ser Arg Lys Tyr
    930                 935                 940
Thr Ser Phe Pro Trp Leu Leu Gly Cys Thr Ala Asn Trp Ile Leu Arg
```

```
                945                 950                 955                 960
        Gly Thr Ser Phe Val Tyr Val Pro Ser Ala Leu Asn Pro Ala Asp Asp
                        965                 970                 975

Pro Ser Arg Gly Arg Leu Gly Leu Tyr Arg Pro Leu Leu Arg Leu Pro
                        980                 985                 990

Tyr Arg Pro Thr Thr Gly Arg Thr  Ser Leu Tyr Ala Val  Ser Pro Ser
                    995                 1000                1005

Val Pro  Ser His Leu Pro Val  Arg Val His Phe Ala  Ser Pro Leu
            1010                1015                1020

His Val  Ala Trp Arg Pro Pro
            1025                1030

<210> SEQ ID NO 16
<211> LENGTH: 1026
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Pro Leu Ser Tyr Gln His Phe Arg
            180                 185                 190

Lys Leu Leu Leu Leu Asp Asp Glu Ala Gly Pro Leu Glu Glu Glu Leu
        195                 200                 205

Pro Arg Leu Ala Asp Glu Gly Leu Asn Arg Arg Val Ala Glu Asp Leu
    210                 215                 220

Asn Leu Gly Asn Leu Asn Val Ser Ile Pro Trp Thr His Lys Val Gly
225                 230                 235                 240

Asn Phe Thr Gly Leu Tyr Ser Ser Thr Val Pro Val Phe Asn Pro Glu
                245                 250                 255

Trp Gln Thr Pro Ser Phe Pro His Ile His Leu Gln Glu Asp Ile Ile
            260                 265                 270
```

-continued

Asn Arg Cys Gln Gln Tyr Val Gly Pro Leu Thr Val Asn Glu Lys Arg
        275                 280                 285

Arg Leu Lys Leu Ile Met Pro Ala Arg Phe Tyr Pro Asn Leu Thr Lys
    290                 295                 300

Tyr Leu Pro Leu Asp Lys Gly Ile Lys Pro Tyr Tyr Pro Glu His Val
305                 310                 315                 320

Val Asn His Tyr Phe Gln Thr Arg His Tyr Leu His Thr Leu Trp Lys
                325                 330                 335

Ala Gly Ile Leu Tyr Lys Arg Glu Ser Thr Arg Ser Ala Ser Phe Cys
            340                 345                 350

Gly Ser Pro Tyr Ser Trp Glu Gln Asp Leu Gln His Gly Arg Leu Val
        355                 360                 365

Phe Gln Thr Ser Lys Arg His Gly Asp Lys Ser Phe Cys Pro Gln Ser
    370                 375                 380

Pro Gly Ile Leu Pro Arg Ser Ser Val Gly Pro Cys Ile Gln Asn Gln
385                 390                 395                 400

Leu Arg Lys Ser Arg Leu Gly Pro Gln Pro Ala Gln Gly Gln Leu Ala
                405                 410                 415

Gly Arg Gln Gln Gly Ser Gly Ser Ile Arg Ala Arg Val His Pro
            420                 425                 430

Ser Pro Trp Gly Thr Val Gly Val Glu Pro Ser Gly Ser Gly His Ile
        435                 440                 445

His Asn Cys Ala Ser Asn Ser Ser Cys Leu His Gln Ser Ala Val
    450                 455                 460

Arg Lys Ala Ala Tyr Ser His Ile Ser Thr Ser Lys Gly His Ser Ser
465                 470                 475                 480

Ser Gly His Ala Val Glu Leu His His Phe Pro Ser Ser Ser Arg
                485                 490                 495

Ser Gln Ser Gln Gly Pro Val Leu Ser Cys Trp Trp Leu Gln Phe Arg
            500                 505                 510

Asn Ser Glu Pro Cys Ser Glu Tyr Cys Leu Cys His Ile Val Asn Leu
        515                 520                 525

Ile Glu Asp Trp Gly Pro Cys Thr Glu His Gly Glu His Arg Ile Arg
530                 535                 540

Thr Pro Arg Thr Pro Ala Arg Val Thr Gly Gly Val Phe Leu Val Asp
545                 550                 555                 560

Lys Asn Pro His Asn Thr Thr Glu Ser Arg Leu Val Val Asp Phe Ser
                565                 570                 575

Gln Phe Ser Arg Gly Asn Thr Arg Val Ser Trp Pro Lys Phe Ala Val
            580                 585                 590

Pro Asn Leu Gln Ser Leu Thr Asn Leu Leu Ser Ser Asn Leu Ser Trp
        595                 600                 605

Leu Ser Leu Asp Val Ser Ala Ala Phe Tyr His Leu Pro Leu His Pro
610                 615                 620

Ala Ala Met Pro His Leu Leu Val Gly Ser Ser Gly Leu Ser Arg Tyr
625                 630                 635                 640

Val Ala Arg Leu Ser Ser Asn Ser Arg Ile Ile Asn Asn Gln His Arg
                645                 650                 655

Thr Met Gln Asn Leu His Asp Ser Cys Ser Arg Asn Leu Tyr Val Ser
            660                 665                 670

Leu Met Leu Leu Tyr Lys Thr Tyr Gly Arg Lys Leu His Leu Tyr Ser
        675                 680                 685

His Pro Ile Ile Leu Gly Phe Arg Lys Ile Pro Met Gly Val Gly Leu

```
                690                 695                 700
Ser Pro Phe Leu Leu Ala Gln Phe Thr Ser Ala Ile Cys Ser Val Val
705                 710                 715                 720

Arg Arg Ala Phe Pro His Cys Leu Ala Phe Ser Tyr Met His Asp Val
                725                 730                 735

Val Leu Gly Ala Lys Ser Val Gln His Leu Glu Ser Leu Tyr Ala Ala
                740                 745                 750

Val Thr Asn Phe Leu Leu Ser Leu Gly Ile His Leu Asn Pro His Lys
                755                 760                 765

Thr Lys Arg Trp Gly Tyr Ser Leu Asn Phe Met Gly Tyr Val Ile Gly
770                 775                 780

Ser Trp Gly Thr Leu Pro Gln Glu His Ile Val Gln Lys Ile Lys Met
785                 790                 795                 800

Cys Phe Arg Lys Leu Pro Val Asn Arg Pro Ile Asp Trp Lys Val Cys
                805                 810                 815

Gln Arg Ile Val Gly Leu Leu Gly Phe Ala Ala Pro Phe Thr Gln Cys
                820                 825                 830

Gly Tyr Pro Ala Leu Met Pro Leu Tyr Ala Cys Ile Gln Ala Lys Gln
                835                 840                 845

Ala Phe Thr Phe Ser Pro Thr Tyr Lys Ala Phe Leu Ser Lys Gln Tyr
                850                 855                 860

Leu His Leu Tyr Pro Val Ala Arg Gln Arg Pro Gly Leu Cys Gln Val
865                 870                 875                 880

Phe Ala Asp Ala Thr Pro Thr Gly Trp Gly Leu Ala Ile Gly His Gln
                885                 890                 895

Arg Met Arg Gly Ala Phe Val Ser Pro Leu Pro Ile His Thr Ala His
                900                 905                 910

Leu Leu Ala Ala Cys Phe Ala Arg Ser Arg Ser Gly Ala Lys Leu Ile
                915                 920                 925

Gly Thr Asp Asn Ser Val Val Leu Ser Arg Lys Tyr Thr Ser Phe Pro
930                 935                 940

Trp Leu Leu Gly Cys Ala Ala Asn Trp Ile Leu Arg Gly Thr Ser Phe
945                 950                 955                 960

Val Tyr Val Pro Ser Ala Leu Asn Pro Ala Asp Asp Pro Ser Arg Gly
                965                 970                 975

Arg Leu Gly Leu Tyr Arg Pro Leu Leu Arg Leu Leu Tyr Arg Pro Thr
                980                 985                 990

Thr Gly Arg Thr Ser Leu Tyr Ala Asp Ser Pro Ser Val Pro Ser His
                995                 1000                1005

Leu Pro Asp Arg Val His Phe Ala Ser Pro Leu His Val Ala Trp
    1010                1015                1020

Arg Pro  Pro
    1025

<210> SEQ ID NO 17
<211> LENGTH: 1026
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Ile Asp Pro Tyr Lys Glu Phe Gly Ala Ser Val Glu Leu Leu
1               5                   10                  15
```

```
Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
 50                  55                  60

Leu Met Asn Leu Ala Thr Trp Val Gly Ser Asn Leu Glu Asp Pro Ala
 65                  70                  75                  80

Ser Arg Glu Leu Val Val Ser Tyr Val Asn Val Asn Met Gly Leu Lys
                 85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
130                 135                 140

Glu Thr Thr Val Val Arg Arg Gly Arg Ser Pro Arg Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Pro Leu Ser Tyr Gln His Phe Arg
            180                 185                 190

Lys Leu Leu Leu Leu Asp Asp Glu Ala Gly Pro Leu Glu Glu Glu Leu
                195                 200                 205

Pro Arg Leu Ala Asp Glu Asp Leu Asn Arg Arg Val Ala Glu Asp Leu
210                 215                 220

Asn Leu Gly Asn Leu Asn Val Ser Ile Pro Trp Thr His Lys Val Gly
225                 230                 235                 240

Asn Phe Thr Gly Leu Tyr Ser Ser Thr Val Pro Val Phe Asn Pro Glu
                245                 250                 255

Trp Gln Thr Pro Ser Phe Pro His Ile His Leu Gln Glu Asp Ile Ile
            260                 265                 270

Asn Arg Cys Gln Gln Tyr Val Gly Pro Leu Thr Val Asn Glu Lys Arg
            275                 280                 285

Arg Leu Lys Leu Ile Met Pro Ala Arg Phe Tyr Pro Asn Leu Thr Lys
290                 295                 300

Tyr Leu Pro Leu Asp Lys Gly Ile Lys Pro Tyr Tyr Pro Glu His Thr
305                 310                 315                 320

Val Asn His Tyr Phe Lys Thr Arg His Tyr Leu His Thr Leu Trp Lys
                325                 330                 335

Ala Gly Ile Leu Tyr Lys Arg Glu Thr Thr Arg Ser Ala Ser Phe Cys
            340                 345                 350

Gly Ser Pro Tyr Ser Trp Glu Gln Glu Leu Gln His Gly Arg Leu Val
            355                 360                 365

Phe Gln Thr Ser Thr Arg His Gly Asp Glu Ser Phe Cys Ser Gln Ser
            370                 375                 380

Ser Gly Ile Leu Ser Arg Ser Pro Val Gly Pro Cys Ile Arg Ser Gln
385                 390                 395                 400

Leu Lys Gln Ser Arg Leu Gly Leu Gln Pro Gln Gln Gly Ser Leu Ala
                405                 410                 415

Arg Ser Lys Ser Gly Arg Ser Gly Ser Ile Arg Ala Arg Val His Pro
                420                 425                 430

Thr Thr Arg Gln Ser Phe Gly Val Glu Pro Ser Gly Ser Gly His Ile
```

```
            435                 440                 445
Asp Asn Ser Ala Ser Ser Ala Ser Ser Cys Leu His Gln Ser Ala Val
            450                 455                 460
Arg Lys Thr Ala Tyr Ser His Leu Ser Thr Ser Lys Arg Gln Ser Ser
465                 470                 475                 480
Ser Gly His Ala Val Glu Leu His Asn Phe Pro Ser Ser Ala Arg
                485                 490                 495
Ser Gln Ser Glu Gly Pro Leu Leu Ser Cys Trp Trp Leu Gln Phe Arg
            500                 505                 510
Asn Ser Lys Pro Cys Ser Asp Tyr Cys Leu Ser His Ile Val Asn Leu
            515                 520                 525
Leu Glu Asp Trp Gly Pro Cys Thr Glu His Gly Glu His Asn Ile Arg
            530                 535                 540
Ile Pro Arg Thr Pro Ala Arg Val Thr Gly Gly Val Phe Leu Val Asp
545                 550                 555                 560
Lys Asn Pro His Asn Thr Thr Glu Ser Arg Leu Val Val Asp Phe Ser
                565                 570                 575
Gln Phe Ser Arg Gly Ser Thr His Val Ser Trp Pro Lys Phe Ala Val
            580                 585                 590
Pro Asn Leu Gln Ser Leu Thr Asn Leu Leu Ser Ser Asn Leu Ser Trp
            595                 600                 605
Leu Ser Leu Asp Val Ser Ala Ala Phe Tyr His Leu Pro Leu His Pro
            610                 615                 620
Ala Ala Met Pro His Leu Leu Val Gly Ser Ser Gly Leu Ser Arg Tyr
625                 630                 635                 640
Val Ala Arg Leu Ser Ser Thr Ser Arg Asn Ile Asn Tyr Gln His Gly
                645                 650                 655
Ala Met Gln Asp Leu His Asp Ser Cys Ser Arg Asn Leu Tyr Val Ser
            660                 665                 670
Leu Leu Leu Leu Tyr Lys Thr Phe Gly Arg Lys Leu His Leu Tyr Ser
            675                 680                 685
His Pro Ile Ile Leu Gly Phe Arg Lys Ile Pro Met Gly Val Gly Leu
            690                 695                 700
Ser Pro Phe Leu Leu Ala Gln Phe Thr Ser Ala Ile Cys Ser Val Val
705                 710                 715                 720
Arg Arg Ala Phe Pro His Cys Leu Ala Phe Ser Tyr Met His Asp Val
                725                 730                 735
Val Leu Gly Ala Lys Ser Val Gln His Leu Glu Ser Leu Phe Thr Ala
            740                 745                 750
Val Thr Asn Phe Leu Leu Ser Leu Gly Ile His Leu Asn Pro Asn Lys
            755                 760                 765
Thr Lys Arg Trp Gly Tyr Ser Leu Asn Phe Met Gly Tyr Val Ile Gly
            770                 775                 780
Ser Trp Gly Thr Leu Pro Gln Glu His Ile Val Leu Lys Ile Lys Gln
785                 790                 795                 800
Cys Phe Arg Lys Leu Pro Val Asn Arg Pro Ile Asp Trp Lys Val Cys
                805                 810                 815
Gln Arg Ile Val Gly Leu Leu Gly Phe Ala Ala Pro Phe Thr Gln Cys
            820                 825                 830
Gly Tyr Pro Ala Leu Met Pro Leu Tyr Ala Cys Ile Gln Ala Lys Gln
            835                 840                 845
Ala Phe Thr Phe Ser Pro Thr Tyr Lys Ala Phe Leu Cys Lys Gln Tyr
            850                 855                 860
```

```
Leu Asn Leu Tyr Pro Val Ala Arg Gln Arg Ser Gly Leu Cys Gln Val
865                 870                 875                 880

Phe Ala Asp Ala Thr Pro Thr Gly Trp Gly Leu Ala Val Gly His Gln
            885                 890                 895

Arg Met Arg Gly Thr Phe Val Ser Pro Leu Pro Ile His Thr Ala His
        900                 905                 910

Leu Leu Ala Ala Cys Phe Ala Arg Ser Arg Ser Gly Ala Lys Leu Ile
        915                 920                 925

Gly Thr Asp Asn Ser Val Val Leu Ser Arg Lys Tyr Thr Ser Phe Pro
        930                 935                 940

Trp Leu Leu Gly Cys Ala Ala Asn Trp Ile Leu Arg Gly Thr Ser Phe
945                 950                 955                 960

Val Tyr Val Pro Ser Ala Leu Asn Pro Ala Asp Asp Pro Ser Arg Gly
                965                 970                 975

Arg Leu Gly Leu Tyr Arg Pro Leu Leu Arg Leu Pro Phe Arg Pro Thr
            980                 985                 990

Thr Gly Arg Thr Ser Leu Tyr Ala Val Ser Pro Ser Val Pro Ser His
        995                 1000                1005

Leu Pro Val Arg Val His Phe Ala Ser Pro Leu His Val Ala Trp
    1010                1015                1020

Arg Pro Pro
    1025

<210> SEQ ID NO 18
<211> LENGTH: 1015
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Pro Leu Ser Tyr Gln His Phe Arg
```

```
            180                 185                 190
Arg Leu Leu Leu Leu Asp Asp Glu Ala Gly Pro Leu Glu Glu Glu Leu
        195                 200                 205

Pro Arg Leu Ala Asp Glu Gly Leu Asn Arg Arg Val Ala Glu Asp Leu
    210                 215                 220

Asn Leu Gly Asn Leu Asn Val Ser Ile Pro Trp Thr His Lys Val Gly
225                 230                 235                 240

Asn Phe Thr Gly Leu Tyr Ser Ser Thr Val Pro Val Phe Asn Pro His
                245                 250                 255

Trp Lys Thr Pro Ser Phe Pro Asn Ile His Leu His Gln Asp Ile Ile
            260                 265                 270

Lys Lys Cys Glu Gln Phe Val Gly Pro Leu Thr Val Asn Glu Lys Arg
        275                 280                 285

Arg Leu Gln Leu Ile Met Pro Ala Arg Phe Tyr Pro Asn Val Thr Lys
    290                 295                 300

Tyr Leu Pro Leu Asp Lys Gly Ile Lys Pro Tyr Tyr Pro Glu His Leu
305                 310                 315                 320

Val Asn His Tyr Phe Gln Thr Arg His Tyr Leu His Thr Leu Trp Lys
                325                 330                 335

Ala Gly Ile Leu Tyr Lys Arg Glu Thr Thr His Ser Ala Ser Phe Cys
            340                 345                 350

Gly Ser Pro Tyr Ser Trp Glu Gln Glu Leu Gln His Gly Ala Glu Ser
        355                 360                 365

Phe His Gln Gln Ser Ser Gly Ile Leu Ser Arg Pro Pro Val Gly Ser
    370                 375                 380

Ser Leu Gln Ser Lys His Arg Lys Ser Arg Leu Gly Leu Gln Ser Gln
385                 390                 395                 400

Gln Gly His Leu Ala Arg Arg Gln Gln Gly Arg Gly Trp Ser Ile Arg
                405                 410                 415

Ala Gly Ile His Pro Thr Ala Arg Arg Pro Phe Gly Val Glu Pro Ser
            420                 425                 430

Gly Ser Gly His Thr Ala Asn Leu Ala Ser Lys Ser Ala Ser Cys Leu
        435                 440                 445

Tyr Gln Ser Ala Val Arg Lys Ala Ala Tyr Pro Val Val Ser Thr Phe
    450                 455                 460

Lys Lys His Ser Ser Ser Gly His Ala Val Glu Leu His Asn Leu Pro
465                 470                 475                 480

Pro Asn Ser Ala Arg Ser Gln Ser Glu Arg Pro Val Phe Pro Cys Trp
                485                 490                 495

Trp Leu Gln Phe Arg Asn Ser Lys Pro Cys Ser Asp Tyr Cys Leu Ser
            500                 505                 510

His Ile Val Asn Leu Leu Glu Asp Trp Gly Pro Cys Ala Glu His Gly
        515                 520                 525

Glu His His Ile Arg Ile Pro Arg Thr Pro Ala Arg Val Thr Gly Gly
    530                 535                 540

Val Phe Leu Val Asp Lys Asn Pro His Asn Thr Ala Glu Ser Arg Leu
545                 550                 555                 560

Val Val Asp Phe Ser Gln Phe Ser Arg Gly Asn Tyr Arg Val Ser Trp
                565                 570                 575

Pro Lys Phe Ala Val Pro Asn Leu Gln Ser Leu Thr Asn Leu Leu Ser
            580                 585                 590

Ser Asn Leu Ser Trp Leu Ser Leu Asp Val Ser Ala Ala Phe Tyr His
        595                 600                 605
```

Leu Pro Leu His Pro Ala Ala Met Pro His Leu Leu Val Gly Ser Ser
610                 615                 620

Gly Leu Ser Arg Tyr Val Ala Arg Leu Ser Ser Asn Ser Arg Ile Phe
625                 630                 635                 640

Asn Tyr Gln His Gly Thr Met Gln Asn Leu His Asp Ser Cys Ser Arg
                645                 650                 655

Asn Leu Tyr Val Ser Leu Met Leu Leu Tyr Gln Thr Phe Gly Arg Lys
                660                 665                 670

Leu His Leu Tyr Ser His Pro Ile Ile Leu Gly Phe Arg Lys Ile Pro
            675                 680                 685

Met Gly Val Gly Leu Ser Pro Phe Leu Leu Ala Gln Phe Thr Ser Ala
690                 695                 700

Ile Cys Ser Val Val Arg Arg Ala Phe Pro His Cys Leu Ala Phe Ser
705                 710                 715                 720

Tyr Met His Asp Val Val Leu Gly Ala Lys Ser Val Gln His Leu Glu
                725                 730                 735

Ser Leu Phe Thr Ala Val Thr Asn Phe Leu Leu Ser Leu Gly Ile His
                740                 745                 750

Leu Asn Pro Asn Lys Thr Lys Arg Trp Gly Tyr Ser Leu His Phe Met
            755                 760                 765

Gly Tyr Val Ile Gly Cys Tyr Gly Ser Leu Pro Gln Asp His Ile Ile
770                 775                 780

Gln Lys Ile Lys Glu Cys Phe Arg Lys Leu Pro Val Asn Arg Pro Ile
785                 790                 795                 800

Asp Trp Lys Val Cys Gln Arg Ile Val Gly Leu Leu Gly Phe Ala Ala
                805                 810                 815

Pro Phe Thr Gln Cys Gly Tyr Pro Ala Leu Met Pro Leu Tyr Ala Cys
                820                 825                 830

Ile Gln Ser Lys Gln Ala Phe Thr Phe Ser Pro Thr Tyr Lys Ala Phe
            835                 840                 845

Leu Cys Lys Gln Tyr Leu Asn Leu Tyr Pro Val Ala Arg Gln Arg Pro
850                 855                 860

Gly Leu Cys Gln Val Phe Ala Asp Ala Thr Pro Thr Gly Trp Gly Leu
865                 870                 875                 880

Val Met Gly His Gln Arg Met Arg Gly Thr Phe Lys Ala Pro Leu Pro
                885                 890                 895

Ile His Thr Ala His Leu Leu Ala Ala Cys Phe Ala Arg Ser Arg Ser
                900                 905                 910

Gly Ala Asn Ile Leu Gly Thr Asp Asn Ser Val Val Leu Ser Arg Lys
            915                 920                 925

Tyr Thr Ser Phe Pro Trp Leu Leu Gly Cys Ala Ala Asn Trp Ile Leu
930                 935                 940

Arg Gly Thr Ser Phe Val Tyr Val Pro Ser Ala Leu Asn Pro Ala Asp
945                 950                 955                 960

Asp Pro Ser Arg Gly Arg Leu Gly Leu Tyr Arg Pro Leu Leu Arg Leu
                965                 970                 975

Pro Phe Arg Pro Thr Thr Gly Arg Thr Ser Leu Tyr Ala Asp Ser Pro
                980                 985                 990

Ser Val Pro Ser His Leu Pro Asp Arg Val His Phe Ala Ser Pro Leu
            995                 1000                1005

His Val Ala Trp Arg Pro Pro
    1010                1015

-continued

<210> SEQ ID NO 19
<211> LENGTH: 940
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys Met Pro Leu Ser Tyr Gln His
            180                 185                 190

Phe Arg Lys Leu Leu Leu Leu Asp Asp Glu Thr Glu Ala Gly Pro Leu
        195                 200                 205

Glu Glu Glu Leu Pro Arg Leu Ala Asp Glu Asp Leu Asn Arg Arg Val
    210                 215                 220

Ala Glu Asp Leu Asn Leu Gly Asn Leu Asn Val Ser Ile Pro Trp Thr
225                 230                 235                 240

His Lys Val Gly Asn Phe Thr Gly Leu Tyr Ser Ser Thr Val Pro Ile
                245                 250                 255

Phe Asn Pro Glu Trp Gln Thr Pro Ser Phe Pro Lys Ile His Leu His
            260                 265                 270

Glu Asp Ile Ala Asn Arg Cys Gln Gln Phe Val Gly Pro Leu Thr Val
        275                 280                 285

Asn Glu Lys Arg Arg Leu Arg Leu Ile Met Pro Ala Arg Phe Tyr Pro
    290                 295                 300

Asn Ser Thr Lys Tyr Leu Pro Leu Asp Lys Gly Ile Lys Pro Tyr Tyr
305                 310                 315                 320

Pro Asp His Val Val Asn His Tyr Phe Gln Thr Arg His Tyr Leu His
                325                 330                 335

Thr Leu Trp Lys Ala Gly Ile Leu Tyr Lys Arg Glu Thr Thr Arg Ser
            340                 345                 350

Ala Ser Phe Cys Gly Ser Pro Tyr Ser Trp Glu Gln Glu Leu His His
        355                 360                 365

-continued

Gly Arg Leu Val Ile Lys Thr Ser Gln Arg His Gly Asp Glu Pro Phe
    370                 375                 380

Cys Ser Gln Pro Ser Gly Ile Leu Ser Arg Ser Ser Val Gly Pro Glu
385                 390                 395                 400

Phe His Ser Phe Pro Pro Ser Ser Ala Arg Ser Gln Ser Gln Gly Pro
                    405                 410                 415

Val Phe Ser Cys Trp Trp Leu Gln Phe Arg Asn Thr Gln Pro Cys Ser
            420                 425                 430

Lys Tyr Cys Leu Ser His Leu Val Asn Leu Leu Glu Asp Trp Gly Pro
        435                 440                 445

Cys Asp Glu His Gly Glu His His Ile Arg Ile Pro Arg Thr Pro Ala
    450                 455                 460

Arg Val Thr Gly Gly Val Phe Leu Val Asp Lys Asn Pro His Asn Thr
465                 470                 475                 480

Ala Glu Ser Arg Leu Val Val Asp Phe Ser Gln Phe Ser Arg Gly Ile
                485                 490                 495

Thr Arg Val Ser Trp Pro Lys Phe Ala Val Pro Asn Leu Gln Ser Leu
            500                 505                 510

Thr Asn Leu Leu Ser Ser Asn Leu Ser Trp Leu Ser Leu Asp Val Ser
        515                 520                 525

Ala Ala Phe Tyr His Ile Pro Leu His Pro Ala Ala Met Pro His Leu
    530                 535                 540

Leu Val Gly Ser Ser Gly Leu Ser Arg Tyr Val Ala Arg Leu Ser Ser
545                 550                 555                 560

Asn Ser Arg Ile His Asn Asn Gln His Gly Thr Leu Gln Asn Leu His
                565                 570                 575

Asp Ser Cys Ser Arg Gln Leu Tyr Val Ser Leu Met Leu Leu Tyr Lys
            580                 585                 590

Thr Tyr Gly Arg Lys Leu His Leu Tyr Ser His Pro Ile Ile Leu Gly
        595                 600                 605

Phe Arg Lys Ile Pro Met Gly Val Gly Leu Ser Pro Phe Leu Leu Ala
    610                 615                 620

Gln Phe Thr Ser Ala Ile Cys Ser Val Val Arg Arg Ala Phe Pro His
625                 630                 635                 640

Cys Leu Ala Phe Ser Tyr Met His Asp Val Val Leu Gly Ala Lys Ser
                645                 650                 655

Val Gln His Leu Glu Ser Leu Tyr Thr Ala Val Thr Asn Phe Leu Leu
            660                 665                 670

Ser Leu Gly Ile His Leu Asn Pro Asn Lys Thr Lys Arg Trp Gly Tyr
        675                 680                 685

Ser Leu Asn Phe Met Gly Tyr Val Ile Gly Ser Trp Gly Thr Leu Pro
    690                 695                 700

Gln Asp His Ile Val Gln Lys Ile Lys His Cys Phe Arg Lys Leu Pro
705                 710                 715                 720

Ile Asn Arg Pro Ile Asp Trp Lys Val Cys Gln Arg Ile Val Gly Leu
                725                 730                 735

Leu Gly Phe Ala Ala Pro Phe Thr Gln Cys Gly Tyr Pro Ala Leu Met
            740                 745                 750

Pro Leu Tyr Ala Cys Ile Gln Ala Lys Gln Ala Phe Thr Phe Ser Pro
        755                 760                 765

Thr Tyr Lys Ala Phe Leu Ser Lys Gln Tyr Leu Asn Leu Tyr Pro Val
    770                 775                 780

```
Ala Arg Gln Arg Pro Gly Leu Cys Gln Val Phe Ala Asp Ala Thr Pro
785                 790                 795                 800

Thr Gly Trp Gly Leu Ala Ile Gly His Gln Arg Met Arg Gly Thr Phe
            805                 810                 815

Val Ala Pro Leu Pro Ile His Thr Ala His Leu Leu Ala Ala Cys Phe
            820                 825                 830

Ala Arg Ser Arg Ser Gly Ala Lys Leu Ile Gly Thr Asp Asn Ser Val
            835                 840                 845

Val Leu Ser Arg Lys Tyr Thr Ser Phe Pro Trp Leu Leu Gly Cys Thr
850                 855                 860

Ala Asn Trp Ile Leu Arg Gly Thr Ser Phe Val Tyr Val Pro Ser Ala
865                 870                 875                 880

Leu Asn Pro Ala Asp Asp Pro Ser Arg Gly Arg Leu Gly Leu Tyr Arg
                885                 890                 895

Pro Leu Leu Arg Leu Pro Tyr Arg Pro Thr Thr Gly Arg Thr Ser Leu
            900                 905                 910

Tyr Ala Val Ser Pro Ser Val Pro Ser His Leu Pro Val Arg Val His
            915                 920                 925

Phe Ala Ser Pro Leu His Val Ala Trp Arg Pro Pro
930                 935                 940

<210> SEQ ID NO 20
<211> LENGTH: 932
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Pro Leu Ser Tyr Gln His Phe Arg
            180                 185                 190

Lys Leu Leu Leu Leu Asp Asp Glu Ala Gly Pro Leu Glu Glu Glu Leu
        195                 200                 205
```

-continued

Pro Arg Leu Ala Asp Glu Gly Leu Asn Arg Arg Val Ala Glu Asp Leu
    210                 215                 220

Asn Leu Gly Asn Leu Asn Val Ser Ile Pro Trp Thr His Lys Val Gly
225                 230                 235                 240

Asn Phe Thr Gly Leu Tyr Ser Ser Thr Val Pro Val Phe Asn Pro Glu
                245                 250                 255

Trp Gln Thr Pro Ser Phe Pro His Ile His Leu Gln Glu Asp Ile Ile
            260                 265                 270

Asn Arg Cys Gln Gln Tyr Val Gly Pro Leu Thr Val Asn Glu Lys Arg
        275                 280                 285

Arg Leu Lys Leu Ile Met Pro Ala Arg Phe Tyr Pro Asn Leu Thr Lys
290                 295                 300

Tyr Leu Pro Leu Asp Lys Gly Ile Lys Pro Tyr Tyr Pro Glu His Val
305                 310                 315                 320

Val Asn His Tyr Phe Gln Thr Arg His Tyr Leu His Thr Leu Trp Lys
                325                 330                 335

Ala Gly Ile Leu Tyr Lys Arg Glu Ser Thr Arg Ser Ala Ser Phe Cys
            340                 345                 350

Gly Ser Pro Tyr Ser Trp Glu Gln Asp Leu Gln His Gly Arg Leu Val
        355                 360                 365

Phe Gln Thr Ser Lys Arg His Gly Asp Lys Ser Phe Cys Pro Gln Ser
370                 375                 380

Pro Gly Ile Leu Pro Arg Ser Glu Leu His His Phe Pro Pro Ser Ser
385                 390                 395                 400

Ser Arg Ser Gln Ser Gln Gly Pro Val Leu Ser Cys Trp Trp Leu Gln
                405                 410                 415

Phe Arg Asn Ser Glu Pro Cys Ser Glu Tyr Cys Leu Cys His Ile Val
            420                 425                 430

Asn Leu Ile Glu Asp Trp Gly Pro Cys Thr Glu His Gly Glu His Arg
        435                 440                 445

Ile Arg Thr Pro Arg Thr Pro Ala Arg Val Thr Gly Gly Val Phe Leu
450                 455                 460

Val Asp Lys Asn Pro His Asn Thr Thr Glu Ser Arg Leu Val Val Asp
465                 470                 475                 480

Phe Ser Gln Phe Ser Arg Gly Asn Thr Arg Val Ser Trp Pro Lys Phe
                485                 490                 495

Ala Val Pro Asn Leu Gln Ser Leu Thr Asn Leu Leu Ser Ser Asn Leu
            500                 505                 510

Ser Trp Leu Ser Leu Asp Val Ser Ala Ala Phe Tyr His Leu Pro Leu
        515                 520                 525

His Pro Ala Ala Met Pro His Leu Leu Val Gly Ser Ser Gly Leu Ser
530                 535                 540

Arg Tyr Val Ala Arg Leu Ser Ser Asn Ser Arg Ile Ile Asn Asn Gln
545                 550                 555                 560

His Arg Thr Met Gln Asn Leu His Asp Ser Cys Ser Arg Asn Leu Tyr
                565                 570                 575

Val Ser Leu Met Leu Leu Tyr Lys Thr Tyr Gly Arg Lys Leu His Leu
            580                 585                 590

Tyr Ser His Pro Ile Ile Leu Gly Phe Arg Lys Ile Pro Met Gly Val
        595                 600                 605

Gly Leu Ser Pro Phe Leu Leu Ala Gln Phe Thr Ser Ala Ile Cys Ser
610                 615                 620

Val Val Arg Arg Ala Phe Pro His Cys Leu Ala Phe Ser Tyr Met His
625                 630                 635                 640

Asp Val Val Leu Gly Ala Lys Ser Val Gln His Leu Glu Ser Leu Tyr
                645                 650                 655

Ala Ala Val Thr Asn Phe Leu Leu Ser Leu Gly Ile His Leu Asn Pro
            660                 665                 670

His Lys Thr Lys Arg Trp Gly Tyr Ser Leu Asn Phe Met Gly Tyr Val
        675                 680                 685

Ile Gly Ser Trp Gly Thr Leu Pro Gln Glu His Ile Val Gln Lys Ile
690                 695                 700

Lys Met Cys Phe Arg Lys Leu Pro Val Asn Arg Pro Ile Asp Trp Lys
705                 710                 715                 720

Val Cys Gln Arg Ile Val Gly Leu Leu Gly Phe Ala Ala Pro Phe Thr
                725                 730                 735

Gln Cys Gly Tyr Pro Ala Leu Met Pro Leu Tyr Ala Cys Ile Gln Ala
            740                 745                 750

Lys Gln Ala Phe Thr Phe Ser Pro Thr Tyr Lys Ala Phe Leu Ser Lys
        755                 760                 765

Gln Tyr Leu His Leu Tyr Pro Val Ala Arg Gln Arg Pro Gly Leu Cys
770                 775                 780

Gln Val Phe Ala Asp Ala Thr Pro Thr Gly Trp Gly Leu Ala Ile Gly
785                 790                 795                 800

His Gln Arg Met Arg Gly Ala Phe Val Ser Pro Leu Pro Ile His Thr
                805                 810                 815

Ala His Leu Leu Ala Ala Cys Phe Ala Arg Ser Arg Ser Gly Ala Lys
            820                 825                 830

Leu Ile Gly Thr Asp Asn Ser Val Val Leu Ser Arg Lys Tyr Thr Ser
        835                 840                 845

Phe Pro Trp Leu Leu Gly Cys Ala Ala Asn Trp Ile Leu Arg Gly Thr
850                 855                 860

Ser Phe Val Tyr Val Pro Ser Ala Leu Asn Pro Ala Asp Asp Pro Ser
865                 870                 875                 880

Arg Gly Arg Leu Gly Leu Tyr Arg Pro Leu Leu Arg Leu Leu Tyr Arg
                885                 890                 895

Pro Thr Thr Gly Arg Thr Ser Leu Tyr Ala Asp Ser Pro Ser Val Pro
            900                 905                 910

Ser His Leu Pro Asp Arg Val His Phe Ala Ser Pro Leu His Val Ala
        915                 920                 925

Trp Arg Pro Pro
    930

<210> SEQ ID NO 21
<211> LENGTH: 936
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

```
Ser Pro His His Thr Ala Leu Arg Gln Ala Ile Leu Cys Trp Gly Glu
 50                  55                  60

Leu Met Asn Leu Ala Thr Trp Val Gly Ser Asn Leu Glu Asp Pro Ala
 65                  70                  75                  80

Ser Arg Glu Leu Val Val Ser Tyr Val Asn Val Asn Met Gly Leu Lys
                 85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
                130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Pro Leu Ser Tyr Gln His Phe Arg
                180                 185                 190

Lys Leu Leu Leu Leu Asp Asp Glu Ala Gly Pro Leu Glu Glu Glu Leu
                195                 200                 205

Pro Arg Leu Ala Asp Glu Asp Leu Asn Arg Arg Val Ala Glu Asp Leu
210                 215                 220

Asn Leu Gly Asn Leu Asn Val Ser Ile Pro Trp Thr His Lys Val Gly
225                 230                 235                 240

Asn Phe Thr Gly Leu Tyr Ser Ser Thr Val Pro Val Phe Asn Pro Glu
                245                 250                 255

Trp Gln Thr Pro Ser Phe Pro His Ile His Leu Gln Glu Asp Ile Ile
                260                 265                 270

Asn Arg Cys Gln Gln Tyr Val Gly Pro Leu Thr Val Asn Glu Lys Arg
                275                 280                 285

Arg Leu Lys Leu Ile Met Pro Ala Arg Phe Tyr Pro Asn Leu Thr Lys
                290                 295                 300

Tyr Leu Pro Leu Asp Lys Gly Ile Lys Pro Tyr Tyr Pro Glu His Thr
305                 310                 315                 320

Val Asn His Tyr Phe Lys Thr Arg His Tyr Leu His Thr Leu Trp Lys
                325                 330                 335

Ala Gly Ile Leu Tyr Lys Arg Glu Thr Thr Arg Ser Ala Ser Phe Cys
                340                 345                 350

Gly Ser Pro Tyr Ser Trp Glu Gln Glu Leu Gln His Gly Arg Leu Val
                355                 360                 365

Phe Gln Thr Ser Thr Arg His Gly Asp Glu Ser Phe Cys Ser Gln Ser
                370                 375                 380

Ser Gly Ile Leu Ser Arg Ser Pro Val Gly Pro Glu Leu His Asn Phe
385                 390                 395                 400

Pro Pro Ser Ser Ala Arg Ser Gln Ser Glu Gly Pro Leu Leu Ser Cys
                405                 410                 415

Trp Trp Leu Gln Phe Arg Asn Ser Lys Pro Cys Ser Asp Tyr Cys Leu
                420                 425                 430

Ser His Ile Val Asn Leu Leu Glu Asp Trp Gly Pro Cys Thr Glu His
                435                 440                 445

Gly Glu His Asn Ile Arg Ile Pro Arg Thr Pro Ala Arg Val Thr Gly
450                 455                 460
```

```
Gly Val Phe Leu Val Asp Lys Asn Pro His Asn Thr Thr Glu Ser Arg
465                 470                 475                 480

Leu Val Val Asp Phe Ser Gln Phe Ser Arg Gly Ser Thr His Val Ser
            485                 490                 495

Trp Pro Lys Phe Ala Val Pro Asn Leu Gln Ser Leu Thr Asn Leu Leu
        500                 505                 510

Ser Ser Asn Leu Ser Trp Leu Ser Leu Asp Val Ser Ala Ala Phe Tyr
    515                 520                 525

His Leu Pro Leu His Pro Ala Met Pro His Leu Leu Val Gly Ser
    530                 535                 540

Ser Gly Leu Ser Arg Tyr Val Ala Arg Leu Ser Ser Thr Ser Arg Asn
545                 550                 555                 560

Ile Asn Tyr Gln His Gly Ala Met Gln Asp Leu His Asp Ser Cys Ser
                565                 570                 575

Arg Asn Leu Tyr Val Ser Leu Leu Leu Tyr Lys Thr Phe Gly Arg
                580                 585                 590

Lys Leu His Leu Tyr Ser His Pro Ile Ile Leu Gly Phe Arg Lys Ile
        595                 600                 605

Pro Met Gly Val Gly Leu Ser Pro Phe Leu Leu Ala Gln Phe Thr Ser
    610                 615                 620

Ala Ile Cys Ser Val Val Arg Arg Ala Phe Pro His Cys Leu Ala Phe
625                 630                 635                 640

Ser Tyr Met His Asp Val Val Leu Gly Ala Lys Ser Val Gln His Leu
                645                 650                 655

Glu Ser Leu Phe Thr Ala Val Thr Asn Phe Leu Leu Ser Leu Gly Ile
                660                 665                 670

His Leu Asn Pro Asn Lys Thr Lys Arg Trp Gly Tyr Ser Leu Asn Phe
            675                 680                 685

Met Gly Tyr Val Ile Gly Ser Trp Gly Thr Leu Pro Gln Glu His Ile
    690                 695                 700

Val Leu Lys Ile Lys Gln Cys Phe Arg Lys Leu Pro Val Asn Arg Pro
705                 710                 715                 720

Ile Asp Trp Lys Val Cys Gln Arg Ile Val Gly Leu Leu Gly Phe Ala
                725                 730                 735

Ala Pro Phe Thr Gln Cys Gly Tyr Pro Ala Leu Met Pro Leu Tyr Ala
                740                 745                 750

Cys Ile Gln Ala Lys Gln Ala Phe Thr Phe Ser Pro Thr Tyr Lys Ala
            755                 760                 765

Phe Leu Cys Lys Gln Tyr Leu Asn Leu Tyr Pro Val Ala Arg Gln Arg
    770                 775                 780

Ser Gly Leu Cys Gln Val Phe Ala Asp Ala Thr Pro Thr Gly Trp Gly
785                 790                 795                 800

Leu Ala Val Gly His Gln Arg Met Arg Gly Thr Phe Val Ser Pro Leu
                805                 810                 815

Pro Ile His Thr Ala His Leu Leu Ala Ala Cys Phe Ala Arg Ser Arg
                820                 825                 830

Ser Gly Ala Lys Leu Ile Gly Thr Asp Asn Ser Val Val Leu Ser Arg
            835                 840                 845

Lys Tyr Thr Ser Phe Pro Trp Leu Leu Gly Cys Ala Ala Asn Trp Ile
    850                 855                 860

Leu Arg Gly Thr Ser Phe Val Tyr Val Pro Ser Ala Leu Asn Pro Ala
865                 870                 875                 880

Asp Asp Pro Ser Arg Gly Arg Leu Gly Leu Tyr Arg Pro Leu Leu Arg
```

```
                    885                 890                 895
Leu Pro Phe Arg Pro Thr Thr Gly Arg Thr Ser Leu Tyr Ala Val Ser
            900                 905                 910

Pro Ser Val Pro Ser His Leu Pro Val Arg Val His Phe Ala Ser Pro
            915                 920                 925

Leu His Val Ala Trp Arg Pro Pro
            930                 935

<210> SEQ ID NO 22
<211> LENGTH: 925
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Pro Leu Ser Tyr Gln His Phe Arg
            180                 185                 190

Arg Leu Leu Leu Leu Asp Asp Glu Ala Gly Pro Leu Glu Glu Glu Leu
        195                 200                 205

Pro Arg Leu Ala Asp Glu Gly Leu Asn Arg Arg Val Ala Glu Asp Leu
    210                 215                 220

Asn Leu Gly Asn Leu Asn Val Ser Ile Pro Trp Thr His Lys Val Gly
225                 230                 235                 240

Asn Phe Thr Gly Leu Tyr Ser Ser Thr Val Pro Val Phe Asn Pro His
                245                 250                 255

Trp Lys Thr Pro Ser Phe Pro Asn Ile His Leu His Gln Asp Ile Ile
            260                 265                 270

Lys Lys Cys Glu Gln Phe Val Gly Pro Leu Thr Val Asn Glu Lys Arg
        275                 280                 285

Arg Leu Gln Leu Ile Met Pro Ala Arg Phe Tyr Pro Asn Val Thr Lys
    290                 295                 300
```

```
Tyr Leu Pro Leu Asp Lys Gly Ile Lys Pro Tyr Pro Glu His Leu
305                 310                 315                 320

Val Asn His Tyr Phe Gln Thr Arg His Tyr Leu His Thr Leu Trp Lys
            325                 330                 335

Ala Gly Ile Leu Tyr Lys Arg Glu Thr Thr His Ser Ala Ser Phe Cys
                340                 345                 350

Gly Ser Pro Tyr Ser Trp Glu Gln Glu Leu Gln His Gly Ala Glu Ser
        355                 360                 365

Phe His Gln Gln Ser Ser Gly Ile Leu Ser Arg Pro Val Gly Ser
    370                 375                 380

Glu Leu His Asn Leu Pro Pro Asn Ser Ala Arg Ser Gln Ser Glu Arg
385                 390                 395                 400

Pro Val Phe Pro Cys Trp Trp Leu Gln Phe Arg Asn Ser Lys Pro Cys
                405                 410                 415

Ser Asp Tyr Cys Leu Ser His Ile Val Asn Leu Leu Glu Asp Trp Gly
                420                 425                 430

Pro Cys Ala Glu His Gly Glu His His Ile Arg Ile Pro Arg Thr Pro
            435                 440                 445

Ala Arg Val Thr Gly Gly Val Phe Leu Val Asp Lys Asn Pro His Asn
450                 455                 460

Thr Ala Glu Ser Arg Leu Val Val Asp Phe Ser Gln Phe Ser Arg Gly
465                 470                 475                 480

Asn Tyr Arg Val Ser Trp Pro Lys Phe Ala Val Pro Asn Leu Gln Ser
                485                 490                 495

Leu Thr Asn Leu Leu Ser Ser Asn Leu Ser Trp Leu Ser Leu Asp Val
            500                 505                 510

Ser Ala Ala Phe Tyr His Leu Pro Leu His Pro Ala Ala Met Pro His
            515                 520                 525

Leu Leu Val Gly Ser Ser Gly Leu Ser Arg Tyr Val Ala Arg Leu Ser
530                 535                 540

Ser Asn Ser Arg Ile Phe Asn Tyr Gln His Gly Thr Met Gln Asn Leu
545                 550                 555                 560

His Asp Ser Cys Ser Arg Asn Leu Tyr Val Ser Leu Met Leu Leu Tyr
                565                 570                 575

Gln Thr Phe Gly Arg Lys Leu His Leu Tyr Ser His Pro Ile Ile Leu
            580                 585                 590

Gly Phe Arg Lys Ile Pro Met Gly Val Gly Leu Ser Pro Phe Leu Leu
        595                 600                 605

Ala Gln Phe Thr Ser Ala Ile Cys Ser Val Val Arg Arg Ala Phe Pro
            610                 615                 620

His Cys Leu Ala Phe Ser Tyr Met His Asp Val Val Leu Gly Ala Lys
625                 630                 635                 640

Ser Val Gln His Leu Glu Ser Leu Phe Thr Ala Val Thr Asn Phe Leu
            645                 650                 655

Leu Ser Leu Gly Ile His Leu Asn Pro Asn Lys Thr Lys Arg Trp Gly
            660                 665                 670

Tyr Ser Leu His Phe Met Gly Tyr Val Ile Gly Cys Tyr Gly Ser Leu
            675                 680                 685

Pro Gln Asp His Ile Ile Gln Lys Ile Lys Glu Cys Phe Arg Lys Leu
        690                 695                 700

Pro Val Asn Arg Pro Ile Asp Trp Lys Val Cys Gln Arg Ile Val Gly
705                 710                 715                 720

Leu Leu Gly Phe Ala Ala Pro Phe Thr Gln Cys Gly Tyr Pro Ala Leu
```

```
                    725                 730                 735
Met Pro Leu Tyr Ala Cys Ile Gln Ser Lys Gln Ala Phe Thr Phe Ser
                740                 745                 750

Pro Thr Tyr Lys Ala Phe Leu Cys Lys Gln Tyr Leu Asn Leu Tyr Pro
            755                 760                 765

Val Ala Arg Gln Arg Pro Gly Leu Cys Gln Val Phe Ala Asp Ala Thr
        770                 775                 780

Pro Thr Gly Trp Gly Leu Val Met Gly His Gln Arg Met Arg Gly Thr
785                 790                 795                 800

Phe Lys Ala Pro Leu Pro Ile His Thr Ala His Leu Leu Ala Ala Cys
                805                 810                 815

Phe Ala Arg Ser Arg Ser Gly Ala Asn Ile Leu Gly Thr Asp Asn Ser
                820                 825                 830

Val Val Leu Ser Arg Lys Tyr Thr Ser Phe Pro Trp Leu Leu Gly Cys
            835                 840                 845

Ala Ala Asn Trp Ile Leu Arg Gly Thr Ser Phe Val Tyr Val Pro Ser
        850                 855                 860

Ala Leu Asn Pro Ala Asp Asp Pro Ser Arg Gly Arg Leu Gly Leu Tyr
865                 870                 875                 880

Arg Pro Leu Leu Arg Leu Pro Phe Arg Pro Thr Thr Gly Arg Thr Ser
                885                 890                 895

Leu Tyr Ala Asp Ser Pro Ser Val Pro Ser His Leu Pro Asp Arg Val
                900                 905                 910

His Phe Ala Ser Pro Leu His Val Ala Trp Arg Pro Pro
                915                 920                 925

<210> SEQ ID NO 23
<211> LENGTH: 890
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160
```

```
Arg Thr Pro Ser Pro Arg Arg Arg Ser Gln Ser Pro Arg Arg
            165                 170                 175

Arg Ser Gln Ser Arg Glu Ser Gln Cys Met Pro Leu Ser Tyr Gln His
        180                 185                 190

Phe Arg Lys Leu Leu Leu Leu Asp Asp Glu Thr Glu Ala Gly Pro Leu
        195                 200                 205

Glu Glu Glu Leu Pro Arg Leu Ala Asp Glu Asp Leu Asn Arg Arg Val
        210                 215                 220

Ala Glu Asp Leu Asn Leu Gly Asn Leu Asn Val Ser Ile Pro Trp Thr
225                 230                 235                 240

His Lys Val Gly Asn Phe Thr Gly Leu Tyr Ser Ser Thr Val Pro Ile
                245                 250                 255

Phe Asn Pro Glu Trp Gln Thr Pro Ser Phe Pro Lys Ile His Leu His
            260                 265                 270

Glu Asp Ile Ala Asn Arg Cys Gln Gln Phe Val Gly Pro Leu Thr Val
        275                 280                 285

Asn Glu Lys Arg Arg Leu Arg Leu Ile Met Pro Ala Arg Phe Tyr Pro
        290                 295                 300

Asn Ser Thr Lys Tyr Leu Pro Leu Asp Lys Gly Ile Lys Pro Tyr Tyr
305                 310                 315                 320

Pro Asp His Val Val Asn His Tyr Phe Gln Thr Arg His Tyr Leu His
                325                 330                 335

Thr Leu Trp Lys Ala Gly Ile Leu Tyr Lys Arg Glu Thr Thr Arg Ser
            340                 345                 350

Ala Ser Phe Cys Gly Ser Pro Tyr Ser Trp Glu Gln Glu Leu His His
        355                 360                 365

Gly Cys Trp Trp Leu Gln Phe Arg Asn Thr Gln Pro Cys Ser Lys Tyr
        370                 375                 380

Cys Leu Ser His Leu Val Asn Leu Leu Glu Asp Trp Gly Pro Cys Asp
385                 390                 395                 400

Glu His Gly Glu His His Ile Arg Ile Pro Arg Thr Pro Ala Arg Val
                405                 410                 415

Thr Gly Gly Val Phe Leu Val Asp Lys Asn Pro His Asn Thr Ala Glu
            420                 425                 430

Ser Arg Leu Val Val Asp Phe Ser Gln Phe Ser Arg Gly Ile Thr Arg
        435                 440                 445

Val Ser Trp Pro Lys Phe Ala Val Pro Asn Leu Gln Ser Leu Thr Asn
        450                 455                 460

Leu Leu Ser Ser Asn Leu Ser Trp Leu Ser Leu Asp Val Ser Ala Ala
465                 470                 475                 480

Phe Tyr His Ile Pro Leu His Pro Ala Ala Met Pro His Leu Leu Val
                485                 490                 495

Gly Ser Ser Gly Leu Ser Arg Tyr Val Ala Arg Leu Ser Ser Asn Ser
            500                 505                 510

Arg Ile His Asn Asn Gln His Gly Thr Leu Gln Asn Leu His Asp Ser
        515                 520                 525

Cys Ser Arg Gln Leu Tyr Val Ser Leu Met Leu Leu Tyr Lys Thr Tyr
        530                 535                 540

Gly Arg Lys Leu His Leu Tyr Ser His Pro Ile Ile Leu Gly Phe Arg
545                 550                 555                 560

Lys Ile Pro Met Gly Val Gly Leu Ser Pro Phe Leu Leu Ala Gln Phe
                565                 570                 575

Thr Ser Ala Ile Cys Ser Val Val Arg Arg Ala Phe Pro His Cys Leu
```

```
            580                 585                 590
Ala Phe Ser Tyr Met His Asp Val Val Leu Gly Ala Lys Ser Val Gln
            595                 600                 605

His Leu Glu Ser Leu Tyr Thr Ala Val Thr Asn Phe Leu Leu Ser Leu
        610                 615                 620

Gly Ile His Leu Asn Pro Asn Lys Thr Lys Arg Trp Gly Tyr Ser Leu
625                 630                 635                 640

Asn Phe Met Gly Tyr Val Ile Gly Ser Trp Gly Thr Leu Pro Gln Asp
                645                 650                 655

His Ile Val Gln Lys Ile Lys His Cys Phe Arg Lys Leu Pro Ile Asn
            660                 665                 670

Arg Pro Ile Asp Trp Lys Val Cys Gln Arg Ile Val Gly Leu Leu Gly
        675                 680                 685

Phe Ala Ala Pro Phe Thr Gln Cys Gly Tyr Pro Ala Leu Met Pro Leu
690                 695                 700

Tyr Ala Cys Ile Gln Ala Lys Gln Ala Phe Thr Phe Ser Pro Thr Tyr
705                 710                 715                 720

Lys Ala Phe Leu Ser Lys Gln Tyr Leu Asn Leu Tyr Pro Val Ala Arg
                725                 730                 735

Gln Arg Pro Gly Leu Cys Gln Val Phe Ala Asp Ala Thr Pro Thr Gly
            740                 745                 750

Trp Gly Leu Ala Ile Gly His Gln Arg Met Arg Gly Thr Phe Val Ala
        755                 760                 765

Pro Leu Pro Ile His Thr Ala His Leu Leu Ala Ala Cys Phe Ala Arg
770                 775                 780

Ser Arg Ser Gly Ala Lys Leu Ile Gly Thr Asp Asn Ser Val Val Leu
785                 790                 795                 800

Ser Arg Lys Tyr Thr Ser Phe Pro Trp Leu Leu Gly Cys Thr Ala Asn
                805                 810                 815

Trp Ile Leu Arg Gly Thr Ser Phe Val Tyr Val Pro Ser Ala Leu Asn
            820                 825                 830

Pro Ala Asp Asp Pro Ser Arg Gly Arg Leu Gly Leu Tyr Arg Pro Leu
        835                 840                 845

Leu Arg Leu Pro Tyr Arg Pro Thr Thr Gly Arg Thr Ser Leu Tyr Ala
850                 855                 860

Val Ser Pro Ser Val Pro Ser His Leu Pro Val Arg Val His Phe Ala
865                 870                 875                 880

Ser Pro Leu His Val Ala Trp Arg Pro Pro
                885                 890

<210> SEQ ID NO 24
<211> LENGTH: 886
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45
```

```
Ser Pro His His Thr Ala Leu Arg Gln Ala Ile Leu Cys Trp Gly Glu
 50                  55                  60

Leu Met Asn Leu Ala Thr Trp Val Gly Ser Asn Leu Glu Asp Pro Ala
 65                  70                  75                  80

Ser Arg Glu Leu Val Val Ser Tyr Val Asn Val Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys Met Pro Leu Ser Tyr Gln His Phe Arg
            180                 185                 190

Lys Leu Leu Leu Leu Asp Asp Glu Ala Gly Pro Leu Glu Glu Glu Leu
            195                 200                 205

Pro Arg Leu Ala Asp Glu Gly Leu Asn Arg Arg Val Ala Glu Asp Leu
210                 215                 220

Asn Leu Gly Asn Leu Asn Val Ser Ile Pro Trp Thr His Lys Val Gly
225                 230                 235                 240

Asn Phe Thr Gly Leu Tyr Ser Ser Thr Val Pro Val Phe Asn Pro Glu
                245                 250                 255

Trp Gln Thr Pro Ser Phe Pro His Ile His Leu Gln Glu Asp Ile Ile
            260                 265                 270

Asn Arg Cys Gln Gln Tyr Val Gly Pro Leu Thr Val Asn Glu Lys Arg
            275                 280                 285

Arg Leu Lys Leu Ile Met Pro Ala Arg Phe Tyr Pro Asn Leu Thr Lys
            290                 295                 300

Tyr Leu Pro Leu Asp Lys Gly Ile Lys Pro Tyr Tyr Pro Glu His Val
305                 310                 315                 320

Val Asn His Tyr Phe Gln Thr Arg His Tyr Leu His Thr Leu Trp Lys
                325                 330                 335

Ala Gly Ile Leu Tyr Lys Arg Glu Ser Thr Arg Ser Ala Ser Phe Cys
            340                 345                 350

Gly Ser Pro Tyr Ser Trp Glu Gln Asp Leu Gln His Gly Cys Trp Trp
            355                 360                 365

Leu Gln Phe Arg Asn Ser Glu Pro Cys Ser Glu Tyr Cys Leu Cys His
            370                 375                 380

Ile Val Asn Leu Ile Glu Asp Trp Gly Pro Cys Thr Glu His Gly Glu
385                 390                 395                 400

His Arg Ile Arg Thr Pro Arg Thr Pro Ala Arg Val Thr Gly Gly Val
            405                 410                 415

Phe Leu Val Asp Lys Asn Pro His Asn Thr Thr Glu Ser Arg Leu Val
            420                 425                 430

Val Asp Phe Ser Gln Phe Ser Arg Gly Asn Thr Arg Val Ser Trp Pro
            435                 440                 445

Lys Phe Ala Val Pro Asn Leu Gln Ser Leu Thr Asn Leu Leu Ser Ser
450                 455                 460

Asn Leu Ser Trp Leu Ser Leu Asp Val Ser Ala Ala Phe Tyr His Leu
```

-continued

```
465                 470                 475                 480
Pro Leu His Pro Ala Ala Met Pro His Leu Leu Val Gly Ser Ser Gly
                485                 490                 495

Leu Ser Arg Tyr Val Ala Arg Leu Ser Ser Asn Ser Arg Ile Ile Asn
                500                 505                 510

Asn Gln His Arg Thr Met Gln Asn Leu His Asp Ser Cys Ser Arg Asn
                515                 520                 525

Leu Tyr Val Ser Leu Met Leu Leu Tyr Lys Thr Tyr Gly Arg Lys Leu
                530                 535                 540

His Leu Tyr Ser His Pro Ile Ile Leu Gly Phe Arg Lys Ile Pro Met
545                 550                 555                 560

Gly Val Gly Leu Ser Pro Phe Leu Leu Ala Gln Phe Thr Ser Ala Ile
                565                 570                 575

Cys Ser Val Val Arg Arg Ala Phe Pro His Cys Leu Ala Phe Ser Tyr
                580                 585                 590

Met His Asp Val Val Leu Gly Ala Lys Ser Val Gln His Leu Glu Ser
                595                 600                 605

Leu Tyr Ala Ala Val Thr Asn Phe Leu Leu Ser Leu Gly Ile His Leu
                610                 615                 620

Asn Pro His Lys Thr Lys Arg Trp Gly Tyr Ser Leu Asn Phe Met Gly
625                 630                 635                 640

Tyr Val Ile Gly Ser Trp Gly Thr Leu Pro Gln Glu His Ile Val Gln
                645                 650                 655

Lys Ile Lys Met Cys Phe Arg Lys Leu Pro Val Asn Arg Pro Ile Asp
                660                 665                 670

Trp Lys Val Cys Gln Arg Ile Val Gly Leu Leu Gly Phe Ala Ala Pro
                675                 680                 685

Phe Thr Gln Cys Gly Tyr Pro Ala Leu Met Pro Leu Tyr Ala Cys Ile
                690                 695                 700

Gln Ala Lys Gln Ala Phe Thr Phe Ser Pro Thr Tyr Lys Ala Phe Leu
705                 710                 715                 720

Ser Lys Gln Tyr Leu His Leu Tyr Pro Val Ala Arg Gln Arg Pro Gly
                725                 730                 735

Leu Cys Gln Val Phe Ala Asp Ala Thr Pro Thr Gly Trp Gly Leu Ala
                740                 745                 750

Ile Gly His Gln Arg Met Arg Gly Ala Phe Val Ser Pro Leu Pro Ile
                755                 760                 765

His Thr Ala His Leu Leu Ala Ala Cys Phe Ala Arg Ser Arg Ser Gly
                770                 775                 780

Ala Lys Leu Ile Gly Thr Asp Asn Ser Val Val Leu Ser Arg Lys Tyr
785                 790                 795                 800

Thr Ser Phe Pro Trp Leu Leu Gly Cys Ala Ala Asn Trp Ile Leu Arg
                805                 810                 815

Gly Thr Ser Phe Val Tyr Val Pro Ser Ala Leu Asn Pro Ala Asp Asp
                820                 825                 830

Pro Ser Arg Gly Arg Leu Gly Leu Tyr Arg Pro Leu Leu Arg Leu Leu
                835                 840                 845

Tyr Arg Pro Thr Thr Gly Arg Thr Ser Leu Tyr Ala Asp Ser Pro Ser
                850                 855                 860

Val Pro Ser His Leu Pro Asp Arg Val His Phe Ala Ser Pro Leu His
865                 870                 875                 880

Val Ala Trp Arg Pro Pro
                885
```

<210> SEQ ID NO 25
<211> LENGTH: 886
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Pro Leu Ser Tyr Gln His Phe Arg
            180                 185                 190

Lys Leu Leu Leu Leu Asp Asp Glu Ala Gly Pro Leu Glu Glu Glu Leu
        195                 200                 205

Pro Arg Leu Ala Asp Glu Asp Leu Asn Arg Arg Val Ala Glu Asp Leu
    210                 215                 220

Asn Leu Gly Asn Leu Asn Val Ser Ile Pro Trp Thr His Lys Val Gly
225                 230                 235                 240

Asn Phe Thr Gly Leu Tyr Ser Ser Thr Val Pro Val Phe Asn Pro Glu
                245                 250                 255

Trp Gln Thr Pro Ser Phe Pro His Ile His Leu Gln Glu Asp Ile Ile
            260                 265                 270

Asn Arg Cys Gln Gln Tyr Val Gly Pro Leu Thr Val Asn Glu Lys Arg
        275                 280                 285

Arg Leu Lys Leu Ile Met Pro Ala Arg Phe Tyr Pro Asn Leu Thr Lys
    290                 295                 300

Tyr Leu Pro Leu Asp Lys Gly Ile Lys Pro Tyr Tyr Pro Glu His Thr
305                 310                 315                 320

Val Asn His Tyr Phe Lys Thr Arg His Tyr Leu His Thr Leu Trp Lys
                325                 330                 335

Ala Gly Ile Leu Tyr Lys Arg Glu Thr Thr Arg Ser Ala Ser Phe Cys
            340                 345                 350

Gly Ser Pro Tyr Ser Trp Glu Gln Glu Leu Gln His Gly Cys Trp Trp

-continued

```
            355                 360                 365
Leu Gln Phe Arg Asn Ser Lys Pro Cys Ser Asp Tyr Cys Leu Ser His
        370                 375                 380
Ile Val Asn Leu Leu Glu Asp Trp Gly Pro Cys Thr Glu His Gly Glu
385                 390                 395                 400
His Asn Ile Arg Ile Pro Arg Thr Pro Ala Arg Val Thr Gly Gly Val
                405                 410                 415
Phe Leu Val Asp Lys Asn Pro His Asn Thr Thr Glu Ser Arg Leu Val
            420                 425                 430
Val Asp Phe Ser Gln Phe Ser Arg Gly Ser Thr His Val Ser Trp Pro
            435                 440                 445
Lys Phe Ala Val Pro Asn Leu Gln Ser Leu Thr Asn Leu Leu Ser Ser
        450                 455                 460
Asn Leu Ser Trp Leu Ser Leu Asp Val Ser Ala Ala Phe Tyr His Leu
465                 470                 475                 480
Pro Leu His Pro Ala Ala Met Pro His Leu Leu Val Gly Ser Ser Gly
                485                 490                 495
Leu Ser Arg Tyr Val Ala Arg Leu Ser Ser Thr Ser Arg Asn Ile Asn
            500                 505                 510
Tyr Gln His Gly Ala Met Gln Asp Leu His Asp Ser Cys Ser Arg Asn
            515                 520                 525
Leu Tyr Val Ser Leu Leu Leu Leu Tyr Lys Thr Phe Gly Arg Lys Leu
        530                 535                 540
His Leu Tyr Ser His Pro Ile Ile Leu Gly Phe Arg Lys Ile Pro Met
545                 550                 555                 560
Gly Val Gly Leu Ser Pro Phe Leu Leu Ala Gln Phe Thr Ser Ala Ile
                565                 570                 575
Cys Ser Val Val Arg Arg Ala Phe Pro His Cys Leu Ala Phe Ser Tyr
            580                 585                 590
Met His Asp Val Val Leu Gly Ala Lys Ser Val Gln His Leu Glu Ser
            595                 600                 605
Leu Phe Thr Ala Val Thr Asn Phe Leu Leu Ser Leu Gly Ile His Leu
        610                 615                 620
Asn Pro Asn Lys Thr Lys Arg Trp Gly Tyr Ser Leu Asn Phe Met Gly
625                 630                 635                 640
Tyr Val Ile Gly Ser Trp Gly Thr Leu Pro Gln Glu His Ile Val Leu
                645                 650                 655
Lys Ile Lys Gln Cys Phe Arg Lys Leu Pro Val Asn Arg Pro Ile Asp
            660                 665                 670
Trp Lys Val Cys Gln Arg Ile Val Gly Leu Leu Gly Phe Ala Ala Pro
            675                 680                 685
Phe Thr Gln Cys Gly Tyr Pro Ala Leu Met Pro Leu Tyr Ala Cys Ile
        690                 695                 700
Gln Ala Lys Gln Ala Phe Thr Phe Ser Pro Thr Tyr Lys Ala Phe Leu
705                 710                 715                 720
Cys Lys Gln Tyr Leu Asn Leu Tyr Pro Val Ala Arg Gln Arg Ser Gly
                725                 730                 735
Leu Cys Gln Val Phe Ala Asp Ala Thr Pro Thr Gly Trp Gly Leu Ala
            740                 745                 750
Val Gly His Gln Arg Met Arg Gly Thr Phe Val Ser Pro Leu Pro Ile
        755                 760                 765
His Thr Ala His Leu Leu Ala Ala Cys Phe Ala Arg Ser Arg Ser Gly
        770                 775                 780
```

Ala Lys Leu Ile Gly Thr Asp Asn Ser Val Val Leu Ser Arg Lys Tyr
785                 790                 795                 800

Thr Ser Phe Pro Trp Leu Leu Gly Cys Ala Ala Asn Trp Ile Leu Arg
            805                 810                 815

Gly Thr Ser Phe Val Tyr Val Pro Ser Ala Leu Asn Pro Ala Asp Asp
            820                 825                 830

Pro Ser Arg Gly Arg Leu Gly Leu Tyr Arg Pro Leu Leu Arg Leu Pro
            835                 840                 845

Phe Arg Pro Thr Thr Gly Arg Thr Ser Leu Tyr Ala Val Ser Pro Ser
850                 855                 860

Val Pro Ser His Leu Pro Val Arg Val His Phe Ala Ser Pro Leu His
865                 870                 875                 880

Val Ala Trp Arg Pro Pro
                885

<210> SEQ ID NO 26
<211> LENGTH: 886
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Pro Leu Ser Tyr Gln His Phe Arg
            180                 185                 190

Arg Leu Leu Leu Leu Asp Asp Glu Ala Gly Pro Leu Glu Glu Glu Leu
        195                 200                 205

Pro Arg Leu Ala Asp Glu Gly Leu Asn Arg Arg Val Ala Glu Asp Leu
    210                 215                 220

Asn Leu Gly Asn Leu Asn Val Ser Ile Pro Trp Thr His Lys Val Gly
225                 230                 235                 240

Asn Phe Thr Gly Leu Tyr Ser Ser Thr Val Pro Val Phe Asn Pro His

```
            245                 250                 255
Trp Lys Thr Pro Ser Phe Pro Asn Ile His Leu His Gln Asp Ile Ile
            260                 265                 270

Lys Lys Cys Glu Gln Phe Val Gly Pro Leu Thr Val Asn Glu Lys Arg
        275                 280                 285

Arg Leu Gln Leu Ile Met Pro Ala Arg Phe Tyr Pro Asn Val Thr Lys
        290                 295                 300

Tyr Leu Pro Leu Asp Lys Gly Ile Lys Pro Tyr Tyr Pro Glu His Leu
305                 310                 315                 320

Val Asn His Tyr Phe Gln Thr Arg His Tyr Leu His Thr Leu Trp Lys
                325                 330                 335

Ala Gly Ile Leu Tyr Lys Arg Glu Thr Thr His Ser Ala Ser Phe Cys
                340                 345                 350

Gly Ser Pro Tyr Ser Trp Glu Gln Glu Leu Gln His Gly Cys Trp Trp
            355                 360                 365

Leu Gln Phe Arg Asn Ser Lys Pro Cys Ser Asp Tyr Cys Leu Ser His
        370                 375                 380

Ile Val Asn Leu Leu Glu Asp Trp Gly Pro Cys Ala Glu His Gly Glu
385                 390                 395                 400

His His Ile Arg Ile Pro Arg Thr Pro Ala Arg Val Thr Gly Gly Val
                405                 410                 415

Phe Leu Val Asp Lys Asn Pro His Asn Thr Ala Glu Ser Arg Leu Val
                420                 425                 430

Val Asp Phe Ser Gln Phe Ser Arg Gly Asn Tyr Arg Val Ser Trp Pro
            435                 440                 445

Lys Phe Ala Val Pro Asn Leu Gln Ser Leu Thr Asn Leu Leu Ser Ser
        450                 455                 460

Asn Leu Ser Trp Leu Ser Leu Asp Val Ser Ala Ala Phe Tyr His Leu
465                 470                 475                 480

Pro Leu His Pro Ala Ala Met Pro His Leu Leu Val Gly Ser Ser Gly
                485                 490                 495

Leu Ser Arg Tyr Val Ala Arg Leu Ser Ser Asn Ser Arg Ile Phe Asn
            500                 505                 510

Tyr Gln His Gly Thr Met Gln Asn Leu His Asp Ser Cys Ser Arg Asn
        515                 520                 525

Leu Tyr Val Ser Leu Met Leu Leu Tyr Gln Thr Phe Gly Arg Lys Leu
530                 535                 540

His Leu Tyr Ser His Pro Ile Ile Leu Gly Phe Arg Lys Ile Pro Met
545                 550                 555                 560

Gly Val Gly Leu Ser Pro Phe Leu Leu Ala Gln Phe Thr Ser Ala Ile
                565                 570                 575

Cys Ser Val Val Arg Arg Ala Phe Pro His Cys Leu Ala Phe Ser Tyr
                580                 585                 590

Met His Asp Val Val Leu Gly Ala Lys Ser Val Gln His Leu Glu Ser
            595                 600                 605

Leu Phe Thr Ala Val Thr Asn Phe Leu Leu Ser Leu Gly Ile His Leu
        610                 615                 620

Asn Pro Asn Lys Thr Lys Arg Trp Gly Tyr Ser Leu His Phe Met Gly
625                 630                 635                 640

Tyr Val Ile Gly Cys Tyr Gly Ser Leu Pro Gln Asp His Ile Ile Gln
                645                 650                 655

Lys Ile Lys Glu Cys Phe Arg Lys Leu Pro Val Asn Arg Pro Ile Asp
                660                 665                 670
```

```
Trp Lys Val Cys Gln Arg Ile Val Gly Leu Leu Gly Phe Ala Ala Pro
        675                 680                 685

Phe Thr Gln Cys Gly Tyr Pro Ala Leu Met Pro Leu Tyr Ala Cys Ile
        690                 695                 700

Gln Ser Lys Gln Ala Phe Thr Phe Ser Pro Thr Tyr Lys Ala Phe Leu
705                 710                 715                 720

Cys Lys Gln Tyr Leu Asn Leu Tyr Pro Val Ala Arg Gln Arg Pro Gly
                725                 730                 735

Leu Cys Gln Val Phe Ala Asp Ala Thr Pro Thr Gly Trp Gly Leu Val
                740                 745                 750

Met Gly His Gln Arg Met Arg Gly Thr Phe Lys Ala Pro Leu Pro Ile
        755                 760                 765

His Thr Ala His Leu Leu Ala Ala Cys Phe Ala Arg Ser Arg Ser Gly
        770                 775                 780

Ala Asn Ile Leu Gly Thr Asp Asn Ser Val Val Leu Ser Arg Lys Tyr
785                 790                 795                 800

Thr Ser Phe Pro Trp Leu Leu Gly Cys Ala Ala Asn Trp Ile Leu Arg
                805                 810                 815

Gly Thr Ser Phe Val Tyr Val Pro Ser Ala Leu Asn Pro Ala Asp Asp
                820                 825                 830

Pro Ser Arg Gly Arg Leu Gly Leu Tyr Arg Pro Leu Leu Arg Leu Pro
        835                 840                 845

Phe Arg Pro Thr Thr Gly Arg Thr Ser Leu Tyr Ala Asp Ser Pro Ser
        850                 855                 860

Val Pro Ser His Leu Pro Asp Arg Val His Phe Ala Ser Pro Leu His
865                 870                 875                 880

Val Ala Trp Arg Pro Pro
                885

<210> SEQ ID NO 27
<211> LENGTH: 2247
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atgcccctga gctaccagca cttcaggaag ctgctgctgc tggatgatga ggctggccct      60
ctggaggagg agctgcccag gctggcagat gagggcctca acaggagagt ggcagaggac     120
ctgaacctgg caacctgaa tgtgagcatc ccctggaccc acaaagtggg gaacttcact      180
ggcctctaca gcagcacagt gccagtgttc aaccctgagt ggcagacccc ctccttcccc     240
cacatccacc tccaggagga catcatcaac agatgtcagc agtatgtggg ccctctgaca     300
gtcaatgaga gaggaggct gaagctgatc atgcctgcca ggttctaccc caacctgacc     360
aagtacctcc cactgacaa gggcatcaag ccatactatc tgagcatgt ggtgaaccac      420 tactttcaga ccaggcacta cctgcacaca ctgtggaagg ctggcatcct gtacaagagg     480
gagagcacca gatcagcctc tttctgtggc tcccctaca gctgggagca ggatctccag     540
catggcagac tggtgttcca gacctccaag aggcatgggg acaagtcctt tgcccccag     600 agccctggca tctgcccag gagcgagctc accacttcc cccctcctc agcagaagc       660 cagtcccagg gacctgtgct gtcctgctgg tggctccagt tcaggaacag tgagccctgc     720
agtgagtact gtctgtgtca cattgtgaac ctgattgagg actggggcc ctgcactgag      780
```

```
catggagagc acaggatcag aaccccagg accccagcca gagtgactgg aggtgtgttc      840
ctggtggaca agaaccccca caacaccaca gagagcagac tggtggtgga cttctcccag      900
ttttcaaggg gcaacaccag agtgtcctgg cccaagtttg cagtgcccaa cctccagagc      960
ctgaccaacc tgctgtcatc aaacctgagc tggctgtccc tggatgtgtc tgctgccttc     1020
taccacctgc ccctgcaccc tgcagccatg cctcacctcc tggtgggcag ctcaggcctg     1080
agcaggtatg tggccaggct gtcaagcaac tccagaatca tcaacaacca gcacaggacc     1140
atgcagaacc tgcatgactc ttgcagcagg aacctgtatg tgagcctgat gctgctgtac     1200
aagacctatg caggaagct gcacctgtac tcccacccca tcatcctggg tttcaggaag     1260
atccccatgg gagtgggact gtccccttc ctgctggccc agttcacctc tgccatctgc     1320
tctgtggtga ggagagcctt ccccactgc ctggccttct cctacatgca tgatgtggtg     1380
ctgggggcca agtcagtgca gcacctggag tctctgtatg ctgcagtcac caacttcctg     1440
ctcagcctgg gcatccacct gaaccccac aagaccaaga ggtgggggcta ctctctgaac     1500 ttcatgggct atgtgatagg cagctggggc accctgccac aggagcacat agtgcagaag     1560
atcaagatgt gcttcaggaa gctgccagtg aacaggccca ttgattggaa ggtgtgccag     1620
aggattgtgg gcctgctggg cttttgcagca cccttcacac agtgtggcta cccagctctg     1680
atgcccctgt atgcctgcat ccaggccaag caggccttca ccttctcccc cacttacaag     1740
gccttcctgt ccaagcagta cctgcacctg taccctgtgg caaggcagag gccaggcctc     1800
tgccaggtgt ttgcagatgc caccccaca ggctggggcc tggccattgg ccaccagagg     1860
atgagagggg cctttgtgag cccactgcca atccacacag cccacctgct ggcagcatgc     1920
tttgccaggt ccaggtctgg tgcaaagctg attggcactg acaacagtgt ggtgctgtcc     1980
agaaagtaca ccagcttccc ctggctgctg ggatgtgctg ccaactggat tctgaggggc     2040
accagctttg tctatgtgcc ctctgcactg aaccctgcag atgacccctc caggggcaga     2100
ctggggctgt acaggccact gctcagactg ctgtacaggc ccaccactgg cagaacctcc     2160
ctgtatgcag acagcccctc agtgccctct cacctgccag acagagtgca ctttgccagc     2220
cccctgcatg ttgcctggag gccccc                                          2247
```

<210> SEQ ID NO 28
<211> LENGTH: 2109
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 28

```
atgcccctga gctaccagca cttcaggaag ctgctgctgc tggatgatga ggctggccct       60
ctggaggagg agctgcccag gctggcagat gagggcctca acaggagagt ggcagaggac      120
ctgaacctgg gcaacctgaa tgtgagcatc cctggacccc acaaagtggg gaacttcact      180
ggcctctaca gcagcacagt gccagtgttc aaccctgagt ggcagacccc ctccttcccc      240
cacatccacc tccaggagga catcatcaac agatgtcagc agtatgtggg ccctctgaca      300
gtcaatgaga agaggaggct gaagctgatc atgcctgcca ggttctaccc caacctgacc      360
aagtacctcc cactggacaa gggcatcaag ccatactatc tgagcatgt ggtgaaccac      420 tactttcaga ccaggcacta cctgcacaca ctgtggaagg ctggcatcct gtacaagagg      480
gagagcacca gatcagcctc tttctgtggc tccccctaca gctgggagca ggatctccag      540
```

```
catggctgct ggtggctcca gttcaggaac agtgagccct gcagtgagta ctgtctgtgt      600
cacattgtga acctgattga ggactggggg ccctgcactg agcatggaga gcacaggatc      660
agaaccccca ggaccccagc cagagtgact ggaggtgtgt tcctggtgga caagaacccc      720
cacaacacca cagagagcag actggtggtg gacttctccc agttttcaag ggcaacaccc      780
agagtgtcct ggcccaagtt tgcagtgccc aacctccaga gcctgaccaa cctgctgtca      840
tcaaacctga gctggctgtc cctggatgtg tctgctgcct ctaccaccct gcccctgcac      900
cctgcagcca tgcctcacct cctggtgggc agctcaggcc tgagcaggta tgtggccagg      960
ctgtcaagca actccagaat catcaacaac cagcacagga ccatgcagaa cctgcatgac     1020
tcttgcagca ggaacctgta tgtgagcctg atgctgctgt acaagaccta tggcaggaag     1080
ctgcacctgt actcccaccc catcatcctg ggtttcagga agatccccat gggagtggga     1140 ctgtcccct tcctgctggc ccagttcacc tctgccatct gctctgtggt gaggagagcc     1200
ttcccccact gcctggcctt ctcctacatg catgatgtgg tgctgggggc caagtcagtg     1260
cagcacctgg agtctctgta tgctgcagtc accaacttcc tgctcagcct gggcatccac     1320
ctgaaccccc acaagaccaa gaggtggggc tactctctga acttcatggg ctatgtgata     1380
ggcagctggg gcaccctgcc acaggagcac atagtgcaga agatcaagat gtgcttcagg     1440
aagctgccag tgaacaggcc cattgattgg aaggtgtgcc agaggattgt gggcctgctg     1500
ggctttgcag caccccttcac acagtgtggc tacccagctc tgatgcccct gtatgcctgc     1560
atccaggcca agcaggcctt caccttctcc cccacttaca aggccttcct gtccaagcag     1620
tacctgcacc tgtaccctgt ggcaaggcag aggccaggcc tctgccaggt gtttgcagat     1680
gccaccccca caggctgggg cctggccatt ggccaccaga ggatgagagg ggcctttgtg     1740
agcccactgc caatccacac agcccaccctg ctggcagcat gctttgccag tccaggtct     1800 ggtgcaaagc tgattggcac tgacaacagt gtggtgctgt ccagaaagta caccagcttc     1860
ccctggctgc tgggatgtgc tgccaactgg attctgaggg gcaccagctt tgtctatgtg     1920
ccctctgcac tgaaccctgc agatgacccc tccaggggca gactgggct gtacaggcca     1980 ctgctcagac tgctgtacag gcccaccact ggcagaacct ccctgtatgc agacagcccc     2040
tcagtgccct ctcacctgcc agacagagtg cactttgcca gcccctgca tgttgcctgg     2100 aggcccccc                                                             2109
```

<210> SEQ ID NO 29
<211> LENGTH: 1602
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
atgtccagca gaagccagtc ccagggacct gtgctgtcct gctggtggct ccagttcagg       60
aacagtgagc cctgcagtga gtactgtctg tgtcacattg tgaacctgat tgaggactgg      120
gggccctgca ctgagcatgg agagcacagg atcagaaccc ccaggacccc agccagagtg      180
actggaggtg tgttcctggt ggacaagaac ccccacaaca ccacagagag cagactggtg      240
gtggacttct cccagttttc aaggggcaac accagagtgt cctggcccaa gtttgcagtg      300
cccaacctcc agagcctgac caacctgctg tcatcaaacc tgagctggct gtccctggat      360
gtgtctgctg ccttctacca cctgcccctg caccctgcag ccatgcctca cctcctggtg      420
```

```
ggcagctcag gcctgagcag gtatgtggcc aggctgtcaa gcaactccag aatcatcaac    480
aaccagcaca ggaccatgca gaacctgcat gactcttgca gcaggaacct gtatgtgagc    540
ctgatgctgc tgtacaagac ctatggcagg aagctgcacc tgtactccca ccccatcatc    600
ctgggtttca ggaagatccc catgggagtg ggactgtccc ccttcctgct ggcccagttc    660
acctctgcca tctgctctgt ggtgaggaga gccttccccc actgcctggc cttctcctac    720
atgcatgatg tggtgctggg ggccaagtca gtgcagcacc tggagtctct gtatgctgca    780
gtcaccaact tcctgctcag cctgggcatc cacctgaacc cccacaagac caagaggtgg    840
ggctactctc tgaacttcat gggctatgtg ataggcagct ggggcaccct gccacaggag    900
cacatagtgc agaagatcaa gatgtgcttc aggaagctgc cagtgaacag gcccattgat    960
tggaaggtgt gccagaggat tgtgggcctg ctgggctttg cagcaccctt cacacagtgt   1020
ggctacccag ctctgatgcc cctgtatgcc tgcatccagg ccaagcaggc cttcaccttc   1080
tccccacttt acaaggcctt cctgtccaag cagtacctgc acctgtaccc tgtggcaagg   1140
cagaggccag gcctctgcca ggtgtttgca gatgccaccc ccacaggctg ggcctggcc    1200 attggccacc agaggatgag aggggccttt gtgagcccac tgccaatcca cacagccac    1260 ctgctggcag catgctttgc caggtccagg tctggtgcaa agctgattgg cactgacaac   1320
agtgtggtgc tgtccagaaa gtacaccagc ttccctggc tgctgggatg tgctgccaac   1380
tggattctga ggggcaccag ctttgtctat gtgccctctg cactgaaccc tgcagatgac   1440
ccctccaggg gcagactggg gctgtacagg ccactgctca gactgctgta caggcccacc   1500
actggcagaa cctccctgta tgcagacagc ccctcagtgc cctctcacct gccagacaga   1560
gtgcactttg ccagccccct gcatgttgcc tggaggcccc cc                      1602

<210> SEQ ID NO 30
<211> LENGTH: 2226
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atgcccctga gctaccaaca cttcaggaga ctgctgctgc tggatgatga ggcaggccct     60
ctggaggagg agctgcccag gctggcagat gagggcctga caggagggt ggctgaggac    120 ctgaacctgg gcaacctgaa tgtgagcatc ccttggaccc acaaagtggg caacttcaca    180
ggcctgtaca gcagcactgt gcctgtgttc aaccccact ggaagacacc cagcttcccc    240
aacatccacc tgcaccagga catcatcaag aagtgtgagc agtttgtggg cccctgaca     300 gtcaatgaga gaggaggct ccagctgatc atgccagcca ggttctaccc caatgtgacc    360
aagtacctcc ccctggacaa gggcatcaag ccttactatc agagcacct ggtgaaccac     420 tacttccaga ccagacacta cctgcacaca ctgtggaagg caggcatcct gtacaagagg    480
gagaccacac acagtgcctc cttctgtggc agccctact cctgggagca ggagctgcaa    540
catggagctg agtccttcca ccagcagtcc agtggcatcc tgagcaggcc cctgtgggc    600 agcgagctgc acaacctgcc ccccaactct gccagatccc agtctgagag gccagtgttc    660
ccttgctggt ggctccagtt caggaacagc aagccctgct cagactactg cctgagccac    720
attgtgaacc tgctggagga ctggggcccc tgtgcagagc atggggagca ccacatcaga    780
atccccagga cccctgccag ggtgacagga ggggtgttcc tggtggacaa gaaccccac     840
```

```
aacactgcag agtccaggct ggtggtggac ttctcccagt tcagcagggg caactacaga      900
gtctcctggc caaagtttgc tgtgcccaac ctccagagcc tgacaaacct gctgagcagc      960
aacctgtcct ggctctccct ggatgtgagt gcagccttct atcacctgcc cctgcaccca     1020
gcagccatgc cacacctgct ggtgggctcc agtggcctgt ccaggtatgt ggccaggctc     1080
tcctccaact ccaggatctt caactatcag catggcacca tgcagaacct gcatgacagc     1140
tgctccagga acctgtatgt gtccctgatg ctgctctatc agacctttgg caggaagctg     1200
cacctgtaca gccaccccat catcctgggg ttcaggaaga tccccatggg tgtgggcctg     1260
tccccctccc tgctggccca gttccaccagt gccatctgct cagtggtgag gagggccttc     1320
ccacactgcc tggccttctc ttacatgcat gatgtggtcc tgggtgccaa gtctgtgcag     1380
cacctggaga gcctgttcac agctgtgaca aactttctcc tgagcctggg catccacctg     1440
aaccccaaca agaccaagag gtggggttat tcactgcact tcatgggcta tgtgattggc     1500
tgctatggct ctctgccaca ggaccacatc atccagaaga tcaaggagtg cttcagaaag     1560
ctgccagtga acaggccaat tgactggaag gtgtgccaga ggattgtggg cctgctgggc     1620
tttgcagccc ccttcaccca gtgtggctac cctgccctga tgccctgta tgcctgcatc      1680 cagagcaagc aggccttcac cttttcccc acttacaagg ccttcctgtg caagcagtac       1740
ctgaacctgt accctgtggc caggcagaga cctgggctgt gccaggtgtt tgcagatgcc     1800 accccacag gatggggact ggtcatggga caccagagga tgaggggcac cttcaaggca       1860 ccctgccca tccacacagc ccacctgctg gctgcctgct tgccaggag caggagtggg       1920 gccaacatcc tgggcacaga caactctgtg gtgctgagca ggaagtacac atccttcccc     1980
tggctgctgg gatgtgcagc caactggatc ctgaggggca ccagctttgt gtatgtgccc     2040
tctgccctca accctgcaga tgatccaagc aggggcaggc tgggactgta caggccactg     2100
ctcagactgc ccttcaggcc caccactggc aggaccagcc tgtatgctga ctccccatct     2160
gtgccctccc acctgcctga cagagtgcac tttgcctccc cactgcatgt ggcctggagg     2220
cccccca                                                                2226
```

<210> SEQ ID NO 31
<211> LENGTH: 2109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
atgcccctga gctaccaaca cttcaggaga ctgctgctgc tggatgatga ggcaggccct       60
ctggaggagg agctgcccag gctggcagat gagggcctga caggagggt ggctgaggac       120 ctgaacctgg gcaacctgaa tgtgagcatc ccttggaccc acaaagtggg caacttcaca      180
ggcctgtaca gcagcactgt gcctgtgttc aaccccacact ggaagacacc cagcttcccc    240
aacatccacc tgcaccagga catcatcaag aagtgtgagc agtttgtggg ccccctgaca      300
gtcaatgaga agaggaggct ccagctgatc atgccagcca ggttctaccc caatgtgacc      360
aagtacctcc ccctggacaa gggcatcaag ccttactatc agagcaccct ggtgaaccac      420
tacttccaga ccagacacta cctgcacaca ctgtggaagg caggcatcct gtacaagagg      480
gagaccacac acagtgcctc cttctgtggc agccccact cctgggagca ggagctgcaa       540
catggatgct ggtggctcca gttcaggaac agcaagccct gctcagacta ctgcctgagc      600
```

| | |
|---|---:|
| cacattgtga acctgctgga ggactggggc ccctgtgcag agcatgggga gcaccacatc | 660 |
| agaatcccca ggacccctgc cagggtgaca ggagggtgt tcctggtgga caagaacccc | 720 |
| cacaacactg cagagtccag gctggtggtg gacttctccc agttcagcag gggcaactac | 780 |
| agagtctcct ggccaaagtt tgctgtgccc aacctccaga gcctgacaaa cctgctgagc | 840 |
| agcaacctgt cctggctctc cctggatgtg agtgcagcct ctatcacct gcccctgcac | 900 |
| ccagcagcca tgccacacct gctggtgggc tccagtggcc tgtccaggta tgtggccagg | 960 |
| ctctcctcca actccaggat cttcaactat cagcatggca ccatgcagaa cctgcatgac | 1020 |
| agctgctcca ggaacctgta tgtgtccctg atgctgctct atcagacctt ggcaggaag | 1080 |
| ctgcacctgt acagccaccc catcatcctg gggttcagga agatccccat gggtgtgggc | 1140 |
| ctgtccccct tcctgctggc ccagttcacc agtgccatct gctcagtggt gaggagggcc | 1200 |
| ttcccacact gcctggcctt ctcttacatg catgatgtgg tcctgggtgc caagtctgtg | 1260 |
| cagcacctgg agagcctgtt cacagctgtg acaaactttc tcctgagcct gggcatccac | 1320 |
| ctgaacccca caagaccaa gaggtggggt tattcactgc acttcatggg ctatgtgatt | 1380 |
| ggctgctatg gctctctgcc acaggaccac atcatccaga agatcaagga gtgcttcaga | 1440 |
| aagctgccag tgaacaggcc aattgactgg aaggtgtgcc agaggattgt gggcctgctg | 1500 |
| ggctttgcag ccccccttcac ccagtgtggc taccctgccc tgatgcccct gtatgcctgc | 1560 |
| atccagagca agcaggcctt cacctttttcc cccacttaca aggccttcct gtgcaagcag | 1620 |
| tacctgaacc tgtaccctgt ggccaggcag agacctgggc tgtgccaggt gtttgcagat | 1680 |
| gccaccccca caggatgggg actggtcatg ggacaccaga ggatgagggg caccttcaag | 1740 |
| gcaccctgc ccatccacac agcccacctg ctggctgcct gctttgccag gagcaggagt | 1800 |
| ggggccaaca tcctgggcac agacaactct gtggtgctga gcaggaagta cacatccttc | 1860 |
| ccctggctgc tgggatgtgc agccaactgg atcctgaggg gcaccagctt tgtgtatgtg | 1920 |
| ccctctgccc tcaaccctgc agatgatcca agcaggggca ggctgggact gtacaggcca | 1980 |
| ctgctcagac tgcccttcag gcccaccact ggcaggacca gcctgtatgc tgactcccca | 2040 |
| tctgtgccct cccacctgcc tgacagagtg cactttgcct ccccactgca tgtggcctgg | 2100 |
| aggcccccca | 2109 |

<210> SEQ ID NO 32
<211> LENGTH: 1602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

| | |
|---|---:|
| atgtctgcca gatcccagtc tgagaggcca gtgttccctt gctggtggct ccagttcagg | 60 |
| aacagcaagc cctgctcaga ctactgcctg agccacattg tgaacctgct ggaggactgg | 120 |
| ggcccctgtg cagagcatgg ggagcaccac atcagaatcc ccaggacccc tgccagggtg | 180 |
| acaggagggt gttcctggt ggacaagaac cccacaacaa ctgcagagtc caggctggtg | 240 |
| gtggacttct cccagttcag cagggcaac tacagagtct cctggccaaa gtttgctgtg | 300 |
| cccaacctcc agagcctgac aaacctgctg agcagcaacc tgtcctggct ctccctggat | 360 |
| gtgagtgcag ccttctatca cctgcccctg cacccagcag ccatgccaca cctgctggtg | 420 |
| ggctccagtg gcctgtccag gtatgtggcc aggctctcct ccaactccag gatcttcaac | 480 |

| | |
|---|---|
| tatcagcatg gcaccatgca gaacctgcat gacagctgct ccaggaacct gtatgtgtcc | 540 |
| ctgatgctgc tctatcagac ctttggcagg aagctgcacc tgtacagcca ccccatcatc | 600 |
| ctggggttca ggaagatccc catgggtgtg ggcctgtccc ccttcctgct ggcccagttc | 660 |
| accagtgcca tctgctcagt ggtgaggagg gccttccac actgcctggc cttctcttac | 720 |
| atgcatgatg tggtcctggg tgccaagtct gtgcagcacc tggagagcct gttcacagct | 780 |
| gtgacaaact ttctcctgag cctgggcatc cacctgaacc caacaagac caagaggtgg | 840 |
| ggttattcac tgcacttcat gggctatgtg attggctgct atggctctct gccacaggac | 900 |
| cacatcatcc agaagatcaa ggagtgcttc agaaagctgc cagtgaacag gccaattgac | 960 |
| tggaaggtgt gccagaggat tgtgggcctg ctgggctttg cagccccctt cacccagtgt | 1020 |
| ggctaccctg ccctgatgcc cctgtatgcc tgcatccaga gcaagcaggc cttcaccttt | 1080 |
| tcccccactt acaaggcctt cctgtgcaag cagtacctga acctgtaccc tgtggccagg | 1140 |
| cagagacctg ggctgtgcca ggtgtttgca gatgccaccc cacaggatg gggactggtc | 1200 |
| atgggacacc agaggatgag gggcaccttc aaggcacccc tgcccatcca cacagcccac | 1260 |
| ctgctggctg cctgctttgc caggagcagg agtggggcca acatcctggg cacagacaac | 1320 |
| tctgtggtgc tgagcaggaa gtacacatcc ttcccctggc tgctgggatg tgcagccaac | 1380 |
| tggatcctga ggggcaccag ctttgtgtat gtgccctctg ccctcaaccc tgcagatgat | 1440 |
| ccaagcaggg gcaggctggg actgtacagg ccactgctca gactgccctt caggcccacc | 1500 |
| actggcagga ccagcctgta tgctgactcc ccatctgtgc cctcccacct gcctgacaga | 1560 |
| gtgcactttg cctccccact gcatgtggcc tggaggcccc ca | 1602 |

<210> SEQ ID NO 33
<211> LENGTH: 1227
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 33

| | |
|---|---|
| atggacattg accctacaa ggagtttggg gccagtgtgg agctgctgtc ttttctgcca | 60 |
| tctgacttct tccccagtgt gagggacctg ctggacactg cctcagcact gtacagagag | 120 |
| gccctggaga gcccagagca ctgctccccc caccacacag ccctgaggca ggccatcctc | 180 |
| tgctgggggg agctgatgaa cctggccacc tgggtgggct ccaacctgga ggaccctgcc | 240 |
| tcaagggagc tggtggtcag ctatgtcaat gtgaacatgg gcctcaagat caggcagctg | 300 |
| ctgtggttcc acatctcctg cctgaccttt ggcaggagga cagtcctgga gtacctggtg | 360 |
| agctttgggg tgtggatcag gacccccct gcctacaggc ccccaatgc tcccatcctg | 420 |
| tccaccctgc cagagaccac tgtggtcagg agaaggggca ggtcccccag gaggagaacc | 480 |
| ccctctccca ggaggaggag aagccagtcc ccaggagga ggaggagcca gagcagagag | 540 |
| tctcagtgca tggagagcac cacatcaggc ttcctgggcc cctgctggt gctccaggca | 600 |
| ggcttctttc tgctgaccag gattctgacc atccccagt ccctgacag ctggtggacc | 660 |
| tccctgaatt ttctgggggg ggcccctacc tgtcctggcc agaactctca gtctcccacc | 720 |
| tcgaatcact caccaaccag ctgtcccccc atctgtcctg gctacaggtg gatgtgcctg | 780 |
| aggagattca tcatcttcct gtgcatcctg ctgctgtgcc tgatcttct gctggtgctg | 840 |
| ctggactacc agggcatgct gccagtgtgc cctctcatcc caggcagctc caccacatcc | 900 |

```
acaggacctt gcaagacatg caccacacca gcccagggca ccagcatgtt cccctcctgc      960
tgttgcacca agccaacaga tggcaactgc acatgcattc ccatcccctc cagctgggcc     1020
tttgccaggt ttctgtggga gtgggccagt gtgagatttt cctggctgtc tcttctggtg     1080
ccctttgtgc agtggtttgt gggcctgtcc cctacagtgt ggctgagtgt catctggatg     1140
atgtggtact ggggcccctc cctgtacaac atcctctctc cctttctgcc tctgctgcca     1200
atcttctttt gcctgtgggt gtacatc                                         1227

<210> SEQ ID NO 34
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atggacattg ccccctacaa ggagtttggg gccagtgtgg agctgctgtc ttttctgcca       60
tctgacttct tccccagtgt gagggacctg ctggacactg cctcagcact gtacagagag      120
gccctggaga gccagagca ctgctccccc caccacacag ccctgaggca ggccatcctc      180
tgctgggggg agctgatgaa cctggccacc tgggtgggct ccaacctgga ggaccctgcc     240
tcaagggagc tggtggtcag ctatgtcaat gtgaacatgg cctcaagat caggcagctg      300 ctgtggttcc acatctcctg cctgaccttt ggcagggaga cagtcctgga gtacctggtg      360
agctttgggg tgtggatcag gaccccccct gcctacaggc cccccaatgc tcccatcctg     420
tccaccctgc cagagaccac tgtggtcagg agaaggggca ggtcccccag gaggagaacc     480
ccctctccca ggaggaggag aagccagtcc cccaggagga ggaggagcca gagcagagag     540
tctcagtgcg gcagtggggc aaccaacttc agcctcctga acaggcagg ggatgtggag      600 gaaaacccag gccccgagag caccacatca ggcttcctgg gcccctgct ggtgctccag      660 gcaggcttct ttctgctgac caggattctg accatccccc agtccctgga cagctggtgg     720
acctccctga ttttctgggg gggggcccct acctgtcctg gccagaactc tcagtctccc     780
acctcgaatc actcaccaac cagctgtccc cccatctgtc ctggctacag gtggatgtgc     840
ctgaggagat tcatcatctt cctgtgcatc ctgctgctgt gcctgatctt tctgctggtg     900
ctgctggact accagggcat gctgccagtg tgccctctca tccaggcag ctccaccaca     960 tccacaggac cttgcaagac atgcaccaca ccagcccagg gcaccagcat gttcccctcc    1020
tgctgttgca ccaagccaac agatggcaac tgcacatgca ttcccatccc ctccagctgg    1080
gcctttgcca ggtttctgtg ggagtgggcc agtgtgagat tttcctggct gtctcttctg    1140 gtgcccttttg tgcagtggtt tgtgggcctg tcccctacag tgtggctgag tgtcatctgg    1200
atgatgtggt actggggccc ctccctgtac aacatcctct ccctttct gcctctgctg      1260 ccaatcttct tttgcctgtg ggtgtacatc                                     1290

<210> SEQ ID NO 35
<211> LENGTH: 1227
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
```

| | |
|---|---:|
| atggacattg accoctacaa ggagtttggg gccagtgtgg agctgctctc cttcctgccc | 60 |
| tcagacttct ttcccagtgt gagggacctg cttgacacag cctctgccct ctacagagag | 120 |
| gccctggaga gcccagagca ttgctccccc caccacacag cactgaggca ggccatcctg | 180 |
| tgctggggggg agctcatgaa cctggccacc tgggtgggtg tcaacctgga ggacccagct | 240 |
| tccagggatc tggtggtcag ctatgtgaac acaaacatgg cctcaagtt caggcagctg | 300 |
| ctctggttcc acatctcctg cctgaccttt ggcagggaga ctgtgctgga gtacctggtg | 360 |
| agctttggag tgtggatcag gaccccacct gcctacaggc cccccaatgc ccccatcctg | 420 |
| tccaccctgc ctgagaccac agtggtgagg aggaggggga ggtcccccag aaggaggacc | 480 |
| ccttctccca ggaggaggag gagtcagtct cccaggagga ggaggagcca gagcagagag | 540 |
| tcccagtgta tggagaacat cacctctggc tttctgggac cctgctggt gctccaggca | 600 |
| ggcttttttcc tgctgaccag gatcctgacc atccctcaga gcctggactc ctggtggaca | 660 |
| tctctgaatt ttcttggggg caccactgtg tgcctgggac agaactccca gtctcccacc | 720 |
| tccaaccaca gcccaacatc ctgtcccccc atctgcccag gctacaggtg gatgtgcctg | 780 |
| aggaggttca tcatcttcct gttcatcctg ctgctgtgcc tgatcttct gctggtgctc | 840 |
| ctggactatc agggcatgct gccagtgtgc ccactgatcc caggcagctc caccacaagc | 900 |
| acaggacctt gcaggacatg caccacacct gcccagggca cttccatgta cccatcttgc | 960 |
| tgttgcacca agccatctga tggcaattgc acctgcatcc ccatcccctc aagctgggcc | 1020 |
| tttggcaagt tcctgtggga gtgggcaagt gccagattct cttggctgag cctgctggtc | 1080 |
| ccttttgtgc agtggtttgt gggcctgagc cccactgtgt ggctgtctgt gatctggatg | 1140 |
| atgtggtact ggggcccctc cctgtattca atcctgagcc cttttctgcc actgctgccc | 1200 |
| atcttctttt gtctgtgggt gtacatc | 1227 |

<210> SEQ ID NO 36
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

| | |
|---|---:|
| atggacattg accoctacaa ggagtttggg gccagtgtgg agctgctctc cttcctgccc | 60 |
| tcagacttct ttcccagtgt gagggacctg cttgacacag cctctgccct ctacagagag | 120 |
| gccctggaga gcccagagca ttgctccccc caccacacag cactgaggca ggccatcctg | 180 |
| tgctggggggg agctcatgaa cctggccacc tgggtgggtg tcaacctgga ggacccagct | 240 |
| tccagggatc tggtggtcag ctatgtgaac acaaacatgg cctcaagtt caggcagctg | 300 |
| ctctggttcc acatctcctg cctgaccttt ggcagggaga ctgtgctgga gtacctggtg | 360 |
| agctttggag tgtggatcag gaccccacct gcctacaggc cccccaatgc ccccatcctg | 420 |
| tccaccctgc ctgagaccac agtggtgagg aggaggggga ggtcccccag aaggaggacc | 480 |
| ccttctccca ggaggaggag gagtcagtct cccaggagga ggaggagcca gagcagagag | 540 |
| tcccagtgtg gcagtggggc aaccaacttc agctcctga acaggcagg ggatgtggag | 600 |
| gaaaacccag gccccgagaa catcacctct ggctttctgg accctgct ggtgctccag | 660 |
| gcaggctttt tcctgctgac caggatcctg accatccctc agagcctgga ctcctggtgg | 720 |
| acatctctga ttttcttgg gggcaccact gtgtgcctgg gacagaactc ccagtctccc | 780 |

```
acctccaacc acagcccaac atcctgtccc cccatctgcc caggctacag gtggatgtgc    840
ctgaggaggt tcatcatctt cctgttcatc ctgctgctgt gcctgatctt tctgctggtg    900
ctcctggact atcagggcat gctgccagtg tgcccactga tcccaggcag ctccaccaca    960
agcacaggac cttgcaggac atgcaccaca cctgcccagg gcacttccat gtacccatct   1020
tgctgttgca ccaagccatc tgatggcaat tgcacctgca tccccatccc ctcaagctgg   1080
gcctttggca agttcctgtg ggagtgggca agtgccagat tctcttggct gagcctgctg   1140
gtcccttttg tgcagtggtt tgtgggcctg agccccactg tgtggctgtc tgtgatctgg   1200
atgatgtggt actggggccc ctccctgtat caatcctga gccctttcct gccactgctg    1260
cccatcttct tttgtctgtg ggtgtacatc                                    1290
```

<210> SEQ ID NO 37
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
atggacattg acccctacaa ggagtttggg gccagtgtgg agctgctgtc ttttctgcca     60
tctgacttct tccccagtgt gagggacctg ctggacactg cctcagcact gtacagagag    120
gccctggaga gccagagca ctgctccccc caccacacag ccctgaggca ggccatcctc     180
tgctgggggg agctgatgaa cctggccacc tgggtgggcg tcaacctgga ggaccctgcc    240
tcaagggacc tggtggtcag ctatgtcaat acgaacatgg gcctcaagtt caggcagctg    300
ctgtggttcc acatctcctg cctgaccttt ggcaggagaa cagtcctgga gtacctggtg    360
agctttgggg tgtggatcag gacccccccct gcctacaggc cccccaatgc tcccatcctg    420
tccaccctgc cagagaccac tgtggtcagg agaagggggca ggtcccccag gaggagaacc    480
ccctctccca ggaggaggag aagccagtcc cccaggagga ggaggagcca gagcagagag    540
tctcagtgcg gcagtggggc aaccaacttc agcctcctga acaggcagg ggatgtggag     600 gaaaacccag gccccgagaa catcacatca ggcttcctgg gccccctgct ggtgctccag    660
gcaggcttct ttctgctgac caggattctg accatccccc agtccctgga cagctggtgg    720 acctcctga tttttctggg ggggaccact gtctgtcttg gccagaactc tcagtctccc    780
acctcgaatc actcaccaac cagctgtccc ccatctgtc ctggctacag gtggatgtgc     840
ctgaggagat tcatcatctt cctgttcatc ctgctgctgt gcctgatctt tctgctggtg    900
ctgctggact accagggcat gctgccagtg tgcctctca tcccaggcag ctccaccaca    960
tccacaggac cttgcaggac atgcaccaca ccagcccagg gcaccagcat gtaccctcc   1020 tgctgttgca ccaagccatc agatggcaac tgcacatgca ttcccatccc ctccagctgg   1080
gcctttggca agtttctgtg ggagtgggcc agtgcgagat tttcctggct gtctcttctg   1140
gtgccctttg tgcagtggtt tgtgggcctg tcccctacag tgtggctgag tgtcatctgg   1200
atgatgtggt actggggccc ctccctgtac agcatcctct ctccctttct gcctctgctg    1260
ccaatcttct tttgcctgtg ggtgtacatc                                   1290
```

<210> SEQ ID NO 38
<211> LENGTH: 409
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 38

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Glu Ser Thr Thr Ser Gly Phe Leu
            180                 185                 190

Gly Pro Leu Leu Val Leu Gln Ala Gly Phe Phe Leu Leu Thr Arg Ile
        195                 200                 205

Leu Thr Ile Pro Gln Ser Leu Asp Ser Trp Trp Thr Ser Leu Asn Phe
    210                 215                 220

Leu Gly Gly Ala Pro Thr Cys Pro Gly Gln Asn Ser Gln Ser Pro Thr
225                 230                 235                 240

Ser Asn His Ser Pro Thr Ser Cys Pro Pro Ile Cys Pro Gly Tyr Arg
                245                 250                 255

Trp Met Cys Leu Arg Arg Phe Ile Ile Phe Leu Cys Ile Leu Leu Leu
            260                 265                 270

Cys Leu Ile Phe Leu Leu Val Leu Leu Asp Tyr Gln Gly Met Leu Pro
        275                 280                 285

Val Cys Pro Leu Ile Pro Gly Ser Ser Thr Thr Ser Thr Gly Pro Cys
    290                 295                 300

Lys Thr Cys Thr Thr Pro Ala Gln Gly Thr Ser Met Phe Pro Ser Cys
305                 310                 315                 320

Cys Cys Thr Lys Pro Thr Asp Gly Asn Cys Thr Cys Ile Pro Ile Pro
                325                 330                 335

Ser Ser Trp Ala Phe Ala Arg Phe Leu Trp Glu Trp Ala Ser Val Arg
            340                 345                 350

Phe Ser Trp Leu Ser Leu Leu Val Pro Phe Val Gln Trp Phe Val Gly
        355                 360                 365

Leu Ser Pro Thr Val Trp Leu Ser Val Ile Trp Met Met Trp Tyr Trp
    370                 375                 380

Gly Pro Ser Leu Tyr Asn Ile Leu Ser Pro Phe Leu Pro Leu Leu Pro
385                 390                 395                 400
```

```
Ile Phe Phe Cys Leu Trp Val Tyr Ile
                405

<210> SEQ ID NO 39
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Gly Ser Gly Ala Thr Asn Phe Ser Leu
                180                 185                 190

Leu Lys Gln Ala Gly Asp Val Glu Glu Asn Pro Gly Pro Glu Ser Thr
            195                 200                 205

Thr Ser Gly Phe Leu Gly Pro Leu Leu Val Leu Gln Ala Gly Phe Phe
        210                 215                 220

Leu Leu Thr Arg Ile Leu Thr Ile Pro Gln Ser Leu Asp Ser Trp Trp
225                 230                 235                 240

Thr Ser Leu Asn Phe Leu Gly Gly Ala Pro Thr Cys Pro Gly Gln Asn
                245                 250                 255

Ser Gln Ser Pro Thr Ser Asn His Ser Pro Thr Ser Cys Pro Pro Ile
                260                 265                 270

Cys Pro Gly Tyr Arg Trp Met Cys Leu Arg Arg Phe Ile Ile Phe Leu
            275                 280                 285

Cys Ile Leu Leu Leu Cys Leu Ile Phe Leu Leu Val Leu Leu Asp Tyr
        290                 295                 300

Gln Gly Met Leu Pro Val Cys Pro Leu Ile Pro Gly Ser Ser Thr Thr
305                 310                 315                 320

Ser Thr Gly Pro Cys Lys Thr Cys Thr Thr Pro Ala Gln Gly Thr Ser
                325                 330                 335

Met Phe Pro Ser Cys Cys Cys Thr Lys Pro Thr Asp Gly Asn Cys Thr
```

```
            340                 345                 350
Cys Ile Pro Ile Pro Ser Ser Trp Ala Phe Ala Arg Phe Leu Trp Glu
            355                 360                 365

Trp Ala Ser Val Arg Phe Ser Trp Leu Ser Leu Leu Val Pro Phe Val
370                 375                 380

Gln Trp Phe Val Gly Leu Ser Pro Thr Val Trp Leu Ser Val Ile Trp
385                 390                 395                 400

Met Met Trp Tyr Trp Gly Pro Ser Leu Tyr Asn Ile Leu Ser Pro Phe
                405                 410                 415

Leu Pro Leu Leu Pro Ile Phe Phe Cys Leu Trp Val Tyr Ile
                420                 425                 430

<210> SEQ ID NO 40
<211> LENGTH: 409
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Met Glu Asn Ile Thr Ser Gly Phe Leu
            180                 185                 190

Gly Pro Leu Leu Val Leu Gln Ala Gly Phe Phe Leu Leu Thr Arg Ile
        195                 200                 205

Leu Thr Ile Pro Gln Ser Leu Asp Ser Trp Trp Thr Ser Leu Asn Phe
    210                 215                 220

Leu Gly Gly Thr Thr Val Cys Leu Gly Gln Asn Ser Gln Ser Pro Thr
225                 230                 235                 240

Ser Asn His Ser Pro Thr Ser Cys Pro Pro Ile Cys Pro Gly Tyr Arg
                245                 250                 255

Trp Met Cys Leu Arg Arg Phe Ile Ile Phe Leu Phe Ile Leu Leu Leu
            260                 265                 270
```

```
Cys Leu Ile Phe Leu Leu Val Leu Leu Asp Tyr Gln Gly Met Leu Pro
            275                 280                 285

Val Cys Pro Leu Ile Pro Gly Ser Ser Thr Thr Ser Thr Gly Pro Cys
290                 295                 300

Arg Thr Cys Thr Thr Pro Ala Gln Gly Thr Ser Met Tyr Pro Ser Cys
305                 310                 315                 320

Cys Cys Thr Lys Pro Ser Asp Gly Asn Cys Thr Cys Ile Pro Ile Pro
                325                 330                 335

Ser Ser Trp Ala Phe Gly Lys Phe Leu Trp Glu Trp Ala Ser Ala Arg
            340                 345                 350

Phe Ser Trp Leu Ser Leu Leu Val Pro Phe Val Gln Trp Phe Val Gly
            355                 360                 365

Leu Ser Pro Thr Val Trp Leu Ser Val Ile Trp Met Met Trp Tyr Trp
            370                 375                 380

Gly Pro Ser Leu Tyr Ser Ile Leu Ser Pro Phe Leu Pro Leu Leu Pro
385                 390                 395                 400

Ile Phe Phe Cys Leu Trp Val Tyr Ile
                405

<210> SEQ ID NO 41
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Gly Ser Gly Ala Thr Asn Phe Ser Leu
            180                 185                 190

Leu Lys Gln Ala Gly Asp Val Glu Glu Asn Pro Gly Pro Glu Asn Ile
        195                 200                 205

Thr Ser Gly Phe Leu Gly Pro Leu Leu Val Leu Gln Ala Gly Phe Phe
    210                 215                 220
```

```
Leu Leu Thr Arg Ile Leu Thr Ile Pro Gln Ser Leu Asp Ser Trp Trp
225                 230                 235                 240

Thr Ser Leu Asn Phe Leu Gly Gly Thr Thr Val Cys Leu Gly Gln Asn
                245                 250                 255

Ser Gln Ser Pro Thr Ser Asn His Ser Pro Thr Ser Cys Pro Pro Ile
            260                 265                 270

Cys Pro Gly Tyr Arg Trp Met Cys Leu Arg Arg Phe Ile Ile Phe Leu
        275                 280                 285

Phe Ile Leu Leu Leu Cys Leu Ile Phe Leu Leu Val Leu Leu Asp Tyr
    290                 295                 300

Gln Gly Met Leu Pro Val Cys Pro Leu Ile Pro Gly Ser Ser Thr Thr
305                 310                 315                 320

Ser Thr Gly Pro Cys Arg Thr Cys Thr Thr Pro Ala Gln Gly Thr Ser
                325                 330                 335

Met Tyr Pro Ser Cys Cys Cys Thr Lys Pro Ser Asp Gly Asn Cys Thr
            340                 345                 350

Cys Ile Pro Ile Pro Ser Ser Trp Ala Phe Gly Lys Phe Leu Trp Glu
        355                 360                 365

Trp Ala Ser Ala Arg Phe Ser Trp Leu Ser Leu Leu Val Pro Phe Val
    370                 375                 380

Gln Trp Phe Val Gly Leu Ser Pro Thr Val Trp Leu Ser Val Ile Trp
385                 390                 395                 400

Met Met Trp Tyr Trp Gly Pro Ser Leu Tyr Ser Ile Leu Ser Pro Phe
                405                 410                 415

Leu Pro Leu Leu Pro Ile Phe Phe Cys Leu Trp Val Tyr Ile
            420                 425                 430

<210> SEQ ID NO 42
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Cys Ile Arg Ser Gln Phe Lys Gln Ser Arg Leu Gly Leu Gln Pro His
1               5                   10                  15

Gln Gly Pro Leu Ala Thr Ser Gln Ser Gly Arg Ser Gly Ser Ile Arg
            20                  25                  30

Ala Arg Val His Ser Pro Thr Arg Arg Cys Phe Gly Val Glu Pro Ser
        35                  40                  45

Gly Ser Gly His Ile Gly His Ser Ala Ser Ser Ser Ser Cys Leu
    50                  55                  60

His Gln Ser Ala Val Arg Lys Ala Ala Tyr Ser His Leu Ser Thr Ser
65                  70                  75                  80

Lys Arg Gln Ser Ser Ser Gly His Ala Val
            85                  90

<210> SEQ ID NO 43
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43
```

```
Ser Val Gly Pro Cys Ile Gln Asn Gln Leu Arg Lys Ser Arg Leu Gly
1               5                   10                  15

Pro Gln Pro Ala Gln Gly Gln Leu Ala Gly Arg Gln Gln Gly Gly Ser
            20                  25                  30

Gly Ser Ile Arg Ala Arg Val His Pro Ser Pro Trp Gly Thr Val Gly
        35                  40                  45

Val Glu Pro Ser Gly Ser Gly His Ile His Asn Cys Ala Ser Asn Ser
50                  55                  60

Ser Ser Cys Leu His Gln Ser Ala Val Arg Lys Ala Ala Tyr Ser His
65                  70                  75                  80

Ile Ser Thr Ser Lys Gly His Ser Ser Gly His Ala Val
                85                  90
```

```
<210> SEQ ID NO 44
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44
```

```
Cys Ile Arg Ser Gln Leu Lys Gln Ser Arg Leu Gly Leu Gln Pro Gln
1               5                   10                  15

Gln Gly Ser Leu Ala Arg Ser Lys Ser Gly Arg Ser Gly Ser Ile Arg
            20                  25                  30

Ala Arg Val His Pro Thr Thr Arg Gln Ser Phe Gly Val Glu Pro Ser
        35                  40                  45

Gly Ser Gly His Ile Asp Asn Ser Ala Ser Ser Ala Ser Ser Cys Leu
50                  55                  60

His Gln Ser Ala Val Arg Lys Thr Ala Tyr Ser His Leu Ser Thr Ser
65                  70                  75                  80

Lys Arg Gln Ser Ser Ser Gly His Ala Val
                85                  90
```

```
<210> SEQ ID NO 45
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

```
Ser Leu Gln Ser Lys His Arg Lys Ser Arg Leu Gly Leu Gln Ser Gln
1               5                   10                  15

Gln Gly His Leu Ala Arg Arg Gln Gln Gly Arg Gly Trp Ser Ile Arg
            20                  25                  30

Ala Gly Ile His Pro Thr Ala Arg Arg Pro Phe Gly Val Glu Pro Ser
        35                  40                  45

Gly Ser Gly His Thr Ala Asn Leu Ala Ser Lys Ser Ala Ser Cys Leu
50                  55                  60

Tyr Gln Ser Ala Val Arg Lys Ala Ala Tyr Pro Val Val Ser Thr Phe
65                  70                  75                  80

Lys Lys His Ser Ser Ser Gly His Ala Val
                85                  90
```

```
<210> SEQ ID NO 46
```

```
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Arg Leu Val Ile Lys Thr Ser Gln Arg His Gly Asp Glu Pro Phe Cys
1               5                   10                  15

Ser Gln Pro Ser Gly Ile Leu Ser Arg Ser Val Gly Pro Cys Ile
            20                  25                  30

Arg Ser Gln Phe Lys Gln Ser Arg Leu Gly Leu Gln Pro His Gln Gly
        35                  40                  45

Pro Leu Ala Thr Ser Gln Ser Gly Arg Ser Gly Ser Ile Arg Ala Arg
    50                  55                  60

Val His Ser Pro Thr Arg Arg Cys Phe Gly Val Glu Pro Ser Gly Ser
65                  70                  75                  80

Gly His Ile Gly His Ser Ala Ser Ser Ser Ser Cys Leu His Gln
                85                  90                  95

Ser Ala Val Arg Lys Ala Ala Tyr Ser His Leu Ser Thr Ser Lys Arg
                100                 105                 110

Gln Ser Ser Ser Gly His Ala Val Glu Phe His Ser Phe Pro Pro Ser
            115                 120                 125

Ser Ala Arg Ser Gln Ser Gln Gly Pro Val Phe Ser
        130                 135                 140

<210> SEQ ID NO 47
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Arg Leu Val Phe Gln Thr Ser Lys Arg His Gly Asp Lys Ser Phe Cys
1               5                   10                  15

Pro Gln Ser Pro Gly Ile Leu Pro Arg Ser Ser Val Gly Pro Cys Ile
            20                  25                  30

Gln Asn Gln Leu Arg Lys Ser Arg Leu Gly Pro Gln Pro Ala Gln Gly
        35                  40                  45

Gln Leu Ala Gly Arg Gln Gln Gly Gly Ser Gly Ser Ile Arg Ala Arg
    50                  55                  60

Val His Pro Ser Pro Trp Gly Thr Val Gly Val Glu Pro Ser Gly Ser
65                  70                  75                  80

Gly His Ile His Asn Cys Ala Ser Asn Ser Ser Cys Leu His Gln
                85                  90                  95

Ser Ala Val Arg Lys Ala Ala Tyr Ser His Ile Ser Thr Ser Lys Gly
                100                 105                 110

His Ser Ser Ser Gly His Ala Val Glu Leu His His Phe Pro Pro Ser
            115                 120                 125

Ser Ser Arg Ser Gln Ser Gln Gly Pro Val Leu Ser
        130                 135                 140

<210> SEQ ID NO 48
<211> LENGTH: 140
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 48

Arg Leu Val Phe Gln Thr Ser Thr Arg His Gly Asp Glu Ser Phe Cys
1               5                   10                  15

Ser Gln Ser Ser Gly Ile Leu Ser Arg Ser Pro Val Gly Pro Cys Ile
            20                  25                  30

Arg Ser Gln Leu Lys Gln Ser Arg Leu Gly Leu Gln Pro Gln Gln Gly
        35                  40                  45

Ser Leu Ala Arg Ser Lys Ser Gly Arg Ser Gly Ser Ile Arg Ala Arg
50                  55                  60

Val His Pro Thr Thr Arg Gln Ser Phe Gly Val Glu Pro Ser Gly Ser
65                  70                  75                  80

Gly His Ile Asp Asn Ser Ala Ser Ser Ala Ser Ser Cys Leu His Gln
                85                  90                  95

Ser Ala Val Arg Lys Thr Ala Tyr Ser His Leu Ser Thr Ser Lys Arg
            100                 105                 110

Gln Ser Ser Ser Gly His Ala Val Glu Leu His Asn Phe Pro Pro Ser
        115                 120                 125

Ser Ala Arg Ser Gln Ser Glu Gly Pro Leu Leu Ser
130                 135                 140

<210> SEQ ID NO 49
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Glu Ser Phe His Gln Gln Ser Ser Gly Ile Leu Ser Arg Pro Pro
1               5                   10                  15

Val Gly Ser Ser Leu Gln Ser Lys His Arg Lys Ser Arg Leu Gly Leu
            20                  25                  30

Gln Ser Gln Gln Gly His Leu Ala Arg Arg Gln Gln Gly Arg Gly Trp
        35                  40                  45

Ser Ile Arg Ala Gly Ile His Pro Thr Ala Arg Arg Pro Phe Gly Val
    50                  55                  60

Glu Pro Ser Gly Ser Gly His Thr Ala Asn Leu Ala Ser Lys Ser Ala
65                  70                  75                  80

Ser Cys Leu Tyr Gln Ser Ala Val Arg Lys Ala Ala Tyr Pro Val Val
                85                  90                  95

Ser Thr Phe Lys Lys His Ser Ser Ser Gly His Ala Val Glu Leu His
            100                 105                 110

Asn Leu Pro Pro Asn Ser Ala Arg Ser Gln Ser Glu Arg Pro Val Phe
        115                 120                 125

Pro

<210> SEQ ID NO 50
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 50

```
Pro Leu Ser Tyr Gln His Phe Arg Lys Leu Leu Leu Asp Asp Glu
1               5                   10                  15

Ala Gly Pro Leu Glu Glu Leu Pro Arg Leu Ala Asp Glu Gly Leu
            20                  25                  30

Asn Arg Arg Val Ala Glu Asp Leu Asn Leu Gly Asn Leu Asn Val Ser
        35                  40                  45

Ile Pro Trp Thr His Lys Val Gly Asn Phe Thr Gly Leu Tyr Ser Ser
    50                  55                  60

Thr Val Pro Val Phe Asn Pro Glu Trp Gln Thr Pro Ser Phe Pro His
65                  70                  75                  80

Ile His Leu Gln Glu Asp Ile Ile Asn Arg Cys Gln Tyr Val Gly
                85                  90                  95

Pro Leu Thr Val Asn Glu Lys Arg Arg Leu Lys Leu Ile Met Pro Ala
                100                 105                 110

Arg Phe Tyr Pro Asn Leu Thr Lys Tyr Leu Pro Leu Asp Lys Gly Ile
            115                 120                 125

Lys Pro Tyr Tyr Pro Glu His Val Val Asn His Tyr Phe Gln Thr Arg
        130                 135                 140

His Tyr Leu His Thr Leu Trp Lys Ala Gly Ile Leu Tyr Lys Arg Glu
145                 150                 155                 160

Ser Thr Arg Ser Ala Ser Phe Cys Gly Ser Pro Tyr Ser Trp Glu Gln
                165                 170                 175

Asp Leu Gln His Gly Arg Leu Val Phe Gln Thr Ser Lys Arg His Gly
            180                 185                 190

Asp Lys Ser Phe Cys Pro Gln Ser Pro Gly Ile Leu Pro Arg Ser Ser
        195                 200                 205

Val Gly Pro Cys Ile Gln Asn Gln Leu Arg Lys Ser Arg Leu Gly Pro
    210                 215                 220

Gln Pro Ala Gln Gly Gln Leu Ala Gly Arg Gln Gln Gly Gly Ser Gly
225                 230                 235                 240

Ser Ile Arg Ala Arg Val His Pro Ser Pro Trp Gly Thr Val Gly Val
                245                 250                 255

Glu Pro Ser Gly Ser Gly His Ile His Asn Cys Ala Ser Asn Ser Ser
            260                 265                 270

Ser Cys Leu His Gln Ser Ala Val Arg Lys Ala Ala Tyr Ser His Ile
        275                 280                 285

Ser Thr Ser Lys Gly His Ser Ser Ser Gly His Ala Val Glu Leu His
    290                 295                 300

His Phe Pro Pro Ser
305
```

<210> SEQ ID NO 51
<211> LENGTH: 298
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Pro Leu Ser Tyr Gln His Phe Arg Arg Leu Leu Leu Asp Asp Glu
1               5                   10                  15

Ala Gly Pro Leu Glu Glu Glu Leu Pro Arg Leu Ala Asp Glu Gly Leu
            20                  25                  30
```

Asn Arg Arg Val Ala Glu Asp Leu Asn Leu Gly Asn Leu Asn Val Ser
            35                  40                  45

Ile Pro Trp Thr His Lys Val Gly Asn Phe Thr Gly Leu Tyr Ser Ser
 50                  55                  60

Thr Val Pro Val Phe Asn Pro His Trp Lys Thr Pro Ser Phe Pro Asn
 65                  70                  75                  80

Ile His Leu His Gln Asp Ile Ile Lys Lys Cys Gln Phe Val Gly
                85                  90                  95

Pro Leu Thr Val Asn Glu Lys Arg Arg Leu Gln Leu Ile Met Pro Ala
                100                 105                 110

Arg Phe Tyr Pro Asn Val Thr Lys Tyr Leu Pro Leu Asp Lys Gly Ile
            115                 120                 125

Lys Pro Tyr Tyr Pro Glu His Leu Val Asn His Tyr Phe Gln Thr Arg
130                 135                 140

His Tyr Leu His Thr Leu Trp Lys Ala Gly Ile Leu Tyr Lys Arg Glu
145                 150                 155                 160

Thr Thr His Ser Ala Ser Phe Cys Gly Ser Pro Tyr Ser Trp Glu Gln
                165                 170                 175

Glu Leu Gln His Gly Ala Glu Ser Phe His Gln Ser Ser Gly Ile
            180                 185                 190

Leu Ser Arg Pro Pro Val Gly Ser Ser Leu Gln Ser Lys His Arg Lys
            195                 200                 205

Ser Arg Leu Gly Leu Gln Ser Gln Gln Gly His Leu Ala Arg Arg Gln
            210                 215                 220

Gln Gly Arg Gly Trp Ser Ile Arg Ala Gly Ile His Pro Thr Ala Arg
225                 230                 235                 240

Arg Pro Phe Gly Val Glu Pro Ser Gly Ser Gly His Thr Ala Asn Leu
                245                 250                 255

Ala Ser Lys Ser Ala Ser Cys Leu Tyr Gln Ser Ala Val Arg Lys Ala
            260                 265                 270

Ala Tyr Pro Val Val Ser Thr Phe Lys Lys His Ser Ser Ser Gly His
            275                 280                 285

Ala Val Glu Leu His Asn Leu Pro Pro Asn
            290                 295

<210> SEQ ID NO 52
<211> LENGTH: 845
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Pro Leu Ser Tyr Gln His Phe Arg Lys Leu Leu Leu Leu Asp Asp
 1               5                  10                  15

Glu Thr Glu Ala Gly Pro Leu Glu Glu Glu Leu Pro Arg Leu Ala Asp
            20                  25                  30

Glu Asp Leu Asn Arg Arg Val Ala Glu Asp Leu Asn Leu Gly Asn Leu
            35                  40                  45

Asn Val Ser Ile Pro Trp Thr His Lys Val Gly Asn Phe Thr Gly Leu
 50                  55                  60

Tyr Ser Ser Thr Val Pro Ile Phe Asn Pro Glu Trp Gln Thr Pro Ser
 65                  70                  75                  80

Phe Pro Lys Ile His Leu His Glu Asp Ile Ala Asn Arg Cys Gln Gln
                85                  90                  95

```
Phe Val Gly Pro Leu Thr Val Asn Glu Lys Arg Arg Leu Arg Leu Ile
                100                 105                 110
Met Pro Ala Arg Phe Tyr Pro Asn Ser Thr Lys Tyr Leu Pro Leu Asp
                115                 120                 125
Lys Gly Ile Lys Pro Tyr Tyr Pro Asp His Val Val Asn His Tyr Phe
                130                 135                 140
Gln Thr Arg His Tyr Leu His Thr Leu Trp Lys Ala Gly Ile Leu Tyr
145                 150                 155                 160
Lys Arg Glu Thr Thr Arg Ser Ala Ser Phe Cys Gly Ser Pro Tyr Ser
                165                 170                 175
Trp Glu Gln Glu Leu His His Gly Arg Leu Val Ile Lys Thr Ser Gln
                180                 185                 190
Arg His Gly Asp Glu Pro Phe Cys Ser Gln Pro Ser Gly Ile Leu Ser
                195                 200                 205
Arg Ser Ser Val Gly Pro Cys Ile Arg Ser Gln Phe Lys Gln Ser Arg
210                 215                 220
Leu Gly Leu Gln Pro His Gln Gly Pro Leu Ala Thr Ser Gln Ser Gly
225                 230                 235                 240
Arg Ser Gly Ser Ile Arg Ala Arg Val His Ser Pro Thr Arg Arg Cys
                245                 250                 255
Phe Gly Val Glu Pro Ser Gly Ser Gly His Ile Gly His Ser Ala Ser
                260                 265                 270
Ser Ser Ser Ser Cys Leu His Gln Ser Ala Val Arg Lys Ala Ala Tyr
                275                 280                 285
Ser His Leu Ser Thr Ser Lys Arg Gln Ser Ser Ser Gly His Ala Val
                290                 295                 300
Glu Phe His Ser Phe Pro Pro Ser Ser Ala Arg Ser Gln Ser Gln Gly
305                 310                 315                 320
Pro Val Phe Ser Cys Trp Trp Leu Gln Phe Arg Asn Thr Gln Pro Cys
                325                 330                 335
Ser Lys Tyr Cys Leu Ser His Leu Val Asn Leu Leu Glu Asp Trp Gly
                340                 345                 350
Pro Cys Asp Glu His Gly Glu His His Ile Arg Ile Pro Arg Thr Pro
                355                 360                 365
Ala Arg Val Thr Gly Gly Val Phe Leu Val Asp Lys Asn Pro His Asn
                370                 375                 380
Thr Ala Glu Ser Arg Leu Val Val Asp Phe Ser Gln Phe Ser Arg Gly
385                 390                 395                 400
Ile Thr Arg Val Ser Trp Pro Lys Phe Ala Val Pro Asn Leu Gln Ser
                405                 410                 415
Leu Thr Asn Leu Leu Ser Ser Asn Leu Ser Trp Leu Ser Leu Asp Val
                420                 425                 430
Ser Ala Ala Phe Tyr His Ile Pro Leu His Pro Ala Ala Met Pro His
                435                 440                 445
Leu Leu Val Gly Ser Ser Gly Leu Ser Arg Tyr Val Ala Arg Leu Ser
                450                 455                 460
Ser Asn Ser Arg Ile His Asn Asn Gln His Gly Thr Leu Gln Asn Leu
465                 470                 475                 480
His Asp Ser Cys Ser Arg Gln Leu Tyr Val Ser Leu Met Leu Leu Tyr
                485                 490                 495
Lys Thr Tyr Gly Arg Lys Leu His Leu Tyr Ser His Pro Ile Ile Leu
                500                 505                 510
```

```
Gly Phe Arg Lys Ile Pro Met Gly Val Gly Leu Ser Pro Phe Leu Leu
            515                 520                 525

Ala Gln Phe Thr Ser Ala Ile Cys Ser Val Val Arg Arg Ala Phe Pro
530                 535                 540

His Cys Leu Ala Phe Ser Tyr Met His Asp Val Val Leu Gly Ala Lys
545                 550                 555                 560

Ser Val Gln His Leu Glu Ser Leu Tyr Thr Ala Val Thr Asn Phe Leu
                565                 570                 575

Leu Ser Leu Gly Ile His Leu Asn Pro Asn Lys Thr Lys Arg Trp Gly
            580                 585                 590

Tyr Ser Leu Asn Phe Met Gly Tyr Val Ile Gly Ser Trp Gly Thr Leu
        595                 600                 605

Pro Gln Asp His Ile Val Gln Lys Ile Lys His Cys Phe Arg Lys Leu
    610                 615                 620

Pro Ile Asn Arg Pro Ile Asp Trp Lys Val Cys Gln Arg Ile Val Gly
625                 630                 635                 640

Leu Leu Gly Phe Ala Ala Pro Phe Thr Gln Cys Gly Tyr Pro Ala Leu
                645                 650                 655

Met Pro Leu Tyr Ala Cys Ile Gln Ala Lys Gln Ala Phe Thr Phe Ser
            660                 665                 670

Pro Thr Tyr Lys Ala Phe Leu Ser Lys Gln Tyr Leu Asn Leu Tyr Pro
        675                 680                 685

Val Ala Arg Gln Arg Pro Gly Leu Cys Gln Val Phe Ala Asp Ala Thr
    690                 695                 700

Pro Thr Gly Trp Gly Leu Ala Ile Gly His Gln Arg Met Arg Gly Thr
705                 710                 715                 720

Phe Val Ala Pro Leu Pro Ile His Thr Ala His Leu Leu Ala Ala Cys
                725                 730                 735

Phe Ala Arg Ser Arg Ser Gly Ala Lys Leu Ile Gly Thr Asp Asn Ser
            740                 745                 750

Val Val Leu Ser Arg Lys Tyr Thr Ser Phe Pro Trp Leu Leu Gly Cys
        755                 760                 765

Thr Ala Asn Trp Ile Leu Arg Gly Thr Ser Phe Val Tyr Val Pro Ser
    770                 775                 780

Ala Leu Asn Pro Ala Asp Asp Pro Ser Arg Gly Arg Leu Gly Leu Tyr
785                 790                 795                 800

Arg Pro Leu Leu Arg Leu Pro Tyr Arg Pro Thr Thr Gly Arg Thr Ser
                805                 810                 815

Leu Tyr Ala Val Ser Pro Ser Val Pro Ser His Leu Pro Val Arg Val
            820                 825                 830

His Phe Ala Ser Pro Leu His Val Ala Trp Arg Pro Pro
        835                 840                 845

<210> SEQ ID NO 53
<211> LENGTH: 843
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
            20                  25                  30
```

```
Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Leu Lys Leu Ile Met Pro
                100                 105                 110

Ala Arg Phe Tyr Pro Asn Leu Thr Lys Tyr Leu Pro Leu Asp Lys Gly
            115                 120                 125

Ile Lys Pro Tyr Tyr Pro Glu His Val Val Asn His Tyr Phe Gln Thr
        130                 135                 140

Arg His Tyr Leu His Thr Leu Trp Lys Ala Gly Ile Leu Tyr Lys Arg
145                 150                 155                 160

Glu Ser Thr Arg Ser Ala Ser Phe Cys Gly Ser Pro Tyr Ser Trp Glu
                165                 170                 175

Gln Asp Leu Gln His Gly Arg Leu Val Phe Gln Thr Ser Lys Arg His
            180                 185                 190

Gly Asp Lys Ser Phe Cys Pro Gln Ser Pro Gly Ile Leu Pro Arg Ser
        195                 200                 205

Ser Val Gly Pro Cys Ile Gln Asn Gln Leu Arg Lys Ser Arg Leu Gly
    210                 215                 220

Pro Gln Pro Ala Gln Gly Gln Leu Ala Gly Arg Gln Gln Gly Gly Ser
225                 230                 235                 240

Gly Ser Ile Arg Ala Arg Val His Pro Ser Pro Trp Gly Thr Val Gly
                245                 250                 255

Val Glu Pro Ser Gly Ser Gly His Ile His Asn Cys Ala Ser Asn Ser
            260                 265                 270

Ser Ser Cys Leu His Gln Ser Ala Val Arg Lys Ala Ala Tyr Ser His
        275                 280                 285

Ile Ser Thr Ser Lys Gly His Ser Ser Ser Gly His Ala Val Glu Leu
    290                 295                 300

His His Phe Pro Pro Ser Ser Ser Arg Ser Gln Ser Gln Gly Pro Val
305                 310                 315                 320

Leu Ser Cys Trp Trp Leu Gln Phe Arg Asn Ser Glu Pro Cys Ser Glu
                325                 330                 335

Tyr Cys Leu Cys His Ile Val Asn Leu Ile Glu Asp Trp Gly Pro Cys
            340                 345                 350

Thr Glu His Gly Glu His Arg Ile Arg Thr Pro Arg Thr Pro Ala Arg
        355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Leu Pro Leu His Pro Ala Ala Met Pro His Leu Leu
        435                 440                 445
```

```
Val Gly Ser Ser Gly Leu Ser Arg Tyr Val Ala Arg Leu Ser Ser Asn
    450                 455                 460
Ser Arg Ile Ile Asn Asn Gln His Arg Thr Met Gln Asn Leu His Asp
465                 470                 475                 480
Ser Cys Ser Arg Asn Leu Tyr Val Ser Leu Met Leu Leu Tyr Lys Thr
                485                 490                 495
Tyr Gly Arg Lys Leu His Leu Tyr Ser His Pro Ile Ile Leu Gly Phe
            500                 505                 510
Arg Lys Ile Pro Met Gly Val Gly Leu Ser Pro Phe Leu Leu Ala Gln
        515                 520                 525
Phe Thr Ser Ala Ile Cys Ser Val Val Arg Arg Ala Phe Pro His Cys
    530                 535                 540
Leu Ala Phe Ser Tyr Met His Asp Val Val Leu Gly Ala Lys Ser Val
545                 550                 555                 560
Gln His Leu Glu Ser Leu Tyr Ala Ala Val Thr Asn Phe Leu Leu Ser
                565                 570                 575
Leu Gly Ile His Leu Asn Pro His Lys Thr Lys Arg Trp Gly Tyr Ser
            580                 585                 590
Leu Asn Phe Met Gly Tyr Val Ile Gly Ser Trp Gly Thr Leu Pro Gln
        595                 600                 605
Glu His Ile Val Gln Lys Ile Lys Met Cys Phe Arg Lys Leu Pro Val
    610                 615                 620
Asn Arg Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
                645                 650                 655
Leu Tyr Ala Cys Ile Gln Ala Lys Gln Ala Phe Thr Phe Ser Pro Thr
            660                 665                 670
Tyr Lys Ala Phe Leu Ser Lys Gln Tyr Leu His Leu Tyr Pro Val Ala
        675                 680                 685
Arg Gln Arg Pro Gly Leu Cys Gln Val Phe Ala Asp Ala Thr Pro Thr
    690                 695                 700
Gly Trp Gly Leu Ala Ile Gly His Gln Arg Met Arg Gly Ala Phe Val
705                 710                 715                 720
Ser Pro Leu Pro Ile His Thr Ala His Leu Leu Ala Ala Cys Phe Ala
                725                 730                 735
Arg Ser Arg Ser Gly Ala Lys Leu Ile Gly Thr Asp Asn Ser Val Val
            740                 745                 750
Leu Ser Arg Lys Tyr Thr Ser Phe Pro Trp Leu Leu Gly Cys Ala Ala
        755                 760                 765
Asn Trp Ile Leu Arg Gly Thr Ser Phe Val Tyr Val Pro Ser Ala Leu
    770                 775                 780
Asn Pro Ala Asp Asp Pro Ser Arg Gly Arg Leu Gly Leu Tyr Arg Pro
785                 790                 795                 800
Leu Leu Arg Leu Leu Tyr Arg Pro Thr Thr Gly Arg Thr Ser Leu Tyr
                805                 810                 815
Ala Asp Ser Pro Ser Val Pro Ser His Leu Pro Asp Arg Val His Phe
            820                 825                 830
Ala Ser Pro Leu His Val Ala Trp Arg Pro Pro
        835                 840

<210> SEQ ID NO 54
<211> LENGTH: 843
<212> TYPE: PRT
```

<213> ORGANISM: Artificial Sequence
<220> FEATURE:
<223> OTHER INFORMATION: Description of Artificial Sequence: Synthetic
    polypeptide

<400> SEQUENCE: 54

Met Pro Leu Ser Tyr Gln His Phe Arg Lys Leu Leu Leu Leu Asp Asp
1               5                   10                  15

Glu Ala Gly Pro Leu Glu Glu Leu Pro Arg Leu Ala Asp Glu Asp
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Leu Lys Leu Ile Met Pro
            100                 105                 110

Ala Arg Phe Tyr Pro Asn Leu Thr Lys Tyr Leu Pro Leu Asp Lys Gly
        115                 120                 125

Ile Lys Pro Tyr Tyr Pro Glu His Thr Val Asn His Tyr Phe Lys Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Glu Ser Phe Cys Ser Gln Ser Ser Gly Ile Leu Ser Arg Ser
        195                 200                 205

Pro Val Gly Pro Cys Ile Arg Ser Gln Leu Lys Gln Ser Arg Leu Gly
    210                 215                 220

Leu Gln Pro Gln Gln Gly Ser Leu Ala Arg Ser Lys Ser Gly Arg Ser
225                 230                 235                 240

Gly Ser Ile Arg Ala Arg Val His Pro Thr Thr Arg Gln Ser Phe Gly
                245                 250                 255

Val Glu Pro Ser Gly Ser Gly His Ile Asp Asn Ser Ala Ser Ser Ala
            260                 265                 270

Ser Ser Cys Leu His Gln Ser Ala Val Arg Lys Thr Ala Tyr Ser His
        275                 280                 285

Leu Ser Thr Ser Lys Arg Gln Ser Ser Gly His Ala Val Glu Leu
    290                 295                 300

His Asn Phe Pro Pro Ser Ser Ala Arg Ser Gln Ser Glu Gly Pro Leu
305                 310                 315                 320

Leu Ser Cys Trp Trp Leu Gln Phe Arg Asn Ser Lys Pro Cys Ser Asp
                325                 330                 335

Tyr Cys Leu Ser His Ile Val Asn Leu Leu Glu Asp Trp Gly Pro Cys
            340                 345                 350

Thr Glu His Gly Glu His Asn Ile Arg Ile Pro Arg Thr Pro Ala Arg
        355                 360                 365

Val Thr Gly Gly Val Phe Leu Val Asp Lys Asn Pro His Asn Thr Thr
    370                 375                 380

```
Glu Ser Arg Leu Val Val Asp Phe Ser Gln Phe Ser Arg Gly Ser Thr
385                 390                 395                 400

His Val Ser Trp Pro Lys Phe Ala Val Pro Asn Leu Gln Ser Leu Thr
            405                 410                 415

Asn Leu Leu Ser Ser Asn Leu Ser Trp Leu Ser Leu Asp Val Ser Ala
        420                 425                 430

Ala Phe Tyr His Leu Pro Leu His Pro Ala Ala Met Pro His Leu Leu
            435                 440                 445

Val Gly Ser Ser Gly Leu Ser Arg Tyr Val Ala Arg Leu Ser Ser Thr
    450                 455                 460

Ser Arg Asn Ile Asn Tyr Gln His Gly Ala Met Gln Asp Leu His Asp
465                 470                 475                 480

Ser Cys Ser Arg Asn Leu Tyr Val Ser Leu Leu Leu Tyr Lys Thr
                485                 490                 495

Phe Gly Arg Lys Leu His Leu Tyr Ser His Pro Ile Ile Leu Gly Phe
                500                 505                 510

Arg Lys Ile Pro Met Gly Val Gly Leu Ser Pro Phe Leu Leu Ala Gln
            515                 520                 525

Phe Thr Ser Ala Ile Cys Ser Val Val Arg Arg Ala Phe Pro His Cys
530                 535                 540

Leu Ala Phe Ser Tyr Met His Asp Val Val Leu Gly Ala Lys Ser Val
545                 550                 555                 560

Gln His Leu Glu Ser Leu Phe Thr Ala Val Thr Asn Phe Leu Leu Ser
                565                 570                 575

Leu Gly Ile His Leu Asn Pro Asn Lys Thr Lys Arg Trp Gly Tyr Ser
            580                 585                 590

Leu Asn Phe Met Gly Tyr Val Ile Gly Ser Trp Gly Thr Leu Pro Gln
            595                 600                 605

Glu His Ile Val Leu Lys Ile Lys Gln Cys Phe Arg Lys Leu Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
            645                 650                 655

Leu Tyr Ala Cys Ile Gln Ala Lys Gln Ala Phe Thr Phe Ser Pro Thr
            660                 665                 670

Tyr Lys Ala Phe Leu Cys Lys Gln Tyr Leu Asn Leu Tyr Pro Val Ala
        675                 680                 685

Arg Gln Arg Ser Gly Leu Cys Gln Val Phe Ala Asp Ala Thr Pro Thr
    690                 695                 700

Gly Trp Gly Leu Ala Val Gly His Gln Arg Met Arg Gly Thr Phe Val
705                 710                 715                 720

Ser Pro Leu Pro Ile His Thr Ala His Leu Leu Ala Ala Cys Phe Ala
            725                 730                 735

Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
        755                 760                 765

Asn Trp Ile Leu Arg Gly Thr Ser Phe Val Tyr Val Pro Ser Ala Leu
            770                 775                 780

Asn Pro Ala Asp Asp Pro Ser Arg Gly Arg Leu Gly Leu Tyr Arg Pro
785                 790                 795                 800

Leu Leu Arg Leu Pro Phe Arg Pro Thr Thr Gly Arg Thr Ser Leu Tyr
```

```
                        805                 810                 815
Ala Val Ser Pro Ser Val Pro Ser His Leu Pro Val Arg Val His Phe
                820                 825                 830

Ala Ser Pro Leu His Val Ala Trp Arg Pro Pro
        835                 840

<210> SEQ ID NO 55
<211> LENGTH: 832
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Pro Leu Ser Tyr Gln His Phe Arg Arg Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
    50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
                100                 105                 110

Ala Arg Phe Tyr Pro Asn Val Thr Lys Tyr Leu Pro Leu Asp Lys Gly
            115                 120                 125

Ile Lys Pro Tyr Tyr Pro Glu His Leu Val Asn His Tyr Phe Gln Thr
        130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Glu Leu Gln His Gly Ala Glu Ser Phe His Gln Ser Ser Gly
            180                 185                 190

Ile Leu Ser Arg Pro Pro Val Gly Ser Ser Leu Gln Ser Lys His Arg
        195                 200                 205

Lys Ser Arg Leu Gly Leu Gln Ser Gln Gln Gly His Leu Ala Arg Arg
        210                 215                 220

Gln Gln Gly Arg Gly Trp Ser Ile Arg Ala Gly Ile His Pro Thr Ala
225                 230                 235                 240

Arg Arg Pro Phe Gly Val Glu Pro Ser Gly Ser Gly His Thr Ala Asn
                245                 250                 255

Leu Ala Ser Lys Ser Ala Ser Cys Leu Tyr Gln Ser Ala Val Arg Lys
            260                 265                 270

Ala Ala Tyr Pro Val Val Ser Thr Phe Lys Lys His Ser Ser Ser Gly
        275                 280                 285

His Ala Val Glu Leu His Asn Leu Pro Pro Asn Ser Ala Arg Ser Gln
        290                 295                 300

Ser Glu Arg Pro Val Phe Pro Cys Trp Trp Leu Gln Phe Arg Asn Ser
305                 310                 315                 320
```

```
Lys Pro Cys Ser Asp Tyr Cys Leu Ser His Ile Val Asn Leu Leu Glu
            325                 330                 335

Asp Trp Gly Pro Cys Ala Glu His Gly Glu His His Ile Arg Ile Pro
        340                 345                 350

Arg Thr Pro Ala Arg Val Thr Gly Gly Val Phe Leu Val Asp Lys Asn
    355                 360                 365

Pro His Asn Thr Ala Glu Ser Arg Leu Val Val Asp Phe Ser Gln Phe
370                 375                 380

Ser Arg Gly Asn Tyr Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
            405                 410                 415

Leu Asp Val Ser Ala Ala Phe Tyr His Leu Pro Leu His Pro Ala Ala
            420                 425                 430

Met Pro His Leu Leu Val Gly Ser Ser Gly Leu Ser Arg Tyr Val Ala
            435                 440                 445

Arg Leu Ser Ser Asn Ser Arg Ile Phe Asn Tyr Gln His Gly Thr Met
    450                 455                 460

Gln Asn Leu His Asp Ser Cys Ser Arg Asn Leu Tyr Val Ser Leu Met
465                 470                 475                 480

Leu Leu Tyr Gln Thr Phe Gly Arg Lys Leu His Leu Tyr Ser His Pro
            485                 490                 495

Ile Ile Leu Gly Phe Arg Lys Ile Pro Met Gly Val Gly Leu Ser Pro
            500                 505                 510

Phe Leu Leu Ala Gln Phe Thr Ser Ala Ile Cys Ser Val Val Arg Arg
            515                 520                 525

Ala Phe Pro His Cys Leu Ala Phe Ser Tyr Met His Asp Val Val Leu
            530                 535                 540

Gly Ala Lys Ser Val Gln His Leu Glu Ser Leu Phe Thr Ala Val Thr
545                 550                 555                 560

Asn Phe Leu Leu Ser Leu Gly Ile His Leu Asn Pro Asn Lys Thr Lys
            565                 570                 575

Arg Trp Gly Tyr Ser Leu His Phe Met Gly Tyr Val Ile Gly Cys Tyr
            580                 585                 590

Gly Ser Leu Pro Gln Asp His Ile Ile Gln Lys Ile Lys Glu Cys Phe
            595                 600                 605

Arg Lys Leu Pro Val Asn Arg Pro Ile Asp Trp Lys Val Cys Gln Arg
            610                 615                 620

Ile Val Gly Leu Leu Gly Phe Ala Ala Pro Phe Thr Gln Cys Gly Tyr
625                 630                 635                 640

Pro Ala Leu Met Pro Leu Tyr Ala Cys Ile Gln Ser Lys Gln Ala Phe
            645                 650                 655

Thr Phe Ser Pro Thr Tyr Lys Ala Phe Leu Cys Lys Gln Tyr Leu Asn
            660                 665                 670

Leu Tyr Pro Val Ala Arg Gln Arg Pro Gly Leu Cys Gln Val Phe Ala
            675                 680                 685

Asp Ala Thr Pro Thr Gly Trp Gly Leu Val Met Gly His Gln Arg Met
            690                 695                 700

Arg Gly Thr Phe Lys Ala Pro Leu Pro Ile His Thr Ala His Leu Leu
705                 710                 715                 720

Ala Ala Cys Phe Ala Arg Ser Arg Ser Gly Ala Asn Ile Leu Gly Thr
            725                 730                 735

Asp Asn Ser Val Val Leu Ser Arg Lys Tyr Thr Ser Phe Pro Trp Leu
```

```
                    740                 745                 750
Leu Gly Cys Ala Ala Asn Trp Ile Leu Arg Gly Thr Ser Phe Val Tyr
            755                 760                 765

Val Pro Ser Ala Leu Asn Pro Ala Asp Asp Pro Ser Arg Gly Arg Leu
    770                 775                 780

Gly Leu Tyr Arg Pro Leu Leu Arg Leu Pro Phe Arg Pro Thr Thr Gly
785                 790                 795                 800

Arg Thr Ser Leu Tyr Ala Asp Ser Pro Ser Val Pro Ser His Leu Pro
                805                 810                 815

Asp Arg Val His Phe Ala Ser Pro Leu His Val Ala Trp Arg Pro Pro
            820                 825                 830
```

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Ala Thr Asn Phe Ser Leu Leu Lys Gln Ala Gly Asp Val Glu Glu Asn
1               5                   10                  15

Pro Gly Pro
```

<210> SEQ ID NO 57
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Ala Pro Val Lys Gln Thr Leu Asn Phe Asp Leu Leu Lys Leu Ala Gly
1               5                   10                  15

Asp Val Glu Ser Asn Pro Gly Pro
            20
```

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Gln Cys Thr Asn Tyr Ala Leu Leu Lys Leu Ala Gly Asp Val Glu Ser
1               5                   10                  15

Asn Pro Gly Pro
            20
```

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Glu Gly Arg Gly Ser Leu Leu Thr Cys Gly Asp Val Glu Glu Asn Pro
```

```
1               5                   10                  15
Gly Pro

<210> SEQ ID NO 60
<211> LENGTH: 4
<212> TYPE: PRT
<213> ORGANISM: Unknown
<220> FEATURE:
<223> OTHER INFORMATION: Description of Unknown:
      furin recognition/cleavage site

<400> SEQUENCE: 60

Arg Ala Lys Arg
1

<210> SEQ ID NO 61
<211> LENGTH: 4
<212> TYPE: PRT
<213> ORGANISM: Unknown
<220> FEATURE:
<223> OTHER INFORMATION: Description of Unknown:
      furin recognition/cleavage site

<400> SEQUENCE: 61

Arg Glu Lys Arg
1

<210> SEQ ID NO 62
<211> LENGTH: 4
<212> TYPE: PRT
<213> ORGANISM: Unknown
<220> FEATURE:
<223> OTHER INFORMATION: Description of Unknown:
      furin recognition/cleavage site

<400> SEQUENCE: 62

Arg Arg Lys Arg
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gly Gly Ser
1

<210> SEQ ID NO 64
<211> LENGTH: 185
<212> TYPE: PRT
<213> ORGANISM: Hepatitis B virus

<400> SEQUENCE: 64

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60
```

```
Leu Met Thr Leu Ala Thr Trp Val Gly Asn Asn Leu Glu Asp Pro Ala
 65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185

<210> SEQ ID NO 65
<211> LENGTH: 183
<212> TYPE: PRT
<213> ORGANISM: Hepatitis B virus

<400> SEQUENCE: 65

Met Asp Ile Asp Pro Tyr Lys Glu Phe Gly Ala Ser Val Glu Leu Leu
  1               5                  10                  15

Ser Phe Leu Pro Ser Asp Phe Phe Pro Ser Val Arg Asp Leu Leu Asp
                 20                  25                  30

Thr Ala Ser Ala Leu Tyr Arg Glu Ala Leu Glu Ser Pro Glu His Cys
             35                  40                  45

Ser Pro His His Thr Ala Leu Arg Gln Ala Ile Leu Cys Trp Gly Glu
         50                  55                  60

Leu Met Asn Leu Ala Thr Trp Val Gly Ser Asn Leu Glu Asp Pro Ala
 65                  70                  75                  80

Ser Arg Glu Leu Val Val Ser Tyr Val Asn Val Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 66
<211> LENGTH: 183
<212> TYPE: PRT
<213> ORGANISM: Hepatitis B virus

<400> SEQUENCE: 66

Met Asp Ile Asp Pro Tyr Lys Glu Phe Gly Ala Ser Val Glu Leu Leu
  1               5                  10                  15
```

```
Ser Phe Leu Pro Ser Asp Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Asn Leu Ala Thr Trp Val Gly Val Asn Leu Glu Asp Pro Ala
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 67
<211> LENGTH: 18
<212> TYPE: PRT
<213> ORGANISM: Unknown
<220> FEATURE:
<223> OTHER INFORMATION: Description of Unknown:
      CSF2, GM-CSF sequence

<400> SEQUENCE: 67

Met Trp Leu Gln Ser Leu Leu Leu Leu Gly Thr Val Ala Cys Ser Ile
 1               5                  10                  15

Ser Val

<210> SEQ ID NO 68
<211> LENGTH: 23
<212> TYPE: PRT
<213> ORGANISM: Unknown
<220> FEATURE:
<223> OTHER INFORMATION: Description of Unknown:
      PLAT, t-PA sequence

<400> SEQUENCE: 68

Met Asp Ala Met Lys Arg Gly Leu Cys Cys Val Leu Leu Leu Cys Gly
 1               5                  10                  15

Ala Val Phe Val Ser Ala Arg
             20

<210> SEQ ID NO 69
<211> LENGTH: 16
<212> TYPE: PRT
<213> ORGANISM: Unknown
<220> FEATURE:
<223> OTHER INFORMATION: Description of Unknown:
      CD74 sequence

<400> SEQUENCE: 69

Met His Arg Arg Arg Ser Arg Ser Cys Arg Glu Asp Gln Lys Pro Val
```

```
                1               5                  10                 15
```

<210> SEQ ID NO 70
<211> LENGTH: 17
<212> TYPE: PRT
<213> ORGANISM: Unknown
<220> FEATURE:
<223> OTHER INFORMATION: Description of Unknown:
      serum albumin sequence

<400> SEQUENCE: 70

Lys Trp Val Thr Phe Ile Ser Leu Leu Phe Leu Phe Ser Ser Ala Tyr
1               5                   10                  15

Ser

<210> SEQ ID NO 71
<211> LENGTH: 31
<212> TYPE: PRT
<213> ORGANISM: Unknown
<220> FEATURE:
<223> OTHER INFORMATION: Description of Unknown:
      beta-catenin sequence

<400> SEQUENCE: 71

Met Arg Lys Ala Ala Val Ser His Trp Gln Gln Gln Ser Tyr Leu Asp
1               5                   10                  15

Ser Gly Ile His Ser Gly Ala Thr Thr Thr Ala Pro Ser Leu Ser
            20                  25                  30

<210> SEQ ID NO 72
<211> LENGTH: 107
<212> TYPE: PRT
<213> ORGANISM: Unknown
<220> FEATURE:
<223> OTHER INFORMATION: Description of Unknown:
      CCL7, MCP-3 sequence

<400> SEQUENCE: 72

Met Asn Pro Ser Ala Ala Val Ile Phe Cys Leu Ile Leu Leu Gly Leu
1               5                   10                  15

Ser Gly Thr Gln Gly Ile Leu Asp Met Ala Gln Pro Val Gly Ile Asn
            20                  25                  30

Thr Ser Thr Thr Cys Cys Tyr Arg Phe Ile Asn Lys Lys Ile Pro Lys
        35                  40                  45

Gln Arg Leu Glu Ser Tyr Arg Arg Thr Thr Ser Ser His Cys Pro Arg
    50                  55                  60

Glu Ala Val Ile Phe Lys Thr Lys Leu Asp Lys Glu Ile Cys Ala Asp
65                  70                  75                  80

Pro Thr Gln Lys Trp Val Gln Asp Phe Met Lys His Leu Asp Lys Lys
                85                  90                  95

Thr Gln Thr Pro Lys Leu Ala Ser Ala Gly Ala
            100                 105

<210> SEQ ID NO 73
<211> LENGTH: 76
<212> TYPE: PRT
<213> ORGANISM: Unknown
<220> FEATURE:
<223> OTHER INFORMATION: Description of Unknown:
      ubiquitin sequence

<400> SEQUENCE: 73

Met Gln Ile Phe Val Lys Thr Leu Thr Gly Lys Thr Ile Thr Leu Glu

```
                1               5                  10                 15
Val Glu Pro Ser Asp Thr Ile Glu Asn Val Lys Ala Lys Ile Gln Asp
                20                 25                 30

Lys Glu Gly Ile Pro Pro Asp Gln Gln Arg Leu Ile Phe Ala Gly Lys
                35                 40                 45

Gln Leu Glu Asp Gly Arg Thr Leu Ser Asp Tyr Asn Ile Gln Lys Glu
        50                 55                 60

Ser Thr Leu His Leu Val Leu Arg Leu Arg Gly Gly
65                 70                  75

<210> SEQ ID NO 74
<211> LENGTH: 17
<212> TYPE: PRT
<213> ORGANISM: Unknown
<220> FEATURE:
<223> OTHER INFORMATION: Description of Unknown:
      calreticulin sequence

<400> SEQUENCE: 74

Met Leu Leu Ser Val Pro Leu Leu Leu Gly Leu Leu Gly Leu Ala Val
1               5                   10                  15

Ala

<210> SEQ ID NO 75
<211> LENGTH: 16
<212> TYPE: PRT
<213> ORGANISM: Vesicular stomatitis virus

<400> SEQUENCE: 75

Met Lys Cys Leu Leu Tyr Leu Ala Phe Leu Phe Ile Gly Val Asn Cys
1               5                   10                  15

<210> SEQ ID NO 76
<211> LENGTH: 21
<212> TYPE: PRT
<213> ORGANISM: Unknown
<220> FEATURE:
<223> OTHER INFORMATION: Description of Unknown:
      CXCL10, IP-10 sequence

<400> SEQUENCE: 76

Met Asn Gln Thr Ala Ile Leu Ile Cys Cys Leu Ile Phe Leu Thr Leu
1               5                   10                  15

Ser Gly Ile Gln Gly
            20

<210> SEQ ID NO 77
<211> LENGTH: 384
<212> TYPE: PRT
<213> ORGANISM: Unknown
<220> FEATURE:
<223> OTHER INFORMATION: Description of Unknown:
      LAMP-1, N-terminal sequence

<400> SEQUENCE: 77

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
                20                 25                 30

Lys Asn Gly Asn Gly Thr Ala Cys Ile Met Ala Asn Phe Ser Ala Ala
        35                 40                 45

Phe Ser Val Asn Tyr Asp Thr Lys Ser Gly Pro Lys Asn Met Thr Leu
```

```
            50                  55                  60
Asp Leu Pro Ser Asp Ala Thr Val Val Leu Asn Arg Ser Ser Cys Gly
 65                  70                  75                  80

Lys Glu Asn Thr Ser Asp Pro Ser Leu Val Ile Ala Phe Gly Arg Gly
                 85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Gly Thr Thr Val Leu Leu Phe Gln
        275                 280                 285

Phe Gly Met Asn Ala Ser Ser Ser Arg Phe Phe Leu Gln Gly Ile Gln
290                 295                 300

Leu Asn Thr Leu Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Asp Ile
370                 375                 380

<210> SEQ ID NO 78
<211> LENGTH: 39
<212> TYPE: PRT
<213> ORGANISM: Unknown
<220> FEATURE:
<223> OTHER INFORMATION: Description of Unknown:
      LAMP-1, C-terminal sequence

<400> SEQUENCE: 78

Gly Ser Glu Phe Thr Leu Ile Pro Ile Ala Val Gly Gly Ala Leu Ala
 1               5                  10                  15

Gly Leu Val Ile Val Leu Ile Ala Tyr Leu Val Gly Arg Lys Arg Ser
            20                  25                  30
```

His Ala Gly Tyr Gln Thr Ile
        35

<210> SEQ ID NO 79
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: A or T
<220> FEATURE:
<221> NAME/KEY: MOD_RES
<222> LOCATION: (11)..(11)
<223> OTHER INFORMATION: T or A
<220> FEATURE:
<221> NAME/KEY: MOD_RES
<222> LOCATION: (19)..(19)
<223> OTHER INFORMATION: A or G
<220> FEATURE:
<221> NAME/KEY: MOD_RES
<222> LOCATION: (24)..(24)
<223> OTHER INFORMATION: A or G
<220> FEATURE:
<221> NAME/KEY: MOD_RES
<222> LOCATION: (29)..(29)
<223> OTHER INFORMATION: L or S
<220> FEATURE:
<221> NAME/KEY: MOD_RES
<222> LOCATION: (31)..(31)
<223> OTHER INFORMATION: A or T
<220> FEATURE:
<221> NAME/KEY: MOD_RES
<222> LOCATION: (32)..(32)
<223> OTHER INFORMATION: V or I
<220> FEATURE:
<221> NAME/KEY: MOD_RES
<222> LOCATION: (36)..(36)
<223> OTHER INFORMATION: L or P
<220> FEATURE:
<221> NAME/KEY: MOD_RES
<222> LOCATION: (39)..(39)
<223> OTHER INFORMATION: A or V
<220> FEATURE:
<221> NAME/KEY: MOD_RES
<222> LOCATION: (41)..(41)
<223> OTHER INFORMATION: P or H
<220> FEATURE:
<221> NAME/KEY: MOD_RES
<222> LOCATION: (42)..(42)
<223> OTHER INFORMATION: L or I
<220> FEATURE:
<221> NAME/KEY: MOD_RES
<222> LOCATION: (47)..(47)
<223> OTHER INFORMATION: S or A
<220> FEATURE:
<221> NAME/KEY: MOD_RES
<222> LOCATION: (53)..(53)
<223> OTHER INFORMATION: A or V
<220> FEATURE:
<221> NAME/KEY: MOD_RES
<222> LOCATION: (54)..(54)
<223> OTHER INFORMATION: L, M, P, or T

<400> SEQUENCE: 79

Met Gln Trp Asn Ser Thr Xaa Phe His Gln Xaa Leu Gln Asp Pro Arg
1               5                   10                  15

Val Arg Xaa Leu Tyr Phe Pro Xaa Gly Gly Ser Ser Xaa Gly Xaa Xaa
            20                  25                  30

Asn Pro Val Xaa Thr Thr Xaa Ser Xaa Xaa Ser Ser Ile Phe Xaa Arg
            35                  40                  45

```
Ile Gly Asp Pro Xaa Xaa Asn
        50              55

<210> SEQ ID NO 80
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Gln Trp Asn Ser Thr Ala Phe His Gln Ala Leu Gln Asp Pro Arg
1               5                   10                  15

Val Arg Gly Leu Tyr Phe Pro Ala Gly Gly Ser Ser Ser Gly Thr Val
            20                  25                  30

Asn Pro Ala Pro Asn Ile Ala Ser His Ile Ser Ser Ile Ser Ala Arg
        35                  40                  45

Thr Gly Asp Pro Val Thr Asn
    50              55

<210> SEQ ID NO 81
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Gln Trp Asn Ser Thr Thr Phe His Gln Thr Leu Gln Asp Pro Arg
1               5                   10                  15

Val Arg Ala Leu Tyr Phe Pro Ala Gly Gly Ser Ser Ser Gly Thr Val
            20                  25                  30

Ser Pro Ala Gln Asn Thr Val Ser Ala Ile Ser Ser Ile Leu Ser Lys
        35                  40                  45

Thr Gly Asp Pro Val Pro Asn
    50              55

<210> SEQ ID NO 82
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Gln Trp Asn Ser Thr Thr Phe His Gln Ala Leu Leu Asp Pro Arg
1               5                   10                  15

Val Arg Gly Leu Tyr Phe Pro Ala Gly Gly Ser Ser Ser Gly Thr Val
            20                  25                  30

Asn Pro Val Pro Thr Thr Ala Ser Pro Ile Ser Ser Ile Phe Ser Arg
        35                  40                  45

Thr Gly Asp Pro Ala Pro Asn
    50              55

<210> SEQ ID NO 83
<211> LENGTH: 55
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 83

Met Gln Trp Asn Ser Thr Thr Phe His Gln Thr Leu Gln Asp Pro Arg
1               5                   10                  15

Val Arg Gly Leu Tyr Phe Pro Ala Gly Gly Ser Ser Ser Gly Thr Val
            20                  25                  30

Asn Pro Val Pro Thr Thr Ala Ser Pro Ile Ser Ser Ile Phe Ser Arg
        35                  40                  45

Ile Gly Asp Pro Ala Leu Asn
    50                  55

<210> SEQ ID NO 84
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: D or A
<220> FEATURE:
<221> NAME/KEY: MOD_RES
<222> LOCATION: (28)..(28)
<223> OTHER INFORMATION: A, G, or R
<220> FEATURE:
<221> NAME/KEY: MOD_RES
<222> LOCATION: (74)..(74)
<223> OTHER INFORMATION: I or L
<220> FEATURE:
<221> NAME/KEY: MOD_RES
<222> LOCATION: (77)..(77)
<223> OTHER INFORMATION: L or V
<220> FEATURE:
<221> NAME/KEY: MOD_RES
<222> LOCATION: (86)..(86)
<223> OTHER INFORMATION: T or A
<220> FEATURE:
<221> NAME/KEY: MOD_RES
<222> LOCATION: (90)..(90)
<223> OTHER INFORMATION: S or T
<220> FEATURE:
<221> NAME/KEY: MOD_RES
<222> LOCATION: (103)..(103)
<223> OTHER INFORMATION: N or D
<220> FEATURE:
<221> NAME/KEY: MOD_RES
<222> LOCATION: (115)..(115)
<223> OTHER INFORMATION: A or T
<220> FEATURE:
<221> NAME/KEY: MOD_RES
<222> LOCATION: (119)..(119)
<223> OTHER INFORMATION: T or A
<220> FEATURE:
<221> NAME/KEY: MOD_RES
<222> LOCATION: (127)..(127)
<223> OTHER INFORMATION: A or G
<220> FEATURE:
<221> NAME/KEY: MOD_RES
<222> LOCATION: (132)..(132)
<223> OTHER INFORMATION: A or G
<220> FEATURE:
<221> NAME/KEY: MOD_RES
<222> LOCATION: (137)..(137)
<223> OTHER INFORMATION: L or S
<220> FEATURE:
<221> NAME/KEY: MOD_RES
<222> LOCATION: (139)..(139)
<223> OTHER INFORMATION: A or T
<220> FEATURE:
<221> NAME/KEY: MOD_RES
<222> LOCATION: (140)..(140)

```
<223> OTHER INFORMATION: V or I
<220> FEATURE:
<221> NAME/KEY: MOD_RES
<222> LOCATION: (144)..(144)
<223> OTHER INFORMATION: L or P
<220> FEATURE:
<221> NAME/KEY: MOD_RES
<222> LOCATION: (147)..(147)
<223> OTHER INFORMATION: A or V
<220> FEATURE:
<221> NAME/KEY: MOD_RES
<222> LOCATION: (149)..(149)
<223> OTHER INFORMATION: P or H
<220> FEATURE:
<221> NAME/KEY: MOD_RES
<222> LOCATION: (150)..(150)
<223> OTHER INFORMATION: L or I
<220> FEATURE:
<221> NAME/KEY: MOD_RES
<222> LOCATION: (155)..(155)
<223> OTHER INFORMATION: S or A
<220> FEATURE:
<221> NAME/KEY: MOD_RES
<222> LOCATION: (161)..(161)
<223> OTHER INFORMATION: A or V
<220> FEATURE:
<221> NAME/KEY: MOD_RES
<222> LOCATION: (162)..(162)
<223> OTHER INFORMATION: L, M, P, or T

<400> SEQUENCE: 84

Met Gly Gln Asn Leu Ser Thr Ser Asn Pro Leu Gly Phe Phe Pro Asp
1               5                   10                  15

His Gln Leu Xaa Pro Ala Phe Arg Ala Asn Thr Xaa Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Xaa Gln Thr Xaa Pro Ala Asn
65                  70                  75                  80

Pro Pro Pro Ala Ser Xaa Asn Arg Gln Xaa Gly Arg Gln Pro Thr Pro
                85                  90                  95

Leu Ser Pro Pro Leu Arg Xaa Thr His Pro Gln Ala Met Gln Trp Asn
            100                 105                 110

Ser Thr Xaa Phe His Gln Xaa Leu Gln Asp Pro Arg Val Arg Xaa Leu
        115                 120                 125

Tyr Phe Pro Xaa Gly Gly Ser Ser Xaa Gly Xaa Xaa Asn Pro Val Xaa
    130                 135                 140

Thr Thr Xaa Ser Xaa Xaa Ser Ser Ile Phe Xaa Arg Ile Gly Asp Pro
145                 150                 155                 160

Xaa Xaa Asn

<210> SEQ ID NO 85
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
```

```
                    20                  25                  30

Ala Phe Gly Ala Asn Ser Asn Asn Pro Asp Trp Asp Phe Asn Pro Ile
                35                  40                  45

Lys Asp His Trp Pro Ala Ala Asn Gln Val Gly Val Gly Ala Phe Gly
        50                  55                  60

Pro Gly Leu Thr Pro Pro His Gly Gly Ile Leu Gly Trp Ser Pro Gln
65                  70                  75                  80

Ala Gln Gly Ile Leu Thr Thr Val Ser Thr Ile Pro Pro Ala Ser
                85                  90                  95

Thr Asn Arg Gln Ser Gly Arg Gln Pro Thr Pro Ile Ser Pro Pro Leu
                100                 105                 110

Arg Asp Ser His Pro Gln Ala Met Gln Trp Asn Ser Thr Ala Phe His
                115                 120                 125

Gln Ala Leu Gln Asp Pro Arg Val Arg Gly Leu Tyr Phe Pro Ala Gly
                130                 135                 140

Gly Ser Ser Gly Thr Val Asn Pro Ala Pro Asn Ile Ala Ser His
145                 150                 155                 160

Ile Ser Ser Ile Ser Ala Arg Thr Gly Asp Pro Val Thr Asn
                165                 170

<210> SEQ ID NO 86
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Lys Ala Asn Ser Glu Asn Pro Asp Trp Asp Leu Asn Pro His
                35                  40                  45

Lys Asp Asn Trp Pro Asp Ala Asn Lys Val Gly Val Gly Ala Phe Gly
        50                  55                  60

Pro Gly Phe Thr Pro Pro His Gly Gly Leu Leu Gly Trp Ser Pro Gln
65                  70                  75                  80

Ala Gln Gly Leu Leu Thr Thr Val Pro Ala Ala Pro Pro Pro Ala Ser
                85                  90                  95

Thr Asn Arg Gln Ser Gly Arg Gln Pro Thr Pro Leu Ser Pro Pro Leu
                100                 105                 110

Arg Asp Thr His Pro Gln Ala Met Gln Trp Asn Ser Thr Thr Phe His
                115                 120                 125

Gln Thr Leu Gln Asp Pro Arg Val Arg Ala Leu Tyr Phe Pro Ala Gly
                130                 135                 140

Gly Ser Ser Ser Gly Thr Val Ser Pro Ala Gln Asn Thr Val Ser Ala
145                 150                 155                 160

Ile Ser Ser Ile Leu Ser Lys Thr Gly Asp Pro Val Pro Asn
                165                 170

<210> SEQ ID NO 87
<211> LENGTH: 174
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 87

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
50                  55                  60

Pro Gly Phe Thr Pro Pro His Gly Gly Leu Leu Gly Trp Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn
                165                 170

<210> SEQ ID NO 88
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Gly Thr Val Asn Pro Val Pro
130                 135                 140

Thr Thr Ala Ser Pro Ile Ser Ser Ile Phe Ser Arg Ile Gly Asp Pro
145                 150                 155                 160

Ala Leu Asn

<210> SEQ ID NO 89
<211> LENGTH: 1603
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

| | |
|---|---|
| atgtcttcaa gatcccagag tcagggccct gtactttcct gctggtggct ccagttcagg | 60 |
| aacagtgagc cctgctccga atactgtctc tgccatatcg tcaatcttat cgaagactgg | 120 |
| ggaccctgta ccgaacatgg agaacatcgc atcaggactc ctaggacccc tgctcgtgtt | 180 |
| acaggcgggg ttttcttgt tgacaaaaat cctcacaata ccacagagtc tagactcgtg | 240 |
| gtggacttct ctcaattttc taggggaac accgtgtgt cttggccaaa attcgcagtc | 300 |
| ccaaatctcc agtcactcac caacctgttg tcctccaatt tgtcctggtt atcgctggat | 360 |
| gtgtctgcgg cgttttatca tcttcctctg catcctgctg ctatgcctca tcttcttgtt | 420 |
| ggttcttctg gactatcaag gtatgttgcc cgtttgtcct ctaattccag gatcatcaac | 480 |
| aaccagcacc ggaccatgca aaacctgcac gactcctgct caaggaacct ctatgtttcc | 540 |
| ctcatgttgc tgtacaaaac ctacggacgg aaactgcact tgtattccca tcccatcatc | 600 |
| ttgggctttc gcaaaattcc tatgggagtg ggcctcagtc cgtttctctt ggctcagttt | 660 |
| actagtgcca tttgttcagt ggttcgtagg gctttccccc actgtctggc tttcagttat | 720 |
| atgcatgatg tggtattggg ggccaagtct gtacaacatc ttgagtccct ttatgccgct | 780 |
| gttaccaatt ttcttttgtc tttgggtata catttaaacc ctcacaaaac aaaaagatgg | 840 |
| ggatattccc ttaacttcat gggatatgta attgggagtt ggggcacatt gccgcaggaa | 900 |
| catattgtac aaaaaatcaa aatgtgtttt aggaaacttc ctgtaaaccg gcctattgat | 960 |
| tggaaagtat gtcaacgaat tgtgggtctt ttggggtttg ccgccccttt cacgcaatgt | 1020 |
| ggatatcctg ctttaatgcc tttatatgca tgtatacaag caaaacaggc ttttactttc | 1080 |
| tcgccaactt acaaggcctt cctaagtaaa cagtatctgc acctttaccc cgttgctcgg | 1140 |
| caacggcctg gtctgtgcca agtgtttgct gacgcaaccc ccactggttg gggcttggcc | 1200 |
| ataggccatc agcgcatgcg tggagccttc gtgtctcctc tgccgatcca tactgcgcat | 1260 |
| ctcctggccg cttgttttgc tcgcagcagg tctgggcaa aactcatcgg gactgacaat | 1320 |
| tctgtcgtgc tctcccgcaa gtatacatcc tttccatggc tgctaggctg tgctgccaac | 1380 |
| tggatcctgc gcgggacgtc ctttgtttac gtcccgtcgg cgctgaatcc cgcggacgac | 1440 |
| ccctcccggg gccgcttggg gctctaccgc ccgcttctcc gcttgttgta ccgaccgact | 1500 |
| acggggcgca cctctctcta cgcggactcc ccgtctgtgc cttctcatct gccggaccgt | 1560 |
| gtgcacttcg cttcacctct gcacgtcgca tggagaccac cgt | 1603 |

<210> SEQ ID NO 90
<211> LENGTH: 1602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

| | |
|---|---|
| atgtcatcca gatcccagag tcagggccct gtcctttcct gttggtggct ccagttcagg | 60 |

```
aacagtgagc cctgttctga gtactgtctc tgccacattg tcaatctgat tgaggactgg     120
ggcccctgca cagagcatgg tgaacacagg atcaggactc ccaggacccc tgccagggtg     180
actggtgggg ttttccttgt tgacaaaaat cctcacaaca ccacagagtc aaggcttgtg     240
gtggacttct ctcaattttc aagggggaac acaagggtgt cttggcccaa atttgcagtc     300
ccaaatctcc agtctctgac caacctgttg tcctccaatt tgtcctggtt gtctctggat     360
gtctctgctg ccttttatca tcttcctctc catcctgctg ccatgcctca tcttcttgtt     420
ggttcttctg gcctctctag gtatgttgcc agattgtcct ccaattccag gatcatcaac     480
aaccagcaca ggaccatgca aaacctgcat gactcctgct ccagaaacct ctatgtttct     540
ctcatgttgc tgtacaaaac ctatggcagg aaactgcatt tgtattccca tcccatcatc     600
ttgggcttca ggaaaattcc catgggagtg ggcctcagtc ccttcctctt ggctcagttc     660
accagtgcca tttgttctgt tgtcaggagg ctttccccc  actgtcttgc tttcagttac     720
atgcatgatg tggtcttggg ggccaagtct gtccaacatc ttgagtcact ttatgctgct     780
gtgaccaact ttcttttgtc tttgggcatc catttgaacc ctcacaaaac caaaagatgg     840
ggctattccc tcaatttcat gggctatgtc attgggagtt ggggcacttt gccccaggaa     900
cacattgtgc aaaaaatcaa gatgtgtttc aggaaacttc ctgtgaacag gccaattgac     960
tggaaagtct gtcagagaat tgtgggtctt ttggggtttg cagctccttt cacccaatgt    1020
ggctatcctg ctttgatgcc cttgtatgcc tgcatccagg ccaaacaggc tttcactttc    1080 tccccactt  acaaggcctt cctcagcaaa cagtatctcc acctttaccc tgttgcaagg    1140
cagaggcctg gtctgtgcca agtgtttgct gatgcaaccc ccactggttg gggcttggcc    1200
attggccatc agagaatgag aggtgccttt gtgtctcctc tccccatcca cactgctcat    1260
ctcctggcag cttgctttgc aaggagcagg tctggagcca aactcatagg gactgacaat    1320
tctgtggtgc tctccagaaa gtacacctcc tttccttggc tgctgggctg tgcagccaac    1380
tggatcctga gggggacttc ctttgtttat gtccctctg  ccctgaatcc tgcagatgac    1440
ccctccaggg gcaggttggg gctctacaga ccccttctca ggttgttgta cagaccaaca    1500
acagggagga cctctctcta tgcagattcc ccctctgttc cttctcatct tccagacaga    1560
gtgcactttg cttctcctct gcatgtggct tggagacctc cc                       1602
```

<210> SEQ ID NO 91
<211> LENGTH: 1602
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

```
atgtctagca gaagccagtc ccagggacct gtgctgtctt gttggtggct tcagtttcgg      60
aatagcgagc catgtagcga gtattgcctg tgtcacatcg tgaatctgat tgaggattgg     120
ggaccatgca cagagcacgg agagcaccgg atcagaaccc ctaggacacc agcccgcgtg     180
acaggaggcg tgttcctggt ggataagaac ccccataata aacagagag  cagactggtg     240 gtggattttt ctcagttttc tcgggcaat  acaagagtgt cctggccaaa gtttgccgtg     300
cccaatctcc agagcctgac aaacctgctg tcttctaatc tgagctggct gtccctggac     360
gtgtccgccg cctttaccca cctgccactg cacccctgccg ccatgcccca cctgctggtg     420
ggcagctccg gactgagcag atacgtggca aggctgtcta gcaattctag aattattaat     480
```

```
aatcagcaca gaacaatgca gaatctgcat gattcttgta gcaggaatct gtacgtgagc      540
ctgatgctgc tgtataagac atatggacgc aagctgcacc tgtattctca ccctattatt      600
ctgggcttcc ggaagatccc tatgggcgtg ggactgtccc cattcctgct ggcccagttt      660
acctccgcca tctgctctgt ggtgcggaga gccttcccac attgtctggc cttttcttac      720
atgcacgatg tggtgctggg cgccaaatcc gtgcagcacc tggagtctct gtatgccgcc      780
gtgacaaact tcctgctgag cctgggcatc cacctgaatc cacataagac aaagcggtgg      840
ggctattctc tgaattttat gggctatgtg atcggcagct ggggaaccct gccacaggag      900
cacattgtgc agaagatcaa gatgtgcttt cgcaagctgc ccgtgaatcg gcctatcgat      960
tggaaggtgt gccagaggat cgtgggactg ctgggattcg cagcacccct tacccagtgc     1020
ggctacccag ccctgatgcc actgtatgcc tgtatccagg ccaaacaggc cttcaccttt     1080
tcccctacat ataaggcttt tctgtctaag cagtacctgc atctgtatcc agtggcaagg     1140
cagaggccag gactgtgcca ggtgtttgca gatgcaacac caacaggatg ggactggca      1200 atcggacacc agaggatgag aggagccttc gtgagcccac tgccaattca caccgcccac     1260
ctgctggcag catgctttgc aaggtcccgc tctggagcaa agctgattgg caccgataac     1320
agcgtggtgc tgtccagaaa atacaccagc ttccctggc tgctgggatg tgcagcaaat     1380
tggattctga ggggcaccag cttcgtgtat gtgccttccg ccctgaatcc tgccgatgat     1440
ccatctcgag gcagactggg actgtatagg ccactgctga gactgctgta taggcctacc     1500
acaggcagaa catccctgta tgccgacagc ccatccgtgc cctctcacct gccagataga     1560
gtgcatttcg caagcccact gcatgtggca tggaggccac cc                        1602

<210> SEQ ID NO 92
<211> LENGTH: 1602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
atgtcttcaa gatcccagag tcagggccct gtactttcct gctggtggct ccagttcagg       60
aacagtgagc cctgctctga atactgtctc tgccatattg tcaatcttat agaagactgg      120
ggaccctgta ctgaacatgg agaacatagg atcaggactc ctaggacccc tgctagagtt      180
acaggggggg tttttcttgt tgacaaaaat cctcacaata ccacagagtc tagacttgtg      240
gtggacttct ctcaatttc taggggaac accagggtgt cttggccaaa atttgcagtc       300
ccaaatctcc agtcactcac caacctgttg tcctccaatt tgtcctggtt atccctggat      360
gtgtctgcag ccttttatca tcttcctctg catcctgctg ctatgcctca tcttcttgtt      420
ggttcttctg gactatcaag gtatgttgcc aggttgtcct ctaattccag gatcatcaac      480
aaccagcaca ggaccatgca aaacctgcat gactcctgct caaggaacct ctatgtttcc      540
ctcatgttgc tgtacaaaac ctatggaagg aaactgcact tgtattccca tcccatcatc      600
ttgggcttta gaaaaattcc tatggagtg gcctcagtc cctttctctt ggctcagttt       660
actagtgcca tttgttcagt ggttagaagg ctttcccc actgtctggc tttcagttat       720
atgcatgatg tggtattggg ggccaagtct gtacaacatc ttgagtccct ttatgctgct      780
gttaccaatt ttcttttgtc tttgggtata catttaaacc ctcacaaaac aaaaagatgg      840
ggatattccc ttaacttcat gggatatgta attgggagtt ggggcacatt gcctcaggaa      900
```

```
catattgtac aaaaaatcaa aatgtgtttt aggaaacttc ctgtaaacag gcctattgat      960
tggaaagtat gtcaaagaat tgtgggtctt ttggggtttg cagccccttt cacccaatgt     1020
ggatatcctg ctttaatgcc tttatatgca tgtatacaag caaaacaggc ttttactttc     1080
tccccaactt acaaggcctt cctaagtaaa cagtatctgc acctttaccc tgttgctagg     1140
caaaggcctg gtctgtgcca agtgtttgct gatgcaaccc ccactggttg gggcttggcc     1200
ataggccatc agaggatgag gggagccttt gtgtctcctc tgcctatcca tactgcccat     1260
ctcctggcag cttgttttgc taggagcagg tctgggcaa aactcattgg gactgacaat      1320
tctgttgtgc tctccagaaa gtatacatcc tttccatggc tgctaggctg tgctgccaac     1380
tggatcctga gggggacatc ctttgtttat gtcccttcag cactgaatcc tgctgatgac     1440
ccctccaggg gcagattggg gctctacagg ccccttctca ggttgttgta cagacccact     1500
actgggagaa cctctctcta tgcagactcc ccctctgtgc cttctcatct gcctgacagg     1560
gtgcactttg cttcacctct gcatgttgca tggagaccac ct                        1602
```

<210> SEQ ID NO 93
<211> LENGTH: 1602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
atgagttccc gatcacagag tcaggggccc gtcctttcat gttggtggct tcagtttcga       60
aactccgagc catgttctga gtattgtctc tgccacattg tgaatcttat tgaagactgg      120
ggcccctgca ccgagcacgg cgagcaccga atacggacac ctcgaacgcc agcaagagtg      180
acgggcggag tgttcctcgt cgacaagaat ccacacaaca cgacggagag tagattggtc      240
gttgatttca gtcaattttc aagaggcaat acacagagtt tcttggccgaa attcgccgta    300 ccgaatctgc aatccttgac aaatttgctt agttctaatt tgtcttggct ttctctcgat      360
gtttccgccg ctttctatca cttgccccctt cacccagccg cgatgccgca tctcttggtg    420
ggcagctctg gacttagtag atacgtagct agactcagtt ctaactcacg gataataaat      480
aaccaacatc gcactatgca gaacctgcat gattcttgtt cccggaactt gtatgtctcc     540
ttgatgttgt tgtataaaac ttatgggcga agcttcatc tgtatagcca tccgattata       600
ttgggtttta ggaaaattcc tatggtgtt ggcttgagcc cttttctgct ggcgcaattt       660
acttcagcta tctgctcagt agtacgccgg gcgtttcccc attgtcttgc tttctcatac     720
atgcatgatg tagtacttgg ggccaagtct gtacaacacc ttgagagttt gtatgccgcc     780
gtaactaatt tccttctctc tctcgggatc catcttaacc ctcacaaaac gaagaggtgg     840
ggttattctc tgaatttcat gggatatgtt atcgggtctt ggggaacgct gcctcaggaa      900
cacatcgtcc agaaaatcaa gatgtgtttc agaaagttgc cagtgaacag accgatagat     960
tggaaggttt gccaaagaat tgttggcttg ttgggattcg cagccccatt cacacagtgc     1020
gggtatccgg ctttgatgcc cctttatgct tgtatccagg caaaacaggc attcacccttt    1080 tcaccgactt acaaagcatt tctttctaag cagtatctcc atctttaccc tgtcgctcga     1140
cagcggccgg ggcttgcca ggttttcgca gacgcaaccc caactggttg gggtcttgcg      1200
atcggccacc agaggatgcg cggtgcattc gtgtccccgc tcccaatcca tacggcccac    1260
ttgctggcgg cgtgcttcgc tcgaagtaga agcggggcta aattgatcgg cacggacaat     1320
```

```
tcagtcgtgt tgtcacgcaa atatacctcc tttccctggt tgctcggttg cgcagcaaac   1380
tggatacttc ggggaactag tttcgtttat gtgccctctg ctctcaaccc cgccgacgat   1440
ccttcacgag ggaggctggg tctttaccgc ccattgctca ggctgcttta ccggcctacc   1500
actgggagaa caagcttgta cgccgacagc ccgagcgtcc cgtctcatct gcccgacaga   1560
gttcactttg cgagtccatt gcacgtcgct ggcgcccgc cg                       1602
```

<210> SEQ ID NO 94
<211> LENGTH: 1602
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94

```
atgagttcca gatcacagag tcagggggcct gtcctttcat gttggtggct tcagtttaga   60
aactcagagc catgttctga gtattgtctc tgccacattg tgaatcttat tgaagactgg   120
ggcccctgca cagagcatgg agagcacaga ataaggacac ctagaacccc agcaagagtg   180
acaggtggag tgttcctggt agacaagaat ccacacaaca caactgagag tagattggtg   240
gttgatttca gtcaatttc aagaggcaat acaagagttt cttggccaaa atttgctgta    300
cccaatctgc aatccttgac aaatttgctt agttctaatt tgtcttggct ttctctagat   360
gtttctgcag cttctctatca cttgcccctt cacccagcag ctatgcctca tctcttggtg   420
ggcagctctg gacttagtag atatgtagct agactcagtt ctaactcaag gataataaat   480
aaccaacata ggactatgca gaacctgcat gattcttgtt ccaggaactt gtatgtctcc   540
ttgatgttgt tgtataaaac ttatgggaga aagcttcatc tgtatagcca tcctattata   600
ttgggtttta ggaaaattcc tatgggtgtt ggcttgagcc cttttctgct ggcccaattt   660
acttcagcta tctgctcagt agtaaggagg gcctttcccc attgtcttgc tttctcatac   720
atgcatgatg tagtacttgg ggccaagtct gtacaacacc ttgagagttt gtatgcagca   780
gtaactaatt tccttctctc tcttgggatc catcttaacc ctcacaaaac caagaggtgg   840
ggttattctc tgaatttcat gggatatgtt atagggtctt ggggaaccct gcctcaggaa   900
cacattgtcc agaaaatcaa gatgtgtttc agaaagttgc cagtgaacag accaatagat   960
tggaaggttt gccaaagaat tgttggcttg ttgggatttg cagccccatt cacacagtgt   1020
gggtatcctg ctttgatgcc cctttatgct tgtatccagg caaaacaggc attcaccttt   1080
tcacccactt acaaagcatt tctttctaag cagtatctcc atctttaccc tgtggctaga   1140
cagaggccag gctttgcca ggttttttgca gatgcaaccc caactggttg gggtcttgca   1200
attggccacc agaggatgag aggtgcattt gtgtccccac tcccaatcca tactgcccac   1260
ttgctggcag cttgctttgc tagaagtaga agtggggcta aattgattgg cacagacaat   1320
tcagttgtgt tgtcaaggaa atatacctcc tttccctggt tgcttggttg tgcagcaaac   1380
tggatactta ggggaactag ttttgtttat gtgccctctg ctctcaaccc tgcagatgat   1440
ccttcaagag ggaggctggg tctttacagg ccattgctca ggctgcttta caggcctacc   1500
actgggagaa caagcttgta tgcagacagc cccagtgtcc cctctcatct gcctgacaga   1560
gttcactttg caagtccatt gcatgttgct tggagacctc ca                      1602
```

<210> SEQ ID NO 95
<211> LENGTH: 6

```
<212> TYPE: PRT
<213> ORGANISM: Hepatitis B virus

<400> SEQUENCE: 95

Ser Ala Arg Ser Gln Ser
1               5

<210> SEQ ID NO 96
<211> LENGTH: 6
<212> TYPE: PRT
<213> ORGANISM: Hepatitis B virus

<400> SEQUENCE: 96

Ser Ser Arg Ser Gln Ser
1               5

<210> SEQ ID NO 97
<211> LENGTH: 4
<212> TYPE: PRT
<213> ORGANISM: Hepatitis B virus

<400> SEQUENCE: 97

Tyr Met Asp Asp
1

<210> SEQ ID NO 98
<211> LENGTH: 4
<212> TYPE: PRT
<213> ORGANISM: Hepatitis B virus

<400> SEQUENCE: 98

Ala Glu Leu Leu
1

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Tyr Met His Asp
1

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala His Leu Leu
1

<210> SEQ ID NO 101
<211> LENGTH: 8
<212> TYPE: PRT
<213> ORGANISM: Hepatitis B virus

<400> SEQUENCE: 101

Met Gly Leu Lys Phe Arg Gln Leu
1               5
```

```
<210> SEQ ID NO 102
<211> LENGTH: 8
<212> TYPE: PRT
<213> ORGANISM: Hepatitis B virus

<400> SEQUENCE: 102

Met Gly Leu Lys Ile Arg Gln Leu
1               5
```